(12) United States Patent
Pekrun et al.

(10) Patent No.: US 11,608,510 B2
(45) Date of Patent: Mar. 21, 2023

(54) RECOMBINANT ADENO-ASSOCIATED VIRUS CAPSIDS WITH ENHANCED HUMAN PANCREATIC TROPISM

(71) Applicant: The Board of Trustees of the Leland Stanford Junior University, Palo Alto, CA (US)

(72) Inventors: Katja Pekrun, Palo Alto, CA (US); Mark A. Kay, Los Altos, CA (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 758 days.

(21) Appl. No.: 16/370,735

(22) Filed: Mar. 29, 2019

(65) Prior Publication Data

US 2020/0024616 A1 Jan. 23, 2020

Related U.S. Application Data

(60) Provisional application No. 62/651,010, filed on Mar. 30, 2018, provisional application No. 62/745,226, filed on Oct. 12, 2018.

(51) Int. Cl.
| | |
|---|---|
| *C12N 15/86* | (2006.01) |
| *C07K 14/015* | (2006.01) |
| *A61K 47/69* | (2017.01) |
| *C07K 14/075* | (2006.01) |
| *C12N 15/10* | (2006.01) |
| *C12N 7/00* | (2006.01) |
| *C12N 15/90* | (2006.01) |

(52) U.S. Cl.
CPC .......... *C12N 15/86* (2013.01); *A61K 47/6901* (2017.08); *C07K 14/015* (2013.01); *C07K 14/075* (2013.01); *C12N 15/102* (2013.01); *C12N 7/00* (2013.01); *C12N 15/902* (2013.01); *C12N 2710/10041* (2013.01); *C12N 2710/10071* (2013.01); *C12N 2710/10134* (2013.01); *C12N 2710/10141* (2013.01); *C12N 2750/14123* (2013.01)

(58) Field of Classification Search
CPC ................ C12N 15/86; C12N 15/8645; C12N 710/10041; C12N 710/10071; C12N 2750/14111; C12N 2750/14122; C07K 14/00; C07K 14/005; C07K 14/015
See application file for complete search history.

(56) References Cited

U.S. PATENT DOCUMENTS

| | | | |
|---|---|---|---|
| 5,139,941 | A | 8/1992 | Muzyczka et al. |
| 5,173,414 | A | 12/1992 | Lebkowski et al. |
| 6,200,560 | B1 | 3/2001 | Couto et al. |
| 6,221,349 | B1 | 4/2001 | Couto et al. |
| 6,491,907 | B1 | 12/2002 | Rabinowitz et al. |
| 6,951,758 | B2 | 10/2005 | Ferrari et al. |
| 7,271,002 | B2 | 9/2007 | Kotin et al. |
| 7,439,065 | B2 | 10/2008 | Ferrari et al. |
| 9,169,299 | B2 * | 10/2015 | Lisowski ............. C07K 14/005 |
| 10,414,803 | B2 * | 9/2019 | Nathwani ........... C07K 14/005 |
| 11,015,189 | B2 * | 5/2021 | Lisowski ................ C12N 7/00 |
| 11,083,800 | B2 * | 8/2021 | Arbetman .......... A61K 48/0058 |
| 2005/0053922 | A1 | 3/2005 | Schaffer et al. |
| 2005/0075492 | A1 | 4/2005 | Chen et al. |
| 2005/0142581 | A1 | 6/2005 | Griffey et al. |
| 2005/0266552 | A1 | 12/2005 | Doench et al. |
| 2005/0272923 | A1 | 12/2005 | Zhang et al. |
| 2009/0202490 | A1 | 8/2009 | Schaffer et al. |
| 2009/0203071 | A1 | 8/2009 | Chen |
| 2012/0164106 | A1 | 6/2012 | Schaffer et al. |
| 2014/0242031 | A1 | 8/2014 | Schaffer et al. |
| 2014/0348794 | A1 | 11/2014 | Chiorini et al. |
| 2015/0023924 | A1 | 1/2015 | High et al. |
| 2015/0176027 | A1 | 6/2015 | Gao et al. |
| 2016/0017295 | A1 * | 1/2016 | Schaffer ............... A61K 35/761 435/235.1 |

FOREIGN PATENT DOCUMENTS

| | | |
|---|---|---|
| WO | WO 1992/001070 A1 | 1/1992 |
| WO | WO 1993/003769 A1 | 3/1993 |
| WO | WO 1998/010088 A1 | 3/1998 |
| WO | WO 2013/029030 A1 | 2/2013 |
| WO | WO 2016/054557 A1 | 4/2016 |
| WO | WO 2017/143100 A1 | 8/2017 |

OTHER PUBLICATIONS

Lochrie et al, J. Virology 80(2): 821-834, 2006.*
Adachi et al, Nature Communications 5: 3075, 14 pages, doi:10.1038/ncomms4075; 2014.*
Zhong et al, Molecular Therapy 22 (Suppl 1): Abstract 290, May 2014.*
Yan et al, Human Gene Therapy 26: 38-49, 2015.*
Loiler et al, Gene Therapy 10: 1551-1558, 2003.*
Adachi, Kei et al. "Drawing a high-resolution functional map of adeno-associated virus capsid by massively parallel sequencing." Nature communications vol. 5 (2014): 3075. doi:10.1038/ncomms4075.
Adachi, Kei, and Hiroyuki Nakai. "A New Recombinant Adeno-Associated Virus (AAV)-Based Random Peptide Display Library System: Infection-Defective AAV1.9-3 as a Novel Detargeted Platform for Vector Evolution." Gene therapy and regulation vol. 5,1 (2010): 31-55. doi:10.1142/S1568558610000197.

(Continued)

*Primary Examiner* — Kevin K Hill

(74) *Attorney, Agent, or Firm* — Morgan, Lewis & Bockius LLP

(57) ABSTRACT

The present invention relates to variant AAV capsid polypeptides, wherein the variant AAV capsid polypeptides exhibit increased transduction and/or tropism in human pancreatic tissue or human islets as compared non-variant parent capsid polypeptides.

26 Claims, 70 Drawing Sheets

Specification includes a Sequence Listing.

(56) References Cited

OTHER PUBLICATIONS

Aiello, L et al. "Adenovirus 5 DNA sequences present and RNA sequences transcribed in transformed human embryo kidney cells (HEK-Ad-5 or 293)." Virology vol. 94,2 (1979): 460-9. doi:10.1016/0042-6822(79)90476-8.

Andersen, J K et al. "Herpesvirus-mediated gene delivery into the rat brain: specificity and efficiency of the neuron-specific enolase promoter." Cellular and molecular neurobiology vol. 13,5 (1993): 503-15. doi:10.1007/BF00711459.

Apt, Doris et al. "Tetravalent neutralizing antibody response against four dengue serotypes by a single chimeric dengue envelope antigen." Vaccine vol. 24,3 (2006): 335-44. doi:10.1016/j.vaccine.2005.07.100.

Arbuthnot, P B et al. "In vitro and in vivo hepatoma cell-specific expression of a gene transferred with an adenoviral vector." Human gene therapy vol. 7,13 (1996): 1503-14. doi:10.1089/hum.1996.7.13-1503.

Asuri, Prashanth et al. "Directed evolution of adeno-associated virus for enhanced gene delivery and gene targeting in human pluripotent stem cells." Molecular therapy : the journal of the American Society of Gene Therapy vol. 20,2 (2012): 329-38. doi:10.1038/mt.2011.255.

Balazs, Alejandro B et al. "Antibody-based protection against HIV infection by vectored immunoprophylaxis." Nature vol. 481,7379 81-4. Nov. 30, 2011, doi:10.1038/nature10660.

Balazs, Alejandro B et al. "Broad protection against influenza infection by vectored immunoprophylaxis in mice." Nature biotechnology vol. 31,7 (2013): 647-52. doi:10.1038/nbt.2618.

Balazs, Alejandro B et al. "Vectored immunoprophylaxis protects humanized mice from mucosal HIV transmission." Nature medicine vol. 20,3 (2014): 296-300. doi:10.1038/nm.3471.

Bowles, Dawn E et al. "Phase 1 gene therapy for Duchenne muscular dystrophy using a translational optimized AAV vector." Molecular therapy : the journal of the American Society of Gene Therapy vol. 20,2 (2012): 443-55. doi:10.1038/mt.2011.237.

Brantly, Mark L et al. "Sustained transgene expression despite T lymphocyte responses in a clinical trial of rAAV1-AAT gene therapy." Proceedings of the National Academy of Sciences of the United States of America vol. 106,38 (2009): 16363-8. doi:10.1073/pnas.0904514106.

Bruni, Anthony et al. "Islet cell transplantation for the treatment of type 1 diabetes: recent advances and future challenges." Diabetes, metabolic syndrome and obesity : targets and therapy vol. 7 211-23. Jun. 23, 2014, doi:10.2147/DMSO.S50789.

Capecchi, M R. "High efficiency transformation by direct microinjection of DNA into cultured mammalian cells." Cell vol. 22,2 Pt 2 (1980): 479-88. doi:10.1016/0092-8674(80)90358-x.

Carter, B J. "Adeno-associated virus vectors." Current opinion in biotechnology vol. 3,5 (1992): 533-9. doi:10.1016/0958-1669(92)900824.

Chakravarthy, Harini et al. "Converting Adult Pancreatic Islet α Cells into β Cells by Targeting Both Dnmt1 and Arx." Cell metabolism vol. 25,3 (2017): 622-634. doi:10.1016/j.cmet.2017.01.009.

Chakravarti, Dhrubajyoti, and Paula C Mailander. "Formation of template-switching artifacts by linear amplification." Journal of biomolecular techniques : JBT vol. 19,3 (2008): 184-8.

Chang, C C et al. "Evolution of a cytokine using DNA family shuffling." Nature biotechnology vol. 17,8 (1999): 793-7. doi:10.1038/11737.

Charville, Gregory W et al. "Ex Vivo Expansion and In Vivo Self-Renewal of Human Muscle Stem Cells." Stem cell reports vol. 5,4 (2015): 621-32. doi:10.1016/j.stemcr.2015.08.004.

Chen, Haifeng. "Intron splicing-mediated expression of AAV Rep and Cap genes and production of AAV vectors in insect cells." Molecular therapy : the journal of the American Society of Gene Therapy vol. 16,5 (2008): 924-30. doi:10.1038/mt.2008.35.

Chen, J et al. "Expression of rat bone sialoprotein promoter in transgenic mice." Journal of bone and mineral research : the official journal of the American Society for Bone and Mineral Research vol. 11,5 (1996): 654-64. doi:10.1002/jbmr.5650110513.

Chen, Min et al. "Efficient Gene Delivery and Expression in Pancreas and Pancreatic Tumors by Capsid-Optimized AAV8 Vectors." Human gene therapy methods vol. 28,1 (2017): 49-59. doi:10.1089/hgtb.2016.089.

Choudhury, Sourav R et al. "In Vivo Selection Yields AAV-B1 Capsid for Central Nervous System and Muscle Gene Therapy." Molecular therapy : the journal of the American Society of Gene Therapy vol. 24,7 (2016): 1247-57. doi:10.1038/mt.2016.84.

Christians, F C et al. "Directed evolution of thymidine kinase for AZT phosphorylation using DNA family shuffling." Nature biotechnology vol. 17,3 (1999): 259-64. doi:10.1038/7003.

Chu, G, and P A Sharp. "SV40 DNA transfection of cells in suspension: analysis of efficiency of transcription and translation of T-antigen." Gene vol. 13,2 (1981): 197-202. doi:10.1016/0378-1119(81)90008-1.

Coco, W M et al. "DNA shuffling method for generating highly recombined genes and evolved enzymes." Nature biotechnology vol. 19,4 (2001): 354-9. doi:10.1038/86744.

Colella, Pasqualina et al. "Emerging Issues in AAV-Mediated In Vivo Gene Therapy." Molecular therapy. Methods & clinical development vol. 8 87-104. Dec. 1, 2017, doi:10.1016/j.omtm.2017.11.007.

Collombat, Patrick et al. "The ectopic expression of Pax4 in the mouse pancreas converts progenitor cells into alpha and subsequently beta cells." Cell vol. 138,3 (2009): 449-62. doi:10.1016/j.cell.2009.05.035.

Courtney, Monica et al. "The inactivation of Arx in pancreatic α-cells triggers their neogenesis and conversion into functional β-like cells." PLoS genetics vol. 9,10 (2013): e1003934. doi:10.1371/journal.pgen.1003934.

Craig, Anthony T et al. "Transduction of rat pancreatic islets with pseudotyped adeno-associated virus vectors." Virology journal vol. 6 61. May 18, 2009, doi:10.1186/1743-422X-6-61.

Crameri, A et al. "DNA shuffling of a family of genes from diverse species accelerates directed evolution." Nature vol. 391,6664 (1998): 288-91. doi:10.1038/34663.

Crameri, A et al. "Molecular evolution of an arsenate detoxification pathway by DNA shuffling." Nature biotechnology vol. 15,5 (1997): 436-8. doi:10.1038/nbt0597-436.

Dalkara, Deniz et al. "In vivo-directed evolution of a new adeno-associated virus for therapeutic outer retinal gene delivery from the vitreous." Science translational medicine vol. 5,189 (2013): 189ra76. doi:10.1126/scitranslmed.3005708.

Dorrell, Craig et al. "Isolation of major pancreatic cell types and long-term culture-initiating cells using novel human surface markers." Stem cell research vol. 1,3 (2008): 183-94. doi:10.1016/j.scr.2008.04.001.

Doshi, Bhavya S, and Valder R Arruda. "Gene therapy for hemophilia: what does the future hold?." Therapeutic advances in hematology vol. 9,9 273-293. Aug. 27, 2018, doi:10.1177/2040620718791933.

Eisenberg, D et al. "Analysis of membrane and surface protein sequences with the hydrophobic moment plot." Journal of molecular biology vol. 179,1 (1984): 125-42. doi:10.1016/0022-2836(84)90309-7.

Felgner, P L et al. "Lipofection: a highly efficient, lipid-mediated DNA-transfection procedure." Proceedings of the National Academy of Sciences of the United States of America vol. 84,21 (1987): 7413-7. doi:10.1073/pnas.84.21.7413.

Flores, R R et al. "Expression of IL-2 in β cells by AAV8 gene transfer in pre-diabetic NOD mice prevents diabetes through activation of FoxP3-positive regulatory T cells." Gene therapy vol. 21,8 (2014): 715-22. doi:10.1038/gt.2014.45.

Flotte, T et al. "Efficient ex vivo transduction of pancreatic islet cells with recombinant adeno-associated virus vectors." Diabetes vol. 50,3 (2001): 515-20. doi:10.2337/diabetes.50.3.515.

Flotte, Terence R et al. "Phase 2 clinical trial of a recombinant adeno-associated viral vector expressing a1-antitrypsin: interim results." Human gene therapy vol. 22,10 (2011): 1239-47. doi:10.1089/hum.2011.053.

(56) References Cited

OTHER PUBLICATIONS

Flotte, Terence R et al. "Phase I trial of intramuscular injection of a recombinant adeno-associated virus alpha 1-antitrypsin (rAAV2-CB-hAAT) gene vector to AAT-deficient adults." Human gene therapy vol. 15,1 (2004): 93-128. doi:10.1089/10430340460732490.
Furuyama, Kenichiro et al. "Diabetes relief in mice by glucose-sensing insulin-secreting human α-cells." Nature vol. 567,7746 (2019): 43-48. doi:10.1038/s41586-019-0942-8.
Gao, Guangping et al. "Adeno-associated viruses undergo substantial evolution in primates during natural infections." Proceedings of the National Academy of Sciences of the United States of America vol. 100,10 (2003): 6081-6. doi:10.1073/pnas.0937739100.
George, L, et al. (2017). Spk-8011: preliminary results from a phase 1/2 dose escalation trial of an investigational AAV-mediated gene therapy for hemophilia A. Blood 130.
Gillam E.M.J., C, J.N., Ackerley, D.F. (2014). Directed Evolution Library Creation, Methods and Protocols, Humana Press.
Gossen, M et al. "Transcriptional activation by tetracyclines in mammalian cells." Science (New York, N.Y.) vol. 268,5218 (1995): 1766-9. doi:10.1126/science.7792603.
Gossen, M, and H Bujard. "Tight control of gene expression in mammalian cells by tetracycline-responsive promoters." Proceedings of the National Academy of Sciences of the United States of America vol. 89,12 (1992): 5547-51. doi:10.1073/pnas.89.12.5547.
Graham, F L et al. "Characteristics of a human cell line transformed by DNA from human adenovirus type 5." The Journal of general virology vol. 36,1 (1977): 59-74. doi:10.1099/0022-1317-36-1-59.
Graham, F L, and A J van der Eb. "A new technique for the assay of infectivity of human adenovirus 5 DNA." Virology vol. 52,2 (1973): 456-67. doi:10.1016/0042-6822(73)90341-3.
Gray, Steven J et al. "Production of recombinant adeno-associated viral vectors and use in in vitro and in vivo administration." Current protocols in neuroscience vol. Chapter 4 (2011): Unit 4.17. doi:10.1002/0471142301.ns0417s57.
Grimm, D, and M A Kay. "From virus evolution to vector revolution: use of naturally occurring serotypes of adeno-associated virus (AAV) as novel vectors for human gene therapy." Current gene therapy vol. 3,4 (2003): 281-304. doi:10.2174/1566523034578285.
Grimm, Dirk et al. "In vitro and in vivo gene therapy vector evolution via multispecies interbreeding and retargeting of adeno-associated viruses." Journal of virology vol. 82,12 (2008): 5887-911. doi:10.1128/JVI.00254-08.
Grimm, Dirk, and Sergei Zolotukhin. "E Pluribus Unum: 50 Years of Research, Millions of Viruses, and One Goal-Tailored Acceleration of AAV Evolution." Molecular therapy : the journal of the American Society of Gene Therapy vol. 23,12 (2015): 1819-31. doi:10.1038/mt.2015.173.
Grosse, Stefanie et al. "Relevance of Assembly-Activating Protein for Adeno-associated Virus Vector Production and Capsid Protein Stability in Mammalian and Insect Cells." Journal of virology vol. 91,20 e01198-17. Sep. 27, 2017, doi:10.1128/JVI.01198-17.
Hansal, S A et al. "Induction of antigen-specific hyporesponsiveness by transplantation of hemopoietic cells containing an MHC class I transgene regulated by a lymphocyte-specific promoter." Journal of immunology (Baltimore, Md. : 1950) vol. 161,3 (1998): 1063-8.
Harvey, D M, and C T Caskey. "Inducible control of gene expression: prospects for gene therapy." Current opinion in chemical biology vol. 2,4 (1998): 512-8. doi:10.1016/1367-5931(98)80128-2.
Herrmann, Anne-Kathrin et al. "A Robust and All-Inclusive Pipeline for Shuffling of Adeno-Associated Viruses." ACS synthetic biology vol. 8,1 (2019): 194-206. doi:10.1021/acssynbio.8b00373.
Herrmann, Anne-Kathrin et al. "Impact of the Assembly-Activating Protein on Molecular Evolution of Synthetic Adeno-Associated Virus Capsids." Human gene therapy vol. 30,1 (2019): 21-35. doi:10.1089/hum.2018.085.
Hildinger, Markus, and Alberto Auricchio. "Advances in AAV-mediated gene transfer for the treatment of inherited disorders." European journal of human genetics : EJHG vol. 12,4 (2004): 263-71. doi:10.1038/sj.ejhg.5201153.

Huang, Weiliang et al. "ReX: A suite of computational tools for the design, visualization, and analysis of chimeric protein libraries." BioTechniques vol. 60,2 91-4. Feb. 1, 2016, doi:10.2144/000114381.
International Search Report and Written Opinion for International Patent Application No. PCT/US2019/025026 dated Jul. 22, 2019, 18 pages.
Jimenez, V et al. "In vivo genetic engineering of murine pancreatic beta cells mediated by single-stranded adeno-associated viral vectors of serotypes 6, 8 and 9." Diabetologia vol. 54,5 (2011): 1075-86. doi:10.1007/s00125-011-2070-3.
Johnson, Philip R et al. "Vector-mediated gene transfer engenders long-lived neutralizing activity and protection against SIV infection in monkeys." Nature medicine vol. 15,8 (2009): 901-6. doi:10.1038/nm.1967.
Kapturczak, M H et al. "Adeno-associated virus (AAV) as a vehicle for therapeutic gene delivery: improvements in vector design and viral production enhance potential to prolong graft survival in pancreatic islet cell transplantation for the reversal of type 1 diabetes." Current molecular medicine vol. 1,2 (2001): 245-58. doi:10.2174/1566524013363979.
Kay, Mark A. "Selecting the Best AAV Capsid for Human Studies." Molecular therapy : the journal of the American Society of Gene Therapy vol. 23,12 (2015): 1800-1. doi:10.1038/mt.2015.206.
Keiser, Nicholas W et al. "Unique characteristics of AAV1, 2, and 5 viral entry, intracellular trafficking, and nuclear import define transduction efficiency in HeLa cells." Human gene therapy vol. 22,11 (2011): 1433-44. doi:10.1089/hum.2011.044.
Kienle, Eike et al. "Engineering and evolution of synthetic adeno-associated virus (AAV) gene therapy vectors via DNA family shuffling." Journal of visualized experiments : JoVE ,62 3819. Apr. 2, 2012, doi:10.3791/3819.
Kienle, Eike. "Secrets to finding the ideal mate:New insights into parameters that govern successful Adeno-associated virus (AAV) vector evolution." (2014).
Kikuchi, M et al. "Novel family shuffling methods for the in vitro evolution of enzymes." Gene vol. 236,1 (1999): 159-67. doi:10.1016/s0378-1119(99)00240-1.
Klein, T. et al. High-velocity microprojectiles for delivering nucleic acids into living cells. Nature 327, 70-73 (1987). https://doi.org/10.1038/327070a0.
Koerber, James T et al. "DNA shuffling of adeno-associated virus yields functionally diverse viral progeny." Molecular therapy : the journal of the American Society of Gene Therapy vol. 16,10 (2008): 1703-9. doi:10.1038/mt.2008.167.
Koerber, James T et al. "Molecular evolution of adeno-associated virus for enhanced glial gene delivery." Molecular therapy : the journal of the American Society of Gene Therapy vol. 17,12 (2009): 2088-95. doi:10.1038/mt.2009.184.
Kotin, R M. "Prospects for the use of adeno-associated virus as a vector for human gene therapy." Human gene therapy vol. 5,7 (1994): 793-801. doi:10.1089/hum.1994.5.7-793.
Kuck, Dirk et al. "Intranasal vaccination with recombinant adeno-associated virus type 5 against human papillomavirus type 16 L1." Journal of virology vol. 80,6 (2006): 2621-30. doi:10.1128/JVI.80.6.2621-2630.2006.
Lagos-Quintana, M et al. "Identification of novel genes coding for small expressed RNAs." Science (New York, N.Y.) vol. 294,5543 (2001): 853-8. doi:10.1126/science.1064921.
Lagos-Quintana, Mariana et al. "Identification of tissue-specific microRNAs from mouse." Current biology : CB vol. 12,9 (2002): 735-9. doi:10.1016/s0960-9822(02)00809-6.
Lagos-Quintana, Mariana et al. "New microRNAs from mouse and human." RNA (New York, N.Y.) vol. 9,2 (2003): 175-9. doi:10.1261/rna.2146903.
Lau, N C et al. "An abundant class of tiny RNAs with probable regulatory roles in Caenorhabditis elegans." Science (New York, N.Y.) vol. 294,5543 (2001): 858-62. doi:10.1126/science.1065062.
Lebkowski, J S et al. "Adeno-associated virus: a vector system for efficient introduction and integration of DNA into a variety of mammalian cell types." Molecular and cellular biology vol. 8,10 (1988): 3988-96. doi:10.1128/mcb.8.10.3988-3996.1988.

(56) References Cited

OTHER PUBLICATIONS

Lee, R C, and V Ambros. "An extensive class of small RNAs in Caenorhabditis elegans." Science (New York, N.Y.) vol. 294,5543 (2001): 862-4. doi:10.1126/science.1065329.

Leong, Steven R et al. "Optimized expression and specific activity of IL-12 by directed molecular evolution." Proceedings of the National Academy of Sciences of the United States of America vol. 100,3 (2003): 1163-8. doi:10.1073/pnas.0237327100.

Lerch, Thomas F, and Michael S Chapman. "Identification of the heparin binding site on adeno-associated virus serotype 3B (AAV-3B)." Virology vol. 423,1 (2012): 6-13. doi:10.1016/j.virol.2011.10.007.

Li, Chengwen et al. "Adeno-associated virus vectors: potential applications for cancer gene therapy." Cancer gene therapy vol. 12,12 (2005): 913-25. doi:10.1038/sj.cgt.7700876.

Li, Wuping et al. "Engineering and selection of shuffled AAV genomes: a new strategy for producing targeted biological nanoparticles." Molecular therapy : the journal of the American Society of Gene Therapy vol. 16,7 (2008): 1252-60. doi:10.1038/mt.2008.100.

Li, X et al. "Synthetic muscle promoters: activities exceeding naturally occurring regulatory sequences." Nature biotechnology vol. 17,3 (1999): 241-5. doi:10.1038/6981.

Lim, Lee P et al. "The microRNAs of Caenorhabditis elegans." Genes & development vol. 17,8 (2003): 991-1008. doi:10.1101/gad.1074403.

Lim, Lee P et al. "Vertebrate microRNA genes." Science (New York, N.Y.) vol. 299,5612 (2003): 1540. doi:10.1126/science.1080372.

Lima, Maria J et al. "Generation of Functional Beta-Like Cells from Human Exocrine Pancreas." PloS one vol. 11,5 e0156204. May 31, 2016, doi:10.1371/journal.pone.0156204.

Limberis, Maria P et al. "Intranasal antibody gene transfer in mice and ferrets elicits broad protection against pandemic influenza." Science translational medicine vol. 5,187 (2013): 187ra72. doi:10.1126/scitranslmed.3006299.

Limberis, Maria P et al. "Vectored expression of the broadly neutralizing antibody FI6 in mouse airway provides partial protection against a new avian influenza A virus, H7N9." Clinical and vaccine immunology : CVI vol. 20,12 (2013): 1836-7. doi:10.1128/CVI.00545-13.

Lin, Jianping et al. "A new genetic vaccine platform based on an adeno-associated virus isolated from a rhesus macaque." Journal of virology vol. 83,24 (2009): 12738-50. doi:10.1128/JVI.01441-09.

Lisowski, Leszek et al. "Selection and evaluation of clinically relevant AAV variants in a xenograft liver model." Nature vol. 506,7488 (2014): 382-6. doi:10.1038/nature12875.

Magari, S R et al. "Pharmacologic control of a humanized gene therapy system implanted into nude mice." The Journal of clinical investigation vol. 100,11 (1997): 2865-72. doi:10.1172/JCI119835.

Maheshri, Narendra et al. "Directed evolution of adeno-associated virus yields enhanced gene delivery vectors." Nature biotechnology vol. 24,2 (2006): 198-204. doi:10.1038/nbt1182.

Mallol, Cristina et al. "AAV-mediated pancreatic overexpression of Igf1 counteracts progression to autoimmune diabetes in mice." Molecular metabolism vol. 6,7 664-680. May 17, 2017, doi:10.1016/j.molmet.2017.05.007.

Mannino, R J, and S Gould-Fogerite. "Liposome mediated gene transfer." BioTechniques vol. 6,7 (1988): 682-90.

Martini, Sabrina V et al. "Tyrosine Mutation in AAV9 Capsid Improves Gene Transfer to the Mouse Lung." Cellular physiology and biochemistry : international journal of experimental cellular physiology, biochemistry, and pharmacology vol. 39,2 (2016): 544-53. doi:10.1159/000445646.

Matsuoka, Taka-Aki et al. "Mafa Enables Pdx1 to Effectively Convert Pancreatic Islet Progenitors and Committed Islet α-Cells Into β-Cells In Vivo." Diabetes vol. 66,5 (2017): 1293-1300. doi:10.2337/db16-0887.

Mays, Lauren E et al. "Mapping the structural determinants responsible for enhanced T cell activation to the immunogenic adeno-associated virus capsid from isolate rhesus 32.33." Journal of virology vol. 87,17 (2013): 9473-85. doi:10.1128/JVI.00596-13.

Meliani, Amine et al. "Determination of anti-adeno-associated virus vector neutralizing antibody titer with an in vitro reporter system." Human gene therapy methods vol. 26,2 (2015): 45-53. doi:10.1089/hgtb.2015.037.

Miyatake, S et al. "Transcriptional targeting of herpes simplex virus for cell-specific replication." Journal of virology vol. 71,7 (1997): 5124-32. doi:10.1128/JVI.71.7.5124-5132.1997.

Mowat, F M et al. "Tyrosine capsid-mutant AAV vectors for gene delivery to the canine retina from a subretinal or intravitreal approach." Gene therapy vol. 21,1 (2014): 96-105. doi:10.1038/gt.2013.64.

Mueller, Christian et al. "Human Treg responses allow sustained recombinant adeno-associated virus-mediated transgene expression." The Journal of clinical investigation vol. 123,12 (2013): 5310-8. doi:10.1172/JCI70314.

Münch, Robert C et al. "Displaying high-affinity ligands on adeno-associated viral vectors enables tumor cell-specific and safe gene transfer." Molecular therapy : the journal of the American Society of Gene Therapy vol. 21,1 (2013): 109-18. doi:10.1038/mt.2012.186.

Muzyczka, N. "Use of adeno-associated virus as a general transduction vector for mammalian cells." Current topics in microbiology and immunology vol. 158 (1992): 97-129. doi:10.1007/978-3-642-75608-5_5.

Nair, Gopika G et al. "Recapitulating endocrine cell clustering in culture promotes maturation of human stem-cell-derived β cells." Nature cell biology vol. 21,2 (2019): 263-274. doi:10.1038/541556-018-0271-4.

Naumer, Matthias et al. "Properties of the adeno-associated virus assembly-activating protein." Journal of virology vol. 86,23 (2012): 13038-48. doi:10.1128/JVI.01675-12.

Ness, J E et al. "DNA shuffling of subgenomic sequences of subtilisin." Nature biotechnology vol. 17,9 (1999): 893-6. doi:10.1038/12884.

Nieto, Karen et al. "Combined prophylactic and therapeutic intranasal vaccination against human papillomavirus type-16 using different adeno-associated virus serotype vectors." Antiviral therapy vol. 14,8 (2009): 1125-37. doi:10.3851/IMP1469.

Nieto, Karen et al. "Intranasal vaccination with AAV5 and 9 vectors against human papillomavirus type 16 in rhesus macaques." Human gene therapy vol. 23,7 (2012): 733-41. doi:10.1089/hum.2011.202.

No, D et al. "Ecdysone-inducible gene expression in mammalian cells and transgenic mice." Proceedings of the National Academy of Sciences of the United States of America vol. 93,8 (1996): 3346-51. doi:10.1073/pnas.93.8.3346.

Nonnenmacher, Mathieu et al. "High capsid-genome correlation facilitates creation of AAV libraries for directed evolution." Molecular therapy : the journal of the American Society of Gene Therapy vol. 23,4 (2015): 675-82. doi:10.1038/mt.2015.3.

Odelberg, S J et al. "Template-switching during DNA synthesis by Thermus aquaticus DNA polymerase I." Nucleic acids research vol. 23,11 (1995): 2049-57. doi:10.1093/nar/23.11.2049.

Pääbo, S et al. "DNA damage promotes jumping between templates during enzymatic amplification." The Journal of biological chemistry vol. 265,8 (1990): 4718-21.

Paulk, Nicole K et al. "Bioengineered AAV Capsids with Combined High Human Liver Transduction In Vivo and Unique Humoral Seroreactivity." Molecular therapy : the journal of the American Society of Gene Therapy vol. 26,1 (2018): 289-303. doi:10.1016/j.ymthe.2017.09.021.

Paulk, Nicole K et al. "Bioengineered Viral Platform for Intramuscular Passive Vaccine Delivery to Human Skeletal Muscle." Molecular therapy. Methods & clinical development vol. 10 144-155. Jul. 24, 2018, doi:10.1016/j.omtm.2018.06.001.

Pekrun, K. et al. "Screening of Barcoded Capsid Shuffled AAV Libraries Results in the Selection of Capsids with Enhanced Transduction Efficiency for Human Islets", Molecular Therapy,vol. 26, No. 5S1, May 1, 2018 (May 1, 2018), p. 41.

Pekrun, Katja et al. "Evolution of a human immunodeficiency virus type 1 variant with enhanced replication in pig-tailed macaque cells

(56) References Cited

OTHER PUBLICATIONS by DNA shuffling." Journal of virology vol. 76,6 (2002): 2924-35. doi:10.1128/jvi.76.6.2924-2935.2002.
Pekrun, Katja et al. "Using a barcoded AAV capsid library to select for clinically relevant gene therapy vectors." JCI insight vol. 4,22 e131610. Nov. 14, 2019, doi:10.1172/jci.insight.131610.
Piccioli, P et al. "Neuroantibodies: ectopic expression of a recombinant anti-substance P antibody in the central nervous system of transgenic mice." Neuron vol. 15,2 (1995): 373-84. doi:10.1016/0896-6273(95)90041-1.
Piccioli, P et al. "Neuroantibodies: molecular cloning of a monoclonal antibody against substance P forexpression in the central nervous system." Proceedings of the National Academy of Sciences of the United States of America vol. 88,13 (1991): 5611-5. doi:10.1073/pnas.88.13.5611.
Pillay, Sirika, and Jan E Carette. "Host determinants of adeno-associated viral vector entry." Current opinion in virology vol. 24 (2017): 124-131. doi:10.1016/j.coviro.2017.06.003.
Ploquin, Aurélie et al. "Protection against henipavirus infection by use of recombinant adeno-associated virus-vector vaccines." The Journal of infectious diseases vol. 207,3 (2013): 469-78. doi:10.1093/infdis/jis699.
Powell, S K et al. "Breeding of retroviruses by DNA shuffling for improved stability and processing yields." Nature biotechnology vol. 18,12 (2000): 1279-82. doi:10.1038/82391.
Quirin, Kayla A et al. "Safety and Efficacy of AAV Retrograde Pancreatic Ductal Gene Delivery in Normal and Pancreatic Cancer Mice." Molecular therapy. Methods & clinical development vol. 8 8-20. Sep. 30, 2017, doi:10.1016/j.omtm.2017.09.006.
Raillard, S et al. "Novel enzyme activities and functional plasticity revealed by recombining highly homologous enzymes." Chemistry & biology vol. 8,9 (2001): 891-8. doi:10.1016/s1074-5521(01)00061-8.
Russ, Holger A et al. "Controlled induction of human pancreatic progenitors produces functional beta-like cells in vitro." The EMBO journal vol. 34,13 (2015): 1759-72. doi:10.15252/embj.201591058.
Sakata, Naoaki et al. "Pleckstrin homology-like domain family A, member 3 (PHLDA3) deficiency improves islets engraftment through the suppression of hypoxic damage." PloS one vol. 12,11 e0187927. Nov. 9, 2017, doi:10.1371/journal.pone.0187927.
Sandig, V et al. "HBV-derived promoters direct liver-specific expression of an adenovirally transduced LDL receptor gene." Gene therapy vol. 3,11 (1996): 1002-9.
Shelling, A N, and M G Smith. "Targeted integration of transfected and infected adeno-associated virus vectors containing the neomycin resistance gene." Gene therapy vol. 1,3 (1994): 165-9.
Shigekawa, K, and W J Dower. "Electroporation of eukaryotes and prokaryotes: a general approach to the introduction of macromolecules into cells." BioTechniques vol. 6,8 (1988): 742-51.
Sipo, Isaac et al. "Vaccine protection against lethal homologous and heterologous challenge using recombinant AAV vectors expressing codon-optimized genes from pandemic swine origin influenza virus (SOIV)." Vaccine vol. 29,8 (2011): 1690-9. doi:10.1016/j.vaccine.2010.12.037.
Song, Liujiang et al. "High-efficiency transduction of primary human hematopoietic stem cells and erythroid lineage-restricted expression by optimized AAV6 serotype vectors in vitro and in a murine xenograft model in vivo." PloS one vol. 8,3 (2013): e58757. doi:10.1371/journal.pone.0058757.
Song, Liujiang et al. "Optimizing the transduction efficiency of capsid-modified AAV6 serotype vectors in primary human hematopoietic stem cells in vitro and in a xenograft mouse model in vivo." Cytotherapy vol. 15,8 (2013): 986-98. doi:10.1016/j.jcyt.2013.04.003.
Song, Z, Galivo, FH, Adachi, K, Grompe, M, Nakai, H (2017). Strong Alpha Cell Preference of the AAV Strains That Best Transduce Human Pancreatic Islets In Vitro. Molecular Therapy 25: 47.
Sonntag, F et al. "The assembly-activating protein promotes capsid assembly of different adeno-associated virus serotypes." Journal of virology vol. 85,23 (2011): 12686-97. doi:10.1128/JVI.05359-11.
Sonntag, Florian et al. "A viral assembly factor promotes AAV2 capsid formation in the nucleolus." Proceedings of the National Academy of Sciences of the United States of America vol. 107,22 (2010): 10220-5. doi:10.1073/pnas.1001673107.
Soong, N W et al. "Molecular breeding of viruses." Nature genetics vol. 25,4 (2000): 436-9. doi:10.1038/78132.
Stamatakis, A et al. "RAxML-III: a fast program for maximum likelihood-based inference of large phylogenetic trees." Bioinformatics (Oxford, England) vol. 21,4 (2005): 456-63. doi:10.1093/bioinformatics/bti191.
Stamatakis, Alexandros. "Using RAxML to Infer Phylogenies." Current protocols in bioinformatics vol. 51 6.14.1-6.14.14. Sep. 3, 2015, doi:10.1002/0471250953.bi0614s51.
Stein, G S et al. "The osteocalcin gene: a model for multiple parameters of skeletal-specific transcriptional control." Molecular biology reports vol. 24,3 (1997): 185-96. doi: 10.1023/a:1006803615430.
Stemmer, W P. "DNA shuffling by random fragmentation and reassembly: in vitro recombination for molecular evolution." Proceedings of the National Academy of Sciences of the United States of America vol. 91,22 (1994): 10747-51. doi:10.1073/pnas.91.22.10747.
Stemmer, W P. "Rapid evolution of a protein in vitro by DNA shuffling." Nature vol. 370,6488 (1994): 389-91. doi:10.1038/370389a0.
Stutzman-Engwall, Kim et al. "Semi-synthetic DNA shuffling of aveC leads to improved industrial scale production of doramectin by Streptomyces avermitilis." Metabolic engineering vol. 7,1 (2005): 27-37. doi:10.1016/j.ymben.2004.07.003.
Tervo, D Gowanlock R et al. "A Designer AAV Variant Permits Efficient Retrograde Access to Projection Neurons." Neuron vol. 92,2 (2016): 372-382. doi:10.1016/j.neuron.2016.09.021.
Thomas, Clare E et al. "Rapid uncoating of vector genomes is the key to efficient liver transduction with pseudotyped adeno-associated virus vectors." Journal of virology vol. 78,6 (2004): 3110-22. doi:10.1128/jvi.78.6.3110-3122.2004.
Toole, J J et al. "Molecular cloning of a cDNA encoding human antihaemophilic factor." Nature vol. 312,5992 (1984): 342-7. doi:10.1038/312342a0.
Vasileva, Ana, and Rolf Jessberger. "Precise hit: adeno-associated virus in gene targeting." Nature reviews. Microbiology vol. 3,11 (2005): 837-47. doi:10.1038/nrmicro1266.
Vehar, G A et al. "Structure of human factor VIII." Nature vol. 312,5992 (1984): 337-42. doi:10.1038/312337a0.
Vieira, A et al. "β-Cell replacement as a treatment for type 1 diabetes: an overview of possible cell sources and current axes of research." Diabetes, obesity & metabolism vol. 18 Suppl 1 (2016): 137-43. doi:10.1111/dom.12721.
Wang, Xiaojie et al. "Improving islet engraftment by gene therapy." Journal of transplantation vol. 2011 (2011): 594851. doi:10.1155/2011/594851.
Wang, Y et al. "Ligand-inducible and liver-specific target gene expression in transgenic mice." Nature biotechnology vol. 15,3 (1997): 239-43. doi:10.1038/nbt0397-239.
Wang, Y et al. "Positive and negative regulation of gene expression in eukaryotic cells with an inducible transcriptional regulator." Gene therapy vol. 4,5 (1997): 432-41. doi:10.1038/sj.gt.3300402.
Wang, Yuhan et al. "Long-Term Correction of Diabetes in Mice by In Vivo Reprogramming of Pancreatic Ducts." Molecular therapy : the journal of the American Society of Gene Therapy vol. 26,5 (2018): 1327-1342. doi:10.1016/j.ymthe.2018.02.014.
Wang, Zhong et al. "Widespread and stable pancreatic gene transfer by adeno-associated virus vectors via different routes." Diabetes vol. 55,4 (2006): 875-84. doi:10.2337/diabetes.55.04.06.db05-0927.
Ward, Peter, and Christopher E Walsh. "Chimeric AAV Cap sequences alter gene transduction." Virology vol. 386,2 (2009): 237-48. doi:10.1016/j.virol.2009.01.012.
Wood, W I et al. "Expression of active human factor VIII from recombinant DNA clones." Nature vol. 312,5992 (1984): 330-7. doi:10.1038/312330a0.

(56) References Cited

OTHER PUBLICATIONS

Wright, Anne et al. "Diverse plasmid DNA vectors by directed molecular evolution of cytomegalovirus promoters." Human gene therapy vol. 16,7 (2005): 881-92. doi:10.1089/hum.2005.16.881.

Wu, Jianqing et al. "Self-complementary recombinant adeno-associated viral vectors: packaging capacity and the role of rep proteins in vector purity." Human gene therapy vol. 18,2 (2007): 171-82. doi:10.1089/hum.2006.088.

Xiao, Xiangwei et al. "Endogenous Reprogramming of Alpha Cells into Beta Cells, Induced by Viral Gene Therapy, Reverses Autoimmune Diabetes." Cell stem cell vol. 22,1 (2018): 78-90.e4.doi:10.1016/j.stem.2017.11.020.

Xie, Qing et al. "Structure-function analysis of receptor-binding in adeno-associated virus serotype 6 (AAV-6)." Virology vol. 420,1 (2011): 10-9. doi:10.1016/j.virol.2011.08.011.

Yang, Lin et al. "A myocardium tropic adeno-associated virus (AAV) evolved by DNA shuffling and in vivo selection." Proceedings of the National Academy of Sciences of the United States of America vol. 106,10 (2009): 3946-51. doi:10.1073/pnas.0813207106.

Zhang, J H et al. "Directed evolution of a fucosidase from a galactosidase by DNA shuffling and screening." Proceedings of the National Academy of Sciences of the United States of America vol. 94,9 (1997): 4504-9. doi:10.1073/pnas.94.9.4504.

Zhang, Yanqing et al. "PAX4 Gene Transfer Induces α-to-β Cell Phenotypic Conversion and Confers Therapeutic Benefits for Diabetes Treatment." Molecular therapy : the journal of the American Society of Gene Therapy vol. 24,2 (2016): 251-260. doi:10.1038/mt.2015.181.

Zhao, Chunxia et al. "Overcoming Insulin Insufficiency by Forced Follistatin Expression in β-cells of db/db Mice." Molecular therapy : the journal of the American Society of Gene Therapy vol. 23,5 (2015): 866-874. doi:10.1038/mt.2015.29.

Zhao, H et al. "Molecular evolution by staggered extension process (StEP) in vitro recombination." Nature biotechnology vol. 16,3 (1998): 258-61. doi:10.1038/nbt0398-258.

Zhong, Li et al. "Next generation of adeno-associated virus 2 vectors: point mutations in tyrosines lead to high-efficiency transduction at lower doses." Proceedings of the National Academy of Sciences of the United States of America vol. 105,22 (2008): 7827-32. doi:10.1073/pnas.0802866105.

Zhou, Liqiao et al. "Long-term protection against human papillomavirus e7-positive tumor by a single vaccination of adeno-associated virus vectors encoding a fusion protein of inactivated e7 of human papillomavirus 16/18 and heat shock protein 70." Human gene therapy vol. 21,1 (2010): 109-19. doi:10.1089/hum.2009.139.

Zhou, S Z et al. "Adeno-associated virus 2-mediated high efficiency gene transfer into immature and mature subsets of hematopoietic progenitor cells in human umbilical cord blood." The Journal of experimental medicine vol. 179,6 (1994): 1867-75. doi:10.1084/jem.179.6.1867.

Zinn, Eric et al. "In Silico Reconstruction of the Viral Evolutionary Lineage Yields a Potent Gene Therapy Vector." Cell reports vol. 12,6 (2015): 1056-68. doi:10.1016/j.celrep.2015.07.019.

\* cited by examiner

FIGURE 17
I: each cap linked to different BC: mostly
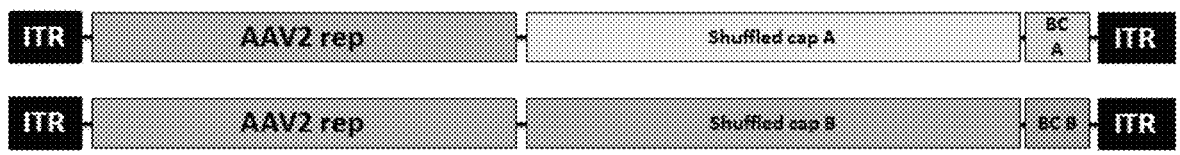
II: different caps linked to identical BC: very rarely (ca. 0.5%)
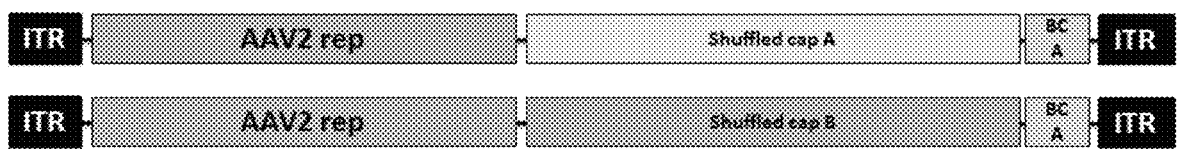
III: identical caps linked to different BC: not found
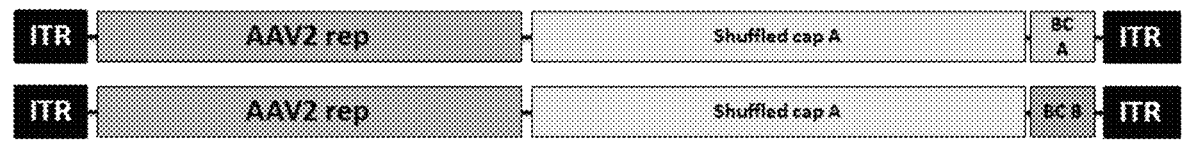

FIGURE 19
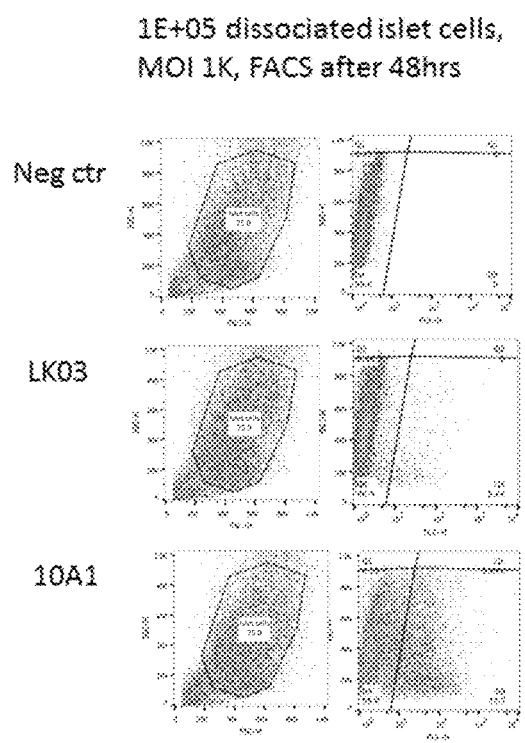
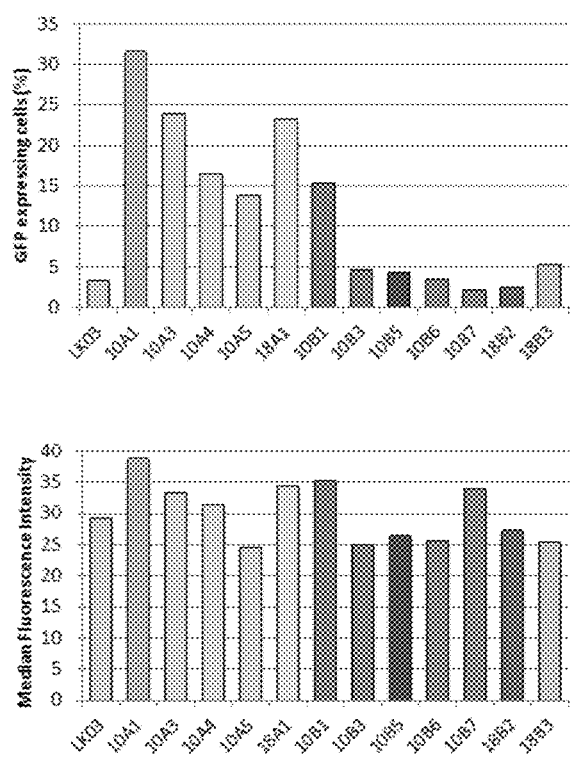

FIGURE 28
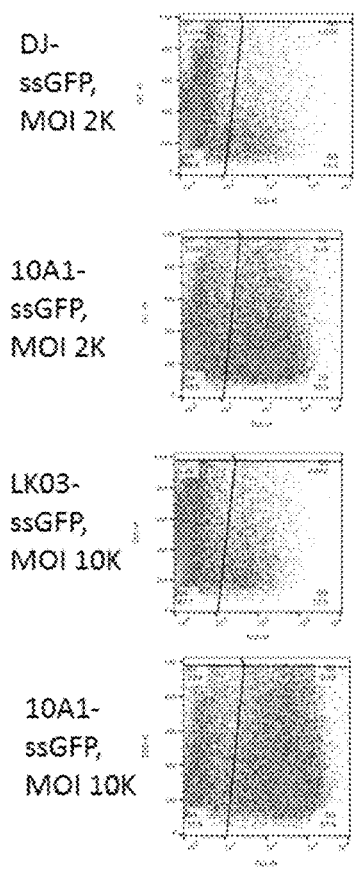
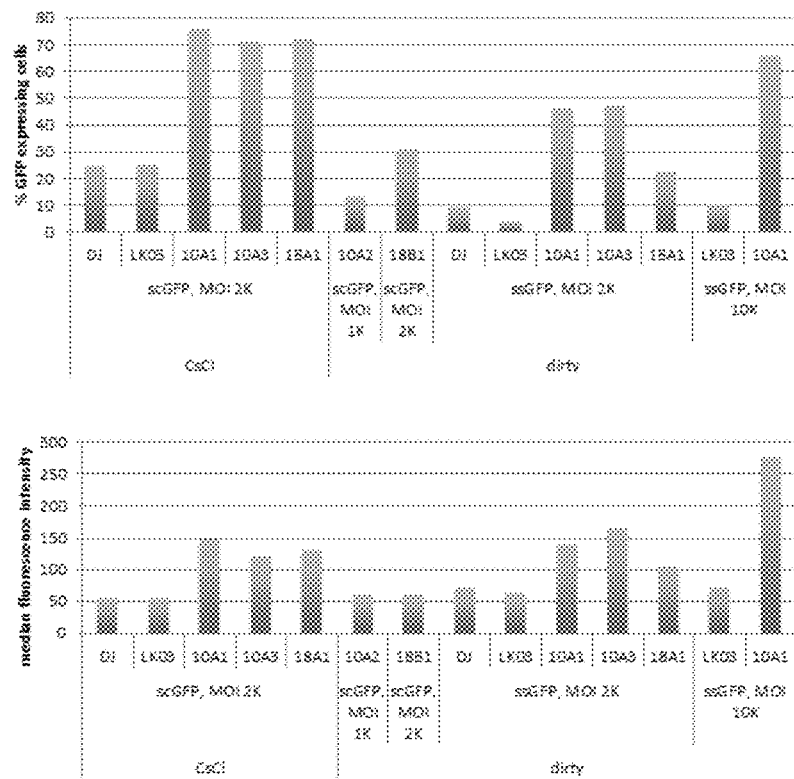

FIGURE 36
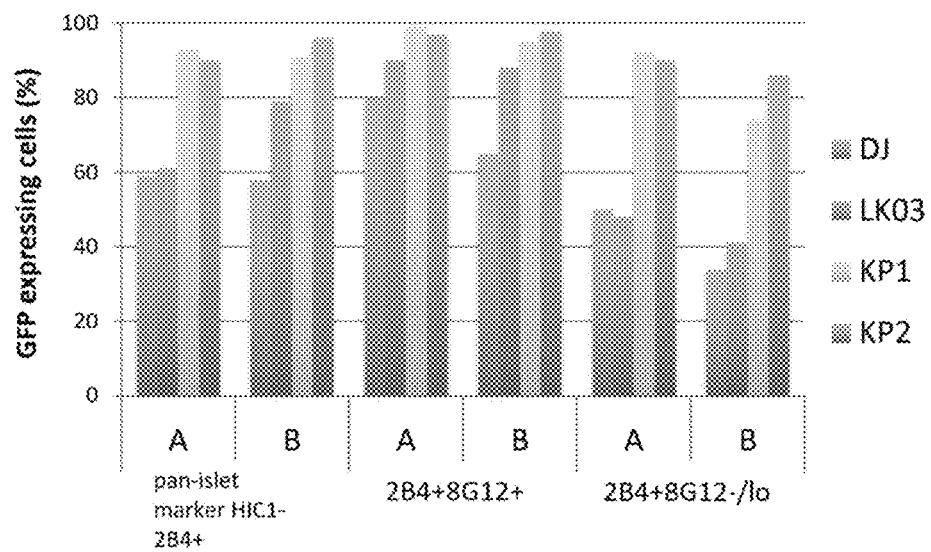
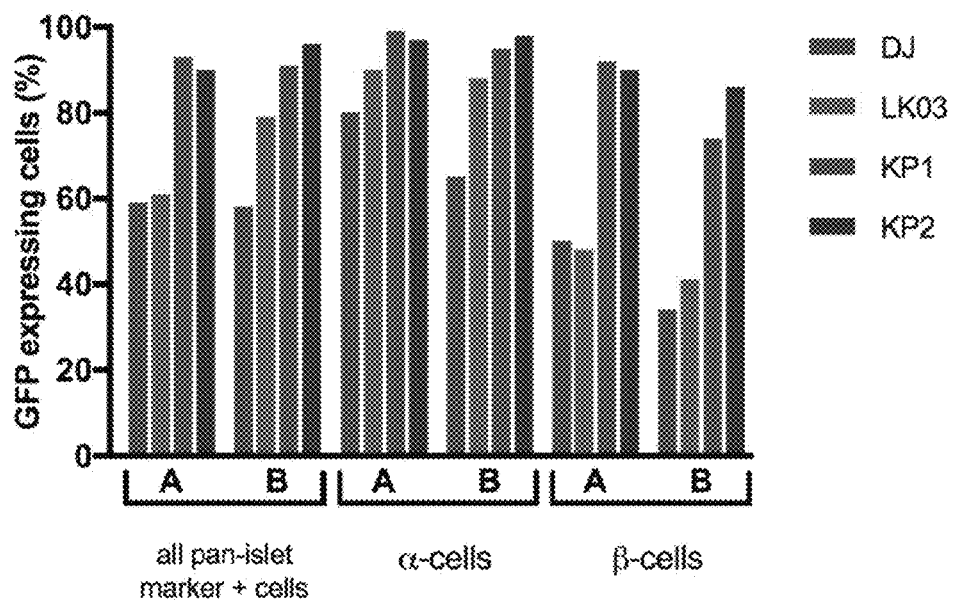

Surface (VP3)   Lumen (VP3)

FIGURE 46
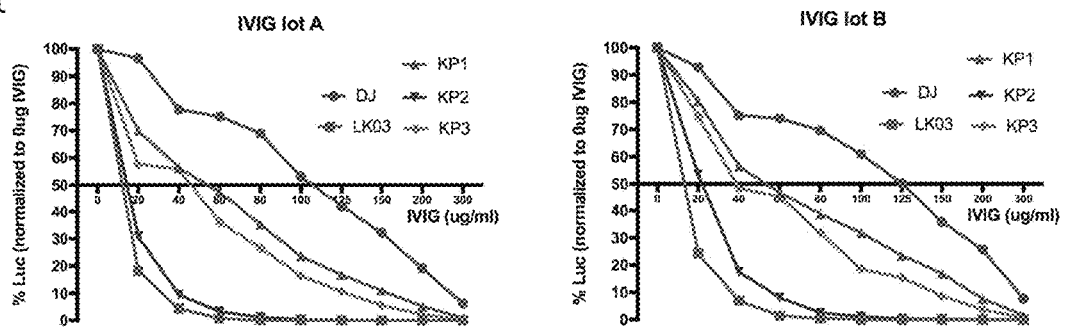
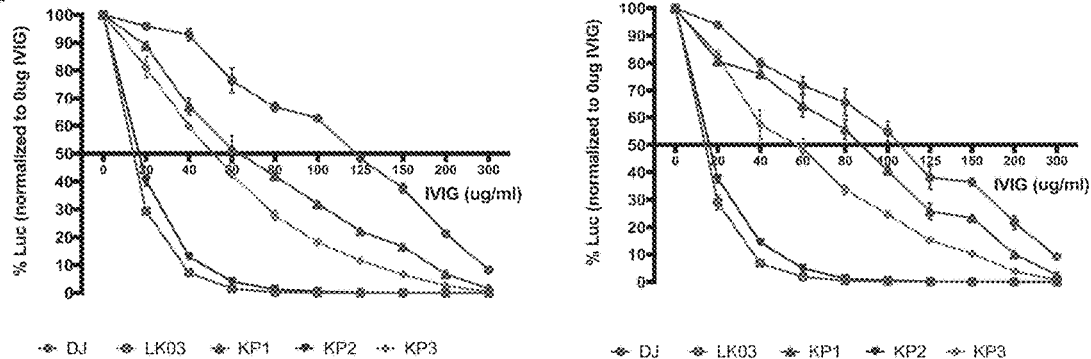

- AAV1
- AAV2
- AAV3B
- AAV4
- AAV5
- AAV6
- AAV8
- AAV9hu14
- AAV12
- DJ
- LK03
- rhesus10
- porcine1
- porcine2
- mouse1
- goat1
- avian
- bovine

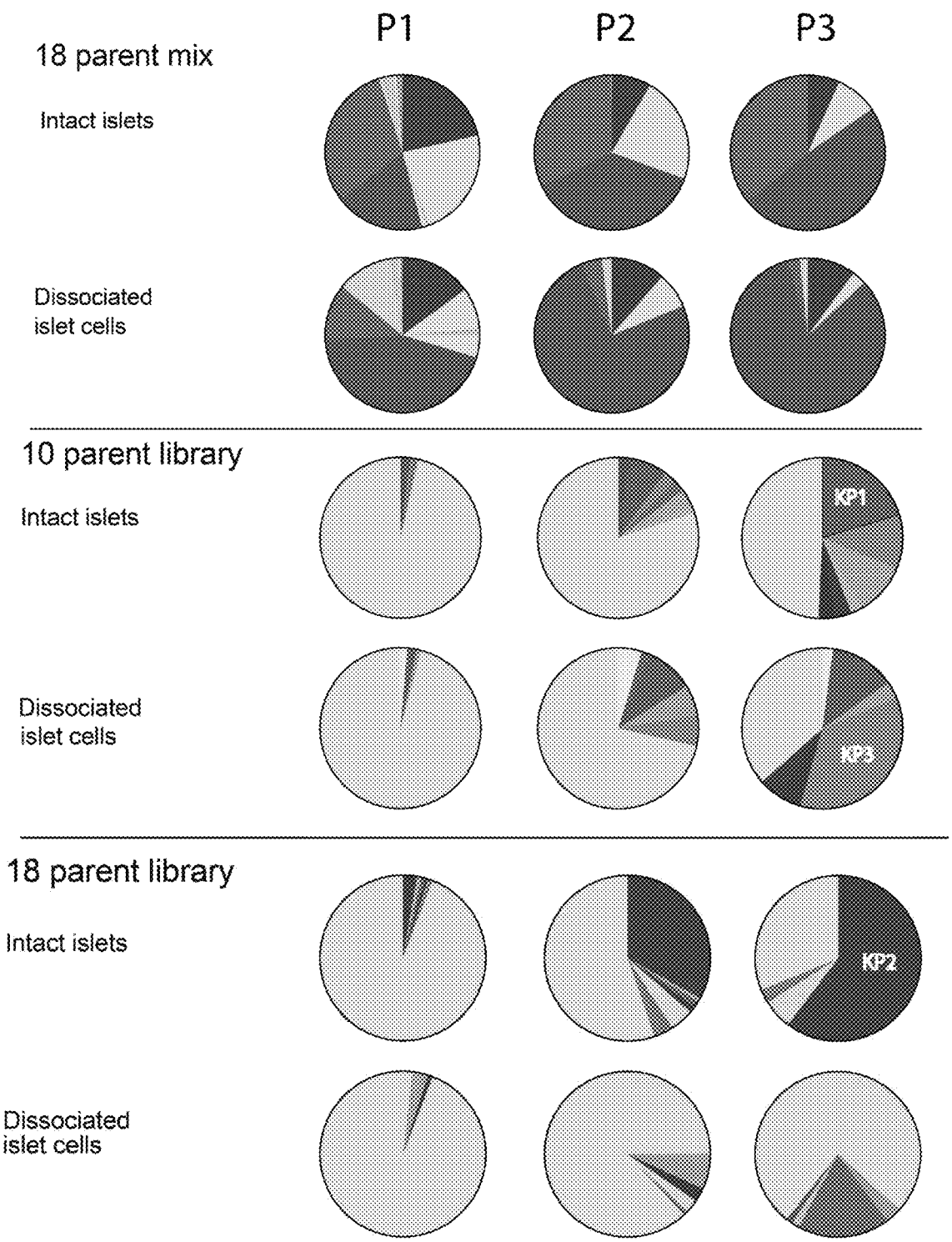

exterior    interior

Plasmid library  AAV library

| Ruler 1 | 1 10 20 30 40 50 60 | |
|---|---|---|
| Consensus | LATGSQs T NLSENxQQPP LVWDL IQWLQAVAHQWQT TKAPTEWVMP QEIGIAI PHGWATESSPPAPE | (SEQ ID NO:117) |
| AAV1_AAP | . . . . . P . H . . . . L . . . . L . . . . L . . . . . . . . . . . . . . . . . . . . . . . . . . . . . . . . . . . . . A | (SEQ ID NO:118) |
| AAV2_AAP | . E . . T . YL . PS . . DSN . . . . . . E . . R . . . . . . . . . . . R . . . . I . R . . . . . . . . . . . . . . . . . | (SEQ ID NO:119) |
| AAV3B_AAP | . . . . . Q . . . . . . . H . . . Q . . . . . . . . . . . . . . RV . M . . I . . . . . . . . . . N . . . . . . . . . . | (SEQ ID NO:120) |
| AAV6_AAP | . . . . . P . H . . . . L . . . . L . . . . L . . . . . . . . . . . . . . . . . . . . . . . . . . . . . . . . . . . . . | (SEQ ID NO:121) |
| AAV8_AAP | . . . . . FQ . . . . . L . . R . . . . . . . . . . . . . . . . . . . . . . . . Y . R . . . . . . . . . . . . . . . . . | (SEQ ID NO:122) |
| AAV9hu14_AAP | . . . . . Q . . . Q . . LP . . . Q . . . . L . . . . Y . . . . . . . . . V . M . . V . R . . . . . . N . . G . . . . . | (SEQ ID NO:123) |
| rhesus_AAP | . . . . . CP . . . Q . . PP . A . . . . . . Y . . . . . . . . L . . . . . . . . . . . . Y . . . . . . . . . . . . . . | (SEQ ID NO:124) |
| porcine2_AAP | . E . PTPPL . PS . . . . H . . . . . . . E . VR . . . . . . . . . . . . . . . . R . . . . . . . . . . . . . . . . . . A | (SEQ ID NO:125) |
| KP1_AAP | . E . PTPPL . PS . . . . H . . . . . . . E . V . . . . . . . L . . . . . . . . . . R . . . . . . . . . . . . . . . . A | (SEQ ID NO:126) |
| KP2_AAP | . . . T . YL . PS . . DSN . . . . . . E . . R . . . . . . . . . . . R . . . . . . . . . . . . . . . . . . . . . . . . | (SEQ ID NO:127) |
| KP3_AAP | . . . . . FQ . . . . . L . . R . . . . . . . . . . . . . . . . . . . . . . . . . . . . . . . . . . . . . . . . . . . A | (SEQ ID NO:128) |

| Ruler 1 | 70 80 90 100 110 120 130 | |
|---|---|---|
| Consensus | PQPEPPTTITSTSKSPv IQR - xPaTTITISATAPPGG ILTSTOSIAISHHVTGSDSSTTTGDSGPPDSTS | (SEQ ID NO:117) |
| AAV1_AAP | . . . . . I . . . . . . . . . . . . . G . . . . . . . . . . . . . . . . . . . F . . . . . . . . . I . . . . . . . . . | (SEQ ID NO:118) |
| AAV2_AAP | . . . . . . . . . . . . N . P . AN . . . E . R . . I . . L . . . . . . L . . . . . . F . . . . K . . . . . . . D . . . . | (SEQ ID NO:119) |
| AAV3B_AAP | . . . . L . . . . . I . . . . . . . AN . . . ELQ . . . . L . . . . L . . . . . . . . . . . . . . . L . . . . . . N . A . | (SEQ ID NO:120) |
| AAV6_AAP | H . . . . I . . . . . . . . . . . . . G . . . . . . . . . . . . . . . . . . . F . . . . . . . . . I . . . . . . . . . | (SEQ ID NO:121) |
| AAV8_AAP | . . . . . . . . . . . . . . . . . TGH . EE . P . . . P . . . . . . . . . L . . . . . F . . . . . . . . . . . . . . . A . | (SEQ ID NO:122) |
| AAV9hu14_AAP | . . . . . I . . . . . . . . TAHLEDLQM . . P . . . . . . . . . . . . . . . . . . . . . . . . . . . . . LS . . . . | (SEQ ID NO:123) |
| rhesus_AAP | . . S . . . . . . . . . . . . . . TGL . EEAP . . P . . . . . . . . . L . . . . . . . . . . . . . . . . . . . . . . . . | (SEQ ID NO:124) |
| porcine2_AAP | . . . . . I . . . . . . ASL . . E . T . . . . L . . . . . T . . . . A . . . PRE . . G . . . . . . G . . . S . . . . | (SEQ ID NO:125) |
| KP1_AAP | . . . . . . . . . . . . . . . . . . . G . . . . . . . . . . . T . . . . A . . . . . . . . . K . . . . . . . . . . . . | (SEQ ID NO:126) |
| KP2_AAP | H . . . . I . . . . . . . . . . . . . G . . . . . . . . . . . T . . . . A . . . PRE . . G . . . . . . G . . . S . . . | (SEQ ID NO:127) |
| KP3_AAP | . . . . . I . . . . . . . . . . . . . G . . . . . . . . . L . . . . . . . F . . . . K . . . . . . . D . . . . | (SEQ ID NO:128) |

| Ruler 1 | 150 160 170 180 190 200 | |
|---|---|---|
| Consensus | SSSTSKSRRSRRMExRPGP ITLPARFRCLRTRSTSSRTsSALRTRAASLRSRRTCs - - - - - - - | (SEQ ID NO:117) |
| AAV1_AAP | N . . . . . . . . . . M . SQ . . L . . . . . . KSS . . . . . . P . . . . . . . . . . . . . . . . . . . . . . . . . . | (SEQ ID NO:118) |
| AAV2_AAP | . . L . P . . K . . . . . TVR . HL . . . . . . . . . . L . . . . . . . . . R . IKD . . R . . QQ . S . WCHSMDTSP | (SEQ ID NO:119) |
| AAV3B_AAP | . . . . LK . . . . . TM . R . LL . . . . . . . . . . . K . . . . . . I . . . C . GR . . K . V . R . FQ . . S . WSLSMDTSP | (SEQ ID NO:120) |
| AAV6_AAP | . . . . . . . . . . . M . S . . . L . . . . . . KSS . . . . . . C . . . . . . . . . . . . . . . . . . . . . . . . . . | (SEQ ID NO:121) |
| AAV8_AAP | . . . . . R . . . . . . . . . . . P . . . . . . . S . . PS . . . . . . C . . F . . . P . . . C . . . . . . . . . . . . | (SEQ ID NO:122) |
| AAV9hu14_AAP | . . . FR . K . L . TTMES . . . . . . . . . S . SS . . OT I . . . . C . GRL . . . . . R . . Q . . P . . . . . . . | (SEQ ID NO:123) |
| rhesus_AAP | . . . . . R . . . . . . . . . . . P . . . . . . . S . . . N . . . . . . . . . . C . . . . . . S . . . . . . . . . . . | (SEQ ID NO:124) |
| porcine2_AAP | . . . . . . . . . . . L . RT . R . . . . . . . . . . . . . S . . . . . . . . . . OQ . . . . . . R . . . . S . WSRSTGI . . | (SEQ ID NO:125) |
| KP1_AAP | . . . . . R . . . . . . . . . . . P . . . . . . . . . . . . . . . L . . . . . C . . F . . . P . . . C . . . . . . . . | (SEQ ID NO:126) |
| KP2_AAP | . . . . . R . . . . . . H . LL . . . . . . . K . . . . . . I . . . . C . . . P . . . C . . . . . . . . . . . . . . . | (SEQ ID NO:127) |
| KP3_AAP | . . L . F . . K . . . . . . P . . . . . . . S . . PS . . . . . . C . . F . . . P . . . C . . . . . . . . . . . . | (SEQ ID NO:128) |

SEQUENCE LISTING

```
<160> NUMBER OF SEQ ID NOS: 128

<210> SEQ ID NO 1
<211> LENGTH: 737
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 1

Met Ala Ala Asp Gly Tyr Leu Pro Asp Trp Leu Glu Asp Thr Leu Ser
1               5                   10                  15

Glu Gly Ile Arg Gln Trp Trp Lys Leu Lys Pro Gly Pro Pro Pro Pro
            20                  25                  30

Lys Pro Ala Glu Arg His Lys Asp Asp Ser Arg Gly Leu Val Leu Pro
        35                  40                  45

Gly Tyr Lys Tyr Leu Gly Pro Gly Asn Gly Leu Asp Lys Gly Glu Pro
    50                  55                  60

Val Asn Ala Ala Asp Ala Ala Leu Glu His Asp Lys Ala Tyr Asp
65                  70                  75                  80

Gln Gln Leu Lys Ala Gly Asp Asn Pro Tyr Leu Arg Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Pro Val Lys Thr Ala Pro Gly Lys Lys Arg
    130                 135                 140

Pro Val Glu His Ser Pro Val Glu Pro Asp Ser Ser Ser Gly Thr Gly
145                 150                 155                 160

Lys Ala Gly Gln Gln Pro Ala Arg Lys Arg Leu Asn Phe Gly Gln Thr
                165                 170                 175

Gly Asp Thr Asp Ser Ala Ala Asp Pro Gln Pro Leu Gly Glu Pro Pro
            180                 185                 190

Ala Ala Pro Ser Gly Leu Gly Thr Gly Thr Met Ala Ala Gly Gly Gly
        195                 200                 205

Ala Pro Met Ala Asp Asn Asn Glu Gly Ala Asp Gly Val Gly Asn Ala
    210                 215                 220

Ser Gly Asn Trp His Cys Asp Ser Thr Trp Leu Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Ser Ala Ser Thr Gly Ala Ser Asn Asp Asn His
            260                 265                 270

Tyr Phe Gly Tyr Ser Thr Pro Trp Gly Tyr Phe Asp Phe Asn Arg Phe
        275                 280                 285
```

```
His Cys His Phe Ser Pro Arg Asp Trp Gln Arg Leu Ile Asn Asn Asn
    290                 295                 300
Trp Gly Phe Arg Pro Lys Arg Leu Asn Phe Lys Leu Phe Asn Ile Gln
305                 310                 315                 320
Val Lys Glu Val Thr Gln Asn Glu Gly Thr Lys Thr Ile Ala Asn Asn
                325                 330                 335
Leu Thr Ser Thr Val Gln Val Phe Thr Asp Ser Glu Tyr Gln Leu Pro
            340                 345                 350
Tyr Val Leu Gly Ser Ala His Gln Gly Cys Leu Pro Pro Phe Pro Ala
                355                 360                 365
Asp Val Phe Met Ile Pro Gln Tyr Gly Tyr Leu Thr Leu Asn Asn Gly
370                 375                 380
Ser Gln Ala Met Gly Arg Ser Ser Phe Tyr Cys Leu Glu Tyr Phe Pro
385                 390                 395                 400
Ser Gln Met Leu Arg Thr Gly Asn Asn Phe Gln Phe Thr Tyr Thr Phe
                405                 410                 415
Glu Asp Val Pro Phe His Ser Ser Tyr Ala His Ser Gln Ser Leu Asp
                420                 425                 430
Arg Leu Met Asn Pro Leu Ile Asp Gln Tyr Leu Tyr Tyr Leu Asn Arg
                435                 440                 445
Thr Gln Gly Thr Thr Ser Gly Thr Thr Asn Gln Ser Arg Leu Leu Phe
            450                 455                 460
Ser Gln Ala Gly Pro Gln Ser Met Ser Leu Gln Ala Arg Asn Trp Leu
465                 470                 475                 480
Pro Gly Pro Cys Tyr Arg Gln Gln Arg Leu Ser Lys Thr Ala Asn Asp
                485                 490                 495
Asn Asn Asn Ser Asn Phe Pro Trp Thr Ala Ala Ser Lys Tyr His Leu
            500                 505                 510
Asn Gly Arg Asp Ser Leu Val Asn Pro Gly Pro Ala Met Ala Ser His
            515                 520                 525
Lys Asp Asp Glu Glu Lys Phe Phe Pro Met His Gly Asn Leu Ile Phe
530                 535                 540
Gly Lys Glu Gly Thr Thr Ala Ser Asn Ala Glu Leu Asp Asn Val Met
545                 550                 555                 560
Ile Thr Asp Glu Glu Glu Ile Arg Thr Thr Asn Pro Val Ala Thr Glu
                565                 570                 575
Gln Tyr Gly Thr Val Ala Asn Asn Leu Gln Ser Ser Asn Thr Ala Pro
            580                 585                 590
Thr Thr Arg Thr Val Asn Asp Gln Gly Ala Leu Pro Gly Met Val Trp
            595                 600                 605
Gln Asp Arg Asp Val Tyr Leu Gln Gly Pro Ile Trp Ala Lys Ile Pro
610                 615                 620
His Thr Asp Gly His Phe His Pro Ser Pro Leu Met Gly Gly Phe Gly
625                 630                 635                 640
Leu Lys His Pro Pro Pro Gln Ile Leu Ile Lys Asn Thr Pro Val Pro
                645                 650                 655
Ala Asp Pro Pro Thr Ala Phe Asn Lys Asp Lys Leu Asn Ser Phe Ile
                660                 665                 670
Thr Gln Tyr Ser Thr Gly Gln Val Ser Val Glu Ile Glu Trp Glu Leu
            675                 680                 685
Gln Lys Glu Asn Ser Lys Arg Trp Asn Pro Glu Ile Gln Tyr Thr Ser
690                 695                 700
Asn Tyr Tyr Lys Ser Thr Ser Val Asp Phe Ala Val Asn Thr Glu Gly
```

```
                      705                 710                 715                 720
            Val Tyr Ser Glu Pro Arg Pro Ile Gly Thr Arg Tyr Leu Thr Arg Asn
                                725                 730                 735

Leu

<210> SEQ ID NO 2
<211> LENGTH: 738
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 2

Met Ala Ala Asp Gly Tyr Leu Pro Asp Trp Leu Glu Asp Thr Leu Ser
  1               5                  10                  15

Glu Gly Ile Arg Gln Trp Trp Lys Leu Lys Pro Gly Pro Pro Pro Pro
                 20                  25                  30

Lys Pro Ala Glu Arg His Lys Asp Asp Ser Arg Gly Leu Val Leu Pro
             35                  40                  45

Gly Tyr Lys Tyr Leu Gly Pro Phe Asn Gly Leu Asp Lys Gly Glu Pro
 50                  55                  60

Val Asn Glu Ala Asp Ala Ala Ala Leu Glu His Asp Lys Ala Tyr Asp
 65                  70                  75                  80

Gln Gln Leu Lys Ala Gly Asp Asn Pro Tyr Leu Arg Tyr Asn His Ala
                 85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Gly Ala Lys Thr Ala Pro Gly Lys Lys Arg
130                 135                 140

Pro Val Glu Pro Ser Pro Gln Arg Ser Pro Asp Ser Ser Thr Gly Ile
145                 150                 155                 160

Gly Lys Lys Gly Gln Gln Pro Ala Arg Lys Arg Leu Asn Phe Gly Gln
                165                 170                 175

Thr Gly Asp Ser Glu Ser Val Pro Asp Pro Gln Pro Leu Gly Glu Pro
            180                 185                 190

Pro Ala Ala Pro Ser Gly Val Gly Pro Asn Thr Met Ala Ala Gly Gly
        195                 200                 205

Gly Ala Pro Met Ala Asp Asn Asn Glu Gly Ala Asp Gly Val Gly Asn
    210                 215                 220

Ala Ser Gly Asn Trp His Cys Asp Ser Thr Trp Leu Gly Asp Arg Val
225                 230                 235                 240

Ile Thr Thr Ser Thr Arg Thr Trp Ala Leu Pro Thr Tyr Asn Asn His
                245                 250                 255

Leu Tyr Lys Gln Ile Ser Ser Ala Ser Thr Gly Ala Ser Asn Asp Asn
            260                 265                 270

His Tyr Phe Gly Tyr Ser Thr Pro Trp Gly Tyr Phe Asp Phe Asn Arg
        275                 280                 285

Phe His Cys His Phe Ser Pro Arg Asp Trp Gln Arg Leu Ile Asn Asn
    290                 295                 300

Asn Trp Gly Phe Arg Pro Lys Arg Leu Asn Phe Lys Leu Phe Asn Ile
305                 310                 315                 320
```

-continued

Gln Val Lys Glu Val Thr Gln Asn Glu Gly Thr Lys Thr Ile Ala Asn
             325                 330                 335

Asn Leu Thr Ser Thr Ile Gln Val Phe Thr Asp Ser Glu Tyr Gln Leu
            340                 345                 350

Pro Tyr Val Leu Gly Ser Ala His Gln Gly Cys Leu Pro Pro Phe Pro
        355                 360                 365

Ala Asp Val Phe Met Ile Pro Gln Tyr Gly Tyr Leu Thr Leu Asn Asn
    370                 375                 380

Gly Ser Gln Ala Val Gly Arg Ser Ser Phe Tyr Cys Leu Glu Tyr Phe
385                 390                 395                 400

Pro Ser Gln Met Leu Arg Thr Gly Asn Asn Phe Gln Phe Ser Tyr Thr
                405                 410                 415

Phe Glu Asp Val Pro Phe His Ser Ser Tyr Ala His Ser Gln Ser Leu
            420                 425                 430

Asp Arg Leu Met Asn Pro Leu Ile Asp Gln Tyr Leu Tyr Tyr Leu Asn
        435                 440                 445

Arg Thr Gln Gly Thr Thr Ser Gly Thr Thr Asn Gln Ser Arg Leu Leu
    450                 455                 460

Phe Ser Gln Ala Gly Pro Gln Ser Met Ser Leu Gln Ala Arg Asn Trp
465                 470                 475                 480

Leu Pro Gly Pro Cys Tyr Arg Gln Gln Arg Leu Ser Lys Thr Ala Asn
                485                 490                 495

Asp Asn Asn Asn Ser Asn Phe Pro Trp Thr Ala Ala Ser Lys Tyr His
            500                 505                 510

Leu Asn Gly Arg Asp Ser Leu Val Asn Pro Gly Pro Ala Met Ala Ser
        515                 520                 525

His Lys Asp Asp Glu Glu Lys Phe Phe Pro Met His Gly Asn Leu Ile
    530                 535                 540

Phe Gly Lys Glu Gly Thr Thr Ala Ser Asn Ala Glu Leu Asp Asn Val
545                 550                 555                 560

Met Ile Thr Asp Glu Glu Glu Ile Arg Thr Thr Asn Pro Val Ala Thr
                565                 570                 575

Glu Gln Tyr Gly Thr Val Ala Asn Asn Leu Gln Ser Ser Asn Thr Ala
            580                 585                 590

Pro Thr Thr Arg Thr Val Asn Asp Gln Gly Ala Leu Pro Gly Met Val
        595                 600                 605

Trp Gln Asp Arg Asp Val Tyr Leu Gln Gly Pro Ile Trp Ala Lys Ile
    610                 615                 620

Pro His Thr Asp Gly Asn Phe His Pro Ser Pro Leu Met Gly Gly Phe
625                 630                 635                 640

Gly Leu Lys His Pro Pro Pro Gln Ile Leu Ile Lys Asn Thr Pro Val
                645                 650                 655

Pro Ala Asp Pro Pro Thr Thr Phe Asn Gln Ser Lys Leu Asn Ser Phe
            660                 665                 670

Ile Thr Gln Tyr Ser Thr Gly Gln Val Ser Val Glu Ile Glu Trp Glu
        675                 680                 685

Leu Gln Lys Glu Asn Ser Lys Arg Trp Asn Pro Glu Ile Gln Tyr Thr
    690                 695                 700

Ser Asn Tyr Tyr Lys Ser Thr Ser Val Asp Phe Ala Val Asn Thr Glu
705                 710                 715                 720

Gly Val Tyr Ser Glu Pro Arg Pro Ile Gly Thr Arg Tyr Leu Thr Arg
                725                 730                 735

Asn Leu

-continued

<210> SEQ ID NO 3
<211> LENGTH: 737
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 3

```
Met Ala Ala Asp Gly Tyr Leu Pro Asp Trp Leu Glu Asp Asn Leu Ser
1               5                   10                  15

Glu Gly Ile Arg Glu Trp Trp Asp Leu Lys Pro Gly Ala Pro Lys Pro
            20                  25                  30

Lys Ala Asn Gln Gln Lys Gln Asp Asp Gly Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Ala Ala Asp Ala Ala Leu Glu His Asp Lys Ala Tyr Asp
65                  70                  75                  80

Gln Gln Leu Lys Ala Gly Asp Asn Pro Tyr Leu Arg Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Leu Leu Glu Pro
        115                 120                 125

Leu Gly Leu Val Glu Glu Ala Lys Thr Ala Pro Gly Lys Lys Arg
130                 135                 140

Pro Val Glu Gln Ser Pro Gln Glu Pro Asp Ser Ser Ser Gly Ile Gly
145                 150                 155                 160

Lys Thr Gly Gln Gln Pro Ala Lys Lys Arg Leu Asn Phe Gly Gln Thr
                165                 170                 175

Gly Asp Thr Glu Ser Val Pro Asp Pro Gln Pro Leu Gly Glu Pro Pro
            180                 185                 190

Ala Ala Pro Thr Ser Leu Gly Ser Asn Thr Met Ala Ser Gly Gly Gly
        195                 200                 205

Ala Pro Met Ala Asp Asn Asn Glu Gly Ala Asp Gly Val Gly Asn Ala
    210                 215                 220

Ser Gly Asn Trp His Cys Asp Ser Thr Trp Leu Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Ser Ala Ser Thr Gly Ala Ser Asn Asp Asn His
            260                 265                 270

Tyr Phe Gly Tyr Ser Thr Pro Trp Gly Tyr Phe Asp Phe Asn Arg Phe
        275                 280                 285

His Cys His Phe Ser Pro Arg Asp Trp Gln Arg Leu Ile Asn Asn Asn
    290                 295                 300

Trp Gly Phe Arg Pro Lys Lys Leu Ser Phe Lys Leu Phe Asn Ile Gln
305                 310                 315                 320

Val Lys Glu Val Thr Gln Asn Asp Gly Thr Thr Ile Ala Asn Asn
                325                 330                 335

Leu Thr Ser Thr Ile Gln Val Phe Thr Asp Ser Glu Tyr Gln Leu Pro
            340                 345                 350
```

Tyr Val Leu Gly Ser Ala His Gln Gly Cys Leu Pro Pro Phe Pro Ala
        355                 360                 365

Asp Val Phe Met Ile Pro Gln Tyr Gly Tyr Leu Thr Leu Asn Asn Gly
    370                 375                 380

Ser Gln Ala Val Gly Arg Ser Ser Phe Tyr Cys Leu Glu Tyr Phe Pro
385                 390                 395                 400

Ser Gln Met Leu Arg Thr Gly Asn Asn Phe Thr Phe Ser Tyr Thr Phe
                405                 410                 415

Glu Glu Val Pro Phe His Ser Ser Tyr Ala His Ser Gln Ser Leu Asp
            420                 425                 430

Arg Leu Met Asn Pro Leu Ile Asp Gln Tyr Leu Tyr Tyr Leu Asn Arg
        435                 440                 445

Thr Gln Gly Thr Thr Ser Gly Thr Thr Asn Gln Ser Arg Leu Leu Phe
    450                 455                 460

Ser Gln Ala Gly Pro Gln Ser Met Ser Leu Gln Ala Arg Asn Trp Leu
465                 470                 475                 480

Pro Gly Pro Cys Tyr Arg Gln Gln Arg Leu Ser Lys Thr Ala Asn Asp
                485                 490                 495

Asn Asn Asn Ser Asn Phe Pro Trp Thr Ala Ala Ser Lys Tyr His Leu
            500                 505                 510

Asn Gly Arg Asp Ser Leu Val Asn Pro Gly Pro Ala Met Ala Ser His
        515                 520                 525

Lys Asp Asp Glu Glu Lys Phe Phe Pro Met His Gly Asn Leu Ile Phe
    530                 535                 540

Gly Lys Glu Gly Thr Thr Ala Ser Asn Ala Glu Leu Asp Asn Val Met
545                 550                 555                 560

Ile Thr Asp Glu Glu Glu Ile Arg Thr Thr Asn Pro Val Ala Thr Glu
                565                 570                 575

Gln Tyr Gly Thr Val Ala Asn Asn Leu Gln Ser Ser Asn Thr Ala Pro
            580                 585                 590

Thr Thr Arg Thr Val Asn Asp Gln Gly Ala Leu Pro Gly Met Val Trp
        595                 600                 605

Gln Asp Arg Asp Val Tyr Leu Gln Gly Pro Ile Trp Ala Lys Ile Pro
    610                 615                 620

His Thr Asp Gly His Phe His Pro Ser Pro Leu Met Gly Gly Phe Gly
625                 630                 635                 640

Leu Lys His Pro Pro Pro Gln Ile Met Ile Lys Asn Thr Pro Val Pro
                645                 650                 655

Ala Asn Pro Pro Thr Thr Phe Ser Pro Ala Lys Phe Ala Ser Phe Ile
            660                 665                 670

Thr Gln Tyr Ser Thr Gly Gln Val Ser Val Glu Ile Glu Trp Glu Leu
        675                 680                 685

Gln Lys Glu Asn Ser Lys Arg Trp Asn Pro Glu Ile Gln Tyr Thr Ser
    690                 695                 700

Asn Tyr Asn Lys Ser Val Asn Val Asp Phe Thr Val Asp Thr Asn Gly
705                 710                 715                 720

Val Tyr Ser Glu Pro Arg Pro Ile Gly Thr Arg Tyr Leu Thr Arg Pro
                725                 730                 735

Leu

<210> SEQ ID NO 4
<211> LENGTH: 737
<212> TYPE: PRT
<213> ORGANISM: Artificial Sequence

```
<220> FEATURE:
<221> NAME/KEY: source
<223> OTHER INFORMATION: /note="Description of Artificial Sequence:
      Synthetic polypeptide"

<400> SEQUENCE: 4

Met Ala Ala Asp Gly Tyr Leu Pro Asp Trp Leu Glu Asp Asn Leu Ser
1               5                   10                  15

Glu Gly Ile Arg Glu Trp Trp Asp Leu Lys Pro Gly Ala Pro Lys Pro
            20                  25                  30

Lys Ala Asn Gln Gln Lys Gln Asp Asp Ala Arg Gly Leu Val Leu Pro
        35                  40                  45

Gly Tyr Lys Tyr Leu Gly Pro Gly Asn Gly Leu Asp Lys Gly Glu Pro
    50                  55                  60

Val Asn Ala Ala Asp Ala Ala Leu Glu His Asp Lys Ala Tyr Asp
65                  70                  75                  80

Gln Gln Leu Gln Ala Gly Asp Asn Pro Tyr Leu Arg Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Ala Ala Lys Thr Ala Pro Gly Lys Lys Arg
    130                 135                 140

Pro Val Glu Gln Ser Pro Gln Glu Pro Asp Ser Ser Ser Gly Ile Gly
145                 150                 155                 160

Lys Thr Gly Gln Gln Pro Ala Lys Lys Arg Leu Asn Phe Gly Gln Thr
                165                 170                 175

Gly Asp Ser Glu Ser Val Pro Asp Pro Gln Pro Leu Gly Glu Pro Pro
            180                 185                 190

Ala Ala Pro Thr Ser Leu Gly Ser Asn Thr Met Ala Ser Gly Gly Gly
        195                 200                 205

Ala Pro Met Ala Asp Asn Asn Glu Gly Ala Asp Gly Val Gly Asn Ser
    210                 215                 220

Ser Gly Asn Trp His Cys Asp Ser Gln Trp Leu Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Ser Ala Ser Thr Gly Ala Ser Asn Asp Asn His
            260                 265                 270

Tyr Phe Gly Tyr Ser Thr Pro Trp Gly Tyr Phe Asp Phe Asn Arg Phe
        275                 280                 285

His Cys His Phe Ser Pro Arg Asp Trp Gln Arg Leu Ile Asn Asn Asn
    290                 295                 300

Trp Gly Phe Arg Pro Lys Arg Leu Asn Phe Lys Leu Phe Asn Ile Gln
305                 310                 315                 320

Val Lys Glu Val Thr Thr Asn Asp Gly Val Thr Thr Ile Ala Asn Asn
                325                 330                 335

Leu Thr Ser Thr Val Gln Val Phe Thr Asp Ser Glu Tyr Gln Leu Pro
            340                 345                 350

Tyr Val Leu Gly Ser Ala His Gln Gly Cys Leu Pro Pro Phe Pro Ala
        355                 360                 365

Asp Val Phe Met Val Pro Gln Tyr Gly Tyr Leu Thr Leu Asn Asn Gly
    370                 375                 380
```

-continued

Ser Gln Ala Val Gly Arg Ser Ser Phe Tyr Cys Leu Glu Tyr Phe Pro
385                 390                 395                 400

Ser Gln Met Leu Arg Thr Gly Asn Asn Phe Gln Phe Ser Tyr Thr Phe
            405                 410                 415

Glu Asp Val Pro Phe His Ser Ser Tyr Ala His Ser Gln Ser Leu Asp
        420                 425                 430

Arg Leu Met Asn Pro Leu Ile Asp Gln Tyr Leu Tyr Tyr Leu Asn Arg
    435                 440                 445

Thr Gln Gly Thr Thr Ser Gly Thr Thr Asn Gln Ser Arg Leu Leu Phe
450                 455                 460

Ser Gln Ala Gly Pro Gln Ser Met Ser Leu Gln Ala Arg Asn Trp Leu
465                 470                 475                 480

Pro Gly Pro Cys Tyr Arg Gln Gln Arg Leu Ser Lys Thr Ala Asn Asp
                485                 490                 495

Asn Asn Asn Ser Asn Phe Pro Trp Thr Ala Ala Ser Lys Tyr His Leu
            500                 505                 510

Asn Gly Arg Asp Ser Leu Val Asn Pro Gly Pro Ala Met Ala Ser His
        515                 520                 525

Lys Asp Asp Glu Glu Lys Phe Phe Pro Met His Gly Asn Leu Ile Phe
530                 535                 540

Gly Lys Glu Gly Thr Thr Ala Ser Asn Ala Glu Leu Asp Asn Val Met
545                 550                 555                 560

Ile Thr Asp Glu Glu Glu Ile Arg Thr Thr Asn Pro Val Ala Thr Glu
                565                 570                 575

Gln Tyr Gly Thr Val Ala Asn Asn Leu Gln Ser Ser Asn Thr Ala Pro
            580                 585                 590

Thr Thr Arg Thr Val Asn Asp Gln Gly Ala Leu Pro Gly Met Val Trp
        595                 600                 605

Gln Asp Arg Asp Val Tyr Leu Gln Gly Pro Ile Trp Ala Lys Ile Pro
610                 615                 620

His Thr Asp Gly His Phe His Pro Ser Pro Leu Met Gly Gly Phe Gly
625                 630                 635                 640

Leu Lys His Pro Pro Pro Gln Ile Leu Ile Lys Asn Thr Pro Val Pro
                645                 650                 655

Ala Asn Pro Pro Ala Glu Phe Ser Ala Thr Lys Phe Ala Ser Phe Ile
            660                 665                 670

Thr Gln Tyr Ser Thr Gly Gln Val Ser Val Glu Ile Glu Trp Glu Leu
        675                 680                 685

Gln Lys Glu Asn Ser Lys Arg Trp Asn Pro Glu Ile Gln Tyr Thr Ser
690                 695                 700

Asn Tyr Asn Lys Ser Val Asn Val Asp Phe Thr Val Asp Thr Asn Gly
705                 710                 715                 720

Val Tyr Ser Glu Pro Arg Pro Ile Gly Thr Arg Tyr Leu Thr Arg Pro
                725                 730                 735

Leu

<210> SEQ ID NO 5
<211> LENGTH: 737
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 5

-continued

```
Met Ala Ala Asp Gly Tyr Leu Pro Asp Trp Leu Glu Asp Asn Leu Ser
1               5                   10                  15

Glu Gly Ile Arg Glu Trp Trp Asp Leu Lys Pro Gly Ala Pro Lys Pro
                20                  25                  30

Lys Ala Asn Gln Gln Lys Gln Asp Asp Gly Arg Gly Leu Val Leu Pro
            35                  40                  45

Gly Tyr Lys Tyr Leu Gly Pro Phe Asn Gly Leu Asp Lys Gly Glu Pro
        50                  55                  60

Val Asn Ala Ala Asp Ala Ala Leu Glu His Asp Lys Ala Tyr Asp
65                  70                  75                  80

Gln Gln Leu Lys Ala Gly Asp Asn Pro Tyr Leu Arg Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Gly Ala Lys Thr Ala Pro Gly Lys Lys Arg
    130                 135                 140

Pro Val Glu His Ser Pro Val Glu Pro Asp Ser Ser Ser Gly Ile Gly
145                 150                 155                 160

Lys Thr Gly Gln Gln Pro Ala Lys Lys Arg Leu Asn Phe Gly Gln Thr
                165                 170                 175

Gly Asp Ala Asp Ser Val Pro Asp Pro Gln Pro Leu Gly Gln Pro Pro
            180                 185                 190

Ala Ala Pro Ser Gly Leu Gly Thr Asn Thr Met Ala Thr Gly Ser Gly
        195                 200                 205

Ala Pro Met Ala Asp Asn Asn Glu Gly Ala Asp Gly Val Gly Asn Ala
    210                 215                 220

Ser Gly Asn Trp His Cys Asp Ser Thr Trp Leu Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Ser Ala Ser Thr Gly Ala Ser Asn Asp Asn His
            260                 265                 270

Tyr Phe Gly Tyr Ser Thr Pro Trp Gly Tyr Phe Asp Phe Asn Arg Phe
        275                 280                 285

His Cys His Phe Ser Pro Arg Asp Trp Gln Arg Leu Ile Asn Asn Asn
    290                 295                 300

Trp Gly Phe Arg Pro Lys Arg Leu Asn Phe Lys Leu Phe Asn Ile Gln
305                 310                 315                 320

Val Lys Glu Val Thr Gln Asn Glu Gly Thr Thr Thr Ile Ala Asn Asn
                325                 330                 335

Leu Thr Ser Thr Val Gln Val Phe Thr Asp Ser Glu Tyr Gln Leu Pro
            340                 345                 350

Tyr Val Leu Gly Ser Ala His Gln Gly Cys Leu Pro Pro Phe Pro Ala
        355                 360                 365

Asp Val Phe Met Ile Pro Gln Tyr Gly Tyr Leu Thr Leu Asn Asn Gly
    370                 375                 380

Ser Gln Ala Val Gly Arg Ser Ser Phe Tyr Cys Leu Glu Tyr Phe Pro
385                 390                 395                 400

Ser Gln Met Leu Arg Thr Gly Asn Asn Phe Thr Phe Ser Tyr Thr Phe
                405                 410                 415
```

```
Glu Asp Val Pro Phe His Ser Ser Tyr Ala His Ser Gln Ser Leu Asp
            420                 425                 430

Arg Leu Met Asn Pro Leu Ile Asp Gln Tyr Leu Tyr Tyr Leu Asn Arg
        435                 440                 445

Thr Gln Gly Thr Thr Ser Gly Thr Thr Asn Gln Ser Arg Leu Leu Phe
    450                 455                 460

Ser Gln Ala Gly Pro Gln Ser Met Ser Leu Gln Ala Arg Asn Trp Leu
465                 470                 475                 480

Pro Gly Pro Cys Tyr Arg Gln Gln Arg Leu Ser Lys Thr Ala Asn Asp
                485                 490                 495

Asn Asn Asn Ser Asn Phe Pro Trp Thr Ala Ala Ser Lys Tyr His Leu
            500                 505                 510

Asn Gly Arg Asp Ser Leu Val Asn Pro Gly Pro Ala Met Ala Ser His
        515                 520                 525

Lys Asp Asp Glu Glu Lys Phe Phe Pro Met His Gly Asn Leu Ile Phe
    530                 535                 540

Gly Lys Glu Gly Thr Thr Ala Ser Asn Ala Glu Leu Asp Asn Val Met
545                 550                 555                 560

Ile Thr Asp Glu Glu Glu Ile Arg Thr Thr Asn Pro Val Ala Thr Glu
                565                 570                 575

Gln Tyr Gly Thr Val Ala Asn Asn Leu Gln Ser Ser Asn Thr Ala Pro
            580                 585                 590

Thr Thr Arg Thr Val Asn Asp Gln Gly Ala Leu Pro Gly Met Val Trp
        595                 600                 605

Gln Asp Arg Asp Val Tyr Leu Gln Gly Pro Ile Trp Ala Lys Ile Pro
    610                 615                 620

His Thr Asp Gly His Phe His Pro Ser Pro Leu Met Gly Gly Phe Gly
625                 630                 635                 640

Leu Lys His Pro Pro Pro Gln Ile Met Ile Lys Asn Thr Pro Val Pro
                645                 650                 655

Ala Asn Pro Pro Thr Thr Phe Ser Pro Ala Lys Phe Ala Ser Phe Ile
            660                 665                 670

Thr Gln Tyr Ser Thr Gly Gln Val Ser Val Glu Ile Glu Trp Glu Leu
        675                 680                 685

Gln Lys Glu Asn Ser Lys Arg Trp Asn Pro Glu Ile Gln Tyr Thr Ser
    690                 695                 700

Asn Tyr Asn Lys Ser Val Asn Val Asp Phe Thr Val Asp Thr Asn Gly
705                 710                 715                 720

Val Tyr Ser Glu Pro Arg Pro Ile Gly Thr Arg Tyr Leu Thr Arg Pro
                725                 730                 735

Leu

<210> SEQ ID NO 6
<211> LENGTH: 737
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 6

Met Ala Ala Asp Gly Tyr Leu Pro Asp Trp Leu Glu Asp Asn Leu Ser
1               5                   10                  15

Glu Gly Ile Arg Gln Trp Trp Lys Leu Lys Pro Gly Pro Pro Pro
                20                  25                  30
```

Lys Pro Ala Glu Arg His Lys Asp Asp Ser Arg Gly Leu Val Leu Pro
    35                  40                  45

Gly Tyr Lys Tyr Leu Gly Pro Phe Asn Gly Leu Asp Lys Gly Glu Pro
 50                  55                  60

Val Asn Ala Ala Asp Ala Ala Leu Glu His Asp Lys Ala Tyr Asp
 65                  70                  75                  80

Gln Gln Leu Lys Ala Gly Asp Asn Pro Tyr Leu Arg Tyr Asn His Ala
             85                  90                  95

Asp Ala Glu Phe Gln Glu Arg Leu Lys Glu Asp Thr Ser Phe Gly Gly
                100                 105                 110

Asn Leu Gly Arg Ala Val Phe Gln Ala Lys Lys Arg Val Leu Glu Pro
            115                 120                 125

Leu Gly Leu Val Glu Glu Gly Ala Lys Thr Ala Pro Gly Lys Lys Arg
130                 135                 140

Pro Val Glu His Ser Pro Val Glu Pro Asp Ser Ser Ser Gly Ile Gly
145                 150                 155                 160

Lys Thr Gly Gln Gln Pro Ala Lys Lys Arg Leu Asn Phe Gly Gln Thr
                165                 170                 175

Gly Asp Ser Glu Ser Val Pro Asp Pro Gln Pro Leu Gly Glu Pro Pro
            180                 185                 190

Ala Ala Pro Ser Gly Leu Gly Thr Asn Thr Met Ala Ser Gly Gly Gly
            195                 200                 205

Ala Pro Met Ala Asp Asn Asn Glu Gly Ala Asp Gly Val Gly Asn Ser
210                 215                 220

Ser Gly Asn Trp His Cys Asp Ser Thr Trp Leu Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Ser Ala Ser Thr Gly Ala Ser Asn Asp Asn His
            260                 265                 270

Tyr Phe Gly Tyr Ser Thr Pro Trp Gly Tyr Phe Asp Phe Asn Arg Phe
            275                 280                 285

His Cys His Phe Ser Pro Arg Asp Trp Gln Arg Leu Ile Asn Asn Asn
            290                 295                 300

Trp Gly Phe Arg Pro Lys Arg Leu Asn Phe Lys Leu Phe Asn Ile Gln
305                 310                 315                 320

Val Lys Glu Val Thr Thr Asn Asp Gly Val Thr Thr Ile Ala Asn Asn
                325                 330                 335

Leu Thr Ser Thr Val Gln Val Phe Thr Asp Ser Glu Tyr Gln Leu Pro
            340                 345                 350

Tyr Val Leu Gly Ser Ala His Gln Gly Cys Leu Pro Pro Phe Pro Ala
            355                 360                 365

Asp Val Phe Met Val Pro Gln Tyr Gly Tyr Leu Thr Leu Asn Asn Gly
370                 375                 380

Ser Gln Ala Val Gly Arg Ser Ser Phe Tyr Cys Leu Glu Tyr Phe Pro
385                 390                 395                 400

Ser Gln Met Leu Arg Thr Gly Asn Asn Phe Gln Phe Thr Tyr Thr Phe
                405                 410                 415

Glu Asp Val Pro Phe His Ser Ser Tyr Ala His Ser Gln Ser Leu Asp
            420                 425                 430

Arg Leu Met Asn Pro Leu Ile Asp Gln Tyr Leu Tyr Tyr Leu Asn Arg
            435                 440                 445

Thr Gln Gly Thr Thr Ser Gly Thr Thr Asn Gln Ser Arg Leu Leu Phe
    450                 455                 460

Ser Gln Ala Gly Pro Gln Ser Met Ser Leu Gln Ala Arg Asn Trp Leu
465                 470                 475                 480

Pro Gly Pro Cys Tyr Arg Gln Gln Arg Leu Ser Lys Thr Ala Asn Asp
            485                 490                 495

Asn Asn Asn Ser Asn Phe Pro Trp Thr Ala Ser Lys Tyr His Leu
            500                 505                 510

Asn Gly Arg Asp Ser Leu Val Asn Pro Gly Pro Ala Met Ala Ser His
            515                 520                 525

Lys Asp Asp Glu Glu Lys Phe Phe Pro Met His Gly Asn Leu Ile Phe
530                 535                 540

Gly Lys Glu Gly Thr Thr Ala Ser Asn Ala Glu Leu Asp Asn Val Met
545                 550                 555                 560

Ile Thr Asp Glu Glu Glu Ile Arg Thr Thr Asn Pro Val Ala Thr Glu
            565                 570                 575

Gln Tyr Gly Thr Val Ala Asn Asn Leu Gln Ser Ser Thr Ala Pro
            580                 585                 590

Thr Thr Arg Thr Val Asn Asp Gln Gly Ala Leu Pro Gly Met Val Trp
            595                 600                 605

Gln Asp Arg Asp Val Tyr Leu Gln Gly Pro Ile Trp Ala Lys Ile Pro
610                 615                 620

His Thr Asp Gly His Phe His Pro Ser Pro Leu Met Gly Gly Phe Gly
625                 630                 635                 640

Leu Lys His Pro Pro Pro Gln Ile Met Ile Lys Asn Thr Pro Val Pro
            645                 650                 655

Ala Asn Pro Pro Thr Thr Phe Ser Pro Ala Lys Phe Ala Ser Phe Ile
            660                 665                 670

Thr Gln Tyr Ser Thr Gly Gln Val Ser Val Glu Ile Glu Trp Glu Leu
            675                 680                 685

Gln Lys Glu Asn Ser Lys Arg Trp Asn Pro Glu Ile Gln Tyr Thr Ser
            690                 695                 700

Asn Tyr Asn Lys Ser Val Asn Val Asp Phe Thr Val Asp Thr Asn Gly
705                 710                 715                 720

Val Tyr Ser Glu Pro Arg Pro Ile Gly Thr Arg Tyr Leu Thr Arg Pro
            725                 730                 735

Leu

<210> SEQ ID NO 7
<211> LENGTH: 737
<212> TYPE: PRT
<213> ORGANISM: Artificial Sequence
<220> FEATURE:
<221> NAME/KEY: source
<223> OTHER INFORMATION: /note="Description of Artificial Sequence:
    Synthetic polypeptide"

<400> SEQUENCE: 7

Met Ala Ala Asp Gly Tyr Leu Pro Asp Trp Leu Glu Asp Thr Leu Ser
1               5                   10                  15

Glu Gly Ile Arg Gln Trp Trp Lys Leu Lys Pro Gly Pro Pro Pro
            20                  25                  30

Lys Pro Ala Glu Arg His Lys Asp Asp Ser Arg Gly Leu Val Leu Pro
            35                  40                  45

Gly Tyr Lys Tyr Leu Gly Pro Phe Asn Gly Leu Asp Lys Gly Glu Pro
    50                  55                  60

-continued

Val Asn Ala Ala Asp Ala Ala Leu Glu His Asp Lys Ala Tyr Asp
65                  70                  75                  80

Gln Gln Leu Lys Ala Gly Asp Asn Pro Tyr Leu Arg Tyr Asn His Ala
            85                  90                  95

Asp Ala Glu Phe Gln Glu Arg Leu Gln Glu Asp Thr Ser Phe Gly Gly
        100                 105                 110

Asn Leu Gly Arg Ala Val Phe Gln Ala Lys Lys Arg Leu Leu Glu Pro
    115                 120                 125

Leu Gly Leu Val Glu Glu Ala Ala Lys Thr Ala Pro Gly Lys Lys Arg
130                 135                 140

Pro Val Glu His Ser Pro Val Glu Pro Asp Ser Ser Gly Thr Gly
145                 150                 155                 160

Lys Ala Gly Gln Gln Pro Ala Lys Lys Arg Leu Asn Phe Gly Gln Thr
                165                 170                 175

Gly Asp Ser Glu Ser Val Pro Asp Pro Gln Pro Leu Gly Glu Pro Pro
            180                 185                 190

Ala Ala Pro Ser Gly Val Gly Pro Asn Thr Met Ala Ala Gly Gly Gly
        195                 200                 205

Ala Pro Met Ala Asp Asn Asn Glu Gly Ala Asp Gly Val Gly Asn Ala
    210                 215                 220

Ser Gly Asn Trp His Cys Asp Ser Thr Trp Leu Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Ser Ala Ser Thr Gly Ala Ser Asn Asp Asn His
            260                 265                 270

Tyr Phe Gly Tyr Ser Thr Pro Trp Gly Tyr Phe Asp Phe Asn Arg Phe
        275                 280                 285

His Cys His Phe Ser Pro Arg Asp Trp Gln Arg Leu Ile Asn Asn Asn
    290                 295                 300

Trp Gly Phe Arg Pro Lys Arg Leu Ser Phe Lys Leu Phe Asn Ile Gln
305                 310                 315                 320

Val Lys Glu Val Thr Thr Asn Asp Gly Val Thr Thr Ile Ala Asn Asn
                325                 330                 335

Leu Thr Ser Thr Val Gln Val Phe Thr Asp Ser Glu Tyr Gln Leu Pro
            340                 345                 350

Tyr Val Leu Gly Ser Ala His Gln Gly Cys Leu Pro Pro Phe Pro Ala
        355                 360                 365

Asp Val Phe Met Val Pro Gln Tyr Gly Tyr Leu Thr Leu Asn Asn Gly
    370                 375                 380

Ser Gln Ala Val Gly Arg Ser Ser Phe Tyr Cys Leu Glu Tyr Phe Pro
385                 390                 395                 400

Ser Gln Met Leu Arg Thr Gly Asn Asn Phe Gln Phe Ser Tyr Thr Phe
                405                 410                 415

Glu Asp Val Pro Phe His Ser Ser Tyr Ala His Ser Gln Ser Leu Asp
            420                 425                 430

Arg Leu Met Asn Pro Leu Ile Asp Gln Tyr Leu Tyr Tyr Leu Asn Arg
        435                 440                 445

Thr Gln Gly Thr Thr Ser Gly Thr Thr Asn Gln Ser Arg Leu Leu Phe
    450                 455                 460

Ser Gln Ala Gly Pro Gln Ser Met Ser Leu Gln Ala Arg Asn Trp Leu
465                 470                 475                 480

```
Pro Gly Pro Cys Tyr Arg Gln Gln Arg Leu Ser Lys Thr Ala Asn Asp
                485                 490                 495

Asn Asn Asn Ser Asn Phe Pro Trp Thr Ala Ala Ser Lys Tyr His Leu
            500                 505                 510

Asn Gly Arg Asp Ser Leu Val Asn Pro Gly Pro Ala Met Ala Ser His
            515                 520                 525

Lys Asp Asp Glu Glu Lys Phe Phe Pro Met His Gly Asn Leu Ile Phe
530                 535                 540

Gly Lys Glu Gly Thr Thr Ala Ser Asn Ala Glu Leu Asp Asn Val Met
545                 550                 555                 560

Ile Thr Asp Glu Glu Glu Ile Arg Thr Thr Asn Pro Val Ala Thr Glu
                565                 570                 575

Gln Tyr Gly Thr Val Ala Asn Asn Leu Gln Ser Ser Asn Thr Ala Pro
            580                 585                 590

Thr Thr Arg Thr Val Asn Asp Gln Gly Ala Leu Pro Gly Met Val Trp
        595                 600                 605

Gln Asp Arg Asp Val Tyr Leu Gln Gly Pro Ile Trp Ala Lys Ile Pro
610                 615                 620

His Thr Asp Gly His Phe His Pro Ser Pro Leu Met Gly Gly Phe Gly
625                 630                 635                 640

Leu Lys His Pro Pro Pro Gln Ile Met Ile Lys Asn Thr Pro Val Pro
                645                 650                 655

Ala Asn Pro Pro Thr Thr Phe Ser Pro Ala Lys Phe Ala Ser Phe Ile
            660                 665                 670

Thr Gln Tyr Ser Thr Gly Gln Val Ser Val Glu Ile Glu Trp Glu Leu
        675                 680                 685

Gln Lys Glu Asn Ser Lys Arg Trp Asn Pro Glu Ile Gln Tyr Thr Ser
690                 695                 700

Asn Tyr Asn Lys Ser Val Asn Val Asp Phe Thr Val Asp Thr Asn Gly
705                 710                 715                 720

Val Tyr Ser Glu Pro Arg Pro Ile Gly Thr Arg Tyr Leu Thr Arg Pro
                725                 730                 735

Leu

<210> SEQ ID NO 8
<211> LENGTH: 737
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 8

Met Ala Ala Asp Gly Tyr Leu Pro Asp Trp Leu Glu Asp Asn Leu Ser
1               5                   10                  15

Glu Gly Ile Arg Glu Trp Trp Ala Leu Gln Pro Gly Ala Pro Lys Pro
                20                  25                  30

Lys Ala Asn Gln Gln Lys Gln Asp Asp Gly Arg Gly Leu Val Leu Pro
            35                  40                  45

Gly Tyr Lys Tyr Leu Gly Pro Phe Asn Gly Leu Asp Lys Gly Glu Pro
        50                  55                  60

Val Asn Ala Ala Asp Ala Ala Ala Leu Glu His Asp Lys Ala Tyr Asp
65                  70                  75                  80

Gln Gln Leu Lys Ala Gly Asp Asn Pro Tyr Leu Arg Tyr Asn His Ala
                85                  90                  95
```

-continued

```
Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
            115                 120                 125

Leu Gly Leu Val Glu Gly Ala Lys Thr Ala Pro Gly Lys Lys Arg
130             135                 140

Pro Val Glu Gln Ser Pro Gln Glu Pro Asp Ser Ser Gly Ile Gly
145                 150                 155                 160

Lys Thr Gly Gln Gln Pro Ala Lys Lys Arg Leu Asn Phe Gly Gln Thr
                165                 170                 175

Gly Asp Ser Glu Ser Val Pro Asp Pro Gln Pro Ile Gly Glu Pro Pro
            180                 185                 190

Ala Gly Pro Ser Gly Leu Gly Thr Gly Thr Met Ala Ser Gly Ser Gly
            195                 200                 205

Ala Pro Met Ala Asp Asn Asn Glu Gly Ala Asp Gly Val Gly Asn Ser
            210                 215                 220

Ser Gly Asn Trp His Cys Asp Ser Gln Trp Leu Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Ser Ala Ser Thr Gly Ala Ser Asn Asp Asn His
                260                 265                 270

Tyr Phe Gly Tyr Ser Thr Pro Trp Gly Tyr Phe Asp Phe Asn Arg Phe
            275                 280                 285

His Cys His Phe Ser Pro Arg Asp Trp Gln Arg Leu Ile Asn Asn Asn
            290                 295                 300

Trp Gly Phe Arg Pro Lys Arg Leu Asn Phe Lys Leu Phe Asn Ile Gln
305                 310                 315                 320

Val Lys Glu Val Thr Thr Asn Asp Gly Val Thr Thr Ile Ala Asn Asn
                325                 330                 335

Leu Thr Ser Thr Ile Gln Val Phe Thr Asp Ser Glu Tyr Gln Leu Pro
            340                 345                 350

Tyr Val Leu Gly Ser Ala His Gln Gly Cys Leu Pro Pro Phe Pro Ala
            355                 360                 365

Asp Val Phe Met Ile Pro Gln Tyr Gly Tyr Leu Thr Leu Asn Asn Gly
            370                 375                 380

Ser Gln Ala Val Gly Arg Ser Ser Phe Tyr Cys Leu Glu Tyr Phe Pro
385                 390                 395                 400

Ser Gln Met Leu Arg Thr Gly Asn Asn Phe Thr Phe Ser Tyr Thr Phe
                405                 410                 415

Glu Asp Val Pro Phe His Ser Ser Tyr Ala His Ser Gln Ser Leu Asp
            420                 425                 430

Arg Leu Met Asn Pro Leu Ile Asp Gln Tyr Leu Tyr Tyr Leu Asn Arg
            435                 440                 445

Thr Gln Gly Thr Thr Ser Gly Thr Thr Asn Gln Ser Arg Leu Leu Phe
            450                 455                 460

Ser Gln Ala Gly Pro Gln Ser Met Ser Leu Gln Ala Arg Asn Trp Leu
465                 470                 475                 480

Pro Gly Pro Cys Tyr Arg Gln Gln Arg Leu Ser Lys Thr Ala Asn Asp
                485                 490                 495

Asn Asn Asn Ser Asn Phe Pro Trp Thr Ala Ala Ser Lys Tyr His Leu
            500                 505                 510
```

Asn Gly Arg Asp Ser Leu Val Asn Pro Gly Pro Ala Met Ala Ser His
            515                 520                 525

Lys Asp Asp Glu Glu Lys Phe Phe Pro Met His Gly Asn Leu Ile Phe
530                 535                 540

Gly Lys Glu Gly Thr Thr Ala Ser Asn Ala Glu Leu Asp Asn Val Met
545                 550                 555                 560

Ile Thr Asp Glu Glu Ile Arg Thr Thr Asn Pro Val Ala Thr Glu
                565                 570                 575

Gln Tyr Gly Thr Val Ala Asn Asn Leu Gln Ser Ser Asn Thr Ala Pro
            580                 585                 590

Thr Thr Arg Thr Val Asn Asp Gln Gly Ala Leu Pro Gly Met Val Trp
            595                 600                 605

Gln Asp Arg Asp Val Tyr Leu Gln Gly Pro Ile Trp Ala Lys Ile Pro
610                 615                 620

His Thr Asp Gly His Phe His Pro Ser Pro Leu Met Gly Gly Phe Gly
625                 630                 635                 640

Leu Lys His Pro Pro Pro Gln Ile Met Ile Lys Asn Thr Pro Val Pro
                645                 650                 655

Ala Asn Pro Pro Thr Thr Phe Ser Pro Ala Lys Phe Ala Ser Phe Ile
            660                 665                 670

Thr Gln Tyr Ser Thr Gly Gln Val Ser Val Glu Ile Glu Trp Glu Leu
            675                 680                 685

Gln Lys Glu Asn Ser Lys Arg Trp Asn Pro Glu Ile Gln Tyr Thr Ser
690                 695                 700

Asn Tyr Asn Lys Ser Val Asn Val Asp Phe Thr Val Asp Thr Asn Gly
705                 710                 715                 720

Val Tyr Ser Glu Pro Arg Pro Ile Gly Thr Arg Tyr Leu Thr Arg Pro
                725                 730                 735

Leu

<210> SEQ ID NO 9
<211> LENGTH: 737
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 9

Met Ala Ala Asp Gly Tyr Leu Pro Asp Trp Leu Glu Asp Thr Leu Ser
1               5                   10                  15

Glu Gly Ile Arg Gln Trp Trp Lys Leu Lys Pro Gly Pro Pro Pro
            20                  25                  30

Lys Pro Ala Glu Arg His Lys Asp Asp Ser Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Ala Ala Asp Ala Ala Ala Leu Glu His Asp Lys Ala Tyr Asp
65                  70                  75                  80

Gln Gln Leu Lys Ala Gly Asp Asn Pro Tyr Leu Arg Tyr Asn His Ala
                85                  90                  95

Asp Ala Glu Phe Gln Glu Arg Leu Lys Glu Asp Thr Ser Phe Gly Gly
            100                 105                 110

Asn Leu Gly Arg Ala Val Phe Gln Ala Lys Lys Arg Val Leu Glu Pro
        115                 120                 125

```
Phe Gly Leu Val Glu Glu Ala Ala Lys Thr Ala Pro Gly Lys Lys Arg
    130                 135                 140
Pro Val Asp Gln Ser Pro Gln Glu Pro Asp Ser Ser Ser Gly Val Gly
145                 150                 155                 160
Lys Ser Gly Lys Gln Pro Ala Arg Lys Arg Leu Asn Phe Gly Gln Thr
                165                 170                 175
Gly Asp Ser Glu Ser Val Pro Asp Pro Gln Pro Leu Gly Glu Pro Pro
            180                 185                 190
Ala Ala Pro Thr Ser Leu Gly Ser Asn Thr Met Ala Ser Gly Gly Gly
        195                 200                 205
Ala Pro Met Ala Asp Asn Asn Glu Gly Ala Asp Gly Val Gly Asn Ala
    210                 215                 220
Ser Gly Asn Trp His Cys Asp Ser Thr Trp Leu Gly Asp Arg Val Ile
225                 230                 235                 240
Thr Thr Ser Thr Arg Thr Trp Ala Leu Pro Thr Tyr Asn Asn His Leu
                245                 250                 255
Tyr Lys Gln Ile Ser Ser Ala Ser Thr Gly Ala Ser Asn Asp Asn His
            260                 265                 270
Tyr Phe Gly Tyr Ser Thr Pro Trp Gly Tyr Phe Asp Phe Asn Arg Phe
        275                 280                 285
His Cys His Phe Ser Pro Arg Asp Trp Gln Arg Leu Ile Asn Asn Asn
    290                 295                 300
Trp Gly Phe Arg Pro Lys Lys Leu Ser Phe Lys Leu Phe Asn Ile Gln
305                 310                 315                 320
Val Lys Glu Val Thr Gln Asn Glu Gly Thr Lys Thr Ile Ala Asn Asn
                325                 330                 335
Leu Thr Ser Thr Ile Gln Val Phe Thr Asp Ser Glu Tyr Gln Leu Pro
            340                 345                 350
Tyr Val Leu Gly Ser Ala His Gln Gly Cys Leu Pro Pro Phe Pro Ala
        355                 360                 365
Asp Val Phe Met Ile Pro Gln Tyr Gly Tyr Leu Thr Leu Asn Asn Gly
    370                 375                 380
Ser Gln Ala Val Gly Arg Ser Ser Phe Tyr Cys Leu Glu Tyr Phe Pro
385                 390                 395                 400
Ser Gln Met Leu Arg Thr Gly Asn Asn Phe Gln Phe Thr Tyr Thr Phe
                405                 410                 415
Glu Asp Val Pro Phe His Ser Ser Tyr Ala His Ser Gln Ser Leu Asp
            420                 425                 430
Arg Leu Met Asn Pro Leu Ile Asp Gln Tyr Leu Tyr Tyr Leu Asn Arg
        435                 440                 445
Thr Gln Gly Thr Thr Ser Gly Thr Thr Asn Gln Ser Arg Leu Leu Phe
    450                 455                 460
Ser Gln Ala Gly Pro Gln Ser Met Ser Leu Gln Ala Arg Asn Trp Leu
465                 470                 475                 480
Pro Gly Pro Cys Tyr Arg Gln Gln Arg Leu Ser Lys Thr Ala Asn Asp
                485                 490                 495
Asn Asn Asn Ser Asn Phe Pro Trp Thr Ala Ala Ser Lys Tyr His Leu
            500                 505                 510
Asn Gly Arg Asp Ser Leu Val Asn Pro Gly Pro Ala Met Ala Ser His
        515                 520                 525
Lys Asp Asp Glu Glu Lys Phe Phe Pro Met His Gly Asn Leu Ile Phe
    530                 535                 540
```

```
Gly Lys Glu Gly Thr Thr Ala Ser Asn Ala Glu Leu Asp Asn Val Met
545                 550                 555                 560

Ile Thr Asp Glu Glu Ile Arg Thr Thr Asn Pro Val Ala Thr Glu
                565                 570                 575

Gln Tyr Gly Thr Val Ala Asn Asn Leu Gln Ser Ser Asn Thr Ala Pro
                580                 585                 590

Thr Thr Arg Thr Val Asn Asp Gln Gly Ala Leu Pro Gly Met Val Trp
            595                 600                 605

Gln Asp Arg Asp Val Tyr Leu Gln Gly Pro Ile Trp Ala Lys Ile Pro
610                 615                 620

His Thr Asp Gly His Phe His Pro Ser Pro Leu Met Gly Gly Phe Gly
625                 630                 635                 640

Met Lys His Pro Pro Pro Gln Ile Leu Ile Lys Asn Thr Pro Val Pro
                645                 650                 655

Ala Asp Pro Pro Thr Ala Phe Asn Lys Asp Lys Leu Asn Ser Phe Ile
                660                 665                 670

Thr Gln Tyr Ser Thr Gly Gln Val Ser Val Glu Ile Glu Trp Glu Leu
            675                 680                 685

Gln Lys Glu Asn Ser Lys Arg Trp Asn Pro Glu Ile Gln Tyr Thr Ser
690                 695                 700

Asn Tyr Tyr Lys Ser Thr Ser Val Asp Phe Ala Val Asn Thr Glu Gly
705                 710                 715                 720

Val Tyr Ser Glu Pro Arg Pro Ile Gly Thr Arg Tyr Leu Thr Arg Asn
                725                 730                 735

Leu

<210> SEQ ID NO 10
<211> LENGTH: 736
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 10

Met Ala Ala Asp Gly Tyr Leu Pro Asp Trp Leu Glu Asp Thr Leu Ser
1               5                   10                  15

Glu Gly Ile Arg Gln Trp Trp Lys Leu Lys Pro Gly Pro Pro Pro
                20                  25                  30

Lys Pro Ala Glu Arg His Lys Asp Asp Ser Arg Gly Leu Val Leu Pro
            35                  40                  45

Gly Tyr Lys Tyr Leu Gly Pro Phe Asn Gly Leu Asp Lys Gly Glu Pro
        50                  55                  60

Val Asn Glu Ala Asp Ala Ala Ala Leu Glu His Asp Lys Ala Tyr Asp
65                  70                  75                  80

Gln Gln Leu Lys Ala Gly Asp Asn Pro Tyr Leu Lys Tyr Asn His Ala
                85                  90                  95

Asp Ala Glu Phe Gln Glu Arg Leu Lys Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Ala Ala Lys Thr Ala Pro Gly Lys Lys Arg
    130                 135                 140

Pro Val Glu His Ser Pro Val Glu Pro Asp Ser Ser Ser Gly Thr Gly
145                 150                 155                 160
```

-continued

```
Lys Ala Gly Gln Gln Pro Ala Arg Lys Arg Leu Asn Phe Gly Gln Thr
                165                 170                 175
Gly Asp Ala Asp Ser Val Pro Asp Pro Gln Pro Leu Gly Glu Pro Pro
            180                 185                 190
Ala Ala Pro Thr Ser Leu Gly Ser Asn Thr Met Ala Ser Gly Gly Gly
        195                 200                 205
Ala Pro Met Ala Asp Asn Asn Glu Gly Ala Asp Gly Val Gly Ser Ser
    210                 215                 220
Ser Gly Asn Trp His Cys Asp Ser Thr Trp Leu Gly Asp Arg Val Ile
225                 230                 235                 240
Thr Thr Ser Thr Arg Thr Trp Ala Leu Pro Thr Tyr Asn Asn His Leu
                245                 250                 255
Tyr Lys Gln Ile Ser Ser Ala Ser Thr Gly Ala Ser Asn Asp Asn His
            260                 265                 270
Tyr Phe Gly Tyr Ser Thr Pro Trp Gly Tyr Phe Asp Phe Asn Arg Phe
        275                 280                 285
His Cys His Phe Ser Pro Arg Asp Trp Gln Arg Leu Ile Asn Asn Asn
    290                 295                 300
Trp Gly Phe Arg Pro Lys Arg Leu Asn Phe Lys Leu Phe Asn Ile Gln
305                 310                 315                 320
Val Lys Glu Val Thr Gln Asn Glu Gly Thr Lys Thr Ile Ala Asn Asn
                325                 330                 335
Leu Thr Ser Thr Ile Gln Val Phe Thr Asp Ser Glu Tyr Gln Leu Pro
            340                 345                 350
Tyr Val Leu Gly Ser Ala His Gln Gly Cys Leu Pro Pro Phe Pro Ala
        355                 360                 365
Asp Val Phe Met Ile Pro Gln Tyr Gly Tyr Leu Thr Leu Asn Asn Gly
    370                 375                 380
Ser Gln Ala Met Gly Arg Ser Ser Phe Tyr Cys Leu Glu Tyr Phe Pro
385                 390                 395                 400
Ser Gln Met Leu Arg Thr Gly Asn Asn Phe Thr Phe Ser Tyr Thr Phe
                405                 410                 415
Glu Asp Val Pro Phe His Ser Ser Tyr Ala His Ser Gln Ser Leu Asp
            420                 425                 430
Arg Leu Met Asn Pro Leu Ile Asp Gln Tyr Leu Tyr Tyr Leu Ser Arg
        435                 440                 445
Thr Gln Ser Thr Gly Gly Thr Ala Gly Thr Gln Gln Leu Leu Phe Ser
    450                 455                 460
Gln Ala Gly Pro Asn Asn Met Ser Ala Gln Ala Arg Asn Trp Leu Pro
465                 470                 475                 480
Gly Pro Cys Tyr Arg Gln Gln Arg Leu Ser Lys Thr Ala Asn Asp Asn
                485                 490                 495
Asn Asn Ser Asn Phe Pro Trp Thr Ala Ala Ser Lys Tyr His Leu Asn
            500                 505                 510
Gly Arg Asp Ser Leu Val Asn Pro Gly Pro Ala Met Ala Ser His Lys
        515                 520                 525
Asp Asp Glu Glu Lys Phe Phe Pro Met His Gly Asn Leu Ile Phe Gly
    530                 535                 540
Lys Glu Gly Thr Thr Ala Ser Asn Ala Glu Leu Asp Asn Val Met Ile
545                 550                 555                 560
Thr Asp Glu Glu Glu Ile Arg Thr Thr Asn Pro Val Ala Thr Glu Gln
                565                 570                 575
```

```
Tyr Gly Thr Val Ala Asn Asn Leu Gln Ser Ser Asn Thr Ala Pro Thr
            580                 585                 590

Thr Arg Thr Val Asn Asp Gln Gly Ala Leu Pro Gly Met Val Trp Gln
        595                 600                 605

Asp Arg Asp Val Tyr Leu Gln Gly Pro Ile Trp Ala Lys Ile Pro His
    610                 615                 620

Thr Asp Gly His Phe His Pro Ser Pro Leu Met Gly Gly Phe Gly Leu
625                 630                 635                 640

Lys His Pro Pro Gln Ile Leu Ile Lys Asn Thr Pro Val Pro Ala
                645                 650                 655

Asp Pro Pro Thr Thr Phe Asn Gln Ser Lys Leu Asn Ser Phe Ile Thr
            660                 665                 670

Gln Tyr Ser Thr Gly Gln Val Ser Val Glu Ile Glu Trp Glu Leu Gln
        675                 680                 685

Lys Glu Asn Ser Lys Arg Trp Asn Pro Glu Ile Gln Tyr Thr Ser Asn
    690                 695                 700

Tyr Asn Lys Ser Val Asn Val Asp Phe Thr Val Asp Thr Asn Gly Val
705                 710                 715                 720

Tyr Ser Glu Pro Arg Pro Ile Gly Thr Arg Tyr Leu Thr Arg Asn Leu
                725                 730                 735
```

<210> SEQ ID NO 11
<211> LENGTH: 737
<212> TYPE: PRT
<213> ORGANISM: Artificial Sequence
<220> FEATURE:
<221> NAME/KEY: source
<223> OTHER INFORMATION: /note="Description of Artificial Sequence:
    Synthetic polypeptide"

<400> SEQUENCE: 11

```
Met Ala Ala Asp Gly Tyr Leu Pro Asp Trp Leu Glu Asp Thr Leu Ser
1               5                   10                  15

Glu Gly Ile Arg Gln Trp Trp Lys Leu Lys Pro Gly Pro Pro Pro
            20                  25                  30

Lys Pro Ala Glu Arg His Lys Asp Asp Ser Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Ala Ala Asp Ala Ala Leu Glu His Asp Lys Ala Tyr Asp
65                  70                  75                  80

Gln Gln Leu Lys Ala Gly Asp Asn Pro Tyr Leu Arg Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Leu Leu Glu Pro
        115                 120                 125

Leu Gly Leu Val Glu Glu Ala Ala Lys Thr Ala Pro Gly Lys Lys Arg
    130                 135                 140

Pro Val Glu His Ser Pro Val Glu Pro Asp Ser Ser Ser Gly Thr Gly
145                 150                 155                 160

Lys Ala Gly Gln Gln Pro Ala Arg Lys Arg Leu Asn Phe Gly Gln Thr
                165                 170                 175

Gly Asp Ala Asp Ser Val Pro Asp Pro Gln Pro Leu Gly Glu Pro Pro
            180                 185                 190

Ala Ala Pro Thr Ser Leu Gly Ser Asn Thr Met Ala Thr Gly Ser Gly
```

```
            195                 200                 205
Ala Pro Met Ala Asp Asn Asn Glu Gly Ala Asp Gly Val Gly Asn Ser
210                 215                 220

Ser Gly Asn Trp His Cys Asp Ser Gln Trp Leu Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Ser Ala Ser Thr Gly Ala Ser Asn Asp Asn His
                260                 265                 270

Tyr Phe Gly Tyr Ser Thr Pro Trp Gly Tyr Phe Asp Phe Asn Arg Phe
            275                 280                 285

His Cys His Phe Ser Pro Arg Asp Trp Gln Arg Leu Ile Asn Asn Asn
        290                 295                 300

Trp Gly Phe Arg Pro Lys Arg Leu Asn Phe Lys Leu Phe Asn Ile Gln
305                 310                 315                 320

Val Lys Glu Val Thr Thr Asn Asp Gly Val Thr Thr Ile Ala Asn Asn
                325                 330                 335

Leu Thr Ser Thr Val Gln Val Phe Thr Asp Ser Glu Tyr Gln Leu Pro
            340                 345                 350

Tyr Val Leu Gly Ser Ala His Gln Gly Cys Leu Pro Pro Phe Pro Ala
        355                 360                 365

Asp Val Phe Met Val Pro Gln Tyr Gly Tyr Leu Thr Leu Asn Asn Gly
370                 375                 380

Ser Gln Ala Val Gly Arg Ser Ser Phe Tyr Cys Leu Glu Tyr Phe Pro
385                 390                 395                 400

Ser Gln Met Leu Arg Thr Gly Asn Asn Phe Gln Phe Ser Tyr Thr Phe
                405                 410                 415

Glu Asp Val Pro Phe His Ser Ser Tyr Ala His Ser Gln Ser Leu Asp
            420                 425                 430

Arg Leu Met Asn Pro Leu Ile Asp Gln Tyr Leu Tyr Tyr Leu Asn Arg
        435                 440                 445

Thr Gln Gly Thr Thr Ser Gly Thr Thr Asn Gln Ser Arg Leu Leu Phe
    450                 455                 460

Ser Gln Ala Gly Pro Gln Ser Met Ser Leu Gln Ala Arg Asn Trp Leu
465                 470                 475                 480

Pro Gly Pro Cys Tyr Arg Gln Gln Arg Leu Ser Lys Thr Ala Asn Asp
                485                 490                 495

Asn Asn Asn Ser Asn Phe Pro Trp Thr Ala Ala Ser Lys Tyr His Leu
            500                 505                 510

Asn Gly Arg Asp Ser Leu Val Asn Pro Gly Pro Ala Met Ala Ser His
        515                 520                 525

Lys Asp Asp Glu Glu Lys Phe Phe Pro Met His Gly Asn Leu Ile Phe
    530                 535                 540

Gly Lys Glu Gly Thr Thr Ala Ser Asn Ala Glu Leu Asp Asn Val Met
545                 550                 555                 560

Ile Thr Asp Glu Glu Glu Ile Arg Thr Thr Asn Pro Val Ala Thr Glu
                565                 570                 575

Gln Tyr Gly Thr Val Ala Asn Asn Leu Gln Ser Ser Asn Thr Ala Pro
            580                 585                 590

Thr Thr Arg Thr Val Asn Asp Gln Gly Ala Leu Pro Gly Met Val Trp
        595                 600                 605

Gln Asp Arg Asp Val Tyr Leu Gln Gly Pro Ile Trp Ala Lys Ile Pro
    610                 615                 620
```

His Thr Asp Gly His Phe His Pro Ser Pro Leu Met Gly Gly Phe Gly
625                 630                 635                 640

Leu Lys His Pro Pro Pro Gln Ile Leu Ile Lys Asn Thr Pro Val Pro
                645                 650                 655

Ala Asn Pro Pro Thr Thr Phe Asn Gln Ser Lys Leu Asn Ser Phe Ile
            660                 665                 670

Thr Gln Tyr Ser Thr Gly Gln Val Ser Val Glu Ile Glu Trp Glu Leu
        675                 680                 685

Gln Lys Glu Asn Ser Lys Arg Trp Asn Pro Glu Ile Gln Tyr Thr Ser
690                 695                 700

Asn Tyr Tyr Lys Ser Thr Ser Val Asp Phe Ala Val Asn Thr Glu Gly
705                 710                 715                 720

Val Tyr Ser Glu Pro Arg Pro Ile Gly Thr Arg Tyr Leu Thr Arg Asn
                725                 730                 735

Leu

<210> SEQ ID NO 12
<211> LENGTH: 737
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 12

Met Ala Ala Asp Gly Tyr Leu Pro Asp Trp Leu Glu Asp Thr Leu Ser
1               5                   10                  15

Glu Gly Ile Arg Gln Trp Trp Lys Leu Lys Pro Gly Pro Pro Pro Pro
            20                  25                  30

Lys Pro Ala Glu Arg His Lys Asp Asp Ser Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Ala Ala Asp Ala Ala Ala Leu Glu His Asp Lys Ala Tyr Asp
65                  70                  75                  80

Gln Gln Leu Lys Ala Gly Asp Asn Pro Tyr Leu Arg Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
        115                 120                 125

Phe Gly Leu Val Glu Glu Gly Ala Lys Thr Ala Pro Gly Lys Lys Arg
    130                 135                 140

Pro Val Glu His Ser Pro Val Glu Pro Asp Ser Ser Ser Gly Thr Gly
145                 150                 155                 160

Lys Ala Gly Gln Gln Pro Ala Arg Lys Arg Leu Asn Phe Gly Gln Thr
                165                 170                 175

Gly Asp Ser Glu Ser Val Pro Asp Pro Gln Pro Leu Gly Glu Pro Pro
            180                 185                 190

Ala Ala Pro Ser Gly Val Gly Pro Asn Thr Met Ala Ser Gly Gly Gly
        195                 200                 205

Ala Pro Met Ala Asp Asn Asn Glu Gly Ala Asp Gly Val Gly Asn Ala
    210                 215                 220

Ser Gly Asn Trp His Cys Asp Ser Thr Trp Leu Gly Asp Arg Val Ile

-continued

```
            225                 230                 235                 240
        Thr Thr Ser Thr Arg Thr Trp Ala Leu Pro Thr Tyr Asn Asn His Leu
                        245                 250                 255
        Tyr Lys Gln Ile Ser Ser Ala Ser Thr Gly Ala Ser Asn Asp Asn His
                        260                 265                 270
        Tyr Phe Gly Tyr Ser Thr Pro Trp Gly Tyr Phe Asp Phe Asn Arg Phe
                        275                 280                 285
        His Cys His Phe Ser Pro Arg Asp Trp Gln Arg Leu Ile Asn Asn Asn
                        290                 295                 300
        Trp Gly Phe Arg Pro Lys Arg Leu Asn Phe Lys Leu Phe Asn Ile Gln
        305                 310                 315                 320
        Val Lys Glu Val Thr Gln Asn Asp Gly Thr Thr Ile Ala Asn Asn
                        325                 330                 335
        Leu Thr Ser Thr Val Gln Val Phe Thr Asp Ser Glu Tyr Gln Leu Pro
                        340                 345                 350
        Tyr Val Leu Gly Ser Ala His Gln Gly Cys Leu Pro Pro Phe Pro Ala
                        355                 360                 365
        Asp Val Phe Met Val Pro Gln Tyr Gly Tyr Leu Thr Leu Asn Asn Gly
                        370                 375                 380
        Ser Gln Ala Val Gly Arg Ser Ser Phe Tyr Cys Leu Glu Tyr Phe Pro
        385                 390                 395                 400
        Ser Gln Met Leu Arg Thr Gly Asn Asn Phe Gln Phe Ser Tyr Thr Phe
                        405                 410                 415
        Glu Asp Val Pro Phe His Ser Ser Tyr Ala His Ser Gln Ser Leu Asp
                        420                 425                 430
        Arg Leu Met Asn Pro Leu Ile Asp Gln Tyr Leu Tyr Tyr Leu Asn Arg
                        435                 440                 445
        Thr Gln Gly Thr Thr Ser Gly Thr Thr Asn Gln Ser Arg Leu Leu Phe
                        450                 455                 460
        Ser Gln Ala Gly Pro Gln Ser Met Ser Leu Gln Ala Arg Asn Trp Leu
        465                 470                 475                 480
        Pro Gly Pro Cys Tyr Arg Gln Gln Arg Leu Ser Lys Thr Ala Asn Asp
                        485                 490                 495
        Asn Asn Asn Ser Asn Phe Pro Trp Thr Ala Ala Ser Lys Tyr His Leu
                        500                 505                 510
        Asn Gly Arg Asp Ser Leu Val Asn Pro Gly Pro Ala Met Ala Ser His
                        515                 520                 525
        Lys Asp Asp Glu Glu Lys Phe Phe Pro Met His Gly Asn Leu Ile Phe
        530                 535                 540
        Gly Lys Glu Gly Thr Thr Ala Ser Asn Ala Glu Leu Asp Asn Val Met
        545                 550                 555                 560
        Ile Thr Asp Glu Glu Ile Arg Thr Thr Asn Pro Val Ala Thr Glu
                        565                 570                 575
        Gln Tyr Gly Thr Val Ala Asn Asn Leu Gln Ser Ser Asn Thr Ala Pro
                        580                 585                 590
        Thr Thr Arg Thr Val Asn Asp Gln Gly Ala Leu Pro Gly Met Val Trp
                        595                 600                 605
        Gln Asp Arg Asp Val Tyr Leu Gln Gly Pro Ile Trp Ala Lys Ile Pro
                        610                 615                 620
        His Thr Asp Gly His Phe His Pro Ser Pro Leu Met Gly Gly Phe Gly
        625                 630                 635                 640
        Leu Lys His Pro Pro Pro Gln Ile Met Ile Lys Asn Thr Pro Val Pro
                        645                 650                 655
```

```
Ala Asn Pro Pro Thr Thr Phe Ser Pro Ala Lys Phe Ala Ser Phe Ile
            660                 665                 670

Thr Gln Tyr Ser Thr Gly Gln Val Ser Val Glu Ile Glu Trp Glu Leu
        675                 680                 685

Gln Lys Glu Asn Ser Lys Arg Trp Asn Pro Gly Ile Gln Tyr Thr Ser
690                 695                 700

Asn Tyr Tyr Lys Ser Thr Ser Val Asp Phe Ala Val Asn Thr Glu Gly
705                 710                 715                 720

Val Tyr Ser Glu Pro Arg Pro Ile Gly Thr Arg Tyr Leu Thr Arg Asn
                725                 730                 735

Leu

<210> SEQ ID NO 13
<211> LENGTH: 737
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 13

Met Ala Ala Asp Gly Tyr Leu Pro Asp Trp Leu Glu Asp Asn Leu Ser
1               5                   10                  15

Glu Gly Ile Arg Glu Trp Trp Asp Leu Lys Pro Gly Ala Pro Lys Pro
            20                  25                  30

Lys Ala Asn Gln Gln Lys Gln Asp Asp Gly Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Ala Ala Asp Ala Ala Ala Leu Glu His Asp Lys Ala Tyr Asp
65                  70                  75                  80

Gln Gln Leu Gln Ala Gly Asp Asn Pro Tyr Leu Arg Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Leu Leu Glu Pro
        115                 120                 125

Leu Gly Leu Val Glu Glu Ala Ala Lys Thr Ala Pro Gly Lys Lys Arg
    130                 135                 140

Pro Val Glu His Ser Pro Val Glu Pro Asp Ser Ser Ser Gly Thr Gly
145                 150                 155                 160

Lys Ala Gly Gln Gln Pro Ala Arg Lys Arg Leu Asn Phe Gly Gln Thr
                165                 170                 175

Gly Asp Ala Asp Ser Val Pro Asp Pro Gln Pro Ile Gly Glu Pro Pro
            180                 185                 190

Ala Ala Pro Ser Gly Val Gly Ser Leu Thr Met Ala Ala Gly Gly Gly
        195                 200                 205

Ala Pro Met Ala Asp Asn Asn Glu Gly Ala Asp Gly Val Gly Asn Ser
    210                 215                 220

Ser Gly Asn Trp His Cys Asp Ser Thr Trp Met Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Ser Ala Ser Thr Gly Ala Ser Asn Asp Asn His
```

-continued

```
                260                 265                 270
Tyr Phe Gly Tyr Ser Thr Pro Trp Gly Tyr Phe Asp Phe Asn Arg Phe
            275                 280                 285
His Cys His Phe Ser Pro Arg Asp Trp Gln Arg Leu Ile Asn Asn Asn
290                 295                 300
Trp Gly Phe Arg Pro Lys Arg Leu Asn Phe Lys Leu Phe Asn Ile Gln
305                 310                 315                 320
Val Lys Glu Val Thr Thr Asn Asp Gly Val Thr Thr Ile Ala Asn Asn
                325                 330                 335
Leu Thr Ser Thr Val Gln Val Phe Ser Asp Ser Glu Tyr Gln Leu Pro
            340                 345                 350
Tyr Val Leu Gly Ser Ala His Gln Gly Cys Leu Pro Pro Phe Pro Ala
            355                 360                 365
Asp Val Phe Met Ile Pro Gln Tyr Gly Tyr Leu Thr Leu Asn Asn Gly
            370                 375                 380
Ser Gln Ala Val Gly Arg Ser Ser Phe Tyr Cys Leu Glu Tyr Phe Pro
385                 390                 395                 400
Ser Gln Met Leu Arg Thr Gly Asn Asn Phe Thr Phe Ser Tyr Thr Phe
                405                 410                 415
Glu Asp Val Pro Phe His Ser Ser Tyr Ala His Ser Gln Ser Leu Asp
            420                 425                 430
Arg Leu Met Asn Pro Leu Ile Asp Gln Tyr Leu Tyr Tyr Leu Asn Arg
            435                 440                 445
Thr Gln Gly Thr Thr Ser Gly Thr Thr Asn Gln Ser Arg Leu Leu Phe
            450                 455                 460
Ser Gln Ala Gly Pro Gln Ser Met Ser Leu Gln Ala Arg Asn Trp Leu
465                 470                 475                 480
Pro Gly Pro Cys Tyr Arg Gln Gln Arg Leu Ser Lys Thr Ala Asn Asp
                485                 490                 495
Asn Asn Asn Ser Asn Phe Pro Trp Thr Ala Ala Ser Lys Tyr His Leu
                500                 505                 510
Asn Gly Arg Asp Ser Leu Val Asn Pro Gly Pro Ala Met Ala Ser His
            515                 520                 525
Lys Asp Asp Glu Glu Lys Phe Phe Pro Met His Gly Asn Leu Ile Phe
            530                 535                 540
Gly Lys Glu Gly Thr Thr Ala Ser Asn Ala Glu Leu Asp Asn Val Met
545                 550                 555                 560
Ile Thr Asp Glu Glu Glu Ile Arg Thr Thr Asn Pro Val Ala Thr Glu
                565                 570                 575
Gln Tyr Gly Thr Val Ala Asn Asn Leu Gln Ser Ser Asn Thr Ala Pro
            580                 585                 590
Thr Thr Arg Thr Val Asn Asp Gln Gly Ala Leu Pro Gly Met Val Trp
            595                 600                 605
Gln Asp Arg Asp Val Tyr Leu Gln Gly Pro Ile Trp Ala Lys Ile Pro
            610                 615                 620
His Thr Asp Gly His Phe His Pro Ser Pro Leu Met Gly Gly Phe Gly
625                 630                 635                 640
Leu Lys His Pro Pro Pro Gln Ile Met Ile Lys Asn Thr Pro Val Pro
                645                 650                 655
Ala Asn Pro Pro Thr Thr Phe Ser Pro Ala Lys Phe Ala Ser Phe Ile
                660                 665                 670
Thr Gln Tyr Ser Thr Gly Gln Val Ser Val Glu Ile Glu Trp Glu Leu
            675                 680                 685
```

```
Gln Lys Glu Asn Ser Lys Arg Trp Asn Pro Glu Ile Gln Tyr Thr Ser
    690                 695                 700

Asn Tyr Asn Lys Ser Val Asn Val Asp Phe Thr Val Asp Thr Asn Gly
705                 710                 715                 720

Val Tyr Ser Glu Pro Arg Pro Ile Gly Thr Arg Tyr Leu Thr Arg Pro
                725                 730                 735

Leu

<210> SEQ ID NO 14
<211> LENGTH: 2214
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 14
atggctgccg atggttatct tccagattgg ctcgaggaca ctctctctga aggaataaga      60
cagtggtgga agctcaaacc tggcccacca ccaccaaagc ccgcagagcg cataaggac     120 gacagcaggg gtcttgtgct tccgggttac aaatacctcg acccggcaa cggactcgac     180 aaggggagc ccgtcaacgc ggcggacgca gcggccctcg agcacgacaa ggcctacgac     240
cagcagctca aagcgggtga caatccgtac ctgcggtata accacgccga cgccgagttt     300
caggagcgtc tgcaagaaga tacgtctttt gggggcaacc tcgggcgagc agtcttccag     360
gccaagaagc gggttctcga acctctcggt ctggttgagg aacctgttaa dacggctccg     420
ggaaaaaaga ggccggtaga gcactctcct gtggagccag actcctcctc gggaaccgga     480
aaggcgggcc agcagcctgc gaggaagcga ctcaactttg gtcagactgg agacaccgac     540
tccgccgctg accccagcc tctcggagaa ccaccagcag cccctctgg tctgggaact     600 ggtacaatgg ctgcaggcgg tggcgctcca atggcagaca taacgaagg cgccgacgga     660 gtgggtaatg cctcgggaaa ttggcattgc gattccacat ggctgggcga cagagtcatc     720
accaccagca cccgcacctg ggccttgccc acctacaata accacctcta caagcaaatc     780
tccagtgctt caacggggc cagcaacgac aaccactact tcggctacag cacccctgg     840 gggtactttg acttcaaccg cttccactgc cacttctcac cacgtgactg gcaaagactc     900
atcaacaaca actgggggatt ccggcccaag agactcaact tcaagctctt caacatccag     960
gtcaaggagg tcacgcagaa tgaaggcacc aagaccatcg ccaataacct taccagcacg    1020
gttcaggtgt ttactgactc ggagtaccag ctgccgtacg ttctcggctc tgcccaccag    1080
ggctgcctgc ctccgttccc ggcggacgtg ttcatgattc cgcagtacgg ctacctaacg    1140
ctcaacaatg gcagccaggc gatgggtcgc tcgtccttct actgcctgga gtactttccg    1200
tcgcagatgc tgagaaccgg caacaacttc cagtttactt acaccttcga ggacgtgcct    1260
ttccacagca gctacgctca cagccagagt ttggatcgct tgatgaatcc tcttattgat    1320
cagtatctgt actacctgaa cagaacgcaa ggaacaacct ctggaacaac aaccaatca    1380 cggctgcttt ttagccaggc tgggcctcag tctatgtctt gcaggccag aaattggcta    1440 cctgggccct gctaccggca acagagactt tcaaagactg ctaacgacaa caacaacagt    1500
aactttcctt ggacagcggc cagcaaatat catctcaatg ccgcgactc gctggtgaat    1560 ccaggaccag ctatgccag tcacaaggac gatgaagaaa atttttccc tatgcacggc    1620 aatctaatat ttggcaaaga agggacaacg gcaagtaacg cagaattaga taatgtaatg    1680
```

```
attacggatg aagaagagat tcgtaccacc aatcctgtgg caacagagca gtatggaact   1740
gtggcaaata acttgcagag ctcaaataca gctcccacga ctagaactgt caatgatcag   1800
ggggccttac ctggcatggt gtggcaagat cgtgacgtgt accttcaagg acctatctgg   1860
gcaaagattc ctcacacgga tggacacttt catccttctc ctctgatggg cggctttggc   1920
ctgaaacatc ctccgcctca gatcctgatc aagaacacgc ctgtacctgc ggatcctcca   1980
acggccttca acaaggacaa gctgaactct ttcatcaccc agtattctac tggccaagtc   2040
agcgtggaga tcgagtggga gctgcagaag gaaaacagca agcgctggaa ccccgagatc   2100
cagtacacct ccaactacta caaatctaca agtgtggact tgctgttaa tacagaaggc    2160 gtgtactctg aaccccgccc cattggcacc cgttacctca cccgtaatct gtaa           2214
```

<210> SEQ ID NO 15
<211> LENGTH: 2217
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 15

```
atggctgccg atggttatct tccagattgg ctcgaggaca ctctctctga aggaataaga     60
cagtggtgga agctcaaacc tggcccacca ccaccaaagc ccgcagagcg gcataaggac    120
gacagcaggg gtcttgtgct tcctgggtac aagtacctcg acccttcaa cggactcgac     180 aaaggagagc cggtcaacga ggcggatgca gcggccctcg agcacgacaa ggcctacgac   240
cagcagctca aagcgggtga caatccgtac cttcggtata accacgccga cgccgagttt    300
caggagcgtc tgcaagaaga tacgtctttt gggggcaacc tcgggcgagc agtcttccag   360
gccaagaagc gggttctcga acctctcggt ctggttgagg aaggcgctaa gacggctcct    420
ggaaagaaga gaccggtaga gccatcaccc cagcgttctc cagactcctc tacgggcatc   480
ggcaagaaag ccaacagcc cgccagaaaa agactcaatt ttggtcagac tggcgactca     540
gagtcagttc cagaccctca acctctcgga gaacctccag cagcgccctc tggtgtggga   600
cctaatacaa tggctgcagg cggtggcgca ccaatggcag acaataacga aggcgccgac   660
ggagtgggta atgcctcagg aaattggcat tgcgattcca catggctggg cgacagagtc    720
atcaccacca gcacccgcac ctgggccttg cccacctaca ataaccacct ctacaagcaa   780
atctccagtg cttcaacggg ggccagcaac gacaaccact acttcggcta cagcacccct    840
tgggggtatt ttgacttcaa cagattccac tgccactttt caccacgtga ctggcaaaga    900
ctcatcaaca caactgggg attccgaccc aagagactca acttcaagct ctttaacatt      960
caagtcaaag aggtcacgca gaatgaaggc accaagacca tcgccaataa cctcaccagc   1020
accatccagg tgtttacgga ctcggagtac cagctgccgt acgttctcgg ctctgcccac   1080
cagggctgcc tgcctccgtt cccggcggac gtgttcatga ttccccagta cggctaccta   1140
acactcaaca acggtagtca ggccgtggga cgctcctcct tttactgcct ggagtacttc   1200
ccttcgcaga tgctaaggac tggaaataac ttccaattca gctataccttt cgaggatgta   1260 cctttttcaca gcagctacgc tcacagccag agtttggatc gcttgatgaa tcctcttatt    1320
gatcagtatc tgtactacct gaacagaacg caaggaacaa cctctggaac aaccaaccaa    1380
tcacggctgc tttttagcca ggctgggcct cagtctatgt ctttgcaggc cagaaattgg   1440
```

```
ctacctgggc cctgctaccg gcaacagaga ctttcaaaga ctgctaacga caacaacaac    1500
agtaactttc cttggacagc ggccagcaaa tatcatctca atggccgcga ctcgctggtg    1560
aatccaggac cagctatggc cagtcacaag gacgatgaag aaaaattttt ccctatgcac    1620
ggcaatctaa tatttggcaa agaagggaca acggcaagta acgcagaatt agataatgta    1680
atgattacgg atgaagaaga gattcgtacc accaatcctg tggcaacaga gcagtatgga    1740
actgtggcaa ataacttgca gagctcaaat acagctccca cgactagaac tgtcaatgat    1800 caggggggcct tacctggcat ggtgtggcaa gatagagacg tgtacctgca gggtcctatc    1860
tgggccaaga ttcctcacac ggacggaaac tttcatccct cgccgctgat gggaggcttt    1920
ggactgaaac acccgcctcc tcagatcctg atcaagaaca cgcctgtacc tgcggatcct    1980
ccgaccacct tcaaccagtc aaagctgaac tctttcatca cgcaatacag caccggacag    2040
gtcagcgtgg aaattgaatg ggagctgcag aaggaaaaca gcaagcgctg gaaccccgag    2100
atccagtaca cctccaacta ctacaaatct acaagtgtgg actttgctgt taatacagaa    2160
ggcgtgtact ctgaaccccg ccccattggc acccgttacc tcacccgtaa tctgtaa      2217
```

<210> SEQ ID NO 16
<211> LENGTH: 2214
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 16

```
atggctgccg atggttatct tccagattgg ctcgaggaca acctctctga gggcattcgc      60
gagtggtggg acttgaaacc tggagccccg aaacccaaag ccaaccagca aaagcaggac     120
gacggccggg gtctggtgct tcctggctac aagtacctcg acccttcaa cggactcgac      180 aagggggagc ccgtcaacgc ggcggatgca gcggccctcg agcacgacaa ggcctacgac     240
cagcagctca aagcgggtga caatccgtac ctgcggtata ccacgccga cgccgagttt     300 caggagcgtc tgcaagaaga tacgtctttt gggggcaacc tcgggcgagc agtcttccag     360
gccaaaaaga ggcttcttga acctcttggt ctggttgagg aagcggctaa gacggctcct     420
ggaaagaaac gtccggtaga gcagtcgcca aagagccag actcctcctc gggcatcggc     480
aagacaggcc agcagcccgc taaaaagaga ctcaatttcg gtcagactgg cgacacagag     540
tcagtcccag accctcaacc tctcggagaa ccaccagcag cccccacaag tttgggatct     600
aatacaatgg cttcaggcgg tggcgcacca atggcagaca ataacgaagg cgccgacgga     660
gtgggtaatg cctcaggaaa ttggcattgc gattccacat ggctgggcga cagagtcatc     720
accaccagca cccgcacctg gccttgccc acctacaata accacctcta caagcaaatc     780
tccagtgctt caacggggc cagcaacgac aaccactact cggctacag cacccctgg      840 gggtatttg atttcaacag attccactgc catttctcac cacgtgactg gcagcgactc     900
atcaacaaca attggggatt ccggccaag aaactcagct tcaagctctt caacatccaa     960
gttaaagagg tcacgcagaa cgatggcacg acgactattg ccaataacct taccagcacg    1020
attcaggtct ttacggactc ggagtaccag ctgccgtacg ttctcggctc tgcccaccag    1080
ggctgcctcc ctccgttccc ggcggacgtg ttcatgattc cgcagtacgg ctacctaacg    1140
ctcaacaatg gcagccaagc cgtgggacgt catcctttt actgcctgga gtactttcct    1200
tctcaaatgc tgagaacggg caacaacttt accttcagct acaccttgat ggaagtgcct    1260
```

```
ttccacagca gctacgctca cagccagagt ttggatcgct tgatgaatcc tcttattgat   1320
cagtatctgt actacctgaa cagaacgcaa ggaacaacct ctggaacaac caaccaatca   1380
cggctgcttt ttagccaggc tgggcctcag tctatgtctt tgcaggccag aaattggcta   1440
cctgggccct gctaccggca acagagactt tcaaagactg ctaacgacaa caacaacagt   1500
aactttcctt ggacagcggc cagcaaatat catctcaatg ccgcgactc gctggtgaat    1560 ccaggaccag ctatggccag tcacaaggac gatgaagaaa aattttccc tatgcacggc    1620 aatctaatat ttggcaaaga agggacaacg gcaagtaacg cagaattaga taatgtaatg   1680
attacggatg aagaagagat tcgtaccacc aatcctgtgg caacagagca gtatggaact   1740
gtggcaaata acttgcagag ctcaaataca gctcccacga ctagaactgt caatgatcag   1800
ggggccttac ctggcatggt gtggcaagat cgtgacgtgt accttcaagg acctatctgg   1860
gccaagattc ctcacacgga tggacacttt catccttctc ctctgatggg aggctttgga   1920
ctgaaacatc cgcctcctca aatcatgatc aaaaatactc cggtaccggc aaatcctccg   1980
acgactttca gcccggccaa gtttgcttca tttatcacgc agtacagcac cggacaggtc   2040
agcgtggaaa ttgaatggga gctgcagaaa gaaaacagca acgttggaa tccagagatt   2100 cagtacactt ccaactacaa caagtctgtt aatgtggact ttactgtaga cactaatggt   2160
gtttatagtg aacctcgccc cattggcacc cgttaccta cccgtcccct gtaa           2214
```

<210> SEQ ID NO 17
<211> LENGTH: 2214
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 17

```
atggctgccg atggttatct tccagattgg ctcgaggaca acctttctga aggcattcgc    60
gagtggtggg acttgaaacc tggagccccg aaacccaaag ccaaccagca aaagcaggac   120
gacgctcggg gtcttgtgct tccgggttac aaataccttg acccggcaa cggactcgac    180 aaggggagc ccgtcaacgc ggcggacgca gcggccctcg agcacgacaa agcctacgac    240
cagcagctgc aggcgggtga caatccgtac ctgcggtaca accacgccga cgcggagttt   300
caggagcgtc tgcaagaaga tacgtctttt gggggcaacc tcgggcgagc agtcttccag   360
gccaagaaga gggttctcga acctctcggt ctggttgagg aagcggctaa dacggctcct   420
ggaaagaaac gtccggtaga gcagtcgcca caagagccag actcctcctc gggcatcggc   480
aagacaggcc agcagcccgc taaaaagaga ctcaattttg gtcagactgg cgactcagag   540
tcagtcccag accctcaacc tctcggagaa ccaccagcag cccccacaag tttgggatct   600
aatacaatgg cttcaggcgg tggcgcacca atggcagaca taacgagggg tgccgacgga   660
gtgggtaatt cctcgggaaa ttggcattgc gattcccaat ggctgggcga ccgagtcatc   720
accaccagca cccgcacctg gccttgccc acctacaata accacctcta caagcaaatc    780
tccagtgctt caacggggc cagcaacgac aaccactact cggctacag cacccctgg    840 gggtattttg atttcaacag attccactgc cactttcac cacgtgactg gcaaagactc    900
atcaacaaca ctggggatt ccgacccaag agactcaact tcaaactctt caacatccaa    960
gtcaaggagg tcacgacgaa tgatggcgtc acgaccatcg ccaataacct taccagcacg   1020
```

```
gttcaagtgt tacggactc ggagtatcag ctcccgtacg tgctcgggtc ggcgcaccaa      1080
ggctgtctcc cgccgtttcc agcggacgtc ttcatggtcc ctcagtatgg ataccctcacc   1140 ctgaacaacg gaagtcaagc ggtgggacgc tcatcctttt actgcctgga gtacttccct   1200
tcgcagatgc taaggactgg aaataacttc caattcagct ataccttcga ggatgtacct   1260
tttcacagca gctacgctca cagccagagt ttggatcgct tgatgaatcc tcttattgat   1320
cagtatctgt actacctgaa cagaacgcaa ggaacaacct ctggaacaac caaccaatca   1380
cggctgcttt ttagccaggc tgggcctcag tctatgtctt tgcaggccag aaattggcta   1440
cctgggccct gctaccggca acagagactt tcaaagactg ctaacgacaa caacaacagt   1500
aactttcctt ggacagcggc cagcaaatat catctcaatg gccgcgactc gctggtgaat   1560
ccaggaccag ctatggccag tcacaaggac gatgaagaaa aattttttccc tatgcacggc   1620 aatctaatat ttggcaaaga agggacaacg gcaagtaacg cagaattaga taatgtaatg   1680
attacggatg aagaagagat tcgtaccacc aatcctgtgg caacagagca gtatggaact   1740
gtggcaaata acttgcagag ctcaaataca gctcccacga ctagaactgt caatgatcag   1800
ggggccttac ctggcatggt gtggcaagat cgtgacgtgt accttcaagg acctatctgg   1860
gcaaagattc ctcacacgga tggacacttt cacccgtctc ctctcatggg cggctttgga   1920
cttaagcacc cgcctcctca gatcctcatc aaaaacacgc tgttcctgc gaatcctccg   1980 gcagagtttt cggctacaaa gtttgcttca ttcatcaccc agtattccac aggacaagtg   2040
agcgtggaaa ttgaatggga gctgcagaaa gaaaacagca acgctggaa tccagagatt   2100 cagtacactt ccaactacaa caagtctgtt aatgtggact ttactgtaga cactaatggt   2160
gtttatagtg aacctcgccc cattggcacc cgttacctca cccgtcccct gtaa          2214
```

<210> SEQ ID NO 18
<211> LENGTH: 2214
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 18

```
atggctgccg atggttatct tccagattgg ctcgaggaca acctctctga gggcattcgc      60
gagtggtggg acttgaaacc tggagccccg aaacccaaag ccaaccagca aaagcaggac     120
gacggccggg gtctggtgct tcctggctac aagtacctcg gacccttcaa cggactcgac     180 aaggggagc ccgtcaacgc ggcggatgca gcggccctcg agcacgacaa ggcctacgac     240
cagcagctca aagcgggtga caatccgtac cttcggtata accacgccga cgccgagttt     300
caggagcgtc tgcaagaaga tacgtctttt ggggcaacc tcgggcgagc agtcttccag     360
gccaagaagc gggttctcga acctctcggt ctggttgagg aaggtgctaa gacggctcct     420
ggaaagaaac gtccggtaga gcactctcct gtggagccag actcctcctc gggcatcggc     480
aagacaggcc agcagcccgc taaaaagaga ctcaattttg gtcagactgg cgacgcagac     540
tcagtacctg accccagcc tctcggacag ccaccagcag cccctctgg tctgggaact     600 aatacgatgg ctacaggcag tggcgcacca atggcagaca taacgagggg cgccgacgga     660
gtgggtaatg cctcaggaaa ttggcattgc gattccacat ggctgggcga cagagtcatc     720
accaccagca cccgaacatg ggccttgccc acctataaca accacctcta caagcaaatc     780
tccagtgctt caacggggc cagcaacgac aaccactact cggctacag cacccctgg     840
```

```
gggtactttg acttcaaccg cttccactgc cacttctccc cgcgagactg gcagcggctc    900
atcaacaaca actgggggtt ccggcccaag cgactcaact tcaagctctt caacatccag    960
gtcaaggagg tcacgcagaa tgaaggcacg acgactattg ccaataacct taccagcacg   1020
gttcaagtgt ttacggactc ggagtatcag ctcccgtacg tgctcggctc tgcccaccag   1080
ggctgcctgc ctccgttccc ggcggacgtg ttcatgattc cccagtacgg ctacctaaca   1140
ctcaacaacg gtagtcaggc cgtgggacgc tcctccttct actgcctgga atactttcct   1200
tctcagatgc tgcgtaccgg aaacaacttt accttcagct acacttttga ggacgttcct   1260
ttccacagca gctacgctca cagccagagt ttggatcgct tgatgaatcc tcttattgat   1320
cagtatctgt actacctgaa cagaacgcaa ggaacaacct ctggaacaac caaccaatca   1380
cggctgcttt ttagccaggc tgggcctcag tctatgtctt tgcaggccag aaattggcta   1440
cctgggccct gctaccggca acagagactt tcaaagactg ctaacgacaa caacaacagt   1500
aactttcctt ggacagcggc cagcaaatat catctcaatg gccgcgactc gctggtgaat   1560
ccaggaccag ctatggccag tcacaaggac gatgaagaaa aattttttccc tatgcacggc   1620 aatctaaatat ttggcaaaga agggacaacg gcaagtaacg cagaattaga taatgtaatg   1680
attacggatg aagaagagat tcgtaccacc aatcctgtgg caacagagca gtatggaact   1740
gtggcaaata acttgcagag ctcaaataca gctcccacga ctagaactgt caatgatcag   1800
ggggccttac ctggcatggt gtggcaagat cgtgacgtgt accttcaagg acctatctgg   1860
gcaaagattc ctcacacgga tggacacttt catccttctc ctctgatggg aggctttgga   1920
ctgaaacatc cgcctcctca aatcatgatc aaaaatactc cggtaccggc aaatcctccg   1980
acgactttca gcccggccaa gtttgcttca tttatcactc agtactccac tggacaggtc   2040
agcgtggaaa ttgagtggga gctacagaaa gaaaacagca acgttggaa tccagagatt   2100 cagtacactt ccaactacaa caagtctgtt aatgtggact ttactgtaga cactaatggt   2160
gtttatagtg agcctcgccc cattggcacc cgttacctca cccgtcccct gtaa          2214
```

<210> SEQ ID NO 19
<211> LENGTH: 2214
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 19

```
atggctgccg atggttatct tccagattgg ctcgaggaca acctctctga aggaataaga     60
cagtggtgga agctcaaacc tggcccacca ccaccaaagc ccgcagagcg gcataaggac    120
gacagcaggg gtcttgtgct tcctgggtac aagtacctcg gacccttcaa cggactcgac    180
aagggggagc ccgtcaacgc ggcggatgca gcggccctcg agcacgacaa ggcctacgac    240
cagcagctca agcgggtgga caatccgtac ctgcggtaca accacgccga cgccgagttc    300
caggagcggc tcaaagaaga tacgtctttt ggggggcaacc tcgggcgagc agtcttccag    360
gccaagaagc gggttctcga acctctcggt ctggttgagg aaggcgctaa gacggctcct    420
ggaaagaaga ggcctgtaga gcactctcct gtggagccag actcctcctc gggcatcggc    480
aagacaggcc agcagcccgc taaaaagaga ctcaattttg gtcagactgg cgactcagag    540
tcagtccccg acccacaacc tctcggagaa ccaccagcag ccccctctgg tctgggaact    600
```

| | |
|---|---|
| aatacgatgg cttcaggcgg tgqcgcacca atggcagaca ataacgaggg tgccgatgga | 660 |
| gtgggtaatt cctcaggaaa ttggcattgc gattccacat ggctgggcga cagagtcatc | 720 |
| accaccagca cccgaacctg ggccctgccc acctacaaca atcacctcta caagcaaatc | 780 |
| tccagtgctt caacggggc cagcaacgac aaccactact tcggctacag cacccctgg | 840 |
| gggtattttg atttcaacag attccactgc cacttttcac cacgtgactg gcagcgactc | 900 |
| atcaacaaca attggggatt ccggcccaag agactcaact tcaagctctt caacatccaa | 960 |
| gtcaaggagg tcacgacgaa tgatggcgtc acgaccatcg ccaataacct taccagcacg | 1020 |
| gttcaagtgt ttacggactc ggagtaccag ctcccgtacg tcctcggctc ggcgcatcaa | 1080 |
| ggatgcctcc cgccgttccc agcagacgtc ttcatggtgc cgcagtacgg gtacctgact | 1140 |
| ctgaacaatg gtagtcaggc cgtgggacgc tcctccttct actgcctgga atactttcct | 1200 |
| tcgcagatgc tgagaaccgg caacaacttc cagtttactt acaccttcga ggacgtgcct | 1260 |
| ttccacagca gctacgccca cagccagagc ttggaccggc tgatgaatcc tcttattgat | 1320 |
| cagtatctgt actacctgaa cagaacgcaa ggaacaacct ctggaacaac caccaatca | 1380 |
| cggctgcttt ttagccaggc tgggcctcag tctatgtctt tgcaggccag aaattggcta | 1440 |
| cctgggccct gctaccggca acagagactt tcaaagactg ctaacgacaa caacaacagt | 1500 |
| aactttcctt ggacagcggc cagcaaatat catctcaatg ccgcgactc gctggtgaat | 1560 |
| ccaggaccag ctatggccag tcacaaggac gatgaagaaa aattttttccc tatgcacggc | 1620 |
| aatctaatat ttggcaaaga agggacaacg gcaagtaacg cagaattaga taatgtaatg | 1680 |
| attacgatg aagaagagat tcgtaccacc aatcctgtgg caacagagca gtatggaact | 1740 |
| gtggcaaata acttgcagag ctcaaataca gctcccacga ctagaactgt caatgatcag | 1800 |
| ggggccttac ctggcatggt gtggcaagat cgtgacgtgt accttcaagg acctatctgg | 1860 |
| gcaaagattc ctcacacgga tggacacttt catccttctc ctctgatggg aggctttgga | 1920 |
| ctgaaacatc cgcctcctca aatcatgatc aaaaatactc cggtaccggc aaatcctccg | 1980 |
| acgactttca gcccggccaa gtttgcttca tttatcactc agtactccac gggacaggtc | 2040 |
| agcgtggaaa ttgagtggga gctacagaaa gaaaacagca aacgctggaa tcccgaaatt | 2100 |
| cagtacactt ccaactacaa caagtctgtt aatgtggact ttactgtgga cactaatggt | 2160 |
| gtttatagtg aacctcgccc cattggcacc cgttacctca cccgtcccct gtaa | 2214 |

<210> SEQ ID NO 20
<211> LENGTH: 2214
<212> TYPE: DNA
<213> ORGANISM: Artificial Sequence
<220> FEATURE:
<221> NAME/KEY: source
<223> OTHER INFORMATION: /note="Description of Artificial Sequence:
    Synthetic polynucleotide"

<400> SEQUENCE: 20

| | |
|---|---|
| atggctgctg acggttatct tccagattgg ctcgaggaca ctctctctga aggaataaga | 60 |
| cagtggtgga agctcaaacc tggcccacca ccaccaaagc ccgcagagcg gcataaggac | 120 |
| gacagcaggg gtcttgtgct tcctgggtac aagtacctcg gacccttcaa cggactcgac | 180 |
| aaggggagc ccgtcaacgc ggcggatgca gcggccctcg agcacgacaa ggcctacgac | 240 |
| cagcagctca aagcgggtga caatccgtac ctgcggtata accacgccga cgccgagttt | 300 |
| caggagcgtc tgcaagaaga tacgtctttt gggggcaacc tcgggcgagc agtcttccag | 360 |
| gccaaaaaga ggcttcttga acctcttggt ctggttgagg aagcggctaa gacggctccg | 420 |

-continued

```
ggaaaaaaga ggccggtaga gcactctcct gtggagccag actcctcctc gggaaccgga    480
aaggcgggcc agcagcccgc taaaagagaa ctcaattttg gtcagactgg cgactcagag    540
tcagttccag accctcaacc tctcggagaa cctccagcag cgccctctgg tgtgggacct    600
aatacaatgg ctgcaggcgg tggcgcacca atggcagaca taacgaagg cgccgacgga     660 gtgggtaatg cctcaggaaa ttggcattgc gattccacat ggctgggcga cagagtcatc    720
accaccagca cccgaacctg ggccctgccc acctacaaca accacctcta caagcaaatc    780
tccagtgctt caacgggggc cagcaacgac aaccactact ttggctacag caccccttgg    840
gggtattttg actttaacag attccactgc cacttctcac cacgtgactg gcagcgactc    900
attaacaaca actggggatt ccggcccaag agactcagct tcaagctctt caacatccaa    960
gtcaaggagg tcacgacgaa tgatggcgtc acgaccatcg ccaataacct taccagcacg   1020
gttcaagtgt ttacggactc ggagtatcag ctcccgtacg tcctcggatc agcgcaccaa   1080
ggctgtctcc cgccgtttcc agcggacgtc ttcatggtcc ctcagtatgg ataccctcacc  1140 ctgaacaacg ggagtcaggc agtaggacgc tcttcatttt actgcctgga gtacttccct   1200
tcgcagatgc taaggactgg aaataacttc caattcagct ataccttcga ggatgtacct   1260
tttcacagca gctacgctca cagccagagt ttggatcgct tgatgaatcc tcttattgat   1320
cagtatctgt actacctgaa cagaacgcaa ggaacaacct ctggaacaac caaccaatca   1380
cggctgcttt ttagccaggc tgggcctcag tctatgtctt tgcaggccag aaattggcta   1440
cctgggccct gctaccggca acagagactt tcaaagactg ctaacgacaa caacaacagt   1500
aactttcctt ggacagcggc cagcaaatat catctcaatg gccgcgactc gctggtgaat   1560
ccaggaccag ctatgccagt cacaaggac gatgaagaaa aattttttcc tatgcacggc    1620
aatctaatat ttggcaaaga agggacaacg gcaagtaacg cagaattaga taatgtaatg   1680
attacggatg aagaagagat tcgtaccacc aatcctgtgg caacagagca gtatggaact   1740
gtggcaaata acttgcagag ctcaaataca gctcccacga ctagaactgt caatgatcag   1800
ggggccttac ctggcatggt gtggcaagat cgtgacgtgt accttcaagg acctatctgg   1860
gcaaagattc ctcacacgga tggacacttt catccttctc ctctgatggg aggctttgga   1920
ctgaaacatc cgcctcctca aatcatgatc aaaaatactc cggtaccggc aaatcctccg   1980
acgactttca gccggccaa gtttgcttca tttatcactc agtactccac tggacaggtc   2040
agcgtggaaa ttgagtggga gctacagaaa gaaaacagca acgttggaa tccagagatt    2100 cagtacactt ccaactacaa caagtctgtt aatgtggact ttactgtgga cactaatggc   2160
gtgtattcag agcctcgccc cattggcacc cgttacctca cccgtcccct gtaa         2214
```

<210> SEQ ID NO 21
<211> LENGTH: 2214
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 21

```
atggctgctg acggttatct tccagattgg ctcgaggaca acctttctga aggcattcga     60
gagtggtggg cgctgcaacc tggagccccg aaacccaaag ccaaccagca aaagcaggac    120
gacggccggg gtctggtgct tcctggctac aagtaccctcg gaccccttcaa cggactcgac    180
```

```
aaggggggagc  ccgtcaacgc  ggcggatgca  gcggccctcg  agcacgacaa  ggcctacgac      240
cagcagctca  aagcgggtga  caatccgtac  ctgcggtata  accacgccga  cgccgagttt      300
caggagcgtc  ttcaagaaga  tacgtctttt  gggggcaacc  tcgggcgagc  agtcttccag      360
gccaagaagc  gggttctcga  acctctcggt  ctggttgagg  aaggcgctaa  gacggctcct      420
ggaaagaaac  gtccggtaga  gcagtcgcca  caagagccag  actcctcctc  gggcatcggc      480
aagacaggcc  agcagcccgc  gaaaaagaga  ctcaactttg  gcagactggc  gactcagag      540 tcagtgcccg  accctcaacc  aatcggagaa  ccccccgcag  gcccctctgg  tctgggaact      600
ggtacgatgg  cttcaggcag  tggcgcacca  atggcagaca  taacgaagg  cgccgatgga       660 gtgggtaatt  cctcaggaaa  ttggcattgc  gattcccaat  ggctgggcga  cagagtcatc      720
accaccagca  ccagaacctg  ggccttgccc  acctacaata  accacctcta  caagcaaatc      780
tccagtgctt  caacgggggc  cagcaacgac  aaccactact  tcggctacag  cacccctgg       840 gggtattttg  actttaacag  attccactgc  cacttctcac  cacgtgactg  gcagcgactc      900
attaacaaca  actggggatt  ccggcccaag  agactcaact  tcaagctctt  caacatccaa      960
gtcaaggagg  tcacgacgaa  tgatggcgtc  acgaccattg  ccaataacct  caccagcacc    1020
atccaggtgt  ttacggactc  ggagtaccag  ttgccgtacg  tcctcggctc  tgcgcaccag    1080
ggctgcctcc  ctccgttccc  ggcggacgtg  ttcatgattc  cgcaatacgg  ctacctgacg    1140
ctcaacaatg  gcagccaggc  agtgggacgg  tcatcctttt  actgcctgga  atatttccca    1200
tcgcagatgc  tgagaacggg  caataacttt  accttcagct  acaccttcga  ggacgtgcct    1260
ttccacagca  gctacgctca  cagccagagt  ttggatcgct  tgatgaatcc  tcttattgat    1320
cagtatctgt  actacctgaa  cagaacgcaa  ggaacaacct  ctggaacaac  caaccaatca    1380
cggctgcttt  ttagccaggc  tgggcctcag  tctatgtctt  gcaggccag   aaattggcta    1440 cctgggccct  gctaccggca  acagagactt  tcaaagactg  ctaacgacaa  caacaacagt    1500
aactttcctt  ggacagcggc  cagcaaatat  catctcaatg  gccgcgactc  gctggtgaat    1560
ccaggaccag  ctatggccag  tcacaaggac  gatgaagaaa  aattttttcc  tatgcacggc    1620
aatctaatat  ttggcaaaga  agggacaacg  gcaagtaacg  cagaattaga  taatgtaatg    1680
attacggatg  aagaagagat  tcgtaccacc  aatcctgtgg  caacagagca  gtatggaact    1740
gtggcaaata  acttgcagag  ctcaaataca  gctcccacga  ctagaactgt  caatgatcag    1800
ggggccttac  ctggcatggt  gtggcaagat  cgtgacgtgt  accttcaagg  acctatctgg    1860
gcaaagattc  ctcacacgga  tggacacttt  catccttctc  ctctgatggg  aggctttgga    1920
ctgaaacatc  cgcctcctca  aatcatgatc  aaaaatactc  cggtaccggc  aaatcctccg    1980
acgactttca  gcccggccaa  gtttgcttca  tttatcactc  agtactccac  tggacaggtc    2040
agcgtggaaa  ttgagtggga  gctacagaaa  gaaaacagca  acgttggaa   tccagagatt    2100 cagtacactt  ccaactacaa  caagtctgtt  aatgtggact  ttactgtaga  cactaatggt    2160
gtttatagtg  aacctcgccc  cattggcacc  cgttaccttta cccgtcccct  gtaa          2214
```

<210> SEQ ID NO 22
<211> LENGTH: 2214
<212> TYPE: DNA
<213> ORGANISM: Artificial Sequence
<220> FEATURE:
<221> NAME/KEY: source
<223> OTHER INFORMATION: /note="Description of Artificial Sequence:
   Synthetic polynucleotide"

<400> SEQUENCE: 22

```
atggctgctg acggttatct tccagattgg ctcgaggaca ctctctctga aggaataaga    60
cagtggtgga agctcaaacc tggcccacca ccaccaaagc ccgcagagcg gcataaggac   120
gacagcaggg gtcttgtgct tcctgggtac aagtacctcg gacccttcaa cggactcgac   180
aagggggagc ccgtcaacgc ggcggatgca gcggccctcg agcacgacaa ggcctacgac   240
cagcagctca aagcgggtga caatccgtac ctgcggtata ccacgccga cgcggagttt   300
caggagcgcc ttaaagaaga tacgtctttt gggggcaacc tcggacgagc agtcttccag   360
gccaagaaga gggttctcga accttttggt ctggttgagg aagcggctaa gacggctcct   420
ggaaagaaga ggcctgtaga tcagtctcct caggaaccgg actcatcatc tggtgttggc   480
aaatcgggca acagcctgc cagaaaaaga ctaaatttcg gtcagactgg cgactcagag   540
tcagtcccag accctcaacc tctcggagaa ccaccagcag cccccacaag tttgggatct   600
aatacaatgg cttcaggcgg tggcgcacca atggcagaca taacgaggg tgccgacgga   660
gtgggtaatg cctcaggaaa ttggcattgc gattccacat ggctgggcga ccgagtcatc   720
accaccagca cccgcacctg ggccctgccc acctacaaca accatctcta caagcaaatc   780
tccagtgctt caacggggc cagcaacgac aaccactact tcggctacag cacccccctgg   840
gggtatttg acttaacag attccactgc cacttttcac cacgtgactg cagcgactc   900
atcaacaaca ctggggatt ccggcccaag aaactcagct tcaagctctt caacatccag   960
gtcaaggagg tcacgcagaa tgaaggcacc aagaccatcg ccaataacct caccagcacc  1020
atccaggtgt ttacggactc ggagtaccag ctgccgtacg ttctcggctc tgcgcaccag  1080
ggctgcctcc ctccgttccc ggcggacgtg ttcatgattc cgcaatacgg ctacctgacg  1140
ctcaacaatg cagccaagc cgtgggacgt tcatcctttt actgcctgga atatttccca  1200
tcgcagatgc tgagaaccgg caacaacttc cagtttactt acaccttcga ggatgtacct  1260
tttcacagca gctacgctca cagccagagt ttggatcgct tgatgaatcc tcttattgat  1320
cagtatctgt actacctgaa cagaacgcaa ggaacaacct ctggaacaac caaccaatca  1380
cggctgcttt ttagccaggc tgggcctcag tctatgtctt gcaggccag aaattggcta  1440
cctgggccct gctaccggca acagagactt tcaaagactg ctaacgacaa caacaacagt  1500
aactttcctt ggacagcggc cagcaaatat catctcaatg ccgcgactc gctggtgaat  1560
ccaggaccag ctatgccag tcacaaggac gatgaagaaa aattttttccc tatgcacggc  1620
aatctaatat ttggcaaaga agggacaacg gcaagtaacg cagaattaga taatgtaatg  1680
attacgatg aagaagagat tcgtaccacc aatcctgtgg caacagagca gtatggaact  1740
gtggcaaata acttgcagag ctcaaataca gctcccacga ctagaactgt caatgatcag  1800
ggggccttac ctgcatggt gtggcaagat cgtgacgtgt accttcaagg acctatctgg  1860
gcaaagattc ctcacacgga tggacacttt catccttctc ctctgatggg agggtttgga  1920
atgaaacacc cgcctcctca gatcctcatc aaaaacacac ctgtacctgc ggatcctcca  1980
acggccttca acaaggacaa gctgaactct ttcatcaccc agtattctac tggccaagtc  2040
agcgtggaaa ttgaatggga gctgcagaag gaaaacagca gcgctggaa ccccgagatc  2100
cagtacacct ccaactacta caaatctaca agtgtggact tgctgttaa tacagaaggc  2160
gtgtactctg aaccccgccc cattggcacc cgttacctca cccgtaatct gtaa         2214
```

<210> SEQ ID NO 23
<211> LENGTH: 2211
<212> TYPE: DNA

<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 23

| | | | | | |
|---|---|---|---|---|---|
| atggctgccg | atggttatct | tccagattgg | ctcgaggaca | ctctctctga | aggaataaga | 60 |
| cagtggtgga | agctcaaacc | tggcccacca | ccaccaaagc | ccgcagagcg | gcataaggac | 120 |
| gacagcaggg | gtcttgtgct | tcctgggtac | aagtacctcg | gacccttcaa | cggactcgac | 180 |
| aagggagagc | cggtcaacga | ggcagacgcc | gcggccctcg | agcacgacaa | ggcctacgac | 240 |
| cagcagctca | aagcgggtga | caatccgtac | ctcaagtaca | accacgccga | cgccgagttc | 300 |
| caggagcggc | tcaaagaaga | tacgtctttt | gggggcaacc | tcgggcgagc | agtcttccag | 360 |
| gcgaaaaaga | gggttcttga | acctctgggc | ctggttgagg | aagcggctaa | gacggctcct | 420 |
| ggaaagaaga | ggcctgtaga | gcactctcct | gtggagccag | actcctcctc | gggaaccgga | 480 |
| aaggcgggcc | agcagcctgc | aagaaaaaga | ttgaattttg | gtcagactgg | agacgcagac | 540 |
| tcagtcccag | accctcaacc | tctcggagaa | ccaccagcag | cccccacaag | tttgggatct | 600 |
| aatacaatgg | cttcaggcgg | tggcgcacca | atggcagaca | taacgaagg | cgccgacgga | 660 |
| gtgggtagtt | cctcaggaaa | ttggcattgc | gattccacat | ggctgggcga | cagagtcatc | 720 |
| accaccagca | cccgcacctg | ggccctgccc | acttacaaca | accatctcta | caagcaaatc | 780 |
| tccagtgctt | caacgggggc | cagcaacgac | aaccactact | cggctacag | cacccccctgg | 840 |
| gggtattttg | atttcaacag | attccactgc | catttctcac | cacgtgactg | gcagcgactc | 900 |
| atcaacaaca | actgggggtt | ccggcccaag | cgactcaact | tcaagctctt | caacatccag | 960 |
| gtcaaggagg | tcacgcagaa | tgaaggcacc | aagaccatcg | ccaataacct | taccagcacg | 1020 |
| attcaggtct | ttacggactc | ggaataccag | ctcccgtacg | tcctcggctc | tgcccaccag | 1080 |
| ggctgcctgc | ctccgttccc | ggcggacgtg | ttcatgattc | cccagtacgg | ctacctaaca | 1140 |
| ctcaacaacg | gtagtcaggc | gatgggtcgc | tcgtccttct | actgcctgga | gtactttccg | 1200 |
| tcgcagatgc | tgcggacggg | gaacaacttc | acgttcagct | acaccttcga | ggacgtgccc | 1260 |
| ttccacagca | gctacgcgca | cagccagagt | ctggaccggc | tgatgaatcc | tctgattgac | 1320 |
| cagtacctgt | actacttgtc | tcggactcag | tccacgggag | gtaccgcagg | aactcagcag | 1380 |
| ttgctatttt | ctcaggccgg | gcctaataac | atgtcggctc | aggccagaaa | ttggctacct | 1440 |
| gggcccctgct | accggcaaca | gagactttca | aagactgcta | acgacaacaa | caacagtaac | 1500 |
| tttccttgga | cagcggccag | caaatatcat | ctcaatggcc | gcgactcgct | ggtgaatcca | 1560 |
| ggaccagcta | tggccagtca | caaggacgat | gaagaaaaat | tttttcctat | gcacggcaat | 1620 |
| ctaatatttg | gcaaagaagg | gacaacggca | agtaacgcag | aattagataa | tgtaatgatt | 1680 |
| acggatgaag | aagagattcg | taccaccaat | cctgtggcaa | cagagcagta | tggaactgtg | 1740 |
| gcaaataact | tgcagagctc | aaatacagct | cccacgacta | gaactgtcaa | tgatcagggg | 1800 |
| gccttacctg | gcatggtgtg | gcaagatcgt | gacgtgtacc | ttcaaggacc | tatctgggca | 1860 |
| aagattcctc | acacggatgg | acactttcat | ccctcgccgc | tgatgggagg | ctttggactg | 1920 |
| aaacacccgc | ctcctcagat | cctcatcaaa | aacacacctg | tacctgcgga | tcctccgacc | 1980 |
| accttcaacc | agtcaaagct | gaactctttc | atcacccagt | actccactgg | acaggtcagc | 2040 |
| gtggagatcg | agtgggagct | gcagaaggaa | aacagcaaac | gctggaatcc | cgaaattcag | 2100 |
| tacacttcca | actacaacaa | gtctgttaat | gtggactttta | ctgtggacac | taatggcgtg | 2160 |

```
tattcagagc ctcgccccat tggcacccgt tacctcaccc gtaatctgta a         2211
```

<210> SEQ ID NO 24
<211> LENGTH: 2214
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 24

```
atggctgccg atggttatct tccagattgg ctcgaggaca ctctctctga aggaataaga   60
cagtggtgga agctcaaacc tggcccacca ccaccaaagc ccgcagagcg gcataaggac  120
gacagcaggg gtcttgtgct tcctggctac aagtacctcg gacccttcaa cggactcgac  180
aagggggagc ccgtcaacgc ggcggatgca gcggccctcg agcacgacaa ggcctacgac  240
cagcagctca agcgggtgac aatccgtac ctgcggtata accacgccga cgccgagttt  300
caggagcgtc tgcaagaaga tacgtctttt gggggcaacc tcgggcgagc agtcttccag  360
gccaaaaaga ggcttcttga acctcttggt ctggttgagg aagcggctaa gacggctcct  420
ggaaagaaga ggcctgtaga gcactctcct gtggagccag actcctcctc gggaaccgga  480
aaggcgggcc agcagcctgc aagaaaaaga ttgaattttg gtcagactgg agacgcagac  540
tcagtcccag accctcaacc tctcggagaa ccaccagcag cccccacaag tttgggatct  600
aatacaatgg ctacaggcag tggcgcacca atggcagaca ataacgaggg tgccgatgga  660
gtgggtaatt cctcaggaaa ttggcattgc gattcccaat ggctgggcga cagagtcatc  720
accaccagca cccgaacatg gccttgccc acctataaca accacctcta caagcaaatc  780
tccagtgctt caacgggggc cagcaacgac aaccactact tcggctacag cacccccctgg  840
gggtactttg acttcaaccg cttccactgc cacttctccc cgcgagactg gcagcggctc  900
atcaacaaca actgggggtt ccggcccaag cgactcaact tcaagctctt caacatccaa  960
gtcaaggagg tcacgacgaa tgatggcgtc acgaccatcg ctaataacct taccagcacg 1020
gttcaagtgt ttacggactc ggagtatcag ctcccgtacg tcctcggctc tgcgcaccag 1080
ggctgcctcc ctcgttccc ggcggacgtc ttcatggtcc ctcagtatgg atacctcacc 1140
ctgaacaacg gaagtcaagc ggtgggacgc tcatcctttt actgcctgga gtacttccct 1200
tcgcagatgc taaggactgg aaataacttc caattcagct ataccttcga ggatgtacct 1260
tttcacagca gctacgctca cagccagagt ttggatcgct tgatgaatcc tcttattgat 1320
cagtatctgt actacctgaa cagaacgcaa ggaacaacct ctggaacaac caaccaatca 1380
cggctgcttt ttagccaggc tgggcctcag tctatgtctt tgcaggccag aaattggcta 1440
cctgggccct gctaccggca acagagactt tcaaagactg ctaacgacaa caacaacagt 1500
aactttcctt ggacagcggc cagcaaatat catctcaatg gccgcgactc gctggtgaat 1560
ccaggaccag ctatggccag tcacaaggac gatgaagaaa atttttccc tatgcacggc 1620
aatctaatat ttggcaaaga agggacaacg gcaagtaacg cagaattaga taatgtaatg 1680
attacggatg aagaagagat tcgtaccacc aatcctgtgg caacagagca gtatggaact 1740
gtggcaaata acttgcagag ctcaaataca gctcccacga ctagaactgt caatgatcag 1800
ggggccttac ctggcatggt gtggcaagat cgtgacgtgt accttcaagg acctatctgg 1860
gcaaagattc ctcacacgga tggacacttt catccttctc ctctgatggg aggctttgga 1920
```

| | |
|---|---:|
| ctgaaacacc ctcctccaca gattctcatc aagaacaccc cggtacctgc gaatcctccg | 1980 |
| accaccttca accagtcaaa gctgaactct ttcatcaccc agtattctac tggccaagtc | 2040 |
| agcgtggaga tcgagtggga gctgcagaag gaaaacagca agcgctggaa ccccgagatc | 2100 |
| cagtacacct ccaactacta caaatctaca agtgtggact tgctgttaa tacagaaggc | 2160 |
| gtgtactctg aaccccgccc cattggcacc cgttacctca cccgtaatct gtaa | 2214 |

```
<210> SEQ ID NO 25
<211> LENGTH: 2214
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 25
```

| | |
|---|---:|
| atggctgccg atggttatct tccagattgg ctcgaggaca ctctctctga aggaataaga | 60 |
| cagtggtgga agctcaaacc tggcccacca ccaccaaagc ccgcagagcg gcataaggac | 120 |
| gacagcaggg gtcttgtgct tcctgggtac aagtacctcg gacccttcaa cggactcgac | 180 |
| aaggggggagc ccgtcaacgc ggcggatgca gcggccctcg agcacgacaa ggcctacgac | 240 |
| cagcagctca aagcgggtga caatccgtac ctgcggtata ccacgccga cgccgagttt | 300 |
| caggagcgtc tgcaagaaga tacgtctttt ggggcaacc tcgggcgagc agtcttccag | 360 |
| gccaagaaga gggttctcga accttttggt ctggttgagg aaggtgctaa gacggctcct | 420 |
| ggaaagaaac gtccggtaga gcactctcct gtggagccag actcctcctc gggaaccgga | 480 |
| aaggcgggcc agcagcctgc aagaaaaaga ttgaattttg gtcagactgg cgactcagag | 540 |
| tcagttccag accctcaacc tctcggagaa cctccagcag cgccctctgg tgtgggacct | 600 |
| aatacaatgg cttcaggcgg tggcgcacca atggcagaca taacgaagg cgccgacgga | 660 |
| gtgggtaatg cctcaggaaa ttggcattgc gattccacat ggctgggcga cagagtcatc | 720 |
| accaccagca cccgcacctg ggccttgccc acctacaata accacctcta caagcaaatc | 780 |
| tccagtgctt caacgggggc cagcaacgac aaccactact cggctacag cacccccctgg | 840 |
| gggtattttg acttcaacag attccactgc catttctcac cacgtgactg cagcgactc | 900 |
| atcaacaaca ttggggatt ccggcccaag agactcaact tcaagctctt caacatccaa | 960 |
| gtcaaggagg tcacgcagaa tgacggtacg acgacgattg ccaataacct taccagcacg | 1020 |
| gttcaagtgt ttacggactc ggagtatcag ctcccgtacg tgctcgggtc ggcgcaccaa | 1080 |
| ggctgtctcc cgccgtttcc agcggacgtc ttcatggtcc cgcagtacgg gtatttgacg | 1140 |
| ctgaacaacg gaagtcaagc ggtgggacgc tcatccttt actgcctgga gtacttccct | 1200 |
| tcgcagatgc taaggactgg aaataacttc caattcagct ataccttcga ggatgtacct | 1260 |
| tttcacagca gctacgctca agccagagt ttggatcgct tgatgaatcc tcttattgat | 1320 |
| cagtatctgt actacctgaa cagaacgcaa ggaacaacct ctggaacaac caaccaatca | 1380 |
| cggctgcttt ttagccaggc tgggcctcag tctatgtctt gcaggccag aaattggcta | 1440 |
| cctgggccct gctaccggca acagagactt caaagactg ctaacgacaa caacaacagt | 1500 |
| aactttcctt ggacagcggc cagcaaatat catctcaatg ccgcgactc gctggtgaat | 1560 |
| ccaggaccag ctatggccag tcacaaggac gatgaagaaa attttttccc tatgcacggc | 1620 |
| aatctaatat ttggcaaaga agggacaacg gcaagtaacg cagaattaga taatgtaatg | 1680 |
| attacggatg aagaagagat tcgtaccacc aatcctgtgg caacagagca gtatggaact | 1740 |

```
gtggcaaata acttgcagag ctcaaataca gctcccacga ctagaactgt caatgatcag    1800
ggggccttac ctggcatggt gtggcaagat cgtgacgtgt accttcaagg acctatctgg    1860
gcaaagattc ctcacacgga tggacacttt catccttctc ctctgatggg cggctttgga    1920
ctgaaacatc cgcctcctca aatcatgatc aaaaatactc cggtaccggc aaatcctccg    1980
acgactttca gcccggccaa gtttgcttca tttatcactc agtactccac gggacaggtc    2040
agcgtggaga tcgagtggga gctgcagaag gaaaacagca gcgctggaa ccccgagatc     2100 cagtacacct ccaactacta caaatctaca agtgtggact ttgctgttaa tacagaaggc    2160
gtgtactctg aaccccgccc cattggcacc cgttacctca cccgtaatct gtaa           2214
```

<210> SEQ ID NO 26
<211> LENGTH: 2214
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 26

```
atggctgccg atggttatct tccagattgg ctcgaggaca acctctctga gggcattcgc      60
gagtggtggg acttgaaacc tggagccccg aaacccaaag ccaaccagca aaagcaggac     120
gacggccggg gtctggtgct tcctggctac aagtaccctcg gacccttcaa cggactcgac    180 aaggggagc ccgtcaacgc ggcggatgca gcggccctcg agcacgacaa ggcctacgac     240
cagcagctgc aggcgggtga caatccgtac ctgcggtata accacgccga cgccgagttt    300
caggagcgtc tgcaagaaga tacgtctttt gggggcaacc tcgggcgagc agtcttccag    360
gccaaaaaga ggcttcttga acctcttggt ctggttgagg aagcggctaa gacggctcct    420
ggaaagaaga ggcctgtaga gcactctcct gtggagccag actcctcctc gggaaccgga    480
aaggcgggcc agcagcctgc aagaaaaaga ttgaatttg gtcagactgg agacgcagac    540
tcagtcccag accctcaacc aatcggagaa cctcccgcag cccctcagg tgtgggatct     600 cttacaatgg ctgcaggcgg tggcgcacca atggcagaca taacgagggg tgccgacgga    660
gtgggtaatt cctcgggaaa ttggcattgc gattccacat ggatgggcga cagagtcatc    720
accaccagca cccgaacctg ggccctgccc acctataaca accacctcta caagcaaatc    780
tccagtgctt caacggggc cagcaacgac aaccactact cggctacag caccccctgg    840 gggtatttg atttcaaccg cttccactgc cacttctcac cacgtgactg gcagcgactc    900
atcaacaaca actgggggatt ccggcccaag agactcaact tcaaactctt caacatccaa    960
gtcaaggagg tcacgacgaa tgatggcgtc acgaccatcg ctaataacct taccagcacg   1020
gttcaagtct ctctcggactc ggagtaccag ttgccgtacg tcctcggctc tgcgcaccag   1080
ggctgcctcc ctccgttccc ggcggacgtg ttcatgattc gcagtacgg ctacctaaca    1140 ctcaacaacg gtagtcaggc cgtgggacgc tcctccttct actgcctgga atatttccca    1200
tcgcagatgc tgagaacggg caataacttt accttcagct acaccttcga ggacgtgcct    1260
ttccacagca gctacgcgca cagccagagc ctggaccggc tgatgaaccc cctcatcgac    1320
cagtacctgt actacctgaa cagaacgcaa ggaacaacct ctggaacaac caccaatca    1380 cggctgcttt ttagccaggc tgggcctcag tctatgtctt tgcaggccag aaattggcta    1440
cctgggcccc gctaccggca acagagactt tcaaagactc taacgacaa caacaacagt    1500
```

-continued

```
aacttcctt ggacagcggc cagcaaatat catctcaatg gccgcgactc gctggtgaat    1560
ccaggaccag ctatggccag tcacaaggac gatgaagaaa aattttttcc tatgcacggc    1620
aatctaatat ttggcaaaga agggacaacg gcaagtaacg cagaattaga taatgtaatg    1680
attacggatg aagaagagat tcgtaccacc aatcctgtgg caacagagca gtatggaact    1740
gtggcaaata acttgcagag ctcaaataca gctcccacga ctagaactgt caatgatcag    1800
ggggccttac ctggcatggt gtggcaagat cgtgacgtgt accttcaagg acctatctgg    1860
gcaaagattc ctcacacgga tggacacttt catccttctc ctctgatggg aggctttgga    1920
ctgaaacatc cgcctcctca aatcatgatc aaaaatactc cggtaccggc aaatcctccg    1980
acgactttca gcccggccaa gtttgcttca tttatcactc agtactccac tggacaggtc    2040
agcgtggaaa ttgagtggga gctacagaaa gaaaacagca aacgttggaa tccagagatt    2100
cagtacactt ccaactacaa caagtctgtt aatgtggact ttactgtaga cactaatggt    2160
gtttatagtg aacctcgccc cattggcacc cgttaccta cccgtcccct gtaa         2214
```

<210> SEQ ID NO 27
<211> LENGTH: 743
<212> TYPE: PRT
<213> ORGANISM: Unknown
<220> FEATURE:
<221> NAME/KEY: source
<223> OTHER INFORMATION: /note="Description of Unknown: Parent AAV Capsid sequence"

<400> SEQUENCE: 27

```
Met Ser Leu Ile Ser Asp Ala Ile Pro Asp Trp Leu Glu Arg Leu Val
1               5                   10                  15

Lys Lys Gly Val Asn Ala Ala Asp Phe Tyr His Leu Glu Ser Gly
            20                  25                  30

Pro Pro Arg Pro Lys Ala Asn Gln Gln Thr Gln Glu Ser Leu Glu Lys
        35                  40                  45

Asp Asp Ser Arg Gly Leu Val Phe Pro Gly Tyr Asn Tyr Leu Gly Pro
    50                  55                  60

Phe Asn Gly Leu Asp Lys Gly Glu Pro Val Asn Glu Ala Asp Ala Ala
65                  70                  75                  80

Ala Leu Glu His Asp Lys Ala Tyr Asp Leu Glu Ile Lys Asp Gly His
                85                  90                  95

Asn Pro Tyr Phe Glu Tyr Asn Glu Ala Asp Arg Arg Phe Gln Glu Arg
            100                 105                 110

Leu Lys Asp Asp Thr Ser Phe Gly Gly Asn Leu Gly Lys Ala Ile Phe
        115                 120                 125

Gln Ala Lys Lys Arg Val Leu Glu Pro Phe Gly Leu Val Glu Asp Ser
    130                 135                 140

Lys Thr Ala Pro Thr Gly Asp Lys Arg Lys Gly Glu Asp Glu Pro Arg
145                 150                 155                 160

Leu Pro Asp Thr Pro Gln Thr Pro Lys Asn Lys Lys Pro Arg
                165                 170                 175

Lys Glu Arg Pro Ser Gly Gly Ala Glu Asp Pro Gly Glu Gly Thr Ser
            180                 185                 190

Ser Asn Ala Gly Ala Ala Ala Pro Ala Ser Ser Val Gly Ser Ser Ile
        195                 200                 205

Met Ala Glu Gly Gly Gly Pro Val Gly Asp Ala Gly Gln Gly Ala
    210                 215                 220

Asp Gly Val Gly Asn Ser Ser Gly Asn Trp His Cys Asp Ser Gln Trp
```

-continued

```
            225                 230                 235                 240
Leu Glu Asn Gly Val Val Thr Arg Thr Thr Arg Thr Trp Val Leu Pro
                        245                 250                 255

Ser Tyr Asn Asn His Leu Tyr Lys Arg Ile Gln Gly Pro Ser Gly Gly
                260                 265                 270

Asp Asn Asn Asn Lys Phe Phe Gly Phe Ser Thr Pro Trp Gly Tyr Phe
            275                 280                 285

Asp Tyr Asn Arg Phe His Cys His Phe Ser Pro Arg Asp Trp Gln Arg
            290                 295                 300

Leu Ile Asn Asn Asn Trp Gly Ile Arg Pro Lys Ala Met Arg Phe Arg
305                 310                 315                 320

Leu Phe Asn Ile Gln Val Lys Glu Val Thr Val Gln Asp Ser Asn Thr
                        325                 330                 335

Thr Ile Ala Asn Asn Leu Thr Ser Thr Val Gln Val Phe Ala Asp Lys
                340                 345                 350

Asp Tyr Gln Leu Pro Tyr Val Leu Gly Ser Ala Thr Glu Gly Thr Phe
            355                 360                 365

Pro Pro Phe Pro Ala Asp Ile Tyr Thr Ile Pro Gln Tyr Gly Tyr Cys
        370                 375                 380

Thr Leu Asn Tyr Asn Asn Glu Ala Val Asp Arg Ser Ala Phe Tyr Cys
385                 390                 395                 400

Leu Asp Tyr Phe Pro Ser Asp Met Leu Arg Thr Gly Asn Asn Phe Glu
                405                 410                 415

Phe Thr Tyr Thr Phe Glu Asp Val Pro Phe His Ser Met Phe Ala His
                420                 425                 430

Asn Gln Thr Leu Asp Arg Leu Met Asn Pro Leu Val Asp Gln Tyr Leu
            435                 440                 445

Trp Ala Phe Ser Ser Val Ser Gln Ala Gly Ser Ser Gly Arg Ala Leu
        450                 455                 460

His Tyr Ser Arg Ala Thr Lys Thr Asn Met Ala Ala Gln Tyr Arg Asn
465                 470                 475                 480

Trp Leu Pro Gly Pro Phe Phe Arg Asp Gln Gln Ile Phe Thr Gly Ala
                485                 490                 495

Ser Asn Ile Thr Lys Asn Asn Val Phe Ser Val Trp Glu Lys Gly Lys
            500                 505                 510

Gln Trp Glu Leu Asp Asn Arg Thr Asn Leu Met Gln Pro Gly Pro Ala
        515                 520                 525

Ala Ala Thr Thr Phe Ser Gly Glu Pro Asp Arg Gln Ala Met Gln Asn
    530                 535                 540

Thr Leu Ala Phe Ser Arg Thr Val Tyr Asp Gln Thr Ala Thr Thr
545                 550                 555                 560

Asp Arg Asn Gln Ile Leu Ile Thr Asn Glu Asp Glu Ile Arg Pro Thr
                565                 570                 575

Asn Ser Val Gly Ile Asp Ala Trp Gly Ala Val Pro Thr Asn Asn Gln
            580                 585                 590

Ser Ile Val Thr Pro Gly Thr Arg Ala Ala Val Asn Asn Gln Gly Ala
        595                 600                 605

Leu Pro Gly Met Val Trp Gln Asn Arg Asp Ile Tyr Leu Gln Gly Pro
    610                 615                 620

Ile Trp Ala Lys Ile Pro Asp Thr Asp Asn His Phe His Pro Ser Pro
625                 630                 635                 640

Leu Ile Gly Gly Phe Gly Cys Lys His Pro Pro Pro Gln Ile Phe Ile
                645                 650                 655
```

```
Lys Asn Thr Pro Val Pro Ala Asn Pro Ser Glu Thr Phe Gln Thr Ala
                660                 665                 670

Lys Val Ala Ser Phe Ile Asn Gln Tyr Ser Thr Gly Gln Cys Thr Val
            675                 680                 685

Glu Ile Phe Trp Glu Leu Lys Lys Glu Thr Ser Lys Arg Trp Asn Pro
        690                 695                 700

Glu Ile Gln Phe Thr Ser Asn Phe Gly Asn Ala Ala Asp Ile Gln Phe
705                 710                 715                 720

Ala Val Ser Asp Thr Gly Ser Tyr Ser Glu Pro Arg Pro Ile Gly Thr
                725                 730                 735

Arg Tyr Leu Thr Lys Pro Leu
                740

<210> SEQ ID NO 28
<211> LENGTH: 716
<212> TYPE: PRT
<213> ORGANISM: Unknown
<220> FEATURE:
<221> NAME/KEY: source
<223> OTHER INFORMATION: /note="Description of Unknown:
      Parent AAV Capsid sequence"

<400> SEQUENCE: 28

Met Ser Phe Val Asp His Pro Pro Asp Trp Leu Glu Glu Ile Gly Glu
1               5                   10                  15

Gly Leu Lys Glu Phe Leu Gly Leu Glu Pro Gly Pro Pro Lys Pro Lys
                20                  25                  30

Pro Asn Gln Gln Lys Gln Asp Asp Ala Arg Gly Leu Val Leu Pro Gly
                35                  40                  45

Tyr Asn Tyr Leu Gly Pro Gly Asn Gly Leu Asp Arg Gly Glu Pro Val
        50                  55                  60

Asn Arg Ala Asp Glu Val Ala Arg Glu His Asp Ile Ser Tyr Asn Glu
65                  70                  75                  80

Gln Leu Gln Ala Gly Asp Asn Pro Tyr Leu Lys Tyr Asn His Ala Asp
                85                  90                  95

Ala Glu Phe Gln Glu Lys Leu Ala Asp Asp Thr Ser Phe Gly Gly Asn
                100                 105                 110

Leu Gly Lys Ala Val Phe Gln Ala Lys Lys Arg Val Leu Glu Pro Phe
            115                 120                 125

Gly Leu Val Glu Glu Pro Val Lys Thr Ala Ala Lys Gly Glu Arg Ile
        130                 135                 140

Asp Asp His Tyr Pro Lys Lys Lys Ala Arg Ile Glu Glu Thr Glu
145                 150                 155                 160

Ala Gly Thr Ser Gly Ala Gln Gln Leu Gln Ile Pro Ala Gln Pro Ala
                165                 170                 175

Ser Ser Leu Gly Ala Asp Thr Met Ser Ala Gly Gly Gly Ser Pro Leu
                180                 185                 190

Gly Asp Asn Asn Gln Gly Ala Asp Gly Val Gly Asn Ala Ser Gly Asp
            195                 200                 205

Trp His Cys Asp Ser Thr Trp Met Gly Asp Arg Val Ile Thr Lys Ser
        210                 215                 220

Thr Arg Thr Trp Val Leu Pro Ser Tyr Asn Asn His Gln Tyr Leu Glu
225                 230                 235                 240

Ile His Ser Gly Ser Val Asp Gly Ser Asn Ala Asn Ala Tyr Phe Gly
                245                 250                 255
```

```
Tyr Ser Thr Pro Trp Gly Tyr Phe Asp Phe Asn Arg Phe His Ser His
            260                 265                 270

Trp Ser Pro Arg Asp Trp Gln Arg Leu Val Asn Asn Tyr Trp Gly Phe
        275                 280                 285

Arg Pro Arg Ser Leu Lys Val Lys Ile Phe Asn Ile Gln Val Lys Glu
    290                 295                 300

Val Thr Thr Gln Asp Gly Thr Thr Thr Ile Ala Asn Asn Leu Thr Ser
305                 310                 315                 320

Thr Val Gln Val Phe Thr Asp Asn Asp Tyr Gln Leu Pro Tyr Val Ile
                325                 330                 335

Gly Asn Gly Thr Glu Gly Cys Leu Pro Ala Phe Pro Pro Gln Val Phe
            340                 345                 350

Thr Leu Pro Gln Tyr Gly Tyr Ala Thr Leu Asn Arg Asn Asn Thr Asp
        355                 360                 365

Asp Pro Thr Glu Arg Ser Ser Phe Phe Cys Leu Glu Tyr Phe Pro Ser
    370                 375                 380

Lys Met Leu Arg Thr Gly Asn Asn Phe Glu Phe Thr Tyr Ser Phe Glu
385                 390                 395                 400

Glu Val Pro Phe His Cys Ser Phe Ala Pro Ser Gln Asn Leu Phe Lys
                405                 410                 415

Leu Ala Asn Pro Leu Val Asp Gln Tyr Leu Tyr Arg Phe Val Ser Thr
            420                 425                 430

Asp Thr Ser Gly Asn Leu Gln Phe Gln Lys Asn Leu Lys Ala Arg Tyr
        435                 440                 445

Ala Asn Thr Tyr Lys Asn Trp Phe Pro Gly Pro Met Cys Arg Thr Gln
    450                 455                 460

Gly Trp Tyr Thr Ser Ala Gly Thr Tyr Asn Asn Lys Gly Val Ala Asn
465                 470                 475                 480

Phe Asp Thr Ser Asn Lys Met Glu Leu Glu Gly Ala Ser Tyr Gln Val
                485                 490                 495

Asn Pro Gln Pro Asn Gly Met Thr Asn Thr Leu Gln Asp Ser Asn Lys
            500                 505                 510

Tyr Ala Leu Glu Asn Thr Met Ile Phe Asn Ala Gln Asn Ala Pro Pro
        515                 520                 525

Gly Thr Thr Ser Leu Tyr Gln Glu Asn Asn Leu Leu Ile Thr Ser Glu
530                 535                 540

Ser Glu Thr Gln Pro Val Asn Arg Leu Ala Tyr Asn Thr Gly Gly Gln
545                 550                 555                 560

Val Ser Asn Asn Asn Gln Asn Ser Asn Thr His Pro Thr Val Gly Val
                565                 570                 575

Tyr Asn His Gln Glu Val Leu Pro Gly Ser Val Trp Met Asp Arg Asp
            580                 585                 590

Val Tyr Leu Gln Gly Pro Ile Trp Ala Lys Ile Pro Glu Thr Gly Ala
        595                 600                 605

His Phe His Pro Ser Pro Ala Met Gly Gly Phe Gly Leu Lys His Pro
    610                 615                 620

Pro Pro Met Met Leu Ile Lys Asn Thr Pro Val Pro Ser Asn Val Ala
625                 630                 635                 640

Ala Phe Ser Asp Val Pro Val Lys Ser Phe Ile Thr Gln Tyr Ser Thr
                645                 650                 655

Gly Gln Val Thr Val Glu Ile Glu Trp Glu Leu Lys Lys Glu Asn Ser
            660                 665                 670

Lys Arg Trp Asn Pro Glu Ile Gln Tyr Thr Asn Asn Tyr Asn Asn Pro
```

```
                  675                 680                 685
Thr Phe Val Asp Phe Ala Pro Asp Thr Ser Gly Glu Tyr Arg Thr Thr
         690                 695                 700

Arg Ala Ile Gly Thr Arg Tyr Leu Thr Arg Pro Leu
705                 710                 715

<210> SEQ ID NO 29
<211> LENGTH: 724
<212> TYPE: PRT
<213> ORGANISM: Unknown
<220> FEATURE:
<221> NAME/KEY: source
<223> OTHER INFORMATION: /note="Description of Unknown:
      Parent AAV Capsid sequence"

<400> SEQUENCE: 29

Met Ser Phe Val Asp His Pro Pro Asp Trp Leu Glu Glu Val Gly Glu
1               5                   10                  15

Gly Leu Arg Glu Phe Leu Gly Leu Glu Ala Gly Pro Pro Lys Pro Lys
            20                  25                  30

Pro Asn Gln Gln His Gln Asp Gln Ala Arg Gly Leu Val Leu Pro Gly
        35                  40                  45

Tyr Asn Tyr Leu Gly Pro Gly Asn Gly Leu Asp Arg Gly Glu Pro Val
    50                  55                  60

Asn Arg Ala Asp Glu Val Ala Arg Glu His Asp Ile Ser Tyr Asn Glu
65                  70                  75                  80

Gln Leu Glu Ala Gly Asp Asn Pro Tyr Leu Lys Tyr Asn His Ala Asp
                85                  90                  95

Ala Glu Phe Gln Glu Lys Leu Ala Asp Asp Thr Ser Phe Gly Gly Asn
            100                 105                 110

Leu Gly Lys Ala Val Phe Gln Ala Lys Lys Arg Val Leu Glu Pro Phe
        115                 120                 125

Gly Leu Val Glu Glu Gly Ala Lys Thr Ala Pro Thr Gly Lys Arg Ile
    130                 135                 140

Asp Asp His Phe Pro Lys Arg Lys Lys Ala Arg Thr Glu Glu Asp Ser
145                 150                 155                 160

Lys Pro Ser Thr Ser Ser Asp Ala Glu Ala Gly Pro Ser Gly Ser Gln
                165                 170                 175

Gln Leu Gln Ile Pro Ala Gln Pro Ala Ser Ser Leu Gly Ala Asp Thr
            180                 185                 190

Met Ser Ala Gly Gly Gly Gly Pro Leu Gly Asp Asn Asn Gln Gly Ala
        195                 200                 205

Asp Gly Val Gly Asn Ala Ser Gly Asp Trp His Cys Asp Ser Thr Trp
    210                 215                 220

Met Gly Asp Arg Val Val Thr Lys Ser Thr Arg Thr Trp Val Leu Pro
225                 230                 235                 240

Ser Tyr Asn Asn His Gln Tyr Arg Glu Ile Lys Ser Gly Ser Val Asp
                245                 250                 255

Gly Ser Asn Ala Asn Ala Tyr Phe Gly Tyr Ser Thr Pro Trp Gly Tyr
            260                 265                 270

Phe Asp Phe Asn Arg Phe His Ser His Trp Ser Pro Arg Asp Trp Gln
        275                 280                 285

Arg Leu Ile Asn Asn Tyr Trp Gly Phe Arg Pro Arg Ser Leu Arg Val
    290                 295                 300

Lys Ile Phe Asn Ile Gln Val Lys Glu Val Thr Val Gln Asp Ser Thr
305                 310                 315                 320
```

```
Thr Thr Ile Ala Asn Asn Leu Thr Ser Thr Val Gln Val Phe Thr Asp
            325                 330                 335

Asp Asp Tyr Gln Leu Pro Tyr Val Val Gly Asn Gly Thr Glu Gly Cys
        340                 345                 350

Leu Pro Ala Phe Pro Pro Gln Val Phe Thr Leu Pro Gln Tyr Gly Tyr
            355                 360                 365

Ala Thr Leu Asn Arg Asp Asn Thr Glu Asn Pro Thr Glu Arg Ser Ser
    370                 375                 380

Phe Phe Cys Leu Glu Tyr Phe Pro Ser Lys Met Leu Arg Thr Gly Asn
385                 390                 395                 400

Asn Phe Glu Phe Thr Tyr Asn Phe Glu Glu Val Pro Phe His Ser Ser
                405                 410                 415

Phe Ala Pro Ser Gln Asn Leu Phe Lys Leu Ala Asn Pro Leu Val Asp
            420                 425                 430

Gln Tyr Leu Tyr Arg Phe Val Ser Thr Asn Asn Thr Gly Gly Val Gln
        435                 440                 445

Phe Asn Lys Asn Leu Ala Gly Arg Tyr Ala Asn Thr Tyr Lys Asn Trp
450                 455                 460

Phe Pro Gly Pro Met Gly Arg Thr Gln Gly Trp Asn Leu Gly Ser Gly
465                 470                 475                 480

Val Asn Arg Ala Ser Val Ser Ala Phe Ala Thr Thr Asn Arg Met Glu
                485                 490                 495

Leu Glu Gly Ala Ser Tyr Gln Val Pro Pro Gln Pro Asn Gly Met Thr
            500                 505                 510

Asn Asn Leu Gln Gly Ser Asn Thr Tyr Ala Leu Glu Asn Thr Met Ile
        515                 520                 525

Phe Asn Ser Gln Pro Ala Asn Pro Gly Thr Thr Ala Thr Tyr Leu Glu
    530                 535                 540

Gly Asn Met Leu Ile Thr Ser Glu Ser Glu Thr Gln Pro Val Asn Arg
545                 550                 555                 560

Val Ala Tyr Asn Val Gly Gly Gln Met Ala Thr Asn Asn Gln Ser Ser
                565                 570                 575

Thr Thr Ala Pro Ala Thr Gly Thr Tyr Asn Leu Gln Glu Ile Val Pro
            580                 585                 590

Gly Ser Val Trp Met Glu Arg Asp Val Tyr Leu Gln Gly Pro Ile Trp
        595                 600                 605

Ala Lys Ile Pro Glu Thr Gly Ala His Phe His Pro Ser Pro Ala Met
    610                 615                 620

Gly Gly Phe Gly Leu Lys His Pro Pro Met Met Leu Ile Lys Asn
625                 630                 635                 640

Thr Pro Val Pro Gly Asn Ile Thr Ser Phe Ser Asp Val Pro Val Ser
                645                 650                 655

Ser Phe Ile Thr Gln Tyr Ser Thr Gly Gln Val Thr Val Glu Met Glu
            660                 665                 670

Trp Glu Leu Lys Lys Glu Asn Ser Lys Arg Trp Asn Pro Glu Ile Gln
        675                 680                 685

Tyr Thr Asn Asn Tyr Asn Asp Pro Gln Phe Val Asp Phe Ala Pro Asp
    690                 695                 700

Ser Thr Gly Glu Tyr Arg Thr Thr Arg Pro Ile Gly Thr Arg Tyr Leu
705                 710                 715                 720

Thr Arg Pro Leu
```

<210> SEQ ID NO 30
<211> LENGTH: 726
<212> TYPE: PRT
<213> ORGANISM: Unknown
<220> FEATURE:
<221> NAME/KEY: source
<223> OTHER INFORMATION: /note="Description of Unknown: Parent AAV Capsid sequence"

<400> SEQUENCE: 30

```
Met Ser Phe Val Asp His Pro Pro Asp Trp Leu Glu Glu Val Gly Glu
1               5                   10                  15

Gly Leu Arg Glu Phe Leu Gly Leu Glu Ala Gly Pro Pro Lys Pro Lys
            20                  25                  30

Pro Asn Gln Gln His Gln Asp Gln Ala Arg Gly Leu Val Leu Pro Gly
        35                  40                  45

Tyr Asn Tyr Leu Gly Pro Gly Asn Gly Leu Asp Arg Gly Glu Pro Val
    50                  55                  60

Asn Arg Ala Asp Glu Val Ala Arg Glu His Asp Ile Ser Tyr Asn Glu
65                  70                  75                  80

Gln Leu Glu Ala Gly Asp Asn Pro Tyr Leu Lys Tyr Asn His Ala Asp
                85                  90                  95

Ala Glu Phe Gln Glu Lys Leu Ala Asp Asp Thr Ser Phe Gly Gly Asn
            100                 105                 110

Leu Gly Lys Ala Val Phe Gln Ala Lys Lys Arg Val Leu Glu Pro Phe
        115                 120                 125

Gly Leu Val Glu Glu Gly Ala Lys Thr Ala Pro Thr Gly Lys Arg Ile
    130                 135                 140

Asp Asp His Phe Pro Lys Arg Lys Lys Ala Arg Thr Glu Glu Asp Ser
145                 150                 155                 160

Lys Pro Ser Thr Ser Ser Asp Ala Glu Ala Gly Pro Ser Gly Ser Gln
                165                 170                 175

Gln Leu Gln Ile Pro Ala Gln Pro Ala Ser Ser Leu Gly Ala Asp Thr
            180                 185                 190

Met Ser Ala Gly Gly Gly Gly Pro Leu Gly Asp Asn Asn Gln Gly Ala
        195                 200                 205

Asp Gly Val Gly Asn Ala Ser Gly Asp Trp His Cys Asp Ser Thr Trp
    210                 215                 220

Met Gly Asp Arg Val Val Thr Lys Ser Thr Arg Thr Trp Val Leu Pro
225                 230                 235                 240

Ser Tyr Asn Asn His Gln Tyr Arg Glu Ile Lys Ser Gly Ser Val Asp
                245                 250                 255

Gly Ser Asn Ala Asn Ala Tyr Phe Gly Tyr Ser Thr Pro Trp Gly Tyr
            260                 265                 270

Phe Asp Phe Asn Arg Phe His Ser His Trp Ser Pro Arg Asp Trp Gln
        275                 280                 285

Arg Leu Ile Asn Asn Tyr Trp Gly Phe Arg Pro Arg Ser Leu Arg Val
    290                 295                 300

Lys Ile Phe Asn Ile Gln Val Lys Glu Val Thr Val Gln Asp Ser Thr
305                 310                 315                 320

Thr Thr Ile Ala Asn Asn Leu Thr Ser Thr Val Gln Val Phe Thr Asp
                325                 330                 335

Asp Asp Tyr Gln Leu Pro Tyr Val Val Gly Asn Gly Thr Glu Gly Cys
            340                 345                 350

Leu Pro Ala Phe Pro Pro Gln Val Phe Thr Leu Pro Gln Tyr Gly Tyr
        355                 360                 365
```

Ala Thr Leu Asn Arg Asp Asn Gly Asp Asn Pro Thr Glu Arg Ser Ser
        370                 375                 380

Phe Phe Cys Leu Glu Tyr Phe Pro Ser Lys Met Leu Arg Thr Gly Asn
385                 390                 395                 400

Asn Phe Glu Phe Thr Tyr Ser Phe Glu Glu Val Pro Phe His Cys Ser
                405                 410                 415

Phe Ala Pro Ser Gln Asn Leu Phe Lys Leu Ala Asn Pro Leu Val Asp
            420                 425                 430

Gln Tyr Leu Tyr Arg Phe Val Ser Thr Ser Ala Thr Gly Ala Ile Gln
        435                 440                 445

Phe Gln Lys Asn Leu Ala Gly Arg Tyr Ala Asn Thr Tyr Lys Asn Trp
450                 455                 460

Phe Pro Gly Pro Met Gly Arg Thr Gln Gly Trp Asn Thr Ser Ser Gly
465                 470                 475                 480

Ser Ser Thr Asn Arg Val Ser Val Asn Asn Phe Ser Val Ser Asn Arg
                485                 490                 495

Met Asn Leu Glu Gly Ala Ser Tyr Gln Val Asn Pro Gln Pro Asn Gly
            500                 505                 510

Met Thr Asn Thr Leu Gln Gly Ser Asn Arg Tyr Ala Leu Glu Asn Thr
        515                 520                 525

Met Ile Phe Asn Ala Gln Asn Ala Thr Pro Gly Thr Thr Ser Val Tyr
530                 535                 540

Pro Glu Asp Asn Leu Leu Leu Thr Ser Glu Ser Glu Thr Gln Pro Val
545                 550                 555                 560

Asn Arg Val Ala Tyr Asn Thr Gly Gly Gln Met Ala Thr Asn Ala Gln
                565                 570                 575

Asn Ala Thr Thr Ala Pro Thr Val Gly Thr Tyr Asn Leu Gln Glu Val
            580                 585                 590

Leu Pro Gly Ser Val Trp Met Glu Arg Asp Val Tyr Leu Gln Gly Pro
        595                 600                 605

Ile Trp Ala Lys Ile Pro Glu Thr Gly Ala His Phe His Pro Ser Pro
610                 615                 620

Ala Met Gly Gly Phe Gly Leu Lys His Pro Pro Met Met Leu Ile
625                 630                 635                 640

Lys Asn Thr Pro Val Pro Gly Asn Ile Thr Ser Phe Ser Asp Val Pro
                645                 650                 655

Val Ser Ser Phe Ile Thr Gln Tyr Ser Thr Gly Gln Val Thr Val Glu
            660                 665                 670

Met Glu Trp Glu Leu Lys Lys Glu Asn Ser Lys Arg Trp Asn Pro Glu
        675                 680                 685

Ile Gln Tyr Thr Asn Asn Tyr Asn Asp Pro Gln Phe Val Asp Phe Ala
690                 695                 700

Pro Asp Gly Ser Gly Glu Tyr Arg Thr Thr Arg Ala Ile Gly Thr Arg
705                 710                 715                 720

Tyr Leu Thr Arg Pro Leu
                725

<210> SEQ ID NO 31
<211> LENGTH: 713
<212> TYPE: PRT
<213> ORGANISM: Unknown
<220> FEATURE:
<221> NAME/KEY: source
<223> OTHER INFORMATION: /note="Description of Unknown:
      Parent AAV Capsid sequence"

<400> SEQUENCE: 31

| | | | | | | | | | | | | | | |
|---|---|---|---|---|---|---|---|---|---|---|---|---|---|---|
|Met|Ser|Phe|Phe|Asp|Trp|Leu|Gly|Lys|Gln|Tyr|Ala|Gln|Gly|Ala|Ala|
|1| | | |5| | | | |10| | | | |15| |

Glu Phe Trp Asp Leu Lys Ser Gly Pro Pro Ala Pro Lys Lys Ala Arg
            20                  25                  30

Lys Asp Gly Ser Ala Gly Phe Asn Phe Pro Gly His Lys Tyr Leu Gly
        35                  40                  45

Pro Gly Asn Ser Leu Asp Arg Gly Asp Pro Val Asp Ala Asp Asp Ala
50                  55                  60

Ala Ala Gln Lys His Asp Gln Ser Tyr Gln Glu Gln Leu Glu Ala Gly
65                  70                  75                  80

Asp Asn Pro Tyr Leu Lys Tyr Asn His Ala Asp Arg Glu Phe Gln Glu
                85                  90                  95

Ala Leu Lys Asp Asp Thr Ser Phe Glu Gly Asn Leu Ala Arg Gly Leu
            100                 105                 110

Phe Glu Ala Lys Lys Leu Val Ala Glu Pro Leu Gly Leu Val Glu Pro
            115                 120                 125

Glu Leu Ala Pro Pro Ser Gly Arg Lys Arg Pro Val Gln Ser Ser Gln
130                 135                 140

Glu Ser Gly Tyr Ser Ser Gln Asp Lys Arg Pro Asn Leu Asp Val
145                 150                 155                 160

Asp Glu Glu Asp Arg Glu Phe Ala Ala Ala Ala Glu Thr Glu Thr
                165                 170                 175

Gly Ser Ala Pro Pro Thr Gly Asn Leu Gly Pro Gly Thr Met Ala Gly
            180                 185                 190

Gly Gly Ser Ala Pro Ile Asp Asp Gly Ser Tyr Gly Ala Asp Gly Val
        195                 200                 205

Gly Asn Ala Ser Gly Asp Trp His Cys Asp Ser Thr Trp Leu Asp Asn
210                 215                 220

Cys Val Ile Thr Arg Thr Thr Arg Thr Trp Asn Leu Pro Thr Tyr Asn
225                 230                 235                 240

Asn His Ile Tyr Lys Arg Leu Asn Gly Thr Thr Ser Gly Asp Gln Ser
                245                 250                 255

Tyr Phe Gly Phe Ser Thr Pro Trp Gly Tyr Phe Asp Phe Asn Arg Phe
            260                 265                 270

His Cys His Phe Ser Pro Arg Asp Trp Gln Arg Leu Ile Asn Asn Asn
        275                 280                 285

Trp Gly Leu Arg Pro Lys Ser Leu Arg Phe Lys Ile Phe Asn Ile Gln
290                 295                 300

Val Lys Glu Val Thr Thr Gln Asp Ser Thr Lys Ile Ile Ser Asn Asn
305                 310                 315                 320

Leu Thr Ser Thr Val Gln Val Phe Ala Asp Thr Glu Tyr Gln Leu Pro
                325                 330                 335

Tyr Val Ile Gly Ser Ala His Glu Gly Cys Leu Pro Pro Phe Pro Ala
            340                 345                 350

Asp Val Phe Met Leu Pro Gln Tyr Gly Tyr Cys Thr Arg Gln Asp Gly
        355                 360                 365

Asn Ser Asn Asn Pro Thr Pro Arg Ser Ala Phe Tyr Cys Leu Glu Tyr
370                 375                 380

Phe Pro Ser Lys Met Leu Arg Thr Gly Asn Ser Phe Glu Phe Thr Tyr
385                 390                 395                 400

Asn Phe Glu Lys Val Pro Phe His Ser Met Trp Ala His Asn Gln Ser

```
            405                 410                 415
Leu Asp Arg Leu Met Asn Pro Leu Ile Asp Gln Tyr Leu Tyr Tyr Leu
            420                 425                 430

Asp Val Thr Ser Ser Thr Gly Phe Thr Tyr Gln Lys Gly Val His Thr
            435                 440                 445

Asn Leu Pro Glu Gln Glu Arg Asn Trp Leu Pro Gly Pro Gly Ile Arg
    450                 455                 460

Asn Gln Ala Trp Phe Asn Ser Ala Thr Gly Asn Asn Pro Leu Thr Gly
465                 470                 475                 480

Thr Trp Gln Tyr Ser Asn Lys Tyr Val Leu Glu Asn Arg Ala Ser Lys
                485                 490                 495

Ile Ala Pro Gly Pro Ala Met Gly Ile Glu Ser Thr Lys Phe Asp Gly
            500                 505                 510

Asn Gly Ile Ile Phe Ser Lys Glu Tyr Ile Thr Asn Val Asn Thr Ala
            515                 520                 525

Asn Pro Asn Gln Val Asn Ile Thr Arg Glu Thr Glu Ile Asn Ser Thr
    530                 535                 540

Asn Pro Leu Ala Gly Gly Ser Leu Gly Ala His Ala Asn Asn Ser Gln
545                 550                 555                 560

Asn Thr Thr Thr Ala Pro Thr Leu Asp His Thr Asn Val Met Gly Val
                565                 570                 575

Phe Pro Gly Ser Val Trp Gln Asp Arg Asp Ile Tyr Leu Gln Gly Gln
            580                 585                 590

Ile Trp Ala Lys Ile Pro His Thr Asp Gly His Phe His Pro Ser Pro
            595                 600                 605

Leu Met Gly Gly Phe Gly Leu Lys Asn Pro Pro Gln Ile Leu Ile
    610                 615                 620

Lys Asn Thr Pro Val Pro Ala Asp Pro Thr Glu Phe Asn Ala Asn
625                 630                 635                 640

Lys Ile Ser Ser Phe Ile Thr Gln Tyr Ser Thr Gly Gln Val Thr Val
                645                 650                 655

Glu Met Glu Trp Glu Leu Gln Lys Glu Thr Ser Lys Arg Trp Asn Pro
            660                 665                 670

Glu Ile Gln Tyr Ser Asp Asp Ser Ser Thr Ser Gly Ser Ile Leu
    675                 680                 685

His Phe Ala Pro Asp Asp Val Gly Asn Tyr Lys Glu Phe Arg Ser Ile
    690                 695                 700

Gly Thr Arg Tyr Leu Thr Arg Pro Leu
705                 710

<210> SEQ ID NO 32
<211> LENGTH: 726
<212> TYPE: PRT
<213> ORGANISM: Unknown
<220> FEATURE:
<221> NAME/KEY: source
<223> OTHER INFORMATION: /note="Description of Unknown:
      Parent AAV Capsid sequence"

<400> SEQUENCE: 32

Met Ser Phe Val Asp His Pro Pro Asp Trp Leu Glu Glu Val Gly Glu
1               5                   10                  15

Gly Leu His Glu Phe Leu Glu Leu Glu Ala Gly Pro Pro Lys Pro Lys
            20                  25                  30

Pro Asn Gln Gln Lys Gln Asp Asn Ala Arg Gly Leu Val Leu Pro Gly
        35                  40                  45
```

```
Tyr Asn Tyr Leu Gly Pro Phe Asn Gly Leu Asp Lys Gly Glu Pro Val
     50                  55                  60

Asn Arg Ala Asp Ala Val Ala Arg Glu His Asp Ile Ser Tyr Asn Glu
 65                  70                  75                  80

Gln Leu Gln Ala Gly Asp Asn Pro Tyr Leu Lys Tyr Asn His Ala Asp
                 85                  90                  95

Ala Glu Phe Gln Glu Lys Leu Lys Asp Asp Thr Ser Phe Gly Gly Asn
            100                 105                 110

Leu Gly Lys Ala Ile Phe Gln Ala Lys Lys Arg Val Leu Glu Pro Phe
        115                 120                 125

Gly Leu Val Glu Ala Pro Val Lys Thr Ala Pro Ala Lys Lys Arg Pro
    130                 135                 140

Ile Glu Lys Ser Pro Ala Glu Pro Ser Ser Lys Gly Ile Gly Lys
145                 150                 155                 160

Ala Gly Gln Gln Pro Ala Arg Lys Arg Leu Asn Phe Gly Gln Thr Gly
                165                 170                 175

Asp Thr Asp Ser Ala Ala Asp Pro Gln Pro Leu Gly Glu Pro Pro Ala
            180                 185                 190

Ala Pro Ser Gly Leu Gly Thr Gly Thr Met Ala Ser Gly Ser Gly Ala
        195                 200                 205

Pro Met Ala Asp Asn Asn Glu Gly Ala Asp Gly Val Gly Asn Ala Ser
    210                 215                 220

Gly Asn Trp His Cys Asp Ser Thr Trp Leu Gly Asp Arg Val Ile Thr
225                 230                 235                 240

Thr Ser Thr Arg Thr Trp Ala Leu Pro Thr Tyr Asn Asn His Leu Tyr
                245                 250                 255

Lys Gln Ile Ser Ser Gln Ser Gly Ala Asn Asn Asp Asn His Tyr Phe
            260                 265                 270

Gly Tyr Ser Thr Pro Trp Gly Tyr Phe Asp Phe Asn Arg Phe His Cys
        275                 280                 285

His Phe Ser Pro Arg Asp Trp Gln Arg Leu Ile Asn Asn Asn Trp Gly
    290                 295                 300

Phe Arg Pro Lys Arg Leu Asn Phe Lys Leu Phe Asn Ile Gln Val Lys
305                 310                 315                 320

Glu Val Thr Gln Thr Asp Gly Thr Lys Thr Ile Ala Asn Asn Leu Thr
                325                 330                 335

Ser Thr Val Gln Val Phe Ala Asp Ser Glu Tyr Gln Leu Pro Tyr Val
            340                 345                 350

Leu Gly Ser Ala His Gln Gly Cys Phe Pro Pro Phe Pro Ala Asp Val
        355                 360                 365

Phe Met Val Pro Gln Tyr Gly Tyr Leu Thr Leu Asn Asn Gly Ser Gln
    370                 375                 380

Ala Met Gly Arg Ser Ser Phe Tyr Cys Leu Glu Tyr Phe Pro Ser Gln
385                 390                 395                 400

Met Leu Arg Thr Gly Asn Asn Phe Thr Phe Ser Tyr Thr Phe Glu Asp
                405                 410                 415

Val Pro Phe His Ser Ser Tyr Ala His Ser Gln Ser Leu Asp Arg Leu
            420                 425                 430

Met Asn Pro Leu Ile Asp Gln Tyr Leu Tyr Tyr Leu Ser Lys Thr Asn
        435                 440                 445

Gly Gly Leu Gly Phe Ser Gln Ala Gly Pro Asn Ser Met Arg Asp Gln
    450                 455                 460
```

Ser Arg Asn Trp Leu Pro Gly Pro Cys Phe Arg Gln Gln Arg Ile Ser
465                 470                 475                 480

Thr Val Pro Thr Gln Asn Asn Asn Gly Asp Phe Ser Trp Thr Gly Ala
            485                 490                 495

Thr Lys Tyr His Leu Asn Gly Arg Asn Ser Ala Met Asn Pro Gly Pro
        500                 505                 510

Ala Met Ala Ser His Lys Asp Asp Glu His Arg Phe Phe Pro Gln Asn
    515                 520                 525

Gly Val Leu Ile Phe Gly Lys Gln Gly Ala Asp Lys Thr Asn Ala Ile
530                 535                 540

Leu Glu Lys Val Ile Val Thr Asp Glu Glu Ile Arg Thr Thr Asn
545                 550                 555                 560

Pro Val Ala Thr Glu Glu Tyr Gly Phe Val Ala Thr Asn Leu Gln Ser
            565                 570                 575

Ser Ala Glu Thr Ala Glu Thr Glu Arg Val Asn Ala Gln Gly Ile Leu
        580                 585                 590

Pro Gly Met Val Trp Gln Asp Arg Asp Val Tyr Leu Gln Gly Pro Ile
            595                 600                 605

Trp Ala Lys Ile Pro His Thr Asp Gly His Phe Arg Pro Ser Pro Leu
610                 615                 620

Met Gly Gly Phe Gly Leu Lys His Pro Pro Gln Ile Leu Ile Lys
625                 630                 635                 640

Asn Thr Pro Val Pro Ser Asn Pro Pro Glu Thr Phe Asn Pro Glu Lys
            645                 650                 655

Leu Asn Ser Phe Ile Thr Gln Tyr Ser Thr Gly Gln Val Ser Val Glu
        660                 665                 670

Ile Glu Trp Glu Leu Gln Lys Glu Asn Ser Lys Arg Trp Asn Pro Glu
        675                 680                 685

Val Gln Tyr Thr Ser Asn Tyr Asn Lys Ser Val Asn Val Glu Phe Thr
        690                 695                 700

Val Asp Asn Asn Gly Val Tyr Ser Glu Pro Arg Thr Ile Gly Thr Arg
705                 710                 715                 720

Tyr Leu Thr Arg Asn Leu
                725

<210> SEQ ID NO 33
<211> LENGTH: 736
<212> TYPE: PRT
<213> ORGANISM: Unknown
<220> FEATURE:
<221> NAME/KEY: source
<223> OTHER INFORMATION: /note="Description of Unknown:
      Parent AAV Capsid sequence"

<400> SEQUENCE: 33

Met Ala Ala Asp Gly Tyr Leu Pro Asp Trp Leu Glu Asp Asn Leu Ser
1               5                   10                  15

Glu Gly Ile Arg Glu Trp Trp Ala Leu Lys Pro Gly Ala Pro Gln Pro
            20                  25                  30

Lys Ala Asn Gln Gln His Gln Asp Asn Ala Arg Gly Leu Val Leu Pro
        35                  40                  45

Gly Tyr Lys Tyr Leu Gly Pro Gly Asn Gly Leu Asp Lys Gly Glu Pro
    50                  55                  60

Val Asn Ala Ala Asp Ala Ala Leu Glu His Asp Lys Ala Tyr Asp
65                  70                  75                  80

Gln Gln Leu Lys Ala Gly Asp Asn Pro Tyr Leu Lys Tyr Asn His Ala

-continued

```
                85                  90                  95
Asp Ala Glu Phe Gln Glu Arg Leu Lys Glu Asp Thr Ser Phe Gly Gly
            100                 105                 110

Asn Leu Gly Arg Ala Val Phe Gln Ala Lys Lys Arg Leu Leu Glu Pro
            115                 120                 125

Leu Gly Leu Val Glu Glu Ala Lys Thr Ala Pro Gly Lys Lys Arg
        130                 135                 140

Pro Val Glu Gln Ser Pro Gln Glu Pro Asp Ser Ser Ala Gly Ile Gly
145                 150                 155                 160

Lys Ser Gly Ala Gln Pro Ala Lys Lys Arg Leu Asn Phe Gly Gln Thr
                165                 170                 175

Gly Asp Thr Glu Ser Val Pro Asp Pro Gln Pro Ile Gly Glu Pro Pro
            180                 185                 190

Ala Ala Pro Ser Gly Val Gly Ser Leu Thr Met Ala Ser Gly Gly Gly
            195                 200                 205

Ala Pro Val Ala Asp Asn Asn Glu Gly Ala Asp Gly Val Gly Ser Ser
        210                 215                 220

Ser Gly Asn Trp His Cys Asp Ser Gln Trp Leu Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Asn Ser Thr Ser Gly Gly Ser Ser Asn Asp Asn
            260                 265                 270

Ala Tyr Phe Gly Tyr Ser Thr Pro Trp Gly Tyr Phe Asp Phe Asn Arg
            275                 280                 285

Phe His Cys His Phe Ser Pro Arg Asp Trp Gln Arg Leu Ile Asn Asn
        290                 295                 300

Asn Trp Gly Phe Arg Pro Lys Arg Leu Asn Phe Lys Leu Phe Asn Ile
305                 310                 315                 320

Gln Val Lys Glu Val Thr Asp Asn Asn Gly Val Lys Thr Ile Ala Asn
                325                 330                 335

Asn Leu Thr Ser Thr Val Gln Val Phe Thr Asp Ser Asp Tyr Gln Leu
            340                 345                 350

Pro Tyr Val Leu Gly Ser Ala His Glu Gly Cys Leu Pro Pro Phe Pro
            355                 360                 365

Ala Asp Val Phe Met Ile Pro Gln Tyr Gly Tyr Leu Thr Leu Asn Asp
        370                 375                 380

Gly Ser Gln Ala Val Gly Arg Ser Ser Phe Tyr Cys Leu Glu Tyr Phe
385                 390                 395                 400

Pro Ser Gln Met Leu Arg Thr Gly Asn Asn Phe Gln Phe Ser Tyr Glu
                405                 410                 415

Phe Glu Asn Val Pro Phe His Ser Ser Tyr Ala His Ser Gln Ser Leu
            420                 425                 430

Asp Arg Leu Met Asn Pro Leu Ile Asp Gln Tyr Leu Tyr Tyr Leu Ser
            435                 440                 445

Lys Thr Ile Asn Gly Ser Gly Gln Asn Gln Gln Thr Leu Lys Phe Ser
        450                 455                 460

Val Ala Gly Pro Ser Asn Met Ala Val Gln Gly Arg Asn Tyr Ile Pro
465                 470                 475                 480

Gly Pro Ser Tyr Arg Gln Gln Arg Val Ser Thr Thr Val Thr Gln Asn
                485                 490                 495

Asn Asn Ser Glu Phe Ala Trp Pro Gly Ala Ser Ser Trp Ala Leu Asn
            500                 505                 510
```

Gly Arg Asn Ser Leu Met Asn Pro Gly Pro Ala Met Ala Ser His Lys
            515                 520                 525

Glu Gly Glu Asp Arg Phe Phe Pro Leu Ser Gly Ser Leu Ile Phe Gly
        530                 535                 540

Lys Gln Gly Thr Gly Arg Asp Asn Val Asp Ala Asp Lys Val Met Ile
545                 550                 555                 560

Thr Asn Glu Glu Glu Ile Lys Thr Thr Asn Pro Val Ala Thr Glu Ser
            565                 570                 575

Tyr Gly Gln Val Ala Thr Asn His Gln Ser Ala Gln Ala Gln Ala Gln
        580                 585                 590

Thr Gly Trp Val Gln Asn Gln Gly Ile Leu Pro Gly Met Val Trp Gln
            595                 600                 605

Asp Arg Asp Val Tyr Leu Gln Gly Pro Ile Trp Ala Lys Ile Pro His
        610                 615                 620

Thr Asp Gly Asn Phe His Pro Ser Pro Leu Met Gly Gly Phe Gly Met
625                 630                 635                 640

Lys His Pro Pro Pro Gln Ile Leu Ile Lys Asn Thr Pro Val Pro Ala
            645                 650                 655

Asp Pro Pro Thr Ala Phe Asn Lys Asp Lys Leu Asn Ser Phe Ile Thr
        660                 665                 670

Gln Tyr Ser Thr Gly Gln Val Ser Val Glu Ile Glu Trp Glu Leu Gln
            675                 680                 685

Lys Glu Asn Ser Lys Arg Trp Asn Pro Glu Ile Gln Tyr Thr Ser Asn
        690                 695                 700

Tyr Tyr Lys Ser Asn Asn Val Glu Phe Ala Val Asn Thr Glu Gly Val
705                 710                 715                 720

Tyr Ser Glu Pro Arg Pro Ile Gly Thr Arg Tyr Leu Thr Arg Asn Leu
            725                 730                 735

<210> SEQ ID NO 34
<211> LENGTH: 736
<212> TYPE: PRT
<213> ORGANISM: Unknown
<220> FEATURE:
<221> NAME/KEY: source
<223> OTHER INFORMATION: /note="Description of Unknown:
      Parent AAV Capsid sequence"

<400> SEQUENCE: 34

Met Ala Ala Asp Gly Tyr Leu Pro Asp Trp Leu Glu Asp Asn Leu Ser
1               5                   10                  15

Glu Gly Ile Arg Glu Trp Trp Asp Leu Lys Pro Gly Ala Pro Lys Pro
            20                  25                  30

Lys Ala Asn Gln Gln Lys Gln Asp Asp Gly Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Ala Ala Asp Ala Ala Ala Leu Glu His Asp Lys Ala Tyr Asp
65                  70                  75                  80

Gln Gln Leu Lys Ala Gly Asp Asn Pro Tyr Leu Arg Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
        115                 120                 125

```
Leu Gly Leu Val Glu Glu Gly Ala Lys Thr Ala Pro Gly Lys Lys Arg
130                 135                 140
Pro Val Glu Gln Ser Pro Gln Glu Pro Asp Ser Ser Gly Ile Gly
145                 150                 155                 160
Lys Thr Gly Gln Gln Pro Ala Lys Lys Arg Leu Asn Phe Gly Gln Thr
                165                 170                 175
Gly Asp Ser Glu Ser Val Pro Asp Pro Gln Pro Leu Gly Glu Pro Pro
            180                 185                 190
Ala Thr Pro Ala Ala Val Gly Pro Thr Thr Met Ala Ser Gly Gly Gly
            195                 200                 205
Ala Pro Met Ala Asp Asn Asn Glu Gly Ala Asp Gly Val Gly Asn Ala
210                 215                 220
Ser Gly Asn Trp His Cys Asp Ser Thr Trp Leu Gly Asp Arg Val Ile
225                 230                 235                 240
Thr Thr Ser Thr Arg Thr Trp Ala Leu Pro Thr Tyr Asn Asn His Leu
                245                 250                 255
Tyr Lys Gln Ile Ser Ser Ala Ser Thr Gly Ala Ser Asn Asp Asn His
                260                 265                 270
Tyr Phe Gly Tyr Ser Thr Pro Trp Gly Tyr Phe Asp Phe Asn Arg Phe
            275                 280                 285
His Cys His Phe Ser Pro Arg Asp Trp Gln Arg Leu Ile Asn Asn Asn
290                 295                 300
Trp Gly Phe Arg Pro Lys Arg Leu Asn Phe Lys Leu Phe Asn Ile Gln
305                 310                 315                 320
Val Lys Glu Val Thr Thr Asn Asp Gly Val Thr Thr Ile Ala Asn Asn
                325                 330                 335
Leu Thr Ser Thr Val Gln Val Phe Ser Asp Ser Glu Tyr Gln Leu Pro
                340                 345                 350
Tyr Val Leu Gly Ser Ala His Gln Gly Cys Leu Pro Pro Phe Pro Ala
            355                 360                 365
Asp Val Phe Met Ile Pro Gln Tyr Gly Tyr Leu Thr Leu Asn Asn Gly
370                 375                 380
Ser Gln Ala Val Gly Arg Ser Ser Phe Tyr Cys Leu Glu Tyr Phe Pro
385                 390                 395                 400
Ser Gln Met Leu Arg Thr Gly Asn Asn Phe Thr Phe Ser Tyr Thr Phe
                405                 410                 415
Glu Glu Val Pro Phe His Ser Ser Tyr Ala His Ser Gln Ser Leu Asp
                420                 425                 430
Arg Leu Met Asn Pro Leu Ile Asp Gln Tyr Leu Tyr Tyr Leu Asn Arg
            435                 440                 445
Thr Gln Asn Gln Ser Gly Ser Ala Gln Asn Lys Asp Leu Leu Phe Ser
450                 455                 460
Arg Gly Ser Pro Ala Gly Met Ser Val Gln Pro Lys Asn Trp Leu Pro
465                 470                 475                 480
Gly Pro Cys Tyr Arg Gln Gln Arg Val Ser Lys Thr Lys Thr Asp Asn
                485                 490                 495
Asn Asn Ser Asn Phe Thr Trp Thr Gly Ala Ser Lys Tyr Asn Leu Asn
                500                 505                 510
Gly Arg Glu Ser Ile Ile Asn Pro Gly Thr Ala Met Ala Ser His Lys
            515                 520                 525
Asp Asp Glu Asp Lys Phe Phe Pro Met Ser Gly Val Met Ile Phe Gly
530                 535                 540
Lys Glu Ser Ala Gly Ala Ser Asn Thr Ala Leu Asp Asn Val Met Ile
```

```
                545                 550                 555                 560
Thr Asp Glu Glu Glu Ile Lys Ala Thr Asn Pro Val Ala Thr Glu Arg
                    565                 570                 575

Phe Gly Thr Val Ala Val Asn Phe Gln Ser Ser Thr Asp Pro Ala
            580                 585                 590

Thr Gly Asp Val His Ala Met Gly Ala Leu Pro Gly Met Val Trp Gln
        595                 600                 605

Asp Arg Asp Val Tyr Leu Gln Gly Pro Ile Trp Ala Lys Ile Pro His
        610                 615                 620

Thr Asp Gly His Phe His Pro Ser Pro Leu Met Gly Gly Phe Gly Leu
625                 630                 635                 640

Lys Asn Pro Pro Pro Gln Ile Leu Ile Lys Asn Thr Pro Val Pro Ala
                    645                 650                 655

Asn Pro Pro Ala Glu Phe Ser Ala Thr Lys Phe Ala Ser Phe Ile Thr
                660                 665                 670

Gln Tyr Ser Thr Gly Gln Val Ser Val Glu Ile Glu Trp Glu Leu Gln
            675                 680                 685

Lys Glu Asn Ser Lys Arg Trp Asn Pro Glu Val Gln Tyr Thr Ser Asn
        690                 695                 700

Tyr Ala Lys Ser Ala Asn Val Asp Phe Thr Val Asp Asn Asn Gly Leu
705                 710                 715                 720

Tyr Thr Glu Pro Arg Pro Ile Gly Thr Arg Tyr Leu Thr Arg Pro Leu
                    725                 730                 735

<210> SEQ ID NO 35
<211> LENGTH: 736
<212> TYPE: PRT
<213> ORGANISM: Unknown
<220> FEATURE:
<221> NAME/KEY: source
<223> OTHER INFORMATION: /note="Description of Unknown:
      Parent AAV Capsid sequence"

<400> SEQUENCE: 35

Met Ala Ala Asp Gly Tyr Leu Pro Asp Trp Leu Glu Asp Asn Leu Ser
1               5                   10                  15

Glu Gly Ile Arg Glu Trp Trp Asp Leu Lys Pro Gly Ala Pro Lys Pro
                20                  25                  30

Lys Ala Asn Gln Gln Lys Gln Asp Asp Gly Arg Gly Leu Val Leu Pro
            35                  40                  45

Gly Tyr Lys Tyr Leu Gly Pro Phe Asn Gly Leu Asp Lys Gly Glu Pro
        50                  55                  60

Val Asn Ala Ala Asp Ala Ala Ala Leu Glu His Asp Lys Ala Tyr Asp
65                  70                  75                  80

Gln Gln Leu Lys Ala Gly Asp Asn Pro Tyr Leu Arg Tyr Asn His Ala
                85                  90                  95

Asp Ala Glu Phe Gln Glu Arg Leu Gln Glu Asp Thr Ser Phe Gly Gly
                100                 105                 110

Asn Leu Gly Arg Ala Val Phe Gln Ala Lys Lys Arg Val Leu Glu Pro
            115                 120                 125

Phe Gly Leu Val Glu Glu Gly Ala Lys Thr Ala Pro Gly Lys Lys Arg
        130                 135                 140

Pro Val Glu Gln Ser Pro Gln Glu Pro Asp Ser Ser Ser Gly Ile Gly
145                 150                 155                 160

Lys Thr Gly Gln Gln Pro Ala Lys Lys Arg Leu Asn Phe Gly Gln Thr
                165                 170                 175
```

```
Gly Asp Ser Glu Ser Val Pro Asp Pro Gln Pro Leu Gly Glu Pro Pro
            180                 185                 190

Ala Thr Pro Ala Ala Val Gly Pro Thr Thr Met Ala Ser Gly Gly Gly
            195                 200                 205

Ala Pro Met Ala Asp Asn Asn Glu Gly Ala Asp Gly Val Gly Asn Ala
210                 215                 220

Ser Gly Asn Trp His Cys Asp Ser Thr Trp Leu Gly Asp Arg Val Ile
225                 230                 235                 240

Thr Thr Ser Thr Arg Thr Trp Ala Leu Pro Thr Tyr Asn Asn His Leu
            245                 250                 255

Tyr Lys Gln Ile Ser Ser Ala Ser Thr Gly Ala Ser Asn Asp Asn His
            260                 265                 270

Tyr Phe Gly Tyr Ser Thr Pro Trp Gly Tyr Phe Asp Phe Asn Arg Phe
            275                 280                 285

His Cys His Phe Ser Pro Arg Asp Trp Gln Arg Leu Ile Asn Asn Asn
            290                 295                 300

Trp Gly Phe Arg Pro Lys Arg Leu Asn Phe Lys Leu Phe Asn Ile Gln
305                 310                 315                 320

Val Lys Glu Val Thr Thr Asn Asp Gly Val Thr Thr Ile Ala Asn Asn
            325                 330                 335

Leu Thr Ser Thr Val Gln Val Phe Ser Asp Ser Glu Tyr Gln Leu Pro
            340                 345                 350

Tyr Val Leu Gly Ser Ala His Gln Gly Cys Leu Pro Pro Phe Pro Ala
            355                 360                 365

Asp Val Phe Met Ile Pro Gln Tyr Gly Tyr Leu Thr Leu Asn Asn Gly
            370                 375                 380

Ser Gln Ala Val Gly Arg Ser Ser Phe Tyr Cys Leu Glu Tyr Phe Pro
385                 390                 395                 400

Ser Gln Met Leu Arg Thr Gly Asn Asn Phe Thr Phe Ser Tyr Thr Phe
            405                 410                 415

Glu Asp Val Pro Phe His Ser Ser Tyr Ala His Ser Gln Ser Leu Asp
            420                 425                 430

Arg Leu Met Asn Pro Leu Ile Asp Gln Tyr Leu Tyr Tyr Leu Asn Arg
            435                 440                 445

Thr Gln Asn Gln Ser Gly Ser Ala Gln Asn Lys Asp Leu Leu Phe Ser
            450                 455                 460

Arg Gly Ser Pro Ala Gly Met Ser Val Gln Pro Lys Asn Trp Leu Pro
465                 470                 475                 480

Gly Pro Cys Tyr Arg Gln Gln Arg Val Ser Lys Thr Lys Thr Asp Asn
            485                 490                 495

Asn Asn Ser Asn Phe Thr Trp Thr Gly Ala Ser Lys Tyr Asn Leu Asn
            500                 505                 510

Gly Arg Glu Ser Ile Ile Asn Pro Gly Thr Ala Met Ala Ser His Lys
            515                 520                 525

Asp Asp Lys Asp Lys Phe Phe Pro Met Ser Gly Val Met Ile Phe Gly
            530                 535                 540

Lys Glu Ser Ala Gly Ala Ser Asn Thr Ala Leu Asp Asn Val Met Ile
545                 550                 555                 560

Thr Asp Glu Glu Glu Ile Lys Ala Thr Asn Pro Val Ala Thr Glu Arg
            565                 570                 575

Phe Gly Thr Val Ala Val Asn Leu Gln Ser Ser Ser Thr Asp Pro Ala
            580                 585                 590
```

```
Thr Gly Asp Val His Val Met Gly Ala Leu Pro Gly Met Val Trp Gln
            595                 600                 605
Asp Arg Asp Val Tyr Leu Gln Gly Pro Ile Trp Ala Lys Ile Pro His
    610                 615                 620
Thr Asp Gly His Phe His Pro Ser Pro Leu Met Gly Gly Phe Gly Leu
625                 630                 635                 640
Lys His Pro Pro Gln Ile Leu Ile Lys Asn Thr Pro Val Pro Ala
                645                 650                 655
Asn Pro Pro Ala Glu Phe Ser Ala Thr Lys Phe Ala Ser Phe Ile Thr
                660                 665                 670
Gln Tyr Ser Thr Gly Gln Val Ser Val Glu Ile Glu Trp Glu Leu Gln
        675                 680                 685
Lys Glu Asn Ser Lys Arg Trp Asn Pro Glu Val Gln Tyr Thr Ser Asn
    690                 695                 700
Tyr Ala Lys Ser Ala Asn Val Asp Phe Thr Val Asp Asn Asn Gly Leu
705                 710                 715                 720
Tyr Thr Glu Pro Arg Pro Ile Gly Thr Arg Tyr Leu Thr Arg Pro Leu
                725                 730                 735
```

<210> SEQ ID NO 36
<211> LENGTH: 736
<212> TYPE: PRT
<213> ORGANISM: Unknown
<220> FEATURE:
<221> NAME/KEY: source
<223> OTHER INFORMATION: /note="Description of Unknown:
      Parent AAV Capsid sequence"

<400> SEQUENCE: 36

```
Met Ala Ala Asp Gly Tyr Leu Pro Asp Trp Leu Glu Asp Asn Leu Ser
1                   5                   10                  15
Glu Gly Ile Arg Glu Trp Trp Ala Leu Lys Pro Gly Val Pro Gln Pro
            20                  25                  30
Lys Ala Asn Gln Gln His Gln Asp Asn Arg Arg Gly Leu Val Leu Pro
        35                  40                  45
Gly Tyr Lys Tyr Leu Gly Pro Gly Asn Gly Leu Asp Lys Gly Glu Pro
    50                  55                  60
Val Asn Glu Ala Asp Ala Ala Leu Glu His Asp Lys Ala Tyr Asp
65                  70                  75                  80
Gln Gln Leu Lys Ala Gly Asp Asn Pro Tyr Leu Lys Tyr Asn His Ala
                85                  90                  95
Asp Ala Glu Phe Gln Glu Arg Leu Gln Glu Asp Thr Ser Phe Gly Gly
            100                 105                 110
Asn Leu Gly Arg Ala Val Phe Gln Ala Lys Lys Arg Ile Leu Glu Pro
        115                 120                 125
Leu Gly Leu Val Glu Glu Ala Ala Lys Thr Ala Pro Gly Lys Lys Arg
    130                 135                 140
Pro Val Asp Gln Ser Pro Gln Glu Pro Asp Ser Ser Ser Gly Val Gly
145                 150                 155                 160
Lys Ser Gly Lys Gln Pro Ala Arg Lys Arg Leu Asn Phe Gly Gln Thr
                165                 170                 175
Gly Asp Ser Glu Ser Val Pro Asp Pro Gln Pro Leu Gly Glu Pro Pro
            180                 185                 190
Ala Ala Pro Thr Ser Leu Gly Ser Asn Thr Met Ala Ser Gly Gly Gly
        195                 200                 205
Ala Pro Met Ala Asp Asn Asn Glu Gly Ala Asp Gly Val Gly Asn Ser
```

-continued

```
              210                 215                 220
Ser Gly Asn Trp His Cys Asp Ser Gln Trp Leu Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Ser Gln Ser Gly Ala Ser Asn Asp Asn His Tyr
                260                 265                 270

Phe Gly Tyr Ser Thr Pro Trp Gly Tyr Phe Asp Phe Asn Arg Phe His
                275                 280                 285

Cys His Phe Ser Pro Arg Asp Trp Gln Arg Leu Ile Asn Asn Asn Trp
                290                 295                 300

Gly Phe Arg Pro Lys Lys Leu Ser Phe Lys Leu Phe Asn Ile Gln Val
305                 310                 315                 320

Lys Glu Val Thr Gln Asn Asp Gly Thr Thr Ile Ala Asn Asn Leu
                325                 330                 335

Thr Ser Thr Val Gln Val Phe Thr Asp Ser Glu Tyr Gln Leu Pro Tyr
                340                 345                 350

Val Leu Gly Ser Ala His Gln Gly Cys Leu Pro Pro Phe Pro Ala Asp
                355                 360                 365

Val Phe Met Val Pro Gln Tyr Gly Tyr Leu Thr Leu Asn Asn Gly Ser
370                 375                 380

Gln Ala Val Gly Arg Ser Ser Phe Tyr Cys Leu Glu Tyr Phe Pro Ser
385                 390                 395                 400

Gln Met Leu Arg Thr Gly Asn Asn Phe Gln Phe Ser Tyr Thr Phe Glu
                405                 410                 415

Asp Val Pro Phe His Ser Ser Tyr Ala His Ser Gln Ser Leu Asp Arg
                420                 425                 430

Leu Met Asn Pro Leu Ile Asp Gln Tyr Leu Tyr Tyr Leu Asn Arg Thr
                435                 440                 445

Gln Gly Thr Thr Ser Gly Thr Thr Asn Gln Ser Arg Leu Leu Phe Ser
                450                 455                 460

Gln Ala Gly Pro Gln Ser Met Ser Leu Gln Ala Arg Asn Trp Leu Pro
465                 470                 475                 480

Gly Pro Cys Tyr Arg Gln Gln Arg Leu Ser Lys Thr Ala Asn Asp Asn
                485                 490                 495

Asn Asn Ser Asn Phe Pro Trp Thr Ala Ala Ser Lys Tyr His Leu Asn
                500                 505                 510

Gly Arg Asp Ser Leu Val Asn Pro Gly Pro Ala Met Ala Ser His Lys
                515                 520                 525

Asp Asp Glu Glu Lys Phe Phe Pro Met His Gly Asn Leu Ile Phe Gly
                530                 535                 540

Lys Glu Gly Thr Thr Ala Ser Asn Ala Glu Leu Asp Asn Val Met Ile
545                 550                 555                 560

Thr Asp Glu Glu Ile Arg Thr Thr Asn Pro Val Ala Thr Glu Gln
                565                 570                 575

Tyr Gly Thr Val Ala Asn Asn Leu Gln Ser Ser Asn Thr Ala Pro Thr
                580                 585                 590

Thr Arg Thr Val Asn Asp Gln Gly Ala Leu Pro Gly Met Val Trp Gln
                595                 600                 605

Asp Arg Asp Val Tyr Leu Gln Gly Pro Ile Trp Ala Lys Ile Pro His
                610                 615                 620

Thr Asp Gly His Phe His Pro Ser Pro Leu Met Gly Gly Phe Gly Leu
625                 630                 635                 640
```

```
Lys His Pro Pro Gln Ile Met Ile Lys Asn Thr Pro Val Pro Ala
                645             650                 655
Asn Pro Pro Thr Thr Phe Ser Pro Ala Lys Phe Ala Ser Phe Ile Thr
            660                 665                 670
Gln Tyr Ser Thr Gly Gln Val Ser Val Glu Ile Glu Trp Glu Leu Gln
            675                 680                 685
Lys Glu Asn Ser Lys Arg Trp Asn Pro Glu Ile Gln Tyr Thr Ser Asn
    690                 695                 700
Tyr Asn Lys Ser Val Asn Val Asp Phe Thr Val Asp Thr Asn Gly Val
705                 710                 715                 720
Tyr Ser Glu Pro Arg Pro Ile Gly Thr Arg Tyr Leu Thr Arg Asn Leu
                725                 730                 735

<210> SEQ ID NO 37
<211> LENGTH: 736
<212> TYPE: PRT
<213> ORGANISM: Unknown
<220> FEATURE:
<221> NAME/KEY: source
<223> OTHER INFORMATION: /note="Description of Unknown:
      Parent AAV Capsid sequence"

<400> SEQUENCE: 37

Met Ala Ala Asp Gly Tyr Leu Pro Asp Trp Leu Glu Asp Asn Leu Ser
1               5                   10                  15
Glu Gly Ile Arg Glu Trp Trp Ala Leu Gln Pro Gly Ala Pro Lys Pro
            20                  25                  30
Lys Ala Asn Gln Gln His Gln Asp Asn Ala Arg Gly Leu Val Leu Pro
        35                  40                  45
Gly Tyr Lys Tyr Leu Gly Pro Gly Asn Gly Leu Asp Lys Gly Glu Pro
    50                  55                  60
Val Asn Ala Ala Asp Ala Ala Ala Leu Glu His Asp Lys Ala Tyr Asp
65                  70                  75                  80
Gln Gln Leu Lys Ala Gly Asp Asn Pro Tyr Leu Lys Tyr Asn His Ala
                85                  90                  95
Asp Ala Glu Phe Gln Glu Arg Leu Lys Glu Asp Thr Ser Phe Gly Gly
            100                 105                 110
Asn Leu Gly Arg Ala Val Phe Gln Ala Lys Lys Arg Leu Leu Glu Pro
        115                 120                 125
Leu Gly Leu Val Glu Glu Ala Ala Lys Thr Ala Pro Gly Lys Lys Arg
    130                 135                 140
Pro Val Asp Gln Ser Pro Gln Glu Pro Asp Ser Ser Ser Gly Val Gly
145                 150                 155                 160
Lys Ser Gly Lys Gln Pro Ala Arg Lys Arg Leu Asn Phe Gly Gln Thr
                165                 170                 175
Gly Asp Ser Glu Ser Val Pro Asp Pro Gln Pro Leu Gly Glu Pro Pro
            180                 185                 190
Ala Ala Pro Thr Ser Leu Gly Ser Asn Thr Met Ala Ser Gly Gly Gly
        195                 200                 205
Ala Pro Met Ala Asp Asn Asn Glu Gly Ala Asp Gly Val Gly Asn Ser
    210                 215                 220
Ser Gly Asn Trp His Cys Asp Ser Gln Trp Leu Gly Asp Arg Val Ile
225                 230                 235                 240
Thr Thr Ser Thr Arg Thr Trp Ala Leu Pro Thr Tyr Asn Asn His Leu
                245                 250                 255
```

-continued

```
Tyr Lys Gln Ile Ser Ser Gln Ser Gly Ala Ser Asn Asp Asn His Tyr
                260                 265                 270

Phe Gly Tyr Ser Thr Pro Trp Gly Tyr Phe Asp Phe Asn Arg Phe His
            275                 280                 285

Cys His Phe Ser Pro Arg Asp Trp Gln Arg Leu Ile Asn Asn Asn Trp
        290                 295                 300

Gly Phe Arg Pro Lys Lys Leu Ser Phe Lys Leu Phe Asn Ile Gln Val
305                 310                 315                 320

Lys Glu Val Thr Gln Asn Asp Gly Thr Thr Ile Ala Asn Asn Leu
                325                 330                 335

Thr Ser Thr Val Gln Val Phe Thr Asp Ser Glu Tyr Gln Leu Pro Tyr
            340                 345                 350

Val Leu Gly Ser Ala His Gln Gly Cys Leu Pro Pro Phe Pro Ala Asp
            355                 360                 365

Val Phe Met Val Pro Gln Tyr Gly Tyr Leu Thr Leu Asn Asn Gly Ser
            370                 375                 380

Gln Ala Val Gly Arg Ser Ser Phe Tyr Cys Leu Glu Tyr Phe Pro Ser
385                 390                 395                 400

Gln Met Leu Arg Thr Gly Asn Asn Phe Gln Phe Ser Tyr Thr Phe Glu
                405                 410                 415

Asp Val Pro Phe His Ser Ser Tyr Ala His Ser Gln Ser Leu Asp Arg
            420                 425                 430

Leu Met Asn Pro Leu Ile Asp Gln Tyr Leu Tyr Tyr Leu Asn Arg Thr
            435                 440                 445

Gln Gly Thr Thr Ser Gly Thr Thr Asn Gln Ser Arg Leu Leu Phe Ser
            450                 455                 460

Gln Ala Gly Pro Gln Ser Met Ser Leu Gln Ala Arg Asn Trp Leu Pro
465                 470                 475                 480

Gly Pro Cys Tyr Arg Gln Gln Arg Leu Ser Lys Thr Ala Asn Asp Asn
                485                 490                 495

Asn Asn Ser Asn Phe Pro Trp Thr Ala Ala Ser Lys Tyr His Leu Asn
            500                 505                 510

Gly Arg Asp Ser Leu Val Asn Pro Gly Pro Ala Met Ala Ser His Lys
            515                 520                 525

Asp Asp Glu Glu Lys Phe Phe Pro Met His Gly Asn Leu Ile Phe Gly
            530                 535                 540

Lys Glu Gly Thr Thr Ala Ser Asn Ala Glu Leu Asp Asn Val Met Ile
545                 550                 555                 560

Thr Asp Glu Glu Glu Ile Arg Thr Thr Asn Pro Val Ala Thr Glu Gln
                565                 570                 575

Tyr Gly Thr Val Ala Asn Asn Leu Gln Ser Ser Asn Thr Ala Pro Thr
            580                 585                 590

Thr Arg Thr Val Asn Asp Gln Gly Ala Leu Pro Gly Met Val Trp Gln
            595                 600                 605

Asp Arg Asp Val Tyr Leu Gln Gly Pro Ile Trp Ala Lys Ile Pro His
            610                 615                 620

Thr Asp Gly His Phe His Pro Ser Pro Leu Met Gly Gly Phe Gly Leu
625                 630                 635                 640

Lys His Pro Pro Pro Gln Ile Met Ile Lys Asn Thr Pro Val Pro Ala
                645                 650                 655

Asn Pro Pro Thr Thr Phe Ser Pro Ala Lys Phe Ala Ser Phe Ile Thr
            660                 665                 670

Gln Tyr Ser Thr Gly Gln Val Ser Val Glu Ile Glu Trp Glu Leu Gln
```

-continued

```
                675                 680                 685
Lys Glu Asn Ser Lys Arg Trp Asn Pro Glu Ile Gln Tyr Thr Ser Asn
        690                 695                 700
Tyr Asn Lys Ser Val Asn Val Asp Phe Thr Val Asp Thr Asn Gly Val
705                 710                 715                 720
Tyr Ser Glu Pro Arg Pro Ile Gly Thr Arg Tyr Leu Thr Arg Pro Leu
                725                 730                 735

<210> SEQ ID NO 38
<211> LENGTH: 738
<212> TYPE: PRT
<213> ORGANISM: Unknown
<220> FEATURE:
<221> NAME/KEY: source
<223> OTHER INFORMATION: /note="Description of Unknown:
      Parent AAV Capsid sequence"

<400> SEQUENCE: 38

Met Ala Ala Asp Gly Tyr Leu Pro Asp Trp Leu Glu Asp Asn Leu Ser
1               5                   10                  15
Glu Gly Ile Arg Glu Trp Trp Ala Leu Lys Pro Gly Ala Pro Lys Pro
            20                  25                  30
Lys Ala Asn Gln Gln Lys Gln Asp Asp Gly Arg Gly Leu Val Leu Pro
        35                  40                  45
Gly Tyr Lys Tyr Leu Gly Pro Phe Asn Gly Leu Asp Lys Gly Glu Pro
    50                  55                  60
Val Asn Ala Ala Asp Ala Ala Ala Leu Glu His Asp Lys Ala Tyr Asp
65                  70                  75                  80
Gln Gln Leu Gln Ala Gly Asp Asn Pro Tyr Leu Arg Tyr Asn His Ala
                85                  90                  95
Asp Ala Glu Phe Gln Glu Arg Leu Gln Glu Asp Thr Ser Phe Gly Gly
            100                 105                 110
Asn Leu Gly Arg Ala Val Phe Gln Ala Lys Lys Arg Val Leu Glu Pro
        115                 120                 125
Leu Gly Leu Val Glu Glu Gly Ala Lys Thr Ala Pro Gly Lys Lys Arg
    130                 135                 140
Pro Val Glu Pro Ser Pro Gln Arg Ser Pro Asp Ser Ser Thr Gly Ile
145                 150                 155                 160
Gly Lys Lys Gly Gln Gln Pro Ala Arg Lys Arg Leu Asn Phe Gly Gln
                165                 170                 175
Thr Gly Asp Ser Glu Ser Val Pro Asp Pro Gln Pro Leu Gly Glu Pro
            180                 185                 190
Pro Ala Ala Pro Ser Gly Val Gly Pro Asn Thr Met Ala Ala Gly Gly
        195                 200                 205
Gly Ala Pro Met Ala Asp Asn Asn Glu Gly Ala Asp Gly Val Gly Ser
    210                 215                 220
Ser Ser Gly Asn Trp His Cys Asp Ser Thr Trp Leu Gly Asp Arg Val
225                 230                 235                 240
Ile Thr Thr Ser Thr Arg Thr Trp Ala Leu Pro Thr Tyr Asn Asn His
                245                 250                 255
Leu Tyr Lys Gln Ile Ser Asn Gly Thr Ser Gly Gly Ala Thr Asn Asp
            260                 265                 270
Asn Thr Tyr Phe Gly Tyr Ser Thr Pro Trp Gly Tyr Phe Asp Phe Asn
        275                 280                 285
Arg Phe His Cys His Phe Ser Pro Arg Asp Trp Gln Arg Leu Ile Asn
    290                 295                 300
```

```
Asn Asn Trp Gly Phe Arg Pro Lys Arg Leu Ser Phe Lys Leu Phe Asn
305                 310                 315                 320

Ile Gln Val Lys Glu Val Thr Gln Asn Glu Gly Thr Lys Thr Ile Ala
            325                 330                 335

Asn Asn Leu Thr Ser Thr Ile Gln Val Phe Thr Asp Ser Glu Tyr Gln
            340                 345                 350

Leu Pro Tyr Val Leu Gly Ser Ala His Gln Gly Cys Leu Pro Pro Phe
            355                 360                 365

Pro Ala Asp Val Phe Met Ile Pro Gln Tyr Gly Tyr Leu Thr Leu Asn
            370                 375                 380

Asn Gly Ser Gln Ala Val Gly Arg Ser Ser Phe Tyr Cys Leu Glu Tyr
385                 390                 395                 400

Phe Pro Ser Gln Met Leu Arg Thr Gly Asn Asn Phe Gln Phe Thr Tyr
                405                 410                 415

Thr Phe Glu Asp Val Pro Phe His Ser Ser Tyr Ala His Ser Gln Ser
            420                 425                 430

Leu Asp Arg Leu Met Asn Pro Leu Ile Asp Gln Tyr Leu Tyr Tyr Leu
            435                 440                 445

Ser Arg Thr Gln Thr Thr Gly Gly Thr Ala Asn Thr Gln Thr Leu Gly
450                 455                 460

Phe Ser Gln Gly Gly Pro Asn Thr Met Ala Asn Gln Ala Lys Asn Trp
465                 470                 475                 480

Leu Pro Gly Pro Cys Tyr Arg Gln Gln Arg Val Ser Thr Thr Thr Gly
                485                 490                 495

Gln Asn Asn Asn Ser Asn Phe Ala Trp Thr Ala Gly Thr Lys Tyr His
            500                 505                 510

Leu Asn Gly Arg Asn Ser Leu Ala Asn Pro Gly Ile Ala Met Ala Thr
            515                 520                 525

His Lys Asp Asp Glu Glu Arg Phe Phe Pro Ser Asn Gly Ile Leu Ile
530                 535                 540

Phe Gly Lys Gln Asn Ala Ala Arg Asp Asn Ala Asp Tyr Ser Asp Val
545                 550                 555                 560

Met Leu Thr Ser Glu Glu Glu Ile Lys Thr Thr Asn Pro Val Ala Thr
                565                 570                 575

Glu Glu Tyr Gly Ile Val Ala Asp Asn Leu Gln Gln Gln Asn Thr Ala
            580                 585                 590

Pro Gln Ile Gly Thr Val Asn Ser Gln Gly Ala Leu Pro Gly Met Val
            595                 600                 605

Trp Gln Asn Arg Asp Val Tyr Leu Gln Gly Pro Ile Trp Ala Lys Ile
610                 615                 620

Pro His Thr Asp Gly Asn Phe His Pro Ser Pro Leu Met Gly Gly Phe
625                 630                 635                 640

Gly Leu Lys His Pro Pro Pro Gln Ile Leu Ile Lys Asn Thr Pro Val
                645                 650                 655

Pro Ala Asp Pro Pro Thr Thr Phe Asn Gln Ser Lys Leu Asn Ser Phe
            660                 665                 670

Ile Thr Gln Tyr Ser Thr Gly Gln Val Ser Val Glu Ile Glu Trp Glu
            675                 680                 685

Leu Gln Lys Glu Asn Ser Lys Arg Trp Asn Pro Glu Ile Gln Tyr Thr
            690                 695                 700

Ser Asn Tyr Tyr Lys Ser Thr Ser Val Asp Phe Ala Val Asn Thr Glu
705                 710                 715                 720
```

-continued

```
Gly Val Tyr Ser Glu Pro Arg Pro Ile Gly Thr Arg Tyr Leu Thr Arg
                725                 730                 735
Asn Leu

<210> SEQ ID NO 39
<211> LENGTH: 738
<212> TYPE: PRT
<213> ORGANISM: Unknown
<220> FEATURE:
<221> NAME/KEY: source
<223> OTHER INFORMATION: /note="Description of Unknown:
      Parent AAV Capsid sequence"

<400> SEQUENCE: 39

Met Ala Ala Asp Gly Tyr Leu Pro Asp Trp Leu Glu Asp Asn Leu Ser
1               5                   10                  15

Glu Gly Ile Arg Glu Trp Trp Asp Leu Lys Pro Gly Ala Pro Lys Pro
            20                  25                  30

Lys Ala Asn Gln Gln Lys Gln Asp Asp Gly Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Ala Ala Asp Ala Ala Leu Glu His Asp Lys Ala Tyr Asp
65                  70                  75                  80

Gln Gln Leu Lys Ala Gly Asp Asn Pro Tyr Leu Arg Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Gly Ala Lys Thr Ala Pro Gly Lys Lys Arg
    130                 135                 140

Pro Val Glu Pro Ser Pro Gln Arg Ser Pro Asp Ser Ser Thr Gly Ile
145                 150                 155                 160

Gly Lys Lys Gly Gln Gln Pro Ala Lys Lys Arg Leu Asn Phe Gly Gln
                165                 170                 175

Thr Gly Asp Ser Glu Ser Val Pro Asp Pro Gln Pro Ile Gly Glu Pro
            180                 185                 190

Pro Ala Gly Pro Ser Gly Leu Gly Ser Gly Thr Met Ala Ala Gly Gly
        195                 200                 205

Gly Ala Pro Met Ala Asp Asn Asn Glu Gly Ala Asp Gly Val Gly Ser
    210                 215                 220

Ser Ser Gly Asn Trp His Cys Asp Ser Thr Trp Leu Gly Asp Arg Val
225                 230                 235                 240

Ile Thr Thr Ser Thr Arg Thr Trp Ala Leu Pro Thr Tyr Asn Asn His
                245                 250                 255

Leu Tyr Lys Gln Ile Ser Asn Gly Thr Ser Gly Gly Ser Thr Asn Asp
            260                 265                 270

Asn Thr Tyr Phe Gly Tyr Ser Thr Pro Trp Gly Tyr Phe Asp Phe Asn
        275                 280                 285

Arg Phe His Cys His Phe Ser Pro Arg Asp Trp Gln Arg Leu Ile Asn
    290                 295                 300

Asn Asn Trp Gly Phe Arg Pro Lys Arg Leu Asn Phe Lys Leu Phe Asn
305                 310                 315                 320

Ile Gln Val Lys Glu Val Thr Gln Asn Glu Gly Thr Lys Thr Ile Ala
                325                 330                 335
```

```
Asn Asn Leu Thr Ser Thr Ile Gln Val Phe Thr Asp Ser Glu Tyr Gln
            340                 345                 350

Leu Pro Tyr Val Leu Gly Ser Ala His Gln Gly Cys Leu Pro Pro Phe
            355                 360                 365

Pro Ala Asp Val Phe Met Ile Pro Gln Tyr Gly Tyr Leu Thr Leu Asn
    370                 375                 380

Asn Gly Ser Gln Ala Val Gly Arg Ser Ser Phe Tyr Cys Leu Glu Tyr
385                 390                 395                 400

Phe Pro Ser Gln Met Leu Arg Thr Gly Asn Asn Phe Glu Phe Ser Tyr
                405                 410                 415

Gln Phe Glu Asp Val Pro Phe His Ser Ser Tyr Ala His Ser Gln Ser
            420                 425                 430

Leu Asp Arg Leu Met Asn Pro Leu Ile Asp Gln Tyr Leu Tyr Tyr Leu
        435                 440                 445

Ser Arg Thr Gln Ser Thr Gly Gly Thr Ala Gly Thr Gln Gln Leu Leu
    450                 455                 460

Phe Ser Gln Ala Gly Pro Asn Asn Met Ser Ala Gln Ala Lys Asn Trp
465                 470                 475                 480

Leu Pro Gly Pro Cys Tyr Arg Gln Gln Arg Val Ser Thr Thr Leu Ser
                485                 490                 495

Gln Asn Asn Asn Ser Asn Phe Ala Trp Thr Gly Ala Thr Lys Tyr His
            500                 505                 510

Leu Asn Gly Arg Asp Ser Leu Val Asn Pro Gly Val Ala Met Ala Thr
        515                 520                 525

His Lys Asp Asp Glu Glu Arg Phe Phe Pro Ser Ser Gly Val Leu Met
    530                 535                 540

Phe Gly Lys Gln Gly Ala Gly Lys Asp Asn Val Asp Tyr Ser Ser Val
545                 550                 555                 560

Met Leu Thr Ser Glu Glu Glu Ile Lys Thr Thr Asn Pro Val Ala Thr
                565                 570                 575

Glu Gln Tyr Gly Val Val Ala Asp Asn Leu Gln Gln Gln Asn Ala Ala
            580                 585                 590

Pro Ile Val Gly Ala Val Asn Ser Gln Gly Ala Leu Pro Gly Met Val
        595                 600                 605

Trp Gln Asn Arg Asp Val Tyr Leu Gln Gly Pro Ile Trp Ala Lys Ile
    610                 615                 620

Pro His Thr Asp Gly Asn Phe His Pro Ser Pro Leu Met Gly Gly Phe
625                 630                 635                 640

Gly Leu Lys His Pro Pro Pro Gln Ile Leu Ile Lys Asn Thr Pro Val
                645                 650                 655

Pro Ala Asp Pro Pro Thr Thr Phe Ser Gln Ala Lys Leu Ala Ser Phe
            660                 665                 670

Ile Thr Gln Tyr Ser Thr Gly Gln Val Ser Val Glu Ile Glu Trp Glu
        675                 680                 685

Leu Gln Lys Glu Asn Ser Lys Arg Trp Asn Pro Glu Ile Gln Tyr Thr
    690                 695                 700

Ser Asn Tyr Tyr Lys Ser Thr Asn Val Asp Phe Ala Val Asn Thr Asp
705                 710                 715                 720

Gly Thr Tyr Ser Glu Pro Arg Pro Ile Gly Thr Arg Tyr Leu Thr Arg
                725                 730                 735

Asn Leu
```

```
<210> SEQ ID NO 40
<211> LENGTH: 735
<212> TYPE: PRT
<213> ORGANISM: Unknown
<220> FEATURE:
<221> NAME/KEY: source
<223> OTHER INFORMATION: /note="Description of Unknown:
      Parent AAV Capsid sequence"

<400> SEQUENCE: 40
```

Met Ala Ala Asp Gly Tyr Leu Pro Asp Trp Leu Glu Asp Thr Leu Ser
1               5                   10                  15

Glu Gly Ile Arg Gln Trp Trp Lys Leu Lys Pro Gly Pro Pro Pro Pro
            20                  25                  30

Lys Pro Ala Glu Arg His Lys Asp Asp Ser Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Glu Ala Asp Ala Ala Leu Glu His Asp Lys Ala Tyr Asp
65                  70                  75                  80

Arg Gln Leu Asp Ser Gly Asp Asn Pro Tyr Leu Lys Tyr Asn His Ala
                85                  90                  95

Asp Ala Glu Phe Gln Glu Arg Leu Lys Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Pro Val Lys Thr Ala Pro Gly Lys Lys Arg
    130                 135                 140

Pro Val Glu His Ser Pro Val Glu Pro Asp Ser Ser Ser Gly Thr Gly
145                 150                 155                 160

Lys Ala Gly Gln Gln Pro Ala Arg Lys Arg Leu Asn Phe Gly Gln Thr
                165                 170                 175

Gly Asp Ala Asp Ser Val Pro Asp Pro Gln Pro Leu Gly Gln Pro Pro
            180                 185                 190

Ala Ala Pro Ser Gly Leu Gly Thr Asn Thr Met Ala Thr Gly Ser Gly
        195                 200                 205

Ala Pro Met Ala Asp Asn Asn Glu Gly Ala Asp Gly Val Gly Asn Ser
    210                 215                 220

Ser Gly Asn Trp His Cys Asp Ser Thr Trp Met Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Ser Gln Ser Gly Ala Ser Asn Asp Asn His Tyr
            260                 265                 270

Phe Gly Tyr Ser Thr Pro Trp Gly Tyr Phe Asp Phe Asn Arg Phe His
        275                 280                 285

Cys His Phe Ser Pro Arg Asp Trp Gln Arg Leu Ile Asn Asn Asn Trp
    290                 295                 300

Gly Phe Arg Pro Lys Arg Leu Asn Phe Lys Leu Phe Asn Ile Gln Val
305                 310                 315                 320

Lys Glu Val Thr Gln Asn Asp Gly Thr Thr Thr Ile Ala Asn Asn Leu
                325                 330                 335

Thr Ser Thr Val Gln Val Phe Thr Asp Ser Glu Tyr Gln Leu Pro Tyr
            340                 345                 350

Val Leu Gly Ser Ala His Gln Gly Cys Leu Pro Pro Phe Pro Ala Asp
        355                 360                 365

Val Phe Met Val Pro Gln Tyr Gly Tyr Leu Thr Leu Asn Asn Gly Ser
                370                 375                 380

Gln Ala Val Gly Arg Ser Ser Phe Tyr Cys Leu Glu Tyr Phe Pro Ser
385                 390                 395                 400

Gln Met Leu Arg Thr Gly Asn Asn Phe Thr Phe Ser Tyr Thr Phe Glu
                405                 410                 415

Asp Val Pro Phe His Ser Ser Tyr Ala His Ser Gln Ser Leu Asp Arg
                420                 425                 430

Leu Met Asn Pro Leu Ile Asp Gln Tyr Leu Tyr Tyr Leu Ser Arg Thr
                435                 440                 445

Asn Thr Pro Ser Gly Thr Thr Thr Gln Ser Arg Leu Gln Phe Ser Gln
                450                 455                 460

Ala Gly Ala Ser Asp Ile Arg Asp Gln Ser Arg Asn Trp Leu Pro Gly
465                 470                 475                 480

Pro Cys Tyr Arg Gln Gln Arg Val Ser Lys Thr Ser Ala Asp Asn Asn
                485                 490                 495

Asn Ser Glu Tyr Ser Trp Thr Gly Ala Thr Lys Tyr His Leu Asn Gly
                500                 505                 510

Arg Asp Ser Leu Val Asn Pro Gly Pro Ala Met Ala Ser His Lys Asp
                515                 520                 525

Asp Glu Glu Lys Phe Phe Pro Gln Ser Gly Val Leu Ile Phe Gly Lys
530                 535                 540

Gln Gly Ser Glu Lys Thr Asn Val Asp Ile Glu Lys Val Met Ile Thr
545                 550                 555                 560

Asp Glu Glu Glu Ile Arg Thr Thr Asn Pro Val Ala Thr Glu Gln Tyr
                565                 570                 575

Gly Ser Val Ser Thr Asn Leu Gln Arg Gly Asn Arg Gln Ala Ala Thr
                580                 585                 590

Ala Asp Val Asn Thr Gln Gly Val Leu Pro Gly Met Val Trp Gln Asp
                595                 600                 605

Arg Asp Val Tyr Leu Gln Gly Pro Ile Trp Ala Lys Ile Pro His Thr
                610                 615                 620

Asp Gly His Phe His Pro Ser Pro Leu Met Gly Gly Phe Gly Leu Lys
625                 630                 635                 640

His Pro Pro Pro Gln Ile Leu Ile Lys Asn Thr Pro Val Pro Ala Asn
                645                 650                 655

Pro Ser Thr Thr Phe Ser Ala Ala Lys Phe Ala Ser Phe Ile Thr Gln
                660                 665                 670

Tyr Ser Thr Gly Gln Val Ser Val Glu Ile Glu Trp Glu Leu Gln Lys
                675                 680                 685

Glu Asn Ser Lys Arg Trp Asn Pro Glu Ile Gln Tyr Thr Ser Asn Tyr
                690                 695                 700

Asn Lys Ser Val Asn Val Asp Phe Thr Val Asp Thr Asn Gly Val Tyr
705                 710                 715                 720

Ser Glu Pro Arg Pro Ile Gly Thr Arg Tyr Leu Thr Arg Asn Leu
                725                 730                 735

<210> SEQ ID NO 41
<211> LENGTH: 737
<212> TYPE: PRT
<213> ORGANISM: Unknown
<220> FEATURE:
<221> NAME/KEY: source
<223> OTHER INFORMATION: /note="Description of Unknown:
    Parent AAV Capsid sequence"

<400> SEQUENCE: 41

Met Ala Ala Asp Gly Tyr Leu Pro Asp Trp Leu Glu Asp Thr Leu Ser
1               5                   10                  15

Glu Gly Ile Arg Gln Trp Trp Lys Leu Lys Pro Gly Pro Pro Pro Pro
            20                  25                  30

Lys Pro Ala Glu Arg His Lys Asp Asp Ser Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Glu Ala Asp Ala Ala Leu Glu His Asp Lys Ala Tyr Asp
65                  70                  75                  80

Arg Gln Leu Asp Ser Gly Asp Asn Pro Tyr Leu Lys Tyr Asn His Ala
                85                  90                  95

Asp Ala Glu Phe Gln Glu Arg Leu Lys Glu Asp Thr Ser Phe Gly Gly
            100                 105                 110

Asn Leu Gly Arg Ala Val Phe Gln Ala Lys Lys Arg Leu Leu Glu Pro
        115                 120                 125

Leu Gly Leu Val Glu Glu Ala Ala Lys Thr Ala Pro Gly Lys Lys Arg
    130                 135                 140

Pro Val Glu His Ser Pro Val Glu Pro Asp Ser Ser Ser Gly Thr Gly
145                 150                 155                 160

Lys Ala Gly Gln Gln Pro Ala Arg Lys Arg Leu Asn Phe Gly Gln Thr
                165                 170                 175

Gly Asp Ala Asp Ser Val Pro Asp Pro Gln Pro Ile Gly Glu Pro Pro
            180                 185                 190

Ala Ala Pro Ser Gly Val Gly Ser Leu Thr Met Ala Ala Gly Gly Gly
        195                 200                 205

Ala Pro Met Ala Asp Asn Asn Glu Gly Ala Asp Gly Val Gly Asn Ser
    210                 215                 220

Ser Gly Asn Trp His Cys Asp Ser Thr Trp Met Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Asn Ser Thr Ser Gly Gly Ser Ser Asn Asp Asn
            260                 265                 270

Ala Tyr Phe Gly Tyr Ser Thr Pro Trp Gly Tyr Phe Asp Phe Asn Arg
        275                 280                 285

Phe His Cys His Phe Ser Pro Arg Asp Trp Gln Arg Leu Ile Asn Asn
    290                 295                 300

Asn Trp Gly Phe Arg Pro Lys Arg Leu Ser Phe Lys Leu Phe Asn Ile
305                 310                 315                 320

Gln Val Lys Glu Val Thr Gln Asn Glu Gly Thr Lys Thr Ile Ala Asn
                325                 330                 335

Asn Leu Thr Ser Thr Ile Gln Val Phe Thr Asp Ser Glu Tyr Gln Leu
            340                 345                 350

Pro Tyr Val Leu Gly Ser Ala His Gln Gly Cys Leu Pro Pro Phe Pro
        355                 360                 365

Ala Asp Val Phe Met Ile Pro Gln Tyr Gly Tyr Leu Thr Leu Asn Asn
    370                 375                 380

Gly Ser Gln Ala Val Gly Arg Ser Ser Phe Tyr Cys Leu Glu Tyr Phe
385                 390                 395                 400

Pro Ser Gln Met Leu Arg Thr Gly Asn Asn Phe Gln Phe Thr Tyr Thr

```
                    405                 410                 415
Phe Glu Asp Val Pro Phe His Ser Ser Tyr Ala His Ser Gln Ser Leu
                420                 425                 430

Asp Arg Leu Met Asn Pro Leu Ile Asp Gln Tyr Leu Tyr Tyr Leu Ser
            435                 440                 445

Arg Thr Gln Thr Thr Gly Gly Thr Thr Asn Thr Gln Thr Leu Gly Phe
        450                 455                 460

Ser Gln Gly Gly Pro Asn Thr Met Ala Asn Gln Ala Lys Asn Trp Leu
465                 470                 475                 480

Pro Gly Pro Cys Tyr Arg Gln Gln Arg Val Ser Lys Thr Ser Ala Asp
                485                 490                 495

Asn Asn Asn Ser Glu Tyr Ser Trp Thr Gly Ala Thr Lys Tyr His Leu
            500                 505                 510

Asn Gly Arg Asp Ser Leu Val Asn Pro Gly Pro Ala Met Ala Ser His
        515                 520                 525

Lys Asp Asp Glu Glu Lys Phe Phe Pro Gln Ser Gly Val Leu Ile Phe
530                 535                 540

Gly Lys Gln Gly Ser Glu Lys Thr Asn Val Asp Ile Glu Lys Val Met
545                 550                 555                 560

Ile Thr Asp Glu Glu Glu Ile Arg Thr Thr Asn Pro Val Ala Thr Glu
                565                 570                 575

Gln Tyr Gly Ser Val Ser Thr Asn Leu Gln Arg Gly Asn Arg Gln Ala
            580                 585                 590

Ala Thr Ala Asp Val Asn Thr Gln Gly Val Leu Pro Gly Met Val Trp
        595                 600                 605

Gln Asp Arg Asp Val Tyr Leu Gln Gly Pro Ile Trp Ala Lys Ile Pro
610                 615                 620

His Thr Asp Gly His Phe His Pro Ser Pro Leu Met Gly Gly Phe Gly
625                 630                 635                 640

Leu Lys His Pro Pro Pro Gln Ile Leu Ile Lys Asn Thr Pro Val Pro
                645                 650                 655

Ala Asp Pro Pro Thr Thr Phe Asn Gln Ser Lys Leu Asn Ser Phe Ile
            660                 665                 670

Thr Gln Tyr Ser Thr Gly Gln Val Ser Val Glu Ile Glu Trp Glu Leu
        675                 680                 685

Gln Lys Glu Asn Ser Lys Arg Trp Asn Pro Glu Ile Gln Tyr Thr Ser
690                 695                 700

Asn Tyr Tyr Lys Ser Thr Ser Val Asp Phe Ala Val Asn Thr Glu Gly
705                 710                 715                 720

Val Tyr Ser Glu Pro Arg Pro Ile Gly Thr Arg Tyr Leu Thr Arg Asn
                725                 730                 735

Leu

<210> SEQ ID NO 42
<211> LENGTH: 736
<212> TYPE: PRT
<213> ORGANISM: Unknown
<220> FEATURE:
<221> NAME/KEY: source
<223> OTHER INFORMATION: /note="Description of Unknown:
      Parent AAV Capsid sequence"

<400> SEQUENCE: 42

Met Ser Phe Val Asp His Pro Pro Asp Trp Leu Glu Ser Ile Gly Asp
1               5                   10                  15
```

Gly Phe Arg Glu Phe Leu Gly Leu Glu Ala Gly Pro Pro Lys Pro Lys
                20                  25                  30

Ala Asn Gln Gln Lys Gln Asp Asn Ala Arg Gly Leu Val Leu Pro Gly
            35                  40                  45

Tyr Lys Tyr Leu Gly Pro Gly Asn Gly Leu Asp Lys Gly Asp Pro Val
        50                  55                  60

Asn Phe Ala Asp Glu Val Ala Arg Glu His Asp Leu Ser Tyr Gln Lys
65                  70                  75                  80

Gln Leu Glu Ala Gly Asp Asn Pro Tyr Leu Lys Tyr Asn His Ala Asp
                85                  90                  95

Ala Glu Phe Gln Glu Lys Leu Ala Ser Asp Thr Ser Phe Gly Gly Asn
            100                 105                 110

Leu Gly Lys Ala Val Phe Gln Ala Lys Lys Arg Ile Leu Glu Pro Leu
        115                 120                 125

Gly Leu Val Glu Thr Pro Asp Lys Thr Ala Pro Ala Ala Lys Lys Arg
    130                 135                 140

Pro Leu Glu Gln Ser Pro Gln Glu Pro Asp Ser Ser Gly Val Gly
145                 150                 155                 160

Lys Lys Gly Lys Gln Pro Ala Arg Lys Arg Leu Asn Phe Asp Asp Glu
                165                 170                 175

Pro Gly Ala Gly Asp Gly Pro Pro Glu Gly Pro Ser Ser Gly Ala
            180                 185                 190

Met Ser Thr Glu Thr Glu Met Arg Ala Ala Gly Asn Gly Gly
        195                 200                 205

Asp Ala Gly Gln Gly Ala Glu Gly Val Gly Asn Ala Ser Gly Asp Trp
    210                 215                 220

His Cys Asp Ser Thr Trp Ser Glu Ser His Val Thr Thr Thr Ser Thr
225                 230                 235                 240

Arg Thr Trp Val Leu Pro Thr Tyr Asn Asn His Leu Tyr Leu Arg Leu
                245                 250                 255

Gly Ser Ser Asn Ala Ser Asp Thr Phe Asn Gly Phe Ser Thr Pro Trp
            260                 265                 270

Gly Tyr Phe Asp Phe Asn Arg Phe His Cys His Phe Ser Pro Arg Asp
        275                 280                 285

Trp Gln Arg Leu Ile Asn Asn His Trp Gly Leu Arg Pro Lys Ser Met
    290                 295                 300

Gln Val Arg Ile Phe Asn Ile Gln Val Lys Glu Val Thr Thr Ser Asn
305                 310                 315                 320

Gly Glu Thr Thr Val Ser Asn Asn Leu Thr Ser Thr Val Gln Ile Phe
                325                 330                 335

Ala Asp Ser Thr Tyr Glu Leu Pro Tyr Val Met Asp Ala Gly Gln Glu
            340                 345                 350

Gly Ser Leu Pro Pro Phe Pro Asn Asp Val Phe Met Val Pro Gln Tyr
        355                 360                 365

Gly Tyr Cys Gly Leu Val Thr Gly Gly Ser Ser Gln Asn Gln Thr Asp
    370                 375                 380

Arg Asn Ala Phe Tyr Cys Leu Glu Tyr Phe Pro Ser Gln Met Leu Arg
385                 390                 395                 400

Thr Gly Asn Asn Phe Glu Met Val Tyr Lys Phe Glu Asn Val Pro Phe
                405                 410                 415

His Ser Met Tyr Ala His Ser Gln Ser Leu Asp Arg Leu Met Asn Pro
            420                 425                 430

Leu Leu Asp Gln Tyr Leu Trp Glu Leu Gln Ser Thr Thr Ser Gly Gly

```
                        435                 440                 445
        Thr Leu Asn Gln Gly Asn Ser Ala Thr Asn Phe Ala Lys Leu Thr Lys
            450                 455                 460
        Thr Asn Phe Ser Gly Tyr Arg Lys Asn Trp Leu Pro Gly Pro Met Met
        465                 470                 475                 480
        Lys Gln Gln Arg Phe Ser Lys Thr Ala Ser Gln Asn Tyr Lys Ile Pro
                        485                 490                 495
        Gln Gly Arg Asn Asn Ser Leu Leu His Tyr Glu Thr Arg Thr Thr Leu
                    500                 505                 510
        Asp Gly Arg Trp Ser Asn Phe Ala Pro Gly Thr Ala Met Ala Thr Ala
                515                 520                 525
        Ala Asn Asp Ala Thr Asp Phe Ser Gln Ala Gln Leu Ile Phe Ala Gly
            530                 535                 540
        Pro Asn Ile Thr Gly Asn Thr Thr Thr Asp Ala Asn Asn Leu Met Phe
        545                 550                 555                 560
        Thr Ser Glu Asp Glu Leu Arg Ala Thr Asn Pro Arg Asp Thr Asp Leu
                        565                 570                 575
        Phe Gly His Leu Ala Thr Asn Gln Gln Asn Ala Thr Thr Val Pro Thr
                    580                 585                 590
        Val Asp Asp Val Asp Gly Val Gly Val Tyr Pro Gly Met Val Trp Gln
                595                 600                 605
        Asp Arg Asp Ile Tyr Tyr Gln Gly Pro Ile Trp Ala Lys Ile Pro His
            610                 615                 620
        Thr Asp Gly His Phe His Pro Ser Pro Leu Ile Gly Gly Phe Gly Leu
        625                 630                 635                 640
        Lys Ser Pro Pro Pro Gln Ile Phe Ile Lys Asn Thr Pro Val Pro Ala
                        645                 650                 655
        Asn Pro Ala Thr Thr Phe Ser Pro Ala Arg Ile Asn Ser Phe Ile Thr
                    660                 665                 670
        Gln Tyr Ser Thr Gly Gln Val Ala Val Lys Ile Glu Trp Glu Ile Gln
                675                 680                 685
        Lys Glu Arg Ser Lys Arg Trp Asn Pro Glu Val Gln Phe Thr Ser Asn
            690                 695                 700
        Tyr Gly Ala Gln Asp Ser Leu Leu Trp Ala Pro Asp Asn Ala Gly Ala
        705                 710                 715                 720
        Tyr Lys Glu Pro Arg Ala Ile Gly Ser Arg Tyr Leu Thr Asn His Leu
                        725                 730                 735

<210> SEQ ID NO 43
<211> LENGTH: 734
<212> TYPE: PRT
<213> ORGANISM: Unknown
<220> FEATURE:
<221> NAME/KEY: source
<223> OTHER INFORMATION: /note="Description of Unknown:
      Parent AAV Capsid sequence"

<400> SEQUENCE: 43

Met Thr Asp Gly Tyr Leu Pro Asp Trp Leu Glu Asp Asn Leu Ser Glu
1               5                   10                  15

Gly Val Arg Glu Trp Trp Ala Leu Gln Pro Gly Ala Pro Lys Pro Lys
                20                  25                  30

Ala Asn Gln Gln His Gln Asp Asn Ala Arg Gly Leu Val Leu Pro Gly
            35                  40                  45

Tyr Lys Tyr Leu Gly Pro Gly Asn Gly Leu Asp Lys Gly Glu Pro Val
        50                  55                  60
```

```
Asn Ala Ala Asp Ala Ala Ala Leu Glu His Asp Lys Ala Tyr Asp Gln
 65                  70                  75                  80

Gln Leu Lys Ala Gly Asp Asn Pro Tyr Leu Lys Tyr Asn His Ala Asp
                 85                  90                  95

Ala Glu Phe Gln Gln Arg Leu Gln Gly Asp Thr Ser Phe Gly Gly Asn
            100                 105                 110

Leu Gly Arg Ala Val Phe Gln Ala Lys Lys Arg Val Leu Glu Pro Leu
        115                 120                 125

Gly Leu Val Glu Gln Ala Gly Glu Thr Ala Pro Gly Lys Lys Arg Pro
    130                 135                 140

Leu Ile Glu Ser Pro Gln Pro Asp Ser Ser Thr Gly Ile Gly Lys
145                 150                 155                 160

Lys Gly Lys Gln Pro Ala Lys Lys Leu Val Phe Glu Asp Glu Thr
                165                 170                 175

Gly Ala Gly Asp Gly Pro Pro Glu Gly Ser Thr Ser Gly Ala Met Ser
            180                 185                 190

Asp Asp Ser Glu Met Arg Ala Ala Gly Ala Ala Val Glu Gly
        195                 200                 205

Gly Gln Gly Ala Asp Gly Val Gly Asn Ala Ser Gly Asp Trp His Cys
    210                 215                 220

Asp Ser Thr Trp Ser Glu Gly His Val Thr Thr Thr Ser Thr Arg Thr
225                 230                 235                 240

Trp Val Leu Pro Thr Tyr Asn Asn His Leu Tyr Lys Arg Leu Gly Glu
                245                 250                 255

Ser Leu Gln Ser Asn Thr Tyr Asn Gly Phe Ser Thr Pro Trp Gly Tyr
                260                 265                 270

Phe Asp Phe Asn Arg Phe His Cys His Phe Ser Pro Arg Asp Trp Gln
            275                 280                 285

Arg Leu Ile Asn Asn Asn Trp Gly Met Arg Pro Lys Ala Met Arg Val
        290                 295                 300

Lys Ile Phe Asn Ile Gln Val Lys Glu Val Thr Thr Ser Asn Gly Glu
305                 310                 315                 320

Thr Thr Val Ala Asn Asn Leu Thr Ser Thr Val Gln Ile Phe Ala Asp
                325                 330                 335

Ser Ser Tyr Glu Leu Pro Tyr Val Met Asp Ala Gly Gln Glu Gly Ser
            340                 345                 350

Leu Pro Pro Phe Pro Asn Asp Val Phe Met Val Pro Gln Tyr Gly Tyr
        355                 360                 365

Cys Gly Leu Val Thr Gly Asn Thr Ser Gln Gln Thr Asp Arg Asn
    370                 375                 380

Ala Phe Tyr Cys Leu Glu Tyr Phe Pro Ser Gln Met Leu Arg Thr Gly
385                 390                 395                 400

Asn Asn Phe Glu Ile Thr Tyr Ser Phe Glu Lys Val Pro Phe His Ser
                405                 410                 415

Met Tyr Ala His Ser Gln Ser Leu Asp Arg Leu Met Asn Pro Leu Ile
            420                 425                 430

Asp Gln Tyr Leu Trp Gly Leu Gln Ser Thr Thr Thr Gly Thr Thr Leu
        435                 440                 445

Asn Ala Gly Thr Ala Thr Thr Asn Phe Thr Lys Leu Arg Pro Thr Asn
    450                 455                 460

Phe Ser Asn Phe Lys Lys Asn Trp Leu Pro Gly Pro Ser Ile Lys Gln
465                 470                 475                 480
```

```
Gln Gly Phe Ser Lys Thr Ala Asn Gln Asn Tyr Lys Ile Pro Ala Thr
            485                 490                 495

Gly Ser Asp Ser Leu Ile Lys Tyr Glu Thr His Ser Thr Leu Asp Gly
        500                 505                 510

Arg Trp Ser Ala Leu Thr Pro Gly Pro Pro Met Ala Thr Ala Gly Pro
    515                 520                 525

Ala Asp Ser Lys Phe Ser Asn Ser Gln Leu Ile Phe Ala Gly Pro Glu
530                 535                 540

Gln Asn Gly Asn Thr Ala Thr Val Pro Gly Thr Leu Ile Phe Thr Ser
545                 550                 555                 560

Glu Glu Glu Leu Ala Ala Thr Asn Ala Thr Asp Thr Asp Met Trp Gly
            565                 570                 575

Asn Leu Pro Gly Gly Asp Gln Ser Asn Ser Asn Leu Pro Thr Val Asp
        580                 585                 590

Arg Leu Thr Ala Leu Gly Ala Val Pro Gly Met Val Trp Gln Asn Arg
    595                 600                 605

Asp Ile Tyr Tyr Gln Gly Pro Ile Trp Ala Lys Ile Pro His Thr Asp
610                 615                 620

Gly His Phe His Pro Ser Pro Leu Ile Gly Gly Phe Gly Leu Lys His
625                 630                 635                 640

Pro Pro Pro Gln Ile Phe Ile Lys Asn Thr Pro Val Pro Ala Asn Pro
            645                 650                 655

Ala Thr Thr Phe Ser Ser Thr Pro Val Asn Ser Phe Ile Thr Gln Tyr
        660                 665                 670

Ser Thr Gly Gln Val Ser Val Gln Ile Asp Trp Glu Ile Gln Lys Glu
    675                 680                 685

Arg Ser Lys Arg Trp Asn Pro Glu Val Gln Phe Thr Ser Asn Tyr Gly
690                 695                 700

Gln Gln Asn Ser Leu Leu Trp Ala Pro Asp Ala Ala Gly Lys Tyr Thr
705                 710                 715                 720

Glu Pro Arg Ala Ile Gly Thr Arg Tyr Leu Thr His His Leu
            725                 730

<210> SEQ ID NO 44
<211> LENGTH: 742
<212> TYPE: PRT
<213> ORGANISM: Unknown
<220> FEATURE:
<221> NAME/KEY: source
<223> OTHER INFORMATION: /note="Description of Unknown:
      Parent AAV Capsid sequence"

<400> SEQUENCE: 44

Met Ala Ala Asp Gly Tyr Leu Pro Asp Trp Leu Glu Asp Asn Leu Ser
1               5                   10                  15

Glu Gly Ile Arg Glu Trp Trp Ala Leu Lys Pro Gly Ala Pro Gln Pro
            20                  25                  30

Lys Ala Asn Gln Gln His Gln Asp Asn Gly Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Glu Ala Asp Ala Ala Ala Leu Glu His Asp Lys Ala Tyr Asp
65                  70                  75                  80

Lys Gln Leu Glu Gln Gly Asp Asn Pro Tyr Leu Lys Tyr Asn His Gly
            85                  90                  95

Asp Ala Glu Phe Gln Gln Arg Leu Ala Thr Asp Thr Ser Phe Gly Gly
```

-continued

```
                100                 105                 110
Asn Leu Gly Arg Ala Val Phe Gln Ala Lys Lys Arg Ile Leu Glu Pro
            115                 120                 125
Leu Gly Leu Val Glu Glu Gly Val Lys Thr Ala Pro Gly Lys Lys Arg
        130                 135                 140
Pro Leu Glu Lys Thr Pro Asn Arg Pro Thr Asn Pro Asp Ser Gly Lys
145                 150                 155                 160
Ala Pro Ala Lys Lys Lys Gln Lys Asp Gly Glu Pro Ala Asp Ser Ala
                165                 170                 175
Arg Arg Thr Leu Asp Phe Glu Asp Ser Gly Ala Gly Asp Gly Pro Pro
            180                 185                 190
Glu Gly Ser Ser Ser Gly Glu Met Ser His Asp Ala Glu Met Arg Ala
        195                 200                 205
Ala Pro Gly Gly Asn Ala Val Glu Ala Gly Gln Gly Ala Asp Gly Val
    210                 215                 220
Gly Asn Ala Ser Gly Asp Trp His Cys Asp Ser Thr Trp Ser Glu Gly
225                 230                 235                 240
Arg Val Thr Thr Thr Ser Thr Arg Thr Trp Val Leu Pro Thr Tyr Asn
                245                 250                 255
Asn His Leu Tyr Leu Arg Ile Gly Thr Thr Ala Asn Ser Asn Thr Tyr
            260                 265                 270
Asn Gly Phe Ser Thr Pro Trp Gly Tyr Phe Asp Phe Asn Arg Phe His
        275                 280                 285
Cys His Phe Ser Pro Arg Asp Trp Gln Arg Leu Ile Asn Asn Asn Trp
    290                 295                 300
Gly Leu Arg Pro Lys Ser Met Arg Val Lys Ile Phe Asn Ile Gln Val
305                 310                 315                 320
Lys Glu Val Thr Thr Ser Asn Gly Glu Thr Thr Val Ala Asn Asn Leu
                325                 330                 335
Thr Ser Thr Val Gln Ile Phe Ala Asp Ser Thr Tyr Glu Leu Pro Tyr
            340                 345                 350
Val Met Asp Ala Gly Gln Glu Gly Ser Phe Pro Pro Phe Pro Asn Asp
        355                 360                 365
Val Phe Met Val Pro Gln Tyr Gly Tyr Cys Gly Val Val Thr Gly Lys
    370                 375                 380
Asn Gln Asn Gln Thr Asp Arg Asn Ala Phe Tyr Cys Leu Glu Tyr Phe
385                 390                 395                 400
Pro Ser Gln Met Leu Arg Thr Gly Asn Asn Phe Glu Val Ser Tyr Gln
                405                 410                 415
Phe Glu Lys Val Pro Phe His Ser Met Tyr Ala His Ser Gln Ser Leu
            420                 425                 430
Asp Arg Met Met Asn Pro Leu Leu Asp Gln Tyr Leu Trp His Leu Gln
        435                 440                 445
Ser Thr Thr Thr Gly Asn Ser Leu Asn Gln Gly Thr Ala Thr Thr Thr
    450                 455                 460
Tyr Gly Lys Ile Thr Thr Gly Asp Phe Ala Tyr Tyr Arg Lys Asn Trp
465                 470                 475                 480
Leu Pro Gly Ala Cys Ile Lys Gln Gln Lys Phe Ser Lys Asn Ala Asn
                485                 490                 495
Gln Asn Tyr Lys Ile Pro Ala Ser Gly Gly Asp Ala Leu Leu Lys Tyr
            500                 505                 510
Asp Thr His Thr Thr Leu Asn Gly Arg Trp Ser Asn Met Ala Pro Gly
        515                 520                 525
```

```
Pro Pro Met Ala Thr Ala Gly Ala Gly Asp Ser Asp Phe Ser Asn Ser
    530                 535                 540
Gln Leu Ile Phe Ala Gly Pro Asn Pro Ser Gly Asn Thr Thr Thr Ser
545                 550                 555                 560
Ser Asn Asn Leu Leu Phe Thr Ser Glu Glu Glu Ile Ala Thr Thr Asn
            565                 570                 575
Pro Arg Asp Thr Asp Met Phe Gly Gln Ile Ala Asp Asn Asn Gln Asn
                580                 585                 590
Ala Thr Thr Ala Pro His Ile Ala Asn Leu Asp Ala Met Gly Ile Val
        595                 600                 605
Pro Gly Met Val Trp Gln Asn Arg Asp Ile Tyr Tyr Gln Gly Pro Ile
    610                 615                 620
Trp Ala Lys Val Pro His Thr Asp Gly His Phe His Pro Ser Pro Leu
625                 630                 635                 640
Met Gly Gly Phe Gly Leu Lys His Pro Pro Pro Gln Ile Phe Ile Lys
            645                 650                 655
Asn Thr Pro Val Pro Ala Asn Pro Asn Thr Thr Phe Ser Ala Ala Arg
                660                 665                 670
Ile Asn Ser Phe Leu Thr Gln Tyr Ser Thr Gly Gln Val Ala Val Gln
        675                 680                 685
Ile Asp Trp Glu Ile Gln Lys Glu His Ser Lys Arg Trp Asn Pro Glu
    690                 695                 700
Val Gln Phe Thr Ser Asn Tyr Gly Thr Gln Asn Ser Met Leu Trp Ala
705                 710                 715                 720
Pro Asp Asn Ala Gly Asn Tyr His Glu Leu Arg Ala Ile Gly Ser Arg
                725                 730                 735
Phe Leu Thr His His Leu
            740

<210> SEQ ID NO 45
<211> LENGTH: 2232
<212> TYPE: DNA
<213> ORGANISM: Unknown
<220> FEATURE:
<221> NAME/KEY: source
<223> OTHER INFORMATION: /note="Description of Unknown:
      Parent AAV Capsid sequence"

<400> SEQUENCE: 45
atgtctctca tttctgatgc gattccagat tggttggagc ggttggtcaa aaagggagtg     60
aatgctgcag ctgatttcta ccatttggaa agcggtcctc ctcgtcctaa ggcaaatcag    120
caaactcaag aatctcttga aaaggacgat tcgagaggtc tcgtgttccc aggctacaat    180
tatctaggcc ctttcaacgg tctagataaa ggagaacccg tcaacgaggc agacgctgcc    240
gccttagaac acgacaaggc ttacgacctc gaaatcaagg acgggcacaa cccgtacttt    300
gagtacaacg aggccgacag acgtttccag aacgtctcaa agacgatac ctcctttgga    360 ggcaatttag gtaaagccat cttccaggcc aaaaagaggg ttctcgaacc ctttggtctg    420
gtggaagact caaagacggc tccgaccgga gacaagcgga aggcgaaga cgaacctcgt    480 ctgccccgaca ctcctccaca gactcccaag aaaaacaaga gcctcgcaa ggaaagacct    540 tccggcgggg cagaagatcc gggcgaaggc acctcttcca acgctggagc agcagcaccc    600
gcctctagtg tgggatcatc tatcatggct gaaggaggtg cgggcccagt gggcgatgca    660
ggccagggtg ccgatggagt gggcaattcc tcgggaaatt ggcattgcga ttcccaatgg    720
```

| | |
|---|---|
| ctggaaaacg gagtcgtcac tcgaaccacc cgaacctggg tcttgcccag ctacaacaac | 780 |
| cacctgtaca aacgaatcca aggacccagc ggaggcgaca caacaacaa attctttgga | 840 |
| ttcagcaccc cctggggata ctttgactac aatcgattcc actgccactt tccccgcga | 900 |
| gactggcaac gactcatcaa caacaactgg ggcatccgtc ccaaagcgat gcgctttaga | 960 |
| ctctttaaca tccaggttaa agaggtcacg gtccaagact ccaacaccac catcgccaac | 1020 |
| aacctcacca gtacggtcca ggtctttgcg gacaaggact accaactgcc gtacgtcctc | 1080 |
| ggatcggcta ccgaaggcac cttcccgccg ttcccagcgg atatctacac gatcccgcag | 1140 |
| tacgggtact gcacgctaaa ctacaacaac gaggcggtgg atcgttcggc cttctactgt | 1200 |
| ctggactact ttccctcaga catgctgcgg acaggaaata actttgagtt tacttacacc | 1260 |
| ttcgaggacg ttccttttcca tagcatgttt gcccacaacc agacgctaga ccggctgatg | 1320 |
| aatcccctcg tggatcagta cctctgggct ttcagctccg tcagccaagc aggctcatct | 1380 |
| ggacgagctc ttcattactc gcgggcgact aaaaccaaca tggcggctca atataggaac | 1440 |
| tggttacctg gccttttctt ccgtgatcag caaatcttta cgggcgctag caacatcact | 1500 |
| aaaaataacg tctttagcgt ttgggaaaaa ggcaagcaat gggaactcga caatcggacc | 1560 |
| aacctaatgc agcccggtcc tgcggcagcg accacctta gcggagaacc tgaccgtcaa | 1620 |
| gccatgcaaa acacgctggc ttttagcagg accgtctacg atcaaacgac cgccacgacc | 1680 |
| gatcgtaacc agatactcat caccaacgaa gacgaaatca gacccaccaa ctcggtcggt | 1740 |
| atcgacgcgt ggggagcagt tcccaccaac aaccagtcga tcgtgacccc cggcactcgc | 1800 |
| gcggccgtca acaatcaagg ggcgcttccc gggatggtgt ggcaaaacag agacatttac | 1860 |
| ctacagggac ccatttgggc caaaattccc gacactgaca atcacttcca tccgtccccg | 1920 |
| cttattggcg ggtttggctg caagcatccc cctccccaga ttttcattaa aaacacaccc | 1980 |
| gtccctgcca acccttcgga aacgttccag acggccaaag tggcctcctt catcaaccag | 2040 |
| tactcgaccg gacagtgcac cgtcgaaatc ttttgggaac tcaagaagga aacctccaag | 2100 |
| cgctggaacc ccgaaatcca gttcacctcc aactttggca acgcggccga catccagttt | 2160 |
| gccgtctccg acacgggatc ctattccgaa cctcgtccca tcggtacccg ttaccttacc | 2220 |
| aaacctctgt aa | 2232 |

<210> SEQ ID NO 46
<211> LENGTH: 2151
<212> TYPE: DNA
<213> ORGANISM: Unknown
<220> FEATURE:
<221> NAME/KEY: source
<223> OTHER INFORMATION: /note="Description of Unknown:
    Parent AAV Capsid sequence"

<400> SEQUENCE: 46

| | |
|---|---|
| atgtcgtttg ttgatcaccc tccagattgg cttgaggaga ttggtgaggg tctaaaggag | 60 |
| tttttgggac tcgaacctgg cccacccaaa ccgaagccca accagcagaa gcaagacgac | 120 |
| gcccgtggtc ttgtactgcc tggatataat tacctgggac ccggaaacgg tctcgaccgc | 180 |
| ggagaacctg tcaaccgggc tgacgaggtc gcgcgagagc acgacatctc gtacaacgag | 240 |
| cagctccagg cgggagacaa cccctacctc aagtacaacc acgcggacgc cgagtttcag | 300 |
| gagaagctcg cggacgacac ctccttcggg ggcaacctcg gcaaggcagt ctttcaggcc | 360 |
| aaaaaaaggg ttctcgaacc ttttggcctg gttgaggagc tgttaagac ggctgctaaa | 420 |
| ggcgagcgga tagacgacca ctatcccaaa aagaagaagg ctcggatcga agagaccgaa | 480 |

-continued

```
gctggaacca gcggagccca gcagctgcag atcccagccc aaccagcctc aagtttggga      540
gctgatacaa tgtctgcggg aggtggcagc ccactgggcg acaataacca aggcgccgat      600
ggagtgggca atgcctcggg agattggcat tgcgattcca cgtggatggg ggaccgagtc      660
atcaccaagt ccaccgaac ctgggtgctg cccagctaca caaccatca gtaccttgag       720 atccacagcg gttccgtcga cggaagcaac gctaacgctt attttggata cagcaccccc      780
tgggggtact tgacttcaa ccgcttccac agccactgga gccccgaga ctggcagcga       840 ctcgtcaaca actactgggg attcagaccc cggtccctca aggtcaagat ctttaacatc      900
caagtcaagg aagtcacgac gcaggacggc accaccacca tcgccaacaa cctcacctcc      960
accgtccaag tgtttacgga caacgactac cagctaccgt acgtcatcgg caacggaacg     1020
gaggggtgcc tgccggcctt ccctccgcag gtctttacgc tgccgcagta cggctacgcg     1080
acactgaacc gtaacaacac cgacgatccc accgagcgga cagtttcttt ctgcctggaa    1140
tactttccca gcaagatgct gcggacgggc aacaactttg aattcaccta cagcttcgag     1200
gaggtgccct tccactgcag cttcgctccc agccagaacc tcttcaagct ggccaatccg     1260
ctggtggacc agtacctgta ccgctttgtg agcaccgaca cttccggtaa cctacagttc    1320
caaaagaact tgaaggccag atatgccaac acttacaaga attggtttcc ggggcccatg    1380
tgccggaccc agggctggta cacaagcgcg gcacatata caacaaagg cgttgccaac     1440 tttgatactt caaacaagat ggaactggag ggggctagtt accaagtaaa ccctcaacca     1500 aatgaatga caaacacgct tcaggatagt aacaaatacg cgcttgaaaa caccatgatc     1560
ttcaacgcac agaacgcccc tccgggaacg acctctctgt accaggagaa caatctttttg    1620 ataaccagcg agagcgagac gcagcctgtg aaccgattgg cctacaacac cggtggtcag    1680
gtatcaaaca caaccagaa ttcaaataca catcctacgg tcggagtata caataccag     1740 gaagtgttgc ctggtagcgt gtggatggac agagacgtat accttcaggg ccccatctgg    1800
gccaaaatcc cggagacagg ggcacacttt catccttctc cggctatggg cggattcgga    1860
ctcaaacacc caccgcccat gatgctcatc aagaacacac cggtacctag caacgtcgct    1920
gccttctctg acgtgcccgt taaaagcttc atcacccagt acagcaccgg acaggtcacg     1980
gtggagattg aatgggagct caagaaagaa aactccaaga ggtggaatcc cgagatacag    2040
tacaccaaca actacaacaa ccctacattc gtggactttg ctccagacac ctccggcgag    2100
tacaggacta cgagggctat tggaacccgt taccttaccc gaccctgta a              2151
```

<210> SEQ ID NO 47
<211> LENGTH: 2175
<212> TYPE: DNA
<213> ORGANISM: Unknown
<220> FEATURE:
<221> NAME/KEY: source
<223> OTHER INFORMATION: /note="Description of Unknown:
      Parent AAV Capsid sequence"

<400> SEQUENCE: 47

```
atgtcttttg ttgatcaccc tccagattgg ttggaagaag ttggtgaagg tcttcgcgag       60
tttttgggcc ttgaagcggg cccaccgaaa ccaaaaccca atcagcagca tcaagatcaa      120
gcccgtggtc ttgtgctgcc tggttataac tatctcggac ccggaaacgg tctcgatcga     180
ggagagcctg tcaacagggc agacgaggtc gcgcgagagc acgacatctc gtacaacgag     240
cagcttgagg cgggagacaa cccctacctc aagtacaacc acgcggacgc cgagtttcag     300
```

```
gagaagctcg ccgacgacac atccttcggg ggaaacctcg gaaaggcagt ctttcaggcc    360
aagaaaaggg ttctcgaacc ttttggcctg gttgaagagg gtgctaagac ggcccctacc    420
ggaaagcgga tagacgacca ctttccaaaa agaaagaagg ctcggaccga agaggactcc    480
aagccttcca cctcgtcaga cgccgaagct ggacccagcg gatcccagca gctgcaaatc    540
ccagcccaac cagcctcaag tttgggagct gatacaatgt ctgcgggagg tggcggccca    600
ttgggcgaca ataaccaagg tgccgatgga gtgggcaatg cctcgggaga ttggcattgc    660
gattccacgt ggatggggga cagagtcgtc accaagtcca cccgaacctg ggtgctgccc    720
agctacaaca accaccagta ccgagagatc aaaagcggct ccgtcgacgg aagcaacgcc    780
aacgcctact ttggatacag cacccccctgg gggtactttg actttaaccg cttccacagc    840
cactggagcc cccgagactg gcaaagactc atcaacaact actggggctt cagaccccgg    900
tccctcagag tcaaaatctt caacattcaa gtcaagagg tcacggtgca ggactccacc    960
accaccatcg ccaacaacct cacctccacc gtccaagtgt ttacgacga cgactaccag   1020
ctgcccacg tcgtcggcaa cgggaccgag ggatgcctgc cggccttccc tccgcaggtc   1080
tttacgctgc cgcagtacgg ttacgcgacg ctgaaccgcg acaacacaga aaatcccacc   1140
gagaggagca gcttcttctg cctagagtac tttcccagca agatgctgag aacgggcaac   1200
aactttgagt ttacctacaa cttttgaggag gtgcccttcc actccagctt cgctcccagt   1260
cagaacctct tcaagctggc caacccgctg gtggaccagt acttgtaccg cttcgtgagc   1320
acaaataaca ctggcggagt ccagttcaac aagaacctgg ccgggagata cgccaacacc   1380
tacaaaaact ggttcccggg gcccatgggc cgaacccagg gctggaacct gggctccggg   1440
gtcaaccgcg ccagtgtcag cgccttcgcc acgaccaata ggatggagct cgagggcgcg   1500
agttaccagg tgcccccgca gccgaacggc atgaccaaca cctccagggg cagcaacacc   1560
tatgccctgg agaacactat gatcttcaac agccagccgg cgaacccggg caccaccgcc   1620
acgtacctcg agggcaacat gctcatcacc agcgagagcg agacgcagcc ggtgaaccgc   1680
gtggcgtaca acgtcggcgg gcagatggcc accaacaacc agagctccac cactgccccc   1740
gcgaccggca cgtacaacct ccaggaaatc gtgcccggca gcgtgtggat ggagagggac   1800
gtgtacctcc aaggacccat ctgggccaag atcccagaga cggggcgcgca ctttcacccc   1860
tctccggcca tggcggatt cggactcaaa caccccaccgc ccatgatgct catcaagaac   1920
acgcctgtgc ccggaaatat caccagcttc tcggacgtgc ccgtcagcag cttcatcacc   1980
cagtacagca ccgggcaggt caccgtggag atggagtggg agctcaagaa ggaaaactcc   2040
aagaggtgga acccagagat ccagtacaca aacaactaca acgaccccca gtttgtggac   2100
tttgccccgg acagcaccgg ggaatacaga accaccagac ctatcggaac ccgatacctt   2160
acccgacccc tttaa                                                     2175
```

<210> SEQ ID NO 48
<211> LENGTH: 2181
<212> TYPE: DNA
<213> ORGANISM: Unknown
<220> FEATURE:
<221> NAME/KEY: source
<223> OTHER INFORMATION: /note="Description of Unknown:
      Parent AAV Capsid sequence"

<400> SEQUENCE: 48

```
atgtcttttg ttgatcaccc tccagattgg ttggaagaag ttggtgaagg tcttcgcgag     60
tttttgggcc ttgaagcggg cccaccgaaa ccgaaaccca accagcagca tcaagatcaa    120
```

```
gcccgtggtc ttgtgctgcc tggttataac tatctcggac ccggaaacgg tctcgatcga      180
ggagagcctg tcaacagggc agacgaggtc gcgcgagagc acgacatctc gtacaacgag      240
cagcttgagg cgggagacaa ccctacctc aagtacaacc acgcggacgc cgagttccag       300
gagaagctcg ccgacgacac atccttcggg ggaaacctcg gaaaggcagt ctttcaggcc      360
aagaaaaggg ttctcgaacc ttttggcctg gttgaagagg gtgctaagac ggcccctacc      420
ggaaagcgga tagacgacca cttttccaaaa agaaagaagg ctcggaccga agaggactcc     480
aagccttcca cctcgtcaga cgccgaagct ggacccagcg gatcccagca gctgcaaatc      540
ccagcacaac cagcctcaag tttgggagct gatacaatgt ctgcgggagg tggcggccca     600
ttgggcgaca ataaccaagg tgccgatgga gtgggcaatg cctcgggaga ttggcattgc     660
gattccacgt ggatggggga cagagtcgtc accaagtcca cccgcacctg ggtgctgccc     720
agctacaaca accaccagta ccgagagatc aaaagcggct ccgtcgacgg aagcaacgcc     780
aacgcctact ttggatacag cacccctgg gggtactttg actttaaccg cttccacagc      840
cactggagcc ccgagactg gcaaagactc atcaacaact attggggctt cagaccccgg       900
tctctcagag tcaaaatctt caacatccaa gtcaaagagg tcacggtgca ggactccacc      960
accaccatcg ccaacaacct cacctccacc gtccaagtgt ttacggacga cgactaccaa     1020
ctcccgtacg tcgtcggcaa cgggaccgag ggatgcctgc cggccttccc cccgcaggtc    1080
tttacgctgc cgcagtacgg ctacgcgacg ctgaaccgag acaacggaga caacccgaca     1140
gagcggagca gcttcttttg cctagagtac tttcccagca agatgctgag gacgggcaac     1200
aactttgagt ttacctacag cttttgaagag gtgcccttcc actgcagctt cgccccgagc    1260
cagaacctct ttaagctggc caacccgctg gtggaccagt acctgtaccg cttcgtgagc    1320
acctcggcca cgggcgccat ccagttccaa aagaacctgg cgggcagata cgccaacacc    1380
tacaaaaact ggttcccggg gcccatgggc cgaacccagg gctggaacac gagctctggc   1440
agcagcacca acagagtcag cgtcaacaac tttttccgtct caaaccggat gaacctggag    1500
ggggccagct accaagtgaa cccccagccc aacgggatga caaacacgct ccaaggcagc     1560
aaccgctacg cgctggaaaa caccatgatc ttcaacgctc aaaacgccac gccgggaact     1620
acctcggtgt acccagagga caatctactg ctgaccagcg agagcgagac tcagcccgtc    1680
aaccgggtgg cttacaacac gggcggtcag atggccacca cgcccagaa cgccaccacg    1740 gctcccacgg tcgggaccta caacctccag gaagtgcttc ctggcagcgt atggatggag    1800
agggacgtgt acctccaagg acccatctgg gccaagatcc cagagacggg ggcgcacttt    1860 caccctctc cggccatggg cggattcgga ctcaaacacc cgccgccat gatgctcatc      1920 aaaaacacgc cggtgcccgg caacatcacc agcttctcgg acgtgcccgt cagcagcttc   1980
atcacccagt acagcaccgg gcaggtcacc gtggagatgg aatgggagct caaaaaggaa    2040
aactccaaga ggtggaaccc agagatccag tacaccaaca actacaacga cccccagttt    2100
gtggactttg ctccagacgg ctccggcgaa tacagaacca ccagagccat cggaaccga    2160 tacctcaccc gaccccttta a                                              2181
```

<210> SEQ ID NO 49
<211> LENGTH: 2142
<212> TYPE: DNA
<213> ORGANISM: Unknown
<220> FEATURE:
<221> NAME/KEY: source
<223> OTHER INFORMATION: /note="Description of Unknown:

Parent AAV Capsid sequence"

<400> SEQUENCE: 49

```
atgtctttct tgattggtt aggtaaacag tacgctcaag gagctgctga attctgggat      60
ttgaagtccg gtcctcctgc accaaaaaag gcgcgaaagg acggatcagc cggattcaat     120
ttccctgggc acaaatacct gggtcctggc aattcattgg atcgcggaga tcccgtggac     180
gctgacgacg ccgctgctca aaagcacgac cagtcgtacc aagagcagct tgaggcggga     240
gacaatccct acctcaagta caaccacgcc gaccgcgagt tccaggaggc gttgaaggac     300
gacacctcct tgaaggaaa tctcgcgaga ggactctttg aggccaagaa gctcgtggca     360
gagcctcttg gtctcgtgga accagaactg gcgccaccca gtggccgtaa cgaccggtg     420
caatcgagtc aagagtctgg ttactcgagt agccaagaca gcggcccaa cctcgacgta     480
gacgaggagg accgtgagtt cgctgccgct gcagcggaga ccgaaactgg aagcgctccc     540
cccaccggca atttgggacc tggtacgatg gctggaggcg gtagcgcgcc aatcgacgac     600
ggctcgtatg gtgccgatgg agtgggcaat gcctcgggag attggcattg cgattccaca     660
tggctggaca actgtgtcat cacccgaacc actcggacct ggaatctgcc aacctacaac     720
aaccacatct acaaacgact caacggaacg acctccggag accaaagcta cttcggattc     780
agcacccct ggggatactt tgacttcaac cgcttccact gtcatttctc ccctcgagac     840
tggcaaagac tcatcaacaa taactgggga ctccgaccaa agagcctacg gttcaaaatc     900
tttaacattc aagttaaaga agtcacgacg caagactcaa cgaagatcat ctccaataac     960
cttaccagca cggttcaggt atttgcggac acggagtacc agctcccgta cgtgattgga    1020
tcggctcacg aaggatgtct gcctcctttc ccggctgacg tgttcatgct gccgcagtat    1080
ggatactgta ctcgacaaga cggaaacagc aacaatccga ccccgagaag cgccttctat    1140
tgtttggagt actttcccag caagatgcta agaactggga acagttttga atttacatat    1200
aactttgaga aggtgccgtt ccacagcatg tgggctcaca accagagtct ggatcgattg    1260
atgaatccat tgattgatca gtacctgtac taccttgatg tcacttcgag taccgggttt    1320
acctatcaaa aaggagttca cacgaacttg cccgaacaag agcgcaactg gctgccggga    1380
ccaggaattc gaaatcaagc ttggtttaat tctgcaactg gaaacaaccc actaactggt    1440
acctggcaat attccaacaa atacgtacta gaaaaccgtg cttcgaagat gctcctgga     1500
cctgccatgg gaattgaatc aacaaaattc gacgggaacg gaatcatctt ttctaaagaa    1560
tacatcacca atgtaaatac agccaatccg aatcaagtaa acatcacacg cgagaccgaa    1620
ataaactcaa cgaaccccttt ggctggagga tctctcggag cccacgctaa taattcacaa    1680
aacacaacaa cggcaccgac gctagaccac accaacgtca tgggtgtgtt tccgggtagt    1740
gtctggcaag acagagacat ttaccttcaa ggacaaatct gggccaagat tccccacaca    1800
gacggacatt tccaccttc tcctctcatg ggaggatttg gactgaagaa cccgcctcct    1860
caaattctga tcaaaaacac acctgttccg gctgacccac caactgaatt caatgcgaac    1920
aaaatctctt ctttcatcac tcaatactca accggacaag ttacagtgga aatggaatgg    1980
gaacttcaga agaaacctc caaaagatgg aatccagaaa tccagtacag cgacgactcg    2040
tcttcgacgt ctggctccat tctgcacttt gctccggatg atgttggaaa ctacaaagag    2100
ttccgctcta tcggaactcg ttaccttacc cgtcctctgt aa                       2142
```

<210> SEQ ID NO 50
<211> LENGTH: 2181

<212> TYPE: DNA
<213> ORGANISM: Unknown
<220> FEATURE:
<221> NAME/KEY: source
<223> OTHER INFORMATION: /note="Description of Unknown:
      Parent AAV Capsid sequence"

<400> SEQUENCE: 50

```
atgtcgtttg ttgatcaccc tccagattgg ttagaagaag ttggtgaagg ccttcacgag    60
tttttggagc tcgaagctgg cccacccaaa ccgaagccca accagcagaa gcaggacaac   120
gcccgtggtc ttgtactgcc tggatataat tatctgggac ccttcaacgg actcgacaag   180
ggagagcccg tcaaccgagc ggacgctgtt gcgcgagagc acgacatctc gtacaacgag   240
cagctccagg cgggagacaa ccccctacctc aagtacaacc acgcggacgc cgagtttcag   300
gagaagctca aggacgacac ctcctttggg ggcaacctcg gaaaggcaat ctttcaggcc   360
aagaaaaggg ttctcgaacc ttttggcctg gttgaggcac tgttaagac ggctccagcc   420
aagaagcggc cgatagagaa gtctccggcg gaaccgagct cttcgaaggg catcggcaag   480
gcgggccagc agcctgcgag gaagcgactc aactttggtc agactggaga caccgactcc   540
gccgctgacc cccagcctct cggagaacca ccagcagccc cctctggtct gggaactggt   600
acgatggctt caggcagtgg cgcaccaatg gcagacaata cgaaggcgc cgacggagtg   660
ggtaatgcct cggaaattg gcattgcgat tccacatggc tgggcgaccg agtcatcacc   720
accagcaccc gcacctgggc cctgcccacc tacaacaacc atctctacaa gcaaatctcc   780
agccagtctg gagccaacaa cgacaaccac tactttggct acagcacccc ctggggtac   840
tttgacttca accgcttcca ctgccacttc tccccgcgag actggcagcg gctcatcaac   900
aacaactggg ggttccggcc caagcgactc aacttcaagc tcttcaacat ccaagtcaag   960
gaggtcactc agacggacgg cacgaagacc atcgccaata accttaccag cacggttcag  1020
gtctttgcgg actcggagta ccagctcccg tacgtcctcg gatcagcgca ccagggctgc  1080
ttcccgccgt tccggcggga cgtcttcatg gtcccgcagt acgggtattt gacgctgaac  1140
aacggcagcc aggcgatggg tcgctcgtcc ttctactgcc tggagtactt tccgtcgcag  1200
atgctgcgga cggggaacaa cttcacgttc agctacacct tcgaggacgt gcccttccac  1260
agcagctacg cgcacagcca gagtctggac cggctcatga cccactcat cgaccagtac  1320
ctgtactacc taagcaagac aaatgccggt ctaggatttt cccaagcggg acccaacagc  1380
atgcgcgacc agtccaggaa ttggctgccg ggaccctgct tcagacaaca acggatttca  1440
actgtaccta cacaaaataa caacggagac ttttcgtgga cgggagccac aaagtatcat  1500
ctcaatggaa gaaactcagc aatgaatccc ggcccggcca tggccagcca caaagacgac  1560
gaacacagat tcttccctca gacggtgtg ctcatctttg gaaaacaggg cgcagacaag  1620
acaaatgcga tactagaaaa agtgatcgtt acagacgaag aggagattag gacaacaaat  1680
cctgtagcca cggaggagta tgggtttgtc gccactaatc tacaaagctc ggcagaaaca  1740
gccgagaccg aaagagtcaa cgcgcaaggc atcctccctg gcatggtgtg gcaagaccga  1800
gatgtgtatc tgcaggggcc catctgggc aagatccccc acaccgacgg acacttccgc  1860
ccctcaccac tcatgggagg attcggcctc aagcacccgc ctccgcagat cctcatcaag  1920
aacacgcctg tgccttcgaa tcctccagag acgttcaacc cggaaaagct caattctttc  1980
ataactcaat attctacggg ccaggtcagc gtggagatcg agtgggagct gcagaaggag  2040
aacagcaagc gctggaaccc cgaggtccag tacacgtcca actacaacaa gtccgtcaac  2100
```

```
gtggaattta cagtggacaa caacggcgtg tattcggaac cgcgcaccat cggcacccgc    2160
taccttactc gtaatctgta a                                              2181

<210> SEQ ID NO 51
<211> LENGTH: 2211
<212> TYPE: DNA
<213> ORGANISM: Unknown
<220> FEATURE:
<221> NAME/KEY: source
<223> OTHER INFORMATION: /note="Description of Unknown:
      Parent AAV Capsid sequence"

<400> SEQUENCE: 51
atggctgccg atggttatct tccagattgg ctcgaggaca accttagtga aggaattcgc      60
gagtggtggg ctttgaaacc tggagcccct caacccaagg caaatcaaca acatcaagac     120
aacgctcgag gtcttgtgct tccgggttac aaataccttg acccggcaa cggactcgac      180 aaggggagc cggtcaacgc agcagacgcg gcggccctcg agcacgacaa ggcctacgac      240
cagcagctca aggccggaga caacccgtac ctcaagtaca ccacgccga cgccgagttc      300 caggagcggc tcaaagaaga tacgtctttt ggggcaacc tcgggcgagc agtcttccag      360
gccaaaaaga ggcttcttga acctcttggt ctggttgagg aagcggctaa gacggctcct     420
ggaaagaaga ggcctgtaga gcagtctcct caggaaccgg actcctccgc gggtattggc     480
aaatcgggtg cacagcccgc taaaaagaga ctcaatttcg gtcagactgg cgacacagag     540
tcagtcccag accctcaacc aatcggagaa cctcccgcag cccctcagg tgtgggatct      600 cttacaatgg cttcaggtgg tggcgcacca gtggcagaca taacgaagg tgccgatgga     660 gtgggtagtt cctcgggaaa ttggcattgc gattcccaat ggctggggga cagagtcatc     720
accaccagca cccgaacctg ggccctgccc acctacaaca tcacctcta caagcaaatc     780 tccaacagca catctggagg atcttcaaat gacaacgcct acttcggcta cagcaccccc     840
tgggggtatt ttgacttcaa cagattccac tgccacttct caccacgtga ctggcagcga     900
ctcatcaaca caactggg attccggcct aagcgactca acttcaagct cttcaacatt     960
caggtcaaag aggttacgga caacaatgga gtcaagacca tcgccaataa ccttaccagc    1020
acggtccagg tcttcacgga ctcagactat cagctcccgt acgtgctcgg tcggctcac     1080 gagggctgcc tccgcgcgtt cccagcggac gttttcatga ttcctcagta cgggtatctg    1140
acgcttaatg atggaagcca ggccgtgggt cgttcgtcct tttactgcct ggaatatttc    1200
ccgtcgcaaa tgctaagaac gggtaacaac ttcagttca gctacgagtt tgagaacgta    1260
cctttccata gcagctacgc tcacagccaa agcctggacc gactaatgaa tccactcatc    1320
gaccaatact tgtactatct ctcaaagact attaacggtt ctggacagaa tcaacaaacg    1380
ctaaaattca gtgtggccgg acccagcaac atggctgtcc agggaagaaa ctacatacct    1440
ggacccagct accgacaaca acgtgtctca accactgtga ctcaaaacaa caacagcgaa    1500
tttgcttggc ctggagcttc ttcttgggct ctcaatggac gtaatagctt gatgaatcct    1560
ggacctgcta tggccagcca caaagaagga gaggaccgtt tctttcctttt gtctggatct    1620 ttaattttttg gcaaacaagg aactggaaga gacaacgtgg atgcggacaa agtcatgata    1680
accaacgaag aagaaattaa aactactaac ccggtagcaa cggagtccta tggacaagtg    1740 gccacaaaacc accagagtgc caagcacag cgcagaccg gctgggttca aaaccaagga    1800
atacttccgg gtatggtttg gcaggacaga gatgtgtacc tgcaaggacc catttgggcc    1860
aaaattcctc acacggacgg caactttcac ccttctccgc tgatgggagg gtttggaatg    1920
```

-continued

```
aaacacccgc ctcctcagat cctcatcaaa aacacacctg tacctgcgga tcctccaacg    1980
gccttcaaca aggacaagct gaactctttc atcacccagt attctactgg ccaagtcagc    2040
gtggagatcg agtgggagct gcagaaggaa aacagcaagc gctggaaccc ggagatccag    2100
tacacttcca actattacaa gtctaataat gttgaatttg ctgttaatac tgaaggtgta    2160
tatagtgaac cccgccccat tggcaccaga tacctgactc gtaatctgta a             2211
```

<210> SEQ ID NO 52
<211> LENGTH: 2211
<212> TYPE: DNA
<213> ORGANISM: Unknown
<220> FEATURE:
<221> NAME/KEY: source
<223> OTHER INFORMATION: /note="Description of Unknown:
    Parent AAV Capsid sequence"

<400> SEQUENCE: 52

```
atggctgccg atggttatct tccagattgg ctcgaggaca acctctctga gggcattcgc      60
gagtggtggg acttgaaacc tggagccccg aagcccaaag ccaaccagca aaagcaggac     120
gacggccggg gtctggtgct tcctggctac aagtacctcg acccttcaa cggactcgac      180 aagggggagc ccgtcaacgc ggcggacgca gcggccctcg agcacgacaa ggcctacgac     240
cagcagctca aagcgggtga caatccgtac cttcggtata accacgccga cgccgagttt     300
caggagcgtc tgcaagaaga tacgtctttt gggggcaacc tcgggcgagc agtcttccag     360
gccaagaagc gggttctcga acctctcggt ctggttgagg aaggcgctaa gacggctcct     420
ggaaagaaac gtccggtaga gcagtcgcca aagagccag actcctcctc gggcatcggc     480
aagacaggcc agcagcccgc taaaaagaga ctcaattttg gtcagactgg cgactcagag     540
tcagtccccg acccacaacc tctcggagaa cctccagcaa ccccgctgc tgtgggacct     600 actacaatgg cttcaggcgg tggcgcacca atggcagaca taacgaagg cgccgacgga     660 gtgggtaatg cctcaggaaa ttggcattgc gattccacat ggctgggcga cagagtcatc     720
accaccagca cccgcacctg gccttgccc acctacaata accacctcta caagcaaatc     780
tccagtgctt caacggggc cagcaacgac aaccactact cggctacag cacccctgg      840 gggtattttg atttcaacag attccactgc cacttttcac cacgtgactg cagcgactc      900 atcaacaaca attggggatt ccggcccaag agactcaact tcaaactctt caacatccaa     960
gtcaaggagg tcacgacgaa tgatggcgtc acaaccatcg ctaataacct taccagcacg    1020
gttcaagtct ctctcggactc ggagtaccag cttccgtacg tcctcggctc tgcgcaccag    1080
ggctgcctcc ctccgttccc ggcggacgtg ttcatgattc cgcaatacgg ctacctgacg    1140
ctcaacaatg gcagccaagc cgtgggacgt tcatcctttt actgcctgga atatttccct    1200
tctcagatgc tgagaacggg caacaacttt accttcagct acacctttga ggaagtgcct    1260
ttccacagca gctacgcgca cagccagagc ctggaccggc tgatgaatcc tctcatcgac    1320
caatacctgt attacctgaa cagaactcaa aatcagtccg gaagtgccca aaacaaggac    1380
ttgctgttta gccgtgggtc tccagctggc atgtctgttc agcccaaaaa ctggctacct    1440
ggaccctgtt atcggcagca gcgcgtttct aaaacaaaaa cagacaacaa caacagcaat    1500
tttacctgga ctggtgcttc aaaatataac ctcaatgggc gtgaatccat catcaaccct    1560
ggcactgcta tggcctcaca caaagacgac gaagacaagt tctttccat gagcggtgtc    1620 atgatttttg gaaagagag cgccggagct tcaaacactg cattggacaa tgtcatgatt    1680
```

| | |
|---|---|
| acagacgaag aggaaattaa agccactaac cctgtggcca ccgaaagatt tgggaccgtg | 1740 |
| gcagtcaatt tccagagcag cagcacagac cctgcgaccg agatgtgca tgctatggga | 1800 |
| gcattacctg gcatggtgtg gcaagataga gacgtgtacc tgcagggtcc catttgggcc | 1860 |
| aaaattcctc acacagatgg acactttcac ccgtctcctc ttatgggcgg ctttggactc | 1920 |
| aagaacccgc tcctcagat cctcatcaaa acacgcctg ttcctgcgaa tcctccggcg | 1980 |
| gagttttcag ctacaaagtt tgcttcattc atcacccaat actccacagg acaagtgagt | 2040 |
| gtggaaattg aatgggagct gcagaaagaa acagcaagc gctggaatcc cgaagtgcag | 2100 |
| tacacatcca attatgcaaa atctgccaac gttgatttta ctgtggacaa caatggactt | 2160 |
| tatactgagc ctcgccccat tggcacccgt tacctcaccc gtcccctgta a | 2211 |

```
<210> SEQ ID NO 53
<211> LENGTH: 2211
<212> TYPE: DNA
<213> ORGANISM: Unknown
<220> FEATURE:
<221> NAME/KEY: source
<223> OTHER INFORMATION: /note="Description of Unknown:
      Parent AAV Capsid sequence"

<400> SEQUENCE: 53
```

| | |
|---|---|
| atggctgccg atggttatct tccagattgg ctcgaggaca acctctctga gggcattcgc | 60 |
| gagtggtggg acttgaaacc tggagccccg aaacccaaag ccaaccagca aaagcaggac | 120 |
| gacggccggg gtctggtgct tcctggctac aagtacctcg acccttcaa cggactcgac | 180 |
| aagggggagc ccgtcaacgc ggcggatgca gcggccctcg agcacgacaa ggcctacgac | 240 |
| cagcagctca agcgggtga caatccgtac ctgcggtata ccacgccga cgccgagttt | 300 |
| caggagcgtc tgcaagaaga tacgtctttt ggggcaacc tcgggcgagc agtcttccag | 360 |
| gccaagaaga gggttctcga acctttggt ctggttgagg aaggtgctaa gacggctcct | 420 |
| ggaaagaaac gtccggtaga gcagtcgcca aagagccag actcctcctc gggcattggc | 480 |
| aagacaggcc agcagcccgc taaaagaga ctcaattttg gtcagactgg cgactcagag | 540 |
| tcagtccccg acccacaacc tctcggagaa cctccagcaa cccccgctgc tgtgggacct | 600 |
| actacaatgg cttcaggcgg tggcgcacca atggcagaca taacgaagg cgccgacgga | 660 |
| gtgggtaatg cctcaggaaa ttggcattgc gattccacat ggctgggcga cagagtcatc | 720 |
| accaccagca cccgaacatg gccttgccc acctataaca accacctcta caagcaaatc | 780 |
| tccagtgctt caacggggc cagcaacgac aaccactact cggctacag caccccctgg | 840 |
| gggtatttg atttcaacag attccactgc catttctcac acgtgactg cagcgactc | 900 |
| atcaacaaca ttggggatt ccggcccaag agactcaact tcaagctctt caacatccaa | 960 |
| gtcaaggagg tcacgacgaa tgatggcgtc acgaccatcg ctaataacct taccagcacg | 1020 |
| gttcaagtct ctctcggactc ggagtaccag ttgccgtacg tcctcggctc tgcgcaccag | 1080 |
| ggctgcctcc ctccgttccc ggcggacgtg ttcatgattc gcagtacgg ctacctaacg | 1140 |
| ctcaacaatg gcagccaggc agtgggacgg tcatcctttt actgcctgga atatttccca | 1200 |
| tcgcagatgc tgagaacggg caataacttt accttcagct acaccttcga ggacgtgcct | 1260 |
| ttccacagca gctacgcgca gccagagc ctggaccggc tgatgaatcc tctcatcgac | 1320 |
| cagtacctgt attactgaa cagaactcag aatcagtccg gaagtgccca aaacaaggac | 1380 |
| ttgctgttta gccgggggtc tccagctggc atgtctgttc agcccaaaaa ctggctacct | 1440 |
| ggaccctgtt accggcagca gcgcgtttct aaaacaaaaa cagacaacaa caacagcaac | 1500 |

```
tttacctgga ctggtgcttc aaaatataac cttaatgggc gtgaatctat aatcaaccct    1560
ggcactgcta tggcctcaca caaagacgac aaagacaagt tctttcccat gagcggtgtc    1620 atgattttg gaaaggagag cgccggagct tcaaacactg cattggacaa tgtcatgatc    1680
acagacgaag aggaaatcaa agccactaac cccgtggcca ccgaaagatt tgggactgtg    1740
gcagtcaatc tccagagcag cagcacagac cctgcgaccg agatgtgca tgttatggga    1800 gccttacctg gaatggtgtg gcaagacaga gacgtatacc tgcagggtcc tatttgggcc    1860
aaaattcctc acacggatgg acactttcac ccgtctcctc tcatgggcgg ctttggactt    1920
aagcacccgc ctcctcagat cctcatcaaa aacacgcctg ttcctgcgaa tcctccggca    1980
gagttttcgg ctacaaagtt tgcttcattc atcacccagt attccacagg acaagtgagc    2040
gtggagattg aatgggagct gcagaaagaa acagcaaac gctggaatcc cgaagtgcag    2100
tatacatcta actatgcaaa atctgccaac gttgatttca ctgtggacaa caatggactt    2160
tatactgagc ctcgccccat tggcacccgt tacctcaccc gtcccctgta a             2211
```

<210> SEQ ID NO 54
<211> LENGTH: 2211
<212> TYPE: DNA
<213> ORGANISM: Unknown
<220> FEATURE:
<221> NAME/KEY: source
<223> OTHER INFORMATION: /note="Description of Unknown:
    Parent AAV Capsid sequence"

<400> SEQUENCE: 54

```
atggctgctg acggttatct tccagattgg ctcgaggaca acctttctga aggcattcgt      60
gagtggtggg ctctgaaacc tggagtccct caacccaaag cgaaccaaca acaccaggac     120
aaccgtcggg gtcttgtgct tccgggttac aaatacctcg acccggtaa cggactcgac     180 aaaggagagc cggtcaacga ggcggacgcg cagccctcg aacacgacaa agcctacgac     240
cagcagctca aggccggtga caacccgtac ctcaagtaca ccacgccga cgccgagttt     300 caggagcgtc ttcaagaaga tacgtctttt gggggcaacc ttggcagagc agtcttccag     360
gccaaaaaga ggatccttga gcctcttggt ctggttgagg aagcagctaa aacggctcct     420
ggaaagaaga ggcctgtaga tcagtctcct caggaaccgg actcatcatc tggtgttggc     480
aaatcgggca aacagcctgc cagaaaaaga ctaaatttcg gtcagactgg cgactcagag     540
tcagtcccag accctcaacc tctcggagaa ccaccagcag cccccacaag tttgggatct     600
aatacaatgg cttcaggcgg tggcgcacca atggcagaca taacgagggg tgccgatgga     660
gtgggtaatt cctcaggaaa ttggcattgc gattcccaat ggctgggcga cagagtcatc     720
accaccagca ccgaaacctg gccctgccc acttacaaca accatctcta caagcaaatc     780
tccagccaat caggagcttc aaacgacaac cactactttg gctacagcac cccttgggg     840 tatttttgact ttaacagatt ccactgccac ttctcaccac gtgactggca gcgactcatt     900
aacaacaact ggggattccg gcccaagaaa ctcagcttca gctcttcaa catccaagtt     960 aaagaggtca cgcagaacga tggcacgacg actattgcca ataacctac cagcacggtt    1020 caagtgttta cggactcgga gtatcagctc ccgtacgtgc tcgggtcggc gcaccaaggc    1080
tgtctcccgc cgtttccagc ggacgtcttc atggtccctc agtatggata cctcaccctg    1140
aacaacggaa gtcaagcggt gggacgctca tccttttact gcctggagta cttcccttcg    1200
cagatgctaa ggactggaaa taacttccaa ttcagctata ccttcgagga tgtacctttt    1260
```

```
cacagcagct acgctcacag ccagagtttg gatcgcttga tgaatcctct tattgatcag   1320
tatctgtact acctgaacag aacgcaagga acaacctctg gaacaaccaa ccaatcacgg   1380
ctgcttttta gccaggctgg gcctcagtct atgtctttgc aggccagaaa ttggctacct   1440
gggccctgct accggcaaca gagactttca aagactgcta acgacaacaa caacagtaac   1500
tttccttgga cagcggccag caaatatcat ctcaatggcc gcgactcgct ggtgaatcca   1560
ggaccagcta tggccagtca caaggacgat gaagaaaaat ttttccctat gcacggcaat   1620
ctaatatttg gcaaagaagg gacaacggca agtaacgcag aattagataa tgtaatgatt   1680
acggatgaag aagagattcg taccaccaat cctgtggcaa cagagcagta tggaactgtg   1740
gcaaataact tgcagagctc aaatacagct cccacgacta gaactgtcaa tgatcagggg   1800
gccttacctg gcatggtgtg gcaagatcgt gacgtgtacc ttcaaggacc tatctgggca   1860
aagattcctc acacggatgg acactttcat ccttctcctc tgatgggagg ctttggactg   1920
aaacatccgc ctcctcaaat catgatcaaa aatactccgg taccggcaaa tcctccgacg   1980
actttcagcc cggccaagtt tgcttcattt atcactcagt actccactgg acaggtcagc   2040
gtggaaattg agtgggagct acagaaagaa acagcaaac gttggaatcc agagattcag   2100
tacacttcca actacaacaa gtctgttaat gtggacttta ctgtagacac taatggtgtt   2160
tatagtgaac ctcgccctat tggaacccgg tatctcacac gaaacttgta a            2211

<210> SEQ ID NO 55
<211> LENGTH: 2211
<212> TYPE: DNA
<213> ORGANISM: Unknown
<220> FEATURE:
<221> NAME/KEY: source
<223> OTHER INFORMATION: /note="Description of Unknown:
      Parent AAV Capsid sequence"

<400> SEQUENCE: 55
atggctgctg acggttatct tccagattgg ctcgaggaca acctttctga aggcattcga     60
gagtggtggg cgctgcaacc tggagcccct aaacccaagg caaatcaaca acatcaggac    120
aacgctcggg gtcttgtgct tccgggttac aaataccctg accccggcaa cggactcgac    180
aaggggggaac ccgtcaacgc agcggacgcg gcagccctcg agcacgacaa ggcctacgac    240
cagcagctca aggccggtga caaccccctac ctcaagtaca accacgccga cgccgagttc    300
caggagcggc tcaaagaaga tacgtctttt gggggcaacc tcgggcgagc agtcttccag    360
gccaaaaaga ggcttcttga acctcttggt ctggttgagg aagcggctaa gacggctcct    420
ggaaagaaga ggcctgtaga tcagtctcct caggaaccgg actcatcatc tggtgttggc    480
aaatcgggca acagcctgc cagaaaaaga ctaaatttcg gtcagactgg cgactcagag    540
tcagtcccag accctcaacc tctcggagaa ccaccagcag cccccacaag tttgggatct    600
aatacaatgg cttcaggcgg tggcgcacca atggcagaca taacgagggg tgccgatgga    660
gtgggtaatt cctcaggaaa ttggcattgc gattcccaat ggctgggcga cagagtcatc    720
accaccagca ccagaacctg ggccctgccc acttacaaca accatctcta caagcaaatc    780
tccagccaat caggagcttc aaacgacaac cactactttg gctacagcac ccctggggg    840
tattttgact ttaacagatt ccactgccac ttctcaccac gtgactggca gcgactcatt    900
aacaacaact ggggattccg gcccaagaaa ctcagcttca agctcttcaa catccaagtt    960
aaagaggtca cgcagaacga tggcacgacg actattgcca ataaccttac cagcacggtt   1020
caagtgttta cggactcgga gtatcagctc ccgtacgtgc tcgggtcggc gcaccaaggc   1080
```

```
tgtctcccgc cgtttccagc ggacgtcttc atggtccctc agtatggata cctcaccctg    1140
aacaacggaa gtcaagcggt gggacgctca tccttttact gcctggagta cttcccttcg    1200
cagatgctaa ggactggaaa taacttccaa ttcagctata ccttcgagga tgtaccttt     1260 cacagcagct acgctcacag ccagagtttg gatcgcttga tgaatcctct tattgatcag    1320
tatctgtact acctgaacag aacgcaagga caacctctg gaacaaccaa ccaatcacgg     1380
ctgcttttta gccaggctgg gcctcagtct atgtctttgc aggccagaaa ttggctacct    1440
gggccctgct accggcaaca gagactttca aagactgcta cgacaacaa caacagtaac     1500 tttccttgga cagcggccag caaatatcat ctcaatggcc gcgactcgct ggtgaatcca    1560
ggaccagcta tggccagtca caaggacgat gaagaaaaat ttttccctat gcacggcaat    1620
ctaatatttg gcaaagaagg gacaacggca agtaacgcag aattagataa tgtaatgatt    1680
acggatgaag aagagattcg taccaccaat cctgtggcaa cagagcagta tggaactgtg    1740
gcaaataact gcagagctc aaatacagct cccacgacta gaactgtcaa tgatcagggg    1800
gccttacctg gcatggtgtg gcaagatcgt gacgtgtacc ttcaaggacc tatctgggca    1860
aagattcctc acacgatgg acactttcat ccttctcctc tgatgggagg ctttggactg     1920
aaacatccgc tcctcaaat catgatcaaa atactccgg taccggcaaa tcctccgacg      1980
actttcagcc cggccaagtt tgcttcattt atcactcagt actccactgg acaggtcagc    2040
gtggaaattg agtgggagct acagaaagaa aacagcaaac gttggaatcc agagattcag    2100
tacacttcca actacaacaa gtctgttaat gtggacttta ctgtagacac taatggtgtt    2160
tatagtgaac ctcgccccat tggcaccgt taccttaccc gtccctgta a              2211
```

<210> SEQ ID NO 56
<211> LENGTH: 2217
<212> TYPE: DNA
<213> ORGANISM: Unknown
<220> FEATURE:
<221> NAME/KEY: source
<223> OTHER INFORMATION: /note="Description of Unknown:
      Parent AAV Capsid sequence"

<400> SEQUENCE: 56

```
atggctgccg atggttatct tccagattgg ctcgaggaca acctctctga gggcattcgc     60
gagtggtggg cgctgaaacc tggagccccg aagcccaaag ccaaccagca aaagcaggac    120
gacggccggg gtctggtgct tcctggctac aagtacctcg acccttcaa cggactcgac     180 aagggggagc ccgtcaacgc ggcggacgca gcggccctcg agcacgacaa ggcctacgac    240
cagcagctgc aggcgggtga caatccgtac ctgcggtata ccacgccga cgccgagttt    300 caggagcgtc tgcaagaaga tacgtctttt gggggcaacc tcgggcgagc agtcttccag    360
gccaagaagc gggttctcga acctctcggt ctggttgagg aaggcgctaa gacggctcct    420
ggaaagaaga gaccggtaga gccatcaccc agcgttctc cagactcctc tacgggcatc    480
ggcaagaaag gccaacagcc cgccagaaaa agactcaatt ttggtcagac tggcgactca    540
gagtcagttc cagaccctca acctctcgga gaacctccag cagcgccctc tggtgtggga    600
cctaatacaa tggctgcagg cggtggcgca ccaatgcgca acaataacga aggcgccgac    660
ggagtgggta gttcctcggg aaattggcat tgcgattcca catggctggg cgacagagtc    720
atcaccacca gcacccgaac ctgggcccct cccacctaca acaaccct ctacaagcaa     780 atctccaacg ggacatcggg aggagccacc aacgacaaca cctacttcgg ctacagcacc    840
```

```
ccctgggggt attttgactt taacagattc cactgccact tttcaccacg tgactggcag    900
cgactcatca acaacaactg gggattccgg cccaagagac tcagcttcaa gctcttcaac    960
atccaggtca aggaggtcac gcagaatgaa ggcaccaaga ccatcgccaa taacctcacc   1020
agcaccatcc aggtgtttac ggactcggag taccagctgc cgtacgttct cggctctgcc   1080
caccagggct gcctgcctcc gttcccggcg gacgtgttca tgattcccca gtacggctac   1140
ctaacactca caacggtag tcaggccgtg ggacgctcct ccttctactg cctggaatac    1200
tttccttcgc agatgctgag aaccggcaac aacttccagt ttacttacac cttcgaggac   1260
gtgcctttcc acagcagcta cgcccacagc cagagcttgg accggctgat gaatcctctg   1320
attgaccagt acctgtacta cttgtctcgg actcaaacaa caggaggcac ggcaaatacg    1380
cagactctgg gcttcagcca aggtgggcct aatacaatgg ccaatcaggc aaagaactgg    1440
ctgccaggac cctgttaccg ccaacaacgc gtctcaacga caaccgggca aaacaacaat    1500
agcaactttg cctggactgc tgggaccaaa taccatctga atggaagaaa ttcattggct    1560
aatcctggca tcgctatggc aacacacaaa gacgacgagg agcgtttttt tcccagtaac    1620
gggatcctga tttttggcaa acaaaatgct gccagagaca tgcggatta cagcgatgtc     1680 atgctcacca gcgaggaaga aatcaaaacc actaaccctg tggctacaga ggaatacggt    1740
atcgtggcag ataacttgca gcagcaaaac acggctcctc aaattggaac tgtcaacagc    1800 caggggggcct acccggtat ggtctggcag aaccgggacg tgtacctgca gggtcccatc    1860
tgggccaaga ttcctcacac ggacggcaac ttccacccgt ctccgctgat gggcggcttt    1920
ggcctgaaac atcctccgcc tcagatcctg atcaagaaca gcctgtacc tgcggatcct    1980 ccgaccacct tcaaccagtc aaagctgaac tctttcatca cgcaatacag caccggacag    2040
gtcagcgtgg aaattgaatg ggagctgcag aaggaaaaca gcaagcgctg gaaccccgag    2100
atccagtaca cctccaacta ctacaaatct acaagtgtgg actttgctgt taatacagaa    2160
ggcgtgtact ctgaaccccg ccccattggc acccgttacc tcacccgtaa tctgtaa      2217
```

<210> SEQ ID NO 57
<211> LENGTH: 2217
<212> TYPE: DNA
<213> ORGANISM: Unknown
<220> FEATURE:
<221> NAME/KEY: source
<223> OTHER INFORMATION: /note="Description of Unknown:
    Parent AAV Capsid sequence"

<400> SEQUENCE: 57

```
atggctgccg atggttatct tccagattgg ctcgaggaca acctctctga gggcattcgc     60
gagtggtggg acttgaaacc tggagccccg aaacccaaag ccaaccagca aaagcaggac    120
gacggccggg gtctggtgct tcctggctac aagtacctcg gacccttcaa cggactcgac    180
aagggggagc ccgtcaacgc ggcggacgca gcggccctcg agcacgacaa ggcctacgac    240
cagcagctca agcgggtga caatccgtac ctgcggtata accacgccga cgccgagttt    300
caggagcgtc tgcaagaaga tacgtctttt ggggcaacc tcgggcgagc agtcttccag    360
gccaagaagc gggttctcga acctctcggt ctggttgagg aaggcgctaa gacggctcct    420
ggaaagaaga gaccggtaga gccatcaccc agcgttctc cagactcctc tacgggcatc    480
ggcaagaaag ccagcagcc cgcgaaaaag agactcaact ttgggcagac tggcgactca    540
gagtcagtgc cgaccctca accaatcgga gaaccccccg caggcccctc tggtctggga    600
tctggtacaa tggctgcagg cggtggcgct ccaatggcag acaataacga aggcgccgac    660
```

```
ggagtgggta gttcctcagg aaattggcat tgcgattcca catggctggg cgacagagtc      720
atcaccacca gcacccgaac ctgggccctc cccacctaca caaccacct  ctacaagcaa      780
atctccaacg ggacttcggg aggaagcacc aacgacaaca cctacttcgg ctacagcacc      840
ccctgggggt attttgactt taacagattc cactgccact tctcaccacg tgactggcag      900
cgactcatca caacaactg  gggattccgg cccaagagac tcaacttcaa gctcttcaac      960
atccaggtca aggaggtcac gcagaatgaa ggcaccaaga ccatcgccaa taaccttacc     1020
agcacgattc aggtctttac ggactcggaa taccagctcc cgtacgtcct cggctctgcg     1080
caccagggct gcctgcctcc gttcccggcg gacgtcttca tgattcctca gtacgggtac     1140
ctgactctga caatggcag  tcaggccgtg ggccgttcct ccttctactg cctggagtac     1200
tttccttctc aaatgctgag aacgggcaac aactttgagt tcagctacca gtttgaggac     1260
gtgccttttc acagcagcta cgcgcacagc caaagcctgg accggctgat gaacccctc      1320
atcgaccagt acctgtacta cctgtctcgg actcagtcca cggaggtac  cgcaggaact     1380
cagcagttgc tattttctca ggccgggcct aataacatgt cggctcaggc caaaaactgg     1440
ctacccgggc cctgctaccg gcagcaacgc gtctccacga cactgtcgca aaataacaac     1500
agcaactttg cctggaccgg tgccaccaag tatcatctga atggcagaga ctctctggta     1560
aatcccggtg tcgctatggc aacccacaag gacgacgaag agcgatttt  tccgtccagc     1620
ggagtcttaa tgtttgggaa acagggagct ggaaaagaca acgtggacta tagcagcgtt     1680
atgctaacca gtgaggaaga aattaaaacc accaacccag tggccacaga acagtacggc     1740
gtggtggccg ataacctgca acagcaaaac gccgctccta ttgtaggggc cgtcaacagt     1800
caaggagcct tacctggcat ggtctggcag aaccgggacg tgtacctgca gggtcctatc     1860
tgggccaaga ttcctcacac ggacggaaac tttcatccct cgccgctgat gggaggcttt     1920
ggactgaaac acccgcctcc tcagatcctg attaagaata cacctgttcc cgcggatcct     1980
ccaactacct tcagtcaagc taagctggcg tcgttcatca cgcagtacag caccggacag     2040
gtcagcgtgg aaattgaatg ggagctgcag aaagaaaaca gcaaacgctg gaacccagag     2100
attcaataca cttccaacta ctacaaatct acaaatgtgg actttgctgt taacacagat     2160
ggcacttatt ctgagcctcg ccccatcggc acccgttacc tcacccgtaa tctgtaa       2217
```

<210> SEQ ID NO 58
<211> LENGTH: 2208
<212> TYPE: DNA
<213> ORGANISM: Unknown
<220> FEATURE:
<221> NAME/KEY: source
<223> OTHER INFORMATION: /note="Description of Unknown: Parent AAV Capsid sequence"

<400> SEQUENCE: 58

```
atggctgccg atggttatct tccagattgg ctcgaggaca ctctctctga aggaataaga       60
cagtggtgga agctcaaacc tggcccacca ccaccaaagc ccgcagagcg gcataaggac      120
gacagcaggg gtcttgtgct tcctgggtac aagtacctcg gacccttcaa cggactcgac      180
aagggagagc cggtcaacga ggcagacgcc gcggccctcg agcacgacaa agcctacgac      240
cggcagctcg acagcggaga caacccgtac ctcaagtaca accacgccga cgcggagttt      300
caggagcgcc ttaaagaaga tacgtctttt gggggcaacc tcggacgagc agtcttccag      360
gcgaaaaaga gggttcttga acctctgggc ctggttgagg aacctgttaa gacggctccg      420
```

| | |
|---|---|
| ggaaaaaaga ggccggtaga gcactctcct gtggagccag actcctcctc gggaaccgga | 480 |
| aaggcgggcc agcagcctgc aagaaaaaga ttgaattttg gtcagactgg agacgcagac | 540 |
| tcagtacctg accccccagcc tctcggacag ccaccagcag cccctctgg tctgggaact | 600 |
| aatacgatgg ctacaggcag tggcgcacca atggcagaca ataacgaggg cgccgacgga | 660 |
| gtgggtaatt cctcgggaaa ttggcattgc gattccacat ggatgggcga cagagtcatc | 720 |
| accaccagca cccgaacctg ggccctgccc acctacaaca accacctcta caaacaaatt | 780 |
| tccagccaat caggagcctc gaacgacaat cactactttg ctacagcac cccttggggg | 840 |
| tattttgact caacagatt ccactgccac ttttcaccac gtgactggca aagactcatc | 900 |
| aacaacaact ggggattccg acccaagaga ctcaacttca agctctttaa cattcaagtc | 960 |
| aaagaggtca cgcagaatga cggtacgacg acgattgcca ataaccttac cagcacggtt | 1020 |
| caggtgttta ctgactcgga gtaccagctc ccgtacgtcc tcggctcggc gcatcaagga | 1080 |
| tgcctcccgc cgttcccagc agacgtcttc atggtgccac agtatggata cctcaccctg | 1140 |
| aacaacggga gtcaggcagt aggacgctct tcatttttact gcctggagta ctttcctttct | 1200 |
| cagatgctgc gtaccggaaa caactttacc ttcagctaca cttttgagga cgttcctttc | 1260 |
| cacagcagct acgctcacag ccagagtctg gaccgtctca tgaatcctct catcgaccag | 1320 |
| tacctgtatt acttgagcag aacaaacact ccaagtggaa ccaccacgca gtcaaggctt | 1380 |
| cagtttttctc aggccggagc gagtgacatt cgggaccagt ctaggaactg gcttcctgga | 1440 |
| ccctgttacc gccagcagcg agtatcaaag acatctgcgg ataacaacaa cagtgaatac | 1500 |
| tcgtggactg gagctaccaa gtaccacctc aatggcagag actctctggt gaatccgggc | 1560 |
| ccggccatgg caagccacaa ggacgatgaa gaaaagtttt ttcctcagag cggggttctc | 1620 |
| atctttggga agcaaggctc agagaaaaca aatgtggaca ttgaaaaggt catgattaca | 1680 |
| gacgaagagg aaatcaggac aaccaatccc gtggctacgg agcagtatgg ttctgtatct | 1740 |
| accaacctcc agagaggcaa cagacaagca gctaccgcag atgtcaacac acaaggcgtt | 1800 |
| cttccaggca tggtctggca ggacagagat gtgtaccttc aggggcccat ctgggcaaag | 1860 |
| attccacaca cggacggaca ttttcacccc tctcccctca tgggtggatt cggacttaaa | 1920 |
| caccctcctc cacagattct catcaagaac accccggtac ctgcgaatcc ttcgaccacc | 1980 |
| ttcagtgcgg caaagtttgc ttccttcatc acacagtact ccacgggaca ggtcagcgtg | 2040 |
| gagatcgagt gggagctgca gaaggaaaac agcaaacgct ggaatcccga aattcagtac | 2100 |
| acttccaact acaacaagtc tgttaatgtg gactttactg tggacactaa tggcgtgtat | 2160 |
| tcagagcctc gccccattgg caccagatac ctgactcgta atctgtaa | 2208 |

<210> SEQ ID NO 59
<211> LENGTH: 2214
<212> TYPE: DNA
<213> ORGANISM: Unknown
<220> FEATURE:
<221> NAME/KEY: source
<223> OTHER INFORMATION: /note="Description of Unknown:
    Parent AAV Capsid sequence"

<400> SEQUENCE: 59

| | |
|---|---|
| atggctgccg atggttatct tccagattgg ctcgaggaca ctctctctga aggaataaga | 60 |
| cagtggtgga agctcaaacc tggcccacca ccaccaaagc ccgcagagcg cataaggac | 120 |
| gacagcaggg gtcttgtgct tcctgggtac aagtacctcg gacccttcaa cggactcgac | 180 |
| aagggagagc cggtcaacga ggcagacgcc gcggccctcg agcacgacaa agcctacgac | 240 |

```
cggcagctcg acagcggaga caacccgtac ctcaagtaca accacgccga cgccgagttc    300
caggagcggc tcaaagaaga tacgtctttt gggggcaacc tcgggcgagc agtcttccag    360
gccaaaaaga ggcttcttga acctcttggt ctggttgagg aagcggctaa dacggctcct    420
ggaaagaaga ggcctgtaga gcactctcct gtggagccag actcctcctc gggaaccgga    480
aaggcgggcc agcagcctgc aagaaaaaga ttgaattttg gtcagactgg agacgcagac    540
tcagtcccag accctcaacc aatcggaaa cctcccgcag cccctcagg tgtgggatct    600
cttacaatgg ctgcaggcgg tggcgcacca atggcagaca ataacgaggg cgccgacgga    660
gtgggtaatt cctcgggaaa ttggcattgc gattccacat ggatgggcga cagagtcatc    720
accaccagca cccgaacctg ggccctgccc acctacaaca accacctcta caagcaaatc    780
tccaacagca catctggagg atcttcaaat gacaacgcct acttcggcta cagcaccccc    840
tgggggtatt ttgactttaa cagattccac tgccactttt caccacgtga ctggcagcga    900
ctcatcaaca caactgggg attccggccc aagagactca gcttcaagct cttcaacatc    960
caggtcaagg aggtcacgca gaatgaaggc accaagacca tcgccaataa cctcaccagc    1020
accatccagg tgtttacgga ctcggagtac cagctgccgt acgttctcgg ctctgcccac    1080
cagggctgcc tgcctccgtt cccggcggac gtgttcatga ttccccagta cggctaccta    1140
acactcaaca acggtagtca ggccgtggga cgctcctcct tctactgcct ggaatacttt    1200
ccttcgcaga tgctgagaac cggcaacaac ttccagttta cttcacctt cgaggacgtg    1260
cctttccaca gcagctacgc ccacagccag agcttggacc ggctgatgaa tcctctgatt    1320
gaccagtacc tgtactactt gtctcggact caaacaacag gaggcacgac aaatacgcag    1380
actctgggct tcagccaagg tgggcctaat acaatggcca atcaggcaaa gaactggctg    1440
ccaggaccct gttaccgcca gcagcgagta tcaaagacat ctgcggataa caacaacagt    1500
gaatactcgt ggactggagc taccaagtac cacctcaatg gcagagactc tctggtgaat    1560
ccgggcccgg ccatggcaag ccacaaggac gatgaagaaa agtttttttcc tcagagcggg    1620
gttctcatct ttgggaagca aggctcagag aaaacaaatg tggacattga aaaggtcatg    1680
attacagacg aagaggaaat caggacaacc aatcccgtgg ctacgagca gtatggttct    1740
gtatctacca acctccagag aggcaacaga caagcagcta ccgcagatgt caacacacaa    1800
ggcgttcttc caggcatggt ctggcaggac agagatgtgt accttcaggg gcccatctgg    1860
gcaaagattc acacacggga cggacatttt caccctctc ccctcatggg tggattcgga    1920
cttaaacacc ctccgcctca gatcctgatc aagaacacgc ctgtacctgc ggatcctccg    1980
accaccttca accagtcaaa gctgaactct ttcatcaccc agtattctac tggccaagtc    2040
agcgtggaga tcgagtggga gctgcagaag gaaaacagca gcgctggaa ccccgagatc    2100
cagtacacct ccaactacta caaatctaca agtgtggact tgctgttaa tacagaaggc    2160
gtgtactctg aaccccgccc cattggcacc cgttacctca cccgtaatct gtaa          2214
```

<210> SEQ ID NO 60
<211> LENGTH: 2211
<212> TYPE: DNA
<213> ORGANISM: Unknown
<220> FEATURE:
<221> NAME/KEY: source
<223> OTHER INFORMATION: /note="Description of Unknown:
      Parent AAV Capsid sequence"

<400> SEQUENCE: 60

```
atgtcttttg ttgaccaccc tccagattgg ttggaatcga tcggcgacgg ctttcgtgaa    60
tttctcggcc ttgaggcggg tcccccgaaa cccaaggcca atcaacagaa gcaagataac   120
gctcgaggtc ttgtgcttcc tgggtacaag tatcttggtc ctgggaacgg ccttgataag   180
ggcgatcctg tcaattttgc tgacgaggtt gcccgagagc acgacctctc ctaccagaaa   240
cagcttgagg cgggcgataa cccttacctc aagtacaacc acgcggacgc agagtttcag   300
gagaaactcg cttctgacac ttcttttggg ggaaaccttg ggaaggctgt tttccaggct   360
aaaaagagga ttctcgaacc tcttggcctg gttgagacgc cggataaaac ggcgcctgcg   420
gcaaaaaaga ggcctctaga gcagagtcct caagagccag actcctcgag cggagttggc   480
aagaaaggca aacagcctgc cagaaagaga ctcaactttg acgacgaacc tggagccgga   540
gacgggcctc ccccagaagg accatcttcc ggagctatgt ctactgagac tgaaatgcgt   600
gcagcagctg gcggaaatgg tggcgatgcg ggacaaggtg ccgagggagt gggtaatgcc   660
tccggtgatt ggcattgcga ttccacttgg tcagagagcc acgtcaccac cacctcaacc   720
cgcacctggg tcctgccgac ctacaacaac cacctgtacc tgcggctcgg ctcgagcaac   780
gccagcgaca ccttcaacgg attctccacc ccctggggat actttgactt taaccgcttc   840
cactgccact tctcgccaag agactggcaa aggctcatca caaccactg gggactgcgc   900
cccaaaagca tgcaagtccg catcttcaac atccaagtta aggaggtcac gacgtctaac   960
ggggagacga ccgtatccaa caacctcacc agcacggtcc agatctttgc ggacagcacg  1020
tacgagctcc cgtacgtgat ggatgcaggt caggagggca gcttgcctcc tttccccaac  1080
gacgtgttca tggtgcctca gtacgggtac tgcggactgg taaccggagg cagctctcaa  1140
aaccagacag acagaaatgc cttctactgt ctggagtact ttcccagcca gatgctgaga  1200
accggaaaca actttgagat ggtgtacaag tttgaaaacg tgcccttcca ctccatgtac  1260
gctcacagcc agagcctgga taggctgatg aacccgctgc tggaccagta cctgtgggag  1320
ctccagtcta ccacctctgg aggaactctc aaccagggca attcagccac caactttgcc  1380
aagctgacca aaacaaactt ttctggctac cgcaaaaact ggctcccggg gcccatgatg  1440
aagcagcaga gattctccaa gactgccagt caaaactaca gattccccca gggaagaaac  1500
aacagtctgc tccattatga gaccagaact accctcgacg gaagatggag caattttgcc  1560
ccgggaacgg ccatggcaac cgcagccaac gacgccaccg acttctctca ggcccagctc  1620
atctttgcgg ggcccaacat caccggcaac accaccacag atgccaataa cctgatgttc  1680
acttcagaag atgaacttag ggccaccaac ccccgggaca ctgacctgtt tggccacctg  1740
gcaaccaacc agcaaaacgc caccaccgtt cctaccgtag acgacgtgga cggagtcggc  1800
gtgtacccgg aatggtgtg gcaggacaga gacatttact accaagggcc catttgggcc  1860
aaaattccac acacggatgg acactttcac ccgtctcctc tcattggcgg atttggactg  1920
aaaagcccgc ctcacaaaat attcatcaaa aacactcctg tacccgccaa tcccgcaacg  1980
accttctctc cggccagaat caacagcttc atcacccagt acagcaccgg acaggtggct  2040
gtcaaaatag aatgggaaat ccagaaggag cggtccaaga gatggaaccc agaggtccag  2100
ttcacgtcca actacggagc acaggactcg cttctctggg ctcccgacaa cgccggagcc  2160
tacaaagagc ccagggccat tggatcccga tacctcacca accacctcta a           2211
```

<210> SEQ ID NO 61
<211> LENGTH: 2205
<212> TYPE: DNA
<213> ORGANISM: Unknown

<220> FEATURE:
<221> NAME/KEY: source
<223> OTHER INFORMATION: /note="Description of Unknown:
      Parent AAV Capsid sequence"

<400> SEQUENCE: 61

| | | | | | |
|---|---|---|---|---|---|
| atgactgacg | gttaccttcc | agattggcta | gaggacaacc | tctctgaagg | cgttcgagag | 60 |
| tggtgggcgc | tgcaacctgg | agcccctaaa | cccaaggcaa | atcaacaaca | tcaggacaac | 120 |
| gctcggggtc | ttgtgcttcc | gggttacaaa | tacctcggac | ccggcaacgg | actcgacaag | 180 |
| ggggaacccg | tcaacgcagc | ggacgcggca | gccctcgagc | acgacaaggc | ctacgaccag | 240 |
| cagctcaagg | ccggtgacaa | cccctacctc | aagtacaacc | acgccgacgc | ggagttccag | 300 |
| cagcggcttc | agggcgacac | atcgtttggg | ggcaacctcg | gcagagcagt | cttccaggcc | 360 |
| aaaaagaggg | ttcttgaacc | tcttggtctg | gttgagcaag | cgggtgagac | ggctcctgga | 420 |
| aagaagagac | cgttgattga | atccccccag | cagcccgact | cctccacggg | tatcggcaaa | 480 |
| aaaggcaagc | agccggctaa | aaagaagctc | gttttcgaag | acgaaactgg | agcaggcgac | 540 |
| ggaccccctg | agggatcaac | ttccggagcc | atgtctgatg | acagtgagat | gcgtgcagca | 600 |
| gctggcggag | ctgcagtcga | gggcggacaa | ggtgccgatg | gagtgggtaa | tgcctcgggt | 660 |
| gattggcatt | gcgattccac | ctggtctgag | ggccacgtca | cgaccaccag | caccagaacc | 720 |
| tgggtcttgc | ccacctacaa | caaccacctc | tacaagcgac | tcggagagag | cctgcagtcc | 780 |
| aacacctaca | acggattctc | cacccctgg | ggatactttg | acttcaaccg | cttccactgc | 840 |
| cacttctcac | cacgtgactg | gcagcgactc | atcaacaaca | actggggcat | gcgacccaaa | 900 |
| gccatgcggg | tcaaaatctt | caacatccag | gtcaaggagg | tcacgacgtc | gaacggcgag | 960 |
| acaacggtgg | ctaataacct | taccagcacg | gttcagatct | ttgcggactc | gtcgtacgaa | 1020 |
| ctgccgtacg | tgatggatgc | gggtcaagag | ggcagcctgc | ctccgttttcc | caacgacgtc | 1080 |
| tttatggtgc | cccagtacgg | ctactgtgga | ctggtgaccg | gcaacacttc | gcagcagcag | 1140 |
| actgacagaa | atgccttcta | ctgcctggag | tactttcctt | cgcagatgct | gcggactggc | 1200 |
| aacaactttg | aaattacgta | cagttttgag | aaggtgcctt | tccactcgat | gtacgcgcac | 1260 |
| agccagagcc | tggaccggct | gatgaaccct | ctcatcgacc | agtacctgtg | gggactgcaa | 1320 |
| tcgaccacca | ccggaaccac | cctgaatgcc | gggactgcca | ccaccaactt | taccaagctg | 1380 |
| cggcctacca | acttttccaa | cttttaaaaag | aactggctgc | ccgggccttc | aatcaagcag | 1440 |
| cagggcttct | caaagactgc | caatcaaaac | tacaagatcc | ctgccaccgg | gtcagacagt | 1500 |
| ctcatcaaat | acgagacgca | cagcactctg | acggaagat | ggagtgccct | gacccccgga | 1560 |
| cctccaatgg | ccacggctgg | acctgcggac | agcaagttca | gcaacagcca | gctcatctttt | 1620 |
| gcggggcctg | aacagaacgg | caacacggcc | accgtacccg | ggactctgat | ctttcacctct | 1680 |
| gaggaggagc | tggcagccac | caacgccacc | gatacggaca | tgtggggcaa | cctacctggc | 1740 |
| ggtgaccaga | gcaacagcaa | cctgccgacc | gtggacagac | tgacagcctt | gggagccgtg | 1800 |
| cctggaatgg | tctggcaaaa | cagagacatt | tactaccagg | gtcccatttg | gccaagatt | 1860 |
| cctcataccg | atggacactt | tcaccccctca | ccgctgattg | gtgggtttgg | gctgaaacac | 1920 |
| ccgcctcctc | aaattttttat | caagaacacc | ccggtacctg | cgaatcctgc | aacgaccttc | 1980 |
| agctctactc | cggtaaactc | cttcattact | cagtacagca | ctggccaggt | gtcggtgcag | 2040 |
| attgactggg | agatccagaa | ggagcggtcc | aaacgctgga | accccgaggt | ccagtttacc | 2100 |
| tccaactacg | gacagcaaaa | ctctctgttg | tgggctcccg | atgcggctgg | gaaatacact | 2160 |

```
gagcctaggg ctatcggtac ccgctacctc acccaccacc tgtaa          2205
```

<210> SEQ ID NO 62
<211> LENGTH: 2229
<212> TYPE: DNA
<213> ORGANISM: Unknown
<220> FEATURE:
<221> NAME/KEY: source
<223> OTHER INFORMATION: /note="Description of Unknown:
      Parent AAV Capsid sequence"

<400> SEQUENCE: 62

```
atggctgctg acggttatct tccagattgg ctcgaggaca acctctctga aggcattcgc    60
gagtggtggg cgctgaaacc tggagctcca aacccaagg ccaaccaaca gcatcaggac    120
aacggcaggg gtcttgtgct tcctgggtac aagtacctcg acccttcaa cggactcgac    180 aagggagagc cggtcaacga ggcagacgcc gcggccctcg agcacgacaa ggcctacgac    240
aagcagctcg agcagggga caacccgtat ctcaagtaca accacggcga cgccgagttc    300
cagcagcgct tggcgaccga cacctctttt ggggcaacc tcgggcgagc agtcttccag    360 gccaaaaga ggattctcga gcctctgggt ctggttgaag agggcgttaa acggctcct    420 ggaaagaaac gcccattaga aaagactcca atcggccga ccaacccgga ctctgggaag    480
gccccggcca agaaaagca aaagacggc gaaccagccg actctgctag aaggacactc    540
gactttgaag actctggagc aggagacgga cccctgagg atcatcttc ggagaaatg    600 tctcatgatg ctgagatgcg tgcggcgcca ggcggaaatg ctgtcgaggc gggacaaggt    660
gccgatggag tgggtaatgc ctccggtgat tggcattgcg attccacctg gtcagagggc    720
cgagtcacca ccaccagcac ccgaacctgg gtcctaccca cgtacaacaa ccacctgtac    780
ctgcgaatcg aacaacggc caacagcaac acctacaacg gattctccac ccctgggga    840 tactttgact ttaaccgctt ccactgccac ttttcccac gcgactggca gcgactcatc    900
aacaacaact ggggactcag gccgaaatcg atgcgtgtta aaatcttcaa catacaggtc    960
aaggaggtca cgacgtcaaa cggcgagact acggtcgcta taaccttac cagcacggtt    1020 cagatctttg cggattcgac gtatgaactc ccatacgtga tggacgccgg tcaggagggg    1080
agctttcctc cgtttcccaa cgacgtcttt atggttcccc aatacggata ctgcggagtt    1140
gtcactggaa aaaaccagaa ccagacagac agaaatgcct tttactgcct ggaatacttt    1200
ccatcccaaa tgctaagaac tggcaacaat tttgaagtca gttaccaatt tgaaaaagtt    1260
cctttccatt caatgtacgc gcacagccag agcctggaca gaatgatgaa tcctttactg    1320
gatcagtacc tgtggcatct gcaatcgacc actaccggaa attcccttaa tcaaggaaca    1380
gctaccacca cgtacgggaa aattaccact ggagactttg cctactacag gaaaaactgg    1440
ttgcctggag cctgcattaa caacaaaaa ttttcaagga tgccaatca aaactacaag    1500 attcccgcca gcgggggaga cgccctttta aagtatgaca cgcataccac tctaaatggg    1560
cgatggagta acatggctcc tggacctcca atggcaaccg caggtgccgg ggactcggat    1620
tttagcaaca gccagctgat ctttgccgga cccaatccga gcggtaacac gaccacatct    1680
tcaaacaatt tgttgtttac ctcagaagag gagattgcca aacaaaccc acgagacacg    1740 gacatgtttg gcagattgc agataataat caaaatgcca ccaccgcccc tcacatcgct    1800
aacctggacg ctatgggaat tgttcccgga atggtctggc aaaacagaga catctactac    1860 cagggccta tttgggccaa ggtccctcac acggacggac acttttcaccc ttcgccgctg    1920 atgggaggat ttggactgaa acacccgcct ccacagattt tcatcaaaaa caccccgta    1980
```

```
cccgccaatc ccaatactac ctttagcgct gcaaggatta attcttttct gacgcagtac    2040
agcaccggac aagttgccgt tcagatcgac tgggaaattc agaaggagca ttccaaacgc    2100
tggaatcccg aagttcaatt tacttcaaac tacggcactc aaaattctat gctgtgggct    2160
cccgacaatg ctggcaacta ccacgaactc cgggctattg ggtcccgttt cctcacccac    2220
cacttgtaa                                                           2229
```

<210> SEQ ID NO 63
<211> LENGTH: 42
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (11)..(22)
<223> OTHER INFORMATION: a, c, t, g, unknown or other

<400> SEQUENCE: 63

```
ctaaaccggt nnnnnnnnnn nnacggaaat acgatgtcgg ga                          42
```

<210> SEQ ID NO 64
<211> LENGTH: 42
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (11)..(22)
<223> OTHER INFORMATION: a, c, t, g, unknown or other

<400> SEQUENCE: 64

```
ttctcggccg nnnnnnnnnn nntcccgaca tcgtatttcc gt                          42
```

<210> SEQ ID NO 65
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 65

```
cgcgccacta gtaataaac                                                   19
```

<210> SEQ ID NO 66
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 66

```
tagagcaact agagttcg                                                    18
```

<210> SEQ ID NO 67
<211> LENGTH: 19
<212> TYPE: DNA

```
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 67
aattaaccct cactaaagg                                                   19

<210> SEQ ID NO 68
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 68
gtaatacgac tcactatagg gc                                               22

<210> SEQ ID NO 69
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 69
gtctgagtga ctagcattcg                                                  20

<210> SEQ ID NO 70
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 70
gtctactgaa gctcactgag                                                  20

<210> SEQ ID NO 71
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 71
tggatgactg catctttgaa                                                  20

<210> SEQ ID NO 72
<211> LENGTH: 17
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 72
attggcattg cgattcc                                                     17
```

<210> SEQ ID NO 73
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 73
tagagcaact agagttcg                                                 18

<210> SEQ ID NO 74
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 74
ttcgatcaac tacgcagaca g                                             21

<210> SEQ ID NO 75
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 75
gtccgtgagt gaagcagata tt                                            22

<210> SEQ ID NO 76
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 76
tctgatgctg tttccctgca gaca                                          24

<210> SEQ ID NO 77
<211> LENGTH: 58
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 77
aatgatacgg cgaccaccga gatctacact ctttccctac acgacgctct tccgatct     58

<210> SEQ ID NO 78
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:

Synthetic primer"

<400> SEQUENCE: 78
cgcgccacta gtaataaac                                                19

<210> SEQ ID NO 79
<211> LENGTH: 61
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 79
caagcagaag acggcatacg agatcggtct cggcattcct gctgaaccgc tcttccgatc   60
t                                                                   61

<210> SEQ ID NO 80
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 80
tagagcaact agagttcg                                                 18

<210> SEQ ID NO 81
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 81
cacatatcga ggtggacatt ac                                            22

<210> SEQ ID NO 82
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 82
tgtttgtatt cagcccatag                                               20

<210> SEQ ID NO 83
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 83
cctgtatgcc tctggtcgta                                               20

-continued

```
<210> SEQ ID NO 84
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 84
cctcgtagat gggcacagt                                                   19

<210> SEQ ID NO 85
<211> LENGTH: 42
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (11)..(22)
<223> OTHER INFORMATION: a, c, t, g, unknown or other

<400> SEQUENCE: 85
ctaaaccggt nnnnnnnnnn nnacggaaat acgatgtcgg ga                          42

<210> SEQ ID NO 86
<211> LENGTH: 42
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (11)..(22)
<223> OTHER INFORMATION: a, c, t, g, unknown or other

<400> SEQUENCE: 86
ttctcggccg nnnnnnnnnn nntcccgaca tcgtatttcc gt                          42

<210> SEQ ID NO 87
<211> LENGTH: 62
<212> TYPE: DNA
<213> ORGANISM: Unknown
<220> FEATURE:
<221> NAME/KEY: source
<223> OTHER INFORMATION: /note="Description of Unknown:
      Parent AAV sequence"

<400> SEQUENCE: 87
gtaataaacc ggttgtacgg cagacacgga aatacgatgt cgggaagtac ctcccagcgg      60
cc                                                                     62

<210> SEQ ID NO 88
<211> LENGTH: 62
<212> TYPE: DNA
<213> ORGANISM: Unknown
<220> FEATURE:
<221> NAME/KEY: source
<223> OTHER INFORMATION: /note="Description of Unknown:
      Parent AAV sequence"

<400> SEQUENCE: 88
gtaataaacc ggttgaaact accccacgga aatacgatgt cgggaaccta caagagacgg      60
```

```
cc                                                             62

<210> SEQ ID NO 89
<211> LENGTH: 62
<212> TYPE: DNA
<213> ORGANISM: Unknown
<220> FEATURE:
<221> NAME/KEY: source
<223> OTHER INFORMATION: /note="Description of Unknown:
      Parent AAV sequence"

<400> SEQUENCE: 89
gtaataaacc ggtaggggaa agcggacgga aatacgatgt cgggaaaaaa taaacatcgg   60
cc                                                             62

<210> SEQ ID NO 90
<211> LENGTH: 62
<212> TYPE: DNA
<213> ORGANISM: Unknown
<220> FEATURE:
<221> NAME/KEY: source
<223> OTHER INFORMATION: /note="Description of Unknown:
      Parent AAV sequence"

<400> SEQUENCE: 90
gtaataaacc ggttggcgga tgcagacgga aatacgatgt cgggaaggaa agatcttcgg   60
cc                                                             62

<210> SEQ ID NO 91
<211> LENGTH: 62
<212> TYPE: DNA
<213> ORGANISM: Unknown
<220> FEATURE:
<221> NAME/KEY: source
<223> OTHER INFORMATION: /note="Description of Unknown:
      Parent AAV sequence"

<400> SEQUENCE: 91
gtaataaacc ggtactaagt atcaaacgga aatacgatgt cgggatccac ttcaagacgg   60
cc                                                             62

<210> SEQ ID NO 92
<211> LENGTH: 62
<212> TYPE: DNA
<213> ORGANISM: Unknown
<220> FEATURE:
<221> NAME/KEY: source
<223> OTHER INFORMATION: /note="Description of Unknown:
      Parent AAV sequence"

<400> SEQUENCE: 92
gtaataaacc ggtttttcgc tggaaacgga aatacgatgt cgggacctgc cccgcctcgg   60
cc                                                             62

<210> SEQ ID NO 93
<211> LENGTH: 62
<212> TYPE: DNA
<213> ORGANISM: Unknown
<220> FEATURE:
<221> NAME/KEY: source
<223> OTHER INFORMATION: /note="Description of Unknown:
      Parent AAV sequence"

<400> SEQUENCE: 93
gtaataaacc ggttcgaaag tatgtacgga aatacgatgt cgggactaaa aattacccgg   60
``` cc                                                                      62

<210> SEQ ID NO 94
<211> LENGTH: 62
<212> TYPE: DNA
<213> ORGANISM: Unknown
<220> FEATURE:
<221> NAME/KEY: source
<223> OTHER INFORMATION: /note="Description of Unknown:
      Parent AAV sequence"

<400> SEQUENCE: 94
gtaataaacc ggtccaacaa aatttacgga aatacgatgt cgggatcggt caaaggacgg    60
cc                                                                      62

<210> SEQ ID NO 95
<211> LENGTH: 62
<212> TYPE: DNA
<213> ORGANISM: Unknown
<220> FEATURE:
<221> NAME/KEY: source
<223> OTHER INFORMATION: /note="Description of Unknown:
      Parent AAV sequence"

<400> SEQUENCE: 95
gtaataaacc ggtgtcgtat gtgtgacgga aatacgatgt cgggattatg tcagtcacgg    60
cc                                                                      62

<210> SEQ ID NO 96
<211> LENGTH: 62
<212> TYPE: DNA
<213> ORGANISM: Unknown
<220> FEATURE:
<221> NAME/KEY: source
<223> OTHER INFORMATION: /note="Description of Unknown:
      Parent AAV sequence"

<400> SEQUENCE: 96
gtaataaacc ggtaacgagg tcacgacgga aatacgatgt cgggacgtaa cctagaacgg    60
cc                                                                      62

<210> SEQ ID NO 97
<211> LENGTH: 62
<212> TYPE: DNA
<213> ORGANISM: Unknown
<220> FEATURE:
<221> NAME/KEY: source
<223> OTHER INFORMATION: /note="Description of Unknown:
      Parent AAV sequence"

<400> SEQUENCE: 97
gtaataaacc ggtcaataat gaagaacgga aatacgatgt cgggacgagt tcatattcgg    60
cc                                                                      62

<210> SEQ ID NO 98
<211> LENGTH: 62
<212> TYPE: DNA
<213> ORGANISM: Unknown
<220> FEATURE:
<221> NAME/KEY: source
<223> OTHER INFORMATION: /note="Description of Unknown:
      Parent AAV sequence"

<400> SEQUENCE: 98

```
gtaataaacc ggtgggagtg cagacacgga aatacgatgt cgggaaaccc ttaccaacgg      60
cc                                                                    62
```

<210> SEQ ID NO 99
<211> LENGTH: 62
<212> TYPE: DNA
<213> ORGANISM: Unknown
<220> FEATURE:
<221> NAME/KEY: source
<223> OTHER INFORMATION: /note="Description of Unknown:
      Parent AAV sequence"

<400> SEQUENCE: 99

```
gtaataaacc ggtccatcct attcgacgga aatacgatgt cgggaactgc ctcggtacgg      60
cc                                                                    62
```

<210> SEQ ID NO 100
<211> LENGTH: 62
<212> TYPE: DNA
<213> ORGANISM: Unknown
<220> FEATURE:
<221> NAME/KEY: source
<223> OTHER INFORMATION: /note="Description of Unknown:
      Parent AAV sequence"

<400> SEQUENCE: 100

```
gtaataaacc ggtaagagtt acgccacgga aatacgatgt cgggaccgat aaccacccgg     60
cc                                                                    62
```

<210> SEQ ID NO 101
<211> LENGTH: 62
<212> TYPE: DNA
<213> ORGANISM: Unknown
<220> FEATURE:
<221> NAME/KEY: source
<223> OTHER INFORMATION: /note="Description of Unknown:
      Parent AAV sequence"

<400> SEQUENCE: 101

```
gtaataaacc ggtcgaacgg agataacgga aatacgatgt cgggacccag agtaccacgg     60
cc                                                                    62
```

<210> SEQ ID NO 102
<211> LENGTH: 62
<212> TYPE: DNA
<213> ORGANISM: Unknown
<220> FEATURE:
<221> NAME/KEY: source
<223> OTHER INFORMATION: /note="Description of Unknown:
      Parent AAV sequence"

<400> SEQUENCE: 102

```
gtaataaacc ggtggggccg ctcggacgga aatacgatgt cgggaggtcc gaccctacgg     60
cc                                                                    62
```

<210> SEQ ID NO 103
<211> LENGTH: 62
<212> TYPE: DNA
<213> ORGANISM: Unknown
<220> FEATURE:
<221> NAME/KEY: source
<223> OTHER INFORMATION: /note="Description of Unknown:
      Parent AAV sequence"

<400> SEQUENCE: 103
gtaataaacc ggtattacta catctacgga aatacgatgt cgggaaccat gacttgccgg    60
cc    62

<210> SEQ ID NO 104
<211> LENGTH: 62
<212> TYPE: DNA
<213> ORGANISM: Unknown
<220> FEATURE:
<221> NAME/KEY: source
<223> OTHER INFORMATION: /note="Description of Unknown:
      Parent AAV sequence"

<400> SEQUENCE: 104
gtaataaacc ggtcaatgtt gccatacgga aatacgatgt cgggattacc ttcaattcgg    60
cc    62

<210> SEQ ID NO 105
<211> LENGTH: 736
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: VARIANT
<222> LOCATION: (162)..(162)
<223> OTHER INFORMATION: /replace="Ala" or "Ser" or "Lys"
<220> FEATURE:
<221> NAME/KEY: VARIANT
<222> LOCATION: (200)..(200)
<223> OTHER INFORMATION: /replace="Thr" or "Ser"
<220> FEATURE:
<221> NAME/KEY: VARIANT
<222> LOCATION: (328)..(328)
<223> OTHER INFORMATION: /replace="Glu" or "Asn"
<220> FEATURE:
<221> NAME/KEY: VARIANT
<222> LOCATION: (411)..(411)
<223> OTHER INFORMATION: /replace="Gln" or "Glu"
<220> FEATURE:
<221> NAME/KEY: VARIANT
<222> LOCATION: (494)..(494)
<223> OTHER INFORMATION: /replace="Ala" or "Asn" or "Gly" or "Ser"
<220> FEATURE:
<221> NAME/KEY: VARIANT
<222> LOCATION: (548)..(548)
<223> OTHER INFORMATION: /replace="Ser" or "Thr"
<220> FEATURE:
<221> NAME/KEY: VARIANT
<222> LOCATION: (549)..(549)
<223> OTHER INFORMATION: /replace="Glu" or "Thr" or "Ala" or "Asp"
<220> FEATURE:
<221> NAME/KEY: VARIANT
<222> LOCATION: (554)..(554)
<223> OTHER INFORMATION: /replace="Asp" or "Glu" or "Ile"
<220> FEATURE:
<221> NAME/KEY: VARIANT
<222> LOCATION: (664)..(664)
<223> OTHER INFORMATION: /replace="Pro" or "Gln" or "Lys"
<220> FEATURE:
<221> NAME/KEY: VARIANT
<222> LOCATION: (709)..(709)
<223> OTHER INFORMATION: /replace="Val" or "Thr" or "Asn"
<220> FEATURE:
<221> NAME/KEY: SITE
<222> LOCATION: (1)..(736)
<223> OTHER INFORMATION: /note="Variant residues given in the sequence
      have no preference with respect to those in the annotations
      for variant positions"

<400> SEQUENCE: 105

```
Met Ala Ala Asp Gly Tyr Leu Pro Asp Trp Leu Glu Asp Asn Leu Ser
1               5                   10                  15
Glu Gly Ile Arg Glu Trp Trp Asp Leu Lys Pro Gly Ala Pro Lys Pro
            20                  25                  30
Lys Ala Asn Gln Gln Lys Gln Asp Asp Gly Arg Gly Leu Val Leu Pro
                35                  40                  45
Gly Tyr Lys Tyr Leu Gly Pro Phe Asn Gly Leu Asp Lys Gly Glu Pro
    50                  55                  60
Val Asn Ala Ala Asp Ala Ala Leu Glu His Asp Lys Ala Tyr Asp
65                  70                  75                  80
Gln Gln Leu Lys Ala Gly Asp Asn Pro Tyr Leu Arg Tyr Asn His Ala
            85                  90                  95
Asp Ala Glu Phe Gln Glu Arg Leu Gln Glu Asp Thr Ser Phe Gly Gly
                100                 105                 110
Asn Leu Gly Arg Ala Val Phe Gln Ala Lys Lys Arg Val Leu Glu Pro
            115                 120                 125
Leu Gly Leu Val Glu Glu Gly Ala Lys Thr Ala Pro Gly Lys Lys Arg
    130                 135                 140
Pro Val Glu Gln Ser Pro Gln Glu Pro Asp Ser Ser Gly Ile Gly
145                 150                 155                 160
Lys Thr Gly Gln Gln Pro Ala Arg Lys Arg Leu Asn Phe Gly Gln Thr
            165                 170                 175
Gly Asp Ser Glu Ser Val Pro Asp Pro Gln Pro Leu Gly Glu Pro Pro
                180                 185                 190
Ala Ala Pro Ser Gly Leu Gly Pro Asn Thr Met Ala Ser Gly Gly Gly
            195                 200                 205
Ala Pro Met Ala Asp Asn Asn Glu Gly Ala Asp Gly Val Gly Asn Ala
    210                 215                 220
Ser Gly Asn Trp His Cys Asp Ser Thr Trp Leu Gly Asp Arg Val Ile
225                 230                 235                 240
Thr Thr Ser Thr Arg Thr Trp Ala Leu Pro Thr Tyr Asn Asn His Leu
            245                 250                 255
Tyr Lys Gln Ile Ser Ser Ala Ser Thr Gly Ala Ser Asn Asp Asn His
            260                 265                 270
Tyr Phe Gly Tyr Ser Thr Pro Trp Gly Tyr Phe Asp Phe Asn Arg Phe
    275                 280                 285
His Cys His Phe Ser Pro Arg Asp Trp Gln Arg Leu Ile Asn Asn Asn
    290                 295                 300
Trp Gly Phe Arg Pro Lys Arg Leu Asn Phe Lys Leu Phe Asn Ile Gln
305                 310                 315                 320
Val Lys Glu Val Thr Gln Asn Asp Gly Thr Lys Thr Ile Ala Asn Asn
            325                 330                 335
Leu Thr Ser Thr Val Gln Val Phe Thr Asp Ser Glu Tyr Gln Leu Pro
            340                 345                 350
Tyr Val Leu Gly Ser Ala His Gln Gly Cys Leu Pro Pro Phe Pro Ala
    355                 360                 365
Asp Val Phe Met Ile Pro Gln Tyr Gly Tyr Leu Thr Leu Asn Asn Gly
    370                 375                 380
Ser Gln Ala Val Gly Arg Ser Ser Phe Tyr Cys Leu Glu Tyr Phe Pro
385                 390                 395                 400
Ser Gln Met Leu Arg Thr Gly Asn Asn Phe Thr Phe Ser Tyr Thr Phe
            405                 410                 415
Glu Asp Val Pro Phe His Ser Ser Tyr Ala His Ser Gln Ser Leu Asp
```

420             425             430
Arg Leu Met Asn Pro Leu Ile Asp Gln Tyr Leu Tyr Tyr Leu Asn Arg
            435                 440                 445

Thr Gln Gly Thr Ser Gly Thr Thr Asn Gln Ser Arg Leu Leu Phe Ser
        450                 455                 460

Gln Ala Gly Pro Gln Ser Met Ser Ile Gln Ala Arg Asn Trp Leu Pro
465                 470                 475                 480

Gly Pro Cys Tyr Arg Gln Gln Arg Val Ser Lys Thr Ala Thr Asp Asn
                485                 490                 495

Asn Asn Ser Asn Phe Pro Trp Thr Gly Ala Ser Lys Tyr His Leu Asn
            500                 505                 510

Gly Arg Asp Ser Leu Val Asn Pro Gly Pro Ala Met Ala Ser His Lys
        515                 520                 525

Asp Asp Glu Glu Lys Phe Phe Pro Met Ser Gly Val Leu Ile Phe Gly
530                 535                 540

Lys Glu Gly Ala Gly Ala Ser Asn Ala Ala Leu Asp Asn Val Met Ile
545                 550                 555                 560

Thr Asp Glu Glu Glu Ile Arg Thr Thr Asn Pro Val Ala Thr Glu Gln
                565                 570                 575

Tyr Gly Thr Val Ala Asn Asn Leu Gln Ser Ser Asn Thr Ala Pro Thr
            580                 585                 590

Thr Gly Thr Val Asn Asp Gln Gly Ala Leu Pro Gly Met Val Trp Gln
        595                 600                 605

Asp Arg Asp Val Tyr Leu Gln Gly Pro Ile Trp Ala Lys Ile Pro His
610                 615                 620

Thr Asp Gly His Phe His Pro Ser Pro Leu Met Gly Gly Phe Gly Leu
625                 630                 635                 640

Lys His Pro Pro Pro Gln Ile Leu Ile Lys Asn Thr Pro Val Pro Ala
                645                 650                 655

Asn Pro Pro Thr Thr Phe Ser Ala Ala Lys Leu Ala Ser Phe Ile Thr
            660                 665                 670

Gln Tyr Ser Thr Gly Gln Val Ser Val Glu Ile Glu Trp Glu Leu Gln
        675                 680                 685

Lys Glu Asn Ser Lys Arg Trp Asn Pro Glu Ile Gln Tyr Thr Ser Asn
690                 695                 700

Tyr Tyr Lys Ser Ala Asn Val Asp Phe Thr Val Asp Thr Asn Gly Val
705                 710                 715                 720

Tyr Ser Glu Pro Arg Pro Ile Gly Thr Arg Tyr Leu Thr Arg Asn Leu
                725                 730                 735

<210> SEQ ID NO 106
<211> LENGTH: 736
<212> TYPE: PRT
<213> ORGANISM: Unknown
<220> FEATURE:
<221> NAME/KEY: source
<223> OTHER INFORMATION: /note="Description of Unknown:
      Parent AAV Capsid sequence"

<400> SEQUENCE: 106

Met Ala Ala Asp Gly Tyr Leu Pro Asp Trp Leu Glu Asp Asn Leu Ser
1               5                   10                  15

Glu Gly Ile Arg Glu Trp Trp Asp Leu Lys Pro Gly Ala Pro Lys Pro
            20                  25                  30

Lys Ala Asn Gln Gln Lys Gln Asp Asp Gly Arg Gly Leu Val Leu Pro
        35                  40                  45

```
Gly Tyr Lys Tyr Leu Gly Pro Phe Asn Gly Leu Asp Lys Gly Glu Pro
     50                  55                  60

Val Asn Ala Ala Asp Ala Ala Leu Glu His Asp Lys Ala Tyr Asp
 65              70                  75                  80

Gln Gln Leu Lys Ala Gly Asp Asn Pro Tyr Leu Arg Tyr Asn His Ala
                 85                  90                  95

Asp Ala Glu Phe Gln Glu Arg Leu Gln Glu Asp Thr Ser Phe Gly Gly
                100                 105                 110

Asn Leu Gly Arg Ala Val Phe Gln Ala Lys Lys Arg Val Leu Glu Pro
            115                 120                 125

Leu Gly Leu Val Glu Glu Gly Ala Lys Thr Ala Pro Gly Lys Lys Arg
        130                 135                 140

Pro Val Glu Gln Ser Pro Gln Glu Pro Asp Ser Ser Ser Gly Ile Gly
145                 150                 155                 160

Lys Thr Gly Gln Gln Pro Ala Lys Lys Arg Leu Asn Phe Gly Gln Thr
                165                 170                 175

Gly Asp Ser Glu Ser Val Pro Asp Pro Gln Pro Leu Gly Glu Pro Pro
                180                 185                 190

Ala Thr Pro Ala Ala Val Gly Pro Thr Thr Met Ala Ser Gly Gly Gly
            195                 200                 205

Ala Pro Met Ala Asp Asn Asn Glu Gly Ala Asp Gly Val Gly Asn Ala
210                 215                 220

Ser Gly Asn Trp His Cys Asp Ser Thr Trp Leu Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Ser Ala Ser Thr Gly Ala Ser Asn Asp Asn His
                260                 265                 270

Tyr Phe Gly Tyr Ser Thr Pro Trp Gly Tyr Phe Asp Phe Asn Arg Phe
            275                 280                 285

His Cys His Phe Ser Pro Arg Asp Trp Gln Arg Leu Ile Asn Asn Asn
290                 295                 300

Trp Gly Phe Arg Pro Lys Arg Leu Asn Phe Lys Leu Phe Asn Ile Gln
305                 310                 315                 320

Val Lys Glu Val Thr Thr Asn Asp Gly Val Thr Thr Ile Ala Asn Asn
                325                 330                 335

Leu Thr Ser Thr Val Gln Val Phe Ser Asp Ser Glu Tyr Gln Leu Pro
            340                 345                 350

Tyr Val Leu Gly Ser Ala His Gln Gly Cys Leu Pro Pro Phe Pro Ala
        355                 360                 365

Asp Val Phe Met Ile Pro Gln Tyr Gly Tyr Leu Thr Leu Asn Asn Gly
370                 375                 380

Ser Gln Ala Val Gly Arg Ser Ser Phe Tyr Cys Leu Glu Tyr Phe Pro
385                 390                 395                 400

Ser Gln Met Leu Arg Thr Gly Asn Asn Phe Thr Phe Ser Tyr Thr Phe
                405                 410                 415

Glu Glu Val Pro Phe His Ser Ser Tyr Ala His Ser Gln Ser Leu Asp
                420                 425                 430

Arg Leu Met Asn Pro Leu Ile Asp Gln Tyr Leu Tyr Tyr Leu Asn Arg
            435                 440                 445

Thr Gln Asn Gln Ser Gly Ser Ala Gln Asn Lys Asp Leu Leu Phe Ser
450                 455                 460
```

Arg Gly Ser Pro Ala Gly Met Ser Val Gln Pro Lys Asn Trp Leu Pro
465                 470                 475                 480

Gly Pro Cys Tyr Arg Gln Gln Arg Val Ser Lys Thr Lys Thr Asp Asn
            485                 490                 495

Asn Asn Ser Asn Phe Thr Trp Thr Gly Ala Ser Lys Tyr Asn Leu Asn
        500                 505                 510

Gly Arg Glu Ser Ile Ile Asn Pro Gly Thr Ala Met Ala Ser His Lys
    515                 520                 525

Asp Asp Glu Asp Lys Phe Phe Pro Met Ser Gly Val Met Ile Phe Gly
530                 535                 540

Lys Glu Ser Ala Gly Ala Ser Asn Thr Ala Leu Asp Asn Val Met Ile
545                 550                 555                 560

Thr Asp Glu Glu Glu Ile Lys Ala Thr Asn Pro Val Ala Thr Glu Arg
                565                 570                 575

Phe Gly Thr Val Ala Val Asn Phe Gln Ser Ser Ser Thr Asp Pro Ala
                580                 585                 590

Thr Gly Asp Val His Ala Met Gly Ala Leu Pro Gly Met Val Trp Gln
            595                 600                 605

Asp Arg Asp Val Tyr Leu Gln Gly Pro Ile Trp Ala Lys Ile Pro His
610                 615                 620

Thr Asp Gly His Phe His Pro Ser Pro Leu Met Gly Gly Phe Gly Leu
625                 630                 635                 640

Lys Asn Pro Pro Pro Gln Ile Leu Ile Lys Asn Thr Pro Val Pro Ala
                645                 650                 655

Asn Pro Pro Ala Glu Phe Ser Ala Thr Lys Phe Ala Ser Phe Ile Thr
            660                 665                 670

Gln Tyr Ser Thr Gly Gln Val Ser Val Glu Ile Glu Trp Glu Leu Gln
        675                 680                 685

Lys Glu Asn Ser Lys Arg Trp Asn Pro Glu Val Gln Tyr Thr Ser Asn
690                 695                 700

Tyr Ala Lys Ser Ala Asn Val Asp Phe Thr Val Asp Asn Asn Gly Leu
705                 710                 715                 720

Tyr Thr Glu Pro Arg Pro Ile Gly Thr Arg Tyr Leu Thr Arg Pro Leu
                725                 730                 735

<210> SEQ ID NO 107
<211> LENGTH: 735
<212> TYPE: PRT
<213> ORGANISM: Unknown
<220> FEATURE:
<221> NAME/KEY: source
<223> OTHER INFORMATION: /note="Description of Unknown:
      Parent AAV Capsid sequence"

<400> SEQUENCE: 107

Met Ala Ala Asp Gly Tyr Leu Pro Asp Trp Leu Glu Asp Thr Leu Ser
1               5                   10                  15

Glu Gly Ile Arg Gln Trp Trp Lys Leu Lys Pro Gly Pro Pro Pro
            20                  25                  30

Lys Pro Ala Glu Arg His Lys Asp Asp Ser Arg Gly Leu Val Leu Pro
            35                  40                  45

Gly Tyr Lys Tyr Leu Gly Pro Phe Asn Gly Leu Asp Lys Gly Glu Pro
        50                  55                  60

Val Asn Glu Ala Asp Ala Ala Ala Leu Glu His Asp Lys Ala Tyr Asp
65                  70                  75                  80

Arg Gln Leu Asp Ser Gly Asp Asn Pro Tyr Leu Lys Tyr Asn His Ala

```
            85              90               95
Asp Ala Glu Phe Gln Glu Arg Leu Lys Glu Asp Thr Ser Phe Gly Gly
            100             105              110

Asn Leu Gly Arg Ala Val Phe Gln Ala Lys Lys Arg Val Leu Glu Pro
            115             120              125

Leu Gly Leu Val Glu Glu Pro Val Lys Thr Ala Pro Gly Lys Lys Arg
            130             135              140

Pro Val Glu His Ser Pro Val Glu Pro Asp Ser Ser Gly Thr Gly
145             150             155              160

Lys Ala Gly Gln Gln Pro Ala Arg Lys Arg Leu Asn Phe Gly Gln Thr
                165             170             175

Gly Asp Ala Asp Ser Val Pro Asp Pro Gln Pro Leu Gly Gln Pro Pro
                180             185             190

Ala Ala Pro Ser Gly Leu Gly Thr Asn Thr Met Ala Thr Gly Ser Gly
                195             200             205

Ala Pro Met Ala Asp Asn Asn Glu Gly Ala Asp Gly Val Gly Asn Ser
            210             215              220

Ser Gly Asn Trp His Cys Asp Ser Thr Trp Met Gly Asp Arg Val Ile
225             230             235              240

Thr Thr Ser Thr Arg Thr Trp Ala Leu Pro Thr Tyr Asn Asn His Leu
                245             250             255

Tyr Lys Gln Ile Ser Ser Gln Ser Gly Ala Ser Asn Asp Asn His Tyr
                260             265             270

Phe Gly Tyr Ser Thr Pro Trp Gly Tyr Phe Asp Phe Asn Arg Phe His
            275             280             285

Cys His Phe Ser Pro Arg Asp Trp Gln Arg Leu Ile Asn Asn Asn Trp
290             295             300

Gly Phe Arg Pro Lys Arg Leu Asn Phe Lys Leu Phe Asn Ile Gln Val
305             310             315              320

Lys Glu Val Thr Gln Asn Asp Gly Thr Thr Thr Ile Ala Asn Asn Leu
                325             330             335

Thr Ser Thr Val Gln Val Phe Thr Asp Ser Glu Tyr Gln Leu Pro Tyr
            340             345             350

Val Leu Gly Ser Ala His Gln Gly Cys Leu Pro Pro Phe Pro Ala Asp
            355             360             365

Val Phe Met Val Pro Gln Tyr Gly Tyr Leu Thr Leu Asn Asn Gly Ser
            370             375             380

Gln Ala Val Gly Arg Ser Ser Phe Tyr Cys Leu Glu Tyr Phe Pro Ser
385             390             395              400

Gln Met Leu Arg Thr Gly Asn Asn Phe Thr Phe Ser Tyr Thr Phe Glu
                405             410             415

Asp Val Pro Phe His Ser Ser Tyr Ala His Ser Gln Ser Leu Asp Arg
            420             425             430

Leu Met Asn Pro Leu Ile Asp Gln Tyr Leu Tyr Tyr Leu Ser Arg Thr
            435             440             445

Asn Thr Pro Ser Gly Thr Thr Thr Gln Ser Arg Leu Gln Phe Ser Gln
            450             455             460

Ala Gly Ala Ser Asp Ile Arg Asp Gln Ser Arg Asn Trp Leu Pro Gly
465             470             475              480

Pro Cys Tyr Arg Gln Gln Arg Val Ser Lys Thr Ser Ala Asp Asn Asn
                485             490             495

Asn Ser Glu Tyr Ser Trp Thr Gly Ala Thr Lys Tyr His Leu Asn Gly
            500             505             510
```

```
Arg Asp Ser Leu Val Asn Pro Gly Pro Ala Met Ala Ser His Lys Asp
    515                 520                 525
Asp Glu Glu Lys Phe Phe Pro Gln Ser Gly Val Leu Ile Phe Gly Lys
    530                 535                 540
Gln Gly Ser Glu Lys Thr Asn Val Asp Ile Glu Lys Val Met Ile Thr
545                 550                 555                 560
Asp Glu Glu Glu Ile Arg Thr Thr Asn Pro Val Ala Thr Glu Gln Tyr
                565                 570                 575
Gly Ser Val Ser Thr Asn Leu Gln Arg Gly Asn Arg Gln Ala Ala Thr
                580                 585                 590
Ala Asp Val Asn Thr Gln Gly Val Leu Pro Gly Met Val Trp Gln Asp
    595                 600                 605
Arg Asp Val Tyr Leu Gln Gly Pro Ile Trp Ala Lys Ile Pro His Thr
    610                 615                 620
Asp Gly His Phe His Pro Ser Pro Leu Met Gly Gly Phe Gly Leu Lys
625                 630                 635                 640
His Pro Pro Pro Gln Ile Leu Ile Lys Asn Thr Pro Val Pro Ala Asn
                645                 650                 655
Pro Ser Thr Thr Phe Ser Ala Ala Lys Phe Ala Ser Phe Ile Thr Gln
                660                 665                 670
Tyr Ser Thr Gly Gln Val Ser Val Glu Ile Glu Trp Glu Leu Gln Lys
            675                 680                 685
Glu Asn Ser Lys Arg Trp Asn Pro Glu Ile Gln Tyr Thr Ser Asn Tyr
            690                 695                 700
Asn Lys Ser Val Asn Val Asp Phe Thr Val Asp Thr Asn Gly Val Tyr
705                 710                 715                 720
Ser Glu Pro Arg Pro Ile Gly Thr Arg Tyr Leu Thr Arg Asn Leu
                725                 730                 735

<210> SEQ ID NO 108
<211> LENGTH: 736
<212> TYPE: PRT
<213> ORGANISM: Unknown
<220> FEATURE:
<221> NAME/KEY: source
<223> OTHER INFORMATION: /note="Description of Unknown:
      Parent AAV Capsid sequence"

<400> SEQUENCE: 108

Met Ala Ala Asp Gly Tyr Leu Pro Asp Trp Leu Glu Asp Asn Leu Ser
1               5                   10                  15
Glu Gly Ile Arg Glu Trp Trp Ala Leu Lys Pro Gly Val Pro Gln Pro
            20                  25                  30
Lys Ala Asn Gln Gln His Gln Asp Asn Arg Arg Gly Leu Val Leu Pro
        35                  40                  45
Gly Tyr Lys Tyr Leu Gly Pro Gly Asn Gly Leu Asp Lys Gly Glu Pro
    50                  55                  60
Val Asn Glu Ala Asp Ala Ala Ala Leu Glu His Asp Lys Ala Tyr Asp
65                  70                  75                  80
Gln Gln Leu Lys Ala Gly Asp Asn Pro Tyr Leu Lys Tyr Asn His Ala
                85                  90                  95
Asp Ala Glu Phe Gln Glu Arg Leu Gln Glu Asp Thr Ser Phe Gly Gly
            100                 105                 110
Asn Leu Gly Arg Ala Val Phe Gln Ala Lys Lys Arg Ile Leu Glu Pro
        115                 120                 125
```

```
Leu Gly Leu Val Glu Glu Ala Ala Lys Thr Ala Pro Gly Lys Lys Arg
    130                 135                 140
Pro Val Asp Gln Ser Pro Gln Glu Pro Asp Ser Ser Gly Val Gly
145                 150                 155                 160
Lys Ser Gly Lys Gln Pro Ala Arg Lys Arg Leu Asn Phe Gly Gln Thr
                165                 170                 175
Gly Asp Ser Glu Ser Val Pro Asp Pro Gln Pro Leu Gly Glu Pro Pro
            180                 185                 190
Ala Ala Pro Thr Ser Leu Gly Ser Asn Thr Met Ala Ser Gly Gly Gly
        195                 200                 205
Ala Pro Met Ala Asp Asn Asn Glu Gly Ala Asp Gly Val Gly Asn Ser
    210                 215                 220
Ser Gly Asn Trp His Cys Asp Ser Gln Trp Leu Gly Asp Arg Val Ile
225                 230                 235                 240
Thr Thr Ser Thr Arg Thr Trp Ala Leu Pro Thr Tyr Asn Asn His Leu
                245                 250                 255
Tyr Lys Gln Ile Ser Ser Gln Ser Gly Ala Ser Asn Asp Asn His Tyr
            260                 265                 270
Phe Gly Tyr Ser Thr Pro Trp Gly Tyr Phe Asp Phe Asn Arg Phe His
        275                 280                 285
Cys His Phe Ser Pro Arg Asp Trp Gln Arg Leu Ile Asn Asn Asn Trp
    290                 295                 300
Gly Phe Arg Pro Lys Lys Leu Ser Phe Lys Leu Phe Asn Ile Gln Val
305                 310                 315                 320
Lys Glu Val Thr Gln Asn Asp Gly Thr Thr Thr Ile Ala Asn Asn Leu
                325                 330                 335
Thr Ser Thr Val Gln Val Phe Thr Asp Ser Glu Tyr Gln Leu Pro Tyr
            340                 345                 350
Val Leu Gly Ser Ala His Gln Gly Cys Leu Pro Pro Phe Pro Ala Asp
        355                 360                 365
Val Phe Met Val Pro Gln Tyr Gly Tyr Leu Thr Leu Asn Asn Gly Ser
    370                 375                 380
Gln Ala Val Gly Arg Ser Ser Phe Tyr Cys Leu Glu Tyr Phe Pro Ser
385                 390                 395                 400
Gln Met Leu Arg Thr Gly Asn Asn Phe Gln Phe Ser Tyr Thr Phe Glu
                405                 410                 415
Asp Val Pro Phe His Ser Ser Tyr Ala His Ser Gln Ser Leu Asp Arg
            420                 425                 430
Leu Met Asn Pro Leu Ile Asp Gln Tyr Leu Tyr Tyr Leu Asn Arg Thr
        435                 440                 445
Gln Gly Thr Thr Ser Gly Thr Thr Asn Gln Ser Arg Leu Leu Phe Ser
    450                 455                 460
Gln Ala Gly Pro Gln Ser Met Ser Ile Gln Ala Arg Asn Trp Leu Pro
465                 470                 475                 480
Gly Pro Cys Tyr Arg Gln Gln Arg Leu Ser Lys Thr Ala Asn Asp Asn
                485                 490                 495
Asn Asn Ser Asn Phe Pro Trp Thr Ala Ala Ser Lys Tyr His Leu Asn
            500                 505                 510
Gly Arg Asp Ser Leu Val Asn Pro Gly Pro Ala Met Ala Ser His Lys
        515                 520                 525
Asp Asp Glu Glu Lys Phe Phe Pro Met His Gly Asn Leu Ile Phe Gly
    530                 535                 540
Lys Glu Gly Thr Thr Ala Ser Asn Ala Glu Leu Asp Asn Val Met Ile
```

```
545                 550                 555                 560
Thr Asp Glu Glu Glu Ile Arg Thr Thr Asn Pro Val Ala Thr Glu Gln
                    565                 570                 575
Tyr Gly Thr Val Ala Asn Asn Leu Gln Ser Ser Asn Thr Ala Pro Thr
                580                 585                 590
Thr Arg Thr Val Asn Asp Gln Gly Ala Leu Pro Gly Met Val Trp Gln
            595                 600                 605
Asp Arg Asp Val Tyr Leu Gln Gly Pro Ile Trp Ala Lys Ile Pro His
        610                 615                 620
Thr Asp Gly His Phe His Pro Ser Pro Leu Met Gly Gly Phe Gly Leu
625                 630                 635                 640
Lys His Pro Pro Pro Gln Ile Met Ile Lys Asn Thr Pro Val Pro Ala
                    645                 650                 655
Asn Pro Pro Thr Thr Phe Ser Pro Ala Lys Phe Ala Ser Phe Ile Thr
                660                 665                 670
Gln Tyr Ser Thr Gly Gln Val Ser Val Glu Ile Glu Trp Glu Leu Gln
            675                 680                 685
Lys Glu Asn Ser Lys Arg Trp Asn Pro Glu Ile Gln Tyr Thr Ser Asn
        690                 695                 700
Tyr Asn Lys Ser Val Asn Val Asp Phe Thr Val Asp Thr Asn Gly Val
705                 710                 715                 720
Tyr Ser Glu Pro Arg Pro Ile Gly Thr Arg Tyr Leu Thr Arg Asn Leu
                    725                 730                 735

<210> SEQ ID NO 109
<211> LENGTH: 736
<212> TYPE: PRT
<213> ORGANISM: Unknown
<220> FEATURE:
<221> NAME/KEY: source
<223> OTHER INFORMATION: /note="Description of Unknown:
      Parent AAV Capsid sequence"

<400> SEQUENCE: 109

Met Ala Ala Asp Gly Tyr Leu Pro Asp Trp Leu Glu Asp Asn Leu Ser
1               5                   10                  15
Glu Gly Ile Arg Glu Trp Trp Asp Leu Lys Pro Gly Ala Pro Lys Pro
                20                  25                  30
Lys Ala Asn Gln Gln Lys Gln Asp Asp Gly Arg Gly Leu Val Leu Pro
            35                  40                  45
Gly Tyr Lys Tyr Leu Gly Pro Phe Asn Gly Leu Asp Lys Gly Glu Pro
        50                  55                  60
Val Asn Ala Ala Asp Ala Ala Leu Glu His Asp Lys Ala Tyr Asp
65                  70                  75                  80
Gln Gln Leu Lys Ala Gly Asp Asn Pro Tyr Leu Arg Tyr Asn His Ala
                85                  90                  95
Asp Ala Glu Phe Gln Glu Arg Leu Gln Glu Asp Thr Ser Phe Gly Gly
                100                 105                 110
Asn Leu Gly Arg Ala Val Phe Gln Ala Lys Lys Arg Val Leu Glu Pro
            115                 120                 125
Phe Gly Leu Val Glu Glu Gly Ala Lys Thr Ala Pro Gly Lys Lys Arg
        130                 135                 140
Pro Val Glu Gln Ser Pro Gln Glu Pro Asp Ser Ser Ser Gly Ile Gly
145                 150                 155                 160
Lys Thr Gly Gln Gln Pro Ala Lys Lys Arg Leu Asn Phe Gly Gln Thr
                165                 170                 175
```

```
Gly Asp Ser Glu Ser Val Pro Asp Pro Gln Pro Leu Gly Glu Pro Pro
            180                 185                 190

Ala Thr Pro Ala Ala Val Gly Pro Thr Thr Met Ala Ser Gly Gly Gly
            195                 200                 205

Ala Pro Met Ala Asp Asn Asn Glu Gly Ala Asp Gly Val Gly Asn Ala
210                 215                 220

Ser Gly Asn Trp His Cys Asp Ser Thr Trp Leu Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Ser Ala Ser Thr Gly Ala Ser Asn Asp Asn His
            260                 265                 270

Tyr Phe Gly Tyr Ser Thr Pro Trp Gly Tyr Phe Asp Phe Asn Arg Phe
            275                 280                 285

His Cys His Phe Ser Pro Arg Asp Trp Gln Arg Leu Ile Asn Asn Asn
        290                 295                 300

Trp Gly Phe Arg Pro Lys Arg Leu Asn Phe Lys Leu Phe Asn Ile Gln
305                 310                 315                 320

Val Lys Glu Val Thr Thr Asn Asp Gly Val Thr Thr Ile Ala Asn Asn
                325                 330                 335

Leu Thr Ser Thr Val Gln Val Phe Ser Asp Ser Glu Tyr Gln Leu Pro
            340                 345                 350

Tyr Val Leu Gly Ser Ala His Gln Gly Cys Leu Pro Pro Phe Pro Ala
            355                 360                 365

Asp Val Phe Met Ile Pro Gln Tyr Gly Tyr Leu Thr Leu Asn Asn Gly
            370                 375                 380

Ser Gln Ala Val Gly Arg Ser Ser Phe Tyr Cys Leu Glu Tyr Phe Pro
385                 390                 395                 400

Ser Gln Met Leu Arg Thr Gly Asn Asn Phe Thr Phe Ser Tyr Thr Phe
                405                 410                 415

Glu Asp Val Pro Phe His Ser Ser Tyr Ala His Ser Gln Ser Leu Asp
            420                 425                 430

Arg Leu Met Asn Pro Leu Ile Asp Gln Tyr Leu Tyr Tyr Leu Asn Arg
            435                 440                 445

Thr Gln Asn Gln Ser Gly Ser Ala Gln Asn Lys Asp Leu Leu Phe Ser
            450                 455                 460

Arg Gly Ser Pro Ala Gly Met Ser Val Gln Pro Lys Asn Trp Leu Pro
465                 470                 475                 480

Gly Pro Cys Tyr Arg Gln Gln Arg Val Ser Lys Thr Lys Thr Asp Asn
                485                 490                 495

Asn Asn Ser Asn Phe Thr Trp Thr Gly Ala Ser Lys Tyr Asn Leu Asn
            500                 505                 510

Gly Arg Glu Ser Ile Ile Asn Pro Gly Thr Ala Met Ala Ser His Lys
            515                 520                 525

Asp Asp Lys Asp Lys Phe Phe Pro Met Ser Gly Val Met Ile Phe Gly
            530                 535                 540

Lys Glu Ser Ala Gly Ala Ser Asn Thr Ala Leu Asp Asn Val Met Ile
545                 550                 555                 560

Thr Asp Glu Glu Glu Ile Lys Ala Thr Asn Pro Val Ala Thr Glu Arg
                565                 570                 575

Phe Gly Thr Val Ala Val Asn Leu Gln Ser Ser Ser Thr Asp Pro Ala
            580                 585                 590
```

Thr Gly Asp Val His Val Met Gly Ala Leu Pro Gly Met Val Trp Gln
            595                 600                 605

Asp Arg Asp Val Tyr Leu Gln Gly Pro Ile Trp Ala Lys Ile Pro His
610                 615                 620

Thr Asp Gly His Phe His Pro Ser Pro Leu Met Gly Gly Phe Gly Leu
625                 630                 635                 640

Lys His Pro Pro Gln Ile Leu Ile Lys Asn Thr Pro Val Pro Ala
            645                 650                 655

Asn Pro Pro Ala Glu Phe Ser Ala Thr Lys Phe Ala Ser Phe Ile Thr
            660                 665                 670

Gln Tyr Ser Thr Gly Gln Val Ser Val Glu Ile Glu Trp Glu Leu Gln
            675                 680                 685

Lys Glu Asn Ser Lys Arg Trp Asn Pro Glu Val Gln Tyr Thr Ser Asn
            690                 695                 700

Tyr Ala Lys Ser Ala Asn Val Asp Phe Thr Val Asp Asn Asn Gly Leu
705                 710                 715                 720

Tyr Thr Glu Pro Arg Pro Ile Gly Thr Arg Tyr Leu Thr Arg Pro Leu
            725                 730                 735

<210> SEQ ID NO 110
<211> LENGTH: 738
<212> TYPE: PRT
<213> ORGANISM: Unknown
<220> FEATURE:
<221> NAME/KEY: source
<223> OTHER INFORMATION: /note="Description of Unknown:
      Parent AAV Capsid sequence"

<400> SEQUENCE: 110

Met Ala Ala Asp Gly Tyr Leu Pro Asp Trp Leu Glu Asp Asn Leu Ser
1               5                   10                  15

Glu Gly Ile Arg Glu Trp Trp Ala Leu Lys Pro Gly Ala Pro Lys Pro
            20                  25                  30

Lys Ala Asn Gln Gln Lys Gln Asp Asp Gly Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Ala Ala Asp Ala Ala Ala Leu Glu His Asp Lys Ala Tyr Asp
65                  70                  75                  80

Gln Gln Leu Gln Ala Gly Asp Asn Pro Tyr Leu Arg Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Gly Ala Lys Thr Ala Pro Gly Lys Lys Arg
    130                 135                 140

Pro Val Glu Pro Ser Pro Gln Arg Ser Pro Asp Ser Ser Thr Gly Ile
145                 150                 155                 160

Gly Lys Lys Gly Gln Gln Pro Ala Arg Lys Arg Leu Asn Phe Gly Gln
                165                 170                 175

Thr Gly Asp Ser Glu Ser Val Pro Asp Pro Gln Pro Leu Gly Glu Pro
            180                 185                 190

Pro Ala Ala Pro Ser Gly Val Gly Pro Asn Thr Met Ala Ala Gly Gly
        195                 200                 205

Gly Ala Pro Met Ala Asp Asn Asn Glu Gly Ala Asp Gly Val Gly Ser

```
          210                 215                 220
Ser Ser Gly Asn Trp His Cys Asp Ser Thr Trp Leu Gly Asp Arg Val
225                 230                 235                 240

Ile Thr Thr Ser Thr Arg Thr Trp Ala Leu Pro Thr Tyr Asn Asn His
                245                 250                 255

Leu Tyr Lys Gln Ile Ser Asn Gly Thr Ser Gly Gly Ala Thr Asn Asp
                260                 265                 270

Asn Thr Tyr Phe Gly Tyr Ser Thr Pro Trp Gly Tyr Phe Asp Phe Asn
            275                 280                 285

Arg Phe His Cys His Phe Ser Pro Arg Asp Trp Gln Arg Leu Ile Asn
        290                 295                 300

Asn Asn Trp Gly Phe Arg Pro Lys Arg Leu Ser Phe Lys Leu Phe Asn
305                 310                 315                 320

Ile Gln Val Lys Glu Val Thr Gln Asn Glu Gly Thr Lys Thr Ile Ala
                325                 330                 335

Asn Asn Leu Thr Ser Thr Ile Gln Val Phe Thr Asp Ser Glu Tyr Gln
                340                 345                 350

Leu Pro Tyr Val Leu Gly Ser Ala His Gln Gly Cys Leu Pro Pro Phe
            355                 360                 365

Pro Ala Asp Val Phe Met Ile Pro Gln Tyr Gly Tyr Leu Thr Leu Asn
        370                 375                 380

Asn Gly Ser Gln Ala Val Gly Arg Ser Ser Phe Tyr Cys Leu Glu Tyr
385                 390                 395                 400

Phe Pro Ser Gln Met Leu Arg Thr Gly Asn Asn Phe Gln Phe Thr Tyr
                405                 410                 415

Thr Phe Glu Asp Val Pro Phe His Ser Ser Tyr Ala His Ser Gln Ser
                420                 425                 430

Leu Asp Arg Leu Met Asn Pro Leu Ile Asp Gln Tyr Leu Tyr Tyr Leu
            435                 440                 445

Ser Arg Thr Gln Thr Thr Gly Gly Thr Ala Asn Thr Gln Thr Leu Gly
        450                 455                 460

Phe Ser Gln Gly Gly Pro Asn Thr Met Ala Asn Gln Ala Lys Asn Trp
465                 470                 475                 480

Leu Pro Gly Pro Cys Tyr Arg Gln Gln Arg Val Ser Thr Thr Thr Gly
                485                 490                 495

Gln Asn Asn Asn Ser Asn Phe Ala Trp Thr Ala Gly Thr Lys Tyr His
                500                 505                 510

Leu Asn Gly Arg Asn Ser Leu Ala Asn Pro Gly Ile Ala Met Ala Thr
            515                 520                 525

His Lys Asp Asp Glu Glu Arg Phe Phe Pro Ser Asn Gly Ile Leu Ile
        530                 535                 540

Phe Gly Lys Gln Asn Ala Ala Arg Asp Asn Ala Asp Tyr Ser Asp Val
545                 550                 555                 560

Met Leu Thr Ser Glu Glu Glu Ile Lys Thr Thr Asn Pro Val Ala Thr
                565                 570                 575

Glu Glu Tyr Gly Ile Val Ala Asp Asn Leu Gln Gln Gln Asn Thr Ala
                580                 585                 590

Pro Gln Ile Gly Thr Val Asn Ser Gln Gly Ala Leu Pro Gly Met Val
            595                 600                 605

Trp Gln Asn Arg Asp Val Tyr Leu Gln Gly Pro Ile Trp Ala Lys Ile
        610                 615                 620

Pro His Thr Asp Gly Asn Phe His Pro Ser Pro Leu Met Gly Gly Phe
625                 630                 635                 640
```

-continued

Gly Leu Lys His Pro Pro Gln Ile Leu Ile Lys Asn Thr Pro Val
            645             650             655

Pro Ala Asp Pro Pro Thr Thr Phe Asn Gln Ser Lys Leu Asn Ser Phe
            660             665             670

Ile Thr Gln Tyr Ser Thr Gly Gln Val Ser Val Glu Ile Glu Trp Glu
            675             680             685

Leu Gln Lys Glu Asn Ser Lys Arg Trp Asn Pro Glu Ile Gln Tyr Thr
690             695             700

Ser Asn Tyr Tyr Lys Ser Thr Ser Val Asp Phe Ala Val Asn Thr Glu
705             710             715             720

Gly Val Tyr Ser Glu Pro Arg Pro Ile Gly Thr Arg Tyr Leu Thr Arg
            725             730             735

Asn Leu

<210> SEQ ID NO 111
<211> LENGTH: 736
<212> TYPE: PRT
<213> ORGANISM: Unknown
<220> FEATURE:
<221> NAME/KEY: source
<223> OTHER INFORMATION: /note="Description of Unknown:
      Parent AAV Capsid sequence"

<400> SEQUENCE: 111

Met Ala Ala Asp Gly Tyr Leu Pro Asp Trp Leu Glu Asp Asn Leu Ser
1               5                   10                  15

Glu Gly Ile Arg Glu Trp Trp Ala Leu Lys Pro Gly Ala Pro Gln Pro
            20                  25                  30

Lys Ala Asn Gln Gln His Gln Asp Asn Ala Arg Gly Leu Val Leu Pro
        35                  40                  45

Gly Tyr Lys Tyr Leu Gly Pro Gly Asn Gly Leu Asp Lys Gly Glu Pro
    50                  55                  60

Val Asn Ala Ala Asp Ala Ala Ala Leu Glu His Asp Lys Ala Tyr Asp
65                  70                  75                  80

Gln Gln Leu Lys Ala Gly Asp Asn Pro Tyr Leu Lys Tyr Asn His Ala
                85                  90                  95

Asp Ala Glu Phe Gln Glu Arg Leu Lys Glu Asp Thr Ser Phe Gly Gly
            100                 105                 110

Asn Leu Gly Arg Ala Val Phe Gln Ala Lys Lys Arg Leu Leu Glu Pro
        115                 120                 125

Leu Gly Leu Val Glu Glu Ala Lys Thr Ala Pro Gly Lys Lys Arg
    130                 135                 140

Pro Val Glu Gln Ser Pro Gln Glu Pro Asp Ser Ser Ala Gly Ile Gly
145                 150                 155                 160

Lys Ser Gly Ala Gln Pro Ala Lys Lys Arg Leu Asn Phe Gly Gln Thr
                165                 170                 175

Gly Asp Thr Glu Ser Val Pro Asp Pro Gln Pro Ile Gly Glu Pro Pro
            180                 185                 190

Ala Ala Pro Ser Gly Val Gly Ser Leu Thr Met Ala Ser Gly Gly Gly
        195                 200                 205

Ala Pro Val Ala Asp Asn Asn Glu Gly Ala Asp Gly Val Gly Ser Ser
    210                 215                 220

Ser Gly Asn Trp His Cys Asp Ser Gln Trp Leu Gly Asp Arg Val Ile
225                 230                 235                 240

Thr Thr Ser Thr Arg Thr Trp Ala Leu Pro Thr Tyr Asn Asn His Leu

-continued

```
                245                 250                 255
Tyr Lys Gln Ile Ser Asn Ser Thr Ser Gly Ser Ser Asn Asp Asn
            260                 265                 270
Ala Tyr Phe Gly Tyr Ser Thr Pro Trp Gly Tyr Phe Asp Phe Asn Arg
            275                 280                 285
Phe His Cys His Phe Ser Pro Arg Asp Trp Gln Arg Leu Ile Asn Asn
            290                 295                 300
Asn Trp Gly Phe Arg Pro Lys Arg Leu Asn Phe Lys Leu Phe Asn Ile
305                 310                 315                 320
Gln Val Lys Glu Val Thr Asp Asn Asn Gly Val Lys Thr Ile Ala Asn
                325                 330                 335
Asn Leu Thr Ser Thr Val Gln Val Phe Thr Asp Ser Asp Tyr Gln Leu
                340                 345                 350
Pro Tyr Val Leu Gly Ser Ala His Glu Gly Cys Leu Pro Pro Phe Pro
                355                 360                 365
Ala Asp Val Phe Met Ile Pro Gln Tyr Gly Tyr Leu Thr Leu Asn Asp
            370                 375                 380
Gly Ser Gln Ala Val Gly Arg Ser Ser Phe Tyr Cys Leu Glu Tyr Phe
385                 390                 395                 400
Pro Ser Gln Met Leu Arg Thr Gly Asn Asn Phe Gln Phe Ser Tyr Glu
                405                 410                 415
Phe Glu Asn Val Pro Phe His Ser Ser Tyr Ala His Ser Gln Ser Leu
                420                 425                 430
Asp Arg Leu Met Asn Pro Leu Ile Asp Gln Tyr Leu Tyr Tyr Leu Ser
                435                 440                 445
Lys Thr Ile Asn Gly Ser Gly Gln Asn Gln Gln Thr Leu Lys Phe Ser
            450                 455                 460
Val Ala Gly Pro Ser Asn Met Ala Val Gln Gly Arg Asn Tyr Ile Pro
465                 470                 475                 480
Gly Pro Ser Tyr Arg Gln Gln Arg Val Ser Thr Thr Val Thr Gln Asn
                485                 490                 495
Asn Asn Ser Glu Phe Ala Trp Pro Gly Ala Ser Ser Trp Ala Leu Asn
            500                 505                 510
Gly Arg Asn Ser Leu Met Asn Pro Gly Pro Ala Met Ala Ser His Lys
            515                 520                 525
Glu Gly Glu Asp Arg Phe Phe Pro Leu Ser Gly Ser Leu Ile Phe Gly
            530                 535                 540
Lys Gln Gly Thr Gly Arg Asp Asn Val Asp Ala Asp Lys Val Met Ile
545                 550                 555                 560
Thr Asn Glu Glu Glu Ile Lys Thr Thr Asn Pro Val Ala Thr Glu Ser
                565                 570                 575
Tyr Gly Gln Val Ala Thr Asn His Gln Ser Ala Gln Ala Gln Ala Gln
            580                 585                 590
Thr Gly Trp Val Gln Asn Gln Gly Ile Leu Pro Gly Met Val Trp Gln
            595                 600                 605
Asp Arg Asp Val Tyr Leu Gln Gly Pro Ile Trp Ala Lys Ile Pro His
            610                 615                 620
Thr Asp Gly Asn Phe His Pro Ser Pro Leu Met Gly Gly Phe Gly Met
625                 630                 635                 640
Lys His Pro Pro Pro Gln Ile Leu Ile Lys Asn Thr Pro Val Pro Ala
                645                 650                 655
Asp Pro Pro Thr Ala Phe Asn Lys Asp Lys Leu Asn Ser Phe Ile Thr
                660                 665                 670
```

```
Gln Tyr Ser Thr Gly Gln Val Ser Val Glu Ile Glu Trp Glu Leu Gln
            675                 680                 685
Lys Glu Asn Ser Lys Arg Trp Asn Pro Glu Ile Gln Tyr Thr Ser Asn
        690                 695                 700
Tyr Tyr Lys Ser Asn Asn Val Glu Phe Ala Val Asn Thr Glu Gly Val
705                 710                 715                 720
Tyr Ser Glu Pro Arg Pro Ile Gly Thr Arg Tyr Leu Thr Arg Asn Leu
                725                 730                 735

<210> SEQ ID NO 112
<211> LENGTH: 738
<212> TYPE: PRT
<213> ORGANISM: Unknown
<220> FEATURE:
<221> NAME/KEY: source
<223> OTHER INFORMATION: /note="Description of Unknown:
      Parent AAV Capsid sequence"

<400> SEQUENCE: 112

Met Ala Ala Asp Gly Tyr Leu Pro Asp Trp Leu Glu Asp Asn Leu Ser
1               5                   10                  15
Glu Gly Ile Arg Glu Trp Trp Asp Leu Lys Pro Gly Ala Pro Lys Pro
            20                  25                  30
Lys Ala Asn Gln Gln Lys Gln Asp Asp Gly Arg Gly Leu Val Leu Pro
        35                  40                  45
Gly Tyr Lys Tyr Leu Gly Pro Phe Asn Gly Leu Asp Lys Gly Glu Pro
    50                  55                  60
Val Asn Ala Ala Asp Ala Ala Leu Glu His Asp Lys Ala Tyr Asp
65                  70                  75                  80
Gln Gln Leu Lys Ala Gly Asp Asn Pro Tyr Leu Arg Tyr Asn His Ala
                85                  90                  95
Asp Ala Glu Phe Gln Glu Arg Leu Gln Glu Asp Thr Ser Phe Gly Gly
            100                 105                 110
Asn Leu Gly Arg Ala Val Phe Gln Ala Lys Lys Arg Val Leu Glu Pro
        115                 120                 125
Leu Gly Leu Val Glu Glu Gly Ala Lys Thr Ala Pro Gly Lys Lys Arg
    130                 135                 140
Pro Val Glu Pro Ser Pro Gln Arg Ser Pro Asp Ser Ser Thr Gly Ile
145                 150                 155                 160
Gly Lys Lys Gly Gln Gln Pro Ala Lys Lys Arg Leu Asn Phe Gly Gln
                165                 170                 175
Thr Gly Asp Ser Glu Ser Val Pro Asp Pro Gln Pro Ile Gly Glu Pro
            180                 185                 190
Pro Ala Gly Pro Ser Gly Leu Gly Ser Gly Thr Met Ala Ala Gly Gly
        195                 200                 205
Gly Ala Pro Met Ala Asp Asn Asn Glu Gly Ala Asp Gly Val Gly Ser
    210                 215                 220
Ser Ser Gly Asn Trp His Cys Asp Ser Thr Trp Leu Gly Asp Arg Val
225                 230                 235                 240
Ile Thr Thr Ser Thr Arg Thr Trp Ala Leu Pro Thr Tyr Asn Asn His
                245                 250                 255
Leu Tyr Lys Gln Ile Ser Asn Gly Thr Ser Gly Gly Ser Thr Asn Asp
            260                 265                 270
Asn Thr Tyr Phe Gly Tyr Ser Thr Pro Trp Gly Tyr Phe Asp Phe Asn
        275                 280                 285
```

```
Arg Phe His Cys His Phe Ser Pro Arg Asp Trp Gln Arg Leu Ile Asn
    290                 295                 300
Asn Asn Trp Gly Phe Arg Pro Lys Arg Leu Asn Phe Lys Leu Phe Asn
305                 310                 315                 320
Ile Gln Val Lys Glu Val Thr Gln Asn Glu Gly Thr Lys Thr Ile Ala
                325                 330                 335
Asn Asn Leu Thr Ser Thr Ile Gln Val Phe Thr Asp Ser Glu Tyr Gln
                340                 345                 350
Leu Pro Tyr Val Leu Gly Ser Ala His Gln Gly Cys Leu Pro Pro Phe
            355                 360                 365
Pro Ala Asp Val Phe Met Ile Pro Gln Tyr Gly Tyr Leu Thr Leu Asn
370                 375                 380
Asn Gly Ser Gln Ala Val Gly Arg Ser Ser Phe Tyr Cys Leu Glu Tyr
385                 390                 395                 400
Phe Pro Ser Gln Met Leu Arg Thr Gly Asn Asn Phe Glu Phe Ser Tyr
                405                 410                 415
Gln Phe Glu Asp Val Pro Phe His Ser Ser Tyr Ala His Ser Gln Ser
                420                 425                 430
Leu Asp Arg Leu Met Asn Pro Leu Ile Asp Gln Tyr Leu Tyr Tyr Leu
            435                 440                 445
Ser Arg Thr Gln Ser Thr Gly Gly Thr Ala Gly Thr Gln Gln Leu Leu
450                 455                 460
Phe Ser Gln Ala Gly Pro Asn Asn Met Ser Ala Gln Ala Lys Asn Trp
465                 470                 475                 480
Leu Pro Gly Pro Cys Tyr Arg Gln Gln Arg Val Ser Thr Thr Leu Ser
                485                 490                 495
Gln Asn Asn Asn Ser Asn Phe Ala Trp Thr Gly Ala Thr Lys Tyr His
                500                 505                 510
Leu Asn Gly Arg Asp Ser Leu Val Asn Pro Gly Val Ala Met Ala Thr
            515                 520                 525
His Lys Asp Asp Glu Glu Arg Phe Phe Pro Ser Ser Gly Val Leu Met
530                 535                 540
Phe Gly Lys Gln Gly Ala Gly Lys Asp Asn Val Asp Tyr Ser Ser Val
545                 550                 555                 560
Met Leu Thr Ser Glu Glu Glu Ile Lys Thr Thr Asn Pro Val Ala Thr
                565                 570                 575
Glu Gln Tyr Gly Val Val Ala Asp Asn Leu Gln Gln Gln Asn Ala Ala
                580                 585                 590
Pro Ile Val Gly Ala Val Asn Ser Gln Gly Ala Leu Pro Gly Met Val
            595                 600                 605
Trp Gln Asn Arg Asp Val Tyr Leu Gln Gly Pro Ile Trp Ala Lys Ile
610                 615                 620
Pro His Thr Asp Gly Asn Phe His Pro Ser Pro Leu Met Gly Gly Phe
625                 630                 635                 640
Gly Leu Lys His Pro Pro Gln Ile Leu Ile Lys Asn Thr Pro Val
                645                 650                 655
Pro Ala Asp Pro Pro Thr Thr Phe Ser Gln Ala Lys Leu Ala Ser Phe
                660                 665                 670
Ile Thr Gln Tyr Ser Thr Gly Gln Val Ser Val Glu Ile Glu Trp Glu
            675                 680                 685
Leu Gln Lys Glu Asn Ser Lys Arg Trp Asn Pro Glu Ile Gln Tyr Thr
690                 695                 700
Ser Asn Tyr Tyr Lys Ser Thr Asn Val Asp Phe Ala Val Asn Thr Asp
```

```
                    705                 710                 715                 720
Gly Thr Tyr Ser Glu Pro Arg Pro Ile Gly Thr Arg Tyr Leu Thr Arg
                    725                 730                 735

Asn Leu

<210> SEQ ID NO 113
<211> LENGTH: 726
<212> TYPE: PRT
<213> ORGANISM: Unknown
<220> FEATURE:
<221> NAME/KEY: source
<223> OTHER INFORMATION: /note="Description of Unknown:
      Parent AAV Capsid sequence"

<400> SEQUENCE: 113

Met Ser Phe Val Asp His Pro Pro Asp Trp Leu Glu Glu Val Gly Glu
1               5                   10                  15

Gly Leu His Glu Phe Leu Glu Leu Glu Ala Gly Pro Pro Lys Pro Lys
                20                  25                  30

Pro Asn Gln Gln Lys Gln Asp Asn Ala Arg Gly Leu Val Leu Pro Gly
                35                  40                  45

Asn Lys Tyr Leu Gly Pro Phe Asn Gly Leu Asp Lys Gly Glu Pro Val
50                  55                  60

Asn Arg Ala Asp Ala Val Ala Arg Glu His Asp Ile Ser Tyr Asn Glu
65                  70                  75                  80

Gln Leu Gln Ala Gly Asp Asn Pro Tyr Leu Lys Tyr Asn His Ala Asp
                85                  90                  95

Ala Glu Phe Gln Glu Lys Leu Lys Asp Asp Thr Ser Phe Gly Gly Asn
                100                 105                 110

Leu Lys Arg Ile Val Phe Gln Ala Lys Lys Arg Val Leu Glu Pro Phe
                115                 120                 125

Gly Leu Val Glu Ala Pro Val Lys Thr Ala Pro Ala Lys Lys Arg Pro
130                 135                 140

Ile Glu Lys Ser Pro Ala Glu Pro Asp Ser Ser Lys Gly Ile Gly Lys
145                 150                 155                 160

Ala Gly Gln Gln Pro Ala Arg Lys Arg Leu Asn Phe Gly Gln Thr Gly
                165                 170                 175

Asp Thr Asp Ser Ala Ala Asp Pro Gln Pro Leu Gly Glu Pro Pro Ala
                180                 185                 190

Ala Pro Ser Gly Leu Gly Thr Gly Thr Met Ala Ser Gly Ser Gly Ala
                195                 200                 205

Pro Met Ala Asp Asn Asn Glu Gly Ala Asp Gly Val Gly Asn Ala Ser
                210                 215                 220

Gly Asn Trp His Cys Asp Ser Thr Trp Leu Gly Asp Arg Val Ile Thr
225                 230                 235                 240

Thr Ser Thr Arg Thr Trp Ala Leu Pro Thr Tyr Asn Asn His Leu Tyr
                245                 250                 255

Lys Gln Ile Ser Ser Gln Ser Gly Ala Asn Asn Asp Asn His Tyr Phe
                260                 265                 270

Gly Tyr Ser Thr Pro Trp Gly Tyr Phe Asp Phe Asn Arg Phe His Cys
                275                 280                 285

His Phe Ser Pro Arg Asp Trp Gln Arg Leu Ile Asn Asn Asn Trp Gly
                290                 295                 300

Phe Arg Pro Lys Arg Leu Asn Phe Lys Leu Phe Asn Ile Gln Val Lys
305                 310                 315                 320
```

-continued

Glu Val Thr Gln Thr Asp Gly Thr Lys Thr Ile Ala Asn Asn Leu Thr
            325                 330                 335

Ser Thr Val Gln Val Phe Ala Asp Ser Glu Tyr Gln Leu Pro Tyr Val
            340                 345                 350

Leu Gly Ser Ala His Gln Gly Cys Phe Pro Phe Pro Ala Asp Val
            355                 360                 365

Phe Met Ile Pro Val Tyr Gly Tyr Leu Thr Leu Asn Asn Gly Ser Gln
    370                 375                 380

Ala Val Gly Met Ser Ser Phe Tyr Cys Leu Glu Tyr Phe Pro Ser Gln
385                 390                 395                 400

Met Leu Arg Thr Gly Asn Asn Phe Thr Phe Ser Tyr Thr Phe Glu Asp
                405                 410                 415

Val Pro Phe His Ser Ser Tyr Ala His Ser Gln Ser Leu Asp Arg Leu
            420                 425                 430

Met Asn Pro Leu Ile Asp Gln Tyr Leu Tyr Tyr Leu Ser Lys Thr Asn
            435                 440                 445

Gly Gly Leu Gly Phe Ser Gln Ala Gly Pro Asn Ser Met Arg Asp Gln
    450                 455                 460

Ser Arg Asn Trp Leu Pro Gly Pro Cys Phe Arg Gln Gln Arg Ile Ser
465                 470                 475                 480

Thr Val Pro Thr Gln Asn Asn Asn Gly Asp Phe Ser Trp Thr Gly Ala
                485                 490                 495

Thr Lys Tyr His Leu Asn Gly Arg Asn Ser Ala Met Asn Pro Gly Pro
            500                 505                 510

Ala Met Ala Ser His Lys Asp Asp Glu His Arg Phe Phe Pro Gln Asn
            515                 520                 525

Gly Val Leu Ile Phe Gly Lys Gln Gly Ala Asp Lys Thr Asn Ala Ile
    530                 535                 540

Leu Glu Lys Val Ile Val Thr Asp Glu Glu Glu Ile Arg Thr Thr Asn
545                 550                 555                 560

Pro Val Ala Thr Glu Glu Tyr Gly Phe Val Ala Thr Asn Leu Gln Ser
                565                 570                 575

Ser Ala Glu Thr Ala Glu Thr Glu Arg Val Asn Ala Gln Gly Ile Leu
            580                 585                 590

Pro Gly Met Val Trp Gln Asp Arg Asp Val Tyr Leu Gln Gly Pro Ile
    595                 600                 605

Trp Ala Lys Ile Pro His Thr Asp Gly His Phe Arg Pro Ser Pro Leu
610                 615                 620

Met Gly Gly Phe Gly Leu Lys His Pro Pro Pro Gln Ile Leu Ile Lys
625                 630                 635                 640

Asn Thr Pro Val Pro Ser Asn Pro Pro Glu Thr Phe Asn Pro Glu Lys
                645                 650                 655

Leu Asn Ser Phe Ile Thr Gln Tyr Ser Thr Gly Gln Val Ser Val Glu
            660                 665                 670

Ile Glu Trp Glu Leu Gln Lys Glu Asn Ser Lys Arg Trp Asn Pro Glu
            675                 680                 685

Val Gln Tyr Thr Ser Asn Tyr Asn Lys Ser Val Asn Val Glu Phe Thr
    690                 695                 700

Val Asp Asn Asn Gly Val Tyr Ser Glu Pro Arg Thr Ile Gly Thr Arg
705                 710                 715                 720

Tyr Leu Thr Arg Asn Leu
                725

```
<210> SEQ ID NO 114
<211> LENGTH: 737
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 114

Met Ala Ala Asp Gly Tyr Leu Pro Asp Trp Leu Glu Asp Thr Leu Ser
1               5                   10                  15

Glu Gly Ile Arg Gln Trp Trp Lys Leu Lys Pro Gly Pro Pro Pro Pro
            20                  25                  30

Lys Pro Ala Glu Arg His Lys Asp Asp Ser Arg Gly Leu Val Leu Pro
        35                  40                  45

Gly Tyr Lys Tyr Leu Gly Pro Gly Asn Gly Leu Asp Lys Gly Glu Pro
    50                  55                  60

Val Asn Ala Ala Asp Ala Ala Ala Leu Glu His Asp Lys Ala Tyr Asp
65                  70                  75                  80

Gln Gln Leu Lys Ala Gly Asp Asn Pro Tyr Leu Arg Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Pro Val Lys Thr Ala Pro Gly Lys Lys Arg
    130                 135                 140

Pro Val Glu His Ser Pro Val Glu Pro Asp Ser Ser Ser Gly Thr Gly
145                 150                 155                 160

Lys Ala Gly Gln Gln Pro Ala Arg Lys Arg Leu Asn Phe Gly Gln Thr
                165                 170                 175

Gly Asp Thr Asp Ser Ala Ala Asp Pro Gln Pro Leu Gly Glu Pro Pro
            180                 185                 190

Ala Ala Pro Ser Gly Leu Gly Thr Gly Thr Met Ala Ala Gly Gly Gly
        195                 200                 205

Ala Pro Met Ala Asp Asn Asn Glu Gly Ala Asp Gly Val Gly Asn Ala
    210                 215                 220

Ser Gly Asn Trp His Cys Asp Ser Thr Trp Leu Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Ser Ala Ser Thr Gly Ala Ser Asn Asp Asn His
            260                 265                 270

Tyr Phe Gly Tyr Ser Thr Pro Trp Gly Tyr Phe Asp Phe Asn Arg Phe
        275                 280                 285

His Cys His Phe Ser Pro Arg Asp Trp Gln Arg Leu Ile Asn Asn Asn
    290                 295                 300

Trp Gly Phe Arg Pro Lys Arg Leu Asn Phe Lys Leu Phe Asn Ile Gln
305                 310                 315                 320

Val Lys Glu Val Thr Gln Asn Glu Gly Thr Lys Thr Ile Ala Asn Asn
                325                 330                 335

Leu Thr Ser Thr Val Gln Val Phe Thr Asp Ser Glu Tyr Gln Leu Pro
            340                 345                 350

Tyr Val Leu Gly Ser Ala His Gln Gly Cys Leu Pro Pro Phe Pro Ala
        355                 360                 365
```

Asp Val Phe Met Ile Pro Gln Tyr Gly Tyr Leu Thr Leu Asn Asn Gly
    370                 375                 380

Ser Gln Ala Met Gly Arg Ser Ser Phe Tyr Cys Leu Glu Tyr Phe Pro
385                 390                 395                 400

Ser Gln Met Leu Arg Thr Gly Asn Asn Phe Gln Phe Thr Tyr Thr Phe
                405                 410                 415

Glu Asp Val Pro Phe His Ser Ser Tyr Ala His Ser Gln Ser Leu Asp
            420                 425                 430

Arg Leu Met Asn Pro Leu Ile Asp Gln Tyr Leu Tyr Tyr Leu Asn Arg
        435                 440                 445

Thr Gln Gly Thr Thr Ser Gly Thr Thr Asn Gln Ser Arg Leu Leu Phe
    450                 455                 460

Ser Gln Ala Gly Pro Gln Ser Met Ser Ile Gln Ala Arg Asn Trp Leu
465                 470                 475                 480

Pro Gly Pro Cys Tyr Arg Gln Gln Arg Leu Ser Lys Thr Ala Asn Asp
                485                 490                 495

Asn Asn Asn Ser Asn Phe Pro Trp Thr Ala Ala Ser Lys Tyr His Leu
            500                 505                 510

Asn Gly Arg Asp Ser Leu Val Asn Pro Gly Pro Ala Met Ala Ser His
        515                 520                 525

Lys Asp Asp Glu Glu Lys Phe Phe Pro Met His Gly Asn Leu Ile Phe
530                 535                 540

Gly Lys Glu Gly Thr Thr Ala Ser Asn Ala Glu Leu Asp Asn Val Met
545                 550                 555                 560

Ile Thr Asp Glu Glu Ile Arg Thr Thr Asn Pro Val Ala Thr Glu
                565                 570                 575

Gln Tyr Gly Thr Val Ala Asn Asn Leu Gln Ser Ser Asn Thr Ala Pro
            580                 585                 590

Thr Thr Arg Thr Val Asn Asp Gln Gly Ala Leu Pro Gly Met Val Trp
        595                 600                 605

Gln Asp Arg Asp Val Tyr Leu Gln Gly Pro Ile Trp Ala Lys Ile Pro
    610                 615                 620

His Thr Asp Gly His Phe His Pro Ser Pro Leu Met Gly Gly Phe Gly
625                 630                 635                 640

Leu Lys His Pro Pro Pro Gln Ile Leu Ile Lys Asn Thr Pro Val Pro
                645                 650                 655

Ala Asp Pro Pro Thr Ala Phe Asn Lys Asp Lys Leu Asn Ser Phe Ile
            660                 665                 670

Thr Gln Tyr Ser Thr Gly Gln Val Ser Val Glu Ile Glu Trp Glu Leu
        675                 680                 685

Gln Lys Glu Asn Ser Lys Arg Trp Asn Pro Glu Ile Gln Tyr Thr Ser
    690                 695                 700

Asn Tyr Tyr Lys Ser Thr Ser Val Asp Phe Ala Val Asn Thr Glu Gly
705                 710                 715                 720

Val Tyr Ser Glu Pro Arg Pro Ile Gly Thr Arg Tyr Leu Thr Arg Asn
                725                 730                 735

Leu

<210> SEQ ID NO 115
<211> LENGTH: 737
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 115

```
Met Ala Ala Asp Gly Tyr Leu Pro Asp Trp Leu Glu Asp Asn Leu Ser
1               5                   10                  15

Glu Gly Ile Arg Glu Trp Trp Asp Leu Lys Pro Gly Ala Pro Lys Pro
            20                  25                  30

Lys Ala Asn Gln Gln Lys Gln Asp Asp Gly Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Ala Ala Asp Ala Ala Leu Glu His Asp Lys Ala Tyr Asp
65                  70                  75                  80

Gln Gln Leu Lys Ala Gly Asp Asn Pro Tyr Leu Arg Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Gly Ala Lys Thr Ala Pro Gly Lys Lys Arg
    130                 135                 140

Pro Val Glu His Ser Pro Val Glu Pro Asp Ser Ser Ser Gly Ile Gly
145                 150                 155                 160

Lys Thr Gly Gln Gln Pro Ala Lys Lys Arg Leu Asn Phe Gly Gln Thr
                165                 170                 175

Gly Asp Ala Asp Ser Val Pro Asp Pro Gln Pro Leu Gly Gln Pro Pro
            180                 185                 190

Ala Ala Pro Ser Gly Leu Gly Thr Asn Thr Met Ala Thr Gly Ser Gly
        195                 200                 205

Ala Pro Met Ala Asp Asn Asn Glu Gly Ala Asp Gly Val Gly Asn Ala
    210                 215                 220

Ser Gly Asn Trp His Cys Asp Ser Thr Trp Leu Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Ser Ala Ser Thr Gly Ala Ser Asn Asp Asn His
            260                 265                 270

Tyr Phe Gly Tyr Ser Thr Pro Trp Gly Tyr Phe Asp Phe Asn Arg Phe
        275                 280                 285

His Cys His Phe Ser Pro Arg Asp Trp Gln Arg Leu Ile Asn Asn Asn
    290                 295                 300

Trp Gly Phe Arg Pro Lys Arg Leu Asn Phe Lys Leu Phe Asn Ile Gln
305                 310                 315                 320

Val Lys Glu Val Thr Gln Asn Glu Gly Thr Thr Thr Ile Ala Asn Asn
                325                 330                 335

Leu Thr Ser Thr Val Gln Val Phe Thr Asp Ser Glu Tyr Gln Leu Pro
            340                 345                 350

Tyr Val Leu Gly Ser Ala His Gln Gly Cys Leu Pro Pro Phe Pro Ala
        355                 360                 365

Asp Val Phe Met Ile Pro Gln Tyr Gly Tyr Leu Thr Leu Asn Asn Gly
    370                 375                 380

Ser Gln Ala Val Gly Arg Ser Ser Phe Tyr Cys Leu Glu Tyr Phe Pro
385                 390                 395                 400
```

```
Ser Gln Met Leu Arg Thr Gly Asn Asn Phe Thr Phe Ser Tyr Thr Phe
            405                 410                 415

Glu Asp Val Pro Phe His Ser Ser Tyr Ala His Ser Gln Ser Leu Asp
            420                 425                 430

Arg Leu Met Asn Pro Leu Ile Asp Gln Tyr Leu Tyr Tyr Leu Asn Arg
            435                 440                 445

Thr Gln Gly Thr Thr Ser Gly Thr Thr Asn Gln Ser Arg Leu Leu Phe
            450                 455                 460

Ser Gln Ala Gly Pro Gln Ser Met Ser Ile Gln Ala Arg Asn Trp Leu
465                 470                 475                 480

Pro Gly Pro Cys Tyr Arg Gln Gln Arg Leu Ser Lys Thr Ala Asn Asp
            485                 490                 495

Asn Asn Asn Ser Asn Phe Pro Trp Thr Ala Ala Ser Lys Tyr His Leu
            500                 505                 510

Asn Gly Arg Asp Ser Leu Val Asn Pro Gly Pro Ala Met Ala Ser His
            515                 520                 525

Lys Asp Asp Glu Glu Lys Phe Phe Pro Met His Gly Asn Leu Ile Phe
530                 535                 540

Gly Lys Glu Gly Thr Thr Ala Ser Asn Ala Glu Leu Asp Asn Val Met
545                 550                 555                 560

Ile Thr Asp Glu Glu Glu Ile Arg Thr Thr Asn Pro Val Ala Thr Glu
            565                 570                 575

Gln Tyr Gly Thr Val Ala Asn Asn Leu Gln Ser Ser Asn Thr Ala Pro
            580                 585                 590

Thr Thr Arg Thr Val Asn Asp Gln Gly Ala Leu Pro Gly Met Val Trp
            595                 600                 605

Gln Asp Arg Asp Val Tyr Leu Gln Gly Pro Ile Trp Ala Lys Ile Pro
            610                 615                 620

His Thr Asp Gly His Phe His Pro Ser Pro Leu Met Gly Gly Phe Gly
625                 630                 635                 640

Leu Lys His Pro Pro Pro Gln Ile Met Ile Lys Asn Thr Pro Val Pro
            645                 650                 655

Ala Asn Pro Pro Thr Thr Phe Ser Pro Ala Lys Phe Ala Ser Phe Ile
            660                 665                 670

Thr Gln Tyr Ser Thr Gly Gln Val Ser Val Glu Ile Glu Trp Glu Leu
            675                 680                 685

Gln Lys Glu Asn Ser Lys Arg Trp Asn Pro Glu Ile Gln Tyr Thr Ser
            690                 695                 700

Asn Tyr Asn Lys Ser Val Asn Val Asp Phe Thr Val Asp Thr Asn Gly
705                 710                 715                 720

Val Tyr Ser Glu Pro Arg Pro Ile Gly Thr Arg Tyr Leu Thr Arg Pro
            725                 730                 735

Leu

<210> SEQ ID NO 116
<211> LENGTH: 738
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 116

Met Ala Ala Asp Gly Tyr Leu Pro Asp Trp Leu Glu Asp Thr Leu Ser
```

-continued

```
1               5                   10                  15
Glu Gly Ile Arg Gln Trp Trp Lys Leu Lys Pro Gly Pro Pro Pro
            20                  25                  30
Lys Pro Ala Glu Arg His Lys Asp Asp Ser Arg Gly Leu Val Leu Pro
            35                  40                  45
Gly Tyr Lys Tyr Leu Gly Pro Phe Asn Gly Leu Asp Lys Gly Glu Pro
 50                  55                  60
Val Asn Glu Ala Asp Ala Ala Ala Leu Glu His Asp Lys Ala Tyr Asp
 65                  70                  75                  80
Gln Gln Leu Lys Ala Gly Asp Asn Pro Tyr Leu Arg Tyr Asn His Ala
                85                  90                  95
Asp Ala Glu Phe Gln Glu Arg Leu Gln Glu Asp Thr Ser Phe Gly Gly
            100                 105                 110
Asn Leu Gly Arg Ala Val Phe Gln Ala Lys Lys Arg Val Leu Glu Pro
            115                 120                 125
Leu Gly Leu Val Glu Glu Gly Ala Lys Thr Ala Pro Gly Lys Lys Arg
            130                 135                 140
Pro Val Glu Pro Ser Pro Gln Arg Ser Pro Asp Ser Ser Thr Gly Ile
145                 150                 155                 160
Gly Lys Lys Gly Gln Gln Pro Ala Arg Lys Arg Leu Asn Phe Gly Gln
                165                 170                 175
Thr Gly Asp Ser Glu Ser Val Pro Asp Pro Gln Pro Leu Gly Glu Pro
            180                 185                 190
Pro Ala Ala Pro Ser Gly Val Gly Pro Asn Thr Met Ala Ala Gly Gly
            195                 200                 205
Gly Ala Pro Met Ala Asp Asn Asn Glu Gly Ala Asp Gly Val Gly Asn
            210                 215                 220
Ala Ser Gly Asn Trp His Cys Asp Ser Thr Trp Leu Gly Asp Arg Val
225                 230                 235                 240
Ile Thr Thr Ser Thr Arg Thr Trp Ala Leu Pro Thr Tyr Asn Asn His
                245                 250                 255
Leu Tyr Lys Gln Ile Ser Ser Ala Ser Thr Gly Ala Ser Asn Asp Asn
            260                 265                 270
His Tyr Phe Gly Tyr Ser Thr Pro Trp Gly Tyr Phe Asp Phe Asn Arg
            275                 280                 285
Phe His Cys His Phe Ser Pro Arg Asp Trp Gln Arg Leu Ile Asn Asn
            290                 295                 300
Asn Trp Gly Phe Arg Pro Lys Arg Leu Asn Phe Lys Leu Phe Asn Ile
305                 310                 315                 320
Gln Val Lys Glu Val Thr Gln Asn Glu Gly Thr Lys Thr Ile Ala Asn
                325                 330                 335
Asn Leu Thr Ser Thr Ile Gln Val Phe Thr Asp Ser Glu Tyr Gln Leu
            340                 345                 350
Pro Tyr Val Leu Gly Ser Ala His Gln Gly Cys Leu Pro Pro Phe Pro
            355                 360                 365
Ala Asp Val Phe Met Ile Pro Gln Tyr Gly Tyr Leu Thr Leu Asn Asn
            370                 375                 380
Gly Ser Gln Ala Val Gly Arg Ser Ser Phe Tyr Cys Leu Glu Tyr Phe
385                 390                 395                 400
Pro Ser Gln Met Leu Arg Thr Gly Asn Asn Phe Gln Phe Ser Tyr Thr
                405                 410                 415
Phe Glu Asp Val Pro Phe His Ser Ser Tyr Ala His Ser Gln Ser Leu
            420                 425                 430
```

-continued

```
Asp Arg Leu Met Asn Pro Leu Ile Asp Gln Tyr Leu Tyr Leu Asn
        435                 440                 445

Arg Thr Gln Gly Thr Thr Ser Gly Thr Thr Asn Gln Ser Arg Leu Leu
450                 455                 460

Phe Ser Gln Ala Gly Pro Gln Ser Met Ser Ile Gln Ala Arg Asn Trp
465                 470                 475                 480

Leu Pro Gly Pro Cys Tyr Arg Gln Gln Arg Leu Ser Lys Thr Ala Asn
                485                 490                 495

Asp Asn Asn Asn Ser Asn Phe Pro Trp Thr Ala Ala Ser Lys Tyr His
                500                 505                 510

Leu Asn Gly Arg Asp Ser Leu Val Asn Pro Gly Pro Ala Met Ala Ser
                515                 520                 525

His Lys Asp Asp Glu Glu Lys Phe Phe Pro Met His Gly Asn Leu Ile
        530                 535                 540

Phe Gly Lys Glu Gly Thr Thr Ala Ser Asn Ala Glu Leu Asp Asn Val
545                 550                 555                 560

Met Ile Thr Asp Glu Glu Ile Arg Thr Thr Asn Pro Val Ala Thr
                565                 570                 575

Glu Gln Tyr Gly Thr Val Ala Asn Asn Leu Gln Ser Ser Asn Thr Ala
                580                 585                 590

Pro Thr Thr Arg Thr Val Asn Asp Gln Gly Ala Leu Pro Gly Met Val
                595                 600                 605

Trp Gln Asp Arg Asp Val Tyr Leu Gln Gly Pro Ile Trp Ala Lys Ile
        610                 615                 620

Pro His Thr Asp Gly Asn Phe His Pro Ser Pro Leu Met Gly Gly Phe
625                 630                 635                 640

Gly Leu Lys His Pro Pro Pro Gln Ile Leu Ile Lys Asn Thr Pro Val
                645                 650                 655

Pro Ala Asp Pro Pro Thr Thr Phe Asn Gln Ser Lys Leu Asn Ser Phe
                660                 665                 670

Ile Thr Gln Tyr Ser Thr Gly Gln Val Ser Val Glu Ile Glu Trp Glu
        675                 680                 685

Leu Gln Lys Glu Asn Ser Lys Arg Trp Asn Pro Glu Ile Gln Tyr Thr
        690                 695                 700

Ser Asn Tyr Tyr Lys Ser Thr Ser Val Asp Phe Ala Val Asn Thr Glu
705                 710                 715                 720

Gly Val Tyr Ser Glu Pro Arg Pro Ile Gly Thr Arg Tyr Leu Thr Arg
                725                 730                 735

Asn Leu
```

<210> SEQ ID NO 117
<211> LENGTH: 196
<212> TYPE: PRT
<213> ORGANISM: Artificial Sequence
<220> FEATURE:
<221> NAME/KEY: source
<223> OTHER INFORMATION: /note="Description of Artificial Sequence:
    Synthetic polypeptide"
<220> FEATURE:
<221> NAME/KEY: VARIANT
<222> LOCATION: (8)..(8)
<223> OTHER INFORMATION: /replace="Leu" or "Gln"
<220> FEATURE:
<221> NAME/KEY: VARIANT
<222> LOCATION: (16)..(16)
<223> OTHER INFORMATION: /replace="His" or "Pro"
<220> FEATURE:
<221> NAME/KEY: VARIANT

```
<222> LOCATION: (91)..(91)
<223> OTHER INFORMATION: /replace="Glu" or "Asp"
<220> FEATURE:
<221> NAME/KEY: VARIANT
<222> LOCATION: (155)..(155)
<223> OTHER INFORMATION: /replace="Arg" or "Pro"
<220> FEATURE:
<221> NAME/KEY: SITE
<222> LOCATION: (1)..(196)
<223> OTHER INFORMATION: /note="Variant residues given in the sequence
      have no preference with respect to those in the annotations
      for variant positions"

<400> SEQUENCE: 117
```

Leu Ala Thr Gln Ser Gln Ser Pro Thr Ile Asn Leu Ser Glu Asn Leu
1               5                   10                  15

Gln Gln Pro Pro Leu Val Trp Asp Leu Ile Gln Trp Leu Gln Ala Val
            20                  25                  30

Ala His Gln Trp Gln Thr Ile Thr Lys Ala Pro Thr Glu Trp Val Met
        35                  40                  45

Pro Gln Glu Ile Gly Ile Ala Ile Pro His Gly Trp Ala Thr Glu Ser
    50                  55                  60

Ser Pro Pro Ala Pro Glu Pro Gly Pro Cys Pro Pro Thr Thr Thr Thr
65                  70                  75                  80

Ser Thr Ser Lys Ser Pro Val Ile Gln Arg Gly Pro Ala Thr Thr Thr
            85                  90                  95

Thr Thr Ser Ala Thr Ala Pro Pro Gly Gly Ile Leu Thr Ser Thr Asp
            100                 105                 110

Ser Thr Ala Thr Ser His His Val Thr Gly Ser Asp Ser Ser Thr Thr
            115                 120                 125

Thr Gly Asp Ser Gly Pro Arg Asp Ser Thr Ser Ser Ser Ser Thr Ser
130                 135                 140

Lys Ser Arg Arg Ser Arg Arg Met Lys Ala Ser Arg Pro Ser Pro Ile
145                 150                 155                 160

Thr Leu Pro Ala Arg Phe Arg Cys Leu Arg Thr Arg Ser Thr Ser Ser
            165                 170                 175

Arg Thr Ser Ser Ala Leu Arg Thr Arg Ala Ala Ser Leu Arg Ser Arg
            180                 185                 190

Arg Thr Cys Ser
            195

```
<210> SEQ ID NO 118
<211> LENGTH: 196
<212> TYPE: PRT
<213> ORGANISM: Unknown
<220> FEATURE:
<221> NAME/KEY: source
<223> OTHER INFORMATION: /note="Description of Unknown:
      Parent AAV Capsid sequence"

<400> SEQUENCE: 118
```

Leu Ala Thr Gln Ser Gln Ser Pro Thr His Asn Leu Ser Glu Asn Leu
1               5                   10                  15

Gln Gln Pro Pro Leu Leu Trp Asp Leu Leu Gln Trp Leu Gln Ala Val
            20                  25                  30

Ala His Gln Trp Gln Thr Ile Thr Lys Ala Pro Thr Glu Trp Val Met
        35                  40                  45

Pro Gln Glu Ile Gly Ile Ala Ile Pro His Gly Trp Ala Thr Glu Ser
    50                  55                  60

Ser Pro Pro Ala Pro Ala Pro Gly Pro Cys Pro Pro Thr Ile Thr Thr

```
              65                  70                  75                  80
Ser Thr Ser Lys Ser Pro Val Ile Gln Arg Gly Pro Ala Thr Thr Thr
                 85                  90                  95

Thr Thr Ser Ala Thr Ala Pro Pro Gly Gly Ile Leu Ile Ser Thr Asp
            100                 105                 110

Ser Thr Ala Thr Phe His His Val Thr Gly Ser Asp Ser Ser Thr Thr
            115                 120                 125

Ile Gly Asp Ser Gly Pro Arg Asp Ser Thr Ser Asn Ser Ser Thr Ser
            130                 135                 140

Lys Ser Arg Arg Ser Arg Arg Met Met Ala Ser Gln Pro Ser Leu Ile
145                 150                 155                 160

Thr Leu Pro Ala Arg Phe Lys Ser Ser Arg Thr Arg Ser Thr Ser Phe
                165                 170                 175

Arg Thr Ser Ser Ala Leu Arg Thr Arg Ala Ala Ser Leu Arg Ser Arg
                180                 185                 190

Arg Thr Cys Ser
            195

<210> SEQ ID NO 119
<211> LENGTH: 204
<212> TYPE: PRT
<213> ORGANISM: Unknown
<220> FEATURE:
<221> NAME/KEY: source
<223> OTHER INFORMATION: /note="Description of Unknown:
      Parent AAV Capsid sequence"

<400> SEQUENCE: 119

Leu Glu Thr Gln Thr Gln Tyr Leu Thr Pro Ser Leu Ser Asp Ser His
1               5                   10                  15

Gln Gln Pro Pro Leu Val Trp Glu Leu Ile Arg Trp Leu Gln Ala Val
                20                  25                  30

Ala His Gln Trp Gln Thr Ile Thr Arg Ala Pro Thr Glu Trp Val Ile
            35                  40                  45

Pro Arg Glu Ile Gly Ile Ala Ile Pro His Gly Trp Ala Thr Glu Ser
50                  55                  60

Ser Pro Pro Ala Pro Glu Pro Gly Pro Cys Pro Pro Thr Thr Thr Thr
65                  70                  75                  80

Ser Thr Asn Lys Phe Pro Ala Asn Gln Glu Pro Arg Thr Thr Ile Thr
                85                  90                  95

Thr Leu Ala Thr Ala Pro Leu Gly Gly Ile Leu Thr Ser Thr Asp Ser
            100                 105                 110

Thr Ala Thr Phe His His Val Thr Gly Lys Asp Ser Ser Thr Thr Thr
            115                 120                 125

Gly Asp Ser Asp Pro Arg Asp Ser Thr Ser Ser Ser Leu Thr Phe Lys
            130                 135                 140

Ser Lys Arg Ser Arg Arg Met Thr Val Arg Arg Leu Pro Ile Thr
145                 150                 155                 160

Leu Pro Ala Arg Phe Arg Cys Leu Leu Thr Arg Ser Thr Ser Arg
                165                 170                 175

Thr Ser Ser Ala Arg Arg Ile Lys Asp Ala Ser Arg Ser Gln Gln
                180                 185                 190

Thr Ser Ser Trp Cys His Ser Met Asp Thr Ser Pro
            195                 200

<210> SEQ ID NO 120
```

```
<211> LENGTH: 204
<212> TYPE: PRT
<213> ORGANISM: Unknown
<220> FEATURE:
<221> NAME/KEY: source
<223> OTHER INFORMATION: /note="Description of Unknown:
      Parent AAV Capsid sequence"

<400> SEQUENCE: 120
```

Leu Ala Thr Gln Ser Gln Ser Gln Thr Ile Asn Leu Ser Glu Asn His
1               5                   10                  15

Gln Gln Pro Pro Gln Val Trp Asp Leu Ile Gln Trp Leu Gln Ala Val
            20                  25                  30

Ala His Gln Trp Gln Thr Ile Thr Arg Val Pro Met Glu Trp Val Ile
        35                  40                  45

Pro Gln Glu Ile Gly Ile Ala Ile Pro Asn Gly Trp Ala Thr Glu Ser
    50                  55                  60

Ser Pro Pro Ala Pro Glu Pro Gly Pro Cys Pro Leu Thr Thr Thr Ile
65              70                  75                  80

Ser Thr Ser Lys Ser Pro Ala Asn Gln Glu Leu Gln Thr Thr Thr Thr
                85                  90                  95

Thr Leu Ala Thr Ala Pro Leu Gly Gly Ile Leu Thr Leu Thr Asp Ser
            100                 105                 110

Thr Ala Thr Ser His His Val Thr Gly Ser Asp Ser Leu Thr Thr Thr
        115                 120                 125

Gly Asp Ser Gly Pro Arg Asn Ser Ala Ser Ser Ser Thr Ser Lys
    130                 135                 140

Leu Lys Arg Ser Arg Arg Thr Met Ala Arg Arg Leu Leu Pro Ile Thr
145                 150                 155                 160

Leu Pro Ala Arg Phe Lys Cys Leu Arg Thr Arg Ser Ile Ser Ser Arg
                165                 170                 175

Thr Cys Ser Gly Arg Arg Thr Lys Ala Val Ser Arg Arg Phe Gln Arg
            180                 185                 190

Thr Ser Ser Trp Ser Leu Ser Met Asp Thr Ser Pro
        195                 200

```
<210> SEQ ID NO 121
<211> LENGTH: 196
<212> TYPE: PRT
<213> ORGANISM: Unknown
<220> FEATURE:
<221> NAME/KEY: source
<223> OTHER INFORMATION: /note="Description of Unknown:
      Parent AAV Capsid sequence"

<400> SEQUENCE: 121
```

Leu Ala Thr Gln Ser Gln Ser Pro Thr His Asn Leu Ser Glu Asn Leu
1               5                   10                  15

Gln Gln Pro Pro Leu Leu Trp Asp Leu Leu Gln Trp Leu Gln Ala Val
            20                  25                  30

Ala His Gln Trp Gln Thr Ile Thr Lys Ala Pro Thr Glu Trp Val Met
        35                  40                  45

Pro Gln Glu Ile Gly Ile Ala Ile Pro His Gly Trp Ala Thr Glu Ser
    50                  55                  60

Ser Pro Pro Ala Pro Glu His Gly Pro Cys Pro Ile Thr Thr Thr
65              70                  75                  80

Ser Thr Ser Lys Ser Pro Val Ile Gln Arg Gly Pro Ala Thr Thr Thr
                85                  90                  95

Thr Thr Ser Ala Thr Ala Pro Pro Gly Ile Leu Ile Ser Thr Asp
            100             105             110

Ser Thr Ala Ile Ser His His Val Thr Gly Ser Asp Ser Ser Thr Thr
        115                 120             125

Ile Gly Asp Ser Gly Pro Arg Asp Ser Thr Ser Ser Ser Thr Ser
    130             135             140

Lys Ser Arg Arg Ser Arg Arg Met Met Ala Ser Arg Pro Ser Leu Ile
145             150             155             160

Thr Leu Pro Ala Arg Phe Lys Ser Ser Arg Thr Arg Ser Thr Ser Cys
                165             170             175

Arg Thr Ser Ser Ala Leu Arg Thr Arg Ala Ala Ser Leu Arg Ser Arg
            180             185             190

Arg Thr Cys Ser
        195

<210> SEQ ID NO 122
<211> LENGTH: 197
<212> TYPE: PRT
<213> ORGANISM: Unknown
<220> FEATURE:
<221> NAME/KEY: source
<223> OTHER INFORMATION: /note="Description of Unknown:
      Parent AAV Capsid sequence"

<400> SEQUENCE: 122

Leu Ala Thr Gln Ser Gln Phe Gln Thr Ile Asn Leu Ser Glu Asn Leu
1               5                   10                  15

Gln Gln Arg Pro Leu Val Trp Asp Leu Ile Gln Trp Leu Gln Ala Val
            20                  25                  30

Ala His Gln Trp Gln Thr Ile Thr Lys Ala Pro Thr Glu Trp Val Val
        35                  40                  45

Pro Arg Glu Ile Gly Ile Ala Ile Pro His Gly Trp Ala Thr Glu Ser
    50                  55                  60

Ser Pro Pro Ala Pro Glu Pro Gly Pro Cys Pro Pro Thr Thr Thr Thr
65                  70                  75                  80

Ser Thr Ser Lys Ser Pro Thr Gly His Arg Glu Glu Pro Pro Thr Thr
                85                  90                  95

Thr Pro Thr Ser Ala Thr Ala Pro Pro Gly Gly Ile Leu Thr Leu Thr
            100             105             110

Asp Ser Thr Ala Thr Phe His His Val Thr Gly Ser Asp Ser Ser Thr
        115                 120             125

Thr Thr Gly Asp Ser Gly Pro Arg Asp Ser Ala Ser Ser Ser Ser Thr
    130             135             140

Ser Arg Ser Arg Arg Ser Arg Arg Met Lys Ala Pro Arg Pro Ser Pro
145             150             155             160

Ile Thr Ser Pro Ala Pro Ser Arg Cys Leu Arg Thr Arg Ser Thr Ser
                165             170             175

Cys Arg Thr Phe Ser Ala Leu Pro Thr Arg Ala Ala Cys Leu Arg Ser
            180             185             190

Arg Arg Thr Cys Ser
        195

<210> SEQ ID NO 123
<211> LENGTH: 197
<212> TYPE: PRT
<213> ORGANISM: Unknown
<220> FEATURE:
<221> NAME/KEY: source
<223> OTHER INFORMATION: /note="Description of Unknown: Parent AAV Capsid sequence"

<400> SEQUENCE: 123

Leu Ala Thr Gln Ser Gln Ser Gln Thr Ile Asn Gln Ser Glu Asn Leu
1               5                   10                  15

Pro Gln Pro Pro Gln Val Trp Asp Leu Leu Gln Trp Leu Gln Val Val
            20                  25                  30

Ala His Gln Trp Gln Thr Ile Thr Lys Val Pro Met Glu Trp Val Val
        35                  40                  45

Pro Arg Glu Ile Gly Ile Ala Ile Pro Asn Gly Trp Gly Thr Glu Ser
    50                  55                  60

Ser Pro Pro Ala Pro Glu Pro Gly Pro Cys Pro Pro Thr Thr Ile Thr
65              70                  75                  80

Ser Thr Ser Lys Ser Pro Thr Ala His Leu Glu Asp Leu Gln Met Thr
            85                  90                  95

Thr Pro Thr Ser Ala Thr Ala Pro Pro Gly Gly Ile Leu Thr Ser Thr
            100                 105                 110

Asp Ser Thr Ala Thr Ser His His Val Thr Gly Ser Asp Ser Ser Thr
            115                 120                 125

Thr Thr Gly Asp Ser Gly Leu Ser Asp Ser Thr Ser Ser Ser Ser Thr
            130                 135                 140

Phe Arg Ser Lys Arg Leu Arg Thr Thr Met Glu Ser Arg Pro Ser Pro
145             150                 155                 160

Ile Thr Leu Pro Ala Arg Ser Arg Ser Ser Arg Thr Gln Thr Ile Ser
            165                 170                 175

Ser Arg Thr Cys Ser Gly Arg Leu Thr Arg Ala Ala Ser Arg Arg Ser
            180                 185                 190

Gln Arg Thr Phe Ser
            195

<210> SEQ ID NO 124
<211> LENGTH: 197
<212> TYPE: PRT
<213> ORGANISM: Unknown
<220> FEATURE:
<221> NAME/KEY: source
<223> OTHER INFORMATION: /note="Description of Unknown: Parent AAV Capsid sequence"

<400> SEQUENCE: 124

Leu Ala Thr Gln Ser Gln Cys Pro Thr Ile Asn Gln Ser Glu Asn Pro
1               5                   10                  15

Pro Gln Ala Pro Leu Val Trp Asp Leu Val Gln Trp Leu Gln Ala Val
            20                  25                  30

Ala Leu Gln Trp Gln Thr Ile Thr Lys Ala Pro Thr Glu Trp Val Val
        35                  40                  45

Pro Gln Glu Ile Gly Ile Ala Ile Pro His Gly Trp Ala Thr Glu Ser
    50                  55                  60

Ser Pro Pro Ala Pro Glu Pro Gly Pro Ser Pro Pro Thr Thr Thr Thr
65              70                  75                  80

Ser Thr Ser Lys Ser Pro Thr Gly Leu Arg Glu Glu Ala Pro Thr Thr
            85                  90                  95

Thr Pro Thr Ser Ala Thr Ala Pro Pro Gly Gly Ile Leu Thr Leu Thr
            100                 105                 110

Asp Ser Thr Ala Thr Ser His His Val Thr Gly Ser Asp Ser Ser Thr
            115                 120                 125

Thr Thr Gly Asp Ser Gly Pro Arg Asp Ser Ser Ser Ser Thr
        130                 135                 140

Ser Arg Ser Arg Arg Ser Arg Met Lys Ala Pro Arg Pro Ser Pro
145                 150                 155                 160

Ile Thr Leu Pro Ala Arg Phe Arg Ser Leu Arg Thr Arg Asn Thr Ser
                165                 170                 175

Ser Arg Thr Ser Ser Ala Leu Arg Thr Arg Ala Ala Cys Leu Arg Ser
                180                 185                 190

Arg Arg Thr Ser Ser
        195

<210> SEQ ID NO 125
<211> LENGTH: 202
<212> TYPE: PRT
<213> ORGANISM: Unknown
<220> FEATURE:
<221> NAME/KEY: source
<223> OTHER INFORMATION: /note="Description of Unknown:
      Parent AAV Capsid sequence"

<400> SEQUENCE: 125

Leu Glu Thr Pro Thr Pro Pro Leu Thr Pro Ser Leu Ser Glu Asn His
1               5                   10                  15

Gln Gln Pro Pro Leu Val Trp Glu Leu Val Arg Trp Leu Gln Ala Val
                20                  25                  30

Ala His Gln Trp Gln Thr Ile Thr Lys Ala Pro Thr Glu Trp Val Met
            35                  40                  45

Pro Arg Glu Ile Gly Ile Ala Ile Pro His Gly Trp Ala Thr Glu Ser
        50                  55                  60

Ser Pro Pro Ala Pro Ala Pro Gly Pro Cys Pro Pro Thr Thr Thr Ile
65                  70                  75                  80

Ser Thr Ser Lys Ser Pro Ala Ser Leu Glu Pro Thr Thr Thr Thr Thr
                85                  90                  95

Thr Leu Ala Thr Ala Pro Pro Gly Gly Thr Leu Thr Ser Thr Ala Ser
                100                 105                 110

Thr Ala Thr Ser Pro Arg Glu Thr Gly Ser Gly Ser Thr Thr Thr
            115                 120                 125

Gly Gly Ser Gly Pro Ser Asp Ser Thr Ser Ser Ser Thr Ser Lys
        130                 135                 140

Ser Arg Arg Ser Leu Arg Thr Ala Arg Arg Pro Ser Pro Ile Thr
145                 150                 155                 160

Leu Pro Ala Arg Phe Arg Ser Leu Arg Thr Arg Ser Thr Ser Ser Arg
                165                 170                 175

Thr Ser Ser Asp Gln Arg Thr Arg Ala Ala Ser Arg Arg Ser Arg Arg
                180                 185                 190

Thr Ser Ser Trp Ser Arg Ser Thr Gly Ile
                195                 200

<210> SEQ ID NO 126
<211> LENGTH: 196
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 126

```
Leu Glu Thr Pro Thr Pro Pro Leu Thr Pro Ser Leu Ser Glu Asn His
1               5                   10                  15

Gln Gln Pro Pro Leu Val Trp Glu Leu Val Gln Trp Leu Gln Ala Val
            20                  25                  30

Ala Leu Gln Trp Gln Thr Ile Thr Lys Ala Pro Thr Glu Trp Val Met
        35                  40                  45

Pro Arg Glu Ile Gly Ile Ala Ile Pro His Gly Trp Ala Thr Glu Ser
    50                  55                  60

Ser Pro Pro Ala Pro Ala Pro Gly Pro Cys Pro Thr Ile Thr Thr
65                  70                  75                  80

Ser Thr Ser Lys Ser Pro Val Ile Gln Arg Gly Pro Ala Thr Thr
                85                  90                  95

Thr Thr Ser Ala Thr Ala Pro Pro Gly Gly Thr Leu Thr Ser Thr Ala
            100                 105                 110

Ser Thr Ala Thr Ser His His Val Thr Gly Lys Asp Ser Ser Thr Thr
            115                 120                 125

Thr Gly Asp Ser Gly Pro Arg Asp Ser Thr Ser Ser Ser Thr Ser
    130                 135                 140

Arg Ser Arg Arg Ser Arg Arg Met Lys Ala Pro Arg Pro Ser Pro Ile
145                 150                 155                 160

Thr Leu Pro Ala Arg Phe Arg Cys Leu Leu Thr Arg Ser Thr Ser Cys
                165                 170                 175

Arg Thr Phe Ser Ala Leu Pro Thr Arg Ala Ala Cys Leu Arg Ser Arg
                180                 185                 190

Arg Thr Cys Ser
        195
```

<210> SEQ ID NO 127
<211> LENGTH: 196
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 127

```
Leu Ala Thr Gln Thr Gln Tyr Leu Thr Pro Ser Leu Ser Asp Ser His
1               5                   10                  15

Gln Gln Pro Pro Leu Val Trp Glu Leu Ile Arg Trp Leu Gln Ala Val
            20                  25                  30

Ala His Gln Trp Gln Thr Ile Thr Arg Ala Pro Thr Glu Trp Val Met
        35                  40                  45

Pro Gln Glu Ile Gly Ile Ala Ile Pro His Gly Trp Ala Thr Glu Ser
    50                  55                  60

Ser Pro Pro Ala Pro Glu His Gly Pro Cys Pro Pro Ile Thr Thr Thr
65                  70                  75                  80

Ser Thr Ser Lys Ser Pro Val Ile Gln Arg Gly Pro Ala Thr Thr Thr
                85                  90                  95

Thr Thr Ser Ala Thr Ala Pro Pro Gly Gly Thr Leu Thr Ser Thr Ala
            100                 105                 110

Ser Thr Ala Thr Ser Pro Arg Glu Thr Gly Ser Gly Ser Ser Thr Thr
            115                 120                 125

Thr Gly Gly Ser Gly Pro Ser Asp Ser Thr Ser Ser Ser Ser Thr Ser
    130                 135                 140

Arg Ser Arg Arg Ser Arg Arg Met Lys Ala Arg Arg Leu Leu Pro Ile
```

```
                 145                 150                 155                 160
Thr Leu Pro Ala Arg Phe Lys Cys Leu Arg Thr Arg Ser Ile Ser Ser
                165                 170                 175

Arg Thr Cys Ser Ala Leu Pro Thr Arg Ala Ala Cys Leu Arg Ser Arg
                180                 185                 190

Arg Thr Cys Ser
        195

<210> SEQ ID NO 128
<211> LENGTH: 196
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 128

Leu Ala Thr Gln Ser Gln Phe Gln Thr Ile Asn Leu Ser Glu Asn Leu
1               5                   10                  15

Gln Gln Arg Pro Leu Val Trp Asp Leu Ile Gln Trp Leu Gln Ala Val
            20                  25                  30

Ala His Gln Trp Gln Thr Ile Thr Lys Ala Pro Thr Glu Trp Val Met
        35                  40                  45

Pro Gln Glu Ile Gly Ile Ala Ile Pro His Gly Trp Ala Thr Glu Ser
    50                  55                  60

Ser Pro Pro Ala Pro Ala Pro Gly Pro Cys Pro Pro Thr Ile Thr Thr
65                  70                  75                  80

Ser Thr Ser Lys Ser Pro Val Ile Gln Arg Gly Pro Ala Thr Thr Thr
                85                  90                  95

Thr Thr Ser Ala Thr Ala Pro Leu Gly Gly Ile Leu Thr Ser Thr Asp
                100                 105                 110

Ser Thr Ala Thr Phe His His Val Thr Gly Lys Asp Ser Ser Thr Thr
            115                 120                 125

Thr Gly Asp Ser Asp Pro Arg Asp Ser Thr Ser Ser Ser Leu Thr Phe
    130                 135                 140

Lys Ser Lys Arg Ser Arg Arg Met Lys Ala Pro Arg Pro Ser Pro Ile
145                 150                 155                 160

Thr Ser Pro Ala Pro Ser Arg Cys Leu Arg Thr Arg Ser Thr Ser Cys
                165                 170                 175

Arg Thr Phe Ser Ala Leu Pro Thr Arg Ala Ala Cys Leu Arg Ser Arg
                180                 185                 190

Arg Thr Cys Ser
        195
```

RECOMBINANT ADENO-ASSOCIATED VIRUS CAPSIDS WITH ENHANCED HUMAN PANCREATIC TROPISM

CROSS REFERENCE TO RELATED APPLICATION

This application claims priority to U.S. Provisional Application No. 62/651,010, filed Mar. 30, 2018, and U.S. Provisional Application No. 62/745,226, filed Oct. 12, 2018, both of which are hereby incorporated by reference in their entireties.

STATEMENT AS TO RIGHTS TO INVENTIONS MADE UNDER FEDERALLY SPONSORED RESEARCH OR DEVELOPMENT

This invention was made with U.S. Government support under Grant Number U01DK089569. The U.S. Government has certain rights in the invention.

FIELD OF THE INVENTION

The present invention relates to variant AAV capsid polypeptides, wherein the variant AAV capsid polypeptides exhibit increased transduction and/or tropism in human pancreatic tissue or human islets as compared to non-variant parent capsid polypeptides.

REFERENCE TO A "SEQUENCE LISTING," A TABLE, OR A COMPUTER PROGRAM, LISTING APPENDIX SUBMITTED ON A COMPACT DISK

This invention incorporated by reference the Sequence Listing text copy submitted herewith, which was created on Jun. 20, 2019, entitled 068597-5036-US_SL.txt which is 397 kilobytes in size.

BACKGROUND OF THE INVENTION

Genetic disorders caused by absence of or a defect in a desirable gene (loss of function) or expression of an undesirable or defective gene (gain of function) lead to a variety of diseases. At present, adeno-associated virus (AAV) vectors are recognized as the gene transfer vectors of choice for therapeutic applications since they have the best safety (replication deficient, low integration rate and minimum immune response) and efficacy profile for the delivery of genes in vivo. AAV vectors small, non-enveloped, non-pathogenic, helper virus dependent ssDNA virus, and they have numerous serotypes with varying tissue tropisms and transduction efficiencies. Of the AAV serotypes isolated so far, AAV2 and AAV8 have been used to target the liver of humans affected by severe hemophilia B. Both vectors worked efficiently and, in the case of AAV8, long-term expression of the therapeutic transgene was documented. Recent data from humans showed that targeting the liver with an AAV vector achieves long-term expression of the FIX transgene at therapeutic levels. Additionally, several Phase 1 and Phase 2 clinical trials using AAV serotypes 1, 2 and/or chimeric 2.5 have been reported for the treatment of cystic fibrosis, hemophilia, Canavan's disease, Duchenne muscular dystrophy (DMD) and alpha-1 antitrypsin deficiency (M. Hildinger and A. Auricchio. *Eur J Hum Genet,* 12, 263-271 (2004); C. Li, D. E. Bowles, T. V. Dyke and R. J. Samulski, *Cancer Gene Ther.,* 12(12): 913-926 (2005); D. E. Bowles, S. W J McPhee, C. Li, S. J. Gray, J. J. Samulski, A. S. Camp, J. Li, B. Wang, P. E. Monahan, J. E. Rabinowitz, J. C. Grieger, La. Govindasamy, M. Agbandje-McKenna, X. Xiao and R. J. Samulski, *Molecular Therapy,* 20, 443-455 (2012); M. L. Brantly, J. D. Chulay, L. Wang, C. Mueller, M. Humphries, L. T. Spencer, F. Rouhani, T. J. Conlon, R. Calcedo, M. R. Betts, C. Spencer, B. J. Byrne, J. M. Wilson, T. R. Flotte, Sustained transgene expression despite T lymphocyte responses in a clinical trial of rAAV1-AAT gene therapy. *Proceedings of the National Academy of Sciences of the United States of America* 106, 16363-16368 (2009); T. R. Flotte, M. L. Brantly, L. T. Spencer, B. J. Byrne, C. T. Spencer, D. J. Baker, M. Humphries, Phase I trial of intramuscular injection of a recombinant adeno-associated virus alpha 1-antitrypsin (rAAV2-CB-hAAT) gene vector to AAT-deficient adults. *Human gene therapy* 15, 93-128 (2004); T. R. Flotte, B. C. Trapnell, M. Humphries, B. Carey, R. Calcedo, F. Rouhani, M. Campbell-Thompson, A. T. Yachnis, R. A. Sandhaus, N. G. McElvaney, C. Mueller, L. M. Messina, J. M. Wilson, M. Brantly, D. R. Knop, G. J. Ye, J. D. Chulay, Phase 2 clinical trial of a recombinant adeno-associated viral vector expressing alpha1-antitrypsin: interim results. *Human gene therapy* 22, 1239-1247 (2011); C. Mueller, J. D. Chulay, B. C. Trapnell, M. Humphries, B. Carey, R. A. Sandhaus, N. G. McElvaney, L. Messina, Q. Tang, F. N. Rouhani, M. Campbell-Thompson, A. D. Fu, A. Yachnis, D. R. Knop, G. J. Ye, M. Brantly, R. Calcedo, S. Somanathan, L. P. Richman, R. H. Vonderheide, M. A. Hulme, T. M. Brusko, J. M. Wilson, T. R. Flotte, Human Treg responses allow sustained recombinant adeno-associated virus-mediated transgene expression. *The Journal of clinical investigation* 123, 5310-5318 (2013)).

Adeno-associated virus (AAV), a member of the Parvovirus family, is a small nonenveloped, icosahedral virus with single-stranded linear DNA genomes of 4.7 kilobases (kb). AAV is assigned to the genus, Dependovirus, because the virus was discovered as a contaminant in purified adenovirus stocks (D. M Knipe, P. M Howley, *Field's Virology., Lippincott Williams &Wilkins, Philadelphia, ed. Sixth,* 2013). In its wild-type state, AAV depends on a helper virus—typically adenovirus—to provide necessary protein factors for replication, as AAV is naturally replication-defective. The 4.7-kb genome of AAV is flanked by two inverted terminal repeats (ITRs) that fold into a hairpin shape important for replication. Being naturally replication-defective and capable of transducing nearly every cell type in the human body, AAV represents an ideal vector for therapeutic use in gene therapy or vaccine delivery. In it's wild-type state, AAV's life cycle includes a latent phase during which AAV genomes, after infection, are site-specifically integrated into host chromosomes and an infectious phase during which, following either adenovirus or herpes simplex virus infection, the integrated genomes are subsequently rescued, replicated, and packaged into infectious viruses. When vectorized, the viral Rep and Cap genes of AAV are removed and provided in trans during virus production, making the ITRs the only viral DNA that remains (A. Vasileva, R. Jessberger, *Nature reviews. Microbiology,* 3, 837-847 (2005)). Rep and Cap are then replaced with an array of possible transfer vector configurations to perform gene addition or gene targeting. These vectorized recombinant AAVs (rAAV) transduce both dividing and non-dividing cells, and show robust stable expression in quiescent tissues like pancreatic tissue. The number of rAAV gene therapy clinical trials that have been completed or are ongoing to treat various inherited or acquired diseases is increasing dramatically as rAAV-based therapies increase in popularity. Similarly, in the clinical vaccine space, there have been numerous recent preclinical studies and one ongoing clinical trial using rAAV as a vector to deliver antibody expression cassettes in passive vaccine approaches for human/simian immunodeficiency virus (HIV/SIV), influenza virus, henipavirus, and human papilloma virus (HPV). (See, P. R. Johnson, B. C. Schnepp, J. Zhang, M. J. Connell, S. M. Greene, E. Yuste, R. C. Desrosiers, K. R. Clark, *Nature medicine* 15, 901-906 (2009); A. B. Balazs, J. Chen, C. M. Hong, D. S. Rao, L. Yang, D. Baltimore, *Nature* 481, 81-84 (2012); A. B. Balazs, Y. Ouyang, C. M. Hong, J. Chen, S. M. Nguyen, D. S. Rao, D. S. An, D. Baltimore, *Nature medicine* 20, 296-300 (2014); A. B. Balazs, J. D. Bloom, C. M. Hong, D. S. Rao, D. Baltimore, *Nature biotechnology* 31, 647-652 (2013); M. P. Limberis, V. S. Adam, G. Wong, J. Gren, D. Kobasa, T. M. Ross, G. P. Kobinger, A. Tretiakova, J. M., *Science translational medicine* 5, 187ra172 (2013); M. P. Limberis, T. Racine, D. Kobasa, Y. Li, G. F. Gao, G. Kobinger, J. M. Wilson, Vectored expression of the broadly neutralizing antibody FI6 in mouse airway provides partial protection against a new avian influenza A virus, H7N9. *Clinical and vaccine immunology: CVI* 20, 1836-1837 (2013); J. Lin, R. Calcedo, L. H. Vandenberghe, P. Bell, S. Somanathan, J. M. Wilson, *Journal of virology* 83, 12738-12750 (2009); I. Sipo, M. Knauf, H. Fechner, W. Poller, O. Planz, R. Kurth, S. Norley, *Vaccine* 29, 1690-1699 (2011); A. Ploquin, J. Szecsi, C. Mathieu, V. Guillaume, V. Barateau, K. C. Ong, K. T. Wong, F. L. Cosset, B. Horvat, A. Salvetti, *The Journal of infectious diseases* 207, 469-478 (2013); D. Kuck, T. Lau, B. Leuchs, A. Kern, M. Muller, L. Gissmann, J. A. Kleinschmidt, *Journal of virology* 80, 2621-2630 (2006); K. Nieto, A. Kern, B. Leuchs, L. Gissmann, M. Muller, J. A. Kleinschmidt, Antiviral therapy 14, 1125-1137 (2009); K. Nieto, C. Stahl-Hennig, B. Leuchs, M. Muller, L. Gissmann, J. A. Kleinschmidt, *Human gene therapy* 23, 733-741 (2012); and L. Zhou, T. Zhu, X. Ye, L. Yang, B. Wang, X. Liang, L. Lu, Y. P. Tsao, S. L. Chen, J. Li, X. Xiao, *Human gene therapy* 21, 109-119 (2010).) The properties of non-pathogenicity, broad host range of infectivity, including non-dividing cells, and potential site-specific chromosomal integration make AAV an attractive tool for gene transfer.

The first rAAV-based gene therapy to be approved in the Western world (Glybera® for lipoprotein lipase deficiency, approved for use in 2012 in the European Union) has stimulated the gene therapy community, investors and regulators to the real possibility of moving rAAV therapies into the clinic globally. Yet, despite the impressive abilities of rAAV to transduce a variety of tissue and cell types, several drawbacks have limited its use for clinical applications, such as its promiscuity, limited transgene packaging size, and the high prevalence of pre-existing neutralizing antibodies in the general population. For gene therapy purposes, transduction needs to be both efficient and highly cell type specific. Pancreatic tissue has been historically one of the most challenging tissues to transduce at high levels sufficient to provide therapeutic levels of expression of delivered transgene products.

The recent excitement surrounding the possible use of rAAV as a vector for delivery of vaccines providing passive immunoprotection against pathogenic viruses like HIV and influenza virus in particular, has renewed the urgency for rAAV capsids capable of highly efficient pancreas delivery for this unique vaccination approach in humans. Given the limitations with efficient human pancreas transduction with existing rAAV serotypes, bioengineering of a clinical rAAV vector candidate that can efficiently transduce human pancreatic tissue or human islets at a level sufficient to express therapeutic levels of broad-spectrum antibodies for vaccine strategies or genes essential for pancreatic disorder treatment was pursued.

A variety of published US applications describe AAV vectors and virions, including U.S. Publication Nos. 2015/0176027, 2015/0023924, 2014/0348794, 2014/0242031, and 2012/0164106; all of which are incorporated by reference herein in their entireties.

However, high levels of transduction are needed for pancreatic gene therapy trials as there are physical limitations to how much AAV can be delivered in a single intraperitoneal injection which is further complicated by the fact that injections need to ensure that the injected vector targets the diseased pancreatic tissue or islet cells specifically and efficiently. If an AAV had superior human pancreas transduction, a lower dose and fewer injections would be needed to achieve therapeutic relevance. Similarly, for use as a vaccine delivery tool, high efficiency transduction and stability is needed to achieve robust secretion of antibodies encoded within the AAV to reach therapeutic levels of circulating antibodies in the blood.

There remains, therefore, a need in the art for AAV vectors with improved human pancreatic tissue transduction. The present invention meets this need by providing variant AAV capsid polypeptides that demonstrate significantly improved human pancreatic tissue transduction over non-variant parent capsid polypeptides with regard to transducing human pancreatic tissue and/or islet cells. The present invention utilizes directed evolution by DNA gene shuffling and re-programming strategies to characterize and screen for such variant AAV capsid polypeptides that have high transduction efficiency for human islet cells than the best parent (i.e. LK03—mainly α-cell specific), and high cell-type specific transduction (e.g. α- or β-cell specific).

BRIEF SUMMARY OF THE INVENTION

The present invention provides variant adeno-associated virus (AAV) capsid polypeptides. The variant AAV capsid polypeptides exhibit increased transduction or tropism in human pancreatic tissue or human islets as compared to non-variant parent capsid polypeptides.

In some embodiments, the variant AAV capsid polypeptides exhibit increased transduction or tropism in human pancreatic tissue or human islets as compared to non-variant parent capsid polypeptides.

In some embodiments, the variant AAV capsid polypeptides transduced either dissociated or intact human islets.

In some embodiments, the variant AAV capsid polypeptides exhibit increased transduction as compared to non-variant parent capsid polypeptides.

In some embodiments, the variant AAV capsid polypeptides exhibit increased tropism as compared to non-variant parent capsid polypeptides.

In some embodiments, the variant AAV capsid polypeptide further exhibits increased transduction or tropism in one or more types of cells within human islets as compared to a non-variant parent capsid polypeptide.

In some embodiments, the variant AAV capsid polypeptide exhibits increased transduction of human pancreatic tissue or human islets in vivo as compared to a non-variant parent capsid polypeptide.

In some embodiments, the variant AAV capsid polypeptide exhibits increased transduction of human pancreatic tissue or human islets in vitro as compared to a non-variant parent capsid polypeptide.

In some embodiments, the variant AAV capsid polypeptide exhibits increased transduction of a human pancreatic tissue or human islets ex vivo as compared to a non-variant parent capsid polypeptide.

In some embodiments, the variant AAV capsid polypeptide exhibits an enhanced neutralization profile as compared to non-variant parent capsid polypeptides.

In some embodiments, the variant AAV capsid polypeptide exhibits an enhanced neutralization profile against pooled human immunoglobulins as compared to non-variant parent capsid polypeptides.

In some embodiments, the variant AAV capsid polypeptide that exhibits an enhanced neutralization profile is selected from the group consisting of AAV-10A1 (SEQ ID NO:1) and AAV-10A3 (SEQ ID NO:2). In some embodiments, the variant AAV capsid polypeptide that exhibits an enhanced neutralization profile is AAV-10A1 (SEQ ID NO:1). In some embodiments, the variant AAV capsid polypeptide that exhibits an enhanced neutralization profile is AAV-10A3 (SEQ ID NO:2).

In some embodiments, the variant AAV capsid polypeptide is part of a functional AAV capsid, where said functional AAV capsid packages a nucleic acid sequence selected from the group consisting of a non-coding RNA, a protein coding sequence, an expression cassette, a multi-expression cassette, a sequence for homologous recombination, a genomic gene targeting cassette, and a therapeutic expression cassette.

In some embodiments, the nucleic acid sequence is contained within an AAV vector.

In some embodiments, the expression cassette is a CRISPR/CAS expression system.

In some embodiments, the therapeutic expression cassette encodes a therapeutic protein or antibody.

In some embodiments, the variant AAV capsid polypeptide is selected from the group consisting of AAV-10A1 (SEQ ID NO:1), AAV-10A3 (SEQ ID NO:2), AAV-10A4 (SEQ ID NO:3), AAV-10A5 (SEQ ID NO:4), AAV-18A1 (SEQ ID NO:5), AAV-10B1 (SEQ ID NO:6), AAV-10B3 (SEQ ID NO:7), AAV-10B5 (SEQ ID NO:8), AAV-10B6 (SEQ ID NO:9), AAV-10B7 (SEQ ID NO:10), AAV-18B2 (SEQ ID NO:12), and AAV-18B3 (SEQ ID NO:13).

In some embodiments, the variant AAV capsid polypeptide is selected from the group consisting of AAV-10A1 (SEQ ID NO:1), AAV-10A3 (SEQ ID NO:2), and AAV-18A1 (SEQ ID NO:5).

The present invention also provides methods of using the variant AAV capsid polypeptides of the present invention in a therapeutic treatment regimen or vaccine.

In some embodiments, the method is using the variant AAV capsid polypeptide as described above in a therapeutic treatment for an endocrine disorder.

In some embodiments, the method is using the variant AAV capsid polypeptide as described above in a therapeutic treatment for diabetes, including Type I or Type II.

The present invention also provides methods of using the variant AAV capsid polypeptides of the present invention to reduce the amount of total nucleic acid administered to a subject, where the method comprises administering less total nucleic acid amount to the subject when the nucleic acid is transduced using a variant AAV capsid polypeptide as compared to the amount of nucleic acid administered to the subject when the nucleic acid is transduced using a non-variant parent capsid polypeptide in order to obtain a similar therapeutic effect.

The present invention also provides AAV vector comprising a nucleic acid sequence encoding a variant AAV capsid polypeptide, where the variant AAV capsid polypeptide exhibits increased transduction or tropism in human pancreatic tissue or human islets as compared to a non-variant parent capsid polypeptide.

In some embodiments, the variant AAV capsid polypeptide exhibits increased transduction as compared to a non-variant parent capsid polypeptide.

In some embodiments, the variant AAV capsid polypeptide exhibits increased tropism as compared to a non-variant parent capsid polypeptide.

In some embodiments, the variant AAV capsid polypeptide exhibits increased transduction of human pancreatic tissue or human islets in vivo as compared to a non-variant parent capsid polypeptide.

In some embodiments, the variant AAV capsid polypeptide exhibits increased transduction of human pancreatic tissue or human islets in vitro as compared to a non-variant parent capsid polypeptide.

In some embodiments, the variant AAV capsid polypeptide exhibits increased transduction of a human pancreatic tissue or human islets ex vivo as compared to a non-variant parent capsid polypeptide.

In some embodiments, the AAV vector further comprises a nucleic acid sequence selected from the group consisting of a non-coding RNA, a coding sequence, an expression cassette, a multi-expression cassette, a sequence for homologous recombination, a genomic gene targeting cassette, and a therapeutic expression cassette.

In some embodiments, the variant AAV capsid polypeptide allows for nucleic acid expression similarly to a non-variant parent capsid polypeptide.

In some embodiments, the expression cassette is a CRISPR/CAS expression system.

In some embodiments, the therapeutic expression cassette encodes a therapeutic protein or antibody.

In some embodiments, the variant AAV capsid polypeptide sequence is selected from the group consisting of AAV-10A1 (SEQ ID NO:1), AAV-10A3 (SEQ ID NO:2), AAV-10A4 (SEQ ID NO:3), AAV-10A5 (SEQ ID NO:4), AAV-18A1 (SEQ ID NO:5), AAV-10B1 (SEQ ID NO:6), AAV-10B3 (SEQ ID NO:7), AAV-10B5 (SEQ ID NO:8), AAV-10B6 (SEQ ID NO:9), AAV-10B7 (SEQ ID NO:10), AAV-18B2 (SEQ ID NO:12), and AAV-18B3 (SEQ ID NO:13).

In some embodiments, the variant AAV capsid polypeptide sequence is selected from the group consisting of AAV-10A1 (SEQ ID NO:1), AAV-10A3 (SEQ ID NO:2), and AAV-18A1 (SEQ ID NO:5).

The present invention also provides methods of using the AAV vector of the present invention in a therapeutic treatment regimen or vaccine.

In some embodiments, the method is using the AAV vector as described above in a therapeutic treatment for an endocrine disorder.

In some embodiments, the method is using the AAV vector as described above in a therapeutic treatment for diabetes, including Type I or Type II.

The present invention further provides methods of using the variant AAV capsid polypeptides of the present invention to reduce the amount of total AAV vector administered to a subject, where the method comprises administering less total AAV vector amount to the subject when the AAV vector is transduced by a variant AAV capsid polypeptide as compared to the amount of AAV vector administered to the subject when the AAV vector is transduced by a non-variant parent capsid polypeptide in order to obtain a similar therapeutic effect.

In some embodiments, the present invention provides a method for generating a variant AAV capsid polypeptide, wherein said variant AAV capsid polypeptide exhibits increased transduction or tropism in human pancreatic tissue or human islets as compared to a non-variant parent capsid polypeptide, said method comprising:
  a) generating a library of variant AAV capsid polypeptide genes, wherein said variant AAV capsid polypeptide genes include a plurality of variant AAV capsid polypeptide genes comprising sequences from more than one non-variant parent capsid polypeptide;
  b) generating an AAV vector library by cloning said variant AAV capsid polypeptide gene library into AAV vectors, wherein said AAV vectors are replication competent AAV vectors;
  c) screening said AAV vectors library from b) encoding for variant AAV capsid polypeptides for increased transduction or tropism in human pancreatic tissue or human islets as compared to a non-variant parent capsid polypeptide; and
  d) selecting said variant AAV capsid polypeptides from c).

In some embodiments, the method further comprises e) determining the sequence of said variant AAV capsid polypeptides from d).

In some embodiments, the variant AAV capsid polypeptide exhibits increased transduction as compared to a non-variant parent capsid polypeptide.

In some embodiments, the variant AAV capsid polypeptide exhibits increased tropism as compared to a non-variant parent capsid polypeptide.

In some embodiments, the variant AAV capsid polypeptide further exhibits an enhanced neutralization profile as compared to a non-variant parent capsid polypeptide. In some embodiments, the variant AAV capsid polypeptide of the invention further exhibits an enhanced neutralization profile against pooled human immunoglobulins as compared to a non-variant parent capsid polypeptide.

In some embodiments, the variant AAV capsid polypeptide that further rexhibits an enhanced neutralization profile is selected from the group consisting of AAV-10A1 (SEQ ID NO:1) and AAV-10A3 (SEQ ID NO:2). In some embodiments, the variant AAV capsid polypeptide that further exhibits an enhanced neutralization profile is AAV-10A1 (SEQ ID NO:1). In some embodiments, the variant AAV capsid polypeptide that further exhibits an enhanced neutralization profile is AAV-10A3 (SEQ ID NO:2).

In some embodiments, the variant AAV capsid polypeptides further exhibit increased transduction or tropism in one or more non-muscle human tissues as compared to non-variant parent capsid polypeptides.

In some embodiments, the variant AAV capsid polypeptide exhibits increased transduction of human pancreatic tissue or human islets in vivo as compared to a non-variant parent capsid polypeptide.

In some embodiments, the variant AAV capsid polypeptides exhibits increased transduction of human pancreatic tissue or human islets in vitro as compared to a non-variant parent capsid polypeptide.

In some embodiments, the variant AAV capsid polypeptides exhibits increased transduction of a human pancreatic tissue or human islets ex vivo as compared to a non-variant parent capsid polypeptide.

Other objects, advantages and embodiments of the invention will be apparent from the detailed description following.

BRIEF DESCRIPTION OF THE DRAWINGS

FIG. 17. PacBio Sequencing reveals good cap-BC linkage.

FIG. 19. Transduction efficiency in islet cells.

FIG. 28. Quantification of GFP expressing cells and median fluorescence intensity in different groups.

FIG. 36. Transduction of human islets from two different donors (MOI 10,000). Islet subpopulation specific transduction efficiency of AAV DJ, AAV LK03, and two of the new variants. Intact islets from two different donors (A and B) were transduced with GFP expressing rAAV at an MOI of 10,000. After two days islets were dissociated into single cell suspensions and analyzed for α-cell or β-cell specific transduction using staining of surface markers followed by FACS.

FIG. 46. Neutralization profile of new AAV variants. Sensitivity of the novel capsid variants towards neutralization by pooled human immune globulin (WIG). The indicated concentrations of IVIG from two different batches were incubated with 2.2E+07 vector copies of rAAV in a volume of 100 ul for 1 hour at 37° C. followed by transduction of permissive Huh7 cells with an MOI of 100 in duplicates. Luciferase activity from cell lysates was determined 24 hours post transduction. Sensitivity of the novel capsid variants towards neutralization by pooled human immune globulin (IVIG). The indicated concentrations of IVIG from two different batches were incubated with 2.2E+

07 vector copies of rAAV in a volume of 100 ul for 1 hour at 37° C. followed by transduction of permissive Huh7 cells with an MOI of 100 in duplicates. Luciferase activity from cell lysates was determined 24 hours post transduction.

Figure 47:
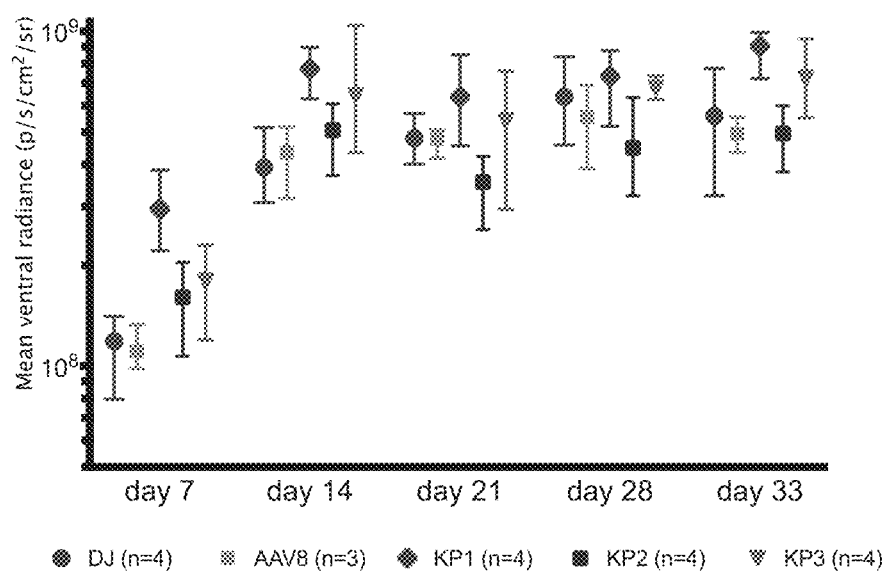

FIG. 47. In vivo liver transduction efficiency of new AAV variants (day 7, 14, 21, and 33). In vivo transduction efficiency of the new capsid variants. Balb/C SCID mice were injected with 2E+10 vg of an AAV luciferase vector packaged with the various capsids and luciferase activity in the liver was monitored over several weeks using an Ami Imaging System. Average values for each group are shown with min and max. In vivo transduction efficiency of the new capsid variants. Balb/C SCID mice were injected with 2E+10 vg of an AAV luciferase vector packaged with the various capsids and luciferase activity in the liver was monitored over several weeks using an Ami Imaging System. Average values for each group are shown with min and max.

Figure 48:
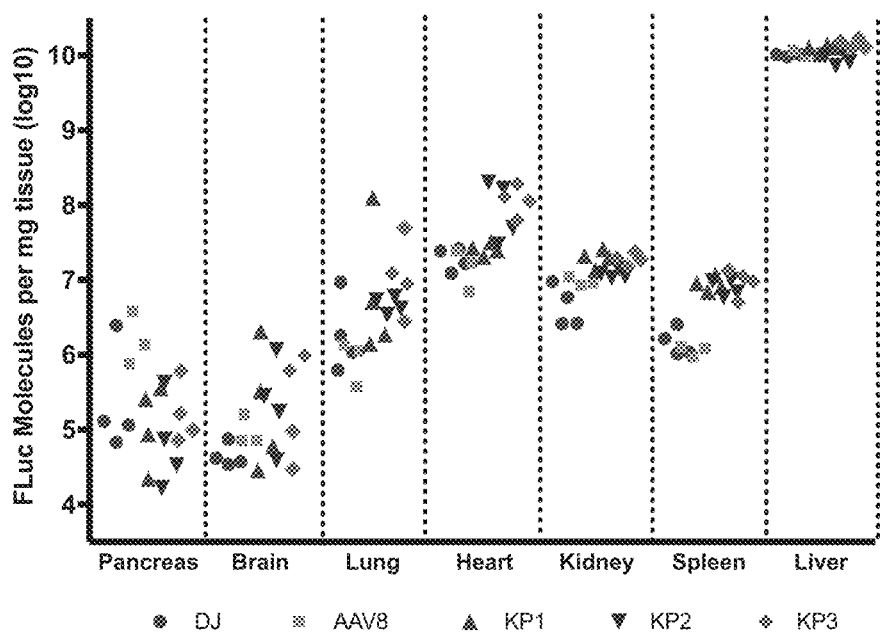

FIG. 48. Luciferase expression in various organs (ex vivo, week 5). Luciferase activity measured in various mouse organs 34 days after injection with rAAV. Organs were homogenized in lysis buffer and assayed for Luciferase activity. Data for each individual mouse are shown and color coded according to group. Luciferase activity measured in various mouse organs 34 days after injection with rAAV. Organs were homogenized in lysis buffer and assayed for Luciferase activity. Data for each individual mouse are shown and color coded according to group.

Figure 13:
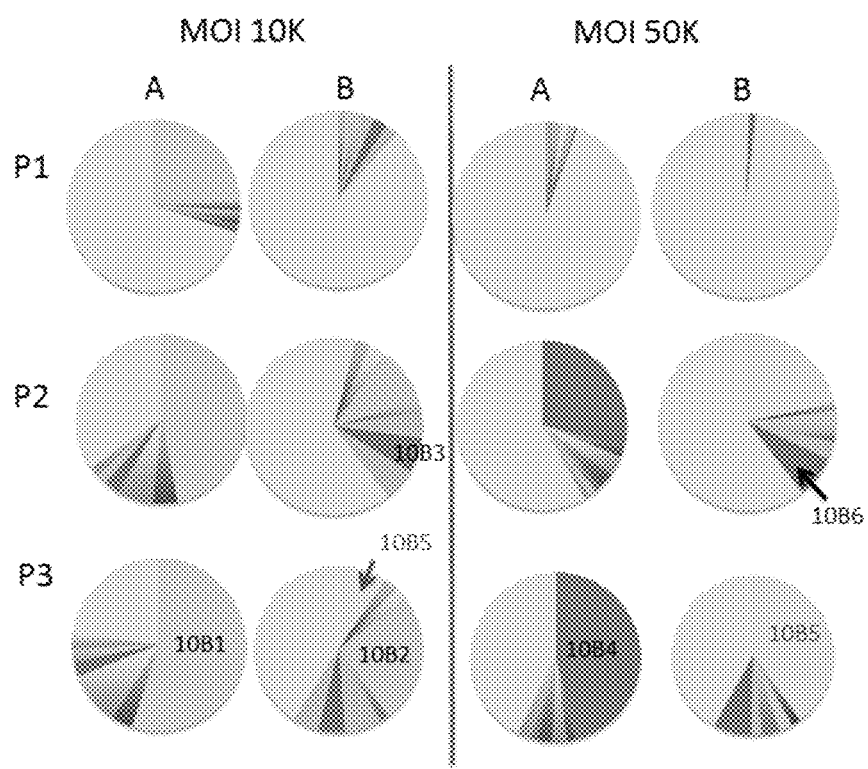
FIG. 13. Enrichment for shuffled AAV cap variants during passaging of the 10 parent library. Only the most enriched AAV variants are shown in different colors, all others are in grey. Variants that were selected for further analysis are indicted by name. The name in red indicate a variant that was enriched in two independent screens.
Figure 49:
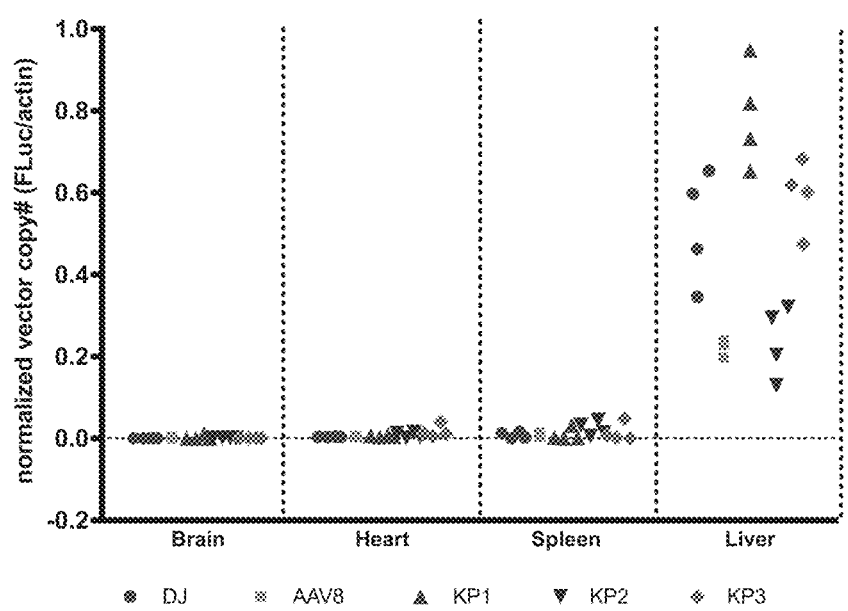

FIG. 49. Vector copy number in various organs (week 5). FIG. 13: Analysis of the new variants for transduction efficiency on various human and nonhuman cell types. Capsid sequences were used to package an AAV luciferase vector and cells were transduced with an MOI of 1,000 in triplicates, except for primary human islets which were transduced in duplicates. Luciferase activity in the cell lysates was determined two days post transduction as a read-out for transduction efficiency. Analysis of the new variants for transduction efficiency on various human and nonhuman cell types. Capsid sequences were used to package an AAV luciferase vector and cells were transduced with an MOI of 1,000 in triplicates, except for primary human islets which were transduced in duplicates. Luciferase activity in the cell lysates was determined two days post transduction as a read-out for transduction efficiency.

FIG. 50. Parental contributions in the 10 parent library and the 18 parent pool. (A, B) Chimeric capsid sequences obtained from the 10 parent library at the plasmid level (A) or at the AAV level (B) were analysed by PacBio sequencing and parental contribution was assigned for each amino acid position. (C) Parental contribution in the 18 parent pool as analysed using high-throughput sequencing of the barcodes. (D) Parental contribution in the 18 parent pool as analysed using PacBio sequencing of the capsid sequences.

Figure 51:
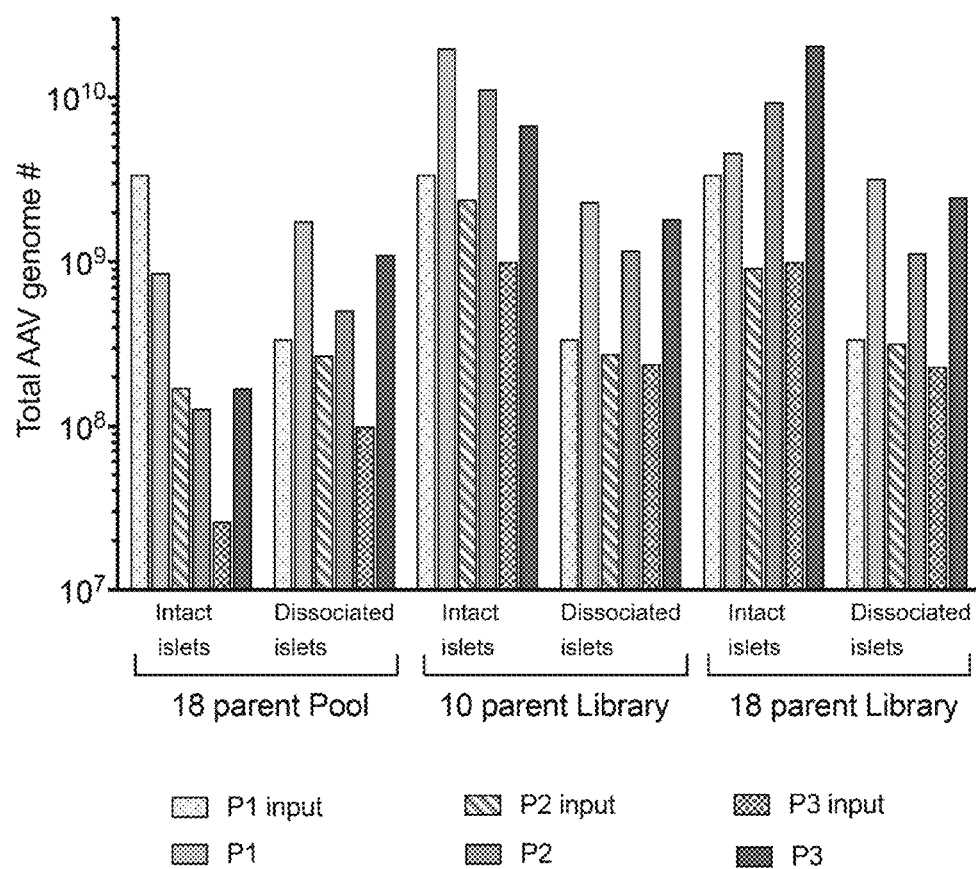

FIG. 51. Replication of the 18 parent mix, the 10 parent library, and the 18 parent library during three rounds of passaging on intact and dissociated islets. Intact islets were infected with the indicated AAV preparations using an MOI of 20,000, dissociated islet cells were infected using an MOI of 2,000. Adenovirus 5 was used to replicate AAV and virus was harvested from the supernatant and cells after 4 days. Replication of viral species was determined by rep qPCR. For each round the total viral genome copies used for infection and the total viral genome copies retrieved are shown.

FIG. 52. Enrichment of distinct capsids during three rounds of passaging. Barcode sequences were amplified from viral genomes after each passage and were analysed by high-throughput sequencing. Color coding of enriched parental capsids for passaging of the 18 parent mix is identical to that of the parental pool depicted in FIG. 1c. Origin of the most improved capsids (KP1, KP2, KP3) is indicted.

FIG. 53. Rescue of enriched capsid sequences and evaluation of selected capsids for islet transduction. (A) The forward primer annealed to a sequence in the 3' end of the rep gene, the reverse primer was specific to the sequence of the right barcode of the variant capsid to be amplified. (B) A self-complementary AAV expressing GFP was packaged with LK03 as well as 12 novel capsid sequences and islet cells were transduced using a low MOI of 1,000. Cells were sorted for GFP expression using FACS 48-hrs later. (C) Dissociated islet cells were transduced with CsCl gradient purified scCAG-GFP rAAV preps generated with the two best parental capsids as well as the novel capsids that were the top transducers in the pre-screen. Three different MOIs were used for transduction. Transduction efficiency is depicted both as the percentage of GFP positive cells (left graph) as well as the median fluorescence intensity within the GFP positive cell population (right graph). (D) α- and β-cell specific transduction efficiency of the novel variants. GFP expressing rAAV packaged with two of the novel variant capsids as well as AAV-DJ and AAV-LK03 capsids were used to transduce intact islets at an MOI of 10,000 and α- and β-cell specific transduction was determined by surface staining followed by FACS. Data are shown as the mean with standard deviation from two individual experiments using islets from two different donors and statistically significant differences are indicated. *: $p<0.1$, : $p<0.01$, *: $p<0.001$ FIG. 54. Amino acid sequence and structural composition of selected shuffled AAV capsid variants. (A) Amino acid sequence mapping analysis of parental capsid fragment crossovers in vectorized shuffled capsids. Library parents are depicted in different colors as indicated on the left. Large dots represent 100% parental match (i.e. the position in question matches only one parent) and small dots represent more than one parental match (i.e. the position matches more than one parent) at each position. The solid line for each chimera represents the library parents identified within the sequence between crossovers. A set of thin horizontal parallel lines between crossovers indicates multiple parents match at an equal probability. A vertical spike indicates a fast single position switch between parents. VP1, VP2, VP3 and AAP ORFs are shown below. (B) Amino acid sequence mapping analysis of parental AAP fragment crossovers in vectorized shuffled capsids. (C) Enrichment scores were calculated for each amino acid position in the sequence of each chimera by comparison of sequences from parental serotypes based on maximum likelihood. Library parents are depicted in different colors as shown. (D) The VP3 sequences of shuffled variants were 3D false-color mapped onto the crystal structure of AAV2 VLP. Color-coding indicates parental amino acid contribution using colors as in (A) and (B). (E) The residues different from AAV3B of shuffled variants were 3D false-color mapped onto the crystal structure of AAV6 VP3. Light gray residues correspond to AAV3B amino acids while colored residues indicate surface exposed amino acids derived from other serotypes. With the exception of AAV3B color coding is as in (A) and (B).

FIG. 55. In vitro transduction experiments using Firefly Luciferase expressing rAAVs. (A) Transduction efficiency of the novel capsids as well as AAV-DJ and AAV-LK03 capsids on a variety of human and non-human derived cell types. Cells were transduced with the different capsid containing rAAVs packaging a firefly luciferase expression cassette at an MOI of 1,000 in triplicates each (with the exception of islet cells) and cell lysates were analysed 48 hrs post transduction in a luciferase activity assay. Two-fold dilutions of recombinant firefly luciferase enzyme were used to prepare a standard curve and raw luminescence units were calculated into luciferase molecules based on the standard curve. (B) Neutralization assay of rAAVs packaged with different capsids using dilutions of two different batches of pooled human immunoglobulin (IVIG). Huh-7 cells were transduced in biological duplicates at a MOI of 100 with Firefly luciferase expressing rAAVs that had been pre-incubated with different concentrations of IVIG for 1-hr at 37° C. Luciferase activity in cell lysates was measured 24-hrs post transduction. Mean values with standard deviations are shown for each sample. Only statistically significant differences are indicated in the legend below the graph. *: $p<0.001$, **: $p<0.0001$.

Figure 56:
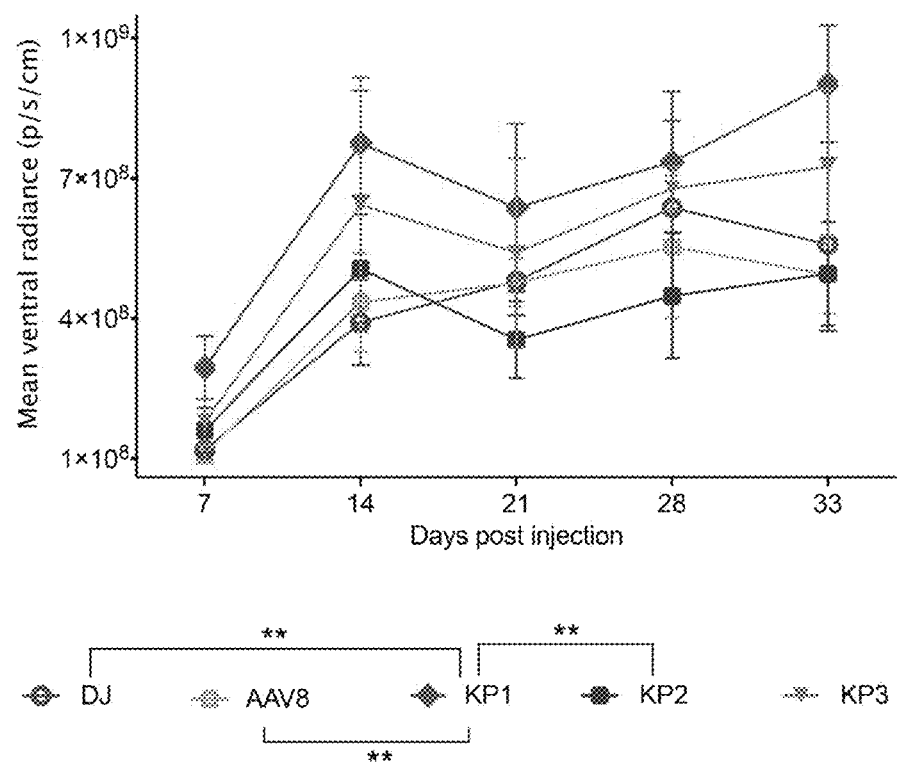

FIG. 56. In vivo transduction efficiency of rAAVs packaged with the novel capsids as well as with AAV8 and DJ capsids. Balb/C SCID mice were injected via tail vein with 2E10 vg each firefly luciferase expressing rAAV and luciferase expression in the livers was monitored over several weeks using live imaging after i.p injection of luciferin substrate. Four animals were injected for each group with the exception of the AAV8 group which contained 3 animals. The mean of each group's mean ventral radiance is shown for each timepoint with standard deviations indicated. One animal from the AAV8 group was omitted from analysis due to a failed substrate injection. Only statistically significant differences are indicated in the legend below the graph. : $p<0.01$ FIG. 57. Validation and Quantification of Human Hepatocyte Transduction in Mice with Humanized Liver In Vivo. (A) Representative immunofluorescence images from treated mice with humanized liver transduced with ssAAV-RFP at 2E11 vg i.v. with varying capsid serotypes. DAPI (blue), human-specific FAH (green), and viral-RFP (red) on liver sections. Scale bar, 50 µM. (B) Quantification of transduction efficiency for all hepatocytes (left panel) as well as human hepatocytes (right panel), and quantification of human hepatocyte repopulation levels (lower panel). Each data point represents an area of interest for each mouse (individual biological replicate, see "Materials and Methods"). A total of six to nine areas of interests for each mouse were scanned and analyzed. The mean and standard deviation for each group are indicated. Only statistically significant differences are shown in the graphs. : $p<0.01$, ****: $p<0.0001$ FIG. 58. Parental capsids used for library generation. (A) Phylogenetic relationship of the 18 parental capsids on the amino acid level. The parental capsids used for generation of the 10 parent library are shown in red. The neighbour-joining tree was constructed using Genious 6.0.6. (B) Crossover analysis of chimeric capsids DJ and LK03 with parental contributions indicated. For simple visualization the same parental capsid sequences are shown for both chimeras although they were derived from different libraries with different parental compositions. AAV-DJ was derived from a library that contained AAV2, AAV4, AAV5, AAV8, AAV9hu14, AAV-bovine, AAV-avian, and AAV-goat1 capsid sequences, AAV-LK03 was derived from a library that contained AAV1, AAV2, AAV3B, AAV4, AAV5, AAV6, AAV8, AAV9hu14, AAV-bovine, AAV-avian, and AAV-goat1 sequences. (C) Crossover analysis of AAP for AAV-DJ and AAV-LK03 with parental contributions indicated.

FIG. 59. Analysis of the 10 parent library by Sanger sequencing of random clones. (A) Crossover analysis of amino acid sequences of several shuffled capsids derived from the plasmid library (left) as well as the AAV library (right). For consistency LK03 and DJ are not shown as individual parents. Positions that are marked with a cross are not de novo mutations, but were derived from AAV-LK03 that contains a short stretch from AAV4. Parental capsids are shown in the following order: AAV1, AAV2, AAV3B, AAV6, AAV8, AAV9hu14, AAV-rhesus10, AAV-porcine2. (B) Conservation analysis along the capsid sequences for the input 8 parental sequences as well as the 10 parent library on the plasmid and on the AAV level (rAAVs).

FIG. 60. Analysis of the 18 parent library by Sanger sequencing of random clones. (A) Crossover analysis of amino acid sequences of several shuffled capsids derived from the plasmid library. Parental capsids are shown in the following order: AAV1, AAV2, AAV3B, AAV6, AAV8, AAV9hu14, AAV-rhesus10, AAV-porcine2, AAV4, AAV5, AAV12, AAV-bovine, AAV-goat1, AAV-porcine1, AAV-mouse1, and AAV-avian. (B) Conservation analysis along the capsid sequences for the input 16 parental sequences as well as the 18 parent library. Capsids DJ and LK03 are not listed as parents since they are chimeras consisting of fragments from the parentals used.

FIG. 61. Results of the second library screen on human islets. (A) Replication of the 10 parent library and the 18 parent library during three rounds of passaging on intact islets. Islets were infected in biological duplicates with the 10 parent library using an MOI of 10,000 or 50,000. Infection with the 18 parent library was performed in biological triplicates using an MOI of 50,000. Adenovirus 5 was used to replicate AAV and virus was harvested from the supernatant and cells after 4 days. Replication of viral species was determined by rep qPCR. For each round the total viral genome copies used for infection and the total viral genome copies retrieved are shown. (B) Enrichment of distinct capsids during three rounds of passaging. Barcode sequences were amplified from viral genomes after each passage and were analysed by high-throughput sequencing.

Figure 62A:
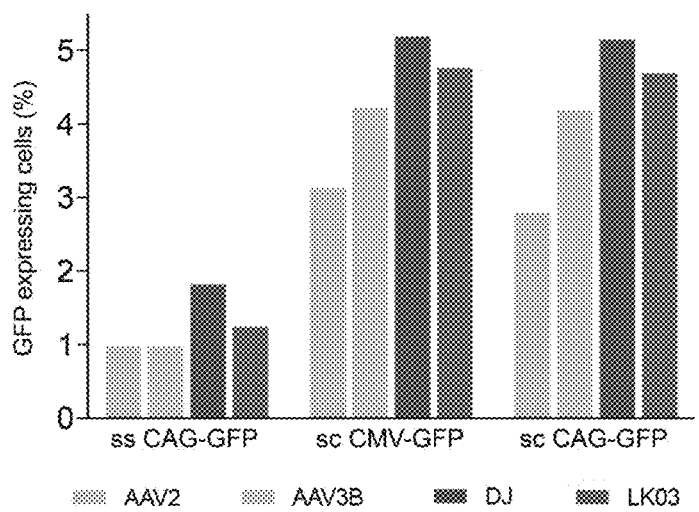
Figure 62B:
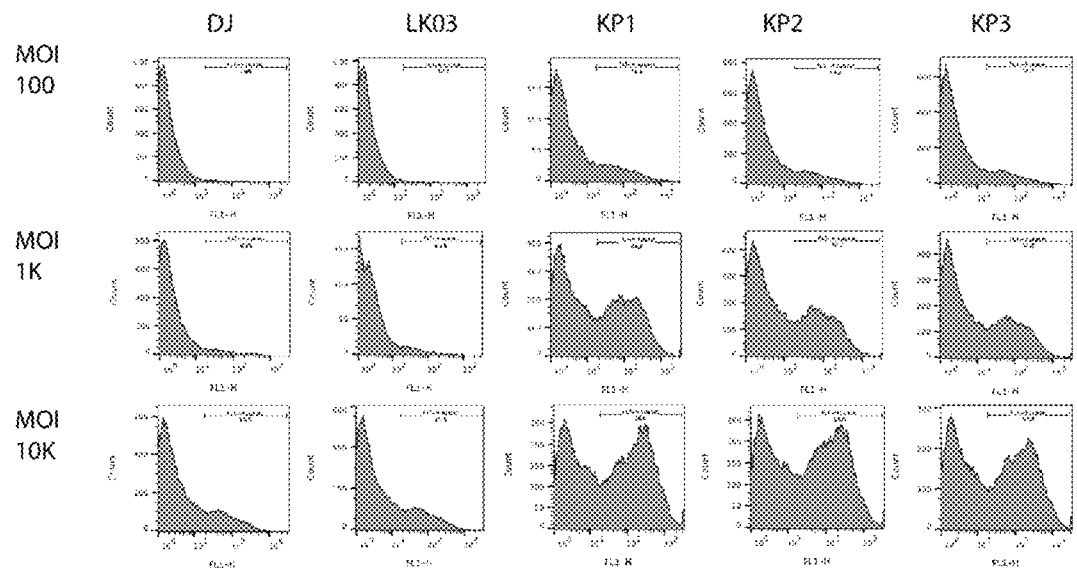

FIG. 62. Transduction efficiency of different chimeric and wildtype AAV capsids. (A) Dissociated islet cells were transduced with rAAVs (AAV2, AAV3B, DJ, and LK03 capsids) at and MOI of 1,000 and transduction efficiency was determined by flow cytometry 48 hrs post transduction. (B) Dissociated islet cells were transduced with CsCl gradient purified scCAG-GFP rAAV preps generated with the two best parental capsids as well as the novel capsids that were the top transducers in the pre-screen. Three different MOIs were used for transduction. Transduction efficiency is measured as a function of the number of GFP expressing cells in conjunction with fluorescence intensity for each cell.

FIG. 63. Analysis of the novel capsids for parental contribution on the nucleotide level as well as for packaging of vector genomes and protein composition. (A) Nucleotide sequence mapping analysis of parental capsid fragment crossovers in vectorized shuffled capsids. VP1, VP2, VP3 and AAP coding sequences are indicated below the crossover analysis for KP1, KP2, and KP3 sequences. (B) Alkaline Southern Blot analysis of ssCAG-FLuc vector genomes packaged with DJ, LK03, as well as the novel capsid variants. 1E09 vg were loaded in each lane. Size standards consisted of plasmids digested with different restriction enzymes to obtain fragments of the desired sizes. Vector genomes were probed with a FLuc specific radiolabeled probe (C) Alkaline Southern Blot analysis of scCAG-GFP vector genomes packaged with DJ, LK03, as well as the novel capsid variants. Size standards consisted of plasmids digested with different restriction enzymes to obtain fragments of the desired sizes. Vector genomes were probed with a GFP specific radiolabeled probe. (D) Western Blot analysis of purified scCAG-GFP vector preparations. Purified virus equivalent to 1E09 vg was loaded on a 4-12% Bis-Tris gel, transferred onto a nitrocellulose membrane and probed with B1 antibody that recognizes a highly conserved epitope in the C terminus of all three capsid proteins.

FIG. 64. In vivo transduction efficiency of rAAVs packaged with the novel capsids as well as with AAV8 and DJ capsids. (A) Balb/C SCID mice were injected via tail vein with 2E10 vg of each Firefly luciferase expressing rAAV and luciferase expression in the livers was monitored over several weeks using live imaging after i.p injection of luciferin substrate. Four animals were injected for each group with the exception of the AAV8 group which contained 3 animals. Maximum radiance was set at 2E09 with a threshold of 5E07. (B) 34 days post injection mice were sacrificed, and several organs were analyzed for luciferase expression ex vivo using the Promega Luciferase assay system. (C) Genomic DNA was isolated from mouse livers and analyzed for vector copy numbers by qPCR. Only statistically significant differences between groups are indicated. *: $p<0.1$, : $p<0.01$, *: $p<0.001$, ****: $p<0.0001$ FIG. 65. Amino acid alignments of the novel variants. (A) Capsid sequences of the novel variants as well as the 8 parental serotypes were aligned using MegAlign. Only differences to the consensus sequence are shown. The start sites for VP1, VP2, and VP3 are indicated. (B) Assembly activating protein (AAP) sequences of the novel variants as well as the 8 parental serotypes were aligned.

Figure 66:
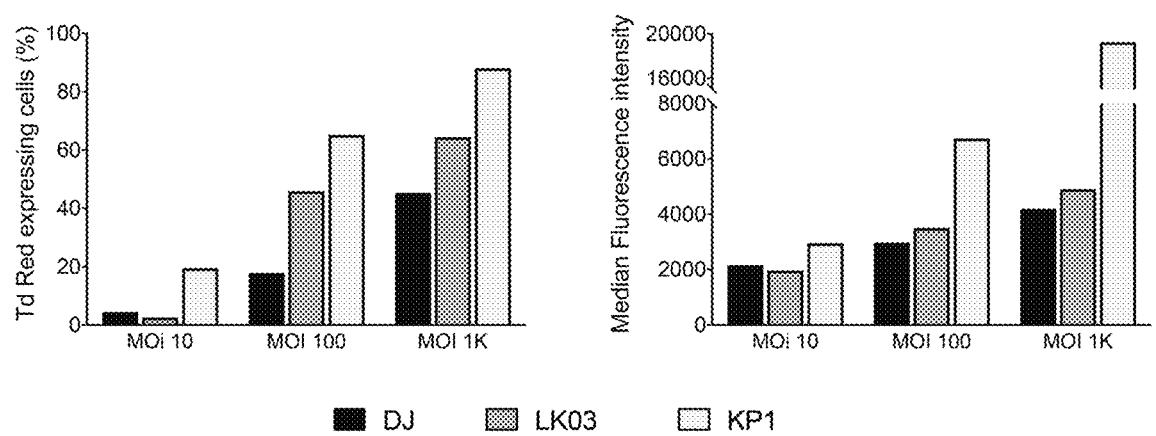

FIG. 66. Transduction efficiency of capsid KP1 for human embryonic stem cell derived β-cells. DJ, LK03 and KP1 capsids were used to package a Tomato Red vector and hESC derived mature β-cells were transduced with the MOIs indicated. Intracellular staining for the β-cell marker C-peptide was performed on day 6 post transduction and cells were analysed by flow cytometry.

Figure 67:
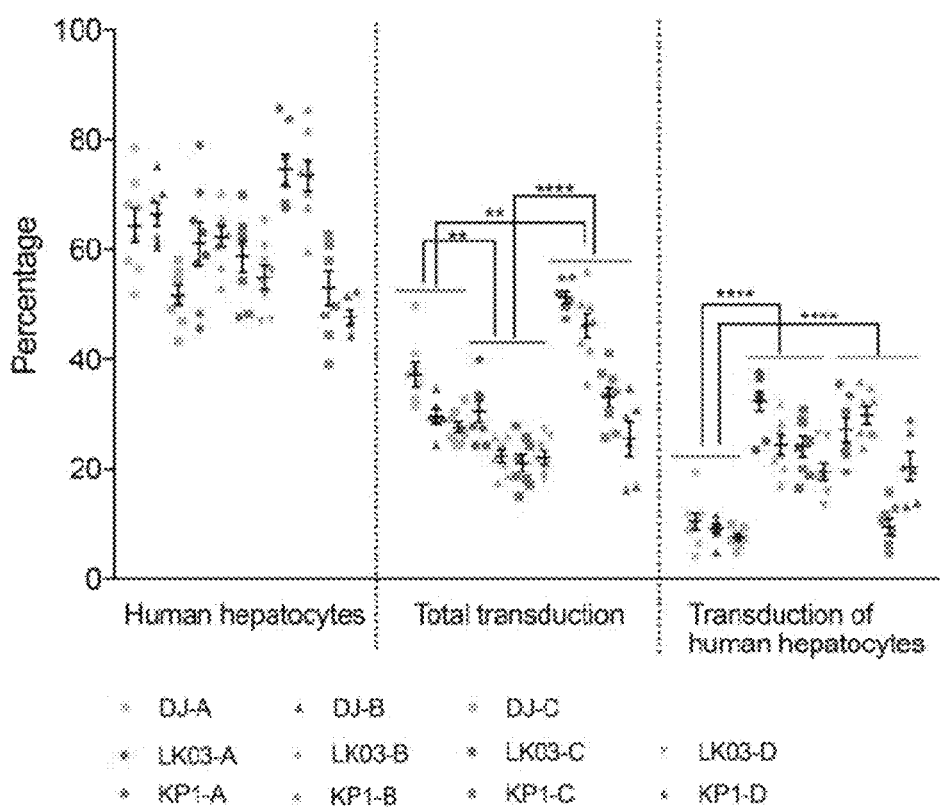

FIG. 67. Quantification of human hepatocyte repopulation levels, transduction efficiency for all hepatocytes as well as human hepatocytes. Each data point represents an area of interest for each mouse. A total of six to nine areas of interest for each mouse were scanned and analyzed. The mean and standard deviation for each mouse are indicated. Only statistically significant differences between the groups are shown in the graphs. : p, 0.01, **: p0.0001

Figure 68A:
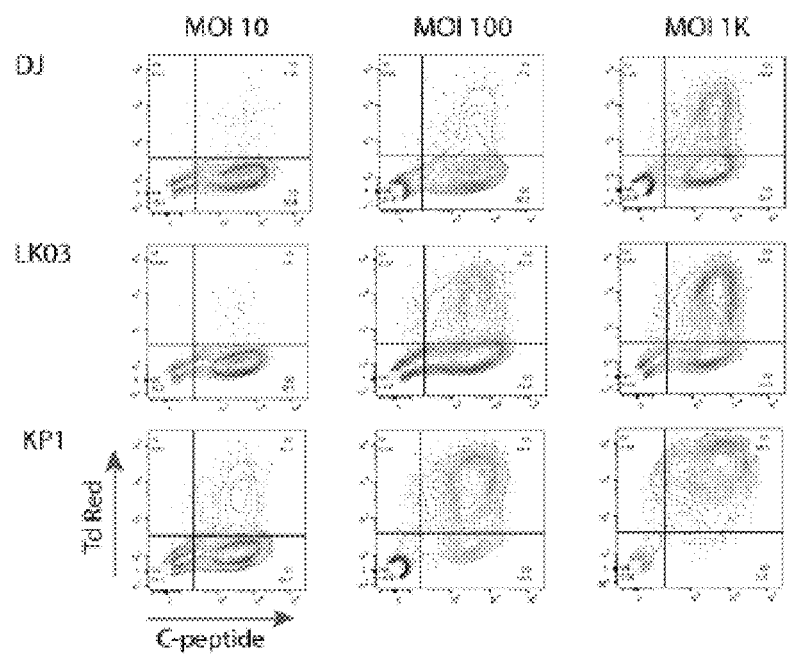
Figure 68B:
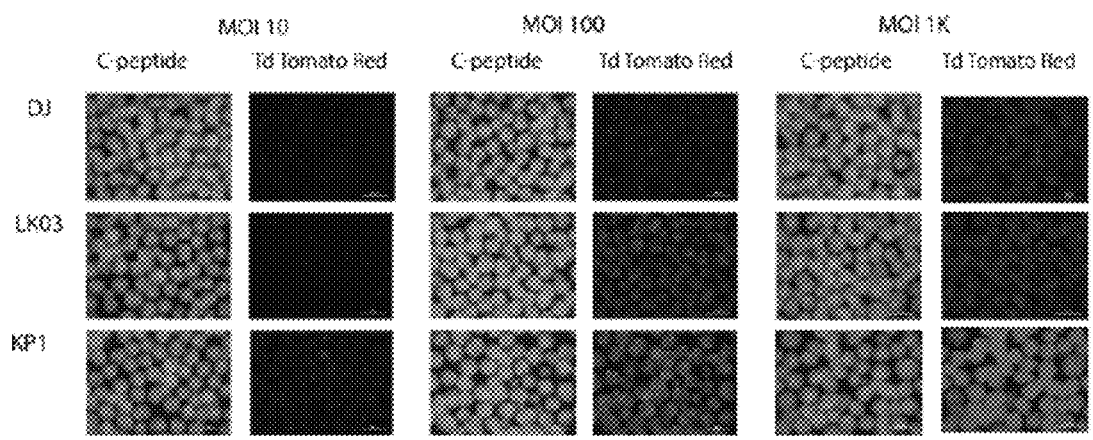

FIG. 68. Transduction efficiency of novel and parental AAV capsids on human islets and on hESC derived β-cells. (A) DJ, LK03 and KP1 capsids were used to package a Tomato Red vector and hESC derived mature β-cells were transduced with the MOIs indicated. Intracellular staining for the β-cell marker C-peptide was performed on day 6 post transduction and cells were analysed by flow cytometry. (B) The same cells were also analysed by immunofluorescent imaging.

DETAILED DESCRIPTION OF THE INVENTION

Introduction

There remains a need in the art for gene therapy vectors capable of increased transduction in human pancreatic tissue or human islets for gene therapy, so that more therapeutic levels of nucleic acid expression can be achieved. The present invention meets this need and provides variant AAV capsid polypeptides that exhibit increased transduction and/or tropism human pancreatic tissue or human islets as compared to non-variant parent capsid polypeptides.

Detailed Description

In various embodiments, the present invention provides variant adeno-associated virus (AAV) capsid polypeptides, wherein the variant AAV capsid polypeptides exhibit increased transduction or tropism human pancreatic tissue or human islets as compared to non-variant parent capsid polypeptides. In some embodiments the variant AAV capsid polypeptide is referred to as a recombinant variant AAV capsid polypeptide or variant rAAV capsid polypeptide.

In other various embodiments, the present invention provides AAV vectors comprising a nucleic acid sequence coding for a variant AAV capsid polypeptide, wherein the variant AAV capsid polypeptide exhibits increased transduction or tropism human pancreatic tissue or human islets as compared to a vector encoding a non-variant parent capsid polypeptide. In some embodiments the AAV vector is referred to as a recombinant AAV or rAAV vector.

In some embodiments, the present invention provides variant AAV capsid polypeptides, wherein the variant AAV capsid polypeptide comprises at least one amino acid difference (e.g., amino acid substitution, amino acid insertion, amino acid deletion) relative to a substantially identical non-variant parent AAV capsid protein, and where the variant AAV capsid protein exhibits increased transduction or tropism human pancreatic tissue or human islets as compared to a vector encoding a non-variant parent capsid polypeptide. In some embodiments, the variant AAV capsid polypeptide does not comprise an amino acid sequence present in a naturally occurring AAV capsid polypeptide.

In some embodiments, the present invention provides AAV vectors comprising: a) a variant AAV capsid protein, wherein the variant AAV capsid polypeptide comprises at least one amino acid difference (e.g., amino acid substitution, amino acid insertion, amino acid deletion) relative to a substantially identical non-variant parent AAV capsid protein, and where the variant AAV capsid protein exhibits increased transduction or tropism human pancreatic tissue or human islets as compared to a vector encoding a non-variant parent capsid polypeptide. In some embodiments, the AAV capsid polypeptide does not comprise an amino acid sequence present in a naturally occurring AAV capsid polypeptide.

Before the invention is described in greater detail, it is to be understood that the invention is not limited to particular embodiments described herein as such embodiments may vary. It is also to be understood that the terminology used herein is for the purpose of describing particular embodiments only, and the terminology is not intended to be limiting. The scope of the invention will be limited only by the appended claims. Unless defined otherwise, all technical and scientific terms used herein have the same meaning as commonly understood by one of ordinary skill in the art to which this invention belongs. Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention. Certain ranges are presented herein with numerical values being preceded by the term "about." The term "about" is used herein to provide literal support for the exact number that it precedes, as well as a number that is near to or approximately the number that the term precedes. In determining whether a number is near to or approximately a specifically recited number, the near or approximating unrecited number may be a number, which, in the context presented, provides the substantial equivalent of the specifically recited number. All publications, patents, and patent applications cited in this specification are incorporated herein by reference to the same extent as if each individual publication, patent, or patent application were specifically and individually indicated to be incorporated by reference. Furthermore, each cited publication, patent, or patent application is incorporated herein by reference to disclose and describe the subject matter in connection with which the publications are cited. The citation of any publication is for its disclosure prior to the filing date and should not be construed as an admission that the invention described herein is not entitled to antedate such publication by virtue of prior invention. Further, the dates of publication provided might be different from the actual publication dates, which may need to be independently confirmed.

It is noted that the claims may be drafted to exclude any optional element. As such, this statement is intended to serve as antecedent basis for use of such exclusive terminology as "solely," "only," and the like in connection with the recitation of claim elements, or use of a "negative" limitation. As will be apparent to those of skill in the art upon reading this disclosure, each of the individual embodiments described and illustrated herein has discrete components and features readily separated from or combined with the features of any of the other several embodiments without departing from the scope or spirit of the invention. Any recited method may be carried out in the order of events recited or in any other order that is logically possible. Although any methods and materials similar or equivalent to those described herein may also be used in the practice or testing of the invention, representative illustrative methods and materials are now described.

As described in the present invention, the following terms will be employed, and are defined as indicated below.

Abbreviations

"AAV" is an abbreviation for adeno-associated virus, and may be used to refer to the virus itself or derivatives thereof. The term covers all subtypes and both naturally occurring and recombinant forms, except where required otherwise. The abbreviation "rAAV" refers to recombinant adeno-associated virus, also referred to as a recombinant AAV vector (or "rAAV vector").

Definitions

The term "AAV" includes AAV type 1 (AAV1), AAV type 2 (AAV2), AAV type 3 (AAV3), AAV type 4 (AAV4), AAV type 5 (AAV5), AAV type 6 (AAV6), AAV type 7 (AAV7), AAV type 8 (AAV8), AAV type 9 (AAV9), AAV 9_hu14, avian AAV, bovine AAV, canine AAV, equine AAV, primate AAV, non-primate AAV, and ovine AAV. "Primate AAV" refers to AAV capable of infecting primates, "non-primate AAV" refers to AAV capable of infecting non-primate mammals, "bovine AAV" refers to AAV capable of infecting bovine mammals, etc.

An "AAV vector" as used herein refers to an AAV vector nucleic acid sequence encoding for various nucleic acid sequences, including in some embodiments a variant capsid polypeptide (i.e., the AAV vector comprises a nucleic acid sequence encoding for a variant capsid polypeptide, also referred to as a variant AAV capsid polypeptide), wherein the variant AAV capsid polypeptides exhibit increased transduction or tropism human pancreatic tissue or human islets as compared to non-variant parent capsid polypeptides. The AAV vectors can also comprise a heterologous nucleic acid sequence not of AAV origin as part of the nucleic acid insert. This heterologous nucleic acid sequence typically comprises a sequence of interest for the genetic transformation of a cell. In general, the heterologous nucleic acid sequence is flanked by at least one, and generally by two AAV inverted terminal repeat sequences (ITRs).

The phrase "non-variant parent capsid polypeptides" includes any naturally occurring AAV capsid polypeptides and/or any AAV wild-type capsid polypeptides. In some embodiments, the non-variant parent capsid polypeptides include AAV1, AAV2, AAV3, AAV4, AAV5, AAV6, AAV7, AAV8, AAV9, bovine AAV and/or avian AAV capsid polypeptides.

The term "substantially identical" in the context of variant AAV capsid polypeptides and non-variant parent capsid polypeptides refers to sequences with 1 or more amino acid changes. In some embodiments, these changes do not affect the packaging function of the capsid polypeptides. In some embodiments, substantially identical include variant AAV capsid polypeptides about 99%, about 98%, about 97%, about 96%, about 95%, about 94%, about 93%, about 92%, about 91%, or about 90% identical to non-variant parent capsid polypeptides. In some embodiments, the variant AAV capsid polypeptides can be substantially identical to non-variant parent capsid polypeptides over a subregion of the variant AAV capsid polypeptide, such as over about 25%, about 50%, about 75%, or about 90% of the total polypeptide sequence length.

An "AAV virion" or "AAV virus" or "AAV viral particle" or "AAV vector particle" refers to a viral particle composed of at least one AAV capsid polypeptide (including both variant AAV capsid polypeptides and non-variant parent capsid polypeptides) and an encapsidated polynucleotide AAV transfer vector. If the particle comprises a heterologous nucleic acid (i.e. a polynucleotide other than a wild-type AAV genome, such as a transgene to be delivered to a mammalian cell), it can be referred to as an "AAV vector particle" or simply an "AAV vector". Thus, production of AAV virion or AAV particle necessarily includes production of AAV vector as such a vector is contained within an AAV virion or AAV particle.

"Packaging" refers to a series of intracellular events resulting in the assembly of AAV virions or AAV particles which encapsidate a nucleic acid sequence and/or other therapeutic molecule. Packaging can refer to encapsidation of nucleic acid sequence and/or other therapeutic molecules into a capsid comprising the variant AAV capsid polypeptides described herein. Generally, AAV have limited packaging capacity of about 5 kb.

The phrase "therapeutic molecule" as used herein can include nucleic acids (including, for example, vectors), polypeptides (including, for example, antibodies), and vaccines, as well as any other therapeutic molecule that could be packaged by the variant AAV capsid polypeptides of the invention.

AAV "rep" and "cap" genes refer to polynucleotide sequences encoding replication and encapsidation proteins of adeno-associated virus (AAV). AAV rep (replication) and cap (capsid) are referred to herein as AAV "packaging genes."

A "helper virus" for AAV refers to a virus allowing AAV (e.g. wild-type AAV) to be replicated and packaged by a mammalian cell. A variety of such helper viruses for AAV are known in the art, including adenoviruses, herpesviruses and poxviruses such as vaccinia. The adenoviruses encompass a number of different subgroups, although Adenovirus type 5 of subgroup C is most commonly used as a helper virus. Numerous adenoviruses of human, non-human mammalian and avian origin are known and available from depositories such as the ATCC. Viruses of the herpes family include, for example, herpes simplex viruses (HSV) and Epstein-Barr viruses (EBV), as well as cytomegaloviruses (CMV) and pseudorabies viruses (PRV); which are also available from depositories such as ATCC.

"Helper virus function(s)" refers to function(s) encoded in a helper virus genome allowing AAV replication and packaging (in conjunction with other requirements for replication and packaging described herein). As described herein, "helper virus function" may be provided in a number of ways, including by providing helper virus or providing, for example, polynucleotide sequences encoding the requisite function(s) to a producer cell in trans.

An "infectious" virion, virus or viral particle is one comprising a polynucleotide component deliverable into a cell tropic for the viral species. The term does not necessarily imply any replication capacity of the virus. As used herein, an "infectious" virus or viral particle is one that upon accessing a target cell, can infect a target cell, and can express a heterologous nucleic acid in a target cell. Thus, "infectivity" refers to the ability of a viral particle to access a target cell, enter a target cell, and express a heterologous nucleic acid in a target cell. Infectivity can refer to in vitro infectivity or in vivo infectivity. Assays for counting infectious viral particles are described elsewhere in this disclosure and in the art. Viral infectivity can be expressed as the ratio of infectious viral particles to total viral particles. Total viral particles can be expressed as the number of viral genome copies. The ability of a viral particle to express a heterologous nucleic acid in a cell can be referred to as "transduction." The ability of a viral particle to express a heterologous nucleic acid in a cell can be assayed using a number of techniques, including assessment of a marker gene, such as a green fluorescent protein (GFP) assay (e.g., where the virus comprises a nucleotide sequence encoding GFP), where GFP is produced in a cell infected with the viral particle and is detected and/or measured; or the measurement of a produced protein, for example by an enzyme-linked immunosorbent assay (ELISA) or fluorescence-activated cell sorting (FACS).

A "replication-competent" virion or virus (e.g. a replication-competent AAV) refers to an infectious phenotypically wild-type virus, and is replicable in an infected cell (i.e. in the presence of a helper virus or helper virus functions). In the case of AAV, replication competence generally requires the presence of functional AAV packaging genes. In some embodiments, AAV vectors, as described herein, lack of one or more AAV packaging genes and are replication-incompetent in mammalian cells (especially in human cells). In some embodiments, AAV vectors lack any AAV packaging gene sequences, minimizing the possibility of generating replication competent AAV by recombination between AAV packaging genes and an incoming AAV vector. In many embodiments, AAV vector preparations as described herein are those containing few if any replication competent AAV (rcAAV, also referred to as RCA) (e.g., less than about 1 rcAAV per $10^2$ AAV particles, less than about 1 rcAAV per $10^4$ AAV particles, less than about 1 rcAAV per $10^8$ AAV particles, less than about 1 rcAAV per $10^{12}$ AAV particles, or no rcAAV).

The terms "polynucleotide" and "nucleic acid" are used interchangeably herein to refer to all forms of nucleic acid, oligonucleotides, including deoxyribonucleic acid (DNA) and ribonucleic acid (RNA). Polynucleotides include genomic DNA, cDNA and antisense DNA, and spliced or unspliced mRNA, rRNA, tRNA, lncRNA, RNA antagomirs, and inhibitory DNA or RNA (RNAi, e.g., small or short hairpin (sh)RNA, microRNA (miRNA), aptamers, small or short interfering (si)RNA, trans-splicing RNA, or antisense RNA). Polynucleotides also include non-coding RNA, which include for example, but are not limited to, RNAi, miRNAs, lncRNAs, RNA antagomirs, aptamers, and any other non-coding RNAs known to those of skill in the art. Polynucleotides include naturally occurring, synthetic, and intentionally altered or modified polynucleotides as well as analogues and derivatives. The term "polynucleotide" also refers to a polymeric form of nucleotides of any length, including deoxyribonucleotides or ribonucleotides, or analogs thereof, and is synonymous with nucleic acid sequence. A polynucleotide may comprise modified nucleotides, such as methylated nucleotides and nucleotide analogs, and may be interrupted by non-nucleotide components. If present, modifications to the nucleotide structure may be imparted before or after assembly of the polymer. The term polynucleotide, as used herein, refers interchangeably to double- and single-stranded molecules. Unless otherwise specified or required, any embodiment as described herein encompassing a polynucleotide encompasses both the double-stranded form and each of two complementary single-stranded forms known or predicted to make up the double-stranded form. Polynucleotides can be single, double, or triplex, linear or circular, and can be of any length. In discussing polynucleotides, a sequence or structure of a particular polynucleotide may be described herein according to the convention of providing the sequence in the 5' to 3' direction.

A "gene" refers to a polynucleotide containing at least one open reading frame capable of encoding a particular protein or polypeptide after being transcribed and translated.

A "small interfering" or "short interfering RNA" or siRNA is a RNA duplex of nucleotides targeted to a gene interest (a "target gene"). An "RNA duplex" refers to the structure formed by the complementary pairing between two regions of a RNA molecule. siRNA is "targeted" to a gene and the nucleotide sequence of the duplex portion of the siRNA is complementary to a nucleotide sequence of the targeted gene. In some embodiments, the length of the duplex of siRNAs is less than 30 nucleotides. In some embodiments, the duplex can be 29, 28, 27, 26, 25, 24, 23, 22, 21, 20, 19, 18, 17, 16, 15, 14, 13, 12, 11 or 10 nucleotides in length. In some embodiments, the length of the duplex is 19-25 nucleotides in length. The RNA duplex portion of the siRNA can be part of a hairpin structure. In addition to the duplex portion, the hairpin structure may contain a loop portion positioned between the two sequences forming the duplex. The loop can vary in length. In some embodiments the loop is 5, 6, 7, 8, 9, 10, 11, 12 or 13 nucleotides in length. The hairpin structure can also contain 3' or 5' overhang portions. In some embodiments, the overhang is a 3' or a 5' overhang 0, 1, 2, 3, 4 or 5 nucleotides in length.

As used herein, the term "microRNA" refers to any type of interfering RNAs, including but not limited to, endogenous microRNAs and artificial microRNAs (e.g., synthetic miRNAs). Endogenous microRNAs are small RNAs naturally encoded in the genome capable of modulating the productive utilization of mRNA. An artificial microRNA can be any type of RNA sequence, other than endogenous microRNA, capable of modulating the activity of an mRNA. A microRNA sequence can be an RNA molecule composed of any one or more of these sequences. MicroRNA (or "miRNA") sequences have been described in publications such as Lim, et al., 2003, Genes & Development, 17, 991-1008, Lim et al., 2003, Science, 299, 1540, Lee and Ambrose, 2001, Science, 294, 862, Lau et al., 2001, Science 294, 858-861, Lagos-Quintana et al., 2002, Current Biology, 12, 735-739, Lagos-Quintana et al., 2001, Science, 294, 853-857, and Lagos-Quintana et al., 2003, RNA, 9, 175-179. Examples of microRNAs include any RNA fragment of a larger RNA or is a miRNA, siRNA, stRNA, sncRNA, tncRNA, snoRNA, smRNA, shRNA, snRNA, or other small non-coding RNA. See, e.g., US Patent Applications 20050272923, 20050266552, 20050142581, and 20050075492. A "microRNA precursor" (or "pre-miRNA") refers to a nucleic acid having a stem-loop structure with a microRNA sequence incorporated therein. A "mature microRNA" (or "mature miRNA") includes a microRNA cleaved from a microRNA precursor (a "pre-miRNA"), or synthesized (e.g., synthesized in a laboratory by cell-free synthesis), and has a length of from about 19 nucleotides to about 27 nucleotides, e.g., a mature microRNA can have a length of 19 nt, 20 nt, 21 nt, 22 nt, 23 nt, 24 nt, 25 nt, 26 nt, or 27 nt. A mature microRNA can bind to a target mRNA and inhibit translation of the target mRNA.

"Recombinant," as applied to a polynucleotide means the polynucleotide is the product of various combinations of cloning, restriction or ligation steps, and other procedures resulting in a construct distinct and/or different from a polynucleotide found in nature. A recombinant virus is a viral particle encapsidating a recombinant polynucleotide. The terms respectively include replicates of the original polynucleotide construct and progeny of the original virus construct.

A "control element" or "control sequence" is a nucleotide sequence involved in an interaction of molecules contributing to the functional regulation of a polynucleotide, including replication, duplication, transcription, splicing, translation, or degradation of the polynucleotide. The regulation may affect the frequency, speed, or specificity of the process, and may be enhancing or inhibitory in nature. Control elements known in the art include, for example, transcriptional regulatory sequences such as promoters, enhancers and degrons. A promoter is a DNA region capable under certain conditions of binding RNA polymerase and initiating transcription of a coding region usually located downstream (in the 3' direction) from the promoter.

"Operatively linked" or "operably linked" refers to a juxtaposition of genetic elements, wherein the elements are in a relationship permitting them to operate in the expected manner. For instance, a promoter is operatively linked to a coding region if the promoter helps initiate transcription of the coding sequence. There may be intervening residues between the promoter and coding region so long as this functional relationship is maintained.

"Heterologous" means derived from a genotypically distinct entity from the rest of the entity to it is being compared too. For example, a polynucleotide introduced by genetic engineering techniques into a plasmid or vector derived from a different species is a heterologous polynucleotide. A promoter removed from its native coding sequence and operatively linked to a coding sequence it is not naturally found linked to a heterologous promoter. For example, an AAV including a heterologous nucleic acid encoding a heterologous gene product is an AAV including a nucleic acid not normally included in a naturally-occurring, wild-type AAV, and the encoded heterologous gene product is a gene product not normally encoded by a naturally-occurring, wild-type AAV. An AAV including a nucleic acid encoding a variant AAV capsid polypeptide includes a heterologous nucleic acid sequence. Once transferred/delivered into a host cell, a heterologous polynucleotide, contained within the virion, can be expressed (e.g., transcribed, and translated if appropriate). Alternatively, a transferred/delivered heterologous polynucleotide into a host cell, contained within the virion, need not be expressed. Although the term "heterologous" is not always used herein in reference to polynucleotides, reference to a polynucleotide even in the absence of the modifier "heterologous" is intended to include heterologous polynucleotides in spite of the omission.

The terms "genetic alteration" and "genetic modification" (and grammatical variants thereof), are used interchangeably herein to refer to a process wherein a genetic element (e.g., a polynucleotide) is introduced into a cell other than by mitosis or meiosis. The element may be heterologous to the cell, or it may be an additional copy or improved version of an element already present in the cell. Genetic alteration may be effected, for example, by transfecting a cell with a recombinant plasmid or other polynucleotide through any process known in the art, such as electroporation, calcium phosphate precipitation, or polynucleotide-liposome complexation. Genetic alteration may also be effected, for example, by transduction or infection with a DNA or RNA virus or viral vector. Generally, the genetic element is introduced into a chromosome or mini-chromosome in the cell; but any alteration changing the phenotype and/or genotype of the cell and its progeny is included in this term.

A cell is said to be "stably" altered, transduced, genetically modified, or transformed with a genetic sequence if the sequence is available to perform its function during extended culture of the cell in vitro. Generally, such a cell is "heritably" altered (genetically modified) in that a genetic alteration is introduced and inheritable by progeny of the altered cell.

The terms "polypeptide," "peptide," and "protein" are used interchangeably herein to refer to polymers of amino acids of any length. The "polypeptides," "proteins" and "peptides" encoded by the "polynucleotide sequences," include full-length native sequences, as with naturally occurring proteins, as well as functional subsequences, modified forms or sequence variants so long as the subsequence, modified form or variant retains some degree of functionality of the native full-length protein. In methods and uses of as described herein, such polypeptides, proteins and peptides encoded by the polynucleotide sequences can be but are not required to be identical to the defective endogenous protein, or whose expression is insufficient, or deficient in the treated mammal. The terms also encompass a modified amino acid polymer; for example, disulfide bond formation, glycosylation, lipidation, phosphorylation, methylation, carboxylation, deamidation, acetylation, or conjugation with a labeling component. Polypeptides such as anti-angiogenic polypeptides, neuroprotective polypeptides, and the like, when discussed in the context of delivering a gene product to a mammalian subject, and compositions therefor, refer to the respective intact polypeptide, or any fragment or genetically engineered derivative thereof, retaining the desired biochemical function of the intact protein.

As used herein, the abbreviations for the genetically encoded L-enantiomeric amino acids used in the disclosure methods are conventional and are as follows in Table 1.

TABLE 1

Amino acid abbreviations

| Amino Acid | One-Letter Symbol | Common Abbreviation |
|---|---|---|
| Alanine | A | Ala |
| Arginine | R | Arg |
| Asparagine | N | Asn |
| Aspartic acid | D | Asp |
| Cysteine | C | Cys |
| Glutamine | Q | Gln |
| Glutamic acid | E | Glu |
| Glycine | G | Gly |
| Histidine | H | His |
| Isoleucine | I | Ile |
| Leucine | L | Leu |
| Lysine | K | Lys |
| Methionine | M | Met |
| Phenylalanine | F | Phe |
| Proline | P | Pro |
| Serine | S | Ser |
| Threonine | T | Thr |
| Tryptophan | W | Trp |
| Tyrosine | Y | Tyr |
| Valine | V | Val |

"Hydrophilic Amino Acid" refers to an amino acid exhibiting a hydrophobicity of less than zero according to the normalized consensus hydrophobicity scale of Eisenberg et al., 1984, J. Mol. Biol. 179: 125-142. Genetically encoded hydrophilic amino acids include Thr (T), Ser (S), His (H), Glu (E), Asn (N), Gln (Q), Asp (D), Lys (K) and Arg (R).

"Acidic Amino Acid" refers to a hydrophilic amino acid having a side chain pK value of less than 7. Acidic amino acids typically have negatively charged side chains at physiological pH due to loss of a hydrogen ion. Genetically encoded acidic amino acids include Glu (E) and Asp (D).

"Basic Amino Acid" refers to a hydrophilic amino acid having a side chain pK value of greater than 7. Basic amino acids typically have positively charged side chains at physiological pH due to association with hydrogen ion. Genetically encoded basic amino acids include His (H), Arg (R) and Lys (K).

"Polar Amino Acid" refers to a hydrophilic amino acid having a side chain uncharged at physiological pH, but which has at least one bond in which the pair of electrons shared in common by two atoms is held more closely by one of the atoms. Genetically encoded polar amino acids include Asn (N), Gln (Q), Ser (S) and Thr (T).

"Hydrophobic Amino Acid" refers to an amino acid exhibiting a hydrophobicity of greater than zero according to the normalized consensus hydrophobicity scale of Eisenberg, 1984, J. Mol. Biol. 179:125-142. Exemplary hydrophobic amino acids include Ile (I), Phe (F), Val (V), Leu (L), Trp (W), Met (M), Ala (A), Gly (G), Tyr (Y), Pro (P), and proline analogues.

"Aromatic Amino Acid" refers to a hydrophobic amino acid with a side chain having at least one aromatic or heteroaromatic ring. The aromatic or heteroaromatic ring may contain one or more substituents such as —OH, —SH, —CN, —F, —Cl, —Br, —I, —NO2, —NO, —NH2, —NHR, —NRR, —C(O)R, —C(O)OH, —C(O)OR, —C(O)NH2, —C(O)NHR, —C(O)NRR and the like where each R is independently (C1-C6) alkyl, substituted (C1-C6) alkyl, (C1-C6) alkenyl, substituted (C1-C6) alkenyl, (C1-C6) alkynyl, substituted (C1-C6) alkynyl, (C1-C21)) aryl, substituted (C5-C20) aryl, (C6-C26) alkaryl, substituted (C6-C26) alkaryl, 5-20 membered heteroaryl, substituted 5-20 membered heteroaryl, 6-26 membered alkheteroaryl or substituted 6-26 membered alkheteroaryl. Genetically encoded aromatic amino acids include Phe (F), Tyr (Y) and Trp (W).

"Nonpolar Amino Acid" refers to a hydrophobic amino acid having a side chain uncharged at physiological pH and which has bonds in which the pair of electrons shared in common by two atoms is generally held equally by each of the two atoms (i.e., the side chain is not polar). Genetically encoded apolar amino acids include Leu (L), Val (V), Ile (I), Met (M), Gly (G) and Ala (A).

"Aliphatic Amino Acid" refers to a hydrophobic amino acid having an aliphatic hydrocarbon side chain. Genetically encoded aliphatic amino acids include Ala (A), Val (V), Leu (L) and Ile (I).

The term "non-naturally" with regard to amino acids can include any amino acid molecule not included as one of the 20 amino acids listed in Table 1 above as well as any modified or derivatized amino acid known to one of skill in the art. Non-naturally amino acids can include but are not limited to β-alanine, α-amino butyric acid, γ-amino butyric acid, γ-(aminophenyl) butyric acid, α-amino isobutyric acid, ε-amino caproic acid, 7-amino heptanoic acid, β-aspartic acid, aminobenzoic acid, aminophenyl acetic acid, aminophenyl butyric acid, γ-glutamic acid, cysteine (ACM), ε-lysine, methionine sulfone, norleucine, norvaline, ornithine, d-ornithine, p-nitro-phenylalanine, hydroxy proline, 1,2,3,4,-tetrahydroisoquinoline-3-carboxylic acid, and thioproline.

The term "variant" or "variants", with regard to polypeptides, such as capsid polypeptides refers to a polypeptide sequence differing by at least one amino acid from a parent polypeptide sequence, also referred to as a non-variant polypeptide sequence. In some embodiments, the polypeptide is a capsid polypeptide and the variant differs by at least one amino acid substitution. Amino acids also include naturally occurring and non-naturally occurring amino acids as well as derivatives thereof. Amino acids also include both D and L forms.

An "isolated" plasmid, nucleic acid, vector, virus, virion, host cell, or other substance refers to a preparation of the substance devoid of at least some of the other components present where the substance or a similar substance naturally occurs or from which it is initially prepared. Thus, for example, an isolated substance may be prepared by using a purification technique to enrich it from a source mixture. Enrichment can be measured on an absolute basis, such as weight per volume of solution, or it can be measured in relation to a second, potentially interfering substance present in the source mixture. Increasing enrichments of the embodiments of this invention are increasingly more isolated. An isolated plasmid, nucleic acid, vector, virus, host cell, or other substance is in some embodiments purified, e.g., from about 80% to about 90% pure, at least about 90% pure, at least about 95% pure, at least about 98% pure, or at least about 99%, or more, pure.

By the term "highly conserved" is meant at least about 80% identity, preferably at least 90% identity, and more preferably, over about 97% identity. Identity is readily determined by one of skill in the art by resort to algorithms and computer programs known by those of skill in the art.

The term "percent sequence identity" or "identical" in the context of nucleic acid sequences refers to the residues in the two sequences that are the same when aligned for maximum correspondence. The length of sequence identity comparison may be over the full-length of the genome, the full-length of a gene coding sequence, or a fragment of at least about 500 to 5000 nucleotides. However, identity among smaller fragments, e.g. of at least about nine nucleotides, usually at least about 20 to about 24 nucleotides, at least about 28 to about 32 nucleotides, at least about 36 or more nucleotides, may also be desired. Similarly, "percent sequence identity" may be readily determined for amino acid sequences, over the full-length of a protein, or a fragment thereof. Suitably, a fragment is at least about 8 amino acids in length, and may be up to about 700 amino acids.

As used herein, the terms "treatment," "treating," and the like, refer to obtaining a desired pharmacologic and/or physiologic effect. The effect may be prophylactic in terms of completely or partially preventing a disease or symptom thereof and/or may be therapeutic in terms of a partial or complete cure for a disease and/or adverse effect attributable to the disease. "Treatment," as used herein, covers any treatment of a disease in a mammal, particularly in a human, and includes: (a) preventing the disease from occurring in a subject predisposed to the disease or at risk of acquiring the disease but has not yet been diagnosed as having it; (b) inhibiting the disease, i.e., arresting its development; and (c) relieving the disease, i.e., causing regression of the disease.

The terms "individual," "subject," and "patient" are used interchangeably herein, and refer to a mammal, including, but not limited to, human and non-human primates, including simians and humans; mammalian sport animals (e.g., horses); mammalian farm animals (e.g., sheep, goats, etc.); mammalian pets (dogs, cats, etc.); and rodents (e.g., mice, rats, etc.).

The terms "pharmaceutically acceptable" and "physiologically acceptable" mean a biologically acceptable formulation, gaseous, liquid or solid, or mixture thereof, suitable for one or more routes of administration, in vivo delivery or contact. A "pharmaceutically acceptable" or "physiologically acceptable" composition is a material that is not biologically or otherwise undesirable, e.g., the material may be administered to a subject without causing substantial undesirable biological effects. Thus, such a pharmaceutical composition may be used, for example in administering an AAV vector or AAV virion as disclosed herein, or transformed cell to a subject.

The phrase a "unit dosage form" as used herein refers to physically discrete units suited as unitary dosages for the subject to be treated; each unit containing a predetermined quantity optionally in association with a pharmaceutical carrier (excipient, diluent, vehicle or filling agent) which, when administered in one or more doses, produces a desired effect (e.g., prophylactic or therapeutic effect). In some embodiments, unit dosage forms may be within, for example, ampules and vials, including a liquid composition, or a composition in a freeze-dried or lyophilized state; a sterile liquid carrier, for example, can be added prior to administration or delivery in vivo. Individual unit dosage forms can be included in multi-dose kits or containers. AAV vectors or AAV virions, and pharmaceutical compositions thereof can be packaged in single or multiple unit dosage form for ease of administration and uniformity of dosage.

A "therapeutically effective amount" will fall in a relatively broad range determinable through experimentation and/or clinical trials. For example, for in vivo injection, e.g., injection directly into the tissue of a subject (for example, pancreatic tissue), a therapeutically effective dose will be on the order of from about $10^6$ to about $10^{15}$ of the AAV virions per kilogram bodyweight of the subject. In some embodiments, a therapeutically effective dose will be on the order of from about $10^8$ to $10^{12}$ AAV virions per kilogram bodyweight of the subject. Other effective dosages can be readily established by one of ordinary skill in the art through routine trials establishing dose response curves.

An "effective amount" or "sufficient amount" refers to an amount providing, in single or multiple doses, alone or in combination, with one or more other compositions (therapeutic agents such as a drug), treatments, protocols, or therapeutic regimens agents (including, for example, vaccine regimens), a detectable response of any duration of time (long or short term), an expected or desired outcome in or a benefit to a subject of any measurable or detectable degree or for any duration of time (e.g., for minutes, hours, days, months, years, or cured).

The doses of an "effective amount" or "sufficient amount" for treatment (e.g., to ameliorate or to provide a therapeutic benefit or improvement) typically are effective to provide a response to one, multiple or all adverse symptoms, consequences or complications of the disease, one or more adverse symptoms, disorders, illnesses, pathologies, or complications, for example, caused by or associated with the disease, to a measurable extent, although decreasing, reducing, inhibiting, suppressing, limiting or controlling progression or worsening of the disease is also a satisfactory outcome.

"Prophylaxis" and grammatical variations thereof mean a method in which contact, administration or in vivo delivery to a subject is prior to disease. Administration or in vivo delivery to a subject can be performed prior to development of an adverse symptom, condition, complication, etc. caused by or associated with the disease. For example, a screen (e.g., genetic) can be used to identify such subjects as candidates for the described methods and uses, but the subject may not manifest the disease. Such subjects therefore include those screened positive for an insufficient amount or a deficiency in a functional gene product (protein), or producing an aberrant, partially functional or non-functional gene product (protein), leading to disease; and subjects screening positive for an aberrant, or defective (mutant) gene product (protein) leading to disease, even though such subjects do not manifest symptoms of the disease.

The phrase "enhanced neutralization profile" refers to the ability of an AAV vector or virion to better evade neutralizing antibody binding in the subject. In some instances, fewer neutralization antibodies allow for the AAV infection to generate higher levels of transduction, making the variant AAV capsid polypeptides, AAV vectors and virions of the present invention better suited for gene therapy purposes.

The phrases "tropism" and "transduction" are interrelated, but there are differences. The term "tropism" as used herein refers to the ability of an AAV vector or virion to infect one or more specified cell types, but can also encompass how the vector functions to transduce the cell in the one or more specified cell types; i.e., tropism refers to preferential entry of the AAV vector or virion into certain cell or tissue type(s) and/or preferential interaction with the cell surface that facilitates entry into certain cell or tissue types, optionally and preferably followed by expression (e.g., transcription and, optionally, translation) of sequences carried by the AAV vector or virion in the cell, e.g., for a recombinant virus, expression of the heterologous nucleotide sequence(s). As used herein, the term "transduction" refers to the ability of an AAV vector or virion to infect one or more particular cell types; i.e., transduction refers to entry of the AAV vector or virion into the cell and the transfer of genetic material contained within the AAV vector or virion into the cell to obtain expression from the vector genome. In some cases, but not all cases, transduction and tropism may correlate.

The term "tropism profile" refers to the pattern of transduction of one or more target cells, tissues and/or organs. For example, some shuffled AAV capsids (variant AAV capsid polypeptides) provide for efficient transduction of human pancreatic tissue or human islets. Conversely, some shuffled AAV capsids have only low level transduction of liver, gonads and/or germ cells. The variant AAV capsid polypeptides disclosed herein provide for efficient and/or enhanced transduction of human pancreatic tissue or human islets.

Unless indicated otherwise, "efficient transduction" or "efficient tropism," or similar terms, can be determined by reference to a suitable control (e.g., at least about 50%, 60%, 70%, 80%, 85%, 90%, 95%, 100%, 110%, 125%, 150%, 175%, or 200% or more of the transduction or tropism, respectively, of the control). Suitable controls will depend on a variety of factors including the desired tropism profile. Similarly, it can be determined if a capsid and/or virus "does not efficiently transduce" or "does not have efficient tropism" for a target tissue, or similar terms, by reference to a suitable control.

As used herein and in the appended claims, the singular forms "a," "an," and "the" include plural referents unless the context clearly dictates otherwise. Thus, for example, reference to "an AAV virion" includes a plurality of such virions and reference to "a host cell" includes reference to one or more host cells and equivalents thereof known to those skilled in the art, and so forth. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

Before the invention is further described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

AAV Capsid and Vector Features

AAV vectors of the present invention have numerous features. In some embodiments, the vectors comprise nucleic acid sequences encoding for variant AAV capsid polypeptides. Such AAV vectors and their features are described in detail below.

An exemplary AAV vector of the present invention comprises a nucleic acid encoding for a variant AAV capsid protein differing in amino acid sequence by at least one amino acid from a wild-type or non-variant parent capsid protein. The amino acid difference(s) can be located in a solvent accessible site in the capsid, e.g., a solvent-accessible loop, or in the lumen (i.e., the interior space of the AAV capsid). In some embodiments, the lumen includes the interior space of the AAV capsid. For example, the amino acid substitution(s) can be located in a GH loop in the AAV capsid polypeptide. In some embodiments, the variant AAV capsid polypeptide comprises an amino acid substitution in AAV1, AAV2, AAV3, AAV4, AAV5, AAV6, AAV7, AAV8, or AAV9 capsid polypeptides.

In some embodiments, the present invention provides an isolated nucleic acid comprising a nucleotide sequence that encodes a variant adeno-associated virus (AAV) capsid protein, where the variant AAV capsid protein comprises an amino acid sequence having at least about 85% at least about 90%, at least about 95%, at least about 98%, at least about 99%, or 100%, to non-variant capsid amino acid sequences or to sub-portions of a non-variant parent capsid polypeptide sequence, and exhibits increased transduction or tropism human pancreatic tissue or human islets as compared to a vector encoding a non-variant parent capsid polypeptide. In some embodiments, the present invention provides an isolated nucleic acid comprising a nucleotide sequence that encodes a variant adeno-associated virus (AAV) capsid protein, where the variant AAV capsid protein comprises an amino acid sequence having at least about 85% at least about 90%, at least about 95%, at least about 98%, at least about 99%, or 100%, to parental non-variant capsid amino acid sequences or to sub-portions of a non-variant parent capsid polypeptide sequence, such as wild-type AAV1, AAV2, AAV3, AAV4, AAV5, AAV6, AAV7, AAV8, or AAV9 capsid polypeptides, and where the variant AAV capsid polypeptide exhibits increased transduction or tropism human pancreatic tissue or human islets as compared to a vector encoding a non-variant parent capsid polypeptide. In some embodiments, the variant AAV capsid polypeptide comprises one or more regions or sub-portions from non-variant parent capsid polypeptide sequences from AAV serotypes 1, 3, 6, 8, and 9 (i.e., AAV1, AAV6, AAV8, and AAV9). In some embodiments, the variant AAV capsid polypeptide comprises one or more regions or sub-portions from non-variant parent capsid polypeptide sequences selected from any one of SEQ ID NOs: 27-44

In some embodiments, a subject AAV vector can encode variant capsid polypeptides having an amino acid sequence of at least about 85%, at least about 90%, at least about 95%, at least about 98%, or at least about 99%, or 100%, amino acid sequence identity to non-variant parent capsid polypeptides or to sub-portions of non-variant parent capsid polypeptides. In some embodiments, the variant AAV capsid polypeptide is encoded by other vectors/plasmids known in the art. In some embodiments, the non-variant parent capsid polypeptide sequence is any one of SEQ ID NOs: 27-44. In some embodiments, the non-variant parent capsid polypeptide sequence is encoded by any one of SEQ ID NOs: 45-62.

In some embodiments, the variant AAV capsid polypeptides exhibit substantial homology or "substantial similarity," when referring to amino acids or fragments thereof, indicating that, when optimally aligned with appropriate amino acid insertions or deletions with another amino acid (or its complementary strand), there is amino acid sequence identity in at least about 95% to about 99% of the aligned sequences. In some embodiments, the homology is over full-length sequence, or a polypeptide thereof, e.g., a capsid protein, or a fragment thereof of at least 8 amino acids, or more desirably, at least about 15 amino acids in length, including sub-portions of a non-variant parent capsid polypeptide sequence. For example, the variant AAV capsid polypeptide can comprise an amino acid sequence having at least about 85%, at least about 90%, at least about 95%, at least about 98%, at least about 99%, or 100%, amino acid sequence identity to a non-variant parent capsid polypeptide sequence or to sub-portions of a non-variant parent capsid polypeptides. In some embodiments the variant AAV capsid polypeptide sequence comprises any one of SEQ ID NOs: 1-7. In some embodiments, the variant AAV capsid polypeptide sequence is encoded by any one of SEQ ID NOs: 8-14. In some embodiments, the non-variant parent capsid polypeptide sequence is any one of SEQ ID NOs: 27-44. In some embodiments, the non-variant parent capsid polypeptide sequence is encoded by any one of SEQ ID NOs: 45-62.

TABLE 2

Variant AAV Capsid Amino Acid Sequences

| Description SEQ ID NO: | Amino Acid Sequence |
|---|---|
| AAV-10A1 SEQ ID NO: 1 | >10A1_KP1<br>MAADGYLPDWLEDTLSEGIRQWWKLKPGPPPPKPAERHKDDSRGLVLPGYKYLGPGNGLD<br>KGEPVNAADAAALEHDKAYDQQLKAGDNPYLRYNHADAEFQERLQEDTSFGGNLGRAVFQ<br>AKKRVLEPLGLVEEPVKTAPGKKRPVEHSPVEPDSSSGTGKAGQQPARKRLNFGQTGDTD<br>SAADPQPLGEPPAAPSGLGTGTMAAGGGAPMADNNEGADGVGNASGNWHCDSTWLGDRVI<br>TTSTRTWALPTYNNHLYKQISSASTGASNDNHYFGYSTPWGYFDFNRFHCHFSPRDWQRL<br>INNNWGFRPKRLNFKLFNIQVKEVTQNEGTKTIANNLTSTVQVFTDSEYQLPYVLGSAHQ<br>GCLPPFPADVFMIPQYGYLTLNNGSQAMGRSSFYCLEYFPSQMLRTGNNFQFTYTFEDVP<br>FHSSYAHSQSLDRLMNPLIDQYLYYLNRTQGTTSGTTNQSRLLFSQAGPQSMSLQARNWL<br>PGPCYRQQRLSKTANDNNNSNFPWTAASKYHLNGRDSLVNPGPAMASHKDDEEKFFPMHG<br>NLIFGKEGTTASNAELDNVMITDEEEIRTTNPVATEQYGTVANNLQSSNTAPTTRTVNDQ<br>GALPGMVWQDRDVYLQGPIWAKIPHTDGHFHPSPLMGGFGLKHPPPQILIKNTPVPADPP<br>TAFNKDKLNSFITQYSTGQVSVEIEWELQKENSKRWNPEIQYTSNYYKSTSVDFAVNTEG<br>VYSEPRPIGTRYLTRNL |
| AAV-10A3 SEQ ID NO: 2 | >10A3_KP3<br>MAADGYLPDWLEDTLSEGIRQWWKLKPGPPPPKPAERHKDDSRGLVLPGYKYLGPFNGLD<br>KGEPVNEADAAALEHDKAYDQQLKAGDNPYLRYNHADAEFQERLQEDTSFGGNLGRAVFQ<br>AKKRVLEPLGLVEEGAKTAPGKKRPVEPSPQRSPDDSSTGIGKKGQQPARKRLNFGQTGDS<br>ESVPDPQPLGEPPAAPSGVGPNTMAAGGGAPMADNNEGADGVGNASGNWHCDSTWLGDRV<br>ITTSTRTWALPTYNNHLYKQISSASTGASNDNHYFGYSTPWGYFDFNRFHCHFSPRDWQR<br>LINNNWGFRPKRLNFKLFNIQVKEVTQNEGTKTIANNLTSTIQVFTDSEYQLPYVLGSAH<br>QGCLPPFPADVFMIPQYGYLTLNNGSQAVGRSSFYCLEYFPSQMLRTGNNFQFSYTFEDV<br>PFHSSYAHSQSLDRLMNPLIDQYLYYLNRTQGTTSGTTNQSRLLFSQAGPQSMSLQARNW<br>LPGPCYRQQRLSKTANDNNNSNFPWTAASKYHLNGRDSLVNPGPAMASHKDDEEKFFPMH<br>GNLIFGKEGTTASNAELDNVMITDEEEIRTTNPVATEQYGTVANNLQSSNTAPTTRTVND<br>QGALPGMVWQDRDVYLQGPIWAKIPHTDGNFHPSPLMGGFGLKHPPPQILIKNTPVPADP<br>PTTFNQSKLNSFITQYSTGQVSVEIEWELQKENSKRWNPEIQYTSNYYKSTSVDFAVNTE<br>GVYSEPRPIGTRYLTRNL |
| AAV-10A4 SEQ ID NO: 3 | >10A4<br>MAADGYLPDWLEDNLSEGIREWWDLKPGAPKPKANQQKQDDGRGLVLPGYKYLGPFNGLD<br>KGEPVNAADAAALEHDKAYDQQLKAGDNPYLRYNHADAEFQERLQEDTSFGGNLGRAVFQ<br>AKKRLLEPLGLVEEAAKTAPGKKRPVEQSPQEPDSSSGIGKTGQQPAKKRLNFGQTGDTE<br>SVPDPQPLGEPPAAPTSLGSNTMASGGGAPMADNNEGADGVGNASGNWHCDSTWLGDRVI<br>TTSTRTWALPTYNNHLYKQISSASTGASNDNHYFGYSTPWGYFDFNRFHCHFSPRDWQRL<br>INNNWGFRPKKLSFKLFNIQVKEVTQNDGTTTIANNLTSTIQVFTDSEYQLPYVLGSAHQ<br>GCLPPFPADVFMIPQYGYLTLNNGSQAVGRSSFYCLEYFPSQMLRTGNNFTFSYTFEEVP<br>FHSSYAHSQSLDRLMNPLIDQYLYYLNRTQGTTSGTTNQSRLLFSQAGPQSMSLQARNWL<br>PGPCYRQQRLSKTANDNNNSNFPWTAASKYHLNGRDSLVNPGPAMASHKDDEEKFFPMHG<br>NLIFGKEGTTASNAELDNVMITDEEEIRTTNPVATEQYGTVANNLQSSNTAPTTRTVNDQ<br>GALPGMVWQDRDVYLQGPIWAKIPHTDGHFHPSPLMGGFGLKHPPPQIMIKNTPVPANPP<br>TTFSPAKFASFITQYSTGQVSVEIEWELQKENSKRWNPEIQYTSNYNKSVNVDFTVDTNG<br>VYSEPRPIGTRYLTRPL |
| AAV-10A5 SEQ ID NO: 4 | >10A5<br>MAADGYLPDWLEDNLSEGIREWWDLKPGAPKPKANQQKQDDARGLVLPGYKYLGPGNGLD<br>KGEPVNAADAAALEHDKAYDQQLQAGDNPYLRYNHADAEFQERLQEDTSFGGNLGRAVFQ<br>AKKRVLEPLGLVEEAAKTAPGKKRPVEQSPQEPDSSSGIGKTGQQPAKKRLNFGQTGDSE<br>SVPDPQPLGEPPAAPTSLGSNTMASGGGAPMADNNEGADGVGNSSGNWHCDSQWLGDRVI<br>TTSTRTWALPTYNNHLYKQISSASTGASNDNHYFGYSTPWGYFDFNRFHCHFSPRDWQRL<br>INNNWGFRPKRLNFKLFNIQVKEVTTNDGVTTIANNLTSTVQVFTDSEYQLPYVLGSAHQ<br>GCLPPFPADVFMVPQYGYLTLNNGSQAVGRSSFYCLEYFPSQMLRTGNNFQFSYTFEDVP<br>FHSSYAHSQSLDRLMNPLIDQYLYYLNRTQGTTSGTTNQSRLLFSQAGPQSMSLQARNWL<br>PGPCYRQQRLSKTANDNNNSNFPWTAASKYHLNGRDSLVNPGPAMASHKDDEEKFFPMHG<br>NLIFGKEGTTASNAELDNVMITDEEEIRTTNPVATEQYGTVANNLQSSNTAPTTRTVNDQ<br>GALPGMVWQDRDVYLQGPIWAKIPHTDGHFHPSPLMGGFGLKHPPPQILIKNTPVPANPP<br>AEFSATKFASFITQYSTGQVSVEIEWELQKENSKRWNPEIQYTSNYNKSVNVDFTVDTNG<br>VYSEPRPIGTRYLTRPL |
| AAV-18A1 SEQ ID NO: 5 | >18A1_KP2<br>MAADGYLPDWLEDNLSEGIREWWDLKPGAPKPKANQQKQDDGRGLVLPGYKYLGPFNGLD<br>KGEPVNAADAAALEHDKAYDQQLKAGDNPYLRYNHADAEFQERLQEDTSFGGNLGRAVFQ<br>AKKRVLEPLGLVEEGAKTAPGKKRPVEHSPVEPDSSSGIGKTGQQPAKKRLNFGQTGDAD<br>SVPDPQPLGQPPAAPSGLGTNTMATGSGAPMADNNEGADGVGNASGNWHCDSTWLGDRVI<br>TTSTRTWALPTYNNHLYKQISSASTGASNDNHYFGYSTPWGYFDFNRFHCHFSPRDWQRL<br>INNNWGFRPKRLNFKLFNIQVKEVTQNEGTTTIANNLTSTVQVFTDSEYQLPYVLGSAHQ<br>GCLPPFPADVFMIPQYGYLTLNNGSQAVGRSSFYCLEYFPSQMLRTGNNFTFSYTFEDVP<br>FHSSYAHSQSLDRLMNPLIDQYLYYLNRTQGTTSGTTNQSRLLFSQAGPQSMSLQARNWL<br>PGPCYRQQRLSKTANDNNNSNFPWTAASKYHLNGRDSLVNPGPAMASHKDDEEKFFPMHG<br>NLIFGKEGTTASNAELDNVMITDEEEIRTTNPVATEQYGTVANNLQSSNTAPTTRTVNDQ<br>GALPGMVWQDRDVYLQGPIWAKIPHTDGHFHPSPLMGGFGLKHPPPQIMIKNTPVPANPP<br>TTFSPAKFASFITQYSTGQVSVEIEWELQKENSKRWNPEIQYTSNYNKSVNVDFTVDTNG<br>VYSEPRPIGTRYLTRPL |

TABLE 2-continued

Variant AAV Capsid Amino Acid Sequences

| Description SEQ ID NO: | Amino Acid Sequence |
|---|---|
| AAV-10B1 SEQ ID NO: 6 | >10B1<br>MAADGYLPDWLEDNLSEGIRQWWKLKPGPPPPKPAERHKDDSRGLVLPGYKYLGPFNGLD<br>KGEPVNAADAAALEHDKAYDQQLKAGDNPYLRYNHADAEFQERLKEDTSFGGNLGRAVFQ<br>AKKRVLEPLGLVEEGAKTAPGKKRPVEHSPVEPDSSSGIGKTGQQPAKKRLNFGQTGDSE<br>SVPDPQPLGEPPAAPSGLGTNTMASGGGAPMADNNEGADGVGNSSGNWHCDSTWLGDRVI<br>TTSTRTWALPTYNNHLYKQISSASTGASNDNHYFGYSTPWGYFDFNRFHCHFSPRDWQRL<br>INNNWGFRPKRLNFKLFNIQVKEVTTNDGVTTIANNLTSTVQVFTDSEYQLPYVLGSAHQ<br>GCLPPFPADVFMVPQYGYLTLNNGSQAVGRSSFYCLEYFPSQMLRTGNNFQFTYTFEDVP<br>FHSSYAHSQSLDRLMNPLIDQYLYYLNRTQGTTSGTTNQSRLLFSQAGPQSMSLQARNWL<br>PGPCYRQQRLSKTANDNNNSNFPWTAASKYHLNGRDSLVNPGPAMASHKDDEEKFFPMHG<br>NLIFGKEGTTASNAELDNVMITDEEEIRTTNPVATEQYGTVANNLQSSNTAPTTRTVNDQ<br>GALPGMVWQDRDVYLQGPIWAKIPHTDGHFHPSPLMGGFGLKHPPPQIMIKNTPVPANPP<br>TTFSPAKFASFITQYSTGQVSVEIEWELQKENSKRWNPEIQYTSNYNKSVNVDFTVDTNG<br>VYSEPRPIGTRYLTRPL |
| AAV-10B3 SEQ ID NO: 7 | >10B3<br>MAADGYLPDWLEDTLSEGIRQWWKLKPGPPPPKPAERHKDDSRGLVLPGYKYLGPFNGLD<br>KGEPVNAADAAALEHDKAYDQQLKAGDNPYLRYNHADAEFQERLKEDTSFGGNLGRAVFQ<br>AKKRRLLEPLGLVEEAAKTAPGKKRPVEHSPVEPDSSSGTGKAGQQPAKKRLNFGQTGDSE<br>SVPDPQPLGEPPAAPSGVGPNTMAAGGGAPMADNNEGADGVGNASGNWHCDSTWLGDRVI<br>TTSTRTWALPTYNNHLYKQISSASTGASNDNHYFGYSTPWGYFDFNRFHCHFSPRDWQRL<br>INNNWGFRPKRLSFKLFNIQVKEVTTNDGVTTIANNLTSTVQVFTDSEYQLPYVLGSAHQ<br>GCLPPFPADVFMVPQYGYLTLNNGSQAVGRSSFYCLEYFPSQMLRTGNNFQFSYTFEDVP<br>FHSSYAHSQSLDRLMNPLIDQYLYYLNRTQGTTSGTTNQSRLLFSQAGPQSMSLQARNWL<br>PGPCYRQQRLSKTANDNNNSNFPWTAASKYHLNGRDSLVNPGPAMASHKDDEEKFFPMHG<br>NLIFGKEGTTASNAELDNVMITDEEEIRTTNPVATEQYGTVANNLQSSNTAPTTRTVNDQ<br>GALPGMVWQDRDVYLQGPIWAKIPHTDGHFHPSPLMGGFGLKHPPPQIMIKNTPVPANPP<br>TTFSPAKFASFITQYSTGQVSVEIEWELQKENSKRWNPEIQYTSNYNKSVNVDFTVDTNG<br>VYSEPRPIGTRYLTRPL |
| AAV-10B5 SEQ ID NO: 8 | >10B5<br>MAADGYLPDWLEDNLSEGIREWWALQPGAPKPKANQQKQDDGRGLVLPGYKYLGPFNGLD<br>KGEPVNAADAAALEHDKAYDQQLKAGDNPYLRYNHADAEFQERLKEDTSFGGNLGRAVFQ<br>AKKRVLEPLGLVEEGAKTAPGKKRPVEQSPQEPDSSSGIGKTGQQPAKKRLNFGQTGDSE<br>SVPDPQPIGEPPAGPSGLGTGTMASGSGAPMADNNEGADGVGNSSGNWHCDSQWLGDRVI<br>TTSTRTWALPTYNNHLYKQISSASTGASNDNHYFGYSTPWGYFDFNRFHCHFSPRDWQRL<br>INNNWGFRPKRLNFKLFNIQVKEVTTNDGVTTIANNLTSTIQVFTDSEYQLPYVLGSAHQ<br>GCLPPFPADVFMIPQYGYLTLNNGSQAVGRSSFYCLEYFPSQMLRTGNNFTFSYTFEDVP<br>FHSSYAHSQSLDRLMNPLIDQYLYYLNRTQGTTSGTTNQSRLLFSQAGPQSMSLQARNWL<br>PGPCYRQQRLSKTANDNNNSNFPWTAASKYHLNGRDSLVNPGPAMASHKDDEEKFFPMHG<br>NLIFGKEGTTASNAELDNVMITDEEEIRTTNPVATEQYGTVANNLQSSNTAPTTRTVNDQ<br>GALPGMVWQDRDVYLQGPIWAKIPHTDGHFHPSPLMGGFGLKHPPPQIMIKNTPVPANPP<br>TTFSPAKFASFITQYSTGQVSVEIEWELQKENSKRWNPEIQYTSNYNKSVNVDFTVDTNG<br>VYSEPRPIGTRYLTRPL |
| AAV-10B6 SEQ ID NO: 9 | >10B6<br>MAADGYLPDWLEDTLSEGIRQWWKLKPGPPPPKPAERHKDDSRGLVLPGYKYLGPFNGLD<br>KGEPVNAADAAALEHDKAYDQQLKAGDNPYLRYNHADAEFQERLKEDTSFGGNLGRAVFQ<br>AKKRVLEPFGLVEEAAKTAPGKKRPVDQSPQEPDSSSGVGKSGKQPARKRLNFGQTGDSE<br>SVPDPQPLGEPPAAPSLGSNTMASGGGAPMADNNEGADGVGNASGNWHCDSTWLGDRVI<br>TTSTRTWALPTYNNHLYKQISSASTGASNDNHYFGYSTPWGYFDFNRFHCHFSPRDWQRL<br>INNNWGFRPKKLSFKLFNIQVKEVTQNEGTKTIANNLTSTIQVFTDSEYQLPYVLGSAHQ<br>GCLPPFPADVFMIPQYGYLTLNNGSQAVGRSSFYCLEYFPSQMLRTGNNFQFTYTFEDVP<br>FHSSYAHSQSLDRLMNPLIDQYLYYLNRTQGTTSGTTNQSRLLFSQAGPQSMSLQARNWL<br>PGPCYRQQRLSKTANDNNNSNFPWTAASKYHLNGRDSLVNPGPAMASHKDDEEKFFPMHG<br>NLIFGKEGTTASNAELDNVMITDEEEIRTTNPVATEQYGTVANNLQSSNTAPTTRTVNDQ<br>GALPGMVWQDRDVYLQGPIWAKIPHTDGHFHPSPLMGGFGMKHPPPQILIKNTPVPADPP<br>TAFNKDKLNSFITQYSTGQVSVEIEWELQKENSKRWNPEIQYTSNYYKSTSVDFAVNTEG<br>VYSEPRPIGTRYLTRNL |
| AAV-10B7 SEQ ID NO: 10 | >10B7<br>MAADGYLPDWLEDTLSEGIRQWWKLKPGPPPPKPAERHKDDSRGLVLPGYKYLGPFNGLD<br>KGEPVNEADAAALEHDKAYDQQLKAGDNPYLKYNHADAEFQERLKEDTSFGGNLGRAVFQ<br>AKKRVLEPLGLVEEAAKTAPGKKRPVEHSPVEPDSSSGTGKAGQQPARKRLNFGQTGDAD<br>SVPDPQPLGEPPAAPSLGSNTMASGGGAPMADNNEGADGVGSSSGNWHCDSTWLGDRVI<br>TTSTRTWALPTYNNHLYKQISSASTGASNDNHYFGYSTPWGYFDFNRFHCHFSPRDWQRL<br>INNNWGFRPKRLNFKLFNIQVKEVTQNEGTKTIANNLTSTIQVFTDSEYQLPYVLGSAHQ<br>GCLPPFPADVFMIPQYGYLTLNNGSQAMGRSSFYCLEYFPSQMLRTGNNFTFSYTFEDVP<br>FHSSYAHSQSLDRLMNPLIDQYLYYLSRTQSTGGVAGTQQLLFSQAGPNNMSAQARNWLP<br>GPCYRQQRLSKTANDNNNSNFPWTAASKYHLNGRDSLVNPGPAMASHKDDEEKFFPMHGN |

TABLE 2-continued

Variant AAV Capsid Amino Acid Sequences

| Description SEQ ID NO: | Amino Acid Sequence |
|---|---|
| | LIFGKEGTTASNAELDNVMITDEEEIRTTNPVATEQYGTVANNLQSSNTAPTTRTVNDQG<br>ALPGMVWQDRDVYLQGPIWAKIPHTDGHFHPSPLMGGFGLKHPPPQILIKNTPVPADPPT<br>TFNQSKLNSFITQYSTGQVSVEIEWELQKENSKRWNPEIQYTSNYNKSVNVDFTVDTNGV<br>YSEPRPIGTRYLTRNL |
| AAV-18B1<br>SEQ ID<br>NO: 11 | >18B1<br>MAADGYLPDWLEDTLSEGIRQWWKLKPGPPPPKPAERHKDDSRGLVLPGYKYLGPFNGLD<br>KGEPVNAADAAALEHDKAYDQQLKAGDNPYLRYNHADAEFQERLQEDTSFGGNLGRAVFQ<br>AKKRLLEPLGLVEEAAKTAPGKKRPVEHSPVEPDSSSGTGKAGQQPARKRLNFGQTGDAD<br>SVPDPQPLGEPPAAPTSLGSNTMATGSGAPMADNNEGADGVGNSSGNWHCDSQWLGDRVI<br>TTSTRTWALPTYNNHLYKQISSASTGASNDNHYFGYSTPWGYFDFNRFHCHFSPRDWQRL<br>INNNWGFRPKRLNFKLFNIQVKEVTTNDGVTTIANNLTSTVQVFTDSEYQLPYVLGSAHQ<br>GCLPPFPADVFMVPQYGYLTLNNGSQAVGRSSFYCLEYFPSQMLRTGNNFQFSYTFEDVP<br>FHSSYAHSQSLDRLMNPLIDQYLYYLNRTQGTTSGTTNQSRLLFSQAGPQSMSLQARNWL<br>PGPCYRQQRLSKTANDNNNSNFPWTAASKYHLNGRDSLVNPGPAMASHKDDEEKFFPMHG<br>NLIFGKEGTTASNAELDNVMITDEEEIRTTNPVATEQYGTVANNLQSSNTAPTTRTVNDQ<br>GALPGMVWQDRDVYLQGPIWAKIPHTDGHFHPSPLMGGFGLKHPPPQILIKNTPVPANPP<br>TTFNQSKLNSFITQYSTGQVSVEIEWELQKENSKRWNPEIQYTSNYYKSTSVDFAVNTEG<br>VYSEPRPIGTRYLTRNL |
| AAV-18B2<br>SEQ ID<br>NO: 12 | >18B2<br>MAADGYLPDWLEDTLSEGIRQWWKLKPGPPPPKPAERHKDDSRGLVLPGYKYLGPFNGLD<br>KGEPVNAADAAALEHDKAYDQQLKAGDNPYLRYNHADAEFQERLQEDTSFGGNLGRAVFQ<br>AKKRVLEPFGLVEEGAKTAPGKKRPVEHSPVEPDSSSGTGKAGQQPARKRLNFGQTGDSE<br>SVPDPQPLGEPPAAPSGVGPNTMASGGGAPMADNNEGADGVGNASGNWHCDSTWLGDRVI<br>TTSTRTWALPTYNNHLYKQISSASTGASNDNHYFGYSTPWGYFDFNRFHCHFSPRDWQRL<br>INNNWGFRPKRLNFKLFNIQVKEVTQNDGTTTIANNLTSTVQVFTDSEYQLPYVLGSAHQ<br>GCLPPFPADVFMVPQYGYLTLNNGSQAVGRSSFYCLEYFPSQMLRTGNNFQFSYTFEDVP<br>FHSSYAHSQSLDRLMNPLIDQYLYYLNRTQGTTSGTTNQSRLLFSQAGPQSMSLQARNWL<br>PGPCYRQQRLSKTANDNNNSNFPWTAASKYHLNGRDSLVNPGPAMASHKDDEEKFFPMHG<br>NLIFGKEGTTASNAELDNVMITDEEEIRTTNPVATEQYGTVANNLQSSNTAPTTRTVNDQ<br>GALPGMVWQDRDVYLQGPIWAKIPHTDGHFHPSPLMGGFGLKHPPPQIMIKNTPVPANPP<br>TTFSPAKFASFITQYSTGQVSVEIEWELQKENSKRWNPEIQYTSNYYKSTSVDFAVNTEG<br>VYSEPRPIGTRYLTRNL |
| AAV-18B3<br>SEQ ID<br>NO: 13 | >18B3<br>MAADGYLPDWLEDNLSEGIREWWDLKPGAPKPKANQQKQDDGRGLVLPGYKYLGPFNGLD<br>KGEPVNAADAAALEHDKAYDQQLQAGDNPYLRYNHADAEFQERLQEDTSFGGNLGRAVFQ<br>AKKRLLEPLGLVEEAAKTAPGKKRPVEHSPVEPDSSSGTGKAGQQPARKRLNFGQTGDAD<br>SVPDPQPIGEPPAAPSGVGSLTMAAGGGAPMADNNEGADGVGNSSGNWHCDSTWMGDRVI<br>TTSTRTWALPTYNNHLYKQISSASTGASNDNHYFGYSTPWGYFDFNRFHCHFSPRDWQRL<br>INNNWGFRPKRLNFKLFNIQVKEVTTNDGVTTIANNLTSTVQVFSDSEYQLPYVLGSAHQ<br>GCLPPFPADVFMIPQYGYLTLNNGSQAVGRSSFYCLEYFPSQMLRTGNNFTFSYTFEDVP<br>FHSSYAHSQSLDRLMNPLIDQYLYYLNRTQGTTSGTTNQSRLLFSQAGPQSMSLQARNWL<br>PGPCYRQQRLSKTANDNNNSNFPWTAASKYHLNGRDSLVNPGPAMASHKDDEEKFFPMHG<br>NLIFGKEGTTASNAELDNVMITDEEEIRTTNPVATEQYGTVANNLQSSNTAPTTRTVNDQ<br>GALPGMVWQDRDVYLQGPIWAKIPHTDGHFHPSPLMGGFGLKHPPPQIMIKNTPVPANPP<br>TTFSPAKFASFITQYSTGQVSVEIEWELQKENSKRWNPEIQYTSNYNKSVNVDFTVDTNG<br>VYSEPRPIGTRYLTRPL |

TABLE 3

Variant AAV Capsid Nucleic Acid Sequences

| Description SEQ ID NO: | Nucleic Acid Sequence |
|---|---|
| AAV-10A1<br>SEQ ID<br>NO: 14 | >10A1_KP1<br>ATGGCTGCCGATGGTTATCTTCCAGATTGGCTCGAGGACACTCTCTCTGAAGGAATAAGACAGTGGTGGA<br>AGCTCAAACCTGGCCCACCACCACCAAAGCCCGCAGAGCGGCATAAGGACGACAGCAGGGGTCTTGTGCT<br>TCCGGGTTACAAATACCTCGGACCCGGCAACGGACTCGACAAGGGGGAGCCCGTCAACGCGGCGGACGCA<br>GCGGCCCTCGAGCACGACAAGGCCTACGACCAGCAGCTCAAAGCGGGTGACAATCCGTACCTGCGGTATA<br>ACCACGCCGACGCCGAGTTTCAGGAGCGTCTGCAAGAAGATACGTCTTTTGGGGGCAACCTCGGGCGAGC<br>AGTCTTCCAGGCCAAGAAGCGGGTTCTCGAACCTCTCGGTCTGGTTGAGGAACCTGTTAAGACGGCTCCG<br>GGAAAAAAGAGGCCGGTAGAGCACTCTCCTGTGGAGCCAGACTCCTCCTCGGGAACCGGAAAGGCGGGCC<br>AGCAGCCTGCGAGGAAGCGACTCAACTTTGGTCAGACTGGAGACACCGACTCCGCCGCTGACCCCCAGCC<br>TCTCGGAGAACCACCAGCAGCCCCCTCTGGTCTGGGAACTGGTACAATGGCTGCAGGCGGTGGCGCTCCA<br>ATGGCAGACAATAACGAAGGCGCCGACGGAGTGGGTAATGCCTCGGGAAATTGGCATTGCGATTCCACAT<br>GGCTGGGCGACAGAGTCATCACCACCAGCACCCGCACCTGGGCCTTGCCCACCTACAATAACCACCTCTA<br>CAAGCAAATC |

TABLE 3-continued

Variant AAV Capsid Nucleic Acid Sequences

| Description SEQ ID NO: | Nucleic Acid Sequence |
|---|---|
| | TCCAGTGCTTCAACGGGGGCCAGCAACGACAACCACTACTTCGGCTACAGCACCCCCTGGGGGTACTTTG<br>ACTTCAACCGCTTCCACTGCCACTTCTCACCACGTGACTGGCAAAGACTCATCAACAACAACTGGGGATT<br>CCGGCCCAAGAGACTCAACTTCAAGCTCTTCAACATCCAGGTCAAGGAGGTCACGCAGAATGAAGGCACC<br>AAGACCATCGCCAATAACCTTACCAGCACGGTTCAGGTGTTTACTGACTCGGAGTACCAGCTGCCGTACG<br>TTCTCGGCTCTGCCCACCAGGGCTGCCTGCCTCCGTTCCCGGCGGACGTGTTCATGATTCCGCAGTACGG<br>CTACCTAACGCTCAACAATGGCAGCCAGGCGATGGGTCGCTCGTCCTTCTACTGCCTGGAGTACTTTCCG<br>TCGCAGATGCTGAGAACCGGCAACAACTTCCAGTTTACTTACACCTTCGAGGACGTGCCTTTCCACAGCA<br>GCTACGCTCACAGCCAGAGTTTGGATCGCTTGATGAATCCTCTTATTGATCAGTATCTGTACTACCTGAA<br>CAGAACGCAAGGAACAACCTCTGGAACAACCAACCAATCACGGCTGCTTTTTAGCCAGGCTGGGCCTCAG<br>TCTATGTCTTTGCAGGCCAGAAATTGGCTACCTGGGCCCTGCTACCGGCAACAGAGACTTTCAAAGACTG<br>CTAACGACAACAACAGTAACTTTCCTTGGACAGCGGCCAGCAAATATCATCTCAATGGCCGCGACTC<br>GCTGGTGAAT<br>CCAGGACCAGCTATGGCCAGTCACAAGGACGATGAAGAAAATTTTTCCCTATGCACGGCAATCTAATAT<br>TTGGCAAAGAAGGGACAACGGCAAGTAACGCAGAATTAGATAATGTAATGATTACGGATGAAGAAGAGAT<br>TCGTACCACCAATCCTGTGGCAACAGAGCAGTATGGAACTGTGGCAAATAACTTGCAGAGCTCAAATACA<br>GCTCCCACGACTAGAACTGTCAATGATCAGGGGGCCTTACCTGGCATGGTGTGGCAAGATCGTGACGTGT<br>ACCTTCAAGGACCTATCTGGGCAAAGATTCCTCACACGGATGGACACTTTCATCCTTCTCCTCTGATGGG<br>CGGCTTTGGCCTGAAACATCCTCCGCCTCAGATCCTGATCAAGAACACGCCTGTACCTGCGGATCCTCCA<br>ACGGCCTTCAACAAGGACAAGCTGAACTCTTTCATCACCGTATTCTACTGGCCAAGTCAGCGTGGAGA<br>TCGAGTGGGAGCTGCAGAAGGAAAACAGCAAGCGCTGGAACCCCGAGATCCAGTACACCTCCAACTACTA<br>CAAATCTACAAGTGTGGACTTTGCTGTTAATACAGAAGGCGTGTACTCTGAACCCCGCCCCATTGCACC<br>CGTTACCTCACCCGTAATCTGTAA |
| AAV-10A3<br>SEQ ID<br>NO: 15 | >10A3_KP3<br>ATGGCTGCCGATGGTTATCTTCCAGATTGGCTCGAGGACACTCTCTCTGAAGGAATAAGACAGTGGTGGA<br>AGCTCAAACCTGGCCCACCACCACCAAAGCCCGCAGAGCGGCATAAGGACGACAGCAGGGGTCTTGTGCT<br>TCCTGGGTACAAGTACCTCGGACCCTTCAACGGACTCGACAAAGGAGAGCCGGTCAACGAGGCGGATGCA<br>GCGGCCCTCGAGCACGACAAGGCCTACGACCAGCAGCTCAAAGCGGGTGACAATCCGTACCTTCGGTATA<br>ACCACGCCGACGCCGAGTTTCAGGAGCGTCTGCAAGAAGATACGTCTTTTGGGGGCAACCTCGGGCGAGC<br>AGTCTTCCAGGCCAAGAAGCGGGTTCTCGAACCTCTCGGTCTGGTTGAGGAAGGCGCTAAGACGGCTCCT<br>GGAAAGAAGAGACCGGTAGAGCCATCACCCCAGCGTTCTCCAGACTCCTCTACGGGCATCGGCAAGAAAG<br>GCCAACAGCCCGCCAGAAAAAGACTCAATTTTGGTCAGACTGGCGACTCAGAGTCAGTTCCAGACCCTCA<br>ACCTCTCGGAGAACCTCCAGCAGCGCCCTCTGGTGTGGGACCTAATACAATGGCTGCAGGCGGTGGCGCA<br>CCAATGGCAGACAATAACGAAGGCGCCGACGGAGTGGGTAATGCCTCAGGAAATTGGCATTGCGATTCCA<br>CATGGCTGGGCGACAGAGTCATCACCACCAGCACCCGCACCTGGGCCTTGCCCACCTACAATAACCACCT<br>CTACAAGCAA<br>ATCTCCAGTGCTTCAACGGGGGCCAGCAACGACAACCACTACTTCGGCTACAGCACCCCTTGGGGGTATT<br>TTGACTTCAACAGATTCCACTGCCACTTTTCACCACGTGACTGGCAAAGACTCATCAACAACAACTGGGG<br>ATTCCGACCCAAGAGACTCAACTTCAAGCTCTTTAACATTCAAGTCAAAGAGGTCACGCAGAATGAAGGC<br>ACCAAGACCATCGCCAATAACCTCACCAGCACCATCCAGGTGTTTACGGACTCGGAGTACCAGCTGCCGT<br>ACGTTCTCGGCTCTGCCCACCAGGGCTGCCTGCCTCCGTTCCCGGCGGACGTGTTCATGATTCCCCAGTA<br>CGGCTACCTAACACTCAACAACGGTAGTCAGGCCGTGGGACGCTCCTCCTTTTACTGCCTGGAGTACTTC<br>CCTTCGCAGATGCTAAGGACTGGAAATAACTTCCAATTCAGCTATACCTTCGAGGATGTACCTTTTCACA<br>GCAGCTACGCTCACAGCCAGAGTTTGGATCGCTTGATGAATCCTCTTATTGATCAGTATCTGTACTACCT<br>GAACAGAACGCAAGGAACAACCTCTGGAACAACCAACCAATCACGGCTGCTTTTTAGCCAGGCTGGGCCT<br>CAGTCTATGTCTTTGCAGGCCAGAAATTGGCTACCTGGGCCCTGCTACCGGCAACAGAGACTTTCAAAGA<br>CTGCTAACGACAACAACAACAGTAACTTTCCTTGGACAGCGGCCAGCAAATATCATCTCAATGGCCGCGA<br>CTCGCTGGTG<br>AATCCAGGACCAGCTATGGCCAGTCACAAGGACGATGAAGAAAATTTTTCCCTATGCACGGCAATCTAA<br>TATATTGGCAAAGAAGGGACAACGGCAAGTAACGCAGAATTAGATAATGTAATGATTACGGATGAAGAAGA<br>GATTCGTACCACCAATCCTGTGGCAACAGAGCAGTATGGAACTGTGGCAAATAACTTGCAGAGCTCAAAT<br>ACAGCTCCCACGACTAGAACTGTCAATGATCAGGGGGCCTTACCTGGCATGGTGTGGCAAGATAGAGACG<br>TGTACCTGCAGGGTCCTATCTGGGCAAGATTCCTCACACGGACGGAAACTTTCATCCCTCGCCGCTGAT<br>GGGAGGCTTTGGACTGAAACACCCGCCTCCTCAGATCCTGATCAAGAACACGCCTGTACCTGCGGATCCT<br>CCGACCACCTTCAACCAGTCAAAGCTGAACTCTTTCATCACGCAATACAGCACCGGACAGGTCAGCGTGG<br>AAATTGAATGGGAGCTGCAGAAGGAAAACAGCAAGCGCTGGAACCCCGAGATCCAGTACACCTCCAACTA<br>CTACAAATCTACAAGTGTGGACTTTGCTGTTAATACAGAAGGCGTGTACTCTGAACCCCGCCCCATTGGC<br>ACCCGTTACCTCACCCGTAATCTGTAA |
| AAV-10A4<br>SEQ ID<br>NO: 16 | >10A4<br>ATGGCTGCCGATGGTTATCTTCCAGATTGGCTCGAGGACAACCTCTCTGAGGGCATTCGCGAGTGGTGGG<br>ACTTGAAACCTGGAGCCCCGAAACCCAAAGCCAACCAGCAAAAGCAGGACGACGGCCGGGGTCTGGTGCT<br>TCCTGGCTACAAGTACCTCGGACCCTTCAACGGACTCGACAAGGGGGAGCCCGTCAACGCGGCGGATGCA<br>GCGGCCCTCGAGCACGACAAGGCCTACGACCAGCAGCTCAAAGCGGGTGACAATCCGTACCTGCGGTATA<br>ACCACGCCGACGCCGAGTTTCAGGAGCGTCTGCAAGAAGATACGTCTTTTGGGGGCAACCTCGGGCGAGC<br>AGTCTTCCAGGCCAAAAAGAGGCTTCTTGAACCTCTTGGTCTGGTTGAGGAAGCGGCTAAGACGGCTCCT<br>GGAAAGAAACGTCGGTAGACAGTCGCCACAAGAGCCAGACTCCTCCTCGGGCATCGGCAAGACAGGCC<br>AGCAGCCCGCTAAAAAGAGACTCAATTTCGGTCAGACTGGCGACACAGAGTCAGTCCCAGACCCTCAACC<br>TCTCGGAGAACCACCAGCAGCCCCCACAAGTTTGGGATCTAATGGCTTCAGGCGGTGGCGCACA<br>ATGGCAGACAATAACGAAGGCGCCGACGGAGTGGGTAATGCCTCAGGAAATTGGCATTGCGATTCCACAT<br>GGCTGGGCGACAGAGTCATCACCACCAGCACCCGCACCTGGGCCTTGCCCACCTACAATAACCACCTCTA<br>CAAGCAAATCTCCAGTGCTTCAACGGGGGCCAGCAACGACAACCACTACTTCGGCTACAGCACCCCCTGG<br>GGGTATTTTGATTTCAACAGATTCCACTGCCATTTCTCACCACGTGACTGGCAGCGACTCATCAACAACA<br>ATTGGGGATTCCGGCCCAAGAAACTCAGCTTCAAGCTCTTCAACATCCAAGTTAAAGAGGTCACGCAGAA |

TABLE 3-continued

Variant AAV Capsid Nucleic Acid Sequences

| Description SEQ ID NO: | Nucleic Acid Sequence |
|---|---|
| | CGATGGCACGACGACTATTGCCAATAACCTTACCAGCACGATTCAGGTCTTTACGGACTCGGAGTACCAG<br>CTGCCGTACGTTCTCGGCTCTGCCCACCAGGGCTGCCTCCCTCCGTTCCCGGCGGACGTGTTCATGATTC<br>CGCAGTACGGCTACCTAACGCTCAACAATGGCAGCCAAGCCGTGGGACGTTCATCCTTTTACTGCCTGGA<br>GTACTTTCCTTCTCAAATGCTGAGAACGGGCAACAACTTTACCTTCAGCTACACCTTTGAGGAAGTGCCT<br>TTCCACAGCAGCTACGCTCACAGCCAGAGTTTGGATCGCTTGATGAATCCTCTTATTGATCAGTATCTGT<br>ACTACCTGAACAGAACGCAAGGAACAACCTCTGGAACAACCAACCAATCACGGCTGCTTTTTAGCCAGGC<br>TGGGGCCTCAGTCTATGTCTTTGCAGGCCAGAAATTGGCTACCTGGGCCCTGCTACCGGCAACAGAGACTT<br>TCAAAGACTGCTAACGACAACAACAACAGTAACTTTCCTTGGACAGCGGCCAGCAAATATCATCTCAATG<br>GCCGCGACTCGCTGGTGAATCCAGGACCAGCTATGGCCAGTCACAAGGACGATGAAGAAAAATTTTTCCC<br>TATGCACGGCAATCTAATATTTGGCAAAGAAGGGACAACGGCAAGTAACGCAGAATTAGATAATGTAATG<br>ATTACGGATGAAGAAGAGATTCGTACCACCAATCCTGTGGCAACAGAGCAGTATGGAACTGTGGCAAATA<br>ACTTGCAGAGCTCAAATACAGCTCCCACGACTAGAACTGTCAATGATCAGGGGCCTTACCTGGCATGGT<br>GTGGCAAGATCGTGACGTGTACCTTCAAGGACCTATCTGGGCCAAGATTCCTCACACGGATGGACACTTT<br>CATCCTTCTCCTCTGATGGGAGGCTTTGGACTGAAACATCCGCCTCCTCAAATCATGATCAAAAATACTC<br>CGGTACCGGCAAATCCTCCGACGACTTTCAGCCGGCCAAGTTTGCTTCATTTATCACGCAGTACGCAC<br>CGGACAGGTCAGCGTGGAAATTGAATGGGAGCTGCAGAAAGAAAACAGCAAACGTTGGAATCCAGAGATT<br>CAGTACACTTCCAACTACAACAAGTCTGTTAATGTGGACTTTACTGTAGACACTAATGGTGTTTATAGTG<br>AACCTCGCCCCATTGGCACCCGTTACCTTACCCGTCCCCTGTAA |
| AAV-10A5 SEQ ID NO: 17 | >10A5<br>ATGGCTGCCGATGGTTATCTTCCAGATTGGCTCGAGGACAACCTTTCTGAAGGCATTCGCGAGTGGTGGG<br>ACTTGAAACCTGGAGCCCCGAAACCCAAAGCCAACCAGCAAAAGCAGGACGACGCTCGGGGTCTTGTGCT<br>TCCGGGTTACAAATACCTTGGACCCGGCAACGGACTCGACAAGGGGGAGCCCGTCAACGCGGCGGACGCA<br>GCGGCCCTCGAGCACGACAAAGCCTACGACCAGCAGCTGCAGGCGGGTGACAATCCGTACCTGCGGTACA<br>ACCACGCCGACGCGGAGTTTCAGGAGCGTCTGCAAGAAGATACGTCTTTTGGGGGCAACCTCGGGCGAGC<br>AGTCTTCCAGGCCAAGAAGAGGGTTCTCGAACCTCTCGGTCTGGTTGAGGAAGCGGCTAAGACGGCTCCT<br>GGAAAGAAACGTCCGGTAGAGCAGTCGCCACAAGAGCCAGACTCCTCCTCGGGCATCGGCAAGACAGGCC<br>AGCAGCCCGCTAAAAAGAGACTCAATTTTGGTCAGACTGGCGACTCAGAGTCAGTCCCAGACCCTCAACC<br>TCTCGGAGAACCACCAGCAGCCCCCACAAGTTTGGGATCTAATACAATGGCTTCAGGCGGTGGCGCACCA<br>ATGGCAGACAATAACGAGGGTGCCGACGGAGTGGGTAATTCCTCGGGAAATTGGCATTGCGATTCCCAAT<br>GGCTGGGCGACCGAGTCATCACCACCAGCACCCGCACCTGGGCCTTGCCCACCTACAATAACCACCTCTA<br>CAAGCAAATCTCCAGTGCTTCAACGGGGGCCAGCAACGACAACCACTACTTCGGCTACGACACCCCCTGG<br>GGGTATTTTGATTTCAACAGATTCCACTGCCACTTTTCACCACGTGACTGGCAAAGACTCATCAACAACA<br>ACTGGGGATTCCGACCCAAGAGACTCAACTTCAAACTCTTCAACATCCAAGTCAAGGAGGTCACGACGAA<br>TGATGGCGTCACGACCATCGCCAATAACCTTACCAGCACGGTTCAAGTGTTTACGGACTCGGAGTATCAG<br>CTCCCGTACGTGCTCGGGTCGGCGCACCAAGGCTGTCTCCCGCCGTTTCCAGCGGACGTCTTCATGGTCC<br>CTCAGTATGGATACCTCACCCTGAACAACGGAAGTCAAGCGGTGGGACGCTCATCCTTTTACTGCCTGGA<br>GTACTTCCCTTCGCAGATGCTAAGGACTGGAAATAACTTCCAATTCAGCTATACCTTCGAGGATGTACCT<br>TTTCACAGCAGCTACGCTCACAGCCAGAGTTTGGATCGCTTGATGAATCCTCTTATTGATCAGTATCTGT<br>ACTACCTGAACAGAACGCAAGGAACAACCTCTGGAACAACCAACCAATCACGGCTGCTTTTTAGCCAGGC<br>TGGGGCCTCAGTCTATGTCTTTGCAGGCCAGAAATTGGCTACCTGGGCCCTGCTACCGGCAACAGAGACTT<br>TCAAAGACTGCTAACGACAACAACAACAGTAACTTTCCTTGGACAGCGGCCAGCAAATATCATCTCAATG<br>GCCGCGACTCGCTGGTGAATCCAGGACCAGCTATGGCCAGTCACAAGGACGATGAAGAAAAATTTTTCCC<br>TATGCACGGCAATCTAATATTTGGCAAAGAAGGGACAACGGCAAGTAACGCAGAATTAGATAATGTAATG<br>ATTACGGATGAAGAAGAGATTCGTACCACCAATCCTGTGGCAACAGAGCAGTATGGAACTGTGGCAAATA<br>ACTTGCAGAGCTCAAATACAGCTCCCACGACTAGAACTGTCAATGATCAGGGGCCTTACCTGGCATGGT<br>GTGGCAAGATCGTGACGTGTACCTTCAAGGACCTATCTGGGCAAAGATTCCTCACACGGATGGACACTTT<br>CACCCGTCCTCCTCTCATGGGCGGCTTTGGACTTAAGCACCCGCCTCTCAGATCCTCATCAAAAACACGC<br>CTGTTCCTGCGAATCCTCCGGCAGAGTTTTCGGCTACAAAGTTTGCTTCATTCATCACCCAGTATTCCAC<br>AGGACAAGTGAGCGTGGAAATTGAATGGGAGCTGCAGAAAGAAAACAGCAAACGCTGGAATCCAGAGATT<br>CAGTACACTTCCAACTACAACAAGTCTGTTAATGTGGACTTTACTGTAGACACTAATGGTGTTTATAGTG<br>AACCTCGCCCCATTGGCACCCGTTACCTCACCCGTCCCCTGTAA |
| AAV-18A1 SEQ ID NO: 18 | >18A1_KP2<br>ATGGCTGCCGATGGTTATCTTCCAGATTGGCTCGAGGACAACCTCTCTGAGGGCATTCGCGAGTGGTGGG<br>ACTTGAAACCTGGAGCCCCGAAACCCAAAGCCAACCAGCAAAAGCAGGACGACGGCCGGGGTCTGGTGCT<br>TCCTGGCTACAAGTACCTCGGACCCTTCAACGGACTCGACAAGGGGGAGCCCGTCAACGCGGCGGATGCA<br>GCGGCCCTCGAGCACGACAAGGCCTACGACCAGCAGCTCAAAGCGGGTGACAATCCGTACCTTCGGTATA<br>ACCACGCCGACGCCGAGTTTCAGGAGCGTCTGCAAGAAGATACGTCTTTTGGGGGCAACCTCGGGCGAGC<br>AGTCTTCCAGGCCAAGAAGCGGGTTCTCGAACCTCTCGGTCTGGTTGAGGAAGGTGCTAAGACGGCTCCT<br>GGAAAGAAACGTCCGGTAGAGCACTCTCCTGTGGAGCCAGACTCCTCCTCGGGCATCGGCAAGACAGGCC<br>AGCAGCCCGCTAAAAAGAGACTCAATTTTGGTCAGACTGGCGACAGAGACTCAGTACCTGACCCCCAGCC<br>TCTCGGACAGCCACCAGCAGCCCCCTCTGGTCTGGGAACTAATACGATGGCTACAGGCAGTGGCGCACCA<br>ATGGCAGACAATAACGAGGGCGCCGACGGAGTGGGTAATGCCTCAGGAAATTGGCATTGCGATTCCACAT<br>GGCTGGGCGACAGAGTCATCACCACCAGCACCCGAACATGGGCCTTGCCCACCTATAACAACCACCTCTA<br>CAAGCAAATCTCCAGTGCTTCAACGGGGGCCAGCAACGACAACCACTACTTCGGCTACAGCACCCCCTGG<br>GGGTACTTTGACTTCAACCGCTTCCACTGCCACTTCTCCCCGCGAGACTGGCAGCGGCTCATCAACAACA<br>ACTGGGGGTTCCGGCCCAAGGACTCAACTTCAAGCTCTTCAACATCCAGGTCAAGGAGGTCACGCAGAA<br>TGAAGGCACGACGACTATTGCCAATAACCTTACCAGCACGGTTCAAGTGTTTACGGACTCGGAGTACAG<br>CTCCCGTACGTGCTCGGCTCTGCCCACCAGGGCTGCCTGCCTCCGTTCCCGGCGGACGTGTTCATGATTC<br>CCAGTACGGCTACCTAACACTCAACAACGGTAGTCAGGCCGTGGGACGCTCCTCCTTCTACTGCCTGGA<br>ATACTTTCCTTCTCAGATGCTGCGTACCGGAAACAACTTTACCTTCAGCTACACTTTTGAGGACGTTCCT<br>TTCCACAGCAGCTACGCTCACAGCCAGAGTTTGGATCGCTTGATGAATCCTCTTATTGATCAGTATCTGT<br>ACTACCTGAACAGAACGCAAGGAACAACCTCTGGAACAACCAACCAATCACGGCTGCTTTTTAGCCAGGC |

TABLE 3-continued

Variant AAV Capsid Nucleic Acid Sequences

| Description SEQ ID NO: | Nucleic Acid Sequence |
|---|---|
| | TGGGCCTCAGTCTATGTCTTTGCAGGCCAGAAATTGGCTACCTGGGCCCTGCTACCGGCAACAGAGACTT<br>TCAAAGACTGCTAACGACAACAACAACAGTAACTTTCCTTGGACAGCGGCCAGCAAATATCATCTCAATG<br>GCCGCGACTCGCTGGTGAATCCAGGACCAGCTATGGCCAGTCACAAGGACGATGAAGAAAATTTTTCCC<br>TATGCACGGCAATCTAATATTTGGCAAAGAAGGGACAACGGCAAGTAACGCAGAATTAGATAATGTAATG<br>ATTACGGATGAAGAAGAGATTCGTACCACCAATCCTGTGGCAACAGAGCAGTATGGAACTGTGGCAAATA<br>ACTTGCAGAGCTCAAATACAGCTCCCACGACTAGAACTGTCAATGATCAGGGGGCCTTACCTGGCATGGT<br>GTGGCAAGATCGTGACGTGTACCTTCAAGGACCTATCTGGGCAAAGATTCCTCACACGGATGGACACTTT<br>CATCCTTCTCCTCTGATGGGAGGCTTTGGACTGAAACATCCGCCTCCTCAAATCATGATCAAAAATACTC<br>CGGTACCGGCAAATCCTCCGACGACTTTCAGCCCGGCCAAGTTTGCTTCATTTATCACTCAGTACTCCAC<br>TGGACAGGTCAGCGTGGAAATTGAGTGGGAGCTACAGAAAGAAAACAGCAAACGTTGGAATCCAGAGATT<br>CAGTACACTTCCAACTACAACAAGTCTGTTAATGTGGACTTTACTGTAGACACTAATGGTGTTTATAGTG<br>AGCCTCGCCCCATTGGCACCCGTTACCTCACCCGTCCCCTGTAA |
| AAV-10B1<br>SEQ ID<br>NO: 19 | >10B1<br>ATGGCTGCCGATGGTTATCTTCCAGATTGGCTCGAGGACAACCTCTCTGAAGGAATAAGACAGTGGTGGA<br>AGCTCAAACCTGGCCCACCACCACCAAAGCCCGCAGAGCGGCATAAGGACGACAGCAGGGGTCTTGTGCT<br>TCCTGGGTACAAGTACCTCGGACCCTTCAACGGACTCGACAAGGGGGAGCCCGTCAACGCGGCGGATGCA<br>GCGGCCCTCGAGCACGACAAGGCCTACGACCAGCAGCTCAAAGCGGGTGACAATCCGTACCTGCGGTACA<br>ACCACGCCGACGCCGAGTTCCAGGAGCGGCTCAAAGAAGATACGTCTTTTGGGGGCAACCTCGGGCGAGC<br>AGTCTTCCAGGCCAAGAAGCGGGTTCTCGAACCTCTCGGTCTGGTTGAGGAAGGCGCTAAGACGGCTCCT<br>GGAAAGAAGAGGCCTGTAGAGCACTCTCCTGTGGAGCCAGACTCCTCCTCGGGCATCGGCAAGACAGGCC<br>AGCAGCCCGCTAAAAAGAGACTCAATTTTGGTCAGACTGGCGACTCAGAGTCAGTCCCCGACCCACAACC<br>TCTCGGAGAACCACCAGCAGCCCCTCTGGTCTGGGAACTAATACGATGGCTTCAGGCGGTGGCGCACCA<br>ATGGCAGACAATAACGAGGGTGCCGATGGAGTGGGTAATTCCTCAGGAAATTGGCATTGCGATTCCACAT<br>GGCTGGGCGACAGAGTCATCACCACCAGCACCCGAACCTGGGCCCTGCCCACCTACAACAATCACCTCTA<br>CAAGCAAATCTCCAGTGCTTCAACGGGGGCCAGCAACGACAACCACTACTTCGGCTACAGCACCCCCTGG<br>GGGTATTTTGATTTCAACAGATTCCACTGCCACTTTTCACCACGTGACTGGCAGCGACTCATCAACAACA<br>ATTGGGGATTCCGGCCCAAGAGACTCAACTTCAAGCTCTTCAACATCCAAGTCAAGGAGGTCACGACGAA<br>TGATGGCGTCACGACCATCGCCAATAACCTTACCAGCACGGTTCAAGTGTTTACGGACTCGGAGTACCAG<br>CTCCCGTACGTCCTCGGCTCGGCGCATCAAGGATGCCTCCCGCCGTTCCCAGCAGACGTCTTCATGGTGC<br>CGCAGTACGGGTACCTGACTCTGAACAATGGTAGTCAGGCCGTGGGACGTCCTCCTTCTACTGGCTGGA<br>ATACTTTCCTTCGCAGATGCTGAGAACCGGCAACAACTTCCAGTTTACTTACACCTTCGAGGACGTGCCT<br>TTCCACAGCAGCTACGCCCACAGCCAGAGCTTGGACCGGCTGATGAATCCTCTTATTGATCAGTATCTGT<br>ACTACCTGAACAGAACGCAAGGAACAACCTCTGGAACAACCAACCAATCACGGCTGCTTTTTAGCCAGGC<br>TGGGCCTCAGTCTATGTCTTTGCAGGCCAGAAATTGGCTACCTGGGCCCTGCTACCGGCAACAGAGACTT<br>TCAAAGACTGCTAACGACAACAACAACAGTAACTTTCCTTGGACAGCGGCCAGCAAATATCATCTCAATG<br>GCCGCGACTCGCTGGTGAATCCAGGACCAGCTATGGCCAGTCACAAGGACGATGAAGAAAATTTTTCCC<br>TATGCACGGCAATCTAATATTTGGCAAAGAAGGGACAACGGCAAGTAACGCAGAATTAGATAATGTAATG<br>ATTACGGATGAAGAAGAGATTCGTACCACCAATCCTGTGGCAACAGAGCAGTATGGAACTGTGGCAAATA<br>ACTTGCAGAGCTCAAATACAGCTCCCACGACTAGAACTGTCAATGATCAGGGGGCCTTACCTGGCATGGT<br>GTGGCAAGATCGTGACGTGTACCTTCAAGGACCTATCTGGGCAAAGATTCCTCACACGGATGGACACTTT<br>CATCCTTCTCCTCTGATGGGAGGCTTTGGACTGAAACATCCGCCTCCTCAAATCATGATCAAAAATACTC<br>CGGTACCGGCAAATCCTCCGACGACTTTCAGCCCGGCCAAGTTTGCTTCATTTATCACTCAGTACTCCAC<br>GGGACAGGTCAGCGTGGAAATTGAGTGGGAGCTACAGAAAGAAAACAGCAAACGCTGGAATCCGAAATT<br>CAGTACACTTCCAACTACAACAAGTCTGTTAATGTGGACTTTACTGTGGACACTAATGGTGTTTATAGTG<br>AACCTCGCCCCATTGGCACCCGTTACCTCACCCGTCCCCTGTAA |
| AAV-10B3<br>SEQ ID<br>NO: 20 | >10B3<br>ATGGCTGCTGACGGTTATCTTCCAGATTGGCTCGAGGACACTCTCTCTGAAGGAATAAGACAGTGGTGGA<br>AGCTCAAACCTGGCCCACCACCACCAAAGCCCGCAGAGCGGCATAAGGACGACAGCAGGGGTCTTGTGCT<br>TCCTGGGTACAAGTACCTCGGACCCTTCAACGGACTCGACAAGGGGGAGCCCGTCAACGCGGCGGATGCA<br>GCGGCCCTCGAGCACGACAAGGCCTACGACCAGCAGCTCAAAGCGGGTGACAATCCGTACCTGCGGTATA<br>ACCACGCCGACGCCGAGTTTCAGGAGCGTCTGCAAGAAGATACGTCTTTTGGGGCAACCTCGGGCGAGC<br>AGTCTTCCAGGCCAAAAAGAGGCTTCTTGAACCTCTTGGTCTGGTTGAGGAAGCGGCTAAGACGGCTCCG<br>GGAAAAAAGAGGCCGGTAGAGCACTCTCCTGTGGAGCCAGACTCCTCCTCGGGAACCGGAAAGGCGGGCC<br>AGCAGCCCGCTAAAAAGAGACTCAATTTTGGTCAGACTGGCGACACTCAGAGTCAGTTCCAGACCCTCAACC<br>TCTCGGAGAACCTCCAGCAGCGCCCTCTGGTGTGGGACCTAATACAATGGCTGCAGGCGGTGGCGCACCA<br>ATGGCAGACAATAACGAAGGCGCCGACGGAGTGGGTAATGCCTCAGGAAATTGGCATTGCGATTCCACAT<br>GGCTGGGCGACAGAGTCATCACCACCAGCACCCGAACCTGGGCCCTGCCCACCTACAACAACCACCTCTA<br>CAAGCAAATCTCCAGTGCTTCAACGGGGGCCAGCAACGACAACCACTACTTTGGCTACAGCACCCCCTTGG<br>GGGTATTTTGACTTTAACAGATTCCACTGCCACTTTTCACCACGTGACTGGCAGCGACTTCATTAACAACA<br>ACTGGGGATTCCGGCCCAAGAGACTCAGCTTCAAGCTCTTCAACATCCAAGTCAAGGAGGTCACGACGAA<br>TGATGGCGTCACGACCATCGCCAATAACCTTACCAGCACGGTTCAAGTGTTTACGGACTCGGAGTATCAG<br>CTCCCGTACGTCCTCGGATCAGCGCACCAAGGCTGTCTCCCGCCGTTTCCAGCGGACGTCTTCATGGTCC<br>CTCAGTATGGATACCTCACCCTGAACAACGGGAGTCAGGCAGTAGGACGCTCTTCATTTTACTGCCTGGA<br>GTACTTCCCTTCGCAGATGCTAAGGACTGGAATAACTTCCAATTCAGCTATACCTTCGAGGATGTACCT<br>TTTCACAGCAGCTACGCTCACAGCCAGAGTTTGGATCGCTTGATGAATCCTCTTATTGATCAGTATCTGT<br>ACTACCTGAACAGAACGCAAGGAACAACCTCTGGAACAACCAACCAATCACGGCTGCTTTTTAGCCAGGC<br>TGGGCCTCAGTCTATGTCTTTGCAGGCCAGAAATTGGCTACCTGGGCCCTGCTACCGGCAACAGAGACTT<br>TCAAAGACTGCTAACGACAACAACAACAGTAACTTTCCTTGGACAGCGGCCAGCAAATATCATCTCAATG<br>GCCGCGACTCGCTGGTGAATCCAGGACCAGCTATGGCCAGTCACAAGGACGATGAAGAAAATTTTTCCC<br>TATGCACGGCAATCTAATATTTGGCAAAGAAGGGACAACGGCAAGTAACGCAGAATTAGATAATGTAATG<br>ATTACGGATGAAGAAGAGATTCGTACCACCAATCCTGTGGCAACAGAGCAGTATGGAACTGTGGCAAATA<br>ACTTGCAGAGCTCAAATACAGCTCCCACGACTAGAACTGTCAATGATCAGGGGGCCTTACCTGGCATGGT |

TABLE 3-continued

Variant AAV Capsid Nucleic Acid Sequences

| Description SEQ ID NO: | Nucleic Acid Sequence |
|---|---|
| | GTGGCAAGATCGTGACGTGTACCTTCAAGGACCTATCTGGGCAAAGATTCCTCACACGGATGGACACTTT<br>CATCCTTCTCCTCTGATGGGAGGCTTTGGACTGAAACATCCGCCTCCTCAAATCATGATCAAAAATACTC<br>CGGTACCGGCAAATCCTCCGACGACTTTCAGCCCGGCCAAGTTTGCTTCATTTATCACTCAGTACTCCAC<br>TGGACAGGTCAGCGTGGAAATTGAGTGGGAGCTACAGAAAGAAAACAGCAAACGTTGGAATCCAGAGATT<br>CAGTACACTTCCAACTACAACAAGTCTGTTAATGTGGACTTTACTGTGGACACTAATGGCGTGTATTCAG<br>AGCCTCGCCCCATTGGCACCCGTTACCTCACCCGTCCCCTGTAA |
| AAV-10B5<br>SEQ ID<br>NO: 21 | >10B5<br>ATGGCTGCTGACGGTTATCTTCCAGATTGGCTCGAGGACAACCTTTCTGAAGGCATTCGAGAGTGGTGGG<br>CGCTGCAACCTGGAGCCCCGAAACCCAAAGCCAACCAGCAAAAGCAGGACGACGGCCGGGGTCTGGTGCT<br>TCCTGGCTACAAGTACCTCGGACCCTTCAACGGACTCGACAAGGGGGAGCCCGTCAACGCGGCGGATGCA<br>GCGGCCCTCGAGCACGACAAGGCCTACGACCAGCAGCTCAAAGCGGGTGACAATCCGTACCTGCGGTATA<br>ACCACGCCGACGCCGAGTTTCAGGAGCGTCTTCAAGAAGATACGTCTTTTGGGGGCAACCTCGGGCGAGC<br>AGTCTTCCAGGCCAAGAAGCGGGTTCTCGAACCTCTCGGTCTGGTTGAGGAAGGCGCTAAGACGGCTCCT<br>GGAAAGAAACGTCCGGTAGAGCAGTCGCCACAAGAGCCAGATCCTCCTCGGGCATCGGCAAGACAGGCC<br>AGCAGCCCGCGAAAAAGAGACTCAACTTTGGGCAGACTGGCGACTCAGAGTCAGTGCCCGACCCTCAACC<br>AATCGGAGAACCCCCGCAGGCCCCTCTGGTCTGGGAACTGGTACGATGGCTTCAGGCAGTGGCGCACCA<br>ATGGCAGACAATAACGAAGGCGCCGATGGAGTGGGTAATTCCTCAGGAAATTGGCATTGCGATTCCCAAT<br>GGCTGGGCGACAGAGTCATCACCACCAGCACCAATAACCTGGGCCTTGCCCACCTACAATAACCACCTCTA<br>CAAGCAAATCTCCAGTGCTTCAACGGGGGCCAGCAACGACAACCACTACTTCGGCTACAGCACCCCCTGG<br>GGGTATTTTGACTTTAACAGATTCCACTGCCACTTCTCACCACGTGACTGGCAGCGACTCATTAACAACA<br>ACTGGGGATTCCGGCCCAAGAGACTCAACTTCAAGCTCTTCAACATCCAAGTCAAGGAGGTCACGACGAA<br>TGATGGCGTCACGACCATTGCCAATAACCTCACCAGCACCATCCAGGTGTTTACGGACTCGGAGTACCAG<br>TTGCCGTACGTCCTCGGCTCTGCGCACCAGGGCTGCCTCCCTCCGTTCCCGGCGGACGTGTTCATGATTC<br>CGCAATACGGCTACCTGACGCTCAACAATGGCAGCCAGGCAGTGGGACGGTCATCCTTTTACTGCCTGGA<br>ATATTTCCCATCGCAGATGCTGAGAACGGGCAATAACTTTACCTTCAGCTACACCTTCGAGGACGTGCCT<br>TTCCACAGCAGCTACGCTCACAGCCAGAGTTTGGATCGCTTGATGAATCCTCTTATTGATCAGTATCTGT<br>ACTACCTGAACAGAACGCAAGGAACAACCTCTGGAACAACCAACCAATCACGGCTGCTTTTTAGCCAGGC<br>TGGGCCTCAGTCTATGTCTTTGCAGGCCAGAAATTGGCTACCTGGGCCCTGCTACCGGCAACAGAGACTT<br>TCAAAGACTGCTAACGACAACAACAACAGTAACTTTCCTTGGACAGCGGCCAGCAAATATCATCTCAATG<br>GCCGCGACTCGCTGGTGAATCCAGGACCAGCTATGGCCAGTCACAAGGACGATGAAGAAAAATTTTTCCC<br>TATGCACGGCAATCTAATATTTGGCAAAGAAGGGACAACGGCAAGTAACGCAGAATTAGATAATGTAATG<br>ATTACGGATGAAGAAGAGATTCGTACCACCAATCCTGTGGCAACAGAGCAGTATGGAACTGTGGCAAATA<br>ACTTGCAGAGCTCAAATACAGCTCCCACGACTAGAACTGTCAATGATCAGGGGCCCTTACCTGGCATGGT<br>GTGGCAAGATCGTGACGTGTACCTTCAAGGACCTATCTGGGCAAAGATTCCTCACACGGATGGACACTTT<br>CATCCTTCTCCTCTGATGGGAGGCTTTGGACTGAAACATCCGCCTCCTCAAATCATGATCAAAAATACTC<br>CGGTACCGGCAAATCCTCCGACGACTTTCAGCCCGGCCAAGTTTGCTTCATTTATCACTCAGTACTCCAC<br>TGGACAGGTCAGCGTGGAAATTGAGTGGGAGCTACAGAAAGAAAACAGCAAACGTTGGAATCCAGAGATT<br>CAGTACACTTCCAACTACAACAAGTCTGTTAATGTGGACTTTACTGTAGACACTAATGGTGTTTATAGTG<br>AACCTCGCCCCATTGGCACCCGTTACCTTACCCGTCCCCTGTAA |
| AAV-10B6<br>SEQ ID<br>NO: 22 | >10B6<br>ATGGCTGCTGACGGTTATCTTCCAGATTGGCTCGAGGACACTCTCTCTGAAGGAATAAGACAGTGGTGGA<br>AGCTCAAACCTGGCCCACCACCACCAAAGCCCGCAGAGCGGCATAAGGACGACAGCAGGGGTCTTGTGCT<br>TCCTGGGTACAAGTACCTCGGACCCTTCAACGGACTCGACAAGGGGGAGCCCGTCAACGCGGCGGATGCA<br>GCGGCCCTCGAGCACGACAAGGCCTACGACCAGCAGCTCAAAGCGGGTGACAATCCGTACCTGCGGTATA<br>ACCACGCCGACGCGGAGTTTCAGGAGCGCCTTAAGAAGATACGTCTTTTGGGGGCAACCTCGGACGAGC<br>AGTCTTCCAGGCCAAGAAGAGGGTTCTCGAACCTTTTGGTCTGGTTGAGGAAGCGGCTAAGACGGCTCCT<br>GGAAAGAAGAGGCCTGTAGATCAGTCTCCTCAGGAACCGGACTCATCATCTGGTGTTGGCAAATCGGGCA<br>AACAGCCTGCCAGAAAAAGACTAAATTTCGGTCAGACTGGCGACTCAGAGTCAGTCCCAGACCCTCAACC<br>TCTCGGAGAACCACCAGCAGCCCCCACAAGTTTGGGATCTAATACAATGGCTTCAGGCGGTGGCGCACCA<br>ATGGCAGACAATAACGAGGGTGCCGACGGAGTGGGTAATGCCTCAGGAAATTGGCATTGCGATTCCACAT<br>GGCTGGGCGACCGAGTCATCACCACCAGCACCCGCACCTGGGCCCTGCCCACCTACAACAACCATCTCTA<br>CAAGCAAATCTCCAGTGCTTCAACGGGGGCCAGCAACGACAACCACTACTTCGGCTACAGCACCCCCTGG<br>GGGTATTTTGACTTTAACAGATTCCACTGCCACTTTTCACCACGTGACTGGCAGCGACTCATCAACAACA<br>ACTGGGGATTCCGGCCCAAGAACTCAGCTTCAAGCTCTTCAACATCCAGGTCAAGGAGGTCACGACAGAA<br>TGAAGGCACCAAGACCATCGCCAATAACCTCACCAGCACCATCCAGGTGTTTACGGACTCGGAGTACCAG<br>CTGCCGTACGTTCTCGGCTCTGCGCACCAGGGCTGCCTCCCTCCGTTCCCGGCGGACGTGTTCATGATTC<br>CGCAATACGGCTACCTGACGCTCAACAATGGCAGCCAAGCCGTGGGACGTTCATCCTTTTACTGCCTGGA<br>ATATTTCCCATCGCAGATGCTGAGAACGGCAACAACTTCCAGTTTACTTACACCTTCGAGGATGTACCT<br>TTTCACAGCAGCTACGCTCACAGCCAGAGTTTGGATCGCTTGATGAATCCTCTTATTGATCAGTATCTGT<br>ACTACCTGAACAGAACGCAAGGAACAACCTCTGGAACAACCAACCAATCACGGCTGCTTTTTAGCCAGGC<br>TGGGCCTCAGTCTATGTCTTTGCAGGCCAGAAATTGGCTACCTGGGCCCTGCTACCGGCAACAGAGACTT<br>TCAAAGACTGCTAACGACAACAACAACAGTAACTTTCCTTGGACAGCGGCCAGCAAATATCATCTCAATG<br>GCCGCGACTCGCTGGTGAATCCAGGACCAGCTATGGCCAGTCACAAGGACGATGAAGAAAAATTTTTCCC<br>TATGCACGGCAATCTAATATTTGGCAAAGAAGGGACAACGGCAAGTAACGCAGAATTAGATAATGTAATG<br>ATTACGGATGAAGAAGAGATTCGTACCACCAATCCTGTGGCAACAGAGCAGTATGGAACTGTGGCAAATA<br>ACTTGCAGAGCTCAAATACAGCTCCCACGACTAGAACTGTCAATGATCAGGGGCCCTTACCTGGCATGGT<br>GTGGCAAGATCGTGACGTGTACCTTCAAGGACCTATCTGGGCAAAGATTCCTCACACGGATGGACACTTT<br>CATCCTTCTCCTCTGATGGGAGGGTTTGGAATGAAACACCCGCCTCCTCAGATCCTCATCAAAAACACAC<br>CTGTACCTGCGGATCCTCAACGGCCTTCAACAAGGACAAGTCTGAACTCTTTCATCACCCAGTATTCTAC<br>TGGCCAAGTCAGCGTGGAAATTGAATGGGAGCTGCAGAAGGAAAACAGCAAGCGCTGGAACCCCGAGATC<br>CAGTACACCTCCAACTACTACAAATCTACAAGTGTGGACTTTGCTGTTAATACAGAAGGCGTGTACTCTG<br>AACCCCGCCCCATTGGCACCCGTTACCTCACCCGTAATCTGTAA |

TABLE 3-continued

Variant AAV Capsid Nucleic Acid Sequences

| Description SEQ ID NO: | Nucleic Acid Sequence |
|---|---|
| AAV-10B7 SEQ ID NO: 23 | >10B7<br>ATGGCTGCCGATGGTTATCTTCCAGATTGGCTCGAGGACACTCTCTCTGAAGGAATAAGACAGTGGTGGA<br>AGCTCAAACCTGGCCCACCACCACCAAAGCCCGCAGAGCGGCATAAGGACGACAGCAGGGGTCTTGTGCT<br>TCCTGGGTACAAGTACCTCGGACCCTTCAACGGACTCGACAAGGGAGAGCCGGTCAACGAGGCAGACGCC<br>GCGGCCCTCGAGCACGACAAGGCCTACGACCAGCAGCTCAAAGCGGGTGACAATCCGTACCTCAAGTACA<br>ACCACGCCGACGCCGAGTTCCAGGAGCGGCTCAAAGAAGATACGTCTTTTGGGGGCAACCTCGGGCGAGC<br>AGTCTTCCAGGCGAAAAAGAGGGTTCTTGAACCTCTGGGCCTGGTTGAGGAAGCGGCTAAGACGGCTCCT<br>GGAAAGAAGAGGCCTGTAGAGCACTCTCCTGTGGAGCCAGACTCCTCCTCGGGAACCGGAAAGGCGGGCC<br>AGCAGCCTGCAAGAAAAAGATTGAATTTTGGTCAGACTGGAGACGCAGACTCAGTCCCAGACCCTCAACC<br>TCTCGGAGAACCACCAGCAGCCCCCACAAGTTTGGGATCTAATACAATGGCTTCAGGCGGTGGCGCACCA<br>ATGGCAGACAATAACGAAGGCGCCGACGGAGTGGGTAGTTCCTCAGGAAATTGGCATTGCGATTCCACAT<br>GGCTGGGCGACAGAGTCATCACCACCAGCACCCGCACCTGGGCCTGCCCACTTACAACAACCATCTCTA<br>CAAGCAAATCTCCAGTGCTTCAACGGGGCCAGCAACGACAACCACTACTTCGGCTACAGCACCCCCTGG<br>GGGTATTTTGATTTCAACAGATTCCACTGCCATTTCTCACCACGTGACTGGCAGCGACTCATCAACAACA<br>ACTGGGGGTTCCGGCCCAAGCGACTCAACTTCAAGCTCTTCAACATCCAGGTCAAGGAGGTCACGCAGAA<br>TGAAGGCACCAAGACCATCGCCAATAACCTTACCAGCACGATTCAGGTCTTTACGGACTCGGAATACCAG<br>CTCCCCGTACGTCCTCGGCTCTGCCCACCAGGGCTGCCTGCCTCCGTTCCCGGCGGACGTGTTCATGATTC<br>CCCAGTACGGCTACCTAACACTCAACAACGGTAGTCAGGCGGATGGGTCGCTCGTCCTTCTACTGCCTGGA<br>GTACTTTCCGTCGCAGATGCTGCGGACGGGGAACAACTTCACGTTCAGCTACACCTTCGAGGACGTGCCC<br>TTCCACAGCAGCTACGCGCACAGCCAGAGTCTGGACCGGCTGATGAATCCTCTGATTGACCAGTACCTGT<br>ACTACTTGTCTCGGACTCAGTCCACGGGAGGTACCGCAGGAACTCAGCAGTTGCTATTTTCTCAGGCCGG<br>GCCTAATAACATGTCGGCTCAGGCCAGAAATTGGCTACCTGGGCCCTGCTACCGGCAACAGAGACTTTCA<br>AAGACTGCTAACGACAACAACAACAGTAACTTTCCTTGGACAGCGGCCAGCAAATATCATCTCAATGGCC<br>GCGACTCGCTGGTGAATCCAGGACCAGCTATGGCCAGTCACAAGGACGATGAAGAAAAATTTTTCCCTAT<br>GCACGGCAATCTAATATTTGGCAAAGAAGGGACAACGGCAAGTAACGCAGAATTAGATAATGTAATGATT<br>ACGGATGAAGAAGAGATTCGTACCACCAATCCTGTGGCAACAGAGCAGTATGGAACTGTGGCAAATAACT<br>TGCAGAGCTCAAATACAGCTCCCACGACTAGAACTGTCAATGATCAGGGGCCCTTACCTGGCATGGTGTG<br>GCAAGATCGTGACGTGTACCTTCAAGGACCTATCTGGGCAAAGATTCCTCACACGGATGGACACTTTCAT<br>CCCTCGCCGCTGATGGGAGGCTTTGGACTGAAACACCCGCCTCCTCAGATCCTCATCAAAAACACACCTG<br>TACCTGCGGATCCTCCGACCACCTTCAACCAGTCAAAGCTGAACTCTTTCATCACCCAGTACTCCACTGG<br>ACAGGTCAGCGTGGAGATCGAGTGGGAGCTGCAGAAGGAAAACAGCAAACGCTGGAATCCCGAAATTCAG<br>TACACTTCCAACTACAACAAGTCTGTTAATGTGGACTTTACTGTTGGACACTAATGGCGTGTATTCAGAGC<br>CTCGCCCCATTGGCACCCGTTACCTCACCCGTAATCTGTAA |
| AAV-18B1 SEQ ID NO: 24 | >18B1<br>ATGGCTGCCGATGGTTATCTTCCAGATTGGCTCGAGGACACTCTCTCTGAAGGAATAAGACAGTGGTGGA<br>AGCTCAAACCTGGCCCACCACCACCAAAGCCCGCAGAGCGGCATAAGGACGACAGCAGGGGTCTTGTGCT<br>TCCTGGCTACAAGTACCTCGGACCCTTCAACGGACTCGACAAGGGGGAGCCCGTCAACGCGGCGGATGCA<br>GCGGCCCTCGAGCACGACAAGGCCTACGACCAGCAGCTCAAAGCGGGTGACAATCCGTACCTGCGGTATA<br>ACCACGCCGACGCCGAGTTTCAGGAGCGTCTGCAAGAAGATACGTCTTTTGGGGGCAACCTCGGGCGAGC<br>AGTCTTCCAGGCCAAAAAGAGGCTTCTTGAACCTCTTGGTCTGGTTGAGGAAGCGGCTAAGACGGCTCCT<br>GGAAAGAAGAGGCCTGTAGAGCACTCTCCTGTGGAGCCAGACTCCTCCTCGGGAACCGGAAAGGCGGGCC<br>AGCAGCCTGCAAGAAAAAGATTGAATTTTGGTCAGACTGGAGACGCAGACTCAGTCCCAGACCCTCAACC<br>TCTCGGAGAACCACCAGCAGCCCCCACAAGTTTGGGATCTAATACAATGGCTACAGGCAGTGGCGCACCA<br>ATGGCAGACAATAACGAGGGTGCCGATGGAGTGGGTAATTCCTCAGGAAATTGGCATTGCGATTCCCAAT<br>GGCTGGGCGACAGAGTCATCACCACCAGCACCCGAACATGGGCCTTGCCCACCTATAACAACCACCTCTA<br>CAAGCAAATCTCCAGTGCTTCAACGGGGCCAGCAACGACAACCACTACTTCGGCTACAGCACCCCCTGG<br>GGGTACTTTGACTTCAACCGCTTCCACTGCCACTTCTCCCCGCGAGACTGGCAGCGGCTCATCAACAACA<br>ACTGGGGGTTCCGGCCCAAGCGACTCAACTTCAAGCTCTTCAACATCCAAGTCAAGGAGGTCACGACGAA<br>TGATGCGTCACGACCATCGCTAATAACCTTACCAGCACGGTTCAAGTGTTTACGGACTCGGAGTATCAG<br>CTCCCGTACGTCCTCGGCTCTGCGCACCAGGGCTGCCTCCCTCCGTTCCCGGCGGACGTCTTCATGGTCC<br>CTCAGTATGGATACCTCACCCTGAACAACGGAAGTCAAGGCGGTGGGACGCTCATCCTTTTACTGCCTGGA<br>GTACTTCCCTTCGCAGATGCTAAGGACTGGAAATAACTTCCAATTCAGCTATACCTTCGAGGATGTACCT<br>TTTCACAGCAGCTACGCTCACAGCCAGAGTTTGGATCGCTTGATGAATCCTCTTATTGATCAGTATCTGT<br>ACTACCTGAACAGAACGCAAGGAACAACCTCTGGAACAACCAACCAATCACGGCTGCTTTTTAGCCAGGC<br>TGGGCCTCAGTCTATGTCTTTGCAGGCCAGAAATTGGCTACCTGGGCCCTGCTACCGGCAACAGAGACTT<br>TCAAAGACTGCTAACGACAACAACAACAGTAACTTTCCTTGGACAGCGGCCAGCAAATATCATCTCAATG<br>GCCGCGACTCGCTGGTGAATCCAGGACCAGCTATGGCCAGTCACAAGGACGATGAAGAAAAATTTTTCCC<br>TATGCACGGCAATCTAATATTTGGCAAAGAAGGGACAACGGCAAGTAACGCAGAATTAGATAATGTAATG<br>ATTACGGATGAAGAAGAGATTCGTACCACCAATCCTGTGGCAACAGAGCAGTATGGAACTGTGGCAAATA<br>ACTTGCAGAGCTCAAATACAGCTCCCACGACTAGAACTGTCAATGATCAGGGGCCTTACCTGGCATGGT<br>GTGGCAAGATCGTGACGTGTACCTTCAAGGACCTATCTGGGCAAAGATTCCTCACACGGATGGACACTTT<br>CATCCTTCCTCTGATGGGAGGCTTTGGACTGAAACACCCTCCTCCACAGATTCTCATCAAGAACACCC<br>CGGTACCTGCGAATCCTCCGACCACCTTCAACCAGTCAAAGCTGAACTCTTTCATCACCCCAGTATTCTAC<br>TGGCCAAGTCAGCGTGGAGATCGAGTGGGAGCTGCAGAAGGAAAACAGCAAGCGCTGGAACCCCGAGATC<br>CAGTACACCTCCAACTACTACAAATCTACAAGTGTGGACTTTGCTGTTAATACAGAAGGCGTGTACTCTG<br>AACCCCGCCCCATTGGCACCCGTTACCTCACCCGTAATCTGTAA |
| AAV-18B2 SEQ ID NO: 25 | >18B2<br>ATGGCTGCCGATGGTTATCTTCCAGATTGGCTCGAGGACACTCTCTCTGAAGGAATAAGACAGTGGTGGA<br>AGCTCAAACCTGGCCCACCACCACCAAAGCCCGCAGAGCGGCATAAGGACGACAGCAGGGGTCTTGTGCT<br>TCCTGGGTACAAGTACCTCGGACCCTTCAACGGACTCGACAAGGGGGAGCCCGTCAACGCGGCGGATGCA<br>GCGGCCCTCGAGCACGACAAGGCCTACGACCAGCAGCTCAAAGCGGGTGACAATCCGTACCTGCGGTATA |

TABLE 3-continued

Variant AAV Capsid Nucleic Acid Sequences

| Description SEQ ID NO: | Nucleic Acid Sequence |
|---|---|
| | ACCACGCCGACGCCGAGTTTCAGGAGCGTCTGCAAGAAGATACGTCTTTTGGGGGCAACCTCGGGCGAGC<br>AGTCTTCCAGGCCAAGAAGAGGGTTCTCGAACCTTTTGGTCTGGTTGAGGAAGGTGCTAAGACGGCTCCT<br>GGAAAGAAACGTCCGGTAGAGCACTCTCCTGTGGAGCCAGACTCCTCCTCGGGAACCGGAAAGGCGGGCC<br>AGCAGCCTGCAAGAAAAAGATTGAATTTTGGTCAGACTGGCGACTCAGAGTCAGTTCCAGACCCTCAACC<br>TCTCGGAGAACCTCCAGCAGCGCCCTCTGGTGTGGGACCTAATACAATGGCTTCAGGCGGTGGCGCACCA<br>ATGGCAGACAATAACGAAGGCGCCGACGGAGTGGGTAATGCCTCAGGAAATTGGCATTGCGATTCCACAT<br>GGCTGGGCGACAGAGTCATCACCACCAGCACCCGCACCTGGGCCTTGCCCACCTACAATAACCACCTCTA<br>CAAGCAAATCTCCAGTGCTTCAACGGGGGCCAGCAACGACAACCACTACTTCGGCTACAGCACCCCCTGG<br>GGGTATTTTGACTTCAACAGATTCCACTGCCATTTCTCACCACGTGACTGGCAGCGACTCATCAACAACA<br>ATTGGGGATTCCGGCCCAAGAGACTCAACTTCAAGCTCTTCAACATCCAAGTCAAGGAGGTCACGCAGAA<br>TGACGGTACGACGACGATTGCCAATAACCTTACCAGCACGGTTCAAGTGTTTACGGACTCGGAGTATCAG<br>CTCCCGTACGTGCTCGGGTCGGCGCACCAAGGCTGTCTCCCGCCGTTTCCAGCGGACGTCTTCATGGTCC<br>CGCAGTACGGGTATTTGACGCTGAACAACGGAAGTCAAGCGGTGGGACGCTCATCCTTTTACTGCCTGGA<br>GTACTTCCCTTCGCAGATGCTAAGGACTGGAAATAACTTCCAATTCAGCTATACCTTCGAGGATGTACCT<br>TTTCACAGCAGCTACGCTCACAGCCAGAGTTTGGATCGCTTGATGAATCCTCTTATTGATCAGTATCTGT<br>ACTACCTGAACAGAACGCAAGGAACAACCTCTGGAACAACCAACCAATCACGGCTGCTTTTTAGCCAGGC<br>TGGGCCTCAGTCTATGTCTTTGCAGGCCAGAAATTGGCTACCTGGGCCCTGCTACCGGCAACAGAGACTT<br>TCAAAGACTGCTAACGACAACAACAACAGTAACTTTCCTTGGACAGCGGCCAGCAAATATCATCTCAATG<br>GCCGCGACTCGCTGGTGAATCCAGGACCAGCTATGGCCAGTCACAAGGACGATGAAGAAAATTTTTCCC<br>TATGCACGGCAATCTAATATTTGGCAAAGAAGGGACAACGGCAAGTAACGCAGAATTAGATAATGTAATG<br>ATTACGGATGAAGAAGAGATTCGTACCACCAATCCTGTGGCAACAGAGCAGTATGGAACTGTGGCAAATA<br>ACTTGCAGAGCTCAAATACAGCTCCCACGACTAGAACTGTCAATGATCAGGGGGCCTTACCTGGCATGGT<br>GTGGCAAGATCGTGACGTGTACCTTCAAGGACCTATCTGGGCAAAGATTCCTCACACGGATGGACACTTT<br>CATCCTTCTCCTCTGATGGGCGGCTTTGGACTGAAACATCCGCCTCCTCAAATCATGATCAAAATACTC<br>CGGTACCGGCAAATCCTCCGACGACTTTCAGCCCGGCCAAGTTTGCTTCATTTATCACTCAGTACTCCAC<br>GGGACAGGTCAGCGTGGAGATCGAGTGGGAGCTGCAGAAGGAAAACAGCAAGCGCTGGAACCCCGAGATC<br>CAGTACACCTCCAACTACTACAAATCTACAAGTGTGGACTTTGCTGTTAATACAGAAGGCGTGTACTCTG<br>AACCCCGCCCCATTGGCACCCGTTACCTCACCCGTAATCTGTAA |
| AAV-18B3 SEQ ID NO: 26 | >18B3<br>ATGGCTGCCGATGGTTATCTTCCAGATTGGCTCGAGGACAACCTCTCTGAGGGCATTCGCGAGTGGTGGG<br>ACTTGAAACCTGGAGCCCCGAAACCCAAAGCCAACCAGCAAAAGCAGGACGACGGCCGGGGTCTGGTGCT<br>TCCTGGCTACAAGTACCTCGGACCCTTCAACGGACTCGACAAGGGGGAGCCCGTCAACGCGGCGGATGCA<br>GCGGCCCTCGAGCACGACAAGGCCTACGACCAGCAGCTGCAGGCGGGTGACAATCCGTACCTGCGGTATA<br>ACCACGCCGACGCCGAGTTTCAGGAGCGTCTGCAAGAAGATACGTCTTTTGGGGGCAACCTCGGGCGAGC<br>AGTCTTCCAGGCCAAAAAGAGGCTTCTTGAACCTCTTGGTCTGGTTGAGGAAGCGGCTAAGACGGCTCCT<br>GGAAAGAAGAGGCCTGTAGAGCACTCTCCTGTGGAGCCAGACTCCTCCTCGGGAACCGGAAAGGCGGGCC<br>AGCAGCCTGCAAGAAAAAGATTGAATTTTGGTCAGACTGGAGACGCAGACTCAGTCCCAGACCCTCAACC<br>AATCGGAGAACCTCCCGCAGCCCCCTCAGGTGTGGGATCTCTTACAATGGCTGCAGGCGGTGGCGCACCA<br>ATGGCAGACAATAACGAGGGTGCCGACGGAGTGGGTAATTCCTCGGGAAATTGGCATTGCGATTCCACAT<br>GGATGGGCGACAGAGTCATCACCACCAGCACCCGAACCTGGGCCTGCCCACCTATAACAACCACCTCTA<br>CAAGCAAATCTCCAGTGCTTCAACGGGGGCCAGCAACGACAACCACTACTTCGGCTACAGCACCCCCTGG<br>GGGTATTTTGATTTCAACCGCTTCCACTGCCACTTCTCACCACGTGACTGGCAGCGACTCATCAACAACA<br>ACTGGGGATTCCGGCCCAAGAGACTCAACTTCAAACTCTTCAACATCCAAGTCAAGGAGGTCACGACGAA<br>TGATGGCGTCACGACCATCGCTAATAACCTTACCAGCACGGTTCAAGTCTTCTCGGACTCGGAGTACCAG<br>TTGCCGTACGTCCTCGGCTCTGCGCACCAGGGCTGCCTCCCTCGTTCCCGGCGGACGTGTTCATGATTC<br>CGCAGTACGGCTACCTAACACTCAACAACGGTAGTCAGGCCGTGGGACGCTCCTCCTTCTACTGCCTGGA<br>ATATTTCCCATCGCAGATGCTGAGAACGGGCAATAACTTTACCTTCAGCTACACCTTCGAGGACGTGCCT<br>TTCCACAGCAGCTACGCGCACAGCCAGAGCCTGGACCGGCTGATGAACCCCCTCATCGACCAGTACCTGT<br>ACTACCTGAACAGAACGCAAGGAACAACCTCTGGAACAACCAACCAATCACGGCTGCTTTTTAGCCAGGC<br>TGGGCCTCAGTCTATGTCTTTGCAGGCCAGAAATTGGCTACCTGGGCCCTGCTACCGGCAACAGAGACTT<br>TCAAAGACTGCTAACGACAACAACAACAGTAACTTTCCTTGGACAGCGGCCAGCAAATATCATCTCAATG<br>GCCGCGACTCGCTGGTGAATCCAGGACCAGCTATGGCCAGTCACAAGGACGATGAAGAAAATTTTTCCC<br>TATGCACGGCAATCTAATATTTGGCAAAGAAGGGACAACGGCAAGTAACGCAGAATTAGATAATGTAATG<br>ATTACGGATGAAGAAGAGATTCGTACCACCAATCCTGTGGCAACAGAGCAGTATGGAACTGTGGCAAATA<br>ACTTGCAGAGCTCAAATACAGCTCCCACGACTAGAACTGTCAATGATCAGGGGGCCTTACCTGGCATGGT<br>GTGGCAAGATCGTGACGTGTACCTTCAAGGACCTATCTGGGCAAAGATTCCTCACACGGATGGACACTTT<br>CATCCTTCTCCTCTGATGGGAGGCTTTGGACTGAAACATCCGCCTCCTCAAATCATGATCAAAATACTC<br>CGGTACCGGCAAATCCTCCGACGACTTTCAGCCCGGCCAAGTTTGCTTCATTTATCACTCAGTACTCCAC<br>TGGACAGGTCAGCGTGGAAATTGAGTGGGAGCTACAGAAGAAAACAGCAAACGTTGGAATCCAGAGATT<br>CAGTACACTTCCAACTACAACAAGTCTGTTAATGTGGACTTTACTGTAGACACTAATGGTGTTTATAGTG<br>AACCTCGCCCCATTGGCACCCGTTACCTTACCCGTCCCCTGTAA |

TABLE 4

Parent AAV Capsid Amino Acid Sequences

| Description SEQ ID NO: | Amino Acid Sequence |
|---|---|
| Avian AAV SEQ ID NO: 27 | >avian<br>MSLISDAIPDWLERLVKKGVNAAADFYHLESGPPRPKANQQTQESLEKDDSRGLVFPGYNYLGPFNGLDK<br>GEPVNEADAAALEHDKAYDLEIKDGHNPYFEYNEADRRFQERLKDDTSFGGNLGKAIFQAKKRVLEPFGL<br>VEDSKTAPTGDKRKGEDEPRLPDTPPQTPKKNKKPRKERPSGGAEDPGEGTSSNAGAAAPASSVGSSIMA<br>EGGGGPVGDAGQGADGVGNSSGNWHCDSQWLENGVVTRTTRTWVLPSYNNHLYKRIQGPSGGDNNNKFFG<br>FSTPWGYFDYNRFHCHFSPRDWQRLINNNWGIRPKAMRFRLFNIQVKEVTVQDSNTTIANNLTSTVQVFA<br>DKDYQLPYVLGSATEGTFPPFPADIYTIPQYGYCTLNYNNEAVDRSAFYCLDYFPSDMLRTGNNFEFTYT<br>FEDVPFHSMFAHNQTLDRLMNPLVDQYLWAFSSVSQAGSSGRALHYSRATKTNMAAQYRNWLPGPFFRDQ<br>QIFTGASNITKNNVFSVWEKGKQWELDNRTNLMQPGPAAATTFSGEPDRQAMQNTLAFSRTVYDQTTATT<br>DRNQILITNEDEIRPTNSVGIDAWGAVPTNNQSIVTPGTRAAVNNQGALPGMVWQNRDIYLQGPIWAKIP<br>DTDNHFHPSPLIGGFGCKHPPPQIFIKNTPVPANPSETFQTAKVASFINQYSTGQCTVEIFWELKKETSK<br>RWNPEIQFTSNFGNAADIQFAVSDTGSYSEPRPIGTRYLTKPL |
| Procine 1 AAV SEQ ID NO: 28 | >porcine_1<br>MSFVDHPPDWLEEIGEGLKEFLGLEPGPPKPKPNQQKQDDARGLVLPGYNYLGPGNGLDREPVNRADEV<br>AREHDISYNEQLQAGDNPYLKYNHADAEFQEKLADDTSFGGNLGKAVFQAKKRVLEPFGLVEEPVKTAAK<br>GERIDDHYPKKKKARIEETEAGTSGAQQLQIPAQPASSLGADTMSAGGGSPLGDNNQGADGVGNASGDWH<br>CDSTWMGDRVITKSTRTWVLPSYNNHQYLEIHSGSVDGSNANAYFGYSTPWGYFDENREHSHWSPRDWQR<br>LVNNYWGFRPRSLKVIFNIQVKEVTTQDGTTTIANNLTSTVQVFTDNDYQLPYVIGNGTEGCLPAFPPQ<br>VETLPQYGYATLNRNNTDDPTERSSFFCLEYFPSKMLRTGNNFEFTYSFEEVPFHCSFAPSQNLFKLANP<br>LVDQYLYRFVSTDTSGNLQFQKNLKARYANTYKNWFPGPMCRTQGWYTSAGTYNNKGVANFDTSNKMELE<br>GASYQVNPQPNGMTNTLQDSNKYALENTMIFNAQNAPPGTTSLYQENNLLITSESETQPVNRLAYNTGGQ<br>VSNNNQNSNTHPTVGVYNHQEVLPGSVWMDRDVYLQGPIWAKIPETGAHFHPSPAMGGFGLKHPPPMMLI<br>KNTPVPSNVAAFSDVPVKSFITQYSTGQVTVEIEWELKKENSKRWNPEIQYTNNYNNPTFVDFAPDTSGE<br>YRTTRAIGTRYLTRPL |
| AAV5 SEQ ID NO: 29 | >AAV5<br>MSFVDHPPDWLEEVGEGLREFLGLEAGPPPKPKPNQQHQDQARGLVLPGYNYLGPGNGLDREPVNRADEV<br>AREHDISYNEQLEAGDNPYLKYNHADAEFQEKLADDTSFGGNLGKAVFQAKKRVLEPFGLVEEGAKTAPT<br>GKRIDDHFPKRKKARTEEDSKPSTSSDAEAGPSGSQQLQIPAQPASSLGADTMSAGGGGPLGDNNQGADG<br>VGNASGDWHCDSTWMGDRVVTKSTRTWVLPSYNNHQYREIKSGSVDGSNANAYFGYSTPWGYFDENREHS<br>HWSPRDWQRLINNYWGFRPRSLRVKIFNIQVKEVTVQDSTTIANNLTSTVQVFTDDDYQLPYVVGNGTE<br>GCLPAFPPQVFTLPQYGYATLNRDTENPTERSSFFCLEYFPSKMLRTGNNFEFTYNFEEVPFHSSFAPS<br>QNLFKLANPLVDQYLYRFVSTNNTGGVQFNKLAGRYANTYKNWFPGPMGRTQGWNLGSGVNRASVSAFA<br>TTNRMELEGASYQVPPQPNGMTNNLQGSNTYALENTMIFNSQPANPGTTATYLEGNMLITSESETQPVNR<br>VAYNVGGQMATNNQSTTAPATGTYNLQEIVPGSVWMERDVYLQGPIWAKIPETGAHFHPSPAMGGFGLK<br>HPPPMMLIKNTPVPGNITSFSDVPVSSFITQYSTGQVTVEMEWELKKENSKRWNPEIQYTNNYNDPQFVD<br>FAPDSTGEYRTTRPIGTRYLTRPL |
| Goat 1 AAV SEQ ID NO: 30 | >goat_1<br>MSFVDHPPDWLEEVGEGLREFLGLEAGPPPKPKPNQQHQDQARGLVLPGYNYLGPGNGLDREPVNRADEV<br>AREHDISYNEQLEAGDNPYLKYNHADAEFQEKLADDTSFGGNLGKAVFQAKKRVLEPFGLVEEGAKTAPT<br>GKRIDDHFPKRKKARTEEDSKPSTSSDAEAGPSGSQQLQIPAQPASSLGADTMSAGGGGPLGDNNQGADG<br>VGNASGDWHCDSTWMGDRVVTKSTRTWVLPSYNNHQYREIKSGSVDGSNANAYFGYSTPWGYFDENREHS<br>HWSPRDWQRLINNYWGFRPRSLRVKIFNIQVKEVTVQDSTTTIANNLTSTVQVFTDDDYQLPYVVGNGTE<br>GCLPAFPPQVFTLPQYGYATLNRDNGDNPTERSSFFCLEYFPSKMLRTGNNFEFTYSFEEVPFHCSFAPS<br>QNLFKLANPLVDQYLYRFVSTSATGAIQFQKNLAGRYANTYKNWFPGPMGRTQGWNTSSGSSTNRVSVNN<br>FSVSNRMNLEGASYQVNPQPNGMTNTLQGSNRYALENTMIFNAQNATPGTTSVYPEDNLLLTSESETQPV<br>NRVAYNTGGQMATNAQNATTAPTVGTYNLQEVLPGSVWMERDVYLQGPIWAKIPETGAHFHPSPAMGGFG<br>LKHPPPMMLIKNTPVPGNITSFSDVPVSSFITQYSTGQVTVEMEWELKKENSKRWNPEIQYTNNYNDPQF<br>VDFAPDGSGEYRTTRAIGTRYLTRPL |
| Mouse 1 AAV SEQ ID NO: 31 | >mouse_1<br>MSFFDWLGKQYAQGAAEFWDLKSGPPAPKKARKDGSAGFNFPGHKYLGPGNSLDRGDPVDADDAAAQKHD<br>QSYQEQLEAGDNPYLKYNHADREFQEALKDDTSFEGNLARGLFEAKKLVAEPLGLVEPELAPPSGRKRPV<br>QSSQESGYSSSQDKRPNLDVDEEDREFAAAAAETETGSAPPTGNLGPGTMAGGGSAPIDDGSYGADGVGN<br>ASGDWHCDSTWLDNCVITRTTRTWNLPTYNNHIYKRLNGTTSGDQSYFGFSTPWGYFDFNRFHCHFSPRD<br>WQRLINNNWGLRPKSLRFKIFNIQVKEVTTQDSTKIISNNLTSTVQVFADTEYQLPYVIGSAHEGCLPPF<br>PADVFMLPQYGYCTRQDGNSNPTPTRSAFYCLEYFPSKMLRTGNSFEFTYNFEKVPFHSMWAHNQSLDRL<br>MNPLIDQYLYYLDVTSSTGFTYQKGVHTNLPEQERNWLPGPGIRNQAWFNSATGNNPLTGTWQYSNKYVL<br>ENRASKIAPGPAMGIESTKFDGNGIIFSKEYITNVNTANPNQVNITRETEINSTNPLAGGSLGAHANNSQ<br>NTTTAPTLDHTNVMGVFPGSVWQDRDIYLQGQIWAKIPHTDGHFHPSPLMGGFGLKNPPPQILIKNTPVP<br>ADPPTEFNANKISSFITQYSTGQVTVEMEWELQKETSKRWNPEIQYSDDSSSTSGSILHFAPDDVGNYKE<br>FRSIGTRYLTRPL |
| Procine 2 AAV SEQ ID NO: 32 | >porcine_2<br>MSFVDHPPDWLEEVGEGLHEFLELEAGPPKPKPNQQKQDNARGLVLPGYNYLGPFNGLDKGEPVNRADAV<br>AREHDISYNEQLQAGDNPYLKYNHADAEFQEKLKDDTSFGGNLGKAIFQAKKRVLEPFGLVEAPVKTAPA<br>KKRPIEKSPAEPSSSKGIGKAGQQPARKRLNFGQTGDTDSAADPQPLGEPPAAPSGLGTGTMASGSGAPM<br>ADNNEGADGVGNASGNWHCDSTWLGDRVITTSTRTWALPTYNNHLYKQISSQSGANNDNHYFGYSTPWGY<br>FDFNRFHCHFSPRDWQRLINNNWGFRPKRLNFKLFNIQVKEVTQTDGTKTIANNLTSTVQVFADSEYQLP<br>YVLGSAHQGCFPPFPADVFMPQYGYLTLNNGSQAMGRSSFYCLEYFPSQMLRTGNNFTFSYTFEDVPFH<br>SSYAHSQSLDRLMNPLIDQYLYYLSKTNGGLGFSQAGPNSMRDQSRNWLPGPCFRQQRISTVPTQNNNGD<br>FSWTGATKYHLNGRNSAMNPGPAMASHKDDEHRFFPQNGVLIFGKQGADKTNAILEKVIVTDEEEIRTTN |

TABLE 4-continued

Parent AAV Capsid Amino Acid Sequences

| Description SEQ ID NO: | Amino Acid Sequence |
|---|---|
| | PVATEEYGFVATNLQSSAETAETERVNAQGILPGMVWQDRDVYLQGPIWAKIPHTDGHFRPSPLMGGFGL<br>KHPPPQILIKNTPVPSNPPETFNPEKLNSFITQYSTGQVSVEIEWELQKENSKRWNPEVQYTSNYNKSVN<br>VEFTVDNNGVYSEPRTIGTRYLTRNL |
| AAV9hu14<br>SEQ ID<br>NO: 33 | >AAV9hu14<br>MAADGYLPDWLEDNLSEGIREWWALKPGAPQPKANQQHQDNARGLVLPGYKYLGPGNGLDKGEPVNAADA<br>AALEHDKAYDQQLKAGDNPYLKYNHADAEFQERLKEDTSFGGNLGRAVFQAKKRLLEPLGLVEEAAKTAP<br>GKKRPVEQSPQEPDSSAGIGKSGAQPAKKRLNFGQTGDTESVPDPQPIGEPPAAPSGVGSLTMASGGGAP<br>VADNNEGADGVGSSSGNWHCDSQWLGDRVITTSTRTWALPTYNNHLYKQISNSTSGGSSNDNAYFGYSTP<br>WGYFDFNRFHCHFSPRDWQRLINNNWGFRPKRLNFKLFNIQVKEVTDNNGVKTIANNLTSTVQVFTDSDY<br>QLPYVLGSAHEGCLPPFPADVFMIPQYGYLTLNDGSQAVGRSSFYCLEYFPSQMLRTGNNFQFSYEFENV<br>PFHSSYAHSQSLDRLMNPLIDQYLYYLSKTINGSGQNQQTLKFSVAGPSNMAVQGRNYIPGPSYRQQRVS<br>TTVTQNNNSEFAWPGASSWALNGRNSLMNPGPAMASHKEGEDRFFPLSGSLIFGKQGTGRDNVDADKVMI<br>TNEEEIKTTNPVATESYGQVATNHQSAQAQAQTGWVQNQGILPGMVWQDRDVYLQGPIWAKIPHTDGNFH<br>PSPLMGGFGMKHPPPQILIKNTPVPADPPTAFNKDKLNSFITQYSTGQVSVEIEWELQKENSKRWNPEIQ<br>YTSNYYKSNNVEFAVNTEGVYSEPRPIGTRYLTRNL |
| AAV1<br>SEQ ID<br>NO: 34 | >AAV1<br>MAADGYLPDWLEDNLSEGIREWWDLKPGAPKPKANQQKQDDGRGLVLPGYKYLGPFNGLDKGEPVNAADA<br>AALEHDKAYDQQLKAGDNPYLRYNHADAEFQERLQEDTSFGGNLGRAVFQAKKRVLEPLGLVEEGAKTAP<br>GKKRPVEQSPQEPDSSSGIGKTGQQPAKKRLNFGQTGDSESVPDPQPLGEPPATPAAVGPTTMASGGGAP<br>MADNNEGADGVGNASGNWHCDSTWLGDRVITTSTRTWALPTYNNHLYKQISSASTGASNDNHYFGYSTPW<br>GYFDENREHCHFSPRDWQRLINNNWGFRPKRLNFKLFNIQVKEVTTNDGVTTIANNLTSTVQVFSDSEYQ<br>LPYVLGSAHQGCLPPFPADVFMIPQYGYLTLNNGSQAVGRSSFYCLEYFPSQMLRTGNNFTFSYTFEEVP<br>FHSSYAHSQSLDRLMNPLIDQYLYYLNRTQNQSGSAQNKDLLFSRGSPAGMSVQPKNWLPGPCYRQQRVS<br>KTKTDNNNSNFTWTGASKYNLNGRESIINPGTAMASHKDDEDKFFPMSGVMIFGKESAGASNTALDNVMI<br>TDEEEIKATNPVATEREGTVAVNFQSSSTDPATGDVHAMGALPGMVWQDRDVYLQGPIWAKIPHTDGHFH<br>PSPLMGGFGLKNPPPQILIKNTPVPANPPAEFSATKFASFITQYSTGQVSVEIEWELQKENSKRWNPEVQ<br>YTSNYAKSANVDFTVDNNGLYTEPRPIGTRYLTRPL |
| AAV6<br>SEQ ID<br>NO: 35 | >AAV6<br>MAADGYLPDWLEDNLSEGIREWWDLKPGAPKPKANQQKQDDGRGLVLPGYKYLGPFNGLDKGEPVNAADA<br>AALEHDKAYDQQLKAGDNPYLRYNHADAEFQERLQEDTSFGGNLGRAVFQAKKRVLEPFGLVEEGAKTAP<br>GKKRPVEQSPQEPDSSSGIGKTGQQPAKKRLNFGQTGDSESVPDPQPLGEPPATPAAVGPTTMASGGGAP<br>MADNNEGADGVGNASGNWHCDSTWLGDRVITTSTRTWALPTYNNHLYKQISSASTGASNDNHYFGYSTPW<br>GYFDENREHCHFSPRDWQRLINNNWGFRPKRLNFKLFNIQVKEVTTNDGVTTIANNLTSTVQVFTDSEYQ<br>LPYVLGSAHQGCLPPFPADVFMIPQYGYLTLNNGSQAVGRSSFYCLEYFPSQMLRTGNNFTFSYTFEDVP<br>FHSSYAHSQSLDRLMNPLIDQYLYYLNRTQNQSGSAQNKDLLFSRGSPAGMSVQPKNWLPGPCYRQQRVS<br>KTKTDNNNSNFTWTGASKYNLNGRESIINPGTAMASHKDDKDKFFPMSGVMIFGKESAGASNTALDNVMI<br>TDEEEIKATNPVATERFGTVAVNLQSSSTDPATGDVHVMGALPGMVWQDRDVYLQGPIWAKIPHTDGHFH<br>PSPLMGGFGLKHPPPQILIKNTPVPANPPAEFSATKFASFITQYSTGQVSVEIEWELQKENSKRWNPEVQ<br>YTSNYAKSANVDFTVDNNGLYTEPRPIGTRYLTRPL |
| AAV3B<br>SEQ ID<br>NO: 36 | >A7V3B<br>MAADGYLPDWLEDNLSEGIREWWALKPGVPQPKANQQHQDNRRGLVLPGYKYLGPGNGLDKGEPVNEADA<br>AALEHDKAYDQQLKAGDNPYLKYNHADAEFQERLQEDTSFGGNLGRAVFQAKKRILEPLGLVEEAAKTAP<br>GKKRPVDQSPQEPDSSSGVGKSGKQPARKRLNFGQTGDSESVPDPQPLGEPPAAPTSLGSNTMASGGGAP<br>MADNNEGADGVGNSSGNWHCDSQWLGDRVITTSTRTWALPTYNNHLYKQISSQSGASNDNHYFGYSTPWG<br>YEDENREHCHFSPRDWQRLINNNWGFRPKKLSFKLFNIQVKEVTQNDGTTTIANNLTSTVQVFTDSEYQL<br>PYVLGSAHQGCLPPFPADVFMVPQYGYLTLNNGSQAVGRSSFYCLEYFPSQMLRTGNNFQFSYTFEDVPF<br>HSSYAHSQSLDRLMNPLIDQYLYYLNRTQGTTSGTTNQSRLLFSQAGPQSMSLQARNWLPGPCYRQQRLS<br>KTANDNNNSNFPWTAASKYHLNGRDSLVNPGPAMASHKDDEEKFFPMHGNLIFGKEGTTASNAELDNVMI<br>TDEEEIRTTNPVATEQYGTVANNLQSSNTAPTTRTVNDQGALPGMVWQDRDVYLQGPIWAKIPHTDGHFH<br>PSPLMGGFGLKHPPPQIMIKNTPVPANPPTTFSPAKFASFITQYSTGQVSVEIEWELQKENSKRWNPEIQ<br>YTSNYNKSVNVDFTVDTNGVYSEPRPIGTRYLTRNL |
| LK03<br>SEQ ID<br>NO: 37 | >LK03<br>MAADGYLPDWLEDNLSEGIREWWALQPGAPKPKANQQHQDNARGLVLPGYKYLGPGNGLDKGEPVNAADA<br>AALEHDKAYDQQLKAGDNPYLKYNHADAEFQERLKEDTSFGGNLGRAVFQAKKRLLEPLGLVEEAAKTAP<br>GKKRPVDQSPQEPDSSSGVGKSGKQPARKRLNFGQTGDSESVPDPQPLGEPPAAPTSLGSNTMASGGGAP<br>MADNNEGADGVGNSSGNWHCDSQWLGDRVITTSTRTWALPTYNNHLYKQISSQSGASNDNHYFGYSTPWG<br>YEDENREHCHFSPRDWQRLINNNWGFRPKKLSFKLFNIQVKEVTQNDGTTTIANNLTSTVQVFTDSEYQL<br>PYVLGSAHQGCLPPFPADVFMVPQYGYLTLNNGSQAVGRSSFYCLEYFPSQMLRTGNNFQFSYTFEDVPF<br>HSSYAHSQSLDRLMNPLIDQYLYYLNRTQGTTSGTTNQSRLLFSQAGPQSMSLQARNWLPGPCYRQQRLS<br>KTANDNNNSNFPWTAASKYHLNGRDSLVNPGPAMASHKDDEEKFFPMHGNLIFGKEGTTASNAELDNVMI<br>TDEEEIRTTNPVATEQYGTVANNLQSSNTAPTTRTVNDQGALPGMVWQDRDVYLQGPIWAKIPHTDGHFH<br>PSPLMGGFGLKHPPPQIMIKNTPVPANPPTTFSPAKFASFITQYSTGQVSVEIEWELQKENSKRWNPEIQ<br>YTSNYNKSVNVDFTVDTNGVYSEPRPIGTRYLTRPL |
| AAV8<br>SEQ ID<br>NO: 38 | >AAV8<br>MAADGYLPDWLEDNLSEGIREWWALKPGAPKPKANQQKQDDGRGLVLPGYKYLGPFNGLDKGEPVNAADA<br>AALEHDKAYDQQLQAGDNPYLRYNHADAEFQERLQEDTSFGGNLGRAVFQAKKRVLEPLGLVEEGAKTAP<br>GKKRPVEPSPQRSPDSSTGIGKKGQQPARKRLNEGQTGDSESVPDPQPLGEPPAAPSGVGPNTMAAGGGA<br>PMADNNEGADGVGSSSGNWHCDSTWLGDRVITTSTRTWALPTYNNHLYKQISNGTSGGATNDNTYFGYST |

TABLE 4-continued

Parent AAV Capsid Amino Acid Sequences

| Description SEQ ID NO: | Amino Acid Sequence |
|---|---|
| | PWGYFDENREHCHFSPRDWQRLINNNWGFRPKRLSFKLENIQVKEVTQNEGTKTIANNLTSTIQVFTDSE YQLPYVLGSAHQGCLPPEPADVFMIPQYGYLTLNNGSQAVGRSSFYCLEYFPSQMLRTGNNFQFTYTED VPFHSSYAHSQSLDRLMNPLIDQYLYLSRTQTTGGTANTQTLGESQGGPNTMANQAKNWLPGPCYRQQR VSTTTGQNNNSNFAWTAGTKYHLNGRNSLANPGIAMATHKDDEERFFPSNGILIFGKQNAARDNADYSDV MLTSEEEIKTTNPVATEEYGIVADNLQQQNTAPQIGTVNSQGALPGMVWQNRDVYLQGPIWAKIPHTDGN FHPSPLMGGEGLKHPPPQILIKNTPVPADPPTTENQSKLNSFITQYSTGQVSVEIEWELQKENSKRWNPE IQYTSNYYKSTSVDFAVNTEGVYSEPRPIGTRYLTRNL |
| Rhesus 10 AAV SEQ ID NO: 39 | >rhesus_10<br>MAADGYLPDWLEDNLSEGIREWWDLKPGAPKPKANQQKQDDGRGLVLPGYKYLGPFNGLDKGEPVNAADA AALEHDKAYDQQLKAGDNPYLRYNHADAEFQERLQEDTSFGGNLGRAVFQAKKRVLEPLGLVEEGAKTAP GKKRPVEPSPQRSPDSSTGIGKKGQQPAKKRLNEGQTGDSESVPDPQPIGEPPAGPSGLGSGTMAAGGGA PMADNNEGADVGSSSGNWHCDSTWLGDRVITTSTRTWALPTYNNHLYKQISNGTSGGSTNDNTYFGYST PWGYFDENREHCHFSPRDWQRLINNNWGFRPKRLNEKLENIQVKEVTQNEGTKTIANNLTSTIQVFTDSE YQLPYVLGSAHQGCLPPEPADVFMIPQYGYLTLNNGSQAVGRSSFYCLEYFPSQMLRTGNNFEFSYQFED VPFHSSYAHSQSLDRLMNPLIDQYLYLSRTQSTGGTAGTQQLLFSQAGPNNMSAQAKNWLPGPCYRQQR VSTTLSQNNNSNFAWTGATKYHLNGRDSLVNPGVAMATHKDDEERFFPSSGVLMFGKQGAGKDNVDYSSV MLTSEEEIKTTNPVATEQYGVADNLQQQNAAPIVGAVNSQGALPGMVWQNRDVYLQGPIWAKIPHTDGN FHPSPLMGGEGLKHPPPQILIKNTPVPADPPTTESQAKLASFITQYSTGQVSVEIEWELQKENSKRWNPE IQYTSNYYKSTNVDFAVNTDGTYSEPRPIGTRYLTRNL |
| AAV2 SEQ ID NO: 40 | >AAV2<br>MAADGYLPDWLEDTLSEGIRQWWKLKPGPPPPKPAERHKDDSRGLVLPGYKYLGPFNGLDKGEPVNEADA AALEHDKAYDRQLDSGDNPYLKYNHADAEFQERLKEDTSFGGNLGRAVFQAKKRVLEPLGLVEEPVKTAP GKKRPVEHSPVEPDSSSGTGKAGQQPARKRLNFGQTGDADSVPDPQPLGQPPAAPSGLGTNTMATGSGAP MADNNEGADGVGNSSGNWHCDSTWMGDRVITTSTRTWALPTYNNHLYKQISSQSGASNDNHYFGYSTPWG YEDENREHCHFSPRDWQRLINNNWGFRPKRLNFKLENIQVKEVTQNDGTTTIANNLTSTVQVFTDSEYQL PYVLGSAHQGCLPPFADVFMVPQYGYLTLNNGSQAVGRSSFYCLEYFPSQMLRTGNNFTESYTFEDVPF HSSYAHSQSLDRLMNPLIDQYLYLSRTNTPSGTTTQSRLQFSQAGASDIRDQSRNWLPGPCYRQQRVSK TSADNNNSEYSWTGATKYHLNGRDSLVNPGPAMASHKDDEEKFFPQSGVLIFGKQGSEKTNVDIEKVMIT DEEEIRTTNPVATEQYGSVSTNLQRGNRQAATADVNTQGVLPGMVWQDRDVYLQGPIWAKIPHTDGHFHP SPLMGGEGLKHPPPQILIKNTPVPANPSTTESAAKFASFITQYSTGQVSVEIEWELQKENSKRWNPEIQY TSNYNKSVNVDFTVDTNGVYSEPRPIGTRYLTRNL |
| DJ SEQ ID NO: 41 | >DJ<br>MAADGYLPDWLEDTLSEGIRQWWKLKPGPPPPKPAERHKDDSRGLVLPGYKYLGPFNGLDKGEPVNEADA AALEHDKAYDRQLDSGDNPYLKYNHADAEFQERLKEDTSFGGNLGRAVFQAKKRLLEPLGLVEEAAKTAP GKKRPVEHSPVEPDSSSGTGKAGQQPARKRLNEGQTGDADSVPDPQPIGEPPAAPSGVGSLTMAAGGGAP MADNNEGADGVGNSSGNWHCDSTWMGDRVITTSTRTWALPTYNNHLYKQISNSTSGGSSNDNAYEGYSTP WGYFDENREHCHFSPRDWQRLINNNWGFRPKRLSFKLENIQVKEVTQNEGTKTIANNLTSTIQVFTDSEY QLPYVLGSAHQGCLPPEPADVFMIPQYGYLTLNNGSQAVGRSSFYCLEYFPSQMLRTGNNFQFTYTFEDV PFHSSYAHSQSLDRLMNPLIDQYLYLSRTQTTGGTTNTQTLGESQGGPNTMANQAKNWLPGPCYRQQRV SKTSADNNNSEYSWTGATKYHLNGRDSLVNPGPAMASHKDDEEKFFPQSGVLIFGKQGSEKTNVDIEKVM ITDEEEIRTTNPVATEQYGSVSTNLQRGNRQAATADVNTQGVLPGMVWQDRDVYLQGPIWAKIPHTDGHF HPSPLMGGEGLKHPPPQILIKNTPVPADPPTTENQSKLNSFITQYSTGQVSVEIEWELQKENSKRWNPEI QYTSNYYKSTSVDFAVNTEGVYSEPRPIGTRYLTRNL |
| BOVINE AAV SEQ ID NO: 42 | >bovine<br>MSFVDHPPDWLESIGDGFREFLGLEAGPPKPKANQQKQDNARGLVLPGYKYLGPGNGLDKGDPVNFADEV AREHDLSYQKQLEAGDNPYLKYNHADAEFQEKLASDTSEGGNLGKAVFQAKKRILEPLGLVETPDKTAPA AKKRPLEQSPQEPDSSSGVGKKGKQPARKRLNEDDEPGAGDGPPPEGPSSGAMSTETEMRAAAGGNGGDA GQGAEGVGNASGDWHCDSTWSESHVTTTSTRTWVLPTYNNHLYLRLGSSNASDTFNGFSTPWGYFDFNRF HCHFSPRDWQRLINNNHWGLRPKSMQVRIFNIQVKEVTTSNGETTVSNNLTSTVQIFADSTYELPYVMDAG QEGSLPPFPNDVFMVPQYGYCGLVTGGSSQNQTDRNAFYCLEYFPSQMLRTGNNFEMVYKFENVPFHSMY AHSQSLDRLMNPLLDQYLWELQSTTSGGTLNQGNSATNFAKLTKTNESGYRKNWLPGPMMKQQRFSKTAS QNYKIPQGRNNSLLHYETRTTLDGRWSNFAPGTAMATAANDATDFSQAQLIFAGPNITGNTTTDANNLMF TSEDELRATNPRDTDLFGHLATNQQNATTVPTVDDVDGVGVYPGMVWQDRDIYYQGPIWAKIPHTDGHFH PSPLIGGFGLKSPPPQIFIKNTPVPANPATTFSPARINSFITQYSTGQVAVKIEWEIQKERSKRWNPEVQ FTSNYGAQDSLLWAPDNAGAYKEPRAIGSRYLTNHL |
| AAV4 SEQ ID NO: 43 | >AAV4<br>MTDGYLPDWLEDNLSEGVREWWALQPGAPKPKANQQHQDNARGLVLPGYKYLGPGNGLDKGEPVNAADAA ALEHDKAYDQQLKAGDNPYLKYNHADAEFQQRLQGDTSFGGNLGRAVFQAKKRVLEPLGLVEQAGETAPG KKRPLIESPQQPDSSTGIGKKGKQPAKKKLVFEDETGAGDGPPEGSTSGAMSDDSEMRAAAGGAAVEGGQ GADGVGNASGDWHCDSTWSEGHVTTTSTRTWVLPTYNNHLYKRLGESLQSNTYNGFSTPWGYFDFNRFHC HFSPRDWQRLINNNWGMRPKAMRVKIFNIQVKEVTTSNGETTVANNLTSTVQIFADSSYELPYVMDAGEQ GSLPPFPNDVFMVPQYGYCGLVTGNTSQQQTDRNAFYCLEYFPSQMLRTGNNFEITYSFEKVPFHSMYAH SQSLDRLMNPLIDQYLWGLQSTTTGTTLNAGTATTNETKLRPTNESNEKKNWLPGPSIKQQGFSKTANQN YKIPATGSDSLIKYETHSTLDGRWSALTPGPPMATAGPADSKFSNSQLIFAGPEQNGNTATVPGTLIFTS EEELAATNATDTDMWGNLPGGDQSNSNLPTVDRLTALGAVPGMVWQNRDIYYQGPIWAKIPHTDGHFHPS PLIGGFGLKHPPPQIFIKNTPVPANPATTFSSTPVNSFITQYSTGQVSVQIDWEIQKERSKRWNPEVQFT SNYGQQNSLLWAPDAAGKYTEPRAIGTRYLTHHL |

TABLE 4-continued

Parent AAV Capsid Amino Acid Sequences

Description
SEQ ID
NO: Amino Acid Sequence

AAV12
SEQ ID
NO: 44

>AAV12
MAADGYLPDWLEDNLSEGIREWWALKPGAPQPKANQQHQDNGRGLVLPGYKYLGPFNGLDKGEPVNEADA
AALEHDKAYDKQLEQGDNPYLKYNHGDAEFQQRLATDTSFGGNLGRAVFQAKKRILEPLGLVEEGVKTAP
GKKRPLEKTPNRPTNPDSGKAPAKKKQKDGEPADSARRTLDFEDSGAGDGPPEGSSSGEMSHDAEMRAAP
GGNAVEAGQGADGVGNASGDWHCDSTWSEGRVTTTSTRTWVLPTYNNHLYLRIGTTANSNTYNGFSTPWG
YEDENREHCHFSPRDWQRLINNNWGLRPKSMRVKIFNIQVKEVTTSNGETTVANNLTSTVQIFADSTYEL
PYVMDAGQEGSFPPFPNDVFMVPQYGYCGVVTGKNQNQTDRNAFYCLEYFPSQMLRTGNNFEVSYQFEKV
PFHSMYAHSQSLDRMMNPLLDQYLWHLQSTTTGNSLNQGTATTTYGKITTGDFAYYRKNWLPGACIKQQK
FSKNANQNYKIPASGGDALLKYDTHTTLNGRWSNMAPGPPMATAGAGDSDFSNSQLIFAGPNPSGNTTTS
SNNLLFTSEEEIATTNPRDTDMFGQIADNNQNATTAPHIANLDAMGIVPGMVWQNRDIYYQGPIWAKVPH
TDGHFHPSPLMGGFGLKHPPPQIFIKNTPVPANPNTTFSAARINSFLTQYSTGQVAVQIDWEIQKEHSKR
WNPEVQFTSNYGTQNSMLWAPDNAGNYHELRAI GS RFLTHHL

TABLE 5

Parent AAV Capsid Nucleic Acid Sequences

Description
SEQ ID
NO: Nucleic Acid Sequence

Avian AAV
SEQ ID
NO: 45

>avian
ATGTCTCTCATTTCTGATGCGATTCCAGATTGGTTGGAGCGGTTGGTCAAAAAGGGAGTGAATGCTGCAG
CTGATTTCTACCATTTGGAAAGCGGTCCTCCTCGTCCTAAGGCAAATCAGCAAACTCAAGAATCTCTTGA
AAAGGACGATTCGAGAGGTCTCGTGTTCCCAGGCTACAATTATCTAGGCCCCTTCAACGGTCTAGATAAA
GGAGAACCCGTCAACGAGGCAGACGCTGCCGCCTTAGAACACGACAAGGCTTACGACCTCGAAATCAAGG
ACGGGCACAACCCGTACTTTGAGTACAACGAGGCCGACAGACGTTTCCAGGAACGTCTCAAAGACGATAC
CTCCTTTGGAGGCAATTTAGGTAAAGCCATCTTCCAGGCCAAAAAGAGGGTTCTCGAACCCTTTGGTCTG
GTGGAAGACTCAAAGACGGCTCCGACCGGAGACAAGCGGAAAGGCGAAGACGAACCTCGTCTGCCCGACA
CTCCTCCACAGACTCCCAAGAAAACAAGAAGCCTCGCAAGGAAAGACCTTCCGGCGGGGCAGAAGATCC
GGGCGAAGGCACCTCTTCAACGCTGGAGCAGCAGCACCCGCCTCTAGTGTGGGATCATCTATCATGGCT
GAAGGAGGTGGCGGCCCAGTGGGCGATGCAGGCCAGGGTGCCAGTGGAGTGGGCAATTCCTCGGGAAATT
GGCATTGCGATTCCCAATGGCTGGAAAACGGAGTCGTCACTCGAACCACCCGAACCTGGGTCTTGCCCAG
CTACAACAACCACCTGTACAAACGAATCAAGGACCCAGCGGAGGCGACAACAACAACAAATTCTTTGGA
TTCAGCACCCCTGGGGATACTTTGACTACAATCGATTCCACTGCCACTTTTCCCCGCGAGACTGGCAAC
GACTCATCAACAACAACTGGGGCATCCGTCCCAAAGCGATGCGCTTTAGACTCTTTTAACATCCAGGTTAA
AGAGGTCACGGTCCAAGACTCCAACACCACCATCGCCAACAACCTCACCAGTACGGTCCAGGTCTTTGCG
GACAAGGACTACCAACTGCCGTACGTCCTCGGATCGGCTACCGAAGGCACCTTCCCGCGCGTTCCCAGCGG
ATATCTACACGATCCCGCAGTACGGGTACTGCACGTAAACTACAACAACGAGGCGGTGGATCGTTCGGC
CTTCTACTGTCTGGACTACTTTCCCTCAGACATGCTGCGGACAGGAAATAACTTTGAGTTTACTTACACC
TTCGAGGACGTTCCTTTCCCATAGCATGTTTGCCCACAACCAGACGCTAGACCGGCTGATGAATCCCCTCG
TGGATCAGTACCTCTGGGCTTTCAGCTCCGTCAGCCAAGCAGGCTCATCTGGACGAGCTCTTCATTACTC
GCGGGCGACTAAAACCAACATGGC
GGCTCAATATAGGAACTGGTTACCTGGGCCTTTCTTCCGTGATCAGCAAATCTTTACGGGCGCTAGCAAC
ATCACTAAAAATAACGTCTTTAGCGTTTGGGAAAAAGGCAAGCAATGGGAACTCGACAATCGGACCAACC
TAATGCAGCCCGGTCCTGCGGCAGCGACCACCTTTAGCGGAGAACCTGACCGTCAAGCCATGCAAAACAC
GCTGGCTTTTAGCAGGACCGTCTACGATCAAACGACCGCCACGACCGATCGTAACCAGATACTCATCACC
AACGAAGACGAAATCAGACCCACCAACTCGGTCGGTATCGACGCGTGGGGAGCAGTTCCCACCAACAACC
AGTCGATCGTGACCCCCGGCACTCGCGCGGCCGTCAACAATCAAGGGGCGCTTCCCGGGATGGTGTGGCA
AAACAGAGACATTTACCTACAGGGACCCATTTGGGCCAAAATTCCCGACACTGACAATCACTTCCATCCG
TCCCCGCTTATTGGCGGGTTTGGCTGCAAGCATCCCCCTCCCCAGATTTTCATTAAAAACACACCCGTCC
CTGCCAACCCTTCGGAAACGTTCCAGACGGCCAAAGTGGCCTCCTTCATCAACCAGTACTCGACCGGACA
GTGCACCGTCGAAATCTTTTGGGAACTCAAGAAGGAAATCCTCAAGCGCTGGAACCCCGAAATCCAGTTC
ACCTCCAACTTTGGCAACGCGGCCGACATCCAGTTTGCCGTCTCCGACACGGGATCCTATTCCGAACCTC
GTCCCATCGGTACCCGTTACCTTACCAAACCTCTGTAA Procine 1
AAV
SEQ ID
NO: 46

>porcine1
ATGTCGTTTGTTGATCACCCTCCAGATTGGCTTGAGGAGATTGGTGAGGGTCTAAAGGAGTTTTTGGGAC
TCGAACCTGGCCCACCCAAACCGAAGCCCAACCAGCAGAAGCAAGACGACGCCCGTGGTCTTGTACTGCC
TGGATATAATTACCTGGGACCCGGAAACGGTCTCGACCGCGGAGAACCTGTCAACCGGGCTGACGAGGTC
GCGCGAGAGCACGACATCTCGTACAACGAGCAGCTCCAGGCGGGAGACAACCCCTACCTCAAGTACAACC
ACGCGGACGCCGAGTTTCAGGAGAAGCTCGCGGACGACACCTCCTTCGGGGGCAACCTCGGCAAGGCAGT
CTTTCAGGCCAAAAAAGGGTTCTCGAACCTTTTGGCCTGGTTGAGGAGCCTGTTAAGACGGCTGCTAAA
GGCGAGCGGATAGACGACCACTATCCCAAAAAGAAGAAGGCTCGGATCGAAGAGACCGAAGCTGGAACCA
GCGGAGCCCAGCAGCTGCAGATCCCAGCCCAACCAGCCTCAAGTTTGGGAGCTGATACAATGTCTGCGGG
AGGTGCAGCCCACTGGGCGACAATAACCAAGGCGCCGATGGAGTGGGCAATGCCTCGGGAGATTGGCAT
TGCGATTCCACGTGGATGGGGACCGAGTCATCACCAAGTCCACCCGAACCTGGGTGCTGCCCAGCTACA
ACAACCATCAGTACCTTGAGATCCACAGCGGTTCCGTCGACGGAAGCAACGCTAACGCTTATTTTGGATA
CAGCACCCCTGGGGGTACTTTGACTTCAACCGCTTCCACAGCCACTGGAGCCCCGAGACTGGCAGCGA
CTCGTCAACAACTACTGGGGATTCAGACCCCGGTCCCTCAAGGTCAAGATCTTTAACATCCAAGTCAAGG TABLE 5-continued Parent AAV Capsid Nucleic Acid Sequences

| Description SEQ ID NO: | Nucleic Acid Sequence |
|---|---|
| | AAGTCACGACGCAGGACGGCACCACCACCATCGCCAACAACCTCACCTCCACCGTCCAAGTGTTTACGGA<br>CAACGACTACCAGCTACCGTACGTCATCGGCAACGGAACGGAGGGGTGCCTGCCGGCCTTCCCTCCGCAG<br>GTCTTTACGCTGCCGCAGTACGGCTAC<br>GCGACACTGAACCGTAACAACACCGACGATCCCACCGAGCGGAGCAGTTTCTTCTGC<br>CTGGAATACTTTCCCAGCAAGATGCTGCGGACGGGCAACAACTTTGAATTCACCTACAGCTTCGAGGAGG<br>TGCCCTTCCACTGCAGCTTCGCTCCCAGCCAGAACCTCTTCAAGCTGGCCAATCCGCTGGTGGACCAGTA<br>CCTGTACCGCTTTGTGAGCACCGACACTTCCGGTAACCTACAGTTCCAAAAGAACTTGAAGGCCAGATAT<br>GCCAACACTTACAAGAATTGGTTTCCGGGGCCCATGTGCCGGACCCAGGGCTGGTACACAAGCGCGGCA<br>CATATAACAACAAAGGCGTTGCCAACTTTGATACTTCAAACAAGATGGAACTGGAGGGGGCTAGTTACCA<br>AGTAAACCCTCAACCAAATGGAATGACAAACACGCTTCAGGATAGTAACAAATACGCGCTTGAAAACACC<br>ATGATCTTCAACGCACAGAACGCCCCTCCGGGAACGACCTCTCTGTACCAGGAGAACAATCTTTTGATAA<br>CCAGCGAGAGCGAGACGCAGCCTGTGAACCGATTGGCCTACAACACCGGTGGTCAGGTATCAAACAACAA<br>CCAGAATTCAAATACACATCCTACGGTCGGAGTATACAATCACCAGGAAGTGTTGCCTGGTAGCGTGTGG<br>ATGGACAGAGACGTATACCTTCAGGGCCCCATCTGGGCCAAAATCCCGGAGACAGGGGCACACTTTCATC<br>CTTCTCCGGCTATGGGCGGATTCGGACTCAAACACCCACCGCCCATGATGCTCATCAAGAACACACCGGT<br>ACCTAGCAACGTCGCTGCCTTCTCTGACGTGCCCGTTAAAAGCTTCATCACCCAGTACAGCACCGGACAG<br>GTCACGGTGGAGATTAATGGGAGCTCAAGAAAGAAAACTCCAAGAGGTGGAATCCCGAGATACAGTACA<br>CCAACAACTACAACAACCCTACATTCGTGGACTTTGCTCCAGACACCTCCGGCGAGTACAGGACTACGAG<br>GGCTATTGGAACCCGTTACCTTACCCGACCCCTGTAA |
| AAV5<br>SEQ ID<br>NO: 47 | >AAV5<br>ATGTCTTTTGTTGATCACCCTCCAGATTGGTTGGAAGAAGTTGGTGAAGGTCTTCGCGAGTTTTTGGGCC<br>TTGAAGCGGGCCCACCGAAACCAAAACCCAATCAGCAGCATCAAGATCAAGCCCGTGGTCTTGTGCTGCC<br>TGGTTATAACTATCTCGGACCCGGAAACGGTCTCGATCGAGGAGAGCCTGTCAACAGGGCAGACGAGGTC<br>GCGCGAGAGCACGACATCTCGTACAACGAGCAGCTTGAGGCGGGAGACAACCCCTACCTCAAGTACAACC<br>ACGCGGACGCCGAGTTTCAGGAGAAGCTCGCCGACGACACATCCTTCGGGGGAAACCTCGGAAAGGCAGT<br>CTTTCAGGCCAAGAAAAGGGTTCTCGAACCTTTTGGCCTGGTTGAAGAGGGTGCTAAGACGGCCCCTACC<br>GGAAAGCGGATAGACGACCACTTTCCAAAAAGAAAGAAGGCTCGGACCGAAGAGGACTCCAAGCCTTCCA<br>CCTCGTCAGACGCCGAAGCTGGACCCAGCGGATCCCAGCAGCTGCAAATCCCAGCCAACCAGCCTCAAG<br>TTTGGGAGCTGATACAATGTCTGCGGGAGGTGGCGGCCCATTGGGCGACAATAACCAAGGTGCCGATGGA<br>GTGGGCAATGCCTCGGGAGATTGGCATTGCGATTCCACGTGGATGGGGGACAGAGTCGTCACCAAGTCCA<br>CCCGAACCTGGGTGCTGCCCAGCTACAACAACCACCAGTACCGAGAGATCAAAAGCGGCTCCGTCGACGG<br>AAGCAACGCCAACGCCTACTTTGGATACAGCACCCCTGGGGGTACTTTGACTTTAACGCTTCCACAGC<br>CACTGGAGCCCCCGAGACTGGCAAAGACTCATCAACAACTACTGGGGCTTCAGACCCCGGTCCCTCAGAG<br>TCAAAATCTTCAACATTCAAGTCAAAGAGGTCACGGTGCAGGACTCCACCACCACCATCGCCAACAACCT<br>CACCTCCACCGTCCAAGTGTTTACGGACGACGACTACCAGCTCCCTACGTCGTCGGCAACGGGACCGAG<br>GGATGCCTGCCGGCCTTCCCTCCGCAGGTCTTTACGCTGCCGCAGTACGGTTACGCGACGCTGAACCGCG<br>ACAACACAGAAAATCCCACCGAGAGGAGCAGCTTCTTCTGCCTAGAGTACTTTCCCAGCAAGATGCTGAG<br>AACGGGCAACAACTTTGAGTTTACCTACAACTTTGAGGAGGTGCCCTTCCACTCCAGCTTCGCTCCCAGT<br>CAGAACCTCTTCAAGCTGGCCAACCCGCTGGTGGACCAGTACTTGTACCGCTTCGTGAGCACAAATAACA<br>CTGGCGGAGTCCAGTTCAACAAGAACCTGGCCGGGAGATACGCCAACACCTACAAAAACTGGTTCCCGGG<br>GCCCATGGGCCGAACCCAGGGCTGGAACCTGGGCTCCGGGGTCAACCGCGCCAGTGTCAGCGCCTTCGCC<br>ACGACCAATAGGATGGAGCTCGAGGGCGCGAGTTACCAGGTGCCCCCGCAGCCGAACGGCAT<br>GACCAACAACCTCCAGGGCAGCAACACCTATGCCCTGGAGAACACTATGATCTTCAACAGCCAGCCGGCG<br>AACCCGGGCACCACCGCCACGTACCTCGAGGGCAACATGCTCATCACCAGCGAGAGCGAGACGCAGCCGG<br>TGAACCGCGTGGCGTACAACGTCGGCGGCCAGATGGCCACCAACAACCAGAGCTCCACCACTGCCCCCGC<br>GACCGGCACGTACAACCTCCAGGAAATCGTGCCCGGCAGCGTGTGGATGGAGAGGGACGTGTACCTCCAA<br>GGACCCATCTGGGCCAAGATCCCAGAGACGGGGGCGCACTTTCACCCCTCTCCGGCCATGGGCGGATTCG<br>GACTCAAACACCCACCGCCCATGATGCTCATCAAGAACACGCCTGTGCCCGGAAATATCACCAGCTTCTC<br>GGACGTGCCCGTCAGCAGCTTCATCACCCAGTACAGCACCGGGCAGGTCACCGTGGAGATGGAGTGGGAG<br>CTCAAGAAGGAAAACTCCAAGAGGTGGAACCCAGAGATCCAGTACACAAACAACTACAACGACCCCCAGT<br>TTGTGGACTTTGCCCCGGACAGCACCGGGGAATACAGAACCACCAGACCTATCGGAACCCGATACCTTAC<br>CCGACCCCTTTAA |
| Goat 1<br>AAV<br>SEQ ID<br>NO: 48 | >goat1<br>ATGTCTTTTGTTGATCACCCTCCAGATTGGTTGGAAGAAGTTGGTGAAGGTCTTCGCGAGTTTTTGGGCC<br>TTGAAGCGGGCCCACCGAAACCGAAACCCAACCAGCAGCATCAAGATCAAGCCCGTGGTCTTGTGCTGCC<br>TGGTTATAACTATCTCGGACCCGGAAACGGTCTCGATCGAGGAGAGCCTGTCAACAGGGCAGACGAGGTC<br>GCGCGAGAGCACGACATCTCGTACAACGAGCAGCTTGAGGCGGGAGACAACCCCTACCTCAAGTACAACC<br>ACGCGGACGCCGAGTTCCAGGAGAAGCTCGCCGACGACACATCCTTCGGGGGAAACCTCGGAAAGGCAGT<br>CTTTCAGGCCAAGAAAAGGGTTCTCGAACCTTTTGGCCTGGTTGAAGAGGGTGCTAAGACGGCCCCTACC<br>GGAAAGCGGATAGACGACCACTTTCCAAAAAGAAAGAAGGCTCGGACCGAAGAGGACTCCAAGCCTTCCA<br>CCTCGTCAGACGCCGAAGCTGGACCCAGCGGATCCCAGCAGCTGCAAATCCCAGCACAACCAGCCTCAAG<br>TTTGGGAGCTGATACAATGTCTGCGGGAGGTGGCGGCCCATTGGGCGACAATAACCAAGGTGCCGATGGA<br>GTGGGCAATGCCTCGGGAGATTGGCATTGCGATTCCACGTGGATGGGGGACAGAGTCGTCACCAAGTCCA<br>CCCGCACCTGGGTGCTGCCCAGCTACAACAACCACCAGTACCGAGAGATCAAAAGCGGCTCCGTCGACGG<br>AAGCAACGCCAACGCCTACTTTGGATACAGCACCCCTGGGGGTACTTTGACTTTAACGCTTCCACAGC<br>CACTGGAGCCCCCGAGACTGGCAAAGACTCATCAACAACTATTGGGGCTTCAGACCCCGGTCTCTCAGAG<br>TCAAAATCTTCAACATCAAGTCAAAGAGGTCACGGTGCAGGACTCCACCACCACCATCGCCAACAACCT<br>CACCTCCACCGTCCAAGTGTTTACGGACGACGACTACCAACTCCCGTACGTCGTCGGCAACGGGACCGAG<br>GGATGCCTGCCGGCCTTCCCCCCGCAGGTCTTTACGCTGCCGCAGTACGGCTACGCGACGCTGAACCGAG<br>ACAACGGAGACAACCCGACAGAGCGGAGCAGCTTCTTTTGCCTAGAGTACTTTCCCAGCAAGATGCTGAG<br>GACGGGCAACAACTTTGAGTTTACCTACAGCTTTGAAGAGGTGCCCTTCCACTGCAGCTTCGCCCCGAGC<br>CAGAACCTCTTTAAGCTGGCCAACCCGCTGGTGGACCAGTACCTGTACCGCTTCGTGAGCACCTCGGCCA |

TABLE 5-continued

Parent AAV Capsid Nucleic Acid Sequences

| Description SEQ ID NO: | Nucleic Acid Sequence |
|---|---|
| | CGGGCGCCATCCAGTTCCAAAAGAACCTGGCGGGCAGATACGCCAACACCTACAAAAACTGGTTCCCGGG<br>GCCCATGGGCCGAACCCAGGGCTGGAACACGAGCTCTGGCAGCAGCACCAACAGAGTCAGCGTCAACAAC<br>TTTTCCGTCTCAAACCGGATGAACCTGGAGGGGGCCAGCTACCAAGTGAACCCCCAGCCCAACGGGATGA<br>CAAACACGCTCCAAGGCAGCAACCGCTACGCGCTGGAAAACACCATGATCTTCAACGCTCAAAACGCCAC<br>GCCGGGAACTACCTCGGTGTACCCAGAGGACAATCTACTGCTGACCAGCGAGAGCGAGACTCAGCCCGTC<br>AACCGGGTGGCTTACAACACGGGCGGTCAGATGGCCACCAACGCCCAGAACGCCACCACGGCTCCCACGG<br>TCGGGACCTACAACCTCCAGGAAGTGCTTCCTGGCAGCGTATGGATGGAGAGGGACGTGTACCTCCAAGG<br>ACCCATCTGGGCCAAGATCCCAGAGACGGGGGCGCACTTTCACCCCTCTCCGGCCATGGGCGGATTCGGA<br>CTCAAACACCCGCCGCCCATGATGCTCATCAAAAACACGCCGGTGCCCGGCAACATCACCAGCTTCTCGG<br>ACGTGCCCGTCAGCAGCTTCATCACCCAGTACAGCACCGGGCAGGTCACCGTGGAGATGGAATGGGAGCT<br>CAAAAAGGAAAACTCCAAGAGGTGGAACCCAGAGATCCAGTACACCAACAACTACAACGACCCCCAGTTT<br>GTGGACTTTGCTCCAGACGGCTCCGGCGAATACAGAACCACCAGAGCCATCGGAACCCGATACCTCACCC<br>GACCCCTTTAA |
| Mouse 1 AAV SEQ ID NO: 49 | >mouse1<br>ATGTCTTTCTTTGATTGGTTAGGTAAACAGTACGCTCAAGGAGCTGCTGAATTCTGGGATTTGAAGTCCG<br>GTCCTCCTGCACCAAAAAAGGCGCGAAAGGACGGATCAGCCGGATTCAATTTCCCTGGGCACAAATACCT<br>GGGTCCTGGCAATTCATTGGATCGCGGAGATCCCGTGGACGCTGACGACGCCGCTGCTCAAAAGCACGAC<br>CAGTCGTACCAAGAGCAGCTTGAGGCGGGAGACAATCCCTACCTCAAGTACAACCACGCCGACCGCGAGT<br>TCCAGGAGGCGTTGAAGGACGACACCTCCTTTGAAGGAAATCTCGCGAGAGGACTCTTTGAGGCCAAGAA<br>GCTCGTGGCAGAGCCTCTTGGTCTCGTGGAACCAGAACTGGCGCCACCCAGTGGCCGTAAACGACCGGTG<br>CAATCGAGTCAAGAGTCTGGTTACTCGAGTAGCCAAGACAAGCGGCCCAACCTCGACGTAGACGAGGAGG<br>ACCGTGAGTTCGCTGCCGCTGCAGCGGAGACCGAAACTGGAAGCGCTCCCCCCACCGGCAATTTGGGACC<br>TGGTACGATGGCTGGAGGCGGTAGCGCGCCAATCGACGACGGCTCGTATGGTGCCGATGGAGTGGGCAAT<br>GCCTCGGGAGATTGGCATTGCGATTCCACATGGCTGGACAACTGTGTCATCACCCGAACCACTCGGACCT<br>GGAATCTGCCAACCTACAACAACCACATCTACAAACGACTCAACGGAACGACCTCCGGAGACCAAAGCTA<br>CTTCGGATTCAGCACCCCCTGGGGATACTTTGACTTCAACCGCTTCCACTGTCATTTCTCCCCTCGAGAC<br>TGGCAAAGACTCATCAACAATAACTGGGGACTCCGACCAAAGAGCCTACGGTTCAAATCTTTAACATTC<br>AAGTTAAAGAAGTCACGACGCAAGACTCAACGAAGATCATCTCCAATAACCTTACCAGCACGGTTCAGGT<br>ATTTGCGGACACGGAGTACCAGCTCCCGTACGTGATTGGATCGGCTCACGAAGGATGTCTGCCTCCTTTC<br>CCGGCTGACGTGTTCATGCTGCCGCAGTATGGATACTGTACTGACAAGACGGAAACAGCAACAATCCGA<br>CCCCGAGAAGCGCCTTCTATTGTTTGGAGTACTTTCCCAGCAAGATGCTAAGAACTGGGAACAGTTTTGA<br>ATTTACATATAACTTTGAGAAGGTGCCGTTCCACAGCATGTGGGCTCACAACCAGAGTCTGGATCGATTG<br>ATGAATCCATTGATTGATCAGTACCTGTACTACCTTGATGTCACTTCGAG<br>TACCGGGTTTACCTATCAAAAAGGAGTTCACACGAACTTGCCCGAACAAGAGCGCAACTGGCTGCCGGGA<br>CCAGGAATTCGAAATCAAGCTTGGTTTAATTCTGCAACTGGAAACAACCCACTAACTGGTACCTGGCAAT<br>ATTCCAACAAATACGTACTAGAAAACCGTGCTTCGAAGATTGCTCCTGGACCTGCCATGGGAATTGAATC<br>AACAAAATTCGACGGGAACGGAATCATCTTTTCTAAAGAATACATCACCAATGTAAATACAGCCAATCCG<br>AATCAAGTAAACATCACACGCGAGACCGAAATAAACTCAACGAACCCCTTGGCTGGAGGATCTCTCGGAG<br>CCCACGCTAATAATTCACAAAACACAACAACGGCACCGACTAGACCAACACCAACGTCATGGGTGTGTT<br>TCCGGGTAGTGTCTGGCAAGACAGAGACATTTACCTTCAAGGACAAATCTGGGCCAAGATTCCCCACACA<br>GACGGACATTTCCACCCTTCTCCTCTCATGGGAGGATTTGGACTGAAGAACCCGCCTCCTCAAATTCTGA<br>TCAAAAACACACCTGTTCCGGCTGACCCACCAACTGAATTCAATGCGAACAAAATCTCTTCTTTCATCAC<br>TCAATACTCAACCGGACAAGTTACAGTGGAAATGGAATGGGAACTTCAGAAAGAAACCTCCAAAAGATGG<br>AATCCAGAAATCCAGTACAGCGACGACTCGTCTTCGACGTCTGGCTCCATTCTGCACTTTGCTCCGGATG<br>ATGTTGGAAACTACAAAGAGTTCCGCTCTATCGGAACTCGTTACCTTACCCGTCCTCTGTAA |
| Procine 2 AAV SEQ ID NO: 50 | >porcine2<br>ATGTCGTTTGTTGATCACCCTCCAGATTGGTTAGAAGAAGTTGGTGAAGGCCTTCACGAGTTTTTGGAGC<br>TCGAAGCTGGCCCACCCAAACCGAAGCCCAACCAGCAGAAGCAGGACAACGCCCGTGGTCTTGTACTGCC<br>TGGATATAATTATCTGGGACCCTTCAACGGACTCGACAAGGGAGAGCCCGTCAACCGAGCGGACGCTGTT<br>GCGCGAGAGCACGACATCTCGTACAACGAGCAGCTCCAGGCGGGAGACAACCCCTACCTCAAGTACAACA<br>ACGCGGACGCCGAGTTTCAGGAGAAGCTCAAGGACGACACCTCCTTTGGGGGCAACCTCGGAAAGGCAAT<br>CTTTCAGGCCAAGAAAAGGGTTCTCGAACCTTTTGGCCTGGTTGAGGCACCTGTTAAGACGGCTCCAGCC<br>AAGAAGCGGCCGATAGAGAAGCTCTCCGGCGGAACCGAGCTCTTCGAAGGGCATCGGCAAGGCGGGCCAGC<br>AGCCTGCGGAGGAAGCGACTCAACTTTGGTCAGACTGGAGACACCGACTCCGCCGCTGACCCCCAGCCTCT<br>CGGAGAACCACCAGCAGCCCCTCTGGTCTGGGAACTGGTACGATGGCTTCAGGCAGTGGCGCACCAATG<br>GCAGACAATAACGAAGGCGCCGACGAGTGGGTAATGCCTCGGGAAATTGGCATTGCGATTCCACATGGCC<br>TGGGCGACCGAGTCATCACCACCAGCACCCGCACCTGGGCCCTGCCCACCTACAACAACATCTCTACAA<br>GCAAATCTCCAGCCAGTCTGGAGCCAACAACGACAACCACTACTTTGGCTACAGCACCCCCTGGGGGTAC<br>TTTGACTTCAACCGCTTCCACTGCCACTTCTCCCCGCGACGATGGCAGCGGCTCATCAACAACAACTGGG<br>GGTTCCGGCCCAAGCGACTCAACTTCAAGCTCTTCAACATCCAAGTCAAGGAGGTCACTCAGACGACGG<br>CACGAAGACCATCGCCAATAACCTTACCAGCACGGTTCAGGTCTTTGCGGACTCGGAGTACCAGCTCCCG<br>TACGTCCTCGGATCAGCGCACCAGGGCTGCTTCCCGCCGTTCCCGGCGGACGTCTTCATGGTCCCGCAGT<br>ACGGGTATTTGACGCTGAACAACGGCAGCCAGGCGATGGGTCGCTCGTCCTTCTACTGCCTGGAGTACTT<br>TCCGTCGCAGATGCTGCGGACGGGGAACAACTTCACGTTCAGCTACACCTTCGAGGACGTGCCCTTCCAC<br>AGCAGCTACGCGCACAGCCAGAGTCTGGACCGGCTCATGAACCCACTCATCGACCAGTACCTGTACTACC<br>TAAGCAAGACAAATGGCGGTCAGGATTTTCCCAAGCGGGACCCAACAGCATGCGCGACCAGTCCAGGAA<br>TTGGCTGCCGGGACCCTGCTTCAGACAACAACGGATTTCAACTGTACCTACCACAAAATAACAACGGACAA<br>TTTTCGTGGACGGGAGCCACAAAGTATCATCTCAATGGAAGAAACTCAGCAATGAATCCCGGCCCGGCCA<br>TGGCCAGCCACAAAGACGACGAACACAGATTCTTCCCTCAGAACGGTGTGCTCATCTTTGGAAAACAGGG<br>CGCAGACAAGACAAATGCGATACTAGAAAAAGTGATCGTTACAGACGAAGAGGAGATTAGGACAACAAAT<br>CCTGTAGCCACGGAGGAGTATGGGTTTGTCGCCACTAATCTACAAAGCTCGGCAGAAACAGCCGAGACCG<br>AAAGAGTCAACGCGCAAGGCATCCTCCCTGGCATGGTGTGGCAAGACCGAGATGTGTATCTGCAGGGGCC |

TABLE 5-continued

Parent AAV Capsid Nucleic Acid Sequences

| Description SEQ ID NO: | Nucleic Acid Sequence |
|---|---|
| | CATCTGGGCCAAGATCCCCCACACCGACGGACACTTCCGCCCCTCACCACTCATGGGAGGATTCGGCCTC<br>AAGCACCCGCCTCCGCAGATCCTCATCAAGAACACGCCTGTGCCTTCGAATCCTCCAGAGACGTTCAACC<br>CGGAAAAGCTCAATTCTTTCATAACTCAATATTCTACGGGCCAGGTCAGCGTGGAGATCGAGTGGGAGCT<br>GCAGAAGGAGAACAGCAAGCGCTGGAACCCCGAGGTCCAGTACACGTCCAACTACAACAAGTCCGTCAAC<br>GTGGAATTTACAGTGGACAACAACGGCGTGTATTCGGAACCGCGCACCATCGGCACCCGCTACCTTACTC<br>GTAATCTGTAA |
| AAV9hu14<br>SEQ ID<br>NO: 51 | >AAV9hu14<br>ATGGCTGCCGATGGTTATCTTCCAGATTGGCTCGAGGACAACCTTAGTGAAGGAATTCGCGAGTGGTGGG<br>CTTTGAAACCTGGAGCCCCTCAACCCAAGGCAAATCAACAACATCAAGACAACGCTCGAGGTCTTGTGCT<br>TCCGGGTTACAAATACCTTGGACCCGGCAACGGACTCGACAAGGGGGAGCCGGTCAACGCAGCAGACGCG<br>GCGGCCCTCGAGCACGACAAGGCCTACGACCAGCAGCTCAAGGCCGGAGCAACCCGTACCTCAAGTACA<br>ACCACGCCGACGCCGAGTTCCAGGAGCGGCTCAAAGAAGATACGTCTTTTGGGGGCAACCTCGGGCGAGC<br>AGTCTTCCAGGCCAAAAAGAGGGCTTCTTGAACCTCTTGGTCTGGTTGAGGAAGCGGCTAAGACGGCTCCT<br>GGAAAGAAGAGGCCTGTAGAGCAGTCTCCTCAGGAACCGGACTCCTCCGCGGGTATTGGCAAATCGGGTG<br>CACAGCCCGCTAAAAAGAGACTCAATTTCGGTCAGACTGGCGACACAGAGTCAGTCCCAGACCCTCAACC<br>AATCGGAGAACCTCCCGCAGCCCCCTCAGGTGTGGGATCTCTTACAATGGCTTCAGGTGGTGGCGCACCA<br>GTGGCAGACAATAACGAAGGTGCCGATGGAGTGGGTAGTTCCTCGGGAAATTGGCATTGCGATTCCCAAT<br>GGCTGGGGGACAGAGTCATCACCACCAGCACCCGAACCTGGGCCTGCCCACCTACAACAATCACCTCTA<br>CAAGCAAATCTCCAACAGCACATCTGGAGGATCTTCAAATGACAACGCCTACTTCGGCTACAGCACCCCC<br>TGGGGGTATTTTGACTTCAACAGATTCCACTGCCACTTCTCACCACGTGACTGGCAGCGACTCATCAACA<br>ACAACTGGGGATTCCGGCCTAAGCGACTCAACTTCAAGCTCTTCAACATTCAGGTCAAAGAGGTTACGGA<br>CAACAATGGAGTCAAGACCATCGCCAATAACCTTACCAGCACGGTCCAGGTCTTCACGGACTCAGACTAT<br>CAGCTCCCGTACGTGCTCGGGTCGGCT<br>CACGAGGGCTGCCTCCCGCCGTTCCCAGCGGACGTTTTCATGATTCCTCAGTACGGGTATCTGACGCTTA<br>ATGATGGAAGCCAGGCCGTGGGTCGTTCGTCCTTTTACTGCCTGGAATATTTCCCGTCGCAAATGCTAAG<br>AACGGGTAACAACTTCCAGTTCAGCTACGAGTTTGAAAACGTACCTTTCCATAGCAGCTACGCTCACAGC<br>CAAAGCCTGGACCGACTAATGAATCCACTCATCGACCAATACTTGTACTATCTCTCAAAGACTATTAACG<br>GTTCTGG<br>ACAGAATCAACAAACGCTAAAATTCAGTGTGGCCGGACCCAGCAACATGGCTGTCCAGGGAAGAAACTAC<br>ATACCTGGACCCAGCTACCGACAACAACGTGTCTCAACCACTGTGACTCAAAACAACAACAGCGAATTTG<br>CTTGGCCTGGAGCTTCTTCTTGGGCTCAATGGACGTAATAGCTTGATGAATCCTGGACCTGCTATGGC<br>CAGCCACAAAGAAGGAGAGGACCGTTTCTTTCCTTTGTCTGGATCTTTAATTTTTGGCAAACAAGGAACT<br>GGAAGAGACAACGTGGATGCGGACAAAGTCATGATAACCAACGAAGAAGAAATTAAAACTACTAACCCGG<br>TAGCAACGGAGTCCTATGGACAAGTGGCCACAAACCACCAGAGTGCCCAAGCACAGGCGCAGACCGGCTG<br>GGTTCAAAACCAAGGAATACTTCCGGGTATGGTTTGGCAGGACAGAGATGTGTACCTGCAAGGACCCATT<br>TGGGCCAAAATTCCTCACACGGACGGCAACTTTCACCCTTCTCCGCTGATGGGAGGGTTTGGAATGAAAC<br>ACCCGCCTCCTCAGATCCTCATCAAAAACACACCTGTACCTGCGGATCCTCCAACGGCCTTCAACAAGGA<br>CAAGCTGAACTCTTTCATCACCCAGTATTCTACTGGCCAAGTCAGCGTGGAGATCGAGTGGGAGCTGCAG<br>AAGGAAAACAGCAAGCGCTGGAACCCGGAGATCCAGTACACTTCCAACTATTACAAGTCTAATAATGTTG<br>AATTTGCTGTTAATACTGAAGGTGTATATAGTGAACCCCGCCCCATTGGCACCAGATACCTGACTCGTAA<br>TCTGTAA |
| AAV1<br>SEQ ID<br>NO: 52 | >AAV1<br>ATGGCTGCCGATGGTTATCTTCCAGATTGGCTCGAGGACAACCTCTCTGAGGGCATTCGCGAGTGGTGGG<br>ACTTGAAACCTGGAGCCCCGAAGCCCAAAGCCAACCAGCAAAAGCAGGACGACGGCCGGGGTCTGGTGCT<br>TCCTGGCTACAAGTACCTCGGACCCTTCAACGGACTCGACAAGGGGGAGCCCGTCAACGCGGCGGACGCA<br>GCGGCCCTCGAGCACGACAAGGCCTACGACCAGCAGCTCAAAGCGGGTGACAATCCGTACCTTCGGTATA<br>ACCACGCCGACGCCGAGTTTCAGGAGCGTCTGCAAGAAGATACGTCTTTTGGGGGCAACCTCGGGCGAGC<br>AGTCTTCCAGGCCAAGAAGCGGGTTCTCGAACCTCTCGGTCTGGTTGAGGAAGGCGCTAAGACGGCTCCT<br>GGAAAGAAACGTCCGGTAGAGCAGTCGCCACAAGAGCCAGACTCCTCCTCGGGCATCGGCAAGACAGGCC<br>AGCAGCCCGCTAAAAAGAGACTCAATTTTGGTCAGACTGGCGACTCAGAGTCAGTCCCCGACCCACAACC<br>TCTCGGAGAACCTCCAGCAACCCCCGCTGCTGTGGGACCTACTACAATGGCTTCAGGCGGTGGCGCACCA<br>ATGGCAGACAATAACGAAGGCGCCGACGGAGTGGGTAATGCCTCAGGAAATTGGCATTGCGATTCCACAT<br>GGCTGGGCGACAGAGTCATCACCACCAGCACCCGCACCTGGGCCTTGCCCACCTACAATAACCACCTCTA<br>CAAGCAAATCTCCAGTGCTTCAACGGGGCCAGCAACGACAACCACTACTTCGGCTACAGCACCCCCTGG<br>GGGTATTTTGATTTCAACAGATTCCACTGCCACTTTTCACCACGTGACTGGCAGCGACTCATCAACAACA<br>ATTGGGGATTCCGGCCCAAGAGACTCAACTTCAAACTCTTCAACATCCAAGTCAAGGAGGTCACGACGAA<br>TGATGGCGTCACAACCATCGCTAATAACCTTACCAGCACGGTTCAAGTCTTCTCGGACTCGGAGTACCAG<br>CTTCCGTACGTCCTCGGCTCTGCGCACCAGGGCTGCCTCCCTCCGTTCCCGGCGGACGTGTTCATGATTC<br>CGCAATACGGCTACCTGACGCTCAACAATGGCAGCCAAGCCGTGGGACGTTCATCCTTTTACTGCCTGGA<br>ATATTTCCCTTCTCAGATGCTGAGAACGGGCAACAACTTTACCTTCAGCTACACCTTTGAGGAAGTGCCT<br>TTCCACAGCAGCTACGCGCACAGCCAGAGCCTGGACCGGCTGATGAATCCTCTCATCGACCAATACCTGT<br>ATTACCTGAACAGAACTCAAAATCAGTCCGGAAGTGCCCAAAACAAGGACTTGCTGTTTAGCCGTGGGTC<br>TCCAGCTGGCATGTCTGTTCAGCCCAAAAACTGGCTACCTGGACCCTGTTATCGGCAGCAGCGCGTTTCT<br>AAAACAAAAACAGACAACAACAACAGCAATTTTACCTGGACTGGTGCTTCAAAATATAACCTCAATGGGC<br>GTGAATCCATCATCAACCCTGGCACTGCTATGGCCTCACACAAAGACGACGAAGACAAGTTCTTTCCCAT<br>GAGCGGTGTCATGATTTTTGGAAAAGAGAGCGCCGGAGCTTCAAACACTGCATTGGACAATGTCATGATT<br>ACAGACGAAGAGGAAATTAAAGCCACTAACCCTGTGGCCACCGAAAGATTTGGGACCGTGGCAGTCAATT<br>TCCAGAGCAGCAGCACAGACCCTGCGACCGGAGATGTGCATGCTATGGGAGCATTACCTGGCATGGTGTG<br>GCAAGATAGAGACGTGTACCTGCAGGGTCCCATTTGGGCCAAAATTCCTCACACAGATGGACACTTTCAC<br>CCGTCTCCTCTTATGGGCGGCTTTGGACTCAAGAACCCGCCTCCTCAGATCCTCATCAAAAACACGCCTG<br>TTCCTGCGAATCCTCCGGCGGAGTTTTCAGCTACAAGTTTGCTTCATTCATCACCCAATACTCCACAGG<br>ACAAGTGAGTGTGGAAATTGAATGGGAGCTGCAGAAAGAAAACAGCAAGCGCTGGAATCCCGAAGTGCAG |

TABLE 5-continued

Parent AAV Capsid Nucleic Acid Sequences

| Description SEQ ID NO: | Nucleic Acid Sequence |
|---|---|
| | TACACATCCAATTATGCAAAATCTGCCAACGTTGATTTTACTGTGGACAACAATGGACTTTATACTGAGC CTCGCCCCATTGGCACCCGTTACCTCACCCGTCCCCTGTAA |
| AAV6 SEQ ID NO: 53 | >AAV6 ATGGCTGCCGATGGTTATCTTCCAGATTGGCTCGAGGACAACCTCTCTGAGGGCATTCGCGAGTGGTGGG ACTTGAAACCTGGAGCCCCGAAACCCAAAGCCAACCAGCAAAAGCAGGACGACGGCCGGGGTCTGGTGCT TCCTGGCTACAAGTACCTCGGACCCTTCAACGGACTCGACAAGGGGGAGCCCGTCAACGCGGCGGATGCA GCGGCCCTCGAGCACGACAAGGCCTACGACCAGCAGCTCAAAGCGGGTGACAATCCGTACCTGCGGTATA ACCACGCCGACGCCGAGTTTCAGGAGCGTCTGCAAGAAGATACGTCTTTTGGGGGCAACCTCGGGCGAGC AGTCTTCCAGGCCAAGAAGAGGGTTCTCGAACCTTTTGGTCTGGTTGAGGAAGGTGCTAAGACGGCTCCT GGAAAGAAACGTCCGGTAGAGCAGTCGCCACAAGAGCCAGACTCCTCCTCGGGCATTGGCAAGACAGGCC AGCAGCCCGCTAAAAAGAGACTCAATTTTGGTCAGACTGGCGACTCAGAGTCAGTCCCCGACCCACAACC TCTCGGAGAACCTCCAGCAACCCCCGCTGCTGTGGGACCTACTACAATGGCTTCAGGCGGTGGCGCACCA ATGGCAGACAATAACGAAGGCGCCGACGGAGTGGGTAATGCCTCAGGAAATTGGCATTGCGATTCCACAT GGCTGGGCGACAGAGTCATCACCACCAGCACCCGAACATGGGCCTTGCCCACCTATAACAACCACCTCTA CAAGCAAATCTCCAGTGCTTCAACGGGGGCCAGCAACGACAACCACTACTTCGGCTACAGCACCCCCTGG GGGTATTTTGATTTCAACAGATTCCACTGCCATTTCTCACCACGTGACTGGCAGCGACTCATCAACAACA ATTGGGGATTCCGGCCCAAGAGACTCAACTTCAAGCTCTTCAACATCCAAGTCAAGGAGGTCACGACGAA TGATGGCGTCACGACCATCGCTAATAACCTTACCAGCACGGTTCAAGTCTTCTCGGACTCGGAGTACCAG TTGCCGTACGTCCTCGGCTCTGCGCACCAGGGCTGCCTCCCTCCGTTCCCGGCGGACGTGTTCATGATTC CGCAGTACGGCTAC CTAACGCTAACAATGGCAGCCAGGCAGTGGGACGGTCATCCTTTTACTGCCTGGAATATTTCCCATCGC AGATGCTGAGAACGGGCAATAACTTTACCTTCAGCTACACCTTCGAGGACGTGCCTTTCCACAGCAGCTA CGCGCACAGCCAGAGCCTGGACCGGCTGATG AATCCTCTCATCGACCAGTACCTGTATTACCTGAACAGAACTCAGAATCAGTCCGGAAGTGCCCAAAACA AGGACTTGCTGTTTAGCCGGGGGTCTCCAGCTGGCATGTCTGTTCAGCCCAAAAACTGGCTACCTGGACC CTGTTACCGGCAGCAGCGCGTTTCTAAAAC AAAAACAGACAACAACAACAGCAACTTTACCTGGACTGGTGCTTCAAAATATAACCTTAATGGGCGTGAA TCTATAATCAACCCTGGCACTGCTATGGCCTCACACAAAGACGACAAAGACAAGTTCTTTCCCATGAGCG GTGTCATGATTTTTGGAAAGGAGAGCGCCGGAGCTTCAAACACTGCATTGGACAATGTCATGATCACAGA CGAAGAGGAAATCAAAGCCACTAACCCCGTGGCCACCGAAAGATTTGGGACTGTGGCAGTCAATTCCCAG AGCAGCAGCACAGACCCTGCCGACCGGAGATGTGCATGTTATGGGAGCCTTACCTGGAATGGTGTGGCAAG ACAGAGACGTATACCTGCAGGGTCCTATTTGGGCCAAAATTCCTCACACGGATGGACACTTTCACCCGTC TCCTCTCATGGGCGGCTTTGGACTTAAGCACCCGCCTCCTCAGATCCTCATCAAAAACACGCCTGTTCCT GCGAATCCTCCGGCAGAGTTTTCGGCTACAAAGTTTGCTTCATTCATCACCCAGTATTCCACAGGACAAG TGAGCGTGGAGATTGAATGGGAGCTGCAGAAAGAAAACAGCAAACGCTGGAATCCCGAAGTGCAGTATAC ATCTAACTATGCAAAATCTGCCAACGTTGATTTCACTGTGGACAACAATGGACTTTATACTGAGCCTCGC CCCATTGGCACCCGTTACCTCACCCGTCCCCTGTAA |
| AAV3B SEQ ID NO: 54 | >A7V3B ATGGCTGCTGACGGTTATCTTCCAGATTGGCTCGAGGACAACCTTTCTGAAGGCATTCGTGAGTGGTGGG CTCTGAAACCTGGAGTCCCTCAACCCAAAGCGAACCAACAACACCAGGACAACCGTCGGGGTCTTGTGCT TCCGGGTTACAAATACCTCGGACCCGGTAACGGACTCGACAAAGGAGAGCCGGTCAACGAGGCGGACGCG GCAGCCCTCGAACACGACAAAGCCTACGACCAGCAGCTCAAGGCCGGTGACAACCCGTACCTCAAGTACA ACCACGCCGACGCCGAGTTTCAGGAGCGTCTTCAAGAAGATACGTCTTTTGGGGGCAACCTTGGCAGAGC AGTCTTCCAGGCCAAAAAGAGGATCCTTGAGCCTCTTGGTCTGGTTGAGGAAGCAGCTAAAACGGCTCCT GGAAAGAAGAGGCCTGTAGATCAGTCTCCTCAGGAACCGGACTCATCATCTGGTGTTGGCAAATCGGGCA AACAGCCTGCAGAAAAGACTAAATTTCGGTCAGACTGGCGACTCAGAGTCAGTCCCAGACCCTCAACC TCTCGGAGAACCACCAGCAGCCCCCACAAGTTTGGGATCTAATACAATGGCTTCAGGCGGTGGCGCACCA ATGGCAGACAATAACGAGGGTGCCGATGGAGTGGGTAATTCCTCAGGAAATTGGCATTGCGATTCCCAAT GGCTGGGCGACAGAGTCATCACCACCAGCACCAGAACCTGGGCCCTGCCCACTTACAACAACCATCTCTA CAAGCAAATCTCCAGCCAATCAGGAGCTTCAAACGACAACCACTACTTTGGCTACAGCACCCCCTTGGGG TATTTTGACTTTAACAGATTCCACTGCCACTTCTCACCACGTGACTGGCAGCGACTCATTAACAACAACT GGGGATTCCGGCCCAAGAAACTCAGCTTCAAGCTCTTCAACATCCAAGTTAAAGAGGTCACGCAGAACGA TGGCACGACGACTATTGCCAATAACCTTACCAGCACGGTTCAAGTGTTTACGGACTCGGAGTATCAGCTC CCGTACGTCCTCGGGTCGGCGCACCAAGGCTGTCTCCCGCCGTTTCCAGCGGACGTCTTCATGGTCCCTC AGTATGGATACCTCACCCTGAACAACGGAAGTCAAGCGGTGGGACGCTCATCCTTTTACTGCCTGGAGTA CTTCCCTTCGCAGATGCTAAGGACTGGAAATAACTTCCAATTCAGCTATACCTTCGAGGATGTACCTTTT CACAGCAGCTACGCTCACAGCCAGAGTTTGGATCGCTTGATGAATCCTCTTATTGATCAGTATCTGTACT ACCTGAACAGAACGCAAGGACAACCTCTGGAACAACCAACCAATCACGGCTGCTTTTTAGCCAGGCTGG GCCTCAGTCTATGTCTTTGCAGGCCAGAAATTGGCTACCTGGGCCCTGCTACCGGCAACAGAGACTTTCA AAGACTGCTAACGACAACAACAACAGTAACTTTCCTTGGACAGCAGTCCAGCAAATATCATCTCAATGGCC GCGACTCGCTGGTGAATCAGGACCAGCTATGGCCAGTCACAAGGACGATGAAGAAAAATTTTTCCCTAT GCACGGCAATCTAATATTTGGCAAAGAAGGGACAACGGCAAGTAACGCAGAATTAGATAATGTAATGATT ACGGATGAAGAAGAGATTCGTACCACCAATCCTGTGGCAACAGAGCAGTATGGAACTGTGGCAAATAACT TGCAGAGCTCAAATACAGCTCCCACGACTAGAACTGTCAATGATCAGGGGGCCTTACCTGGACTGGTGTG GCAAGATCGTGACGTGTACCTTCAAGGACCTATCTGGGCAAAGATTCCTCACACGGATGGACACTTTCAT CCTTCTCCTCTGATGGGAGGCTTTGGACTGAAACATCCGCCTCCTCAAATCATGATCAAAAATACTCCGG TACCGGCAAATCCTCCGACGACTTTCAGCCCGGCCAAGTTTGCTTCATTTATCACTCAGTACTCCACTGG ACAGGTCAGCGTGGAAATTGAGTGGGAGCTACAGAAAGAAAACAGCAAACGTTGGAATCCAGAGATTCAG TACACTTCCAACTACAACAAGTCTGTTAATGTGGACTTTACTGTAGACACTAATGGTGTTTATAGTGAAC CTCGCCCTATTGGAACCCGGTATCTCACACGAAACTTGTAA |

TABLE 5-continued

Parent AAV Capsid Nucleic Acid Sequences

| Description SEQ ID NO: | Nucleic Acid Sequence |
|---|---|
| LK03 SEQ ID NO: 55 | >LK03<br>ATGGCTGCTGACGGTTATCTTCCAGATTGGCTCGAGGACAACCTTTCTGAAGGCATTCGAGAGTGGTGGG<br>CGCTGCAACCTGGAGCCCCTAAACCCAAGGCAAATCAACAACATCAGGACAACGCTCGGGGTCTTGTGCT<br>TCCGGGTTACAAATACCTCGGACCCGGCAACGGACTCGACAAGGGGGAACCCGTCAACGCAGCGGACGCG<br>GCAGCCCTCGAGCACGACAAGGCCTACGACCAGCAGCTCAAGGCCGGTGACAACCCCTACCTCAAGTACA<br>ACCACGCCGACGCCGAGTTCCAGGAGCGGCTCAAAGAAGATACGTCTTTTGGGGGCAACCTCGGGCGAGC<br>AGTCTTCCAGGCCAAAAAGAGGCTTCTTGAACCTCTTGGTCTGGTTGAGGAAGCGGCTAAGACGGCTCCT<br>GGAAAGAAGAGGCCTGTAGATCAGTCTCCTCAGGAACCGGACTCATCATCTGGTGTTGGCAAATCGGGCA<br>AACAGCCTGCCAGAAAAAGACTAAATTTCGGTCAGACTGGCGACTCAGAGTCAGTCCCAGACCCTCAACC<br>TCTCGGAGAACCACCAGCAGCCCCCACAAGTTTGGGATCTAATACAATGGCTTCAGGCGGTGGCGCACCA<br>ATGGCAGACAATAACGAGGGTGCCGATGGAGTGGGTAATTCCTCAGGAAATTGGCATTGCGATTCCCAAT<br>GGCTGGGCGACAGAGTCATCACCACCAGCACCAGAACCTGGGCCCTGCCCACTTACAACAACCATCTCTA<br>CAAGCAAATCTCCAGCCAATCAGGAGCTTCAAACGACAACCACTACTTTGGCTACAGCACCCCTTGGGGG<br>TATTTTGACTTTAACAGATTCCACTGCCACTTCTCACCACGTGACTGGCAGCGACTCATTAACAACAACT<br>GGGGATTCCGGCCCAAGAAACTCAGCTTCAAGCTCTTCAACATCCAAGTTAAAGAGGTCACGCAGAACGA<br>TGGCACGACGACTATTGCCAATAACCTTACCAGCACGGTTCAAGTGTTTACGGACTCGGAGTATCAGCTC<br>CCGTACGTGCTCGGGTCGGCGCACCAAGGCTGTCTCCCGCCGTTTCCAGCGGACGTCTTCATGGTCCCTC<br>AGTATGGATACCTCACCCTGAACAACGGAAGTCAAGCGGTGGGACGCTCATCCTTTTACTGCCTGGAGTA<br>CTTCCCCTTCGCAGATGCTAAGGACTGGAAATAACTTCCAATTCAGCTATACCTTCGAGGATGTACCTTTT<br>CACAGCAGCTACGCTCACAGCCAGAGTTTGGATCGCTTGATGAATCCTCTTATTGATCAGTATCTGTACT<br>ACCTGAACAGAACGCAAGGAACAACCTCTGGAACAACCAACCAATCACGGCTGCTTTTTAGCCAGGCTGG<br>GCCTCAGTCTATGTCTTTGCAGGCCAGAAATTGGCTACCTGGGCCCTGCTACCGGCAACAGAGACTTTCA<br>AAGACTGCTAACGACAACAACAACAGTAACTTTCCTTGGACAGCGGCCAGCAAATATCATCTCAATGGCC<br>GCGACTCGCTGGTGAATCCAGGACCAGCTATGGCCAGTCACAAGGACGATGAAGAAAAATTTTTCCCTAT<br>GCACGGCAATCTAATATTTGGCAAAGAAGGGACAACGGCAAGTAACGCAGAATTAGATAATGTAATGATT<br>ACGGATGAAGAAGAGATTCGTACCACCAATCCTGTGGCAACAGAGCAGTATGGAACTGTGGCAAATAACT<br>TGCAGAGCTCAAATACAGCTCCCACGACTAGAACTGTCAATGATCAGGGGGCCTTACCTGGCATGGTGTG<br>GCAAGATCGTGACGTGTACCTTCAAGGACCTATCTGGGCAAAGATTCCTCACACGGATGGACACTTTCAT<br>CCTTCTCCTCTGATGGGAGGCTTTGGACTGAAACATCCGCCTCCTCAAATCATGATCAAAAATACTCCGG<br>TACCGGCAAATCCTCCGACGACTTTCAGCCCGGCCAAGTTTGCTTCATTTATCACTCAGTACTTCCACTGG<br>ACAGGTCAGCGTGGAAATTGAGTGGGAGCTACAGAAAGAAAACAGCAAACGTTGGAATCCAGAGATTCAG<br>TACACTTCCAACTACAACAAGTCTGTTAATGTGGACTTTACTGTAGACACTAATGGTGTTTATAGTGAAC<br>CTCGCCCCATTGGCACCCGTTACCTTACCCGTCCCCTGTAA |
| AAV8 SEQ ID NO: 56 | >AAV8<br>ATGGCTGCCGATGGTTATCTTCCAGATTGGCTCGAGGACAACCTCTCTGAGGGCATTCGCGAGTGGTGGG<br>CGCTGAAACCTGGAGCCCCGAAGCCCAAAGCCAACCAGCAAAAGCAGGACGACGGCCGGGGTCTGGTGCT<br>TCCTGGCTACAAGTACCTCGGACCCTTCAACGGACTCGACAAGGGGGAGCCCGTCAACGCGGCGGACGCA<br>GCGGCCCTCGAGCACGACAAGGCCTACGACCAGCAGCTGCAGGCGGGTGACAATCCGTACCTGCGGTATA<br>ACCACGCCGACGCCGAGTTTCAGGAGCGTCTGCAAGAAGATACGTCTTTTGGGGGCAACCTCGGGCGAGC<br>AGTCTTCCAGGCCAAGAAGCGGGTTCTCGAACCTCTCGGTCTGGTTGAGGAAGGCGCTAAGACGGCTCCT<br>GGAAAGAAGAGACCGGTAGAGCCATCACCCCAGCGTTCTCCAGACTCCTCTACGGGCATCGGCAAGAAAG<br>GCCAACAGCCCGCCAGAAAAAGACTCAATTTTGGTCAGACTGGCGACTCAGAGTCAGTTCCAGACCCTCA<br>ACCTCTCGGAGAACCTCCAGCAGCGCCCTCTGGTGTGGGACCTAATACAATGGCTGCAGGCGGTGGCGCA<br>CCAATGGCAGACAATAACGAAGGCGCCGACGGAGTGGGTAGTTCCTCGGGAAATTGGCATTGCGATTCCA<br>CATGGCTGGGCGACAGAGTCATCACCACCAGCACCCGAACCTGGGCCCTGCCCACCTACAACAACCACCT<br>CTACAAGCAAATCTCCAACGGGACATCGGGAGGAGCCACCAACGACAACACCTACTTCGGCTACAGCACC<br>CCCTGGGGGTATTTTGACTTTAACAGATTCCACTGCCACTTTTCACCACGTGACTGGCAGCGACTCATCA<br>ACAACAACTGGGGATTCCGGCCCAAGAGACTCAGCTTCAAGCTCTTCAACA<br>TCCAGGTCAAGGAGGTCACGCAGAATGAAGGCACCAAGACCATCGCCAATAACCTCACCAGCACCATCCA<br>GGTGTTTACGGACTCGGAGTACCAGCTGCCGTACGTTCTCGGCTCTGCCCACCAGGGCTGCCTGCCTCCG<br>TTCCCGGCGGACGTGTTCATGATTCCCCAGTACGGCTACCTAACACTCAACAACGGTAGTCAGGCCGTGG<br>GACGCTCCTCCTTCTACTGCCTGGAATACTTTCCTTCGCAGATGCTGAGAACCGGCAACAACTTCCAGTT<br>TACTTACACCTTCGAGGACGTGCCTTTCCACAGCAGCTACGCCCACAGCCAGAGTTGGACCGGCTGATG<br>AATCCTCTGATTGACCAGTACCTGTACTACTTGTCTCGGACTCAAACAACAGGAGGCACGGCAAATACGC<br>AGACTCTGGGCTTCAGCCAAGGTGGGCCTAATACAATGGCCAATCAGGCAAAGAACTGGCTGCCAGGACC<br>CTGTTACCGCCAACAACGCGTCTCAACGACAACGGGCAAAACAACAATAGCAACTTTGCCTGGACTGCTG<br>GGACCAAATACCATCTGAATGGAAGAATTCATTGGCTAATCCTGGCATCGCTATGGCAACACACAAG<br>ACGACGAGGAGCGTTTTTTTCCCAGTAACGGGATCCTGATTTTTGGCAAACAAAATGCTGCCAGAGACAA<br>TGCGGATTACAGCGATGTCATGCTCACCAGCGAGGAAGAAATCAAAACCACTAACCCTGTGGCTACAGAG<br>GAATACGGTATCGTGGCAGATAACTTGCAGCAGCAAAACACGGCTCCTCAAATTGGAACTGTCAACAGCC<br>AGGGGGCCTTACCCGGTATGGTCTGGCAGAACCGGGACGTGTACCTGCAGGGTCCCATCTGGGCCAAGAT<br>TCCTCACACGGACGGCAACTTCCACCCGTCTCCGCTGATGGGCGGCTTTGGCCTGAAACATCCTCCGCCT<br>CAGATCCTGATCAAGAACACGCCTGTACCTGCGGATCCTCCGACCACCTTCAACCAGTCAAAGCTGAACT<br>CTTTCATCACGCAATACAGCACCGGACAGGTC<br>AGCGTGGAAATTGAATGGGAGCTGCAGAAGGAAAACAGCAAGCGCTGGAACCCCGAGATCCAGTACACCT<br>CCAACTACTACAAATCTACAAGTGTGGACTTTGCTGTTAATACAGAAGGCGTGTACTCTGAACCCCGCCC<br>CATTGGCACCCGTTACCTCACCCGTAATCTGTAA |

TABLE 5-continued

Parent AAV Capsid Nucleic Acid Sequences

| Description SEQ ID NO: | Nucleic Acid Sequence |
|---|---|
| Rhesus 10 AAV SEQ ID NO: 57 | >rhesus10<br>ATGGCTGCCGATGGTTATCTTCCAGATTGGCTCGAGGACAACCTCTCTGAGGGCATTCGCGAGTGGTGGG<br>ACTTGAAACCTGGAGCCCCGAAACCCAAAGCCAACCAGCAAAAGCAGGACGACGGCCGGGGTCTGGTGCT<br>TCCTGGCTACAAGTACCTCGGACCCTTCAACGGACTCGACAAGGGGGAGCCCGTCAACGCGGCGGACGCA<br>GCGGCCCTCGAGCACGACAAGGCCTACGACCAGCAGCTCAAAGCGGGTGACAATCCGTACCTGCGGTATA<br>ACCACGCCGACGCCGAGTTTCAGGAGCGTCTGCAAGAAGATACGTCTTTTGGGGGCAACCTCGGGCGAGC<br>AGTCTTCCAGGCCAAGAAGCGGGTTCTCGAACCTCTCGGTCTGGTTGAGGAAGGCGCTAAGACGGCTCCT<br>GGAAAGAAGAGACCGGTAGAGCCATCACCCCAGCGTTCTCCAGACTCCTCTACGGGCATCGGCAAGAAAG<br>GCCAGCAGCCCGCGAAAAAGAGACTCAACTTTGGGCAGACTGGCGACTCAGAGTCAGTGCCCGACCCTCA<br>ACCAATCGGAGAACCCCCGCAGGCCCCTCTGGTCTGGGATCTGGTACAATGGCTGCAGGCGGTGGCGCT<br>CCAATGGCAGACAATAACGAAGGCGCCGACGGAGTGGGTAGTTCCTCAGGAAATTGGCATTGCGATTCCA<br>CATGGCTGGGCGACAGAGTCATCACCACCAGCACCCGAACCTGGGCCTCCCCACCTACAACAACCACCT<br>CTACAAGCAAATCTCCAACGGGACTTCGGGAGGAAGCACCAACGACAACACCTACTTCGGCTACAGCACC<br>CCCTGGGGGTATTTTGACTTTAACAGATTCCACTGCCACTTCTCACCACGTGACTGGCAGCGACTCATCA<br>ACAACAACTGGGGATTCCGGCCCAAGAGACTCAACTTCAAGCTCTTCAACATCCAGGTCAAGGAGGTCAC<br>GCAGAATGAAGGCACCAAGACCATCGCCAATAACCTTACCAGCACGATTCAGGTCTTTACGGACTCGGAA<br>TACCAGCTCCCGTACGTCCTCGGCTCTGCGCACCAGGGCTGCCTGCCTCCGTTCCCGGCGGACGTCTTCA<br>TGATTCCTCAGTACGGGTACCTGACTCTGAACAATGGCAGTCAGGCCGTGGGCCGTTCCTCCTTCTACTG<br>CCTGGAGTACTTTCCTTCTCAAATGCTGAGAACGGGCAACAACTTTGAGTTCAGCTACCAGTTTGAGGAC<br>GTGCCTTTTCACAGCAGCTACGCGCACAGCCAAAGCCTGGACCGGCTGATGAACCCCCTCATCGACCAGT<br>ACCTGTACTACCTGTCTCGGACTCAGTCCACGGGAGGTACCGCAGGAACTCAGCAGTTGCTATTTTCTCA<br>GGCCGGGCCTAATAACATGTC<br>GGCTCAGGCCAAAAACTGGCTACCCGGGCCCTGCTACCGGCAGCAACGCGTCTCCACGACACTGTCGCAA<br>AATAACAACAGCAACTTTGCCTGGACCGGTGCCACCAAGTATCATCTGAATGGCAGAGACTCTCTGGTAA<br>ATCCCGGTGTCGCTATGGCAACCCACAAGGACGAGAGCGATTTTTTCCGTCCAGCGGAGTCTTAAT<br>GTTTGGGAAACAGGGAGCTGGAAAAGACAACGTGGACTATAGCAGCGTTATGCTAACCAGTGAGGAAGAA<br>ATTAAAACCACCAACCCAGTGGCCACAGAACAGTACGGCGTGGTGGCCGATAACCTGCAACAGCAAAACG<br>CCGCTCCTATTGTAGGGGCCGTCAACAGTCAAGGAGCCTTACCTGGCATGGTCTGGCAGAACCGGGACGT<br>GTACCTGCAGGGTCCTATCTGGGCCAAGATTCCTCACACGGACGGAAACTTTCATCCCTCGCCGCTGATG<br>GGAGGCTTTGGACTGAAACACCCGCCTCCTCAGATCCTGATTAAGAATACACCTGTTCCCGCGGATCCTC<br>CAACTACCTTCAGTCAAGCTAAGCTGGCGTCGTTCATCACGCAGTACAGCACCGGACAGGTCAGCGTGGA<br>AATTGAATGGGAGCTGCAGAAAGAAAACAGCAAACGCTGGAACCCAGAGATT<br>CAATACACTTCCAACTACTACAAATCTACAAATGTGGACTTTGCTGTTAACACAGATGGCACTTATTCTG<br>AGCCCTCGCCCCATCGGCACCCGTTACCTCACCCGTAATCTGTAA |
| AAV2 SEQ ID NO: 58 | >AAV2<br>ATGGCTGCCGATGGTTATCTTCCAGATTGGCTCGAGGACACTCTCTCTGAAGGAATAAGACAGTGGTGGA<br>AGCTCAAACCTGGCCCACCACCACCAAAGCCCGCAGAGCGGCATAAGGACGACAGCAGGGGTCTTGTGCT<br>TCCTGGGTACAAGTACCTCGGACCCTTCAACGGACTCGACAAGGGAGAGCCGGTCAACGAGGCAGACGCC<br>GCGGCCCTCGAGCACGACAAAGCCTACGACCGGCAGCTCGACAGCGGAGACAACCCGTACCTCAAGTACA<br>ACCACGCCGACGCGGAGTTTCAGGAGCGCCTTAAAGAAGATACGTCTTTTGGGGGCAACCTCGGACGAGC<br>AGTCTTCCAGGCGAAAAAGAGGGTTCTTGAACCTCTGGGCCTGGTTGAGGAACCTGTTAAGACGGCTCCG<br>GGAAAAAAGAGGCCGGTAGAGCACTCTCCTGTGGAGCCAGACTCCTCCTCGGGAACCGGAAAGGCGGGCC<br>AGCAGCCTGCAAGAAAAAGATTGAATTTTGGTCAGACTGGAGACGCAGACTCAGTACCTGACCCCCAGCC<br>TCTCGGACAGCCACCAGCAGCCCCCTCTGGTCTGGGAACTAATACGATGGCTACAGGCAGTGGCGCACCA<br>ATGGCAGACAATAACGAGGGCGCCGACGGAGTGGGTAATTCCTCGGGAAATTGGCATTGCGATTCCACAT<br>GGATGGGCGACAGAGTCATCACCACCAGCACCCGAACCTGGGCCTGCCCACCTACAACAACCACCTCTA<br>CAAACAAATTTCCAGCCAATCAGGAGCCTCGAACGACAATCACTACTTTGGCTACAGCACCCCTTGGGGG<br>TATTTTGACTTCAACAGATTCCACTGCCACTTTTCACCACGTGACTGGCAAAGACTCATCAACAACAACT<br>GGGGATTCCGACCCAAGAGACTCAACTTCAAGCTCTTTAACATTCAAGTCAAAGAGGTCACGCAGAATGA<br>CGGTACGACGACGATTGCCAATAACCTTACCAGCACGGTTCAGGTGTTTACTGACTCGGAGTACCAGCTC<br>CCGTACGTCCTCGGCTCGGCGCATCAAGGATGCCTCCCGCCGTTCCCAGCAGACGTCTTCATGGTGCCAC<br>AGTATGGATACCTCACCCTGAACAACGGGAGTCAGGCAGTAGGACGCTCTTCATTTACTGCCTGGAGTA<br>CTTTCCTTCTCAGATGCTGCGTACCGGAAACAACTTTACCTTCAGCTACACTTTTGAGGACGTTCCTTTC<br>CACAGCAGCTACGCTCACAGCCAGAGTCTGGACCGTCTCATGAATCCTCTCATCGACCAGTACCTGTATT<br>ACTTGAGCAGAACAAACACTCCAAGTGGAACACCACCAGCAGTCAAGGCTTCAGTTTTCTCAGGCCGGAG<br>GAGTGACATTCGGGACCAGTCTAGGAACTGGCTTCCTGGACCCTGTTACCGCCAGCAGCGAGTATCAAAG<br>ACATCTGCGGATAACAACAACAGTGAATACTCGTGGACTGGAGCTACCAAGTACCACCTCAATGGCAGAG<br>ACTCTCTGGTGAATCCGGGCCCGGCCATGGCAAGCCACAAGGACGATGAAGAAAAGTTTTTTCCTCAGAG<br>CGGGGTTCTCATCTTTGGGAAGCAAGGCTCAGAGAAAACAAATGTGGACATTGAAAAGGTCATGATTACA<br>GACGAAGAGGAAATCAGGACAACCAATCCCGTGGCTACGGAGCAGTATGGTTCTGTATCTACCAACCTCC<br>AGAGAGGCAACAGACAAGCAGCTACCGCAGATGTCAACACACAAGGCGTTCTTCCAGGCATGGTCTGGCA<br>GGACAGAGATGTGTACCTTCAGGGGCCCATCTGGGCAAAGATTCCACACACGGACGGACATTTTCACCCC<br>TCTCCCCTCATGGGTGGATTCGGACTTAAACACCCTCCTCCACAGATTCTCATCAAGAACACCCCGGTAC<br>CTGCGAATCCTTCGACCACCTTCAGTGCGGCAAAGTTTGCTTCCTTCATCACACAGTACTCCACGGGACA<br>GGTCAGCGTGGAGATCGAGTGGGAGCTGCAGAAGGAAAACAGCAAACGCTGGAATCCCGAAATTCAGTAC<br>ACTTCCAACTACAACAAGTCTGTTAATGTGGACTTTACTGTGGACACTAATGGCGTGTATTCAGAGCCTC<br>GCCCCATTGGCACCAGATACCTGACTCGTAATCTGTAA |

TABLE 5-continued

Parent AAV Capsid Nucleic Acid Sequences

| Description SEQ ID NO: | Nucleic Acid Sequence |
|---|---|
| DJ SEQ ID NO: 59 | >DJ<br>ATGGCTGCCGATGGTTATCTTCCAGATTGGCTCGAGGACACTCTCTCTGAAGGAATAAGACAGTGGTGGA<br>AGCTCAAACCTGGCCCACCACCACCAAAGCCCGCAGAGCGGCATAAGGACGACAGCAGGGGTCTTGTGCT<br>TCCTGGGTACAAGTACCTCGGACCCTTCAACGGACTCGACAAGGGAGAGCCGGTCAACGAGGCAGACGCC<br>GCGGCCCTCGAGCACGACAAAGCCTACGACCGGCAGCTCGACAGCGGAGACAACCCGTACCTCAAGTACA<br>ACCACGCCGACGCCGAGTTCCAGGAGCGGCTCAAAGAAGATACGTCTTTTGGGGGCAACCTCGGGCGAGC<br>AGTCTTCCAGGCCAAAAAGAGGCTTCTTGAACCTCTTGGTCTGGTTGAGGAAGCGGCTAAGACGGCTCCT<br>GGAAAGAAGAGGCCTGTAGAGCACTCTCCTGTGGAGCCAGACTCCTCCTCGGGAACCGGAAAGGCGGGCC<br>AGCAGCCTGCAAGAAAAAGATTGAATTTTGGTCAGACTGGAGACGCAGACTCAGTCCCAGACCCTCAACC<br>AATCGGAGAACCTCCCGCAGCCCCCTCAGGTGTGGGATCTCTTACAATGGCTGCAGGCGGTGGCGCACCA<br>ATGGCAGACAATAACGAGGGCGCCGACGGAGTGGGTAATTCCTCGGGAAATTGGCATTGCGATTCCACAT<br>GGATGGGCGACAGAGTCATCACCACCAGCACCCGAACCTGGGCCCTGCCCACCTACAACAACCACCTCTA<br>CAAGCAAATCTCCAACAGCACATCTGGAGGATCTTCAAATGACAACGCCTACTTCGGCTACAGCACCCCC<br>TGGGGGTATTTTGACTTTAACAGATTCCACTGCCACTTTTCACCACGTGACTGGCAGCGACTCATCAACA<br>ACAACTGGGGATTCCGGCCCAAGAGACTCAGCTTCAAGCTCTTCAACATCCAGGTCAAGGAGGTCACGCA<br>GAATGAAGGCACCAAGACCATCGCCAATAACCTCACCAGCACCATCCAGGTGTTTACGGACTCGGAGTAC<br>CAGCTGCCGTACGTTCTCGGCTCTGCC<br>CACCCAGGGCTGCCTGCCTCCGTTCCCGGCGGACGTGTTCATGATTCCCCAGTACGGCTACCTAACACTCA<br>ACAACGGTAGTCAGGCCGTGGGACGCTCCTCCTTCTACTGCCTGGAATACTTTCCTTCGCAGATGCTGAG<br>AACCGGCAACAACTTCCAGTTTACTTACACCTTCGAGGACGTGCCTTTCCACAGCAGCTACGCCCACAGC<br>CAGAGCTTGGACCGGCTGATGAATCCTCTGATTGACCAGTACCTGTACTACTTGTCTCGGACTCAAACAA<br>CAGGAGG<br>CACGACAAATACGCAGACTCTGGGCTTCAGCCAAGGTGGGCCTAATACAATGGCCAATCAGGCAAAGAAC<br>TGGCTGCCAGGACCCTGTTACCGCCAGCAGCGAGTATCAAAGACATCTGCCGGATAACAACAACAGTGAAT<br>ACTCGTGGACTGGAGCTACCAAGTACCACCTCAATGGGAGAGACTCTCTGGTGAATCCGGGCCCGGCCAT<br>GGCAAGCCACAAGGACGATGAAGAAAAGTTTTTTCCTCAGAGCGGGGTTCTCATCTTTGGGAAGCAAGGC<br>TCAGAGAAAACAAATGTGGACATTGAAAAGGTCATGATTACAGACGAAGAGGAAATCAGGACAACCAATC<br>CCGTGGCTACGGAGCAGTATGGTTCTGTATCTACCAACCTCCAGAGAGGCAACAGACAAGCAGCTACCGC<br>AGATGTCAACACACAAGGCGTTCTTCCAGGCATGGTCTGGCAGGACAGAGATGTGTACCTTCAGGGGCCC<br>ATCTGGGCAAAGATTCCACACACGGACGGACATTTTCACCCCTCTCCCCTCATGGGTGGATTCGGACTTA<br>AACACCCTCCGCCTCAGATCCTGATCAAGAACACGCCTGTACCTGCGGATCCTCCGACCACCTTCAACCA<br>GTCAAAGCTGAACTCTTTCATCACCCAGTATTCTACTGGCCAAGTCAGCGTGGAGATCGAGTGGGAGCTG<br>CAGAAGGAAAACAGCAAGCGCTGGAACCCCGAGATC<br>CAGTACACCTCCAACTACTACAAATCTACAAGTGTGGACTTTGCTGTTAATACAGAAGGCGTGTACTCTG<br>AACCCCGCCCCATTGGCACCCGTTACCTCACCCGTAATCTGTAA |
| BOVINE AAV SEQ ID NO: 60 | >bovine<br>ATGTCTTTTGTTGACCACCCTCCAGATTGGTTGGAATCGATCGGCGACGGCTTTCGTGAATTTCTCGGCC<br>TTGAGGCGGGTCCCCCGAAACCCAAGGCCAATCAACAGAAGCAAGATAACGCTCGAGGTCTTGTGCTTCC<br>TGGGTACAAGTATCTTGGTCCTGGGAACGGCCTTGATAAGGGCGATCCTGTCAATTTTGCTGACGAGGTT<br>GCCCGAGAGCACGACCTCTCCTACCAGAAACAGCTTGAGGCGGGCGATAACCCTTACCTCAAGTACAACC<br>ACGCGGACGCCGAGTTTCAGGAGAAACTCGCTTCTGACACTTCTTTTGGGGGAAACCTTGGGAAGGCTGT<br>TTTCCAGGCTAAAAAGAGGATTCTCGAACCTCTTGGCCTGGTTGAGACGCCGGATAAAACGGCCTGCCG<br>GCAAAAAAGAGGCCTCTAGAGCAGAGTCCTCAAGAGCCAGACTCCTCGAGCGGAGTTGGCAAGAAAGGCA<br>AACAGCCTGCCAGAAAGAGACTCAACTTTGACGACGAACCTGGAGCCGGAGACGGGCCTCCCCAGAAGG<br>ACCATCTTCCGGAGCTATGTCTACTGAGACTGAAATGCGTGCAGCAGCTGGCGGAAATGGTGGCGATGCG<br>GGACAAGGTGCCGAGGGAGTGGGTAATGCCTCCGGTGATTGGCATTGCGATTCCACTTGGTCAGAGAGCC<br>ACGTCACCACCACCTCAACCCGCACCTGGGTCCTGCCGACCTACAACAACCACCTGTACCTGCGGCTCGG<br>CTCGAGCAACGCCAGCGACACCTTCAACGGATTCTCCACCCCCTGGGGATACTTTGACTTTAACCGCTTC<br>CACTGCCACTTCTCGCCAAGAGACTGGCAAAGGCTCATCAACAACCACTGGGGACTGCGCCCAAAAGCA<br>TGCAAGTCCGCATCTTCAACATCCAAGTTAAGGAGGTCACGACGTCTAACGGGGAGACGACCGTATCCAA<br>CAACCTCACCAGCACGGTCCAGATCTTTGCGGACAGCACGTACGAGCTCCCGTACGTGATGGATGCAGGT<br>CAGGAGGGCAGCTTGCCTCCTTTCCCCAACGACGTGTTCATGGTGCCTCAGTACGGGTACTGCGGACTGG<br>TAACCGGAGGCAGCTCTCAAAACCAGACAGACAGAAATGCCTTCTACTGTCTGGAGTACTTTCCCAGCCA<br>GATGCTGAGAACCGGAAACAACTTTGAGATGGTGTACAAGTTTGAAAACGTGCCCTTCCACTCCATGTAC<br>GCTCACAGCCAGAGCCTGGATAGGCTGATGAACCCGCTGCTGGACCAGTACCTGTGGGAGCTCCAGTCTA<br>CCACCTCTGGAGGAACTCTCAACCAGGGCAATTCAGCCACCAACTTTGCCAAGCTGACCAAAACAAACTT<br>TTCTGGCTACCGCAAAAACTGGCTCCCGGGGCCCATGATGAGCAGCAGCAGAGATTCTCCAAGACTGCCAGT<br>CAAAACTACAAGATTCCCCAGGGAAGAAAACAACAGTCTGCTCCATTATGAGACCAGAACTACCCTCGACG<br>GAAGATGGAGCAATTTTGCCCCGGGAACGGCCATGGCAACCGCAGCCAACGACGCCACCGACTTCTCTCA<br>GGCCCAGCTCATCTTTGCGGGGCCCAACATCACCGGCAACACCACCACAGATGCCAATAACCTGATGTTC<br>ACTTCAGAAGATGAACTTAGGGCACCAACCCCCGGGACACTGACCTGTTTGGCCACCTGGCAACCAACC<br>AGCAAAACGCCACCACCGTTCCTACCGTAGACGACGTGGACGGAGTCGGCGTGTACCCGGGAATGGTGTG<br>GCAGGACAGAGACATTTACTACCAAGGGCCCATTTGGGCCAAAATTCCACACACGGATGGACACTTTCAC<br>CCGTCTCCTCTCATTGGCGGATTTGGACTGAAAAGCCCGCCTCCACAAATATTCATCAAAAACACTCCTG<br>TACCCGCCAATCCCGCAACGACCTTCTCTCCGGCCAGAATCAACAGCTTCATCACCCAGTACAGCACCGG<br>ACAGGTGGCTGTCAAAATAGAATGGGAAATCCGAAGGAGCGGTCCAAGAGATGGAACCCAGAGGTCCAG<br>TTCACGTCCAACTACGGAGCACAGGACTCGCTTCTCTGGGCTCCCGACAACGCCGGAGCCTACAAAGAGC<br>CCAGGGCCATTGGATCCCGATACCTCACCAACCACCTCTAA |

TABLE 5-continued

Parent AAV Capsid Nucleic Acid Sequences

| Description SEQ ID NO: | Nucleic Acid Sequence |
|---|---|
| AAV4 SEQ ID NO: 61 | >AAV4<br>ATGACTGACGGTTACCTTCCAGATTGGCTAGAGGACAACCTCTCTGAAGGCGTTCGAGAGTGGTGGGCGC<br>TGCAACCTGGAGCCCCTAAACCCAAGGCAAATCAACAACATCAGGACAACGCTCGGGGTCTTGTGCTTCC<br>GGGTTACAAATACCTCGGACCCGGCAACGGACTCGACAAGGGGGAACCCGTCAACGCAGCGGACGCGGCA<br>GCCCTCGAGCACGACAAGGCCTACGACCAGCAGCTCAAGGCCGGTGACAACCCCTACCTCAAGTACAACC<br>ACGCCGACGCGGAGTTCCAGCAGCGGCTTCAGGGCGACACATCGTTTGGGGGCAACCTCGGCAGAGCAGT<br>CTTCCAGGCCAAAAGAGGGTTCTTGAACCTCTTGGTCTGGTTGAGCAAGCGGGTGAGACGGCTCCTGGA<br>AAGAAGAGACCGTTGATTGAATCCCCCAGCAGCCCGACTCCTCCACGGGTATCGGCAAAAAAGGCAAGC<br>AGCCGGCTAAAAAGAAGCTCGTTTTCGAAGACGAAACTGGAGCAGGCGACGGACCCCCTGAGGGATCAAC<br>TTCCGGAGCCATGTCTGATGACAGTGAGATGCGTGCAGCAGCTGGCGGAGCTGCAGTCGAGGGCGGACAA<br>GGTGCCGATGGAGTGGGTAATGCCTCGGGTGATTGGCATTGCGATTCCACCTGGTCTGAGGGCCACGTCA<br>CGACCACCAGCACCAGAACCTGGGTCTTGCCCACCTACAACAACCACCTCTACAAGCGACTCGGAGAGAG<br>CCTGCAGTCCAACACCTACAACGGATTCTCCACCCCCTGGGGATACTTTGACTTCAACCGCTTCCACTGC<br>CACTTCTCACCACGTGACTGGCAGCGACTCATCAACAACAACTGGGGCATGCGACCCAAAGCCATGCGGG<br>TCAAAATCTTCAACATCCAGGTCAAGGAGGTCACGACGTCGAACGGCGAGACAACGGTGGCTAATAACCT<br>TACCAGCACGGTTCAGATCTTTGCGGACTCGTCGTACGAACTGCCGTACGTGATGGATGCGGGTCAAGAG<br>GGCAGCCTGCCTCCGTTTCCCAACGACGTCTTTATGGTGCCCCAGTACGGCTACTGTGGACTGGTGACCG<br>GCAACACTTCGCAGCAGCAGACTGACAGAAATGCCTTCTACTGCCTGGAGTACTTTCCTTCGCAGATGCT<br>GCGGACTGGCAACAACTTTGAAATTACGTACAGTTTTGAGAAGGTGCCTTTCCACTCGATGTACGCGCAC<br>AGCCAGAGCCTGGACCGGCTGATGAACCCTCTCATCGACCAGTACCTGTGGGACTGCAATGACCACCA<br>CCGGAACCACCCTGAATGCCGGGACTGCCACCACCAACTTTACCAAGCTGCGGCCTACCAACTTTTCCAA<br>CTTTAAAAAGAACTGGCTGCCCGGGCCTTCAATCAAGCAGCAGGGCTTCTCAAAGACTGCCAATCAAAAC<br>TACAAGATCCCTGCCACCGGGTCAGACAGTCTCATCAAATACGAGACGCACAGCACTCTGGACGGAAGAT<br>GGGAGTGCCCTGACCCCCGGACCTCCAATGGCCACGGCTGGACCTGCGGACAGCAAGTTCAGCAACAGCCA<br>GCTCATCTTTGCGGGGCCTGAACAGAACGGCAACACGGCCACCGTACCCGGGACTCTGATCTTCACCTCT<br>GAGGAGGAGCTGGCAGCCACCAACGCCACCGATACGGACATGTGGGGCAACCTACCTGGCGGTGACCAGA<br>GCAACAGCAACCTGCCGACCGTGGACAGACTGACAGCCTTGGGAGCCGTGCCTGGAATGGTCTGGCAAAA<br>CAGAGACATTTACTACCAGGGTCCCATTTGGGCAAGATTCCTCATACCGATGGACACTTTCACCCCTCA<br>CCGCTGATTGGTGGGTTTGGGCTGAAACACCCGCCTCCTCAAATTTTTATCAAGAACACCCCGGTACCTG<br>CGAATCCTGCAACGACCTTCAGCTCTACTCCGGTAAACTCCTTCATTACTCAGTACAGCACTGGCCAGGT<br>GTCGGTGCAGATTGACTGGGAGATCCAGAAGGAGCGGTCCAAACGCTGGAACCCCGAGGTCCAGTTTACC<br>TCCAACTACGACAGCAAAACTCTCTGTTGTGGGCTCCCGATGCGGCTGGGAAATACACTGAGCCTAGGG<br>CTATCGGTACCCGCTACCTCACCCACCACCTGTAA |
| AAV12 SEQ ID NO: 62 | >AAV12<br>ATGGCTGCTGACGGTTATCTTCCAGATTGGCTCGAGGACAACCTCTCTGAAGGCATTCGCGAGTGGTGGG<br>CGCTGAAACCTGGAGCTCCACAACCCAAGGCCAACCAACAGCATCAGGACAACGGCAGGGGTCTTGTGCT<br>TCCTGGGTACAAGTACCTCGGACCCTTCAACGGACTCGACAAGGGAGAGCCGGTCAACGAGGCGACGCC<br>GCGGCCCTCGAGCACGACAAGGCCTACGACAAGCAGCTCGAGCAGGGGGACAACCCGTATCTCAAGTACA<br>ACCACGGCGACGCCGAGTTCCAGCAGCGCTTGGCGACCGACACCTCTTTTGGGGGCAACCTCGGGCGAGC<br>AGTCTTCCAGGCCAAAAGAGGATTCTCGAGCCTCTGGGTCTGGTTGAAGAGGGCGTTAAAACGGCTCCT<br>GGAAAGAAACGCCCATTAGAAAAGACTCCAAATCGGCCGACCAACCCGGACTCTGGGAAGGCCCCGGCCA<br>AGAAAAGCAAAAAGACGGCGAACCAGCCGACTCTGCTAGAAGGACACTCGACTTTGAAGACTCTGGAGC<br>AGGAGACGGACCCCCTGAGGGATCATCTTCCGGAGAAATGTCTCATGATGCTGAGATGCGTGCCGGCGCA<br>GGCGGAAATGCTGTCGAGGCGGGACAAGGTGCCGATGGAGTGGGTAATGCCTCCGGTGATTGGCATTGCG<br>ATTCCACCTGGTCAGAGGGCCGAGTCACCACCACCAGCACCCGAACCTGGGTCCTACCCACGTACAACAA<br>CCACCTGTACCTGCGAATCGGAACAACGGCCAACAGCAACACCTACAACGGATTCTCCACCCCCTGGGGA<br>TACTTTGACTTTAACCGCTTCCACTGCCACTTTTCCCCACGCGACTGGCAGCGACTCATCAACAACAACT<br>GGGGACTCAGGCCGAAATCGATGCGTGTTAAAATCTTCAACATACAGGTCAAGGAGGTCACGACGTCAAA<br>CGGCGAGACTACGGTCGCTAATAACCTTACCAGCACGGTTCAGATCTTTGCGGATTCGACGTATGAACTC<br>CCATACGTGATGGACGCCGGTCAGGAGGGGAGCTTTCCTCCGTTTCCCAACGACGTCTTTATGGTTCCCC<br>AATACGGATACTGCGGAGTTGTCACTGGAAAAAACCAGAACCAGACAGACAGAAATGCCTTTTACTGCCT<br>GGAATACTTTCCATCCCAAATGCTAAGAACTGGCAACAATTTTGAAGTCAGTTACCAATTTGAAAAAGTT<br>CCTTTCCATTCAATGTACGCGCACAGCCAGAGCCTGGACAGAATGATGAATCCTTTACTGGATCAGTACC<br>TGTGGCATCTGCAATCGACCACTACCGGAAATTCCCTTAATCAAGGAACAGCTACCACCACGTACGGGAA<br>AATTACCACTGGAGACTTTGC<br>CTACTACAGGAAAAACTGGTTGCCTGGAGCCTGCATTAAACAACAAAAATTTTCAAAGAATGCCAATCAA<br>AACTACAAGATCCCGCCAGCGGGGAGACGCCCTTTTAAAGTATGACACGCATACCACTCTAAATGGGC<br>GATGGAGTAACATGGCTCCTGGACCTCCAATGGCAACCGCAGGTGCCGGGGACTCGGATTTTAGCAACAG<br>CCAGCTGATCTTTGCCGG<br>ACCCAATCCGAGCGGTAACACGACCACATCTTCAAACAATTTGTTGTTTACCTCAGAAGAGGAGATTGCC<br>ACAACAAACCCACGAGACACGGACATGTTTGGACAGATTGCAGATAATAATCAAATGCCACCACCGCCC<br>CTCACATCGCTAACCTGGACGCTATGGGAATTGTTCCCGGAATGGTCTGGCAAAACAGAGACATTCTACTA<br>CCAGGGCCCTATTTGGGCAAGGTCCCTCACACGGACGGACACTTTCACCCTTCGCCGCTGATGGGAGGA<br>TTTGGACTGAAACACCCGCCTCCACAGATTTTTCATCAAAAACACCCCCGTACCCGCCAATCCCAATACTA<br>CCTTTTAGCGCTGCAAGGATTAATTCTTTTCTGACGCAGTACAGCACCGGACAAGTTGCCGTTCAGATCGA<br>CTGGGAAATTCAGAAGGAGCATTCCAAACGCTGGAATCCCGAAGTTCAATTTACTTCAAACTACGGCACT<br>CAAAATTCTATGCTGTGGGCTCCCGACAATGCTGGCAACTACCACGAACTCCGGGCTATTGGGTCCCGTT<br>TCCTCACCCACCACTTGTAA |

In some embodiments, the variant AAV capsid polypeptides of the invention exhibit increased transduction human pancreatic tissue or human islets as compared to non-variant parent capsid polypeptides. In some embodiments, transduction is increased by about 5%, about 10%, about 15%, about 20%, about 25%, about 30%, about 35%, about 40%, about 45%, about 50%, about 55%, about 60%, 65%, about 70%%, about 75%, about 80%, about 85%, about 90%, about 95%, about 99%, or about 100%. In some embodiments, transduction is increased by about 5% to about 80%, about 10% to about 70%, about 20% to about 60%, about 30% to about 60%, or about 40% to about 50%. In some embodiments, the non-variant parent capsid polypeptide sequence is any one of SEQ ID NOs: 27-44. In some embodiments, the non-variant parent capsid polypeptide sequence is encoded by any one of SEQ ID NOs: 45-62.

In some embodiments, the variant AAV capsid polypeptides of the invention exhibit increased tropism human pancreatic tissue or human islets as compared to non-variant parent capsid polypeptides. In some embodiments, tropism is increased by about 5%, about 10%, about 15%, about 20%, about 25%, about 30%, about 35%, about 40%, about 45%, about 50%, about 55%, about 60%, 65%, about 70%%, about 75%, about 80%, about 85%, about 90%, about 95%, about 99%, or about 100%. In some embodiments, tropism is increased by about 5% to about 80%, about 10% to about 70%, about 20% to about 60%, about 30% to about 60%, or about 40% to about 50%. In some embodiments, the non-variant parent capsid polypeptide sequence is any one of SEQ ID NOs: 27-44. In some embodiments, the non-variant parent capsid polypeptide sequence is encoded by any one of SEQ ID NOs: 45-62.

In some embodiments, the variant AAV capsid polypeptides of the invention further exhibit an enhanced neutralization profile as compared to non-variant parent capsid polypeptides. In some embodiments, the variant AAV capsid polypeptides of the invention further exhibit an enhanced neutralization profile against pooled human immunoglobulins as compared to non-variant parent capsid polypeptides. In some embodiments, the neutralization profile is enhanced by about 5%, about 10%, about 15%, about 20%, about 25%, about 30%, about 35%, about 40%, about 45%, about 50%, about 55%, about 60%, 65%, about 70%%, about 75%, about 80%, about 85%, about 90%, about 95%, about 99%, or about 100%. In some embodiments, the neutralization profile is enhanced by about 5% to about 80%, about 10% to about 70%, about 20% to about 60%, about 30% to about 60%, or about 40% to about 50%. In some embodiments, an enhanced neutralization profile is determined by a reduction in the generation of neutralizing antibodies in a host. In some embodiments, the reduction in generation of neutralizing antibodies is a reduction of about 5%, about 10%, about 15%, about 20%, about 25%, about 30%, about 35%, about 40%, about 45%, about 50%, about 55%, about 60%, 65%, about 70%%, about 75%, about 80%, about 85%, about 90%, about 95%, about 99%, or about 100%. In some embodiments, the reduction in generation of neutralizing antibodies is a reduction of about 5% to about 80%, about 10% to about 70%, about 20% to about 60%, about 30% to about 60%, or about 40% to about 50%. In some embodiments, the non-variant parent capsid polypeptide sequence is any one of SEQ ID NOs: 27-44. In some embodiments, the non-variant parent capsid polypeptide sequence is encoded by any one of SEQ ID NOs: 45-62.

In some embodiments, the variant AAV capsid polypeptide that exhibits an enhanced neutralization profile is selected from the group consisting of AAV-10A1 (SEQ ID NO:1) and AAV-10A3 (SEQ ID NO:2). In some embodiments, the variant AAV capsid polypeptide that exhibits an enhanced neutralization profile is AAV-10A1 (SEQ ID NO:1). In some embodiments, the variant AAV capsid polypeptide that exhibits an enhanced neutralization profile is AAV-10A3 (SEQ ID NO:2).

In some embodiments, the variant AAV capsid polypeptides of the invention further exhibit increased transduction or tropism in one or more human stem cell types as compared to non-variant parent capsid polypeptides. In some embodiments, the human stem cell types include but are not limited to embryonic stem cells, adult tissue stem cells (i.e., somatic stem cells), bone marrow, progenitor cells, induced pluripotent stem cells, and reprogrammed stem cells. In some embodiments, adult stem cells can include organoid stem cells (i.e., stem cells derived from any organ or organ system of interest within the body). Organs of the body include for example but are not limited to skin, hair, nails, sense receptors, sweat gland, oil glands, bones, muscles, brain, spinal cord, nerve, pituitary gland, pineal gland, hypothalamus, thyroid gland, parathyroid, thymus, adrenals, pancreas (islet tissue), heart, blood vessels, lymph nodes, lymph vessels, thymus, spleen, tonsils, nose, pharynx, larynx, trachea, bronchi, lungs, mouth, pharynx, esophagus, stomach, small intestine, large intestine, rectum, anal canal, teeth, salivary glands, tongue, liver, gallbladder, pancreas, appendix, kidneys, ureters, urinary bladder, urethra, testes, ductus (vas) deferens, urethra, prostate, penis, scrotum, ovaries, uterus, uterine (fallopian) tubes, vagina, vulva, and mammary glands (breasts). Organ systems of the body include but are not limited to the integumentary system, skeletal system, muscular system, nervous system, endocrine system, cardiovascular system, lymphatic system, respiratory system, digestive system, urinary system, and reproductive system. In some embodiments, transduction and/or tropism is increased by about 5%, about 10%, about 15%, about 20%, about 25%, about 30%, about 35%, about 40%, about 45%, about 50%, about 55%, about 60%, 65%, about 70%%, about 75%, about 80%, about 85%, about 90%, about 95%, about 99%, or about 100%. In some embodiments, transduction and/or tropism is increased by about 5% to about 80%, about 10% to about 70%, about 20% to about 60% or about 30% to about 60%. In some embodiments, the non-variant parent capsid polypeptide sequence is any one of SEQ ID NOs: 27-44. In some embodiments, the non-variant parent capsid polypeptide sequence is encoded by any one of SEQ ID NOs: 45-62.

In some embodiments, the variant AAV capsid polypeptides of the invention further exhibit increased transduction or tropism in one or more non-pancreas human tissues as compared to non-variant parent capsid polypeptides. In some embodiments, the variant AAV capsid polypeptides further exhibit increased transduction in one or more non-pancreas human tissues as compared to a vector encoding non-variant parent capsid polypeptides. In some embodiments, the variant AAV capsid polypeptides further exhibit increased tropism in one or more non-pancreas human tissues as compared to a vector encoding non-variant parent capsid polypeptides. In some embodiments, transduction and/or tropism is increased by about 5%, about 10%, about 15%, about 20%, about 25%, about 30%, about 35%, about 40%, about 45%, about 50%, about 55%, about 60%, 65%, about 70%%, about 75%, about 80%, about 85%, about 90%, about 95%, about 99%, or about 100%. In some embodiments, transduction and/or tropism is increased by about 5% to about 80%, about 10% to about 70%, about 20% to about 60% or about 30% to about 60%. In some embodiments, the non-variant parent capsid polypeptide sequence is any one of SEQ ID NOs: 27-44. In some embodiments, the non-variant parent capsid polypeptide sequence is encoded by any one of SEQ ID NOs: 45-62.

In some embodiments, the variant AAV capsid polypeptides of the invention further exhibit increased transduction or tropism in one or more non-pancreas human tissues as compared to non-variant parent capsid polypeptides. In some embodiments, the variant AAV capsid polypeptides further exhibit increased transduction in one or more non-pancreas human tissues as compared to a vector encoding non-variant parent capsid polypeptides. In some embodiments, the variant AAV capsid polypeptides further exhibit increased tropism in one or more non-pancreas human tissues as compared to a vector encoding non-variant parent capsid polypeptides. In some embodiments, transduction and/or tropism is increased by about 5%, about 10%, about 15%, about 20%, about 25%, about 30%, about 35%, about 40%, about 45%, about 50%, about 55%, about 60%, 65%, about 70%%, about 75%, about 80%, about 85%, about 90%, about 95%, about 99%, or about 100%. In some embodiments, transduction and/or tropism is increased by about 5% to about 80%, about 10% to about 70%, about 20% to about 60% or about 30% to about 60%. In some embodiments, the non-variant parent capsid polypeptide sequence is any one of SEQ ID NOs: 27-44. In some embodiments, the non-variant parent capsid polypeptide sequence is encoded by any one of SEQ ID NOs: 45-62.

In some embodiments, the variant AAV capsid polypeptide sequence is selected from the group consisting of AAV-10A1 (SEQ ID NO:1), AAV-10A3 (SEQ ID NO:2), AAV-10A4 (SEQ ID NO:3), AAV-10A5 (SEQ ID NO:4), AAV-18A1 (SEQ ID NO:5), AAV-10B1 (SEQ ID NO:6), AAV-10B3 (SEQ ID NO:7), AAV-10B5 (SEQ ID NO:8), AAV-10B6 (SEQ ID NO:9), AAV-10B7 (SEQ ID NO:10), AAV-18B2 (SEQ ID NO:12), and AAV-18B3 (SEQ ID NO:13). In some embodiments, the variant AAV capsid polypeptide sequence is selected from the group consisting of AAV-10A1 (SEQ ID NO:1), AAV-10A3 (SEQ ID NO:2), and AAV-18A1 (SEQ ID NO:5). In some embodiments, the variant AAV capsid polypeptides comprise further de novo mutations. In some embodiments, the variant AAV capsid polypeptides exhibit about 99%, about 98%, about 97%, about 96%, about 95%, about 94%, about 93%, about 92%, about 91%, or about 90% identity to non-variant parent capsid polypeptides. In some embodiments, the variant AAV capsid polypeptides exhibit about 99%, about 98%, about 97%, about 96%, about 95%, about 94%, about 93%, about 92%, about 91%, or about 90% identity to AAV-10A1 (SEQ ID NO:1), AAV-10A3 (SEQ ID NO:2), AAV-10A4 (SEQ ID NO:3), AAV-10A5 (SEQ ID NO:4), AAV-18A1 (SEQ ID NO:5), AAV-10B1 (SEQ ID NO:6), AAV-10B3 (SEQ ID NO:7), AAV-10B5 (SEQ ID NO:8), AAV-10B6 (SEQ ID NO:9), AAV-10B7 (SEQ ID NO:10), AAV-18B2 (SEQ ID NO:12), and AAV-18B3 (SEQ ID NO:13). In some embodiments, the variant AAV capsid polypeptides exhibit about 99%, about 98%, about 97%, about 96%, about 95%, about 94%, about 93%, about 92%, about 91%, or about 90% identity to one or more subregions of AAV-10A1 (SEQ ID NO:1), AAV-10A3 (SEQ ID NO:2), and AAV-18A1 (SEQ ID NO:5). In some embodiments, the non-variant parent capsid polypeptide sequence is any one of SEQ ID NOs: 27-44. In some embodiments, the non-variant parent capsid polypeptide sequence is encoded by any one of SEQ ID NOs: 45-62.

The present invention also provides for generating variant AAV capsid polypeptides, such as AAV-10A1 (SEQ ID NO:1), AAV-10A3 (SEQ ID NO:2), AAV-10A4 (SEQ ID NO:3), AAV-10A5 (SEQ ID NO:4), AAV-18A1 (SEQ ID NO:5), AAV-10B1 (SEQ ID NO:6), AAV-10B3 (SEQ ID NO:7), AAV-10B5 (SEQ ID NO:8), AAV-10B6 (SEQ ID NO:9), AAV-10B7 (SEQ ID NO:10), AAV-18B2 (SEQ ID NO:12), and AAV-18B3 (SEQ ID NO:13). In some embodiments, the present invention also provides for generating variant AAV capsid polypeptides, such as AAV-10A1 (SEQ ID NO:1), AAV-10A3 (SEQ ID NO:2), and AAV-18A1 (SEQ ID NO:5). These methods employ known techniques of library generation; however, the methods are novel in that they employ replication competent AAV vectors during the variant AAV capsid polypeptide generation (i.e., selection and evolution of the variant AAV capsid polypeptides). The present invention provides methods for generating variant AAV capsid polypeptides, wherein the variant AAV capsid polypeptides exhibit increased transduction or tropism human pancreatic tissue or human islets as compared to non-variant parent capsid polypeptides, the method comprising:
  a) generating a library of variant AAV capsid polypeptide genes, wherein said variant AAV capsid polypeptide genes include a plurality of variant AAV capsid polypeptide genes comprising sequences from more than one non-variant parent capsid polypeptide;
  b) generating an AAV vector library by cloning said variant AAV capsid polypeptide gene library into AAV vectors, wherein said AAV vectors are replication competent AAV vectors;
  c) screening said AAV vector library from b) encoding for variant AAV capsid polypeptides exhibiting increased transduction or tropism human pancreatic tissue or human islets as compared to a non-variant parent capsid polypeptide; and
  d) selecting said variant AAV capsid polypeptides from c).

In some embodiments, the method further comprises e) determining the sequence of said variant AAV capsid polypeptides from d).

In some embodiments, the variant AAV capsid polypeptides generated by screening methods of the invention exhibit increased transduction human pancreatic tissue or human islets as compared to a vector encoding non-variant parent capsid polypeptides. In some embodiments, transduction is increased by about 5%, about 10%, about 15%, about 20%, about 25%, about 30%, about 35%, about 40%, about 45%, about 50%, about 55%, about 60%, 65%, about 70%%, about 75%, about 80%, about 85%, about 90%, about 95%, about 99%, or about 100%. In some embodiments, transduction is increased by about 5% to about 80%, about 10% to about 70%, about 20% to about 60%, about 30% to about 60%, or about 40% to about 50%. In some embodiments, the non-variant parent capsid polypeptide sequence is any one of SEQ ID NOs: 27-44. In some embodiments, the non-variant parent capsid polypeptide sequence is encoded by any one of SEQ ID NOs: 45-62.

In some embodiments, the variant AAV capsid polypeptides generated by screening methods of the invention exhibit increased tropism human pancreatic tissue or human islets as compared to a vector encoding non-variant parent capsid polypeptides. In some embodiments, tropism is increased by about 5%, about 10%, about 15%, about 20%, about 25%, about 30%, about 35%, about 40%, about 45%, about 50%, about 55%, about 60%, 65%, about 70%%, about 75%, about 80%, about 85%, about 90%, about 95%, about 99%, or about 100%. In some embodiments, tropism is increased by about 5% to about 80%, about 10% to about 70%, about 20% to about 60%, about 30% to about 60%, or about 40% to about 50%. In some embodiments, the non-variant parent capsid polypeptide sequence is any one of SEQ ID NOs: 27-44. In some embodiments, the non-variant parent capsid polypeptide sequence is encoded by any one of SEQ ID NOs: 45-62.

In some embodiments, the variant AAV capsid polypeptides generated by screening methods of the invention further exhibit an enhanced neutralization profile as compared to a vector encoding non-variant parent capsid polypeptides. In some embodiments, the neutralization profile is enhanced by about 5%, about 10%, about 15%, about 20%, about 25%, about 30%, about 35%, about 40%, about 45%, about 50%, about 55%, about 60%, 65%, about 70%%, about 75%, about 80%, about 85%, about 90%, about 95%, about 99%, or about 100%. In some embodiments, the neutralization profile is enhanced by about 5% to about 80%, about 10% to about 70%, about 20% to about 60%, about 30% to about 60%, or about 40% to about 50%. In some embodiments, an enhanced neutralization profile is determined by a reduction in the generation of neutralizing antibodies in a host. In some embodiments, the reduction in generation of neutralizing antibodies is a reduction of about 5%, about 10%, about 15%, about 20%, about 25%, about 30%, about 35%, about 40%, about 45%, about 50%, about 55%, about 60%, 65%, about 70%%, about 75%, about 80%, about 85%, about 90%, about 95%, about 99%, or about 100%. In some embodiments, the reduction in generation of neutralizing antibodies is a reduction of about 5% to about 80%, about 10% to about 70%, about 20% to about 60%, about 30% to about 60%, or about 40% to about 50%. In some embodiments, the non-variant parent capsid polypeptide sequence is any one of SEQ ID NOs: 27-44. In some embodiments, the non-variant parent capsid polypeptide sequence is encoded by any one of SEQ ID NOs: 45-62.

In some embodiments, the variant AAV capsid polypeptides generated by screening methods of the invention further exhibit increased transduction or tropism in one or more non-pancreatic human tissues as compared to a vector encoding non-variant parent capsid polypeptides. In some embodiments, the variant AAV capsid polypeptides further exhibit increased transduction in one or more non-pancreatic human tissues as compared to a vector encoding non-variant parent capsid polypeptides. In some embodiments, the variant AAV capsid polypeptides further exhibit increased tropism in one or more non-pancreatic human tissues as compared to a vector encoding non-variant parent capsid polypeptides. In some embodiments, transduction and/or tropism is increased by about 5%, about 10%, about 15%, about 20%, about 25%, about 30%, about 35%, about 40%, about 45%, about 50%, about 55%, about 60%, 65%, about 70%%, about 75%, about 80%, about 85%, about 90%, about 95%, about 99%, or about 100%. In some embodiments, transduction and/or tropism is increased by about 5% to about 80%, about 10% to about 70%, about 20% to about 60% or about 30% to about 60%. In some embodiments, the non-variant parent capsid polypeptide sequence is any one of SEQ ID NOs: 27-44. In some embodiments, the non-variant parent capsid polypeptide sequence is encoded by any one of SEQ ID NOs: 45-62.

In some embodiments, the variant AAV capsid polypeptides generated by screening methods of the invention further exhibit increased transduction or tropism in one or more non-pancreatic human tissues as compared to a vector encoding non-variant parent capsid polypeptides. In some embodiments, the variant AAV capsid polypeptides further exhibit increased transduction in one or more non-pancreatic human tissues as compared to a vector encoding non-variant parent capsid polypeptides. In some embodiments, the variant AAV capsid polypeptides further exhibit increased tropism in one or more non-pancreatic human tissues as compared to a vector encoding non-variant parent capsid polypeptides. In some embodiments, transduction and/or tropism is increased by about 5%, about 10%, about 15%, about 20%, about 25%, about 30%, about 35%, about 40%, about 45%, about 50%, about 55%, about 60%, 65%, about 70%%, about 75%, about 80%, about 85%, about 90%, about 95%, about 99%, or about 100%. In some embodiments, transduction and/or tropism is increased by about 5% to about 80%, about 10% to about 70%, about 20% to about 60% or about 30% to about 60%. In some embodiments, the non-variant parent capsid polypeptide sequence is any one of SEQ ID NOs: 27-44. In some embodiments, the non-variant parent capsid polypeptide sequence is encoded by any one of SEQ ID NOs: 45-62.

Transduction can be measured by techniques known in the art, including, for example, immunofluorescence and flow-cytometry analysis, including those described in Example 2 below, as well as other methods known in the art. In vitro transduction analysis can be performed in human pancreatic tissue or human islet cells, again as described in the art or as described in Examples 1 and 2 below, including for example by measuring GFP expression (or another marker gene) in order to determine transduction. In vivo or ex vivo transduction analysis can be measured by techniques known in the art, including, for example, Firefly luciferase-based assays, again as described in the art or as described in Examples below, including for example by measuring luciferase expression (or another marker gene) in order to determine transduction. In some embodiments, marker expression from an AAV vector packaged with the variant AAV capsid polypeptides is compared to marker expression from an AAV vector packaged with the non-variant parent capsid polypeptides in order to determine changes in transduction efficiency. In some embodiments, the transduction is compared for different cell types in order to determine tropism, i.e., compare transduction from an AAV vector packaged with the variant AAV capsid polypeptide to transduction from an AAV packaged with the non-variant capsid polypeptide in at least two different cell types in order to determine tropism for a particular cell type, sometimes referred to as a tropism profile. In some embodiments, the at least one cell type is from human pancreatic tissue or human islet cells. In some embodiments, the at least one cell type is human alpha-islet cell or beta-islet cell. In some embodiments, at least a second cell type includes but is not limited to blood cells, blood stem cells, liver cells, gonads, germ cells, joint tissue or cells, pancreas (including α-islet cells and/or (3-islet cells), spleen tissue or cells, the gastrointestinal tract, lung tissue or cells and/or kidney tissue or cells.

Figure 1:
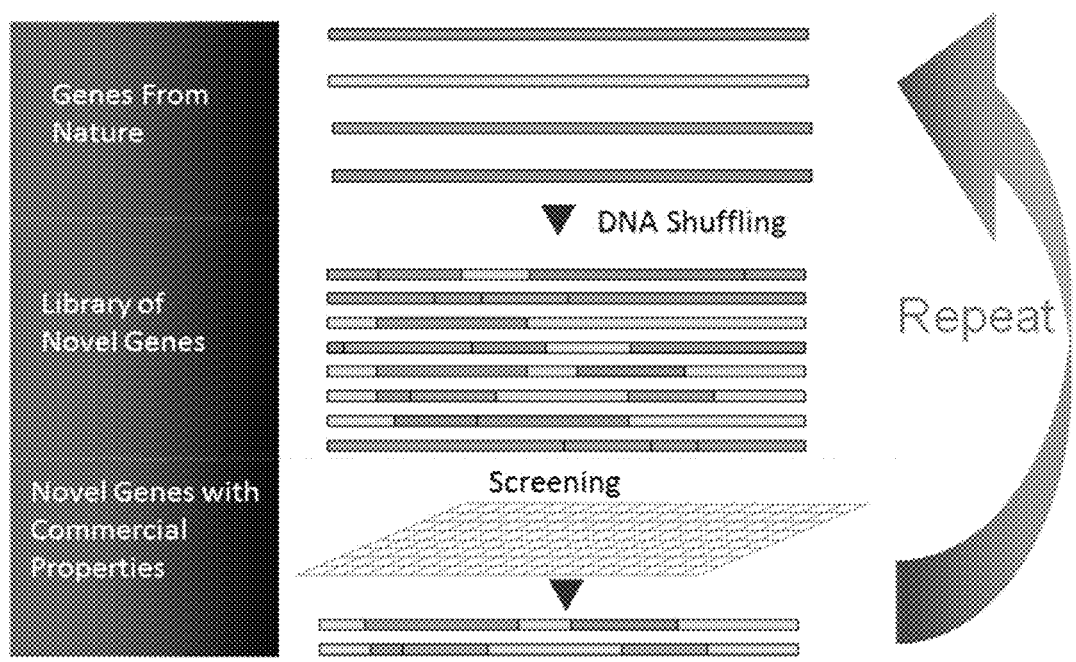
FIG. 1. An illustration for directed molecular evolution.
Figure 3:
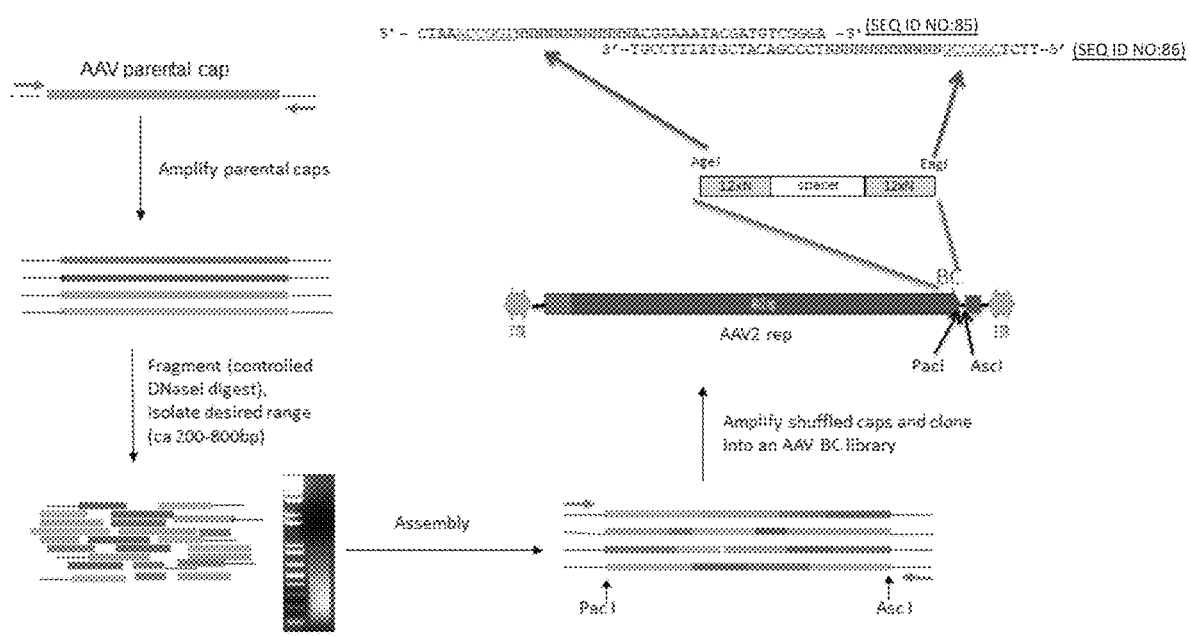
FIG. 3. Generation of barcoded capsid shuffled AAV libraries. Library generation workflow: First, an AAV vector barcode library is generated which was used as backbone for cloning of the shuffled capsid sequences.

Such methods for generating the variant AAV capsid polypeptides include DNA shuffling of capsid proteins, which begins with families of capsid genes from an array or plurality of AAV pseudo-species (for example, AAV1, AAV2, AAV3b, AAV4, AAV5, AAV6, AAV7, AAV8, AAV9, AAV 9_hu14, bovine AAV, avian AAV), that are enzymatically shuffled to create a diverse library of capsid genes that can be cloned back into an AAV shuttle plasmid and utilized to produce live replicating viral libraries (see, for example, FIG. 1 and FIG. 3). To maximize the likelihood that shuffled capsids (i.e., variant AAV capsid polypeptides) could functionally transduce human pancreatic tissue and/or human islets—as compared to non-variant parent capsid polypeptides—the invention contemplates performing two simultaneous screens in primary human intact islets and dissociated human islet cells.

Figure 4:
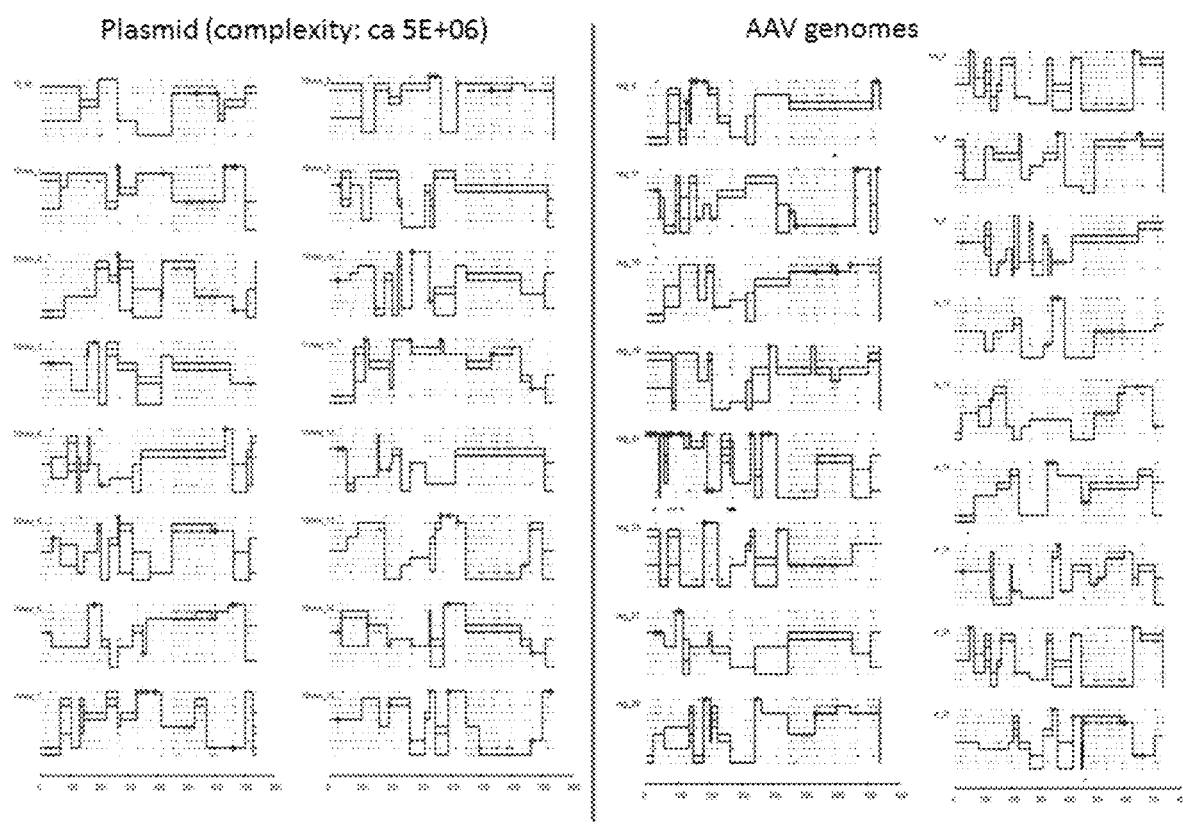
FIG. 4. Crossover analysis of the capsid amino acid sequences in randomly chosen 10 parent library clones on the plasmid and the AAV level. Parental contributions are shown in the following order (top to bottom): po2, AAV1, AAV6, AAV3B, LK03, AAV8, rh10, AAV9hu14, AAV2, DJ.
Figure 10A:
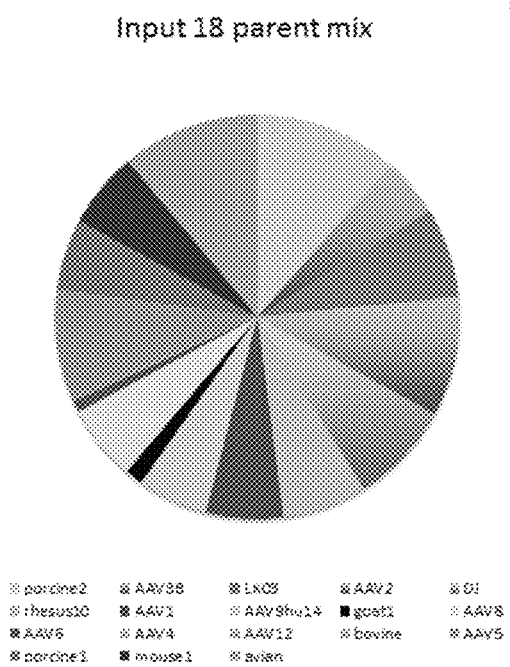
FIG. 10. Composition of the 18 parent control mix (left) and enrichment for parental cap AAVs during passaging (right). Only the most enriched parental AAVs are shown in the right panel. (A) Composition of the 18 parent pool as determined by NGS BC sequencing. (B) Enrichment of parental AAVs through three consecutive passages of the 18 parent mix on intact islets and on dissociated islet.
Figure 10B:
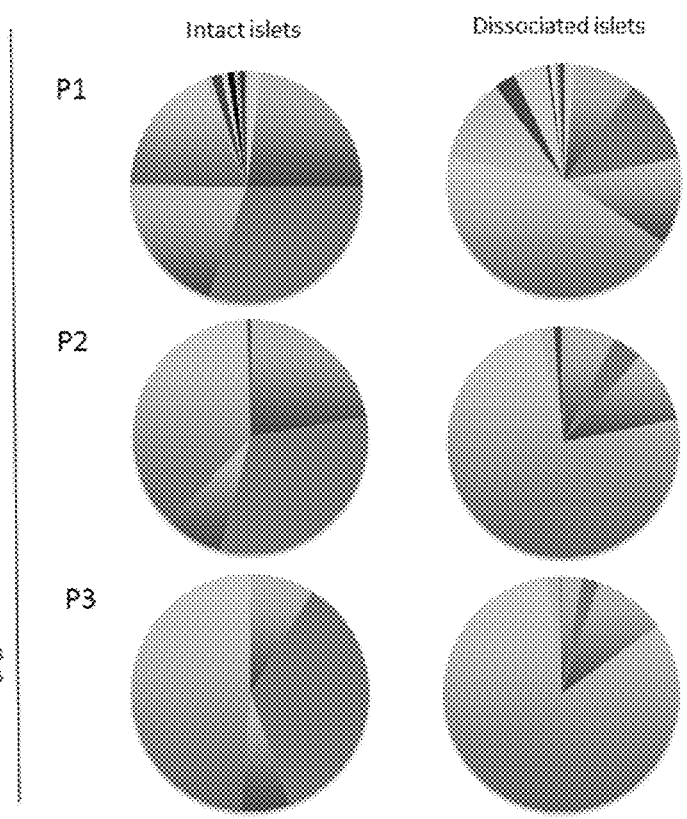
Figure 21:
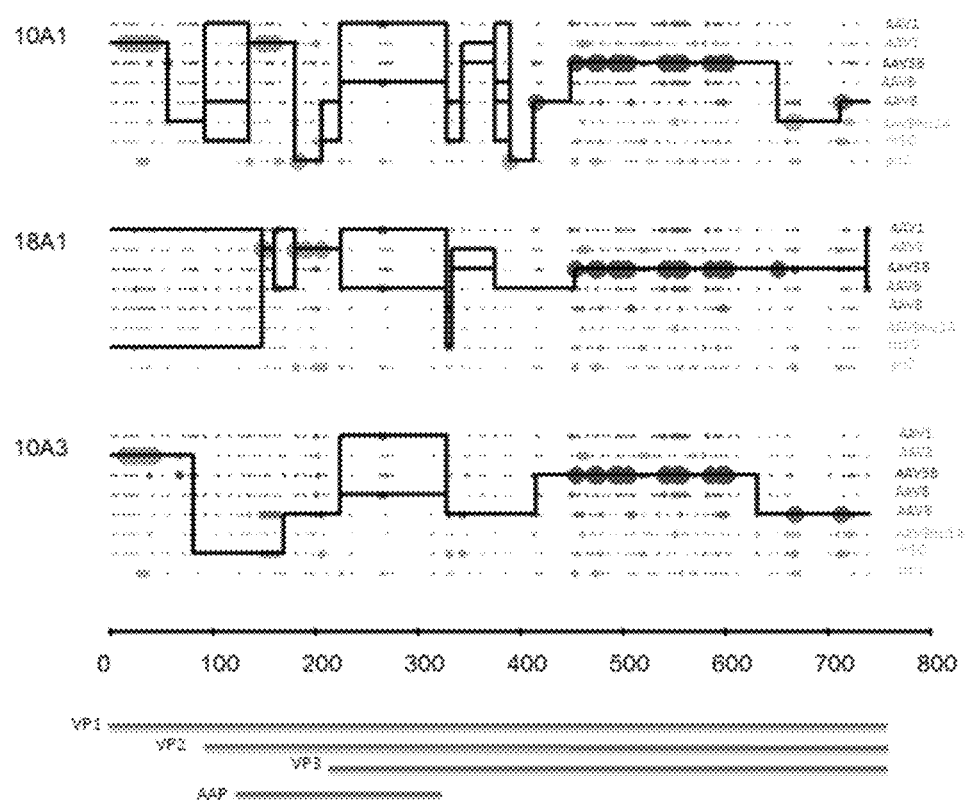
FIG. 21. Composition of the best capsid variants (crossover, amino acids). Library parents are depicted in different colors in order of entry of the parents. Large dots represent 100% parental match (i.e. the position in question matches only one parent) and small dots represent more than one parental match (i.e. the position matches more than one parent) at each position. The solid line for each chimera represents the library parents identified within the sequence between crossovers. A set of thin horizontal parallel lines between crossovers indicates multiple parents match at an equal probability.
Figure 22:
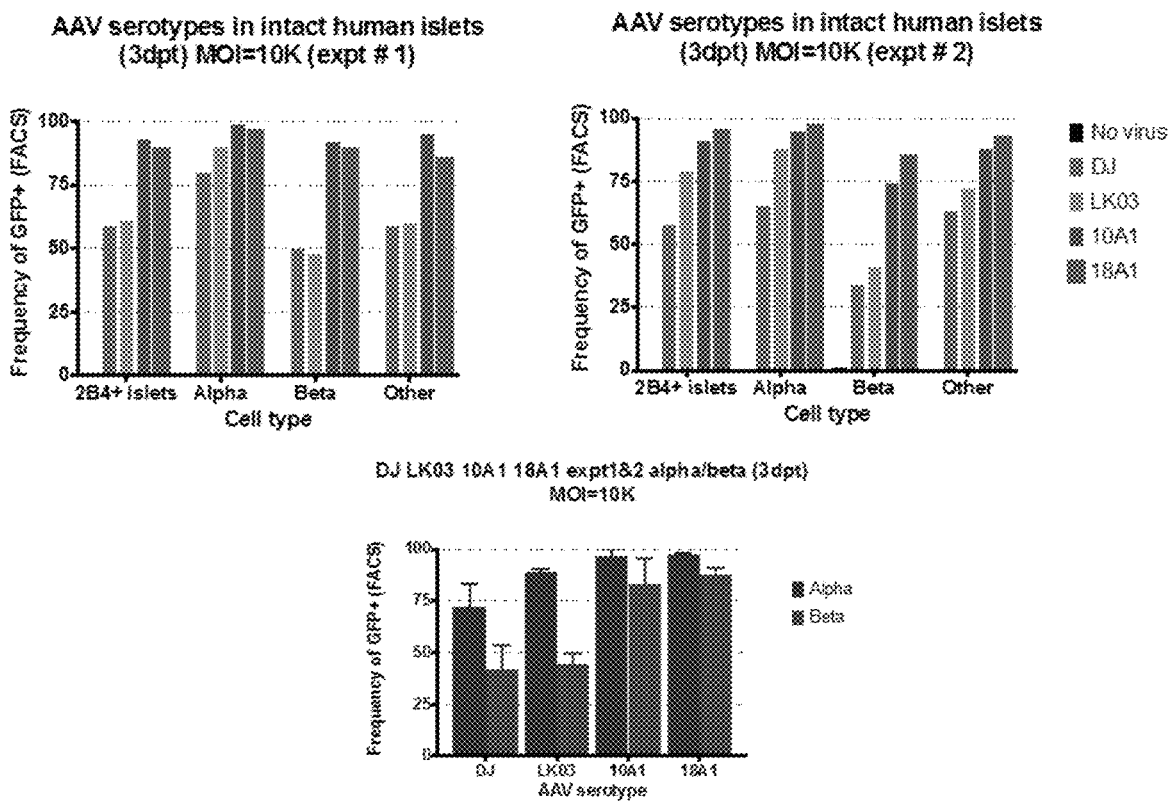
FIG. 22. 10A1 and 18A1 transduce β-cells significantly better than LK03.
Figure 23:
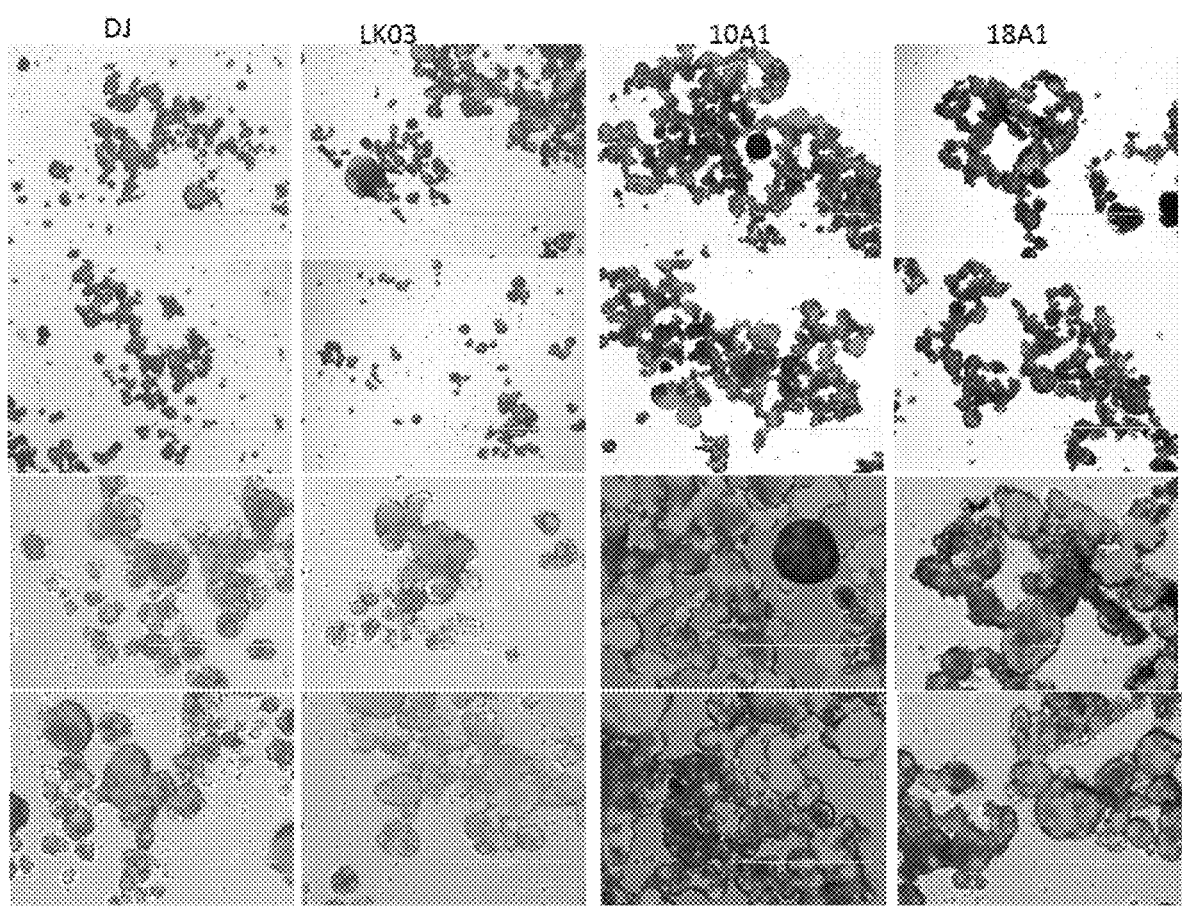
FIG. 23. Grompe Transduction of islets. Intact whole islets were transduced at MOI=10K on ice for 1-2 hours (2% FBS/CMRL) and suspended in culture for 3 days. FACS: 2B4/8G12 mAbs.
Figure 24:
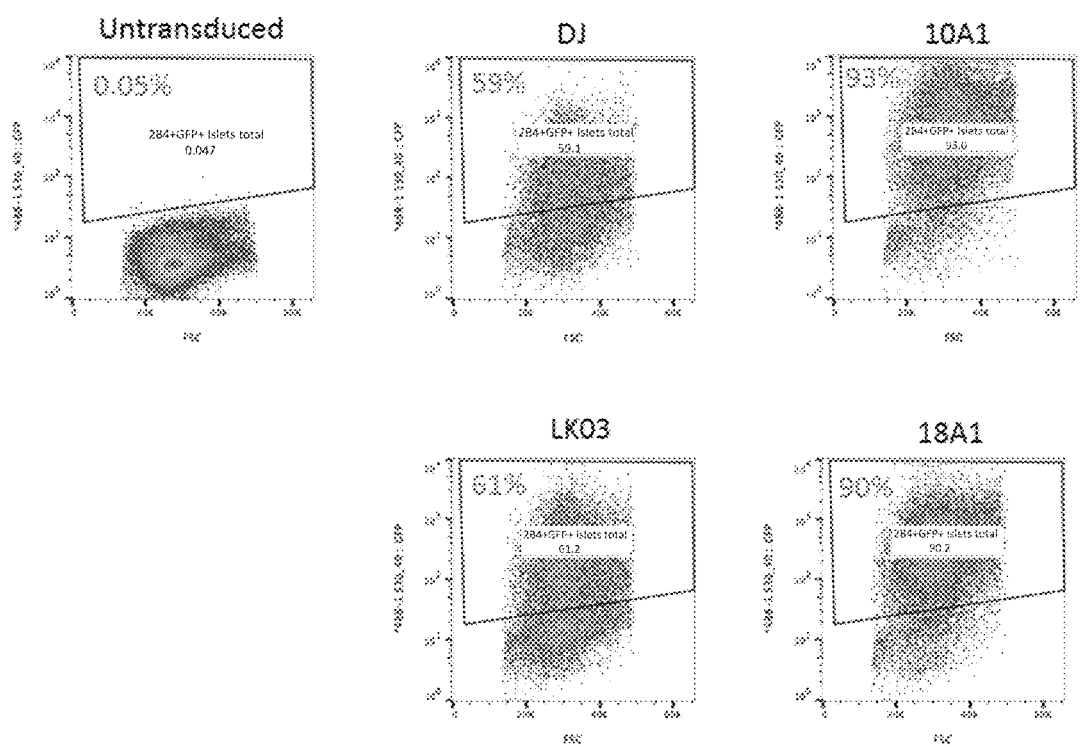
FIG. 24. Quantification of total islets GFP+(HIC1-2B4+ population).
Figure 25:
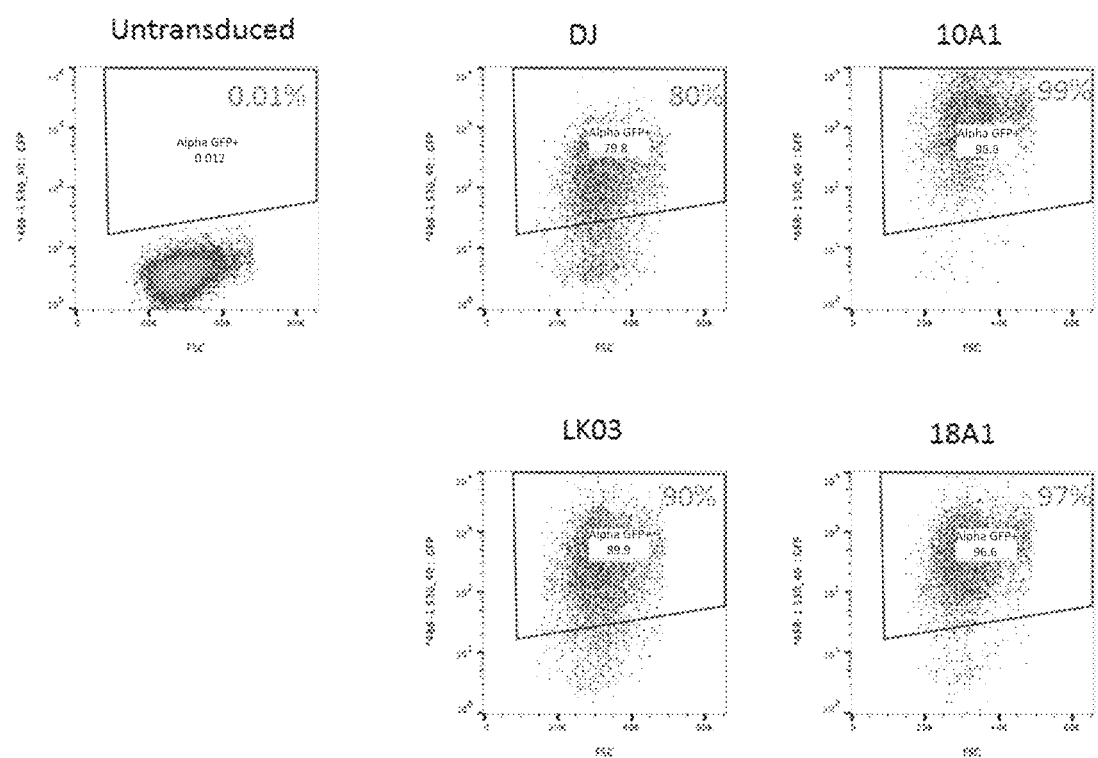
FIG. 25. Quantification of ALPHA GFP+(2B4+8G12+) cells.
Figure 26:
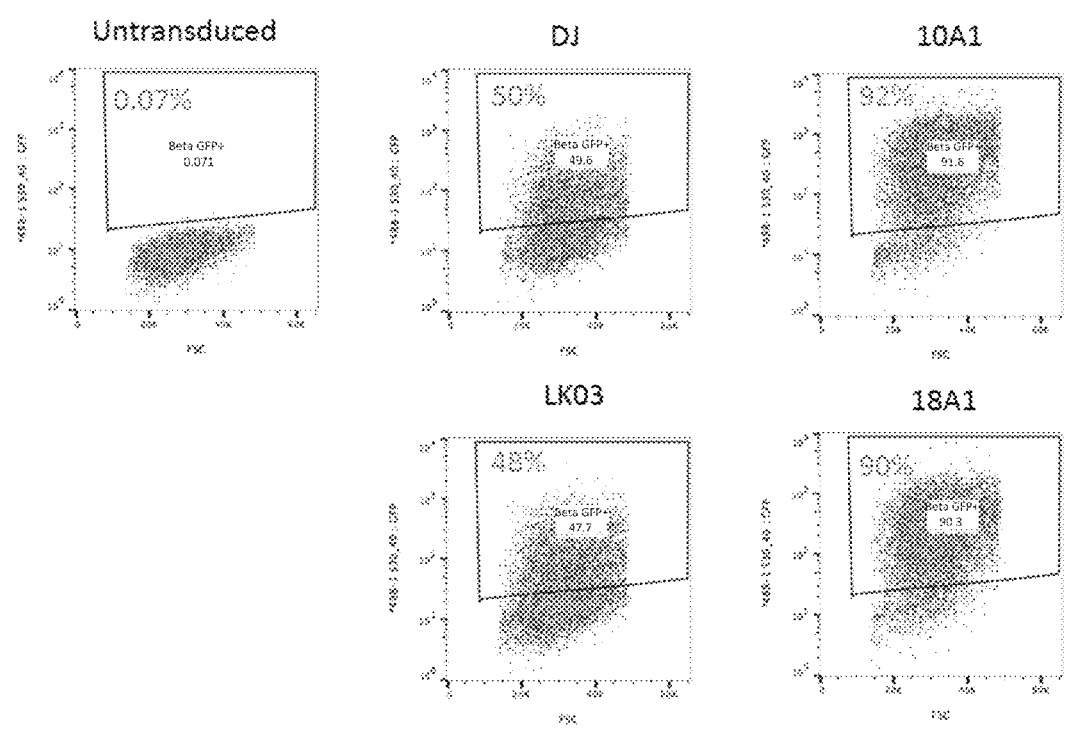
FIG. 26. Quantification of BETA GFP+(2B4+8G12-/lo) cells. (lo=low expression).
Figure 27:
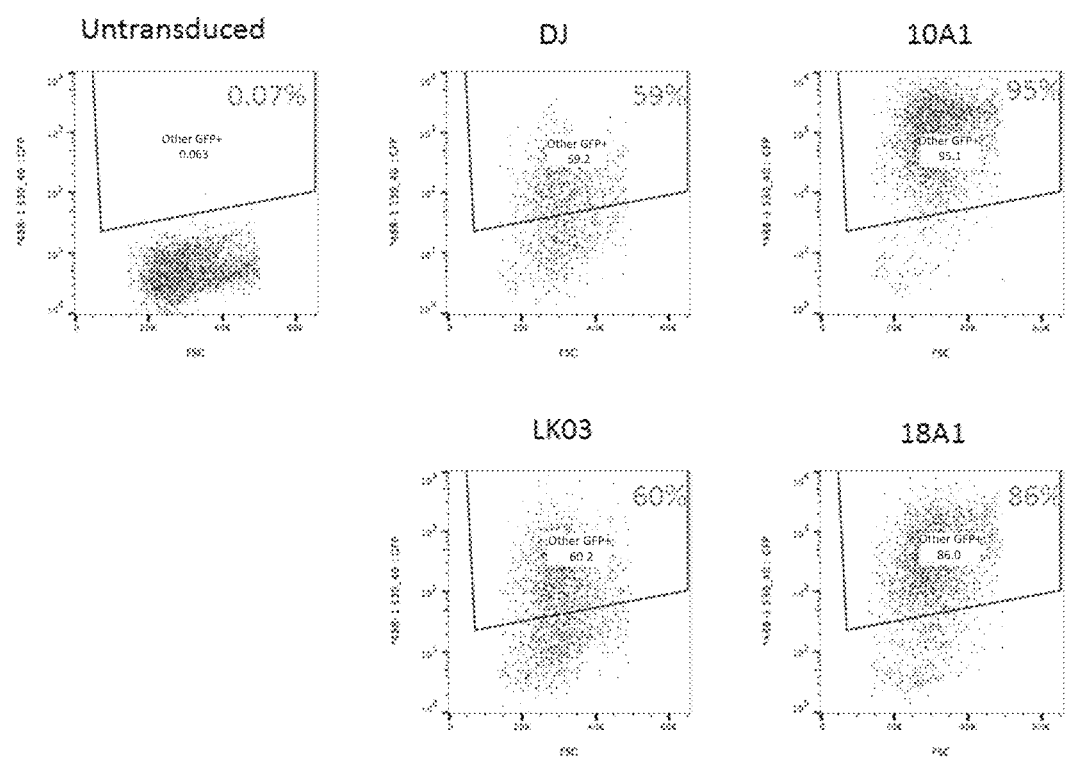
FIG. 27. Quantification of OTHER GFP+(2B4+8G12int) cells. (int=intermediate expression).
Figure 29:
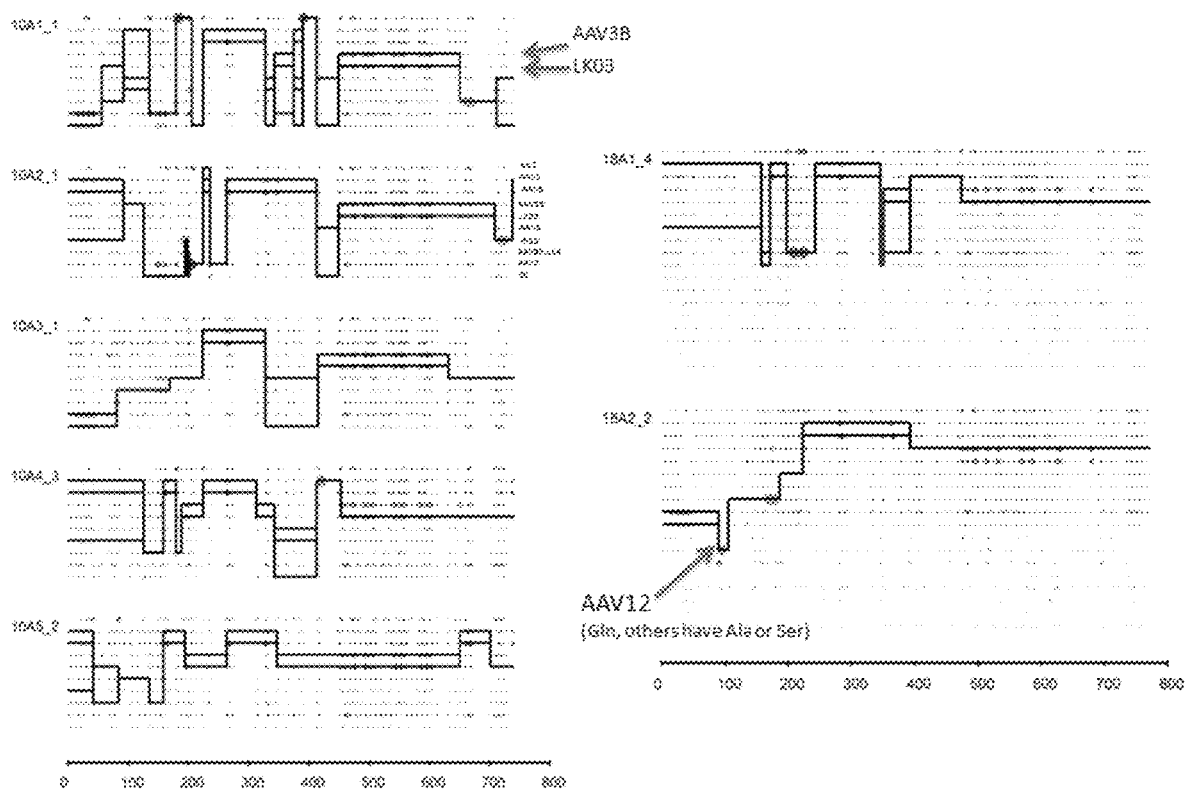
FIG. 29. Vectorized capsid variants from screen A.
Figure 30:
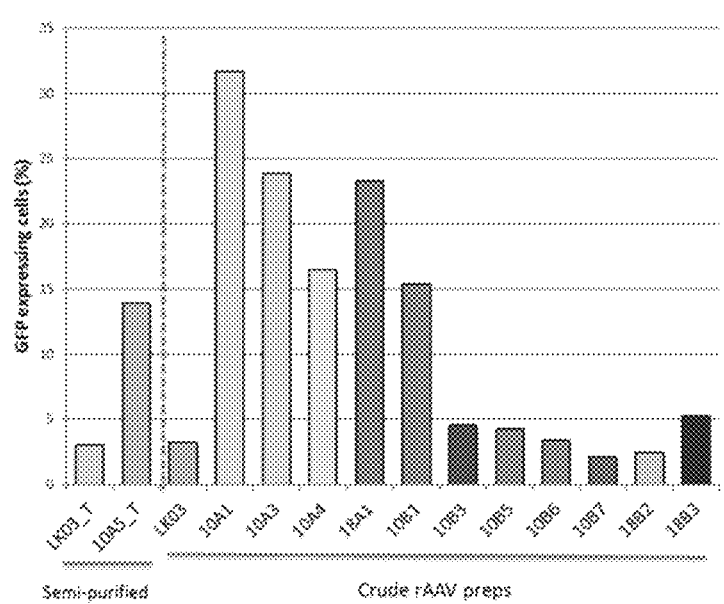
FIG. 30. Transduction efficiency of selected capsid variants on human islet cells. kit 1E+05 dissociated islet cells were transduced with semi-purified or crude rAAV at an MOI of 1K. After 48 hours, transduction efficiency was evaluated by FACS.
Figure 31:
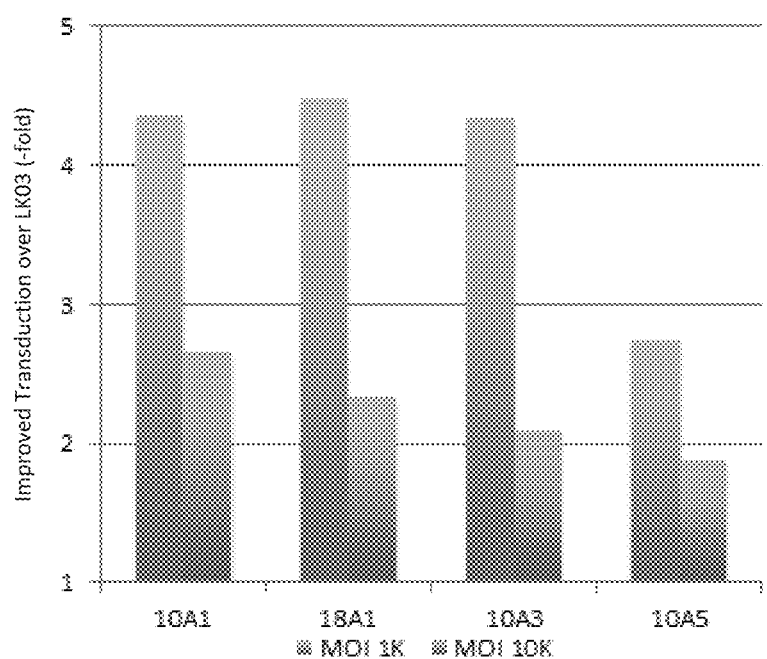
FIG. 31. Transduction efficiency of selected capsid variants on human islet cells. 1E+05 dissociated islet cells were transduced with semi-purified rAAV at an MOI of 1K and 10K. After 48 hrs transduction efficiency was evaluated by FACS. Improvement of transduction over the best parental LK03 is shown.
Figure 32:
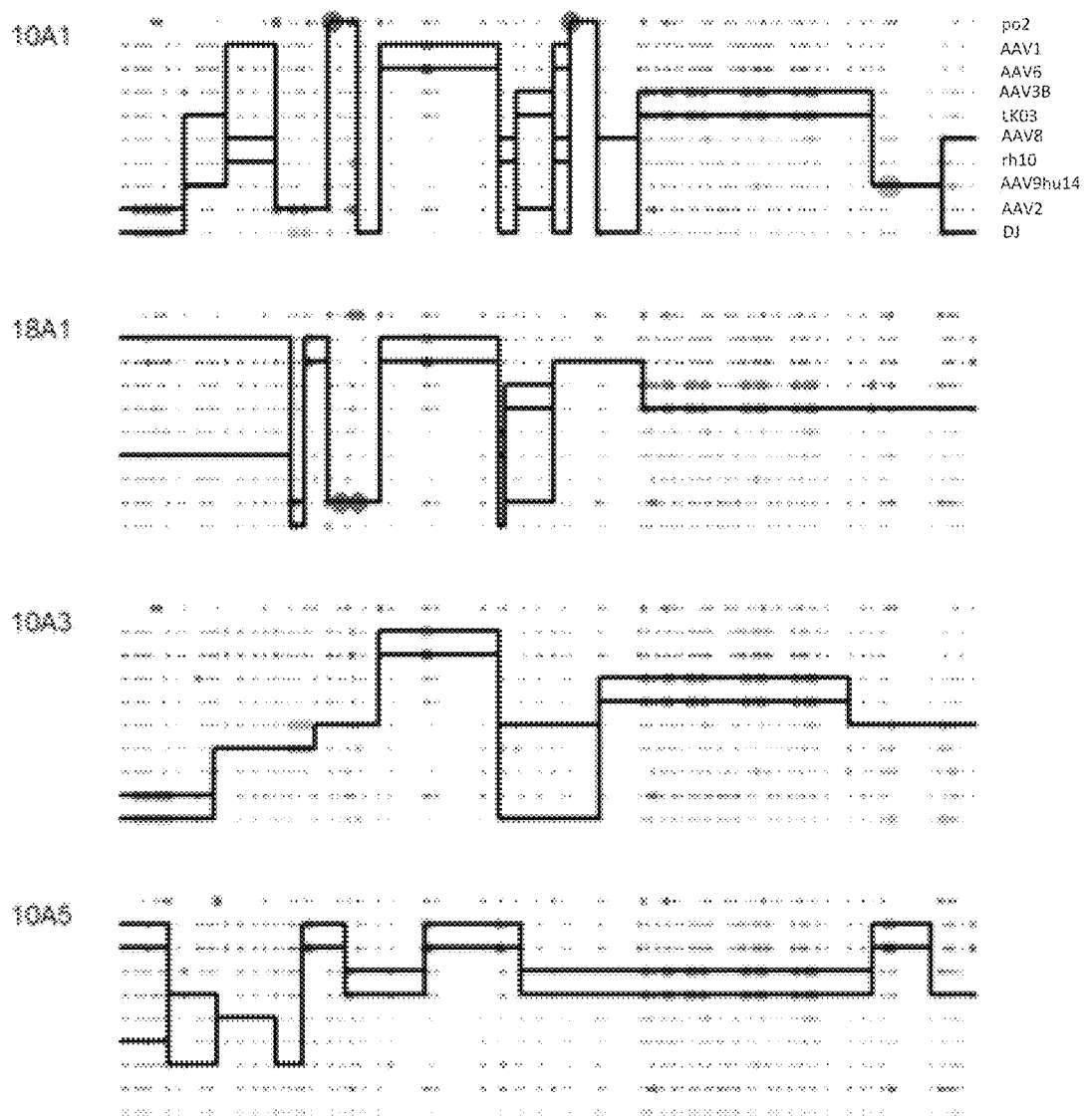
FIG. 32. Crossover analysis of the best capsid variants at the amino acid level.
Figure 33:
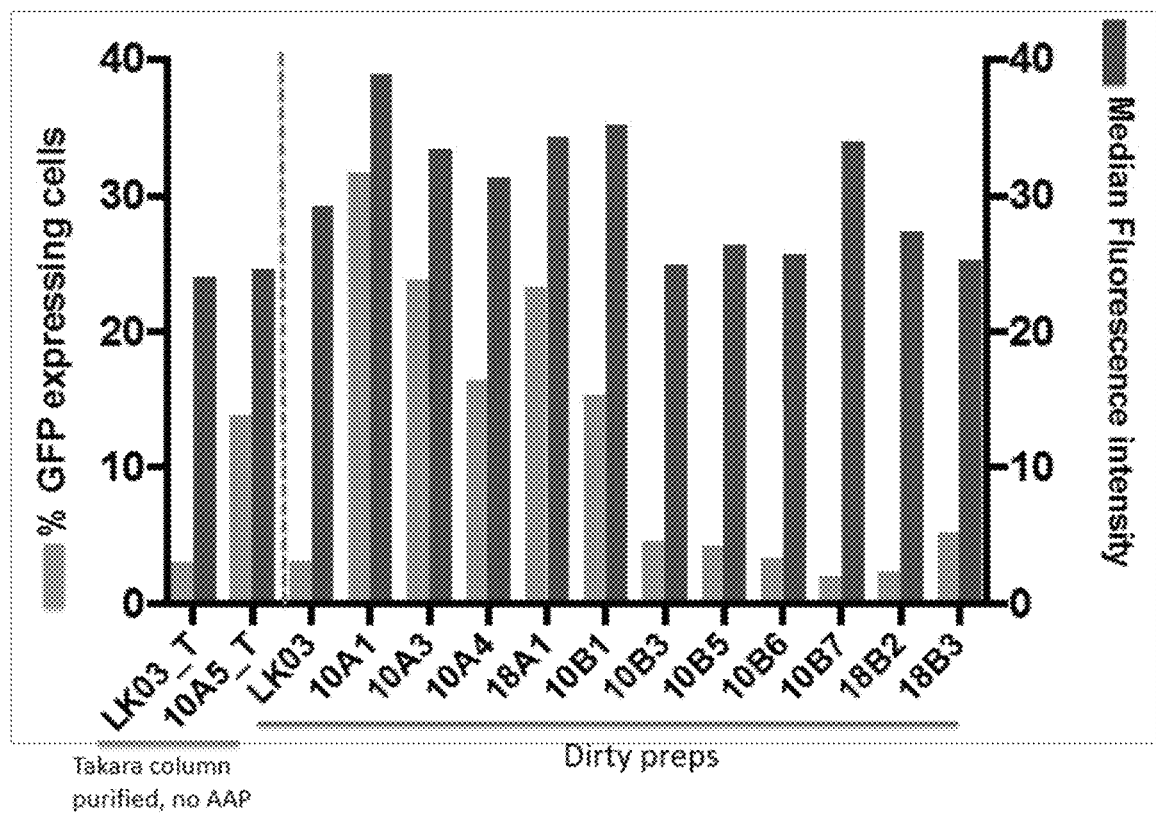
FIG. 33. Quantification of GFP expressing cells after transduction of 1E+05 dissociated islet cells at MOI 1K.
Figure 34:
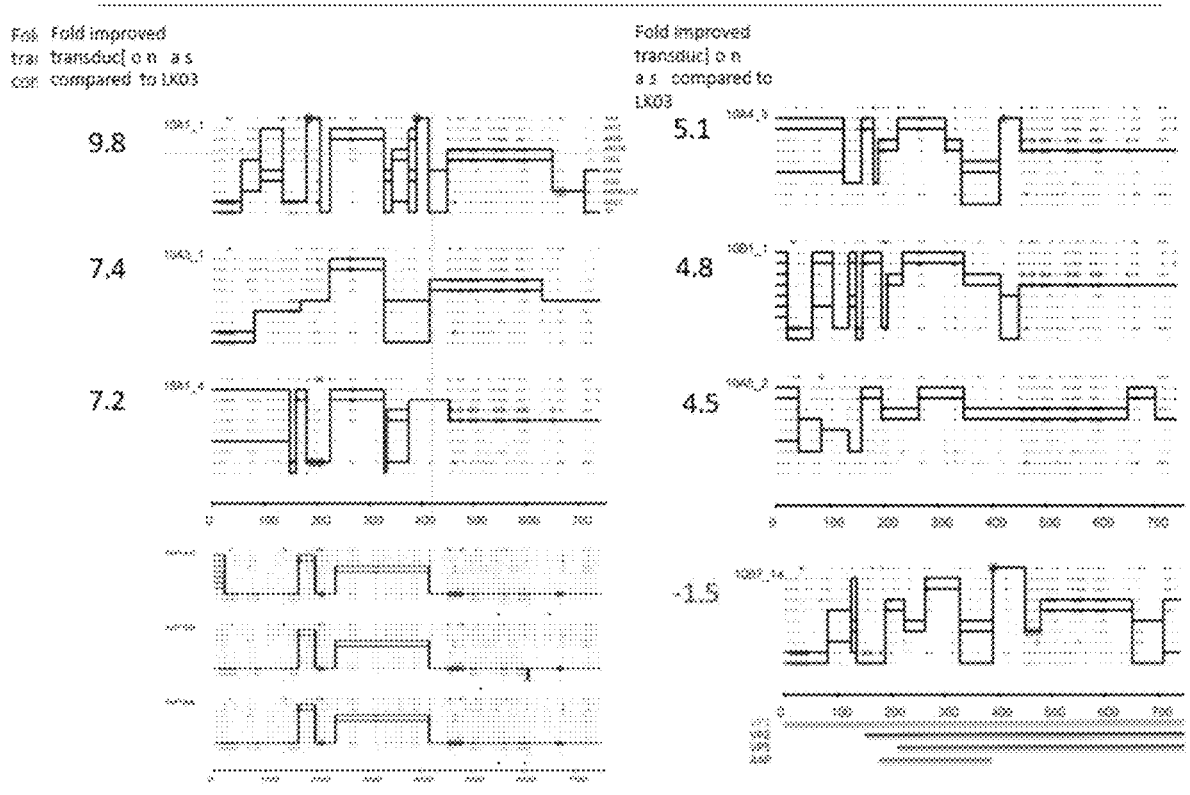
FIG. 34. Capsid variant performance compared to LK03.

At the completion of both screens, variants are chosen from each screen for full Sanger sequencing and phylogenetic comparisons to parental serotypes (i.e., parental non-variant capsid polypeptide sequences). In some embodiments, the parental non-variant capsid polypeptide sequences are those that went into the initial library. The most highly selected variants (for example, those that exhibit the highest increase in transduction and/or tropism) from each screen are isolated and vectorized with expression constructs, in some cases for use in subsequent validation experiments. In some embodiments, in order to assess the genetic contribution of each parental AAV serotype (i.e., non-variant parent capsid polypeptide) to the evolved capsids (i.e., variant AAV capsid polypeptides) selected from each screen, crossover mapping can be performed (see, for example, FIG. 4 and FIG. 21) and bioinformatic prediction analyses (see, for example, FIG. 10 and FIG. 11) to calculate enrichment scores for likelihood of parental (i.e., non-variant parent capsid polypeptide) contribution to each position in the new capsids (i.e., variant AAV capsid polypeptides). Both methodologies demonstrated the highly shuffled nature of the evolved capsid variants and highlighted both unique and shared domains present in selected capsids. In some embodiments, the parental capsids (i.e., non-variant parent capsid polypeptides) that contribute the most to the evolved variants include AAV-10A1 (SEQ ID NO:1), AAV-10A3 (SEQ ID NO:2), and AAV-18A1 (SEQ ID NO:5).

In vitro characterizations are used to demonstrate the significant increase in transduction by variant AAV capsid polypeptides over control serotypes (i.e., non-variant parent capsid polypeptides) in various pancreas-derived cell lines.

For such analyses, large-scale ultrapure productions of AAV vectorized variants (AAV vectors composed of variant AAV capsid polypeptides) can be carried out and those capable of producing high titers sufficient for eventual clinical use (for example, variants AAV-10A1 (SEQ ID NO:1), AAV-10A3 (SEQ ID NO:2), AAV-10A4 (SEQ ID NO:3), AAV-10A5 (SEQ ID NO:4), AAV-18A1 (SEQ ID NO:5), AAV-10B1 (SEQ ID NO:6), AAV-10B3 (SEQ ID NO:7), AAV-10B5 (SEQ ID NO:8), AAV-10B6 (SEQ ID NO:9), AAV-10B7 (SEQ ID NO:10), AAV-18B2 (SEQ ID NO:12), and AAV-18B3 (SEQ ID NO:13), and in particular variants AAV-10A1 (SEQ ID NO:1), AAV-10A3 (SEQ ID NO:2), and AAV-18A1 (SEQ ID NO:5) are considered further for validation.

In order to examine the activity of the AAV vectors encoding the variant AAV capsid polypeptides of the invention, further validation can be performed using ex vivo human pancreatic tissue. Ex vivo human pancreas explant transductions are employed to validate the significantly increased expression in human pancreatic tissue specifically. Samples for use in ex vivo analyses and/or assays can include but are not limited to human pancreas isolation from surgical specimens. Such human pancreas specimens can be obtained from both male and female patients by surgical isolation. Samples for use in ex vivo analyses and/or assays can include but are not limited to non-human pancreas isolation In some embodiments, human pancreas or islets can be used for in vitro analyses and/or assays.

While chimeric humanized pancreas xenografts are powerful tools to model human-like in vivo systems, they are limited in their ability to truly define expected transduction in human patients given the continued presence of mouse cells, as well as the chimeric nature of the fusion products which express both mouse and human protein simultaneously. In some embodiments, islets harvested from deceased organ donors can be treated with rAAV expressing certain transcription factors prior to transplantation into patients. Islet transplantation has been done as treatment for Type 1 diabetes for many years, and is a procedure well-known by those in the art. In some embodiments, islets harvested from deceased organ donors can be treated with the rAAV vectors of the present invention as described herein.

In some embodiments, increased transduction of AAV vectors encoding variant parent capsid polypeptides are exhibited in both dividing and non-dividing human pancreatic cell types. In some embodiments, increased transduction of AAV vectors encoding variant parent capsid polypeptides are exhibited in dividing pancreatic cells. In some embodiments, increased transduction of AAV vectors encoding variant parent capsid polypeptides are exhibited in non-dividing pancreatic cells with long-term transgene expression.

AAV Vector Elements

The nucleic acid insert (also referred to as a heterologous nucleotide sequence) can be operably linked to control elements directing the transcription or expression thereof in the nucleotide sequence in vivo. Such control elements can comprise control sequences normally associated with the selected gene (e.g., endogenous cellular control elements). Alternatively, heterologous control sequences can be employed. Useful heterologous control sequences generally include those derived from sequences encoding mammalian or viral genes. Examples include, but are not limited to, the SV40 early promoter, mouse mammary tumor virus long terminal repeat (LTR) promoter; adenovirus major late promoter (Ad MLP); a herpes simplex virus (HSV) promoter, an endogenous cellular promoter heterologous to the gene of interest, a cytomegalovirus (CMV) promoter such as the CMV immediate early promoter region (CMVIE), a rous sarcoma virus (RSV) promoter, synthetic promoters, hybrid promoters, and the like. In addition, sequences derived from nonviral genes, such as the murine metallothionein gene, can also be used. Such promoter sequences are commercially available from, e.g., Stratagene (San Diego, Calif.).

In some embodiments, a cell type-specific or a tissue-specific promoter can be operably linked to nucleic acid insert (also referred to as a heterologous nucleotide sequence) encoding the heterologous gene product, and allowing for selectively or preferentially producing a gene product in a particular cell type(s) or tissue(s). In some embodiments, an inducible promoter can be operably linked to the heterologous nucleic acid.

In some embodiments, the nucleic acid is packaged with the variant AAV capsid polypeptides of the invention. In some embodiments, the nucleic acid insert or packaged nucleic acid is at least 50, 100, 200, 300, 400, 500, 600, 700, 800, 900, 1000, 1100, 1200, 1300, 1400, or 1500 nucleic acids in length. In some embodiments, the nucleic acid insert or packaged nucleic acid is at least 50 nucleic acids to at least 1500 nucleic acids. In some embodiments, the nucleic acid insert or packaged nucleic acid is at least 100 nucleic acids to at least 1400 nucleic acids. In some embodiments, the nucleic acid insert or packaged nucleic acid is at least 200 nucleic acids to at least 1100 nucleic acids. In some embodiments, the nucleic acid insert or packaged nucleic acid is at least 300 nucleic acids to at least 1000 nucleic acids. In some embodiments, the nucleic acid insert or packaged nucleic acid is at least 100 nucleic acids to at least 900 nucleic acids. In some embodiments, the nucleic acid insert or packaged nucleic acid is at least 200 nucleic acids to at least 900 nucleic acids. In some embodiments, the nucleic acid insert or packaged nucleic acid is at least 300 nucleic acids to at least 900 nucleic acids. In some embodiments, the nucleic acid insert or packaged nucleic acid is at least 100 nucleic acids to at least 600 nucleic acids.

In some embodiments, the AAV vector packaged by the variant AAV capsid polypeptides is at least about 2000 nucleic acids in total length and up to about 5000 nucleic acids in total length. In some embodiments, the AAV vector packaged by the variant AAV capsid polypeptides is about 2000 nucleic acids, about 2400 nucleic acids, about 2800 nucleic acids, about 3000 nucleic acids, about 3200 nucleic acids, about 3400 nucleic acids, about 3600 nucleic acids, about 3800 nucleic acids, about 4000 nucleic acids, about 4200 nucleic acids, about 4400 nucleic acids, about 4600 nucleic acids, about 4700 nucleic acids, or about 4800 nucleic acids. In some embodiments, the AAV vector packaged by the variant AAV capsid polypeptides is between about 2000 nucleic acids (2 kb) and about 5000 nucleic acids (5 kb). In some embodiments, the AAV vector packaged by the variant AAV capsid polypeptides is between about 2400 nucleic acids (2.4 kb) and about 4800 nucleic acids (4.8 kb). In some embodiments, the AAV vector packaged by the variant AAV capsid polypeptides is between about 3000 nucleic acids (3 kb) and about 5000 nucleic acids (5 kb). In some embodiments, the AAV vector packaged by the variant AAV capsid polypeptides is between about 3000 nucleic acids (3 kb) and about 4000 nucleic acids (4 kb).

The AAV vectors or AAV virions disclosed herein can also include conventional control elements operably linked to the nucleic acid insert (also referred to as a heterologous nucleotide sequence) in a manner permitting transcription, translation and/or expression in a cell transfected with the AAV vector or infected with the AAV virion produced according to the present invention. As used herein, "operably linked" sequences include both expression control sequences that are contiguous with the gene of interest and expression control sequences that act in trans or at a distance to control the gene of interest.

Expression control sequences include appropriate transcription initiation, termination, promoter and enhancer sequences; efficient RNA processing signals such as splicing and polyadenylation (polyA) signals; sequences that stabilize cytoplasmic mRNA; sequences that enhance translation efficiency (i.e., Kozak consensus sequence); sequences that enhance protein stability; and when desired, sequences that enhance secretion of the encoded product. A great number of expression control sequences, including promoters selected from native, constitutive, inducible and/or tissue-specific, are known in the art and may be utilized.

Examples of constitutive promoters include, without limitation, the retroviral Rous sarcoma virus (RSV) LTR promoter (optionally with the RSV enhancer), the cytomegalovirus (CMV) promoter (optionally with the CMV enhancer) (see, e.g., Boshart et al., Cell, 41:521-530 (1985)), the SV40 promoter, the dihydrofolate reductase promoter, the beta-actin promoter, the phosphoglycerol kinase (PGK) promoter, and the EF1 promoter (Invitrogen). Inducible promoters allow regulation of gene expression and can be regulated by exogenously supplied compounds, environmental factors such as temperature, or the presence of a specific physiological state, e.g., acute phase, a particular differentiation state of the cell, or in replicating cells only. Inducible promoters and inducible systems are available from a variety of commercial sources, including, without limitation, Invitrogen, Clonetech and Ariad. Many other systems have been described and can be readily selected by one of skill in the art. Examples of inducible promoters regulated by exogenously supplied compounds, include, the zinc-inducible sheep metallothionine (MT) promoter, the dexamethasone (Dex)-inducible mouse mammary tumor virus (MMTV) promoter, the T7 polymerase promoter system (WO 98/10088); the ecdysone insect promoter (No et al., (1996) Proc. Natl. Acad. Sci. USA, 93:3346-3351), the tetracycline-repressible system (Gossen et al., (1992) Proc. Natl. Acad. Sci. USA, 89:5547-5551), the tetracycline-inducible system (Gossen et al., (1995) Science, 268:1766-1769, see also Harvey et al., (1998) Curr. Opin. Chem. Biol., 2:512-518), the RU486-inducible system (Wang et al., (1997) Nat. Biotech., 15:239-243 and Wang et al., (1997) Gene Ther., 4:432-441) and the rapamycin-inducible system (Magari et al., (1997) J Clin. Invest., 100:2865-2872). Other types of inducible promoters useful in this context are those regulated by a specific physiological state, e.g., temperature, acute phase, a particular differentiation state of the cell, or in replicating cells only.

In another embodiment, the native promoter for the nucleic acid insert (also referred to as a heterologous nucleotide sequence) will be used. The native promoter may be preferred when it is desired that expression of the nucleic acid insert (also referred to as a heterologous nucleotide sequence) should mimic the native expression. The native promoter may be used when expression of the nucleic acid insert (also referred to as a heterologous nucleotide sequence) must be regulated temporally or developmentally, or in a tissue-specific manner, or in response to specific transcriptional stimuli. In a further embodiment, other native expression control elements, such as enhancer elements, polyadenylation sites or Kozak consensus sequences may also be used to mimic the native expression.

Another embodiment of the nucleic acid insert (also referred to as a heterologous nucleotide sequence) includes a gene operably linked to a tissue-specific promoter. For instance, if expression in pancreas is desired, a promoter active in pancreas should be used. These include the promoters from genes encoding skeletal β-actin, myosin light chain 2A, dystrophin, and muscle creatine kinase with activities higher than naturally-occurring promoters (see Li et al., Nat. Biotech., 17:241-245 (1999)). Examples of promoters that are tissue-specific are known for liver (albumin, Miyatake et al., (1997) J. Virol., 71:5124-32; hepatitis B virus core promoter, Sandig et al., (1996) Gene Ther., 3:1002-9; alpha-fetoprotein (AFP), Arbuthnot et al., (1996) Hum. Gene Ther., 7:1503-14), bone osteocalcin (Stein et al., (1997)Mol. Biol. Rep., 24:185-96); bone sialoprotein (Chen et al., (1996) J Bone Miner. Res., 11:654-64), lymphocytes (CD2, Hansal et al., (1998) J. Immunol., 161:1063-8; immunoglobulin heavy chain; T cell receptor chain), neuronal such as neuron-specific enolase (NSE) promoter (Andersen et al., (1993) Cell. Mol. Neurobiol., 13:503-15), neurofilament light-chain gene (Piccioli et al., (1991) Proc. Natl. Acad. Sci. USA, 88:5611-5), and the neuron-specific vgf gene (Piccioli et al., (1995) Neuron, 15:373-84), among others.

In various embodiments, AAV vectors or AAV virions carrying one or more therapeutically useful nucleic acid inserts (also referred to as a heterologous nucleotide sequence) also include selectable markers or reporter genes, e.g., sequences encoding geneticin, hygromycin or puromycin resistance, among others. Selectable reporters or marker genes can be used to signal the presence of the plasmids/vectors in bacterial cells, including, for example, examining ampicillin resistance. Other components of the plasmid may include an origin of replication. Selection of these and other promoters and vector elements are conventional and many such sequences are available (see, e.g., Sambrook et al., and references cited therein).

Host Cells and Packaging

Host cells are necessary for generating infectious AAV vectors as well as for generating AAV virions based on the disclosed AAV vectors. Accordingly, the present invention provides host cells for generation and packaging of AAV virions based on the AAV vectors of the present invention. A variety of host cells are known in the art and find use in the methods of the present invention. Any host cells described herein or known in the art can be employed with the compositions and methods described herein.

The present invention provides host cells, e.g., isolated (genetically modified) host cells, comprising a subject nucleic acid. A subject host cell can be an isolated cell, e.g., a cell in in vitro culture. A subject host cell is useful for producing a subject AAV vector or AAV virion, as described below. Where a subject host cell is used to produce a subject AAV virion, it is referred to as a "packaging cell." In some embodiments, a subject host cell is stably genetically modified with a subject AAV vector. In other embodiments, a subject host cell is transiently genetically modified with a subject AAV vector.

In some embodiments, a subject nucleic acid is introduced stably or transiently into a host cell, using established techniques, including, but not limited to, electroporation, calcium phosphate precipitation, liposome-mediated transfection, baculovirus infection, and the like. For stable transformation, a subject nucleic acid will generally further include a selectable marker, e.g., any of several well-known selectable markers such as neomycin resistance, and the like.

Generally, when delivering the AAV vector according to the present invention by transfection, the AAV vector is delivered in an amount from about 5 µg to about 100 µg DNA, about 10 to about 50 µg DNA to about $1\times10^4$ cells to about $1\times10^{13}$ cells, or about $1\times10^5$ cells. However, the relative amounts of vector DNA to host cells may be adjusted, taking into consideration such factors as the selected vector, the delivery method and the host cells selected and such adjustments are within the level of skill of one in the art.

In some embodiments, the host cell for use in generating infectious virions can be selected from any biological organism, including prokaryotic (e.g., bacterial) cells, and eukaryotic cells, including, insect cells, yeast cells and mammalian cells. A subject host cell is generated by introducing a subject nucleic acid (i.e., AAV vector) into any of a variety of cells, e.g., mammalian cells, including, e.g., murine cells, and primate cells (e.g., human cells). Particularly desirable host cells are selected from among any mammalian species. In some embodiments, cells include without limitation, cells such as A549, WEHI, 10T1/2, BHK, MDCK, COS 1, COS 7, BSC 1, BSC 40, BMT 10, WI38, HeLa, CHO, 293, Vero, NIH 3T3, PC12, Huh-7 Saos, C2C12, RAT1, Sf9, L cells, HT1080, human embryonic kidney (HEK), human embryonic stem cells, human adult tissue stem cells, pluripotent stem cells, induced pluripotent stem cells, reprogrammed stem cells, organoid stem cells, bone marrow stem cells, HLHepG2, HepG2 and primary fibroblast, hepatocyte and myoblast cells derived from mammals including human, monkey, mouse, rat, rabbit, and hamster. The selection of the mammalian species providing the cells is not a limitation of this invention; nor is the type of mammalian cell, i.e., fibroblast, hepatocyte, tumor cell, etc. The requirement for the cell used is it is capable of infection or transfection by an AAV vector. In some embodiments, the host cell is one that has Rep and Cap stably transfected in the cell, including in some embodiments a variant AAV capsid polypeptide as described herein. In some embodiments, the host cell expresses a variant AAV capsid polypeptide of the invention or part of an AAV vector as described herein, such as a heterologous nucleic acid sequence contained within the AAV vector.

In some embodiments, the preparation of a host cell according to the invention involves techniques such as assembly of selected DNA sequences. This assembly may be accomplished utilizing conventional techniques. Such techniques include cDNA and genomic cloning, which are well known and are described in Sambrook et al., cited above, use of overlapping oligonucleotide sequences of the adenovirus and AAV genomes, combined with polymerase chain reaction, synthetic methods, and any other suitable methods providing the desired nucleotide sequence.

In some embodiments, introduction of the AAV vector into the host cell may also be accomplished using techniques known to the skilled artisan and as discussed throughout the specification. In a preferred embodiment, standard transfection techniques are used, e.g., CaPO4 transfection or electroporation, and/or infection by hybrid adenovirus/AAV vectors into cell lines such as the human embryonic kidney cell line HEK293 (a human kidney cell line containing functional adenovirus E1 genes providing trans-acting E1 proteins).

In some embodiments, a subject genetically modified host cell includes, in addition to a nucleic acid comprising a nucleotide sequence encoding a variant AAV capsid protein, as described above, a nucleic acid that comprises a nucleotide sequence encoding one or more AAV Rep proteins. In other embodiments, a subject host cell further comprises an AAV vector. An AAV virion can be generated using a subject host cell. Methods of generating an AAV virion are described in, e.g., U.S. Patent Publication No. 2005/0053922 and U.S. Patent Publication No. 2009/0202490.

In addition to the AAV vector, in exemplary embodiments, the host cell contains the sequences driving expression of the AAV capsid polypeptide (including variant AAV capsid polypeptides and non-variant parent capsid polypeptides) in the host cell and Rep sequences of the same serotype as the serotype of the AAV Inverted Terminal Repeats (ITRs) found in the nucleic acid insert (also referred to as a heterologous nucleotide sequence), or a cross-complementing serotype. The AAV Cap and Rep sequences may be independently obtained from an AAV source and may be introduced into the host cell in any manner known to one of skill in the art or as described herein. Additionally, when pseudotyping an AAV vector in an AAV8 capsid for example, the sequences encoding each of the essential Rep proteins may be supplied by AAV8, or the sequences encoding the Rep proteins may be supplied by different AAV serotypes (e.g., AAV1, AAV2, AAV3, AAV4, AAV5, AAV6, AAV7, and/or AAV9).

In some embodiments, the host cell stably contains the capsid protein under the control of a suitable promoter (including, for example, the variant AAV capsid polypeptides of the invention), such as those described above. In some embodiments, the capsid protein is expressed under the control of an inducible promoter. In some embodiments, the capsid protein is supplied to the host cell in trans. When delivered to the host cell in trans, the capsid protein may be delivered via a plasmid containing the sequences necessary to direct expression of the selected capsid protein in the host cell. In some embodiments, when delivered to the host cell in trans, the vector encoding the capsid protein (including, for example, the variant AAV capsid polypeptides of the invention) also carries other sequences required for packaging the AAV, e.g., the Rep sequences.

In some embodiments, the host cell stably contains the Rep sequences under the control of a suitable promoter, such as those described above. In some embodiments, the essential Rep proteins are expressed under the control of an inducible promoter. In another embodiment, the Rep proteins are supplied to the host cell in trans. When delivered to the host cell in trans, the Rep proteins may be delivered via a plasmid containing the sequences necessary to direct expression of the selected Rep proteins in the host cell. In some embodiments, when delivered to the host cell in trans, the vector encoding the capsid protein (including, for example, the variant AAV capsid polypeptides of the invention) also carries other sequences required for packaging the AAV vector, e.g., the Rep sequences.

In some embodiments, the Rep and Cap sequences may be transfected into the host cell on a single nucleic acid molecule and exist stably in the cell as an unintegrated episome. In another embodiment, the Rep and Cap sequences are stably integrated into the chromosome of the cell. Another embodiment has the Rep and Cap sequences transiently expressed in the host cell. For example, a useful nucleic acid molecule for such transfection comprises, from 5' to 3', a promoter, an optional spacer interposed between the promoter and the start site of the Rep gene sequence, an AAV Rep gene sequence, and an AAV Cap gene sequence.

Although the molecule(s) providing Rep and capsid can exist in the host cell transiently (i.e., through transfection), in some embodiments, one or both of the Rep and capsid proteins and the promoter(s) controlling their expression be stably expressed in the host cell, e.g., as an episome or by integration into the chromosome of the host cell. The methods employed for constructing embodiments of the invention are conventional genetic engineering or recombinant engineering techniques such as those described in the references above.

In some embodiments, the packaging host cell can require helper functions in order to package the AAV vector of the invention into an AAV virion. In some embodiments, these functions may be supplied by a herpesvirus. In some embodiments, the necessary helper functions are each provided from a human or non-human primate adenovirus source, and are available from a variety of sources, including the American Type Culture Collection (ATCC), Manassas, Va. (US). In some embodiments, the host cell is provided with and/or contains an E1a gene product, an E1b gene product, an Eta gene product, and/or an E4 ORF6 gene product. In some embodiments, the host cell may contain other adenoviral genes such as VAI RNA. In some embodiments, no other adenovirus genes or gene functions are present in the host cell.

Heterologous Nucleic Acid, Nucleic Acid Gene Products, and Polypeptide Gene Products In various embodiments, the invention provides variant AAV capsid polypeptides capable of forming capsids capable of packaging a variety of therapeutic molecules, including nucleic acids and polypeptides. In some embodiments, the therapeutic molecule is a vaccine. In various embodiments, the invention provides for AAV vectors capable of containing nucleic acid inserts, including for example, transgene inserts or other nucleic acid inserts. This allows for vectors capable of expressing polypeptides. Such nucleic acids can comprise heterologous nucleic acid, nucleic acid gene products, and polypeptide gene products. Features of the nucleic acid inserts are described below.

In some embodiments, the AAV vectors described herein contain nucleic acid inserts. In some embodiments, the nucleic acid insert includes but is not limited to nucleic acid sequences selected from the group consisting of a non-coding RNA, a protein coding sequence, an expression cassette, a multi-expression cassette, a sequence for homologous recombination, a genomic gene targeting cassette, and a therapeutic expression cassette.

In some embodiments, the expression cassette is a CRISPR/CAS expression system.

In some embodiments, a nucleic acid insert comprises a heterologous nucleic acid comprising a nucleotide sequence encoding a heterologous gene product, e.g., a nucleic acid gene product or a polypeptide gene product. In some embodiments, the gene product is an interfering RNA (e.g., shRNA, siRNA, miRNA). In some embodiments, the gene product is an aptamer. The gene product can be a self-complementary nucleic acid. In some embodiments, the gene product is a polypeptide.

Suitable heterologous gene product includes interfering RNA, antisense RNA, ribozymes, and aptamers. Where the gene product is an interfering RNA (RNAi), suitable RNAi include RNAi that decrease the level of a target polypeptide in a cell.

In some embodiments, exemplary polypeptides, nucleic acids, or other therapeutic molecules include those useful in the treatment of pancreatic tissue related diseases. Exemplary pancreatic tissue related diseases include but are not limited to diabetes mellitus (e.g. Type I and Type II), acute pancreatitis, chronic pancreatitis, hereditary pancreatitis, autoimmune pancreatitis, pancreatic cancer (e.g. pancreatic adenocarcinoma, acinar cell carcinoma of the pancreas, cystadenocarcinomas, pancreatoblastoma, pancreatic mucinous cystic neoplasms, etc.), pancreatic benign tumors (e.g. pancreatic serous cystadenoma, solid pseudopapillary tumor of the pancreas, etc.), pancreatic neuroendocrine tumor, cystic fibrosis, exocrine pancreatic insufficiency (EPI), pancreatic pseudocyst, pancreatic cyst, Shwachman-Diamond syndrome, Johanson-Blizzard syndrome, Common Channel syndrome, Zollinger-Ellison syndrome, choledochal cyst, Hemosuccus pancreaticus, and congenital pancreatic abnormalities (e.g. Pancreas divisum, Annular Pancreas, ectopic pancreatic tissue).

In some embodiments, exemplary polypeptides include neuroprotective polypeptides and anti-angiogenic polypeptides. Suitable polypeptides include, but are not limited to, glial derived neurotrophic factor (GDNF), fibroblast growth factor 2 (FGF-2), nurturin, ciliary neurotrophic factor (CNTF), nerve growth factor (NGF; e.g., nerve growth factor-.beta.), brain derived neurotrophic factor (BDNF), neurotrophin-3 (NT-3), neurotrophin-4 (NT-4), neurotrophin-6 (NT-6), epidermal growth factor (EGF), pigment epithelium derived factor (PEDF), a Wnt polypeptide, soluble Flt-1, angiostatin, endostatin, VEGF, an anti-VEGF antibody, a soluble VEGFR, Factor VIII (FVIII), Factor IX (FIX), and a member of the hedgehog family (sonic hedgehog, Indian hedgehog, and desert hedgehog, etc.).

In some embodiments, useful therapeutic products encoded by the heterologous nucleic acid sequence include hormones and growth and differentiation factors including, without limitation, insulin, glucagon, growth hormone (GH), parathyroid hormone (PTH), growth hormone releasing factor (GRF), follicle stimulating hormone (FSH), luteinizing hormone (LH), human chorionic gonadotropin (hCG), vascular endothelial growth factor (VEGF), angiopoietins, angiostatin, granulocyte colony stimulating factor (GCSF), erythropoietin (EPO), connective tissue growth factor (CTGF), basic fibroblast growth factor (bFGF), acidic fibroblast growth factor (aFGF), epidermal growth factor (EGF), platelet-derived growth factor (PDGF), insulin growth factors I and II (IGF-I and IGF-II), any one of the transforming growth factor alpha superfamily, including TGFα, activins, inhibins, or any of the bone morphogenic proteins (BMP) BMPs 1-15, any one of the heregluin/neuregulin/ARIA/neu differentiation factor (NDF) family of growth factors, nerve growth factor (NGF), brain-derived neurotrophic factor (BDNF), neurotrophins NT-3 and NT-4/5, ciliary neurotrophic factor (CNTF), glial cell line derived neurotrophic factor (GDNF), neurturin, agrin, any one of the family of semaphorins/collapsins, netrin-1 and netrin-2, hepatocyte growth factor (HGF), ephrins, noggin, sonic hedgehog and tyrosine hydroxylase.

In some embodiments, useful heterologous nucleic acid sequence products include proteins that regulate the immune system including, without limitation, cytokines and lymphokines such as thrombopoietin (TPO), interleukins (IL) IL-1 through IL-25 (including IL-2, IL-4, IL-12 and IL-18), monocyte chemoattractant protein, leukemia inhibitory factor, granulocyte-macrophage colony stimulating factor, Fas ligand, tumor necrosis factors alpha and beta., interferons (alpha, beta, and gamma), stem cell factor, flk-2/flt3 ligand. Gene products produced by the immune system are also useful in the present invention. These include, without limitations, immunoglobulins IgG, IgM, IgA, IgD and IgE, chimeric immunoglobulins, humanized antibodies, single chain antibodies, T cell receptors, chimeric T cell receptors, single chain T cell receptors, class I and class II MHC molecules, as well as engineered immunoglobulins and MHC molecules. Useful gene products also include complement regulatory proteins such as complement regulatory proteins, membrane cofactor protein (MCP), decay accelerating factor (DAF), CR1, CF2 and CD59.

In some embodiments, useful heterologous nucleic acid sequence products include any one of the receptors for the hormones, growth factors, cytokines, lymphokines, regulatory proteins and immune system proteins. Useful heterologous nucleic acid sequences also include receptors for cholesterol regulation and/or lipid modulation, including the low density lipoprotein (LDL) receptor, high density lipoprotein (HDL) receptor, the very low density lipoprotein (VLDL) receptor, and scavenger receptors. The invention also encompasses the use of gene products such as members of the steroid hormone receptor superfamily including glucocorticoid receptors and estrogen receptors, Vitamin D receptors and other nuclear receptors. In addition, useful gene products include transcription factors such as jun, fos, max, mad, serum response factor (SRF), AP-1, AP-2, myb, MyoD and myogenin, ETS-box containing proteins, TFE3, E2F, ATF1, ATF2, ATF3, ATF4, ZF5, NFAT, CREB, HNF-4, C/EBP, SP1, CCAAT-box binding proteins, interferon regulation factor (IRF-1), Wilms tumor protein, ETS-binding protein, STAT, GATA-box binding proteins, e.g., GATA-3, and the forkhead family of winged helix proteins.

In some embodiments, useful heterologous nucleic acid sequence products include, carbamoyl synthetase I, ornithine transcarbamylase, arginosuccinate synthetase, arginosuccinate lyase, arginase, fumarylacetacetate hydrolase, phenylalanine hydroxylase, alpha-1 antitrypsin, glucose-6-phosphatase, porphobilinogen deaminase, cystathione beta-synthase, branched chain ketoacid decarboxylase, albumin, isovaleryl-coA dehydrogenase, propionyl CoA carboxylase, methyl malonyl CoA mutase, glutaryl CoA dehydrogenase, insulin, beta-glucosidase, pyruvate carboxylate, hepatic phosphorylase, phosphorylase kinase, glycine decarboxylase, H-protein, T-protein, a cystic fibrosis transmembrane regulator (CFTR) sequence, and a dystrophin cDNA sequence. Still other useful gene products include enzymes useful in enzyme replacement therapy, and which are useful in a variety of conditions resulting from deficient activity of enzyme. For example, enzymes containing mannose-6-phosphate may be utilized in therapies for lysosomal storage diseases (e.g., a suitable gene includes that encoding β-glucuronidase (GUSB)).

In some embodiments, useful heterologous nucleic acid sequence products include those used for treatment of hemophilia, including hemophilia B (including Factor IX) and hemophilia A (including Factor VIII and its variants, such as the light chain and heavy chain of the heterodimer and the B-deleted domain; U.S. Pat. Nos. 6,200,560 and 6,221,349). The Factor VIII gene codes for 2351 amino acids and the protein has six domains, designated from the amino to the terminal carboxy terminus as A1-A2-B-A3-C1-C2 (Wood et al., (1984) *Nature,* 312:330; Vehar et al., (1984) *Nature* 312:337; and Toole et al., (1984) *Nature,* 342:337). Human Factor VIII is processed within the cell to yield a heterodimer primarily comprising a heavy chain containing the A1, A2 and B domains and a light chain containing the A3, C1 and C2 domains. Both the single chain polypeptide and the heterodimer circulate in the plasma as inactive precursors, until activated by thrombin cleavage between the A2 and B domains, releasing the B domain and results in a heavy chain consisting of the A1 and A2 domains. The B domain is deleted in the activated procoagulant form of the protein. Additionally, in the native protein, two polypeptide chains ("a" and "b"), flanking the B domain, are bound to a divalent calcium cation.

In some embodiments, useful gene products include non-naturally occurring polypeptides, such as chimeric or hybrid polypeptides having a non-naturally occurring amino acid sequence containing insertions, deletions or amino acid substitutions. For example, single-chain engineered immunoglobulins could be useful in certain immunocompromised patients. Other types of non-naturally occurring gene sequences include antisense molecules and catalytic nucleic acids, such as ribozymes, used to reduce overexpression of a target.

In some embodiments, the present invention provides methods for treatment of a stem cell disorder, for example a disorder in either bone marrow stem cells or adult tissue stem cells (i.e., somatic stem cells). In some embodiments, adult stem cells can include organoid stem cells (i.e., stem cells derived from any organ or organ system of interest within the body). Organs of the body include for example but are not limited to skin, hair, nails, sense receptors, sweat gland, oil glands, bones, muscles, brain, spinal cord, nerve, pituitary gland, pineal gland, hypothalamus, thyroid gland, parathyroid, thymus, adrenals, pancreas (islet tissue), heart, blood vessels, lymph nodes, lymph vessels, thymus, spleen, tonsils, nose, pharynx, larynx, trachea, bronchi, lungs, mouth, pharynx, esophagus, stomach, small intestine, large intestine, rectum, anal canal, teeth, salivary glands, tongue, liver, gallbladder, pancreas, appendix, kidneys, ureters, urinary bladder, urethra, testes, ductus (vas) deferens, urethra, prostate, penis, scrotum, ovaries, uterus, uterine (fallopian) tubes, vagina, vulva, and mammary glands (breasts). Organ systems of the body include but are not limited to the integumentary system, skeletal system, muscular system, nervous system, endocrine system, cardiovascular system, lymphatic system, respiratory system, digestive system, urinary system, and reproductive system. In some embodiments, the disorder for treatment is a disorder in any one or more organoid stem cells (i.e., stem cells derived from any organ or organ system of interest within the body). In some embodiments, the treatment is in vivo (for example, administration of the variant AAV capsid polypeptides is directly to the subject). In some embodiments, the treatment is ex vivo (for example, administration of the variant AAV capsid polypeptides is to stem cells isolated from the subject and the treated stem cells are then returned to the subject).

Reduction and/or modulation of expression of a heterologous nucleic acid sequence is particularly desirable for treatment of hyperproliferative conditions characterized by hyperproliferating cells, such as cancers and psoriasis. Target polypeptides include those polypeptides produced exclusively or at higher levels in hyperproliferative cells as compared to normal cells. Target antigens include polypeptides encoded by oncogenes such as myb, myc, fyn, and the translocation gene bcr/abl, ras, src, P53, neu, trk and EGRF. In addition to oncogene products as target antigens, target polypeptides for anti-cancer treatments and protective regimens include variable regions of antibodies made by B cell lymphomas and variable regions of T cell receptors of T cell lymphomas which, in some embodiments, are used as target antigens for autoimmune disease. Other tumor-associated polypeptides can be used as target polypeptides such as polypeptides found at higher levels in tumor cells including the polypeptide recognized by monoclonal antibody 17-1A and folate binding polypeptides.

In some embodiments, suitable therapeutic polypeptides and proteins include those useful for treating individuals suffering from autoimmune diseases and disorders by conferring a broad based protective immune response against targets that are associated with autoimmunity including cell receptors and cells producing "self"-directed antibodies. T cell mediated autoimmune diseases include Rheumatoid arthritis (RA), multiple sclerosis (MS), Sjogren's syndrome, sarcoidosis, insulin-dependent diabetes mellitus (IDDM), autoimmune thyroiditis, reactive arthritis, ankylosing spondylitis, scleroderma, polymyositis, dermatomyositis, psoriasis, vasculitis, Wegener's granulomatosis, Crohn's disease and ulcerative colitis. Each of these diseases is characterized by T-cell receptors (TCRs) that bind to endogenous antigens and initiate the inflammatory cascade associated with autoimmune diseases.

In some embodiments, heterologous nucleic acid sequences encode for immunogens useful to immunize (i.e., useful as, for example, a vaccine) a human or non-human animal against other pathogens including bacteria, viruses, fungi, parasitic microorganisms or multicellular parasites infecting human and non-human vertebrates, or from a cancer cell or tumor cell. Examples of bacterial pathogens include pathogenic gram-positive cocci include pneumococci; staphylococci (and the toxins produced thereby, e.g., enterotoxin B); and streptococci. Pathogenic gram-negative cocci include meningococcus; gonococcus. Pathogenic enteric gram-negative bacilli include enterobacteriaceae; *Pseudomonas*, acinetobacteria and eikenella; melioidosis; *Salmonella*; *Shigella*; *Haemophilus*; *Moraxella*; *H. ducreyi* (causes chancroid); *brucella* species (brucellosis); *Francisella tularensis* (causes tularemia); *Yersinia pestis* (plague) and other *Yersinia* (*Pasteurella*); *Streptobacillus moniliformis* and spirillum; Gram-positive bacilli include *Listeria monocytogenes*; *Erysipelothrix rhusiopathiae*; *Corynebacterium diphtheria* (causes *diphtheria*); cholera; *Bacillus. anthracia* (causes anthrax); donovanosis (granuloma inguinale; caused by *Klebsiella granulomatis*); and bartonellosis. Diseases caused by pathogenic anaerobic bacteria include tetanus; botulism (*Clostridium botulinum* and its toxin); *Clostridium perfringens* and its epsilon toxin; other clostridia; tuberculosis; leprosy; and other mycobacteria. Pathogenic spirochetal diseases include syphilis; treponematoses: yaws, pinta and endemic syphilis; and leptospirosis. Other infections caused by higher pathogen bacteria and pathogenic fungi include glanders (*Burkholderia mallei*); actinomycosis; nocardiosis; cryptococcosis, blastomycosis, histoplasmosis and coccidioidomycosis; candidiasis; aspergillosis, and mucormycosis; sporotrichosis; paracoccidioidomycosis, petriellidiosis, torulopsosis, mycetoma and chromomycosis; and dermatophytosis. Rickettsial infections include Typhus fever; Rocky Mountain spotted fever; Q fever (*Coxiella burnetti*); and Rickettsialpox. Examples of *Mycoplasma* and chlamydial infections include: *Mycoplasma pneumoniae*; lymphogranuloma venereum (caused by *Chlamydia trachomatis*); psittacosis; and perinatal chlamydial infections. Pathogenic eukaryotes encompassing pathogenic protozoans and helminths and infections produced thereby include: amebiasis (caused by *Entamoeba histolytica*); malaria (caused by *Plasmodium*); Leishmaniasis (caused by *Leishmania*); trypanosomiasis (caused by *Trypanosoma*); toxoplasmosis (caused by *Toxoplasma gondii*); *Pneumocystis carinii*; babesiosis (caused by *Babesia*); giardiasis (caused by *Giardia lamblia*); trichinosis (caused by roundworms of the genus *Trichinella*); filariasis (caused by roundworms of *Filarioidea*); schistosomiasis (carried by fresh water snails infected with one of the five varieties of the parasite *Schistosoma*); nematodes (*Nematoda*); trematodes or flukes (*Platyhelminthes*); and cestode (*Cestoidea*; tapeworm) infections. Examples of viruses include, but are not limited to, human immunodeficiency virus (HIV; e.g., HIV-1 and HIV-2), influenza (e.g., influenza A, influenza B, and influenza C), parainfluenza hepatitis virus (e.g., hepatitis A, hepatitis B, hepatitis C, hepatitis D, and hepatitis E), herpes viruses (HSV; HHV; e.g., herpes virus types 1, 2, 3, 4, 5, 6A, 6B, 7, and 8, including herpes simplex virus types 1 and 2, aka, HSV-1; HSV-2), varicella-zoster virus (HHV-3), Epstein Barr virus (HHV-4), Roseolovirus (HHV-6A and HHV-6B); Rous sarcoma virus, cytomegalovirus (HHV-5), Kaposi's sarcoma-associated herpesvirus; KSHV; HHV-8), papovirus (e.g., human papilloma virus; HPV; HPV-1, HPV-2, HPV-16, and HPV-18), parvovirus (e.g., Parvovirus B19), orthomyxovirus, paramyxovirus (e.g., morbillivirus, respirovirus, rubulavirus, ferlavirus, pneumovirus, and metapneumovirus), picornavirus (e.g., foot-and-mouth disease virus, aquamavirus A, encephalomyocarditis virus, theilovirus, cosavirus A, cadicivirus A, enterovirus A, enterovirus B, enterovirus C, enterovirus D, enterovirus E, enterovirus F, enterovirus G, enterovirus H, enterovirus J, rhinovirus A, rhinovirus B, rhinovirus C, 0, aichivirus B, aichivirus C, melegrivirus A, human parechovirus, ljungan virus, and salivirus A), togavirus (e.g., flavivirus, alphavirus, and rubivirus), Cowpox virus, Horsepox virus, Crimean-Congo hemorrhagic fever virus, Dengue virus, Eastern equine encephalitis virus, Ebola virus, Hantaan virus, Human coronavirus, Human enterovirus 68, Human enterovirus 70, non-HIV retroviruses, rhinovirus, respiratory syncytial virus (RSV), SARS coronavirus, Human spumaretrovirus, Human T-lymphotropic virus, Isfahan virus, Japanese encephalitis virus, Lassa virus, Lymphocytic choriomeningitis virus, MERS coronavirus, measles virus, Mengo encephalomyocarditis virus, Monkeypox virus, mumps virus, Norwalk virus, Pichinde virus, Poliovirus, Rabies virus, rotavirus (e.g., rotavirus A, rotavirus B, and rotavirus C), Rubella virus, St. louis encephalitis virus, Toscana virus, Uukuniemi virus, Venezuelan equine encephalitis virus, Western equine encephalitis virus, West Nile virus, Yellow fever virus, and ZIKA virus, as well as any other viruses known to those of skill in the art.

Methods for Generating an AAV Virion

In various embodiments, the invention provides a method for generating an AAV virion of the invention. A variety of methods for generating AAV virions are known in the art and can be used to generate AAV virions comprising the AAV vectors described herein. Generally, the methods involve inserting or transducing an AAV vector of the invention into a host cell capable of packaging the AAV vector into an AAV virion. Exemplary methods are described and referenced below; however, any method known to one of skill in the art can be employed to generate the AAV virions of the invention.

An AAV vector comprising a heterologous nucleic acid and used to generate an AAV virion can be constructed using methods that are well known in the art. See, e.g., Koerber et al. (2009) *Mol. Ther.*, 17:2088; Koerber et al. (2008) *Mol Ther.*, 16: 1703-1709; as well as U.S. Pat. Nos. 7,439,065, 6,951,758, and 6,491,907. For example, the heterologous sequence(s) can be directly inserted into an AAV genome with the major AAV open reading frames ("ORFs") excised therefrom. Other portions of the AAV genome can also be deleted, so long as a sufficient portion of the ITRs remain to allow for replication and packaging functions. Such constructs can be designed using techniques well known in the art. See, e.g., U.S. Pat. Nos. 5,173,414 and 5,139,941; International Publication Nos. WO 92/01070 (published Jan. 23, 1992) and WO 93/03769 (published Mar. 4, 1993); Lebkowski et al. (1988)*Molec. Cell. Biol.* 8:3988-3996; Vincent et al. (1990) Vaccines 90 (Cold Spring Harbor Laboratory Press); Carter, B. J. (1992) *Current Opinion in Biotechnology* 3:533-539; Muzyczka, N. (1992) *Curr. Topics Microbiol. Immunol.* 158:97-129; Kotin, R. M. (1994) *Human Gene Therapy* 5:793-801; Shelling and Smith (1994) *Gene Therapy* 1:165-169; and Zhou et al. (1994) *J. Exp. Med.* 179:1867-1875.

In order to produce AAV virions, an AAV vector is introduced into a suitable host cell using known techniques, such as by transfection. A number of transfection techniques are generally known in the art. See, e.g., Graham et al. (1973) *Virology*, 52:456, Sambrook et al. (1989) *Molecular Cloning, A Laboratory Manual*, Cold Spring Harbor Laboratories, New York, Davis et al. (1986) *Basic Methods in Molecular Biology*, Elsevier, and Chu et al. (1981) *Gene* 13:197. Particularly suitable transfection methods include calcium phosphate co-precipitation (Graham et al. (1973) *Virol.* 52:456-467), direct micro-injection into cultured cells (Capecchi, M. R. (1980) *Cell* 22:479-488), electroporation (Shigekawa et al. (1988) *BioTechniques* 6:742-751), liposome-mediated gene transfer (Mannino et al. (1988) *BioTechniques* 6:682-690), lipid-mediated transduction (Felgner et al. (1987) *Proc. Natl. Acad. Sci. USA* 84:7413-7417), and nucleic acid delivery using high-velocity microprojectiles (Klein et al. (1987) *Nature* 327:70-73).

Suitable host cells for producing AAV virions include any species and/or type of cell that can be, or have been, used as recipients of a heterologous AAV DNA molecule, and can support the expression of required AAV production cofactors from helper viruses. Such host cells can include but are not limited to microorganisms, yeast cells, insect cells, and mammalian cells, that can be, or have been, used as recipients of a heterologous DNA molecule. The term includes the progeny of the original cell transfected. Thus, a "host cell" as used herein generally refers to a cell transfected with an exogenous DNA sequence. Cells from the stable human cell line, HEK293 (readily available through, e.g., the American Type Culture Collection under Accession Number ATCC CRL1573) can be used. The human cell line HEK293 is a human embryonic kidney cell line that has been transformed with adenovirus type-5 DNA fragments (Graham et al. (1977) J. Gen. Virol. 36:59), and expresses the adenoviral Ela and Elb genes (Aiello et al. (1979) Virology 94:460). The HEK293 cell line is readily transfected, and provides a convenient platform in which to produce AAV virions.

Methods of producing an AAV virion in insect cells are known in the art, and can be used to produce a subject AAV virion. See, e.g., U.S. Patent Publication No. 2009/0203071; U.S. Pat. No. 7,271,002; and Chen (2008) *Mol. Ther.* 16:924.

In some embodiments, the AAV virion or AAV vector is packaged into an infectious virion or virus particle, by any of the methods described herein or known in the art.

In some embodiments, the variant AAV capsid polypeptide allows for similar packaging as compared to a non-variant parent capsid polypeptide.

In some embodiments, an AAV vector packaged with the variant AAV capsid polypeptides transduce into cells in vivo better than a vector packaged from non-variant parent capsid polypeptides.

In some embodiments, the AAV vector packaged with the variant AAV capsid polypeptides transduce into cells in vitro better than a vector packaged from non-variant parent capsid polypeptides.

In some embodiments, the variant AAV capsid polypeptides result in nucleic acid expression higher than a nucleic acid packaged from non-variant parent capsid polypeptides.

In some embodiments, the AAV vector packaged with said variant AAV capsid polypeptides result in transgene expression better than a transgene packaged from non-variant parent capsid polypeptides.

Pharmaceutical Compositions & Dosing

The present invention provides pharmaceutical compositions useful in treating subjects according to the methods of the invention as described herein. Further, the present invention provides dosing regimens for administering the described pharmaceutical compositions. The present invention provides pharmaceutical compositions comprising: a) a subject AAV vector or AAV virion, as described herein as well as therapeutic molecules packaged by or within capsids comprising variant polypeptides as described herein; and b) a pharmaceutically acceptable carrier, diluent, excipient, or buffer. In some embodiments, the pharmaceutically acceptable carrier, diluent, excipient, or buffer is suitable for use in a human.

Such excipients, carriers, diluents, and buffers include any pharmaceutical agent that can be administered without undue toxicity. Pharmaceutically acceptable excipients include, but are not limited to, liquids such as water, saline, glycerol and ethanol. Pharmaceutically acceptable salts can be included therein, for example, mineral acid salts such as hydrochlorides, hydrobromides, phosphates, sulfates, and the like; and the salts of organic acids such as acetates, propionates, malonates, benzoates, and the like. Additionally, auxiliary substances, such as wetting or emulsifying agents, pH buffering substances, and the like, may be present in such vehicles. A wide variety of pharmaceutically acceptable excipients are known in the art and need not be discussed in detail herein. Pharmaceutically acceptable excipients have been amply described in a variety of publications, including, for example, A. Gennaro, (2000) *Remington: The Science and Practice of Pharmacy*, 20th edition, Lippincott, Williams, & Wilkins; *Pharmaceutical Dosage*

*Forms and Drug Delivery Systems* (1999) H. C. Ansel et al., eds., 7th ed., Lippincott, Williams, & Wilkins; and *Handbook of Pharmaceutical Excipients* (2000) A. H. Kibbe et al., eds., 3rd ed. Amer. Pharmaceutical Assoc.

A subject composition can comprise a liquid comprising a subject variant AAV capsid polypeptide of the invention or AAV virion comprising a variant AAV capsid polypeptide in solution, in suspension, or both. As used herein, liquid compositions include gels. In some cases, the liquid composition is aqueous. In some embodiments, the composition is an in situ gellable aqueous composition, e.g., an in situ gellable aqueous solution. Aqueous compositions have opthalmically compatible pH and osmolality.

Such compositions include solvents (aqueous or non-aqueous), solutions (aqueous or non-aqueous), emulsions (e.g., oil-in-water or water-in-oil), suspensions, syrups, elixirs, dispersion and suspension media, coatings, isotonic and absorption promoting or delaying agents, compatible with pharmaceutical administration or in vivo contact or delivery. Aqueous and non-aqueous solvents, solutions and suspensions may include suspending agents and thickening agents. Such pharmaceutically acceptable carriers include tablets (coated or uncoated), capsules (hard or soft), microbeads, powder, granules and crystals. Supplementary active compounds (e.g., preservatives, antibacterial, antiviral and antifungal agents) can also be incorporated into the compositions.

Pharmaceutical compositions can be formulated to be compatible with a particular route of administration or delivery, as set forth herein or known to one of skill in the art. Thus, pharmaceutical compositions include carriers, diluents, or excipients suitable for administration by various routes.

Compositions suitable for parenteral administration comprise aqueous and non-aqueous solutions, suspensions or emulsions of the active compound. Preparations are typically sterile and can be isotonic with the blood of the intended recipient. Non-limiting illustrative examples include water, saline, dextrose, fructose, ethanol, animal, vegetable or synthetic oils.

For intraperitoneal or intravenous administration (e.g., topical contact), penetrants can be included in the pharmaceutical composition. Penetrants are known in the art, and include, for example, for transmucosal administration, detergents, bile salts, and fusidic acid derivatives. For transdermal administration, the active ingredient can be formulated into aerosols, sprays, ointments, salves, gels, or creams as generally known in the art. For contact with skin, pharmaceutical compositions typically include ointments, creams, lotions, pastes, gels, sprays, aerosols, or oils. Useful carriers include Vaseline®, lanolin, polyethylene glycols, alcohols, transdermal enhancers, and combinations thereof.

Cosolvents and adjuvants may be added to the formulation. Non-limiting examples of cosolvents contain hydroxyl groups or other polar groups, for example, alcohols, such as isopropyl alcohol; glycols, such as propylene glycol, polyethyleneglycol, polypropylene glycol, glycol ether; glycerol; polyoxyethylene alcohols and polyoxyethylene fatty acid esters. Adjuvants include, for example, surfactants such as, soya lecithin and oleic acid; sorbitan esters such as sorbitan trioleate; and polyvinylpyrrolidone.

Pharmaceutical compositions and delivery systems appropriate for the AAV vector or AAV virion and methods and uses of are known in the art (see, e.g., *Remington: The Science and Practice of Pharmacy* (2003) 20th ed., Mack Publishing Co., Easton, Pa.; *Remington's Pharmaceutical Sciences* (1990) 18th ed., Mack Publishing Co., Easton, Pa.; *The Merck Index* (1996) 12th ed., Merck Publishing Group, Whitehouse, N.J.; *Pharmaceutical Principles of Solid Dosage Forms* (1993), Technonic Publishing Co., Inc., Lancaster, Pa.; Ansel and Stoklosa, *Pharmaceutical Calculations* (2001) 11th ed., Lippincott Williams & Wilkins, Baltimore, Md.; and Poznansky et al., *Drug Delivery Systems* (1980), R. L. Juliano, ed., Oxford, N.Y., pp. 253-315).

Doses can vary and depend upon whether the treatment is prophylactic or therapeutic, the type, onset, progression, severity, frequency, duration, or probability of the disease treatment is directed to, the clinical endpoint desired, previous or simultaneous treatments, the general health, age, gender, race or immunological competency of the subject and other factors that will be appreciated by the skilled artisan. The dose amount, number, frequency or duration may be proportionally increased or reduced, as indicated by any adverse side effects, complications or other risk factors of the treatment or therapy and the status of the subject. The skilled artisan will appreciate the factors that may influence the dosage and timing required to provide an amount sufficient for providing a therapeutic or prophylactic benefit.

Methods and uses of the invention as disclosed herein can be practiced within about 1 hour to about 2 hours, about 2 hours to about 4 hours, about 4 hours to about 12 hours, about 12 hours to about 24 hours or about 24 hours to about 72 hours after a subject has been identified as having the disease targeted for treatment, has one or more symptoms of the disease, or has been screened and is identified as positive as set forth herein even though the subject does not have one or more symptoms of the disease. In some embodiments, the invention as disclosed herein can be practiced within about 1 hour, about 2 hours, about 3 hours, about 4 hours, about 5 hours, about 6 hours, about 7 hours, about 8 hours, about 9 hours, about 10 hours, about 11 hours, about 12 hours, about 24 hours, about 36 hours, about 48 hours, or about 72 hours or more. Of course, methods and uses of the invention can be practiced about 1 day to about 7 days, about 7 days to about 14 days, about 14 days to about 21 days, about 21 days to about 48 days or more, months or years after a subject has been identified as having the disease targeted for treatment, has one or more symptoms of the disease, or has been screened and is identified as positive as set forth herein. In some embodiments, the invention as disclosed herein can be practiced within about 1 day, about 2 days, about 3 days, about 4 days, about 5 days, about 6 days, about 7 days, about 8 days, about 9 days, about 10 days, about 11 days, about 12 days, about 14 days, about 21 days, about 36 days, or about 48 days or more.

In some embodiments, the present invention provides kits with packaging material and one or more components therein. A kit typically includes a label or packaging insert including a description of the components or instructions for use in vitro, in vivo, or ex vivo, of the components therein. A kit can contain a collection of such components, e.g., a variant AAV capsid polypeptide, an AAV vector, or AAV virion and optionally a second active, such as another compound, agent, drug or composition.

A kit refers to a physical structure housing one or more components of the kit. Packaging material can maintain the components sterilely, and can be made of material commonly used for such purposes (e.g., paper, corrugated fiber, glass, plastic, foil, ampules, vials, tubes, etc.).

Labels or inserts can include identifying information of one or more components therein, dose amounts, clinical pharmacology of the active ingredient(s) including mechanism of action, pharmacokinetics and pharmacodynamics. Labels or inserts can include information identifying the manufacturer, lot numbers, manufacturer location and date, expiration dates. Labels or inserts can include information identifying manufacturer information, lot numbers, manufacturer location and date. Labels or inserts can include information on a disease a kit component may be used for. Labels or inserts can include instructions for the clinician or subject for using one or more of the kit components in a method, use, or treatment protocol or therapeutic regimen. Instructions can include dosage amounts, frequency or duration, and instructions for practicing any of the methods, uses, treatment protocols or prophylactic or therapeutic regimes described herein.

Labels or inserts can include information on any benefit that a component may provide, such as a prophylactic or therapeutic benefit. Labels or inserts can include information on potential adverse side effects, complications or reactions, such as warnings to the subject or clinician regarding situations where it would not be appropriate to use a particular composition. Adverse side effects or complications could also occur when the subject has, will be or is currently taking one or more other medications that may be incompatible with the composition, or the subject has, will be or is currently undergoing another incompatible treatment protocol or therapeutic regimen and, therefore, instructions could include information regarding such incompatibilities.

Labels or inserts include "printed matter," e.g., paper or cardboard, or separate or affixed to a component, a kit or packing material (e.g., a box), or attached to an ampule, tube or vial containing a kit component. Labels or inserts can additionally include a computer readable medium, such as a bar-coded printed label, a disk, optical disk such as CD- or DVD-ROM/RAM, DVD, MP3, magnetic tape, or an electrical storage media such as RAM and ROM or hybrids of these such as magnetic/optical storage media, FLASH media or memory type cards.

Method of Treating a Disease

The present invention also provides methods for treatment of disease in a subject by administering the AAV vectors and/or nucleic acids of the present invention, where AAV vectors and/or nucleic acids described herein packaged within a functional AAV capsid, wherein the functional AAV capsid comprises one or more variant AAV capsid polypeptides of the present invention. In an exemplary embodiment, the invention provides a method of administering a pharmaceutical composition of the invention to a subject in need thereof to treat a disease of a subject. In various embodiments, the subject is not otherwise in need of administration of a composition of the invention. In some embodiments, the invention provides methods for vaccine administration.

In some embodiments, the variant AAV capsid polypeptides package a therapeutic expression cassette comprised of a heterologous nucleic acid comprising a nucleotide sequence encoding a heterologous gene product, such as for example a therapeutic protein or vaccine. In some embodiments, the AAV virion or AAV vector comprises a therapeutic expression cassette comprised of a heterologous nucleic acid comprising a nucleotide sequence encoding a heterologous gene product, such as for example a therapeutic protein or vaccine.

In some embodiments, the variant AAV capsid polypeptides of the invention are employed as part of vaccine delivery. Vaccine delivery can include delivery of any of the therapeutic proteins as well as nucleic acids described herein. In some embodiments, variant AAV capsid polypeptides of the invention are employed as part of a vaccine regimen and dosed according to the methods described herein.

In some embodiments, the variant AAV capsid polypeptides, the AAV virions, or AAV vectors of the invention are used in a therapeutic treatment regimen.

In some embodiments, the variant AAV capsid polypeptides, the AAV virions, or AAV vectors of the invention are used for therapeutic polypeptide production.

In some cases, a subject variant AAV capsid polypeptides or AAV vector, when introduced into the cells of a subject, provides for high level production of the heterologous gene product packaged by the variant AAV capsid polypeptides or encoded by the AAV vector. For example, a heterologous polypeptide packaged by the variant AAV capsid polypeptides or encoded by the AAV can be produced at a level of from about 1 µg to about 50 µg or more.

In some cases, subject variant AAV capsid polypeptides, AAV virion, or AAV vector, when introduced into a subject, provide for production of the heterologous gene product packaged by the variant AAV capsid polypeptides or encoded by the AAV vector in at least about 10%, at least about 15%, at least about 20%, at least about 25%, at least about 30%, at least about 35%, at least about 40%, at least about 50% at least about 60%, at least about 70%, at least about 80%, or more than 80%, of the target cells.

In some embodiments, the present invention provides a method of treating a disease, the method comprising administering to an individual in need thereof an effective amount of a therapeutic molecule packaged by the variant AAV capsid polypeptides or subject AAV vector as described above.

Subject variant AAV capsid polypeptides or subject AAV vectors can be administered systemically, regionally or locally, or by any route, for example, by injection, infusion, orally (e.g., ingestion or inhalation), or topically (e.g., transdermally). Such delivery and administration methods include intravenously, intramuscularly, intraperitoneally, intradermally, subcutaneously, intracavity, intracranially, transdermally (topical), parenterally, e.g. transmucosally or rectally. Exemplary administration and delivery routes include intravenous, intraperitoneal, intrarterial, intramuscular, parenteral, subcutaneous, intra-pleural, topical, dermal, intradermal, transdermal, parenterally, e.g. transmucosal, intra-cranial, intra-spinal, oral (alimentary), mucosal, respiration, intranasal, intubation, intrapulmonary, intrapulmonary instillation, buccal, sublingual, intravascular, intrathecal, intracavity, iontophoretic, intraocular, ophthalmic, optical, intraglandular, intraorgan, and intralymphatic.

In some cases, a therapeutically effective amount of a therapeutic molecule packaged by the variant AAV capsid polypeptides or a subject AAV vectors is an amount that, when administered to an individual in one or more doses, is effective to slow the progression of the disease or disorder in the individual, or is effective to ameliorate symptoms. For example, a therapeutically effective amount of a therapeutic molecule packaged by the variant AAV capsid polypeptides or a subject AAV vectors can be an amount that, when administered to an individual in one or more doses, is effective to slow the progression of the disease by at least about 15%, at least about 20%, at least about 25%, at least about 30%, at least about 40%, at least about 50%, at least about 60%, at least about 70%, at least about 80%, or more than about 80%, compared to the progression of the disease in the absence of treatment with the therapeutic molecule packaged by the variant AAV capsid polypeptides or AAV vectors.

A therapeutic or beneficial effect of treatment is therefore any objective or subjective measurable or detectable improvement or benefit provided to a particular subject. A therapeutic or beneficial effect can but need not be complete ablation of all or any particular adverse symptom, disorder, illness, or complication of a disease. Thus, a satisfactory clinical endpoint is achieved when there is an incremental improvement or a partial reduction in an adverse symptom, disorder, illness, or complication caused by or associated with a disease, or an inhibition, decrease, reduction, suppression, prevention, limit or control of worsening or progression of one or more adverse symptoms, disorders, illnesses, or complications caused by or associated with the disease, over a short or long duration (hours, days, weeks, months, etc.).

Improvement of clinical symptoms can also be monitored by one or more methods known to the art, and used as an indication of therapeutic effectiveness. Clinical symptoms may also be monitored by anatomical or physiological means, such as indirect ophthalmoscopy, fundus photography, fluorescein angiopathy, optical coherence tomography, electroretinography (full-field, multifocal, or other), external eye examination, slit lamp biomicroscopy, applanation tonometry, pachymetry, autorefaction, or other measures of functional vision. In some embodiments, a therapeutic molecule (including, for example, a vaccine) packaged by the variant AAV capsid polypeptides, a subject AAV vector, or AAV virus, when introduced into a subject, provides for production of the heterologous gene product for a period of time of from about 2 days to about 6 months, e.g., from about 2 days to about 7 days, from about 1 week to about 4 weeks, from about 1 month to about 2 months, or from about 2 months to about 6 months. In some embodiments, therapeutic molecules (including, for example, a vaccine) packaged by the variant AAV capsid polypeptides, a subject AAV vector or virus, when introduced into a subject provides for production of the heterologous gene product encoded for a period of time of more than 6 months, e.g., from about 6 months to 20 years or more, or greater than 1 year, e.g., from about 6 months to about 1 year, from about 1 year to about 2 years, from about 2 years to about 5 years, from about 5 years to about 10 years, from about 10 years to about 15 years, from about 15 years to about 20 years, or more than 20 years. In some embodiments, the administration regimen is part of a vaccination regimen.

Multiple doses of a subject AAV virion can be administered to an individual in need thereof. Where multiple doses are administered over a period of time, an active agent is administered once a month to about once a year, from about once a year to once every 2 years, from about once every 2 years to once every 5 years, or from about once every 5 years to about once every 10 years, over a period of time. For example, a subject AAV virion is administered over a period of from about 3 months to about 2 years, from about 2 years to about 5 years, from about 5 years to about 10 years, from about 10 years to about 20 years, or more than 20 years. The actual frequency of administration, and the actual duration of treatment, depends on various factors. In some embodiments, the administration regimen is part of a vaccination regimen.

The dose to achieve a therapeutic effect, e.g., the dose in vector genomes/per kilogram of body weight (vg/kg), will vary based on several factors including, but not limited to: route of administration, the level of heterologous polynucleotide expression required to achieve a therapeutic effect, the specific disease treated, any host immune response to the viral vector, a host immune response to the heterologous polynucleotide or expression product (protein), and the stability of the protein expressed. One skilled in the art can readily determine a virion dose range to treat a patient having a particular disease or disorder based on the aforementioned factors, as well as other factors. Generally, doses will range from at least about, or more, for example, $1 \times 10^9$, $1 \times 10^{10}$, $1 \times 10^{11}$, $1 \times 10^{12}$, $1 \times 10^{13}$ or $1 \times 10^{14}$, or more, vector genomes per kilogram (vg/kg) of the weight of the subject, to achieve a therapeutic effect.

In some embodiments, the variant AAV polypeptides of the present invention can be employed to reduce the amount of total AAV vector or other therapeutic molecule administered to a subject, wherein less total AAV vector or other therapeutic molecule is administered to a subject when said AAV vector or other therapeutic molecule is transduced using variant AAV capsid polypeptides as compared to the amount of AAV vector or other therapeutic molecule administered to a subject when the AAV vector or other therapeutic molecule is transduced using non-variant parent capsid polypeptides in order to obtain a similar therapeutic effect (i.e., both dosages induce similar therapeutic effects or indistinguishable therapeutic effects). In some embodiments, the total vector or other therapeutic molecule administered to a subject is reduced by about 5%, about 10%, about 15%, about 20%, about 25%, about 30%, about 35%, about 40%, about 50%, about 55%, about 60%, about 65%, about 70%, about 75%, about 80% or more when an AAV vector or other therapeutic molecule is transduced using variant AAV capsid polypeptides as compared to when an AAV vector or other therapeutic molecule is transduced using non-variant parent capsid polypeptides in order to obtain a similar therapeutic effect (i.e., both dosages induce similar therapeutic effects or indistinguishable therapeutic effects). In some embodiments, the total AAV vector or other therapeutic molecule administered to a subject is reduced by about 5% to about 80%, about 10% to about 75%, about 15% to about 65%, about 20% to about 60%, or about 10% to about 50% when the AAV vector or other therapeutic molecule is transduced using variant AAV capsid polypeptides as compared to when the AAV vector or other therapeutic molecule is transduced using non-variant parent capsid polypeptides in order to obtain a similar therapeutic effect (i.e., both dosages induce similar therapeutic effects or indistinguishable therapeutic effects).

An effective amount or a sufficient amount can, but need not be, provided in a single administration, may require multiple administrations, and, can but need not be, administered alone or in combination with another composition (e.g., agent), treatment, protocol or therapeutic regimen. For example, the amount may be proportionally increased as indicated by the need of the subject, type, status and severity of the disease treated or side effects (if any) of treatment. In addition, an effective amount or a sufficient amount need not be effective or sufficient if given in single or multiple doses without a second composition (e.g., another drug or agent), treatment, protocol or therapeutic regimen, since additional doses, amounts or duration above and beyond such doses, or additional compositions (e.g., drugs or agents), treatments, protocols or therapeutic regimens may be included in order to be considered effective or sufficient in a given subject. Amounts considered effective also include amounts that result in a reduction of the use of another treatment, therapeutic regimen or protocol, such as administration of recombinant clotting factor protein for treatment of a clotting disorder (e.g., hemophilia A or B).

An effective amount or a sufficient amount need not be effective in each and every subject treated, or a majority of treated subjects in a given group or population. An effective amount or a sufficient amount means effectiveness or sufficiency in a particular subject, not a group or the general population. As is typical for such methods, some subjects will exhibit a greater response, or less or no response to a given treatment method or use. Thus, appropriate amounts will depend upon the condition treated, the therapeutic effect desired, as well as the individual subject (e.g., the bioavailability within the subject, gender, age, etc.).

With regard to a disease or symptom thereof, or an underlying cellular response, a detectable or measurable improvement includes a subjective or objective decrease, reduction, inhibition, suppression, limit or control in the occurrence, frequency, severity, progression, or duration of the disease, or complication caused by or associated with the disease, or an improvement in a symptom or an underlying cause or a consequence of the disease, or a reversal of the disease.

Thus, a successful treatment outcome can lead to a "therapeutic effect," or "benefit" of decreasing, reducing, inhibiting, suppressing, limiting, controlling or preventing the occurrence, frequency, severity, progression, or duration of a disease, or one or more adverse symptoms or underlying causes or consequences of the disease in a subject. Treatment methods and uses affecting one or more underlying causes of the disease or adverse symptoms are therefore considered to be beneficial. A decrease or reduction in worsening, such as stabilizing the disease, or an adverse symptom thereof, is also a successful treatment outcome.

A therapeutic benefit or improvement therefore need not be complete ablation of the disease, or any one, most or all adverse symptoms, complications, consequences or underlying causes associated with the disease. Thus, a satisfactory endpoint is achieved when there is an incremental improvement in a subject's disease, or a partial decrease, reduction, inhibition, suppression, limit, control or prevention in the occurrence, frequency, severity, progression, or duration, or inhibition or reversal, of the disease (e.g., stabilizing one or more symptoms or complications), over a short or long duration of time (hours, days, weeks, months, etc.). Effectiveness of a method or use, such as a treatment that provides a potential therapeutic benefit or improvement of a disease, can be ascertained by various methods.

Disclosed methods and uses can be combined with any compound, agent, drug, treatment or other therapeutic regimen or protocol having a desired therapeutic, beneficial, additive, synergistic or complementary activity or effect. Exemplary combination compositions and treatments include second actives, such as, biologics (proteins), agents and drugs. Such biologics (proteins), agents, drugs, treatments and therapies can be administered or performed prior to, substantially contemporaneously with or following any other method or use of the invention, for example, a therapeutic method of treating a subject for a blood clotting disease.

The compound, agent, drug, treatment or other therapeutic regimen or protocol can be administered as a combination composition, or administered separately, such as concurrently or in series or sequentially (prior to or following) delivery or administration of an AAV vector or AAV virion as described herein. The invention therefore provides combinations where a method or use of the invention is in a combination with any compound, agent, drug, therapeutic regimen, treatment protocol, process, remedy or composition, set forth herein or known to one of skill in the art. The compound, agent, drug, therapeutic regimen, treatment protocol, process, remedy or composition can be administered or performed prior to, substantially contemporaneously with or following administration of an AAV vector or AAV virion as described herein, to a subject. Specific non-limiting examples of combination embodiments therefore include the foregoing or other compound, agent, drug, therapeutic regimen, treatment protocol, process, remedy or composition.

Methods and uses of the invention also include, among other things, methods and uses that result in a reduced need or use of another compound, agent, drug, therapeutic regimen, treatment protocol, process, or remedy. For example, for a blood clotting disease, a method or use of the invention has a therapeutic benefit if in a given subject a less frequent or reduced dose or elimination of administration of a recombinant clotting factor protein to supplement for the deficient or defective (abnormal or mutant) endogenous clotting factor in the subject. Thus, in accordance with the invention, methods and uses of reducing need or use of another treatment or therapy are provided.

The invention is useful in animals including veterinary medical applications. Suitable subjects therefore include mammals, such as humans, as well as non-human mammals. The term "subject" refers to an animal, typically a mammal, such as humans, non-human primates (apes, gibbons, gorillas, chimpanzees, orangutans, macaques), a domestic animal (dogs and cats), a farm animal (poultry such as chickens and ducks, horses, cows, goats, sheep, pigs), and experimental animals (mouse, rat, rabbit, guinea pig). Human subjects include fetal, neonatal, infant, juvenile and adult subjects. Subjects include animal disease models, for example, mouse and other animal models of blood clotting diseases and others known to those of skill in the art.

Non-limiting particular examples of diseases treatable in accordance with the invention include those set forth herein as well as a pancreas disease. A pancreas disease includes but is not limited to diabetes mellitus (e.g. Type I and Type II), acute pancreatitis, chronic pancreatitis, hereditary pancreatitis, autoimmune pancreatitis, pancreatic cancer (e.g. pancreatic adenocarcinoma, acinar cell carcinoma of the pancreas, cystadenocarcinomas, pancreatoblastoma, pancreatic mucinous cystic neoplasms, etc.), pancreatic benign tumors (e.g. pancreatic serous cystadenoma, solid pseudopapillary tumor of the pancreas, etc.), pancreatic neuroendocrine tumor, cystic fibrosis, exocrine pancreatic insufficiency (EPI), pancreatic pseudocyst, pancreatic cyst, Shwachman-Diamond syndrome, Johanson-Blizzard syndrome, Common Channel syndrome, Zollinger-Ellison syndrome, choledochal cyst, Hemosuccus pancreaticus, or congenital pancreatic abnormalities (e.g. Pancreas divisum, Annular Pancreas, ectopic pancreatic tissue).

In one embodiment, a method or use of the invention includes: (a) providing an AAV virion whose capsid comprises the variant AAV capsid polypeptides prepared as described herein, wherein the AAV virion comprises a heterologous nucleic acid sequence, wherein the heterologous nucleic acid sequence is operably linked to an expression control element conferring transcription of said nucleic acid sequence; and (b) administering an amount of the AAV virion to the mammal such that said heterologous nucleic acid is expressed in the mammal.

In one embodiment, a method or use of the invention includes: (a) providing a therapeutic molecule (including, for example, a vaccine) packaged by variant AAV capsid polypeptides prepared as described herein, wherein the therapeutic molecule comprises a heterologous nucleic acid sequence, wherein the heterologous nucleic acid sequence is operably linked to an expression control element conferring transcription of said nucleic acid sequence; and (b) administering an amount of the therapeutic molecule (including, for example, a vaccine) packaged by variant AAV capsid polypeptides to the mammal such that said heterologous nucleic acid is expressed in the mammal.

In another embodiment, a method or use of the invention includes delivering or transferring a heterologous polynucleotide sequence into a mammal or a cell of a mammal, by administering a heterologous polynucleotide packaged by the variant AAV capsid polypeptides, a plurality of heterologous polynucleotides packaged by variant AAV capsid polypeptides, an AAV virion prepared as described herein, or a plurality of AAV virions comprising the heterologous nucleic acid sequence to a mammal or a cell of a mammal, thereby delivering or transferring the heterologous polynucleotide sequence into the mammal or cell of the mammal. In some embodiments, the heterologous nucleic acid sequence encodes a protein expressed in the mammal, or where the heterologous nucleic acid sequence encodes an inhibitory sequence or protein that reduces expression of an endogenous protein in the mammal. By way of example, respecting hemophilia, it is believed that, in order to achieve a therapeutic effect, a blood coagulation factor concentration that is greater than 1% of factor concentration found in a normal individual is needed to change a severe disease phenotype to a moderate one. A severe phenotype is characterized by joint damage and life-threatening bleeds. To convert a moderate disease phenotype into a mild one, it is believed that a blood coagulation factor concentration greater than about 5% of normal is needed. With respect to treating such a hemophilic subject, a typical dose is at least $1\times10^{10}$ AAV vector genomes (vg) per kilogram (vg/kg) of the weight of the subject, or between about $1\times10^{10}$ to about $1\times10^{11}$ vg/kg of the weight of the subject, or between about $1\times10^{11}$ to about $1\times10^{12}$ vg/kg of the weight of the subject, or between about $1\times10^{12}$ to about $1\times10^{13}$ vg/kg of the weight of the subject, to achieve a desired therapeutic effect.

EXAMPLES

Example 1: Directed Evolution of AAV for Human Islet Targeting

Introduction

Adeno-associated viruses (AAV) are of great interest as a potent vehicle for gene transfer into various cell types. While AAV has several features that make it a promising vehicle for human gene therapy, several drawbacks have hampered its use for clinical applications, such as its promiscuity, limited transgene packaging size, and the high prevalence of pre-existing neutralizing antibodies in the general population. For gene therapy purposes, transduction needs to be both efficient and highly cell type specific. AAV cell tropism as well as immunogenicity are determined by sequences of the structural capsid proteins VP1, VP2, and VP3.

DNA shuffling is a powerful method for the in vitro evolution of molecules with specific functions and has applications in areas as diverse as medical, pharmaceutical and agricultural research. Shuffling of the AAV capsid sequences has successfully been used in the past to evolve recombinant AAVs (rAAVs) with improved cell transduction capabilities in vitro and in vivo (D. Grimm. *J. Virol.* 82, 5887-5911 (2008); and L. Lisowski. *Nature,* 506, 382-386 (2013)).

Purpose

The goal of this study is to generate AAV vectors for gene therapy applications in the field of diabetes research. A highly complex AAV library containing shuffled capsid sequences tagged with unique barcodes for high-throughput sequencing has been generated and has been screened for improved islet transduction by performing multiple rounds of passaging in primary human islets.

Results

Figure 2:
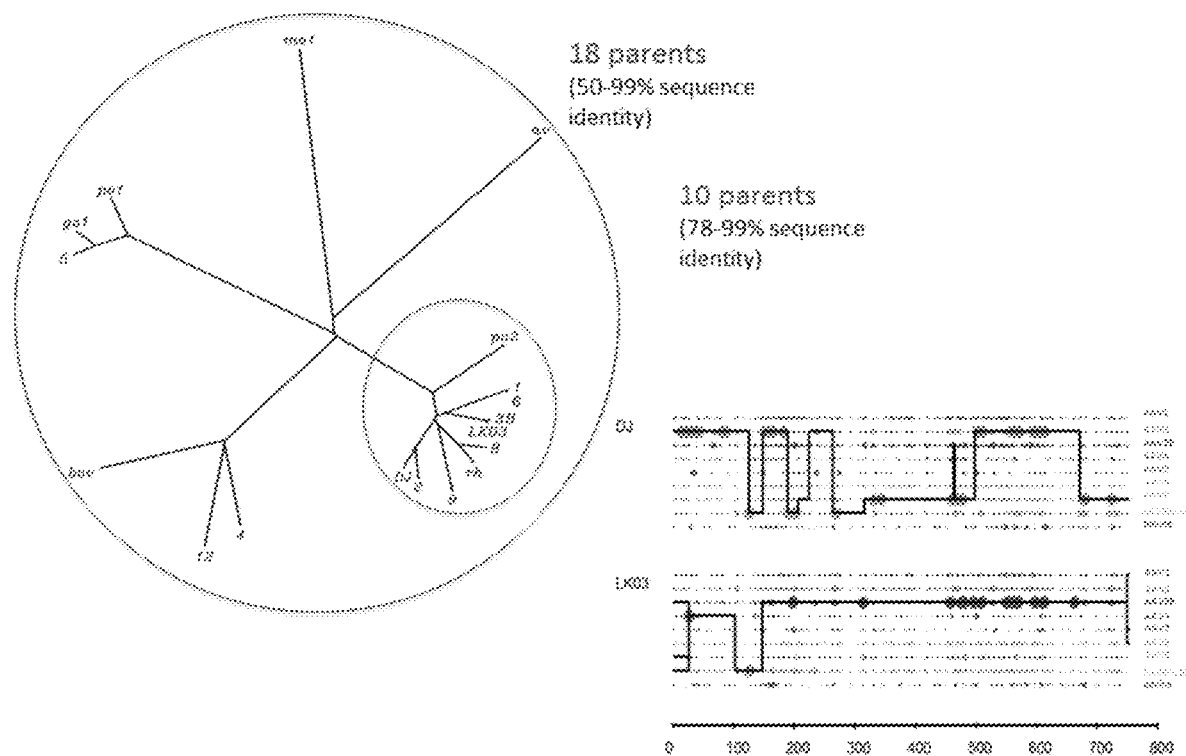
FIG. 2. Phylogenetic relationship of parental capsid amino acid sequences used for shuffling. Phylogenetic distances between the parental capsid sequences used for shuffling. Diversity ranges are shown for amino acid sequences.

Capsid genes from various AAV wild type serotypes and previously described variants (FIG. 2) were shuffled using the DNase shuffling method (W. P. Stemmer. *Proc. Natl. Acad. Sci. USA,* 91, 10747-10751 (1994)) and cloned into an AAV backbone library containing a barcode sequence downstream of the cap polyA (FIG. 3). Tagging each AAV variant with a unique barcode allows for tracking of variant enrichment between rounds of passaging by high-throughput sequencing. The 10 parent library was analyzed in more detail and found to have a good crossover rate by Sanger sequencing (FIG. 4) (W. Huang. *Biotechniques,* 60, 91-94 (2016)). High-throughput capsid+BC sequencing was performed using the PacBio sequencing technology and revealed similar contribution levels of the 10 parental capsid sequences (FIG. 5) as well as good capsid-BC linkage (see, for Example, FIG. 1).

Figure 8:
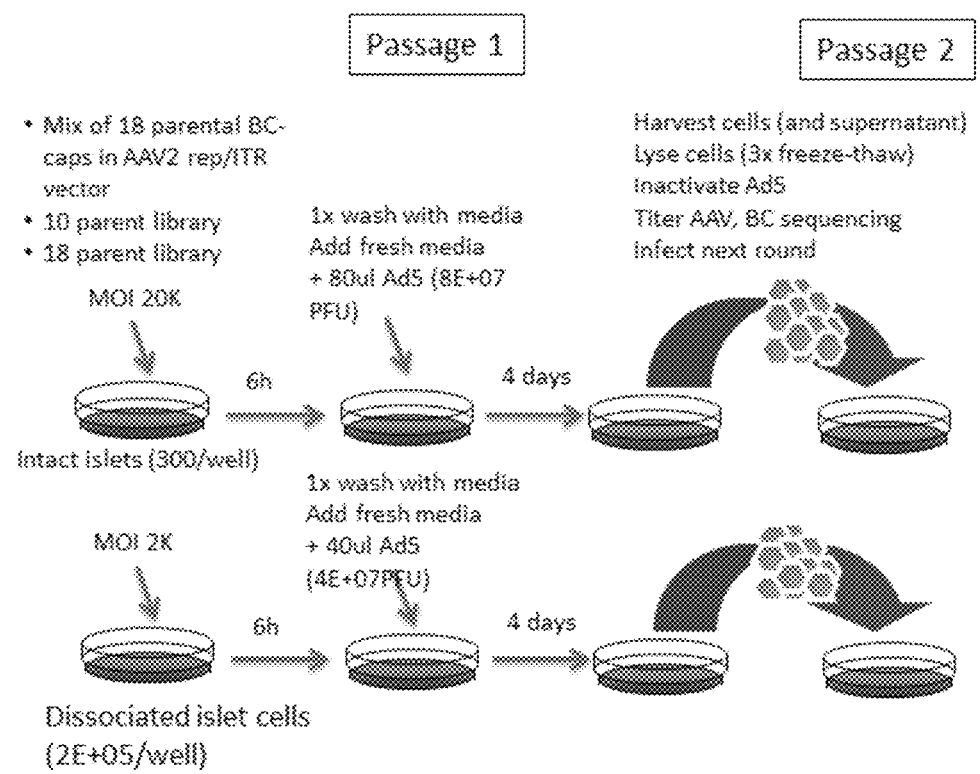
FIG. 8. Passaging regimen of shuffled libraries as well as a parental barcoded AAV mix on intact as well as dissociated islets: Screen A. Passaging regimen of the parental mix as well as the shuffled barcoded AAV libraries on human islets.
Figure 9:
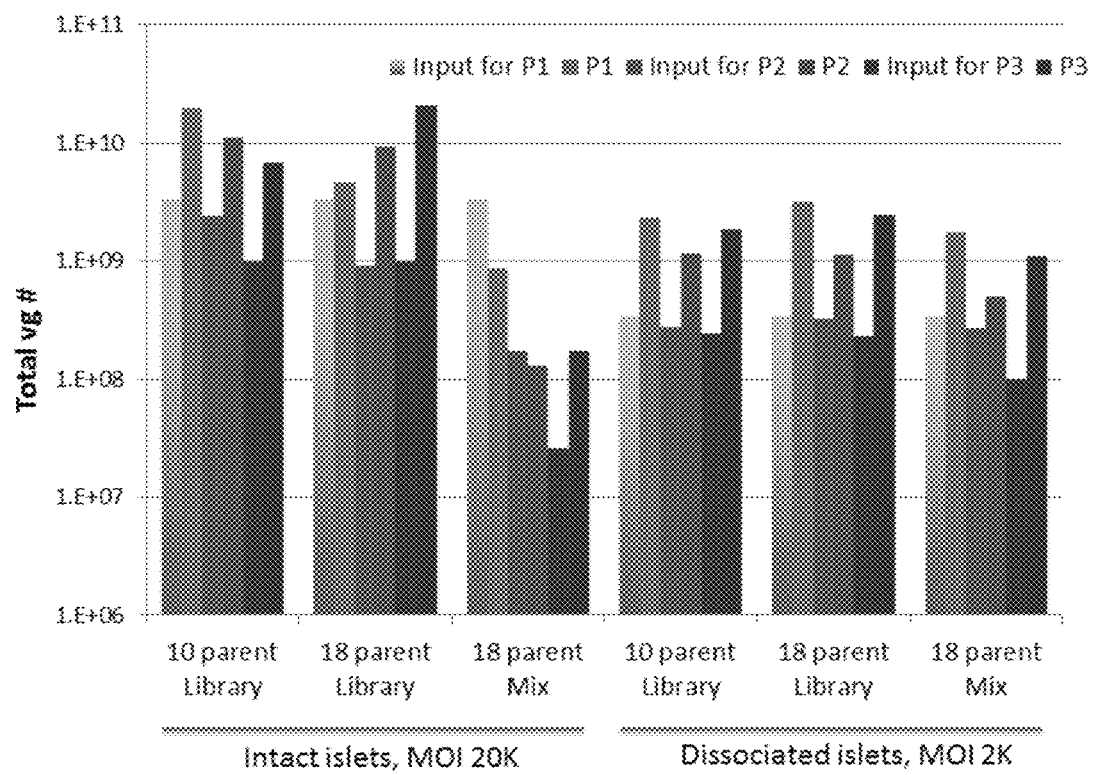
FIG. 9. Replication of AAV libraries and the 18 parent mix.
Figure 12:
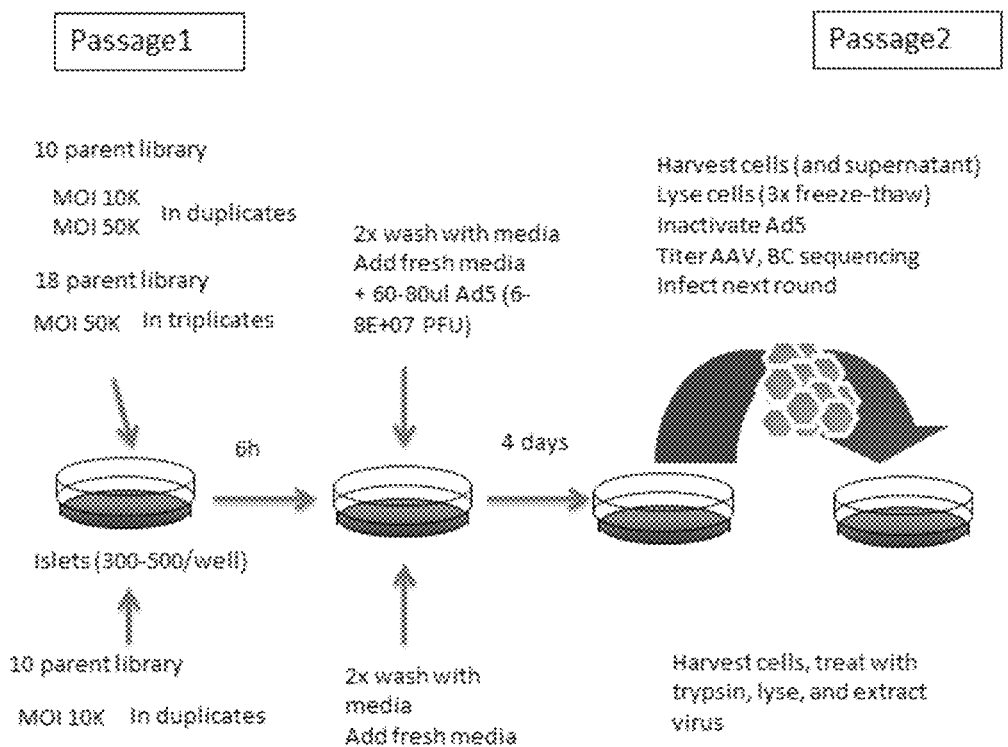
FIG. 12. Passaging regimen of shuffled libraries on intact islets: screen B.

Human islets were infected with high Multiplicity of Infection (MOI) of the cap shuffled barcoded AAV libraries as well as with a control pool of parental cap AAVs each tagged with a unique barcode (FIG. 8 and FIG. 12). Human adenovirus 5 was added as a helper to replicate AAV in most of the screens. Both intact as well as dissociated islets were used in the experiment and three rounds of passaging were performed for each screen. At each round AAV replication was assessed by qPCR and both AAV libraries as well as the 18 parent mix were shown to replicate in the islets (data not shown).

Figure 11:
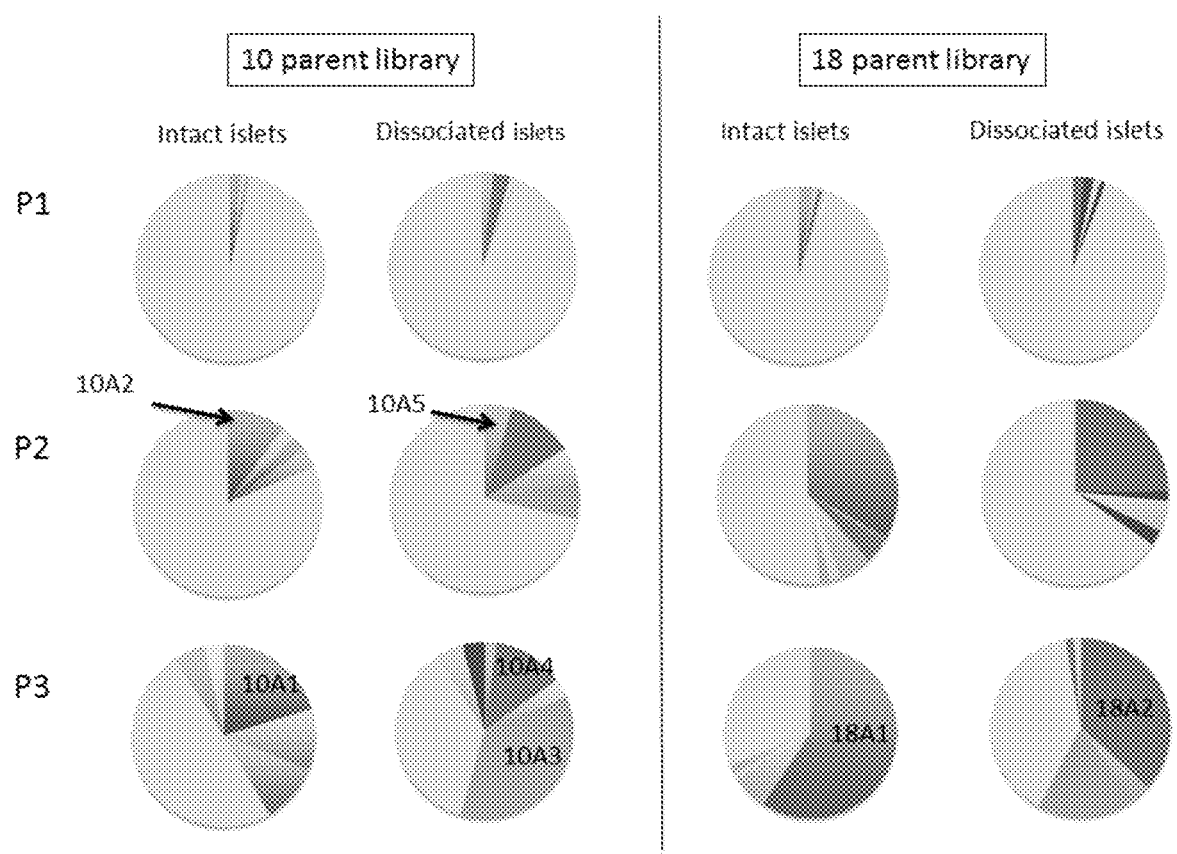
FIG. 11. Enrichment for shuffled AAV cap variants during passaging of the 10 parent (left) and 18 parent (right) libraries. Only the most enriched AAV variants are shown in different colors, all others are in grey. Variants that were selected for further analysis are indicted by name. Enrichment of capsid sequences through three rounds of selection of both libraries on intact islets and dissociated islets. After each passage BC sequences were analyzed by NGS using MiSeq. Colored sections represent enriched AAV populations. Variants with the most improved phenotype are indicated (KP1, KP2, KP3).
Figure 14:
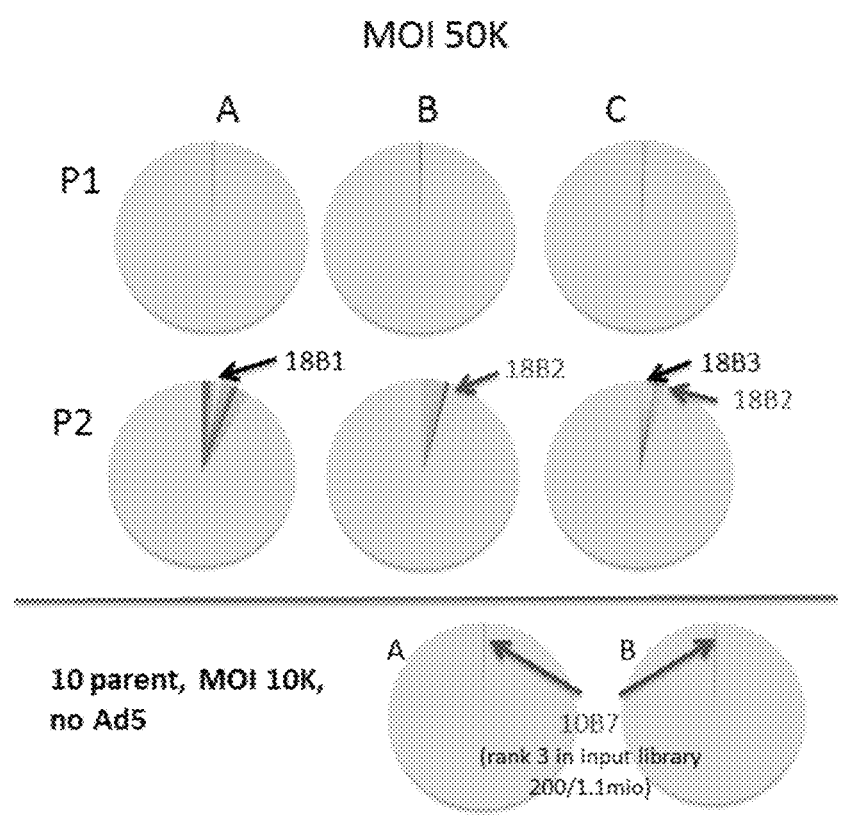
FIG. 14. Enrichment for shuffled AAV cap variants during passaging of the 18 parent library (upper panel), round 1 of the 10 parent library w/o Ad5 (lower panel). Only the most enriched AAV variants are shown in different colors, all others are in grey. Variants that were selected for further analysis are indicted by name. Names in red indicate variants that were enriched in two independent screens.
Figure 15:
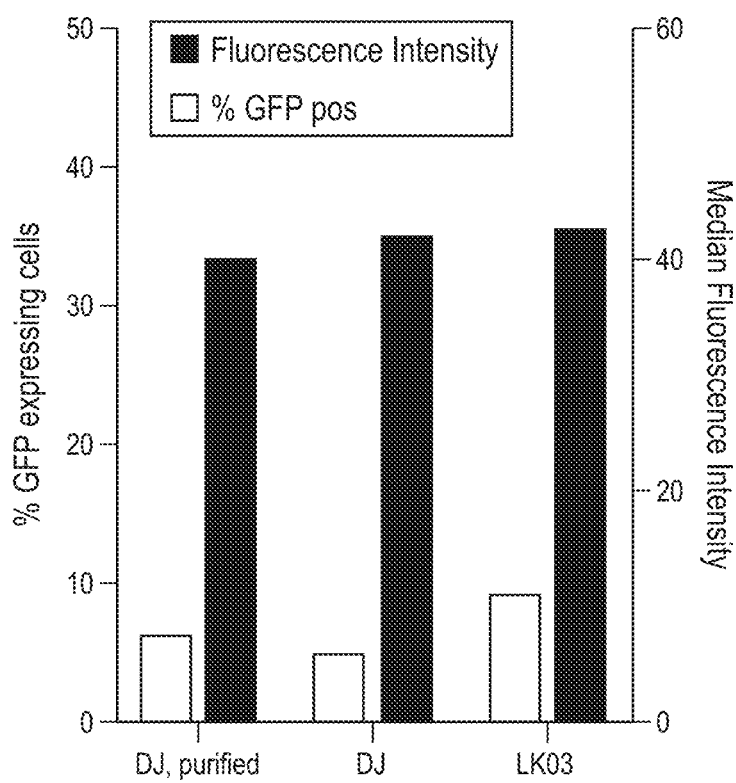
FIG. 15. Transduction of Dissociated Human Islets with AAV-vectors.
Figure 16:
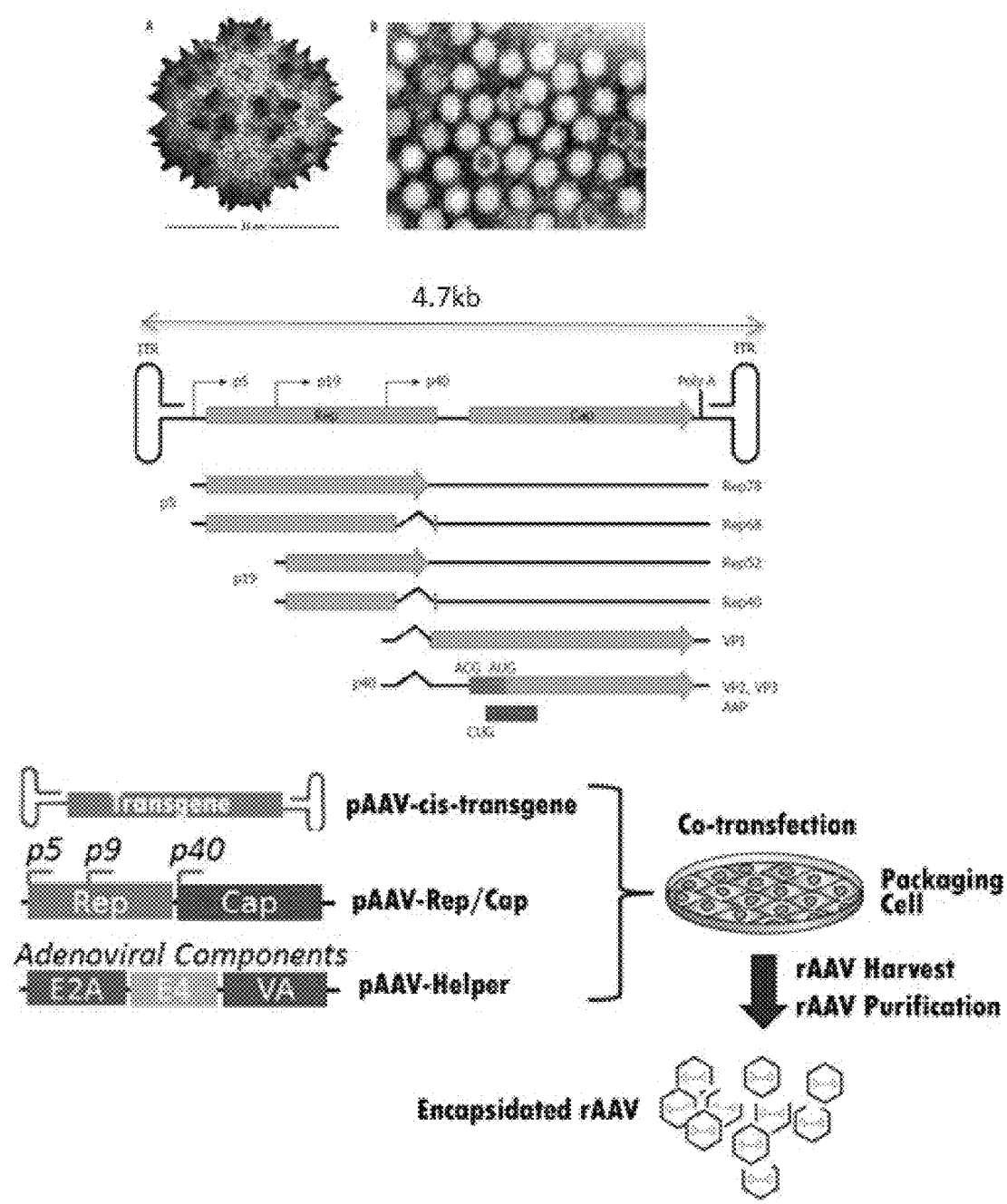
FIG. 16. Recombinant AAV for gene therapy.

High-throughput sequencing using a MiSeq sequencer (Illumina) of the AAV barcodes amplified from viral genomes was performed after each round of passaging. Infection of intact islets with the 18 parent mix revealed selection pressure towards AAVs containing the DJ capsid sequence (FIG. 10) although LK03 was found to be better at islet transduction than DJ. This suggests that variants with capsid sequences that confer improved transduction may be lost during prolonged passaging while those variants that replicate well may take over the population. For this reason, one screen which did not include superinfection with Ad5 was performed using the 10 parent library. Deep sequencing of barcodes obtained after passaging of both libraries revealed rapid enrichment for several capsid variants (FIGS. 11, 13, 14).

Example 2: Novel Recombinant Adeno-Associated Virus Capsids with Enhanced Human Pancreatic Tissue or Human Islet Cell Tropism Purpose The goal of the invention was to find rAAV vectors with enhanced ability to transduce human islet cells. This is useful for new treatments for endocrine disorders specifically diabetes type 1 and 2.

Technical Description

Figure 18:
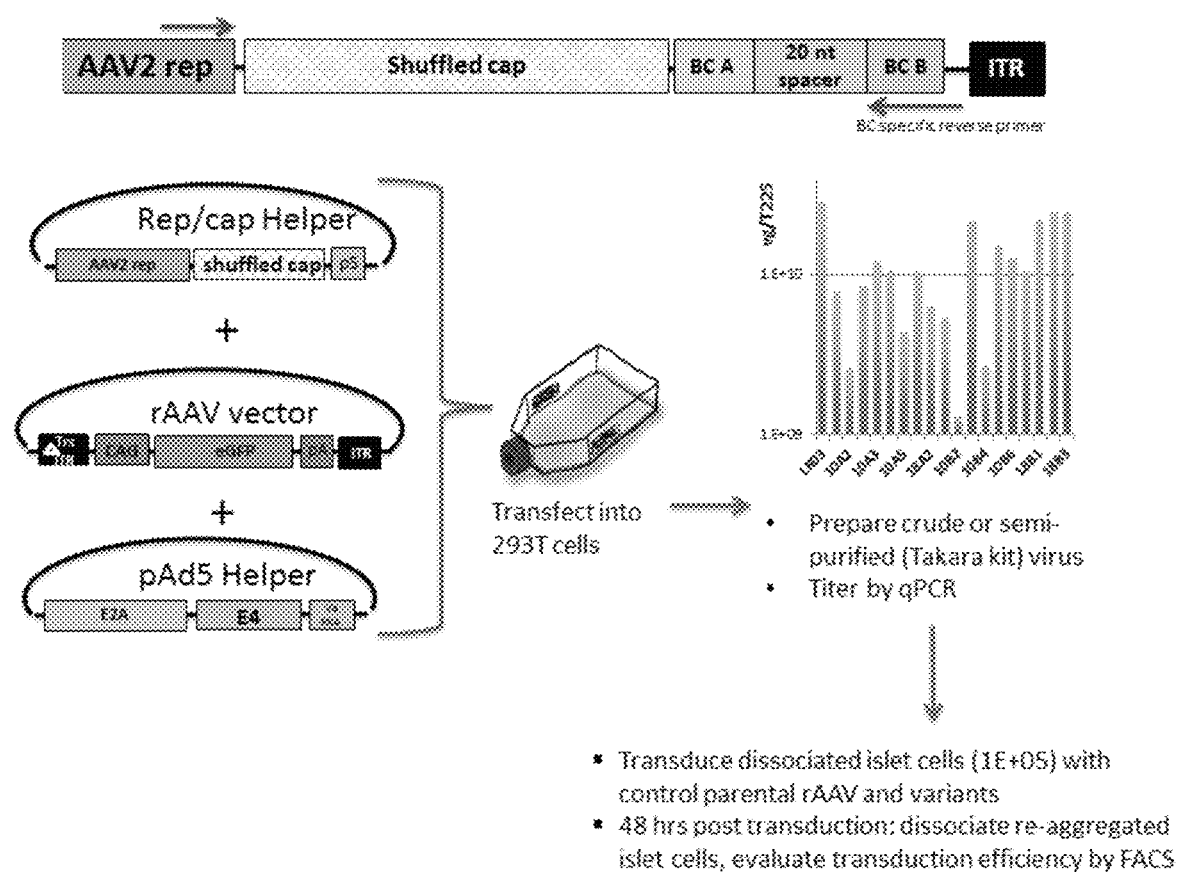
FIG. 18. Generation of rAAV expressing GFP. Capsid sequences from enriched AAV species were amplified using a BC sequence specific reverse primer and rAAV was produced in 293T cells by triple plasmid transfection. Crude or Takara kit purified rAAV preps were then quantified for vector copy numbers by qPCR and used to transduce islet cells.
Figure 20:
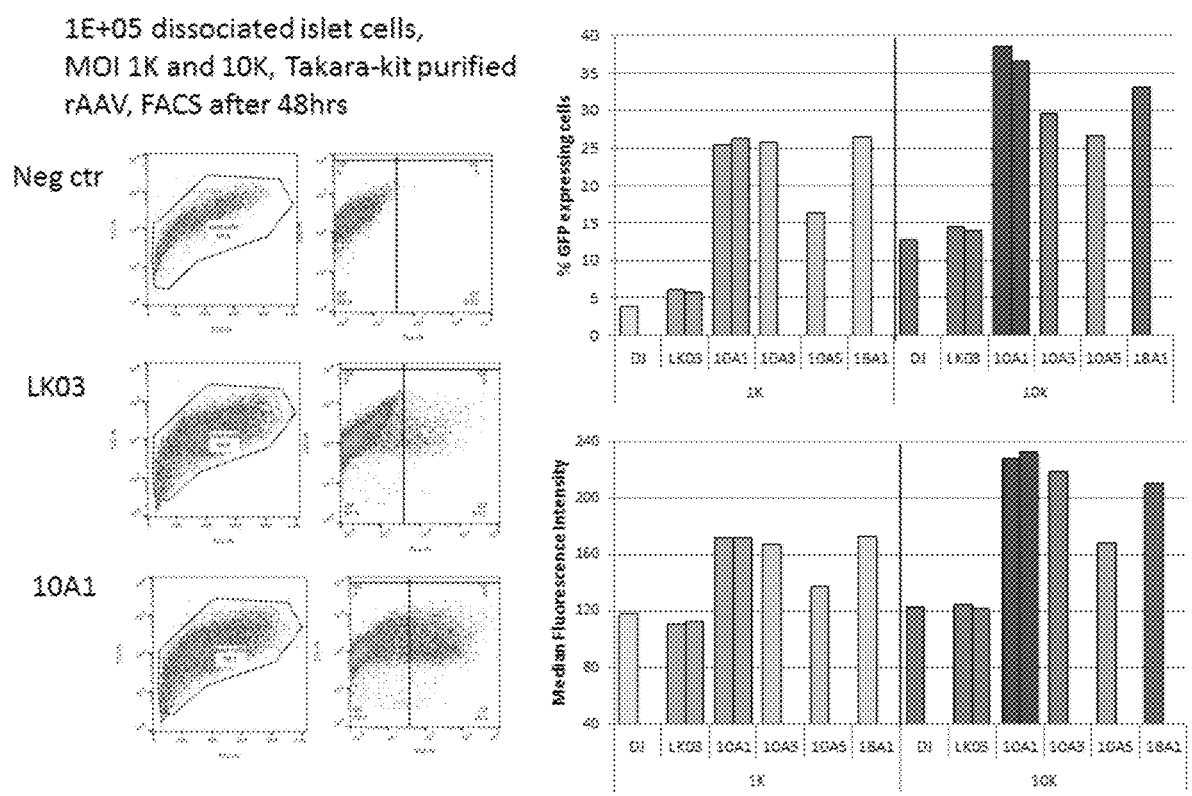
FIG. 20. Transduction repeat: Top variants only, MOI 1K vs 10K.

An AAV capsid library was used to select for AAVs that selectively transduced either dissociated or intact human islets. These capsid sequences were amplified using a barcode specific reverse primer and used to generate rAAV with GFP as a transgene (FIG. 18). Islets were dissociated using Accumax, transduced at MOI=1K or 10K vg/cell at 37° C. for 48 hours (10% FBS/CMRL), plated and analyzed by flow cytometry at 48 hours post transduction. Intact human islets were transduced at MOI=10K vg/cell on ice for 1-2 hours (2% FBS/CMRL) followed by suspension culture for 3 days with media change on day 2 post-transduction, and then were analyzed by flow cytometry. Flow cytometry were done using monoclonal antibodies against 2B4 (an islet surface marker) and 8G12 (an α-cell surface marker). After several rounds of passaging the most prevelant capsids were isolated and sequenced. rAAV vectors expressing a GFP reporter were compared against previously isolated rAAVs that are currently believed to be the most robust at transducing human islets.

Transduction was done on human intact islets from two different donors (MOI 10,000) using the cold transduction protocol. Surface staining was performed using antibodies against pan islet marker and alpha cell specific marker.

Cold transduction protocol. Pelleted whole islets and remove supernatant (in 15 mL Falcon tubes). Added 100 µL of CMRL+2% FBS to the islets. Added AAV, gently flicked tubes several times. Incubated the 15 mL Falcon tube on ice (almost lying flat ~10-15 degree angle) and put ice bucket on top of a horizontal shaker (approximately 100 rpm) in the cold room for 1-2 hours. Pre-warmed islet culture medium (CMRL-1066+10 mM HEPES+0.5% human serum albumin+2% FBS+10 mM nicotinamide+antibiotic/antimycotic+1× glutamax) at 37° C. In 24 well format non-coated/resuspension plate, transferred 350-500 islets (with the AAV) per well. Added 1 mL prewarmed islet culture medium per well. Left in a 37° C., humidified 5% $CO_2$ incubator for 2 days. Changed media on the $2^{nd}$ day. Harvested islets on the $3^{rd}$ day for FACS (Dorrell et al Nature Communications for FACS protocol using surface antibodies to subdivide islets into alpha, beta, non-alpha/non-beta).

Figure 42:
FIG. 42. The new rAAV variants were injected to Balb/SCID mice and transduction efficiency of each variant was tested in vivo.

The transduction efficiencies of new variants were tested in vivo. Different AAVs in four groups (DJ, AAV8, KP1, KP2 and KP3) with CAG-Fluc were injected at 2e10vg/mouse to Balb/SCID mice (n=4 mice/group) (see FIG. 42). In vivo luciferase imaging were performed weekly for 4-6 weeks. Several organs (e.g. liver, pancreas, lung, heart, brain, spleen, kidneys) were harvested, and analyzed for luciferase activities, Fluc transcript levels and vector copy numbers on day 7 and week 5.

Results

Transduction efficiency of primary human islet cells was assessed by FACS. Several capsid variants showed improved transduction when compared to the best parental LK03 (FIGS. 19, 20, 22-28, 30, 31, 33 and 34). Intracellular staining for insulin and glucagon will reveal if any of the variants exhibit selectivity towards α- or β-cells. Their relative transduction efficiencies were compared and the top candidates were approximately 10 times more robust than previous gold standard.

This study demonstrates that additional genetic modifications to the capsid provides enhanced rAAV transduction for efficient gene transfer into the target cells, e.g. islet cells. It provides a critical solution to targeting specificity for pancreatic alpha- and/or beta-cells.

Figure 35:
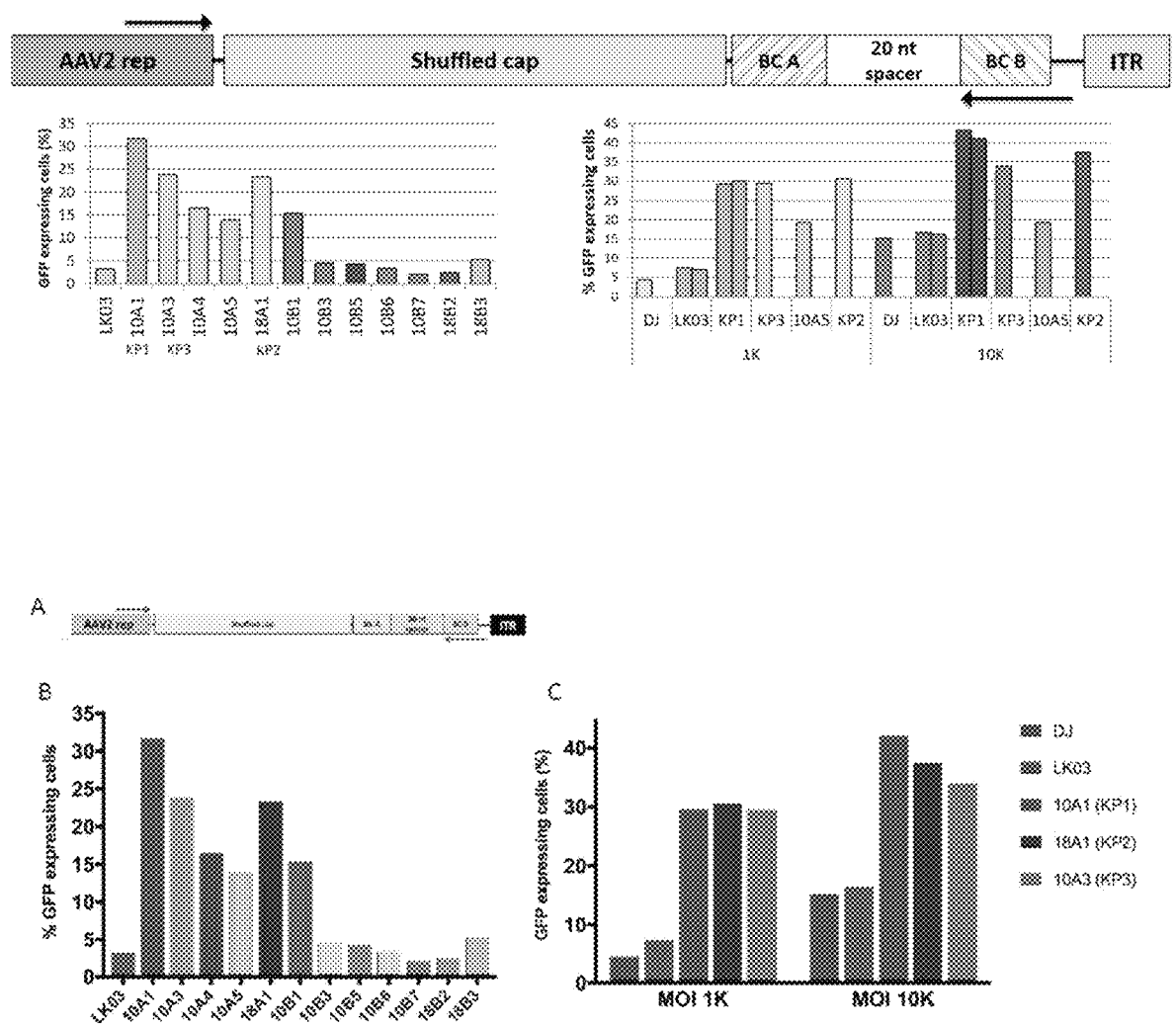
FIG. 35. Vectorization and testing of cap variants for transduction. Validation of enriched variants: (A) Capsid sequences from enriched AAV variants were amplified using a BC specific primer and used to package a sc AAV vector with the GFP transgene. (B) Crude virus preparations of the variants as well as one of the best parents (LK03) were used to transduce dissociated islet cells at an MOI of 1,000. (C) CsCl purified rAAV was prepared for the best variants and transduction of islet cells was analyzed in duplicates using two different MOIs. Validation of enriched variants: (A) Capsid sequences from enriched AAV variants were amplified using a BC specific primer and used to package a sc AAV vector with the GFP transgene. (B) Crude virus preparations of the variants as well as one of the best parents (LK03) were used to transduce dissociated islet cells at an MOI of 1,000. (C) CsCl purified rAAV was prepared for the best variants and transduction of islet cells was analyzed in duplicates using two different MOIs.
Figure 37:
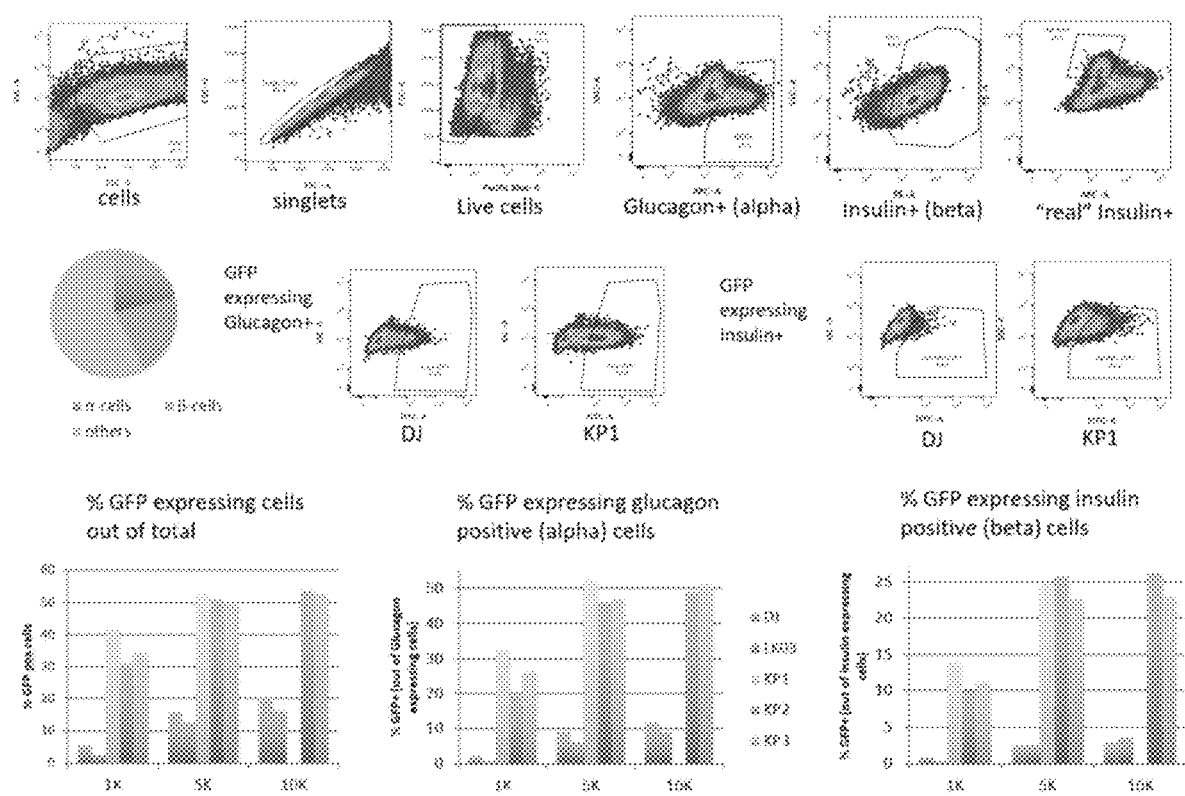
FIG. 37. Islet transduction and intracellular staining.
Figure 38A:
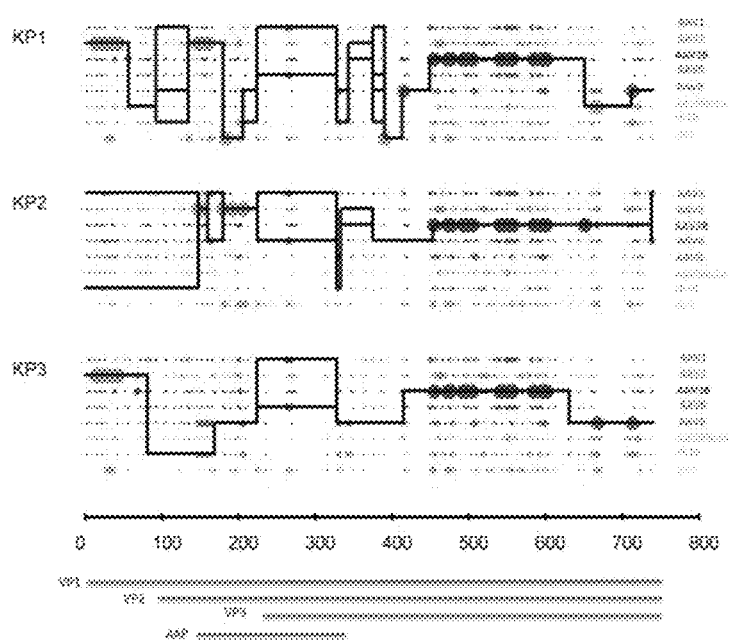
FIG. 38. Composition of the best capsid variants (X-over, amino acids). Library parents are depicted in different colors in order of entry of the parents. Large dots represent 100% parental match (i.e. the position in question matches only one parent) and small dots represent more than one parental match (i.e. the position matches more than one parent) at each position. The solid line for each chimera represents the library parents identified within the sequence between crossovers. A set of thin horizontal parallel lines between crossovers indicates multiple parents match at an equal probability. (A) Crossover analysis of the capsid amino acid sequences for the three best variants. Sequences for DJ and LK03 are not included as parental sequences since they are chimeras consisting of the parental sequences shown. (B) Shuffled variants were 3D false-color mapped onto the crystal structure of AAV2 VP3 using UCSF CHIMERA. Color-coding indicates amino acid contribution using colors as in (A).
Figure 38B:
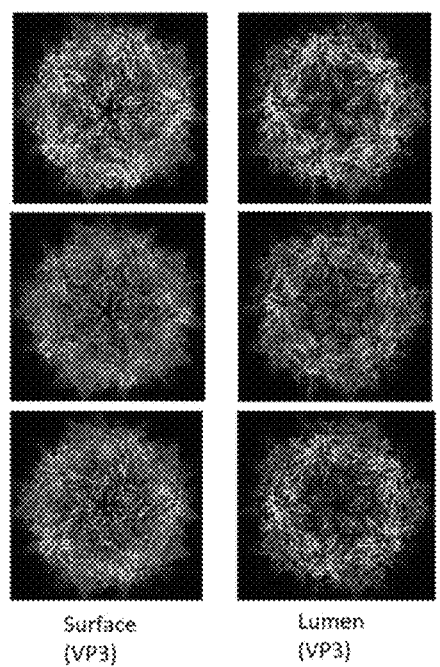
Figure 39:
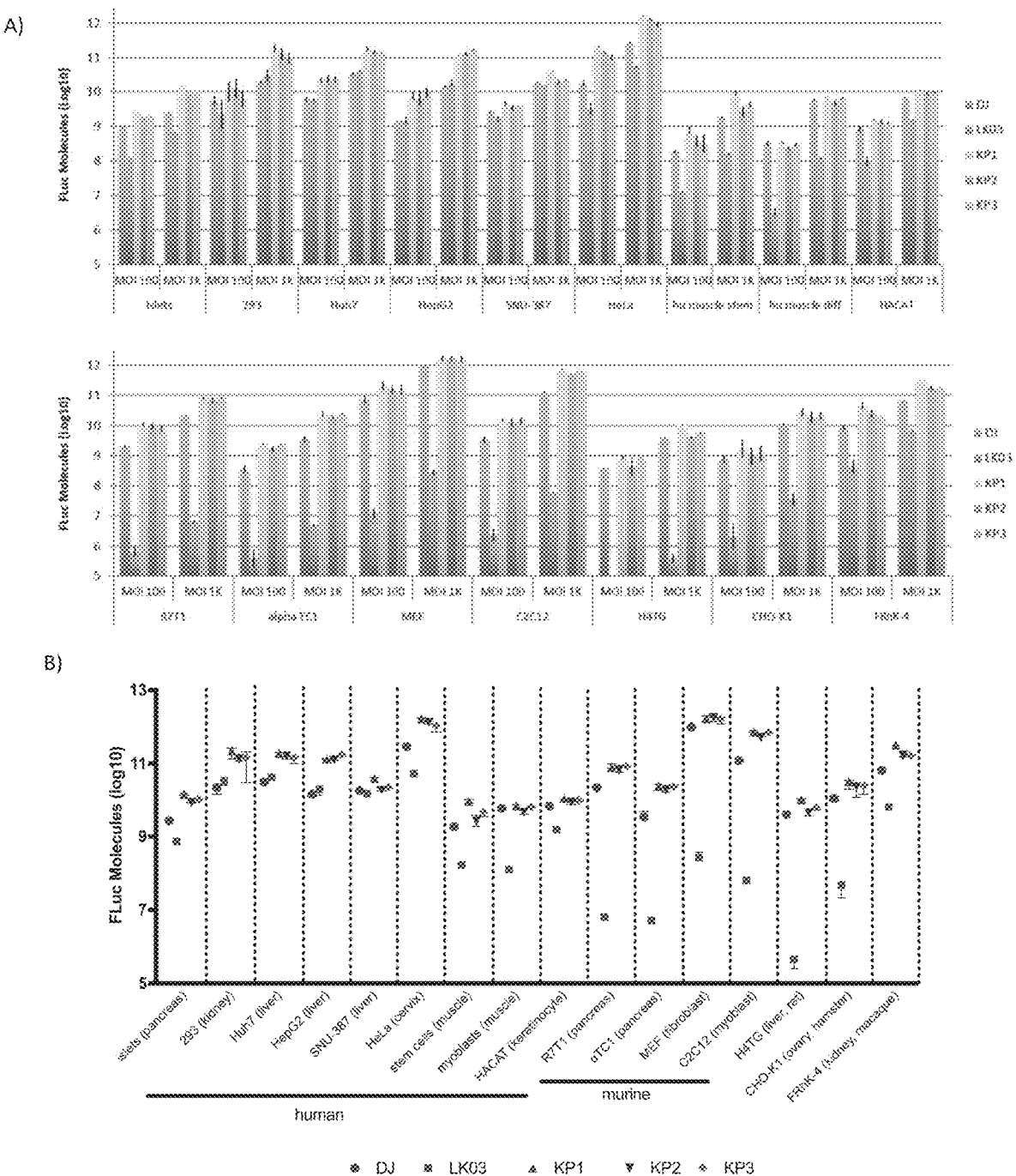
FIG. 39. Transduction efficiency on various human and non-human cell types.
Figure 40:
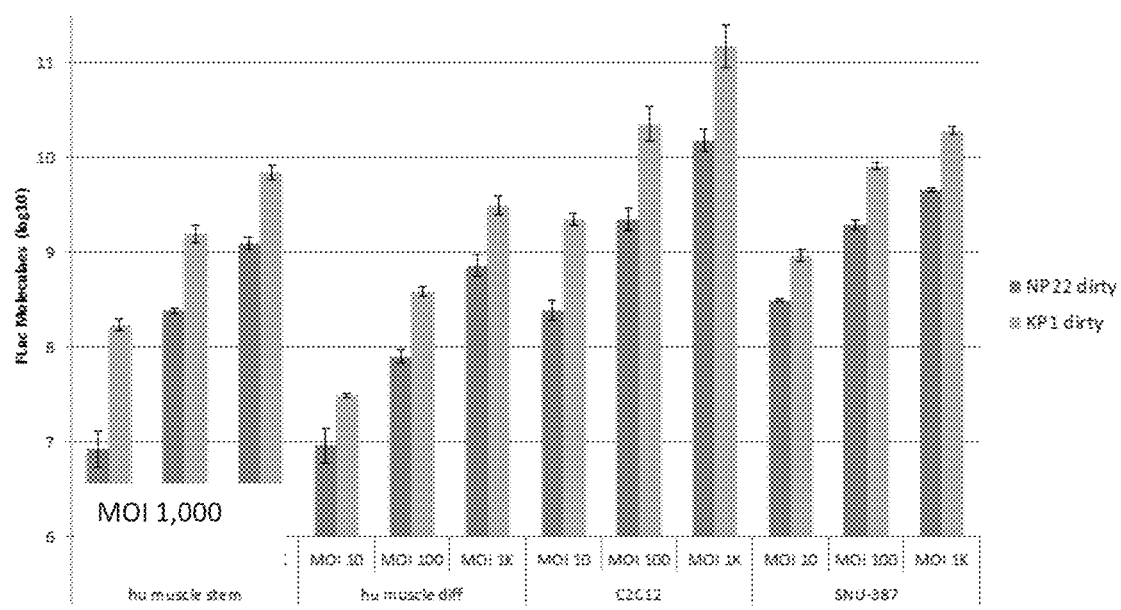
FIG. 40. Islet variant performs better on muscle cells than the best NP22 variant.
Figure 41:
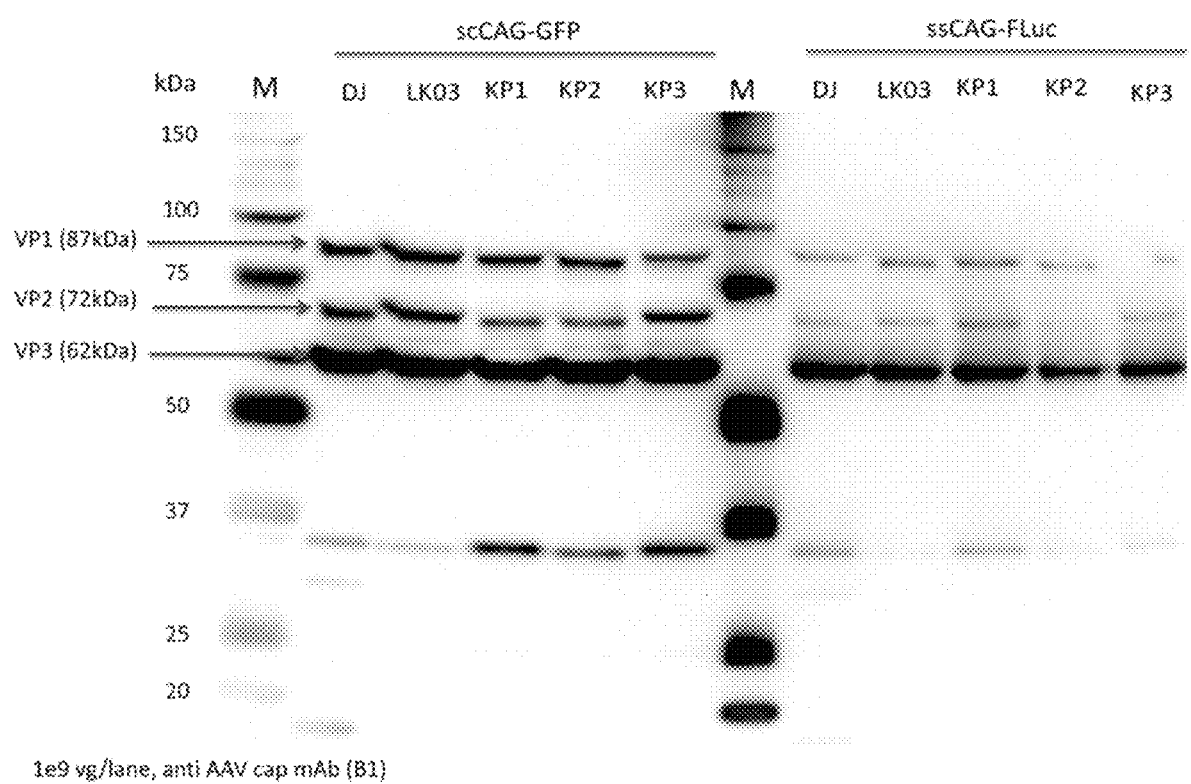
FIG. 41. Western blot results of purified rAAV preparations.

Transduction was done on human intact islets from two different donors (MOI 10,000). Surface staining was performed using antibodies against pan islet marker and alpha cell specific marker, and the results are shown in FIGS. 35-36. Enhanced transduction efficiency of the novel variants was shown on various human and non-human cell lines (FIG. 39). Two of the novel variants, KP1 and KP3, had a better neutralization profile than LK03 (FIG. 46).

Figure 43:
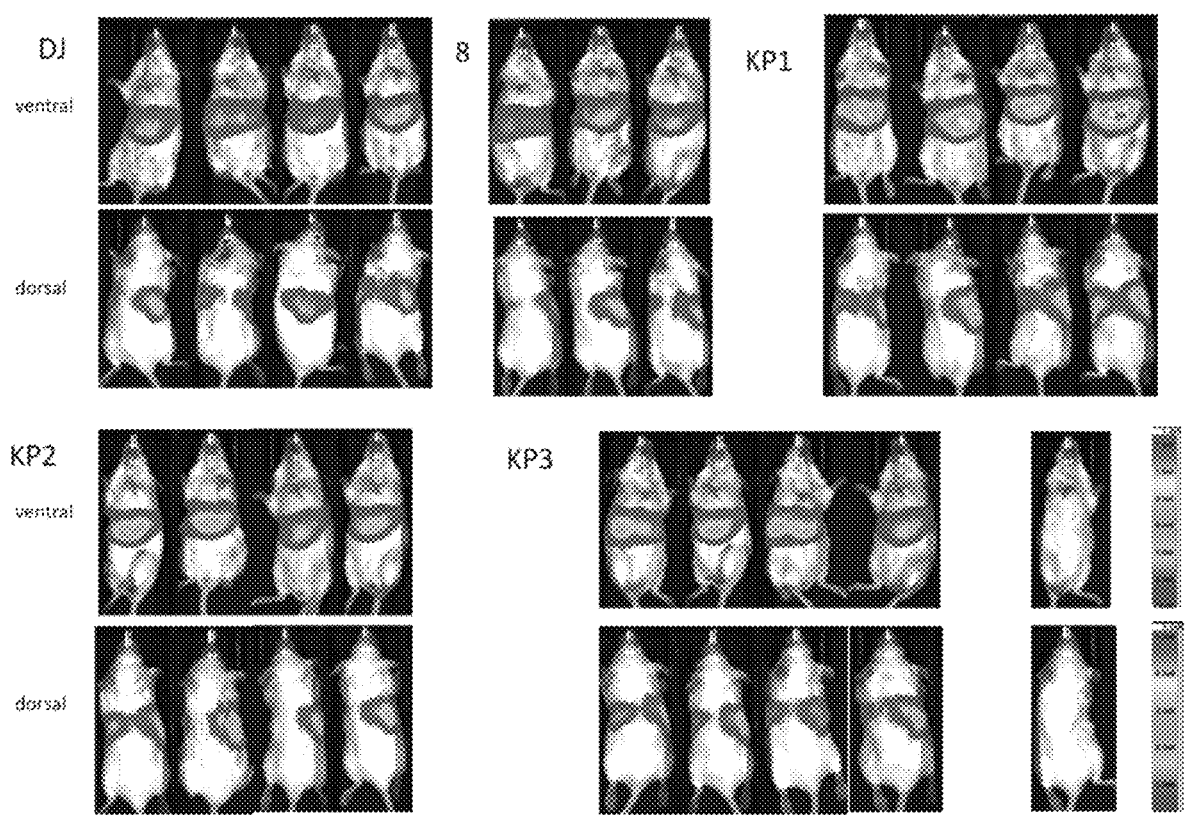
FIG. 43. The in vivo transduction efficiency of new AAV variants was studied via in vivo luciferase imaging.
Figure 44:
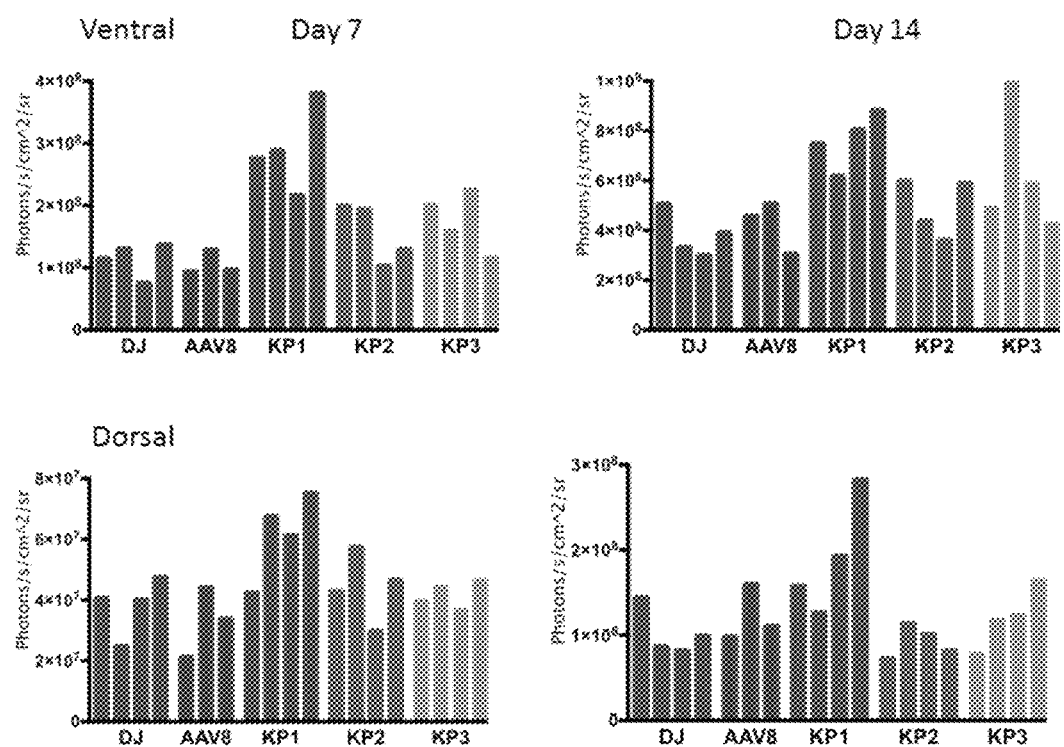
FIG. 44. Quantification of in vivo transduction efficiency of new AAV variants (day 7 and day 14).
Figure 45:
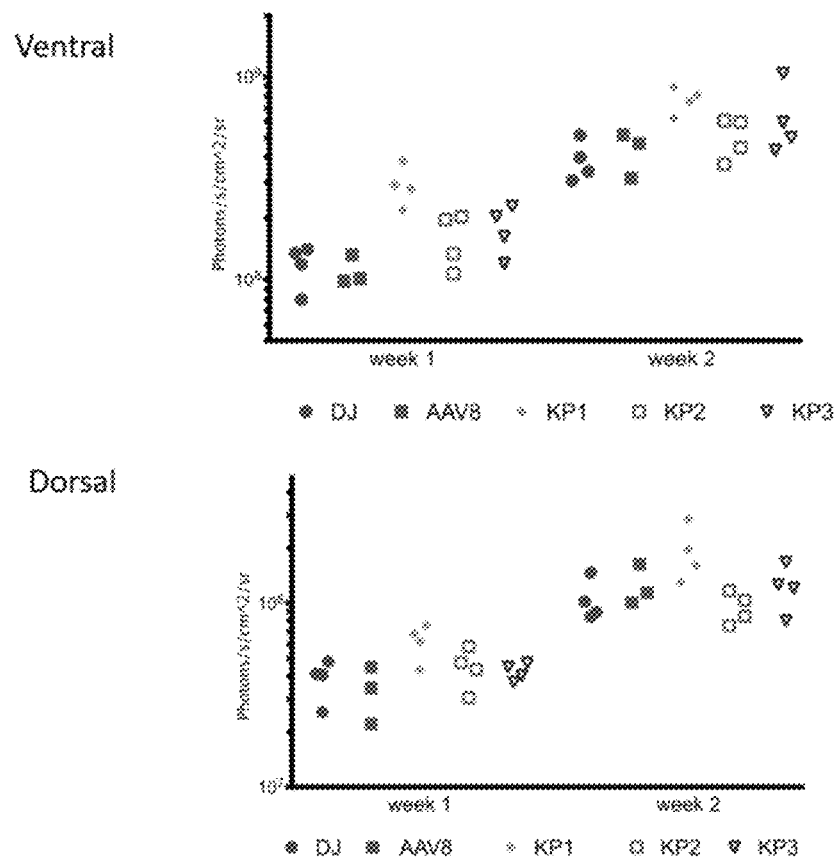
FIG. 45. Results of in vivo transduction efficiency of new AAV variants (week 1 and week 2).

The transduction efficiencies of new variants were tested in Balb/SCID mice in vivo. Balb/C SCID mice were tail-yen injected with 2E+10 vg of luciferase vector packaged with the different capsids. Luciferase expression in liver (ventral and dorsal) was monitored for 7 and 14 days. Luciferase expression (ventral) was then monitored weekly through week 5 (day 33). The results of luciferase imaging at day 7 and 14 are shown in FIG. 43 and quantified in FIGS. 44 and 45. The in-vivo liver transduction efficiency of the novel variants was stable from day 14 through day 33 (FIG. 47). Luciferase expression in various organs was tested ex-vivo at week 5 (FIG. 48). Vector copy number in the liver was elevated compared to brain, heart, and spleen (FIG. 49).

Example 3: Generation and Screening of Barcoded Adeno Associated Virus Capsid Shuffled Libraries for Enhanced Transduction of Primary Human Islet Cells Abstract Safe and effective gene transfer into the islets of Langerhans is a promising approach for the treatment of diabetes. Recombinant AAV-mediated gene transfer into islets is hampered by a lack of AAV serotypes that transduce those cells with high efficacy. In order to identify new AAV serotypes with improved tropism for human islets, two highly complex bar-coded replication competent capsid libraries were constructed, diversity was validated by single-molecule DNA sequencing, and serial selection was performed on human islets. The enriched barcodes were tracked by high throughput sequencing and three capsid variants were identified that were capable of transducing dissociated as well as intact islets with 5- to 10-fold higher efficiency when compared to the previously identified best capsids. These novel AAV capsid variants, capable of penetrating intact human islets, represent a powerful gene therapy tool for the treatment of patients with diabetes. One of the capsids was also robust at transducing both mouse and human hepatocytes in a humanized-chimeric mouse model, thus providing a versatile vector eliminating the requirement of using a surrogate capsid for preclinical testing prior for its use in human clinical trials.

Introduction

The development of viral gene transfer vectors remains an active field of investigation[1]. While recombinant AAV vectors have emerged as a safe vehicle for gene transfer into whole organisms in pre-clinical as well as clinical studies there are still important limitations[2]. Major drawbacks of rAAV are the limited packaging size of around 5 kb, rapid virus clearance due to pre-existing neutralizing antibodies, limited host tropism of the naturally occurring serotypes, as well as loss of transgene expressing in dividing cells due to the episomal nature of AAV. The capsid comprised of VP1, VP2, and VP3 proteins harbors the main determinants for cell tropism based on the recognition of various receptors and co-receptors[3]. In addition, capsid variants may exhibit variable post entry events such as capsid uncoating[4], intracellular trafficking and nuclear entry[5] resulting in differential transduction between tissues and species. Natural and non-natural AAV capsid variants have been isolated using biomining, i.e. isolation and characterization of naturally occurring AAVs[6], screening of capsid peptide display libraries[10], libraries expressing displaying cell specific Designed Ankyrin Repeat Proteins (DARPins)[10], and screening of capsid libraries obtained by random DNA shuffling[11] have been the paths most thoroughly explored to date. Recently, the creation and screening of libraries consisting of ancestral AAV capsid sequences has been described as a valuable tool to obtain AAVs with very specific cell targeting[12].

Directed evolution is a powerful tool to mimic natural evolution in a vastly accelerated manner. Most importantly, no a priori knowledge about sequence-function relationships is needed, which stands in contrast to rational design strategies. Highly diverse libraries of the desired sequences are created, followed by screening for those variants that exhibit the desired phenotype. Several methods for library generation have been described, such as DNase mediated shuffling[13-14,] Staggered Extension Polymerization (STEP)[15], Random Chimeragenesis on Transient Templates[16], restriction enzyme mediated shuffling[17], and others (for detailed protocols see[18]). For this study DNase mediated family shuffling[13, 19] of several full-length AAV capsid sequences was employed to create highly complex and functional libraries. This technology takes advantage of the ability of randomly fragmented DNA derived from a family of related genes to re-assemble into chimeric full-length sequences due to hybridization[13-14.] Crossovers occur when a partially reassembled PCR product primes on the homologous position of a related but not identical template, thus initiating a template switch. Since crossovers based on an identity of less than 15 bases are difficult to obtain[13-14] the degree of library complexity and thus quality tends to negatively correlate with parental sequence diversity. DNA shuffling can be used to create large libraries of genes that can be screened for the desired phenotype. Successful applications of this technology have been described for many areas, such as the improvement of properties of various enzymes, promoters, immune modulating proteins[19-32]. In 2000 Soong et al., were the first to describe the application of DNA shuffling for virus evolution[20]. To take advantage of this highly diverse virus library is subjected to stringent selection pressure throughout several rounds of passaging and enriched variants are recovered. This technology has resulted in the development of Moloney Leukemia virus (MLV) particles with improved envelope stability[26], as well MLV and HIV-1 with novel host cell tropism[25, 28]. In 2008, Grimm, D, et al. were the first to report successful selection of improved AAV variants by capsid shuffling and multiple rounds of selection[8]. A different method for AAV capsid evolution—error-prone PCR combined with STEP—had been described earlier.[33] Soon, others created and screened AAV capsid shuffled libraries[34-40] (for a review see[11]). Some of these screens were performed in presence of human adenovirus 5 to replicate enriched AAV variants between selection rounds, but adenovirus free AAV library screens have also been reported[41-44].

An estimated 30.3 million US Americans are affected by either type 1 or type 2 Diabetes Mellitus[45]. Various strategies to cure diabetes have been evaluated over the years. Transplantation of cadaveric human islets into the hepatic duct has been used to replace β-cells in type 1 diabetic patients, so far with limited success (for a review see[46]). Islets are highly vascularized and require large amounts of oxygen to survive. Because re-vascularization of the transplanted islets takes several weeks those transplants suffer from a large number of cell death due to oxygen deprivation. Ex vivo gene therapy either supplying or repressing certain transcription factors may be used to improve graft survival and function (see [47] for a review). Recently the knockout of PHLDA3 has been shown to lead to increased survival of transplanted islets in mice48. In addition to the approaches described above it is of utmost importance to prevent loss of the transplanted islets due to recurrent autoimmune destruction. Recently a study described the use or AAV to overexpress Igf1 and thus counteract progression to autoimmune diabetes in mice[49].

Another strategy for treatment is the conversion of glucagon producing α-cells or other endocrine or exocrine pancreatic cell types into β-cells by overexpression or repression of certain transcription factors, such as Pdx1, Ngn3, MafA, Pax4, and Arx,[50-58] (for a review, see[59]). Follistatin overexpression in a diabetic mouse model has been shown to preserve β-cell function[60].

To this date only few studies have described the use of AAV as gene therapy vehicle for pancreatic islets and most of the work has been performed with murine islets. AAV8 capsid combined with the β-cell type specific insulin promoter has been described to achieve highly specific transduction of β-cells after intraperitoneal delivery in mice[61]. Another study found AAV6 to transduce mouse islets with high efficiency in vitro as well as via the intraductal route, but AAV8 proved to be the more robust serotype when systemically delivered[62]. Site-directed mutagenesis of surface exposed capsid tyrosine residues to phenylalanine has been described to enhance transduction efficiency of several serotypes due to evasion from intracellular ubiquitination-proteasomal degradation[63-67]. Recently Y-F mutant AAV8 vectors have been reported to achieve up to ten-fold improved gene transfer into mouse islets as compared to wildtype AAV8[68]. Interestingly, studies in rats found that AAV5 was the best capsid for islet transduction in this rodent[69]. AAV2 is the serotype that has been described most frequently for transduction of human islets[70, 71]. More recently capsid variants DJ and LK03 were found to have better transduction efficiency on human islets as compared to AAV2 and AAV3B, however, a strong preference for α-cells was observed for those capsids[72].

This study sought to develop capsid variants with further enhanced human islet cell transduction efficiency. For this purpose, the capsid shuffled barcoded AAV libraries were subject to multiple rounds of selection on human islets and analysed enriched capsid variants for improved transduction efficiency. Barcoding the capsids was performed to follow enrichment of chimeric variants by employing high-throughput sequencing of the barcodes rather than low-throughput Sanger-based sequence analysis of the capsids. This novel technology, termed AAV Barcode Seq has first been described for in vivo tracking of variants derived from small AAV libraries or parental pools[73]. Among all the candidates tested three chimeric variants were found to exhibit considerably improved transduction capacity of human islets—particularly of β-cells as well as other cell types in vitro and in vivo. These novel capsids may be useful for various gene therapy applications besides those targeting pancreatic islets for diabetes treatment.

Results:
Evaluation of Parental Capsids for Human Islet Transduction Efficiency

Figure 50A:
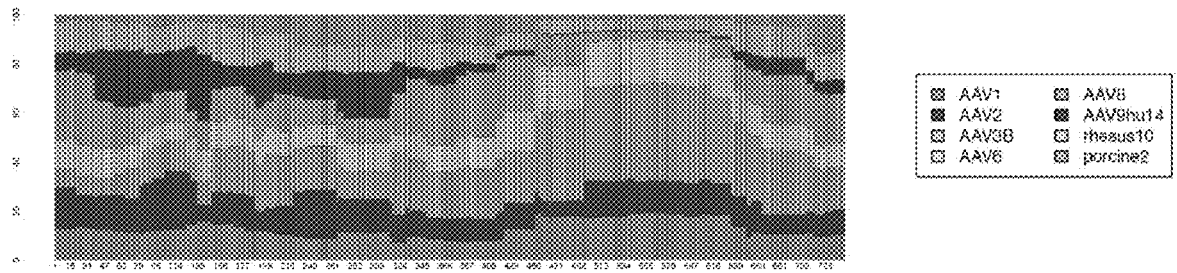
Figure 50B:
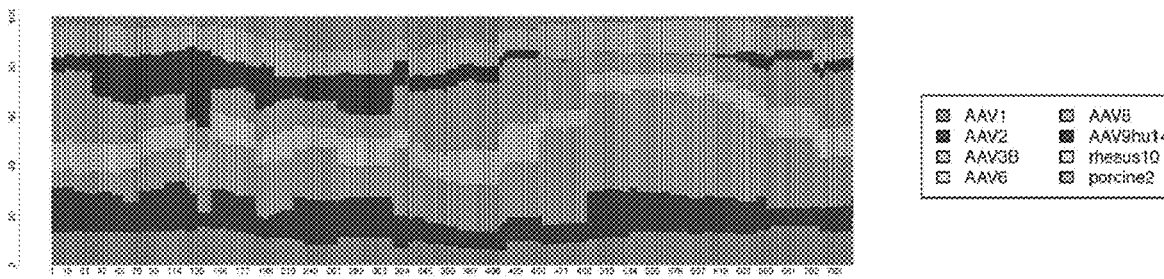
Figure 50C:
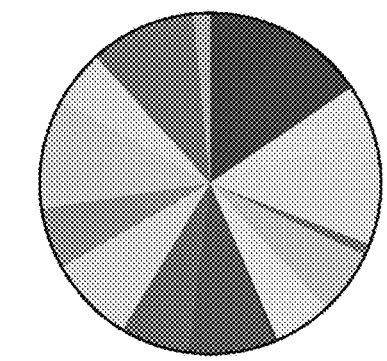
Figure 58A:
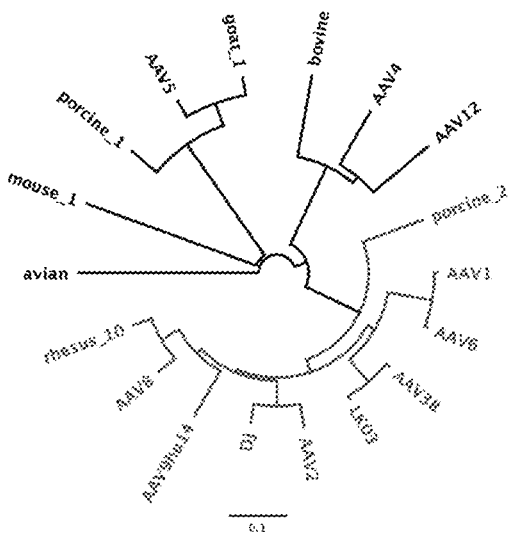
Figure 58B:
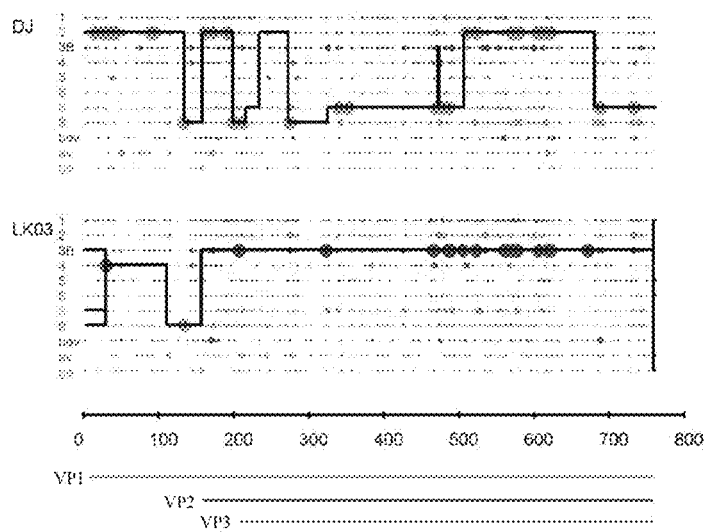
Figure 58C:
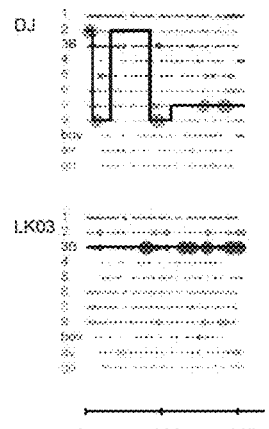

The first step was to confirm previous data showing that AAV-DJ and AAV-LK03 have higher human islet transduction efficiency than the closely related natural serotypes AAV-2 and AAV3B[72]. Human islets were transduced with single stranded (ss) and self-complementary (sc) GFP expressing vectors packaged with the different capsids and measured transduction efficiency using flow cytometry (FIG. 62A). As expected AAV-DJ and AAV-LK03 had higher rates of transduction in human islets than AAV2 and AAV3B. Confirming this result provided the basis of a validation study prior to doing the screening with the shuffled capsid library. For this study a control AAV pool was generated containing parental AAVs that each carried a unique barcode (BC) sequence immediately downstream of the capsid coding sequence. After mixing equal copy numbers of each of the 18 parental AAVs the pool was purified and analysed its composition by high-throughput sequencing of the barcodes (FIG. 50C). Although some of the parental AAVs were under- or overrepresented in the pool, the 18 parent pool was found to be useful in a pilot library screen as the first validation for use of barcode sequencing in a capsid selection screen. To evaluate which capsid was best at transducing human islets human intact as well as dissociated islets were infected with the 18 parent pool and super-infected with human adenovirus 5 to replicate AAVs. A ten-fold higher multiplicity of infection (MOI) for infection of intact than for dissociated islets was used, as it was reasoned that islet cells at the center were harder to infect than those on the periphery. Three consecutive rounds of selection were performed and AAV replication (FIG. 51) as well as composition of the viral pool (FIG. 52) was assessed at each round. For rounds 1 and 2 of selection lower copy numbers of viral genomes were recovered after propagation on intact islets as compared to the input whereas replication picked up at round 3. When a lower MOI of 2K was used to infect dissociated islet cells the amount of virus obtained after islet culture was higher than the input at each round of selection. Next generation sequencing (NGS) of the BC sequences was used to assess the composition of AAVs at each round. Between 400,000 and 1,000,000 sequence reads were obtained for each sample. Certain parental AAVs had a clear advantage over others as the diversity of the pool was already diminished after one round of selection, particularly when intact islets were used (FIG. 52). AAV2, AAV3B, as well as shuffled variants DJ and LK03 were enriched already after the first passage. After the third passage on intact islets as expected AAV-DJ and AAV-LK03 were equally represented while AAV2 and AAV3B were present to a lower extent. Passaging of the 18 parent pool on dissociated islet cells revealed early enrichment of AAV-DJ with lower proportions of AAV2, LK03, AAV3B, and AAV-rhesus10.

by replication studies for wild type AAV with and without the BC (data not shown). High-throughput sequencing of the barcode plasmid library showed a sufficiently high degree of diversity with over 93% of all BC reads having a unique sequence (Table 6). Out of over 1.2 million reads only one single BC sequence was present 6 times, 20 different BC sequences were present in 5 replicates, 342 different BC sequences were found 4 times each, 4844 BC were detected to be present in triplicates each, and 74,433 BC sequences (6%) were found twice. As high-throughput sequencing of the barcodes involved an amplification step it is most likely that the actual number of repetitive barcodes in the BC library was lower than that. The size of the barcode library was estimated to be 1E07 based on the number of colonies obtained from an aliquot of the transformation reaction. Shuffled capsids were then generated using sequences from 10 related AAVs or 18 more diverse AAVs and cloned into the BC library vector. A phylogenetic analysis of the parental sequences used for shuffling is depicted in FIG. 58A. Two of those capsid sequences—DJ and LK03—had been derived from previous screens performed in our laboratory using earlier generation libraries and are hybrids of AAV2, AAV8, and AAV9hu14 for DJ or AAV1, AAV3B, AAV4, AAV8, and AAV9hu14 for LK03 (FIG. 58B). FIG. 58B displays the composition of the DJ and LK03 capsids and FIG. 58C shows the composition of the DJ and LK03 assembly activating protein (AAP). The capsid shuffled barcoded 10 parent library and the 18 parent library each had a size of approximately 5E06 different clones as estimated by the number of colonies that had grown on an agar plate after plating small aliquots of the library transformation reactions. Given the low number of replicates after BC sequencing the complexity was estimated to be at least 1 million for each of the libraries.

TABLE 6

Barcode NGS data of the BC library, and the capsid shuffled libraries at the plasmid as well as the AAV level. The top identical sequences are shown, the number of times each sequence is represented within the sequence reads is shown in paranthesis.

| Sample | BC library | 10 parent plasmid library | 10 parent AAV library | 18 parent plasmid library | 18 parent AAV library |
|---|---|---|---|---|---|
| Total reads (#) | 1,249,614 | 1,256,634 | 1,141,870 | 1,804,277 | 1,000,494 |
| Unique reads (#) | 1,164,408 | 1,110,174 | 866,601 | 1,598,929 | 798,927 |
| Unique reads (%) | 93.18 | 88.35 | 75.89 | 88.62 | 79.85 |
| Identical BC (# of repeats) | 1 (6x) | 7 (7x) | 1 (287x) | 1 (8x) | 1 (232x) |
| Identical BC (# of repeats) | 20 (5x) | 30 (6x) | 1 (195x) | 8 (7x) | 1 (177x) |
| Identical BC (# of repeats) | 342 (4x) | 220 (5x) | 1 (182x) | 63 (6x) | 1 (173x) |
| Identical BC (# of repeats) | 4,844 (3x) | 1,809 (4x) | 1 (177x) | 365 (5x) | 1 (141x) |

This experiment validated our selection screen approach as it confirmed previous transduction studies showing that AAV-DJ and AAV-LK03 robustly transduce primary human islets.

Generation of Highly Diverse Barcoded Capsid Shuffled AAV Libraries

Prior to generating the shuffled AAV libraries a highly diverse AAV Barcode (BC) library was created. For this purpose, a fragment consisting of two 12 nucleotide (nt) long random barcode sequences separated by a 20 nucleotide (nt) long linker was cloned into an ITR containing AAV vector containing the AAV2 p5 promoter and rep gene, but no cap sequences. The barcode fragment was cloned immediately 3' of the cap polyA sequence, thus permitting tracking of variant enrichment throughout the selection process by high-throughput sequencing. Insertion of the BC sequence did not negatively impact virus function as shown The degree of library diversity was assessed using three different methods—high-throughput MiSeq analysis of the barcodes, PacBio sequencing of the capsids including the barcodes, as well as Sanger sequencing of the capsids including the barcodes. Amplification and high-throughput sequencing of the barcodes from the plasmid libraries as well as the AAV libraries revealed a very high degree of complexity with low numbers of replicates. At least 1 million reads were obtained for each sample (Table 6). When the 10 parent library was analysed on the plasmid level, i.e. prior to transfection into 293T cells, it was found that 88.3% of all reads contained unique sequences, with a maximum number of replicates found to be 7 reads out of 1.25 million reads. For the 18 parent plasmid library 88.6% of the reads were unique, the maximum number of reads obtained for one single BC sequence was 8 out of 1.8 million reads. Analysis of the NGS data for the AAV libraries revealed approximately 76% and 80% unique BC sequences for the 10 parent and 18 parent libraries respectively (Table 6). In the 10 parent AAV library one single BC sequence was represented with 287 reads (0.025%), in the 18 parent AAV library the highest number of reads obtained for a single BC was 232 (0.023%). There were also other replicates present in lower numbers, particularly 10 times and less.

Figure 59A:
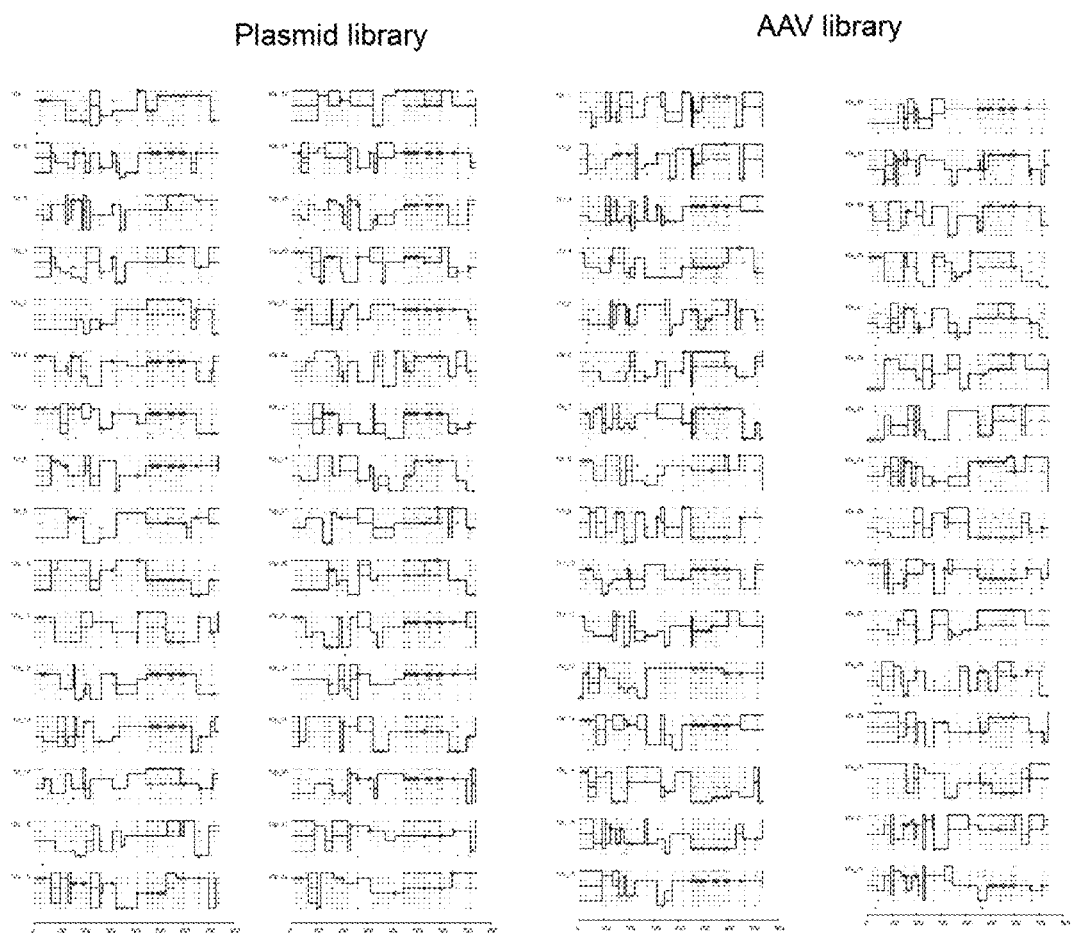
Figure 59B:
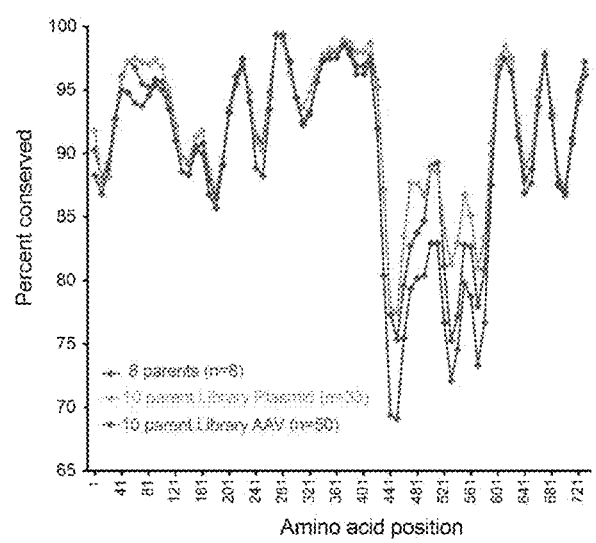
Figure 60A:
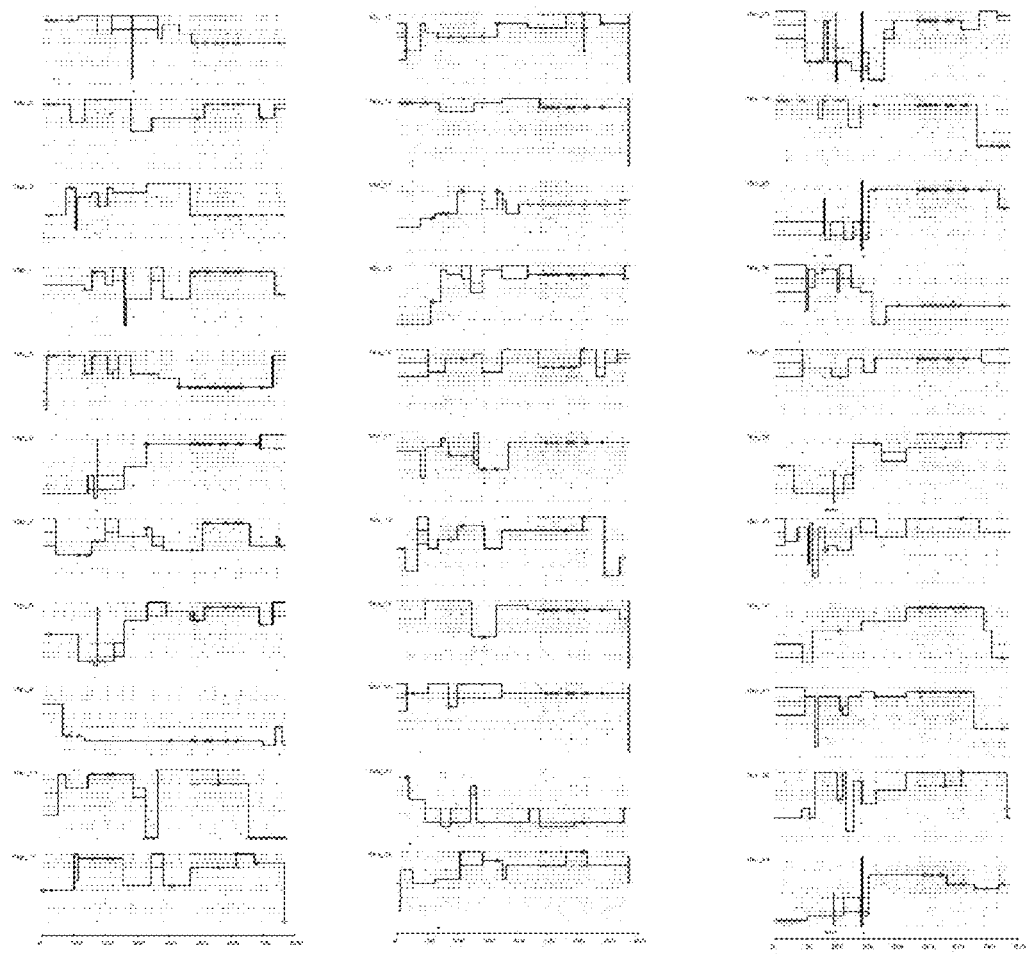
Figure 60B:
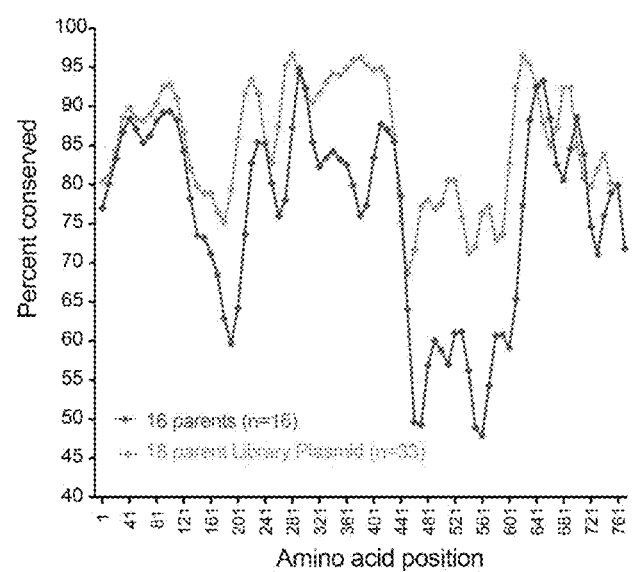

As a low-throughput method several capsids from both plasmid libraries as well as from the 10 parent AAV library were analysed by Sanger sequencing and subjected to recombination analysis using the Xover program made available online by the Gillam lab. (FIG. 59A, FIG. 60A). For analysis of diversity on the AAV level the region spanning capsid and barcodes was amplified from extracted viral genomes, cloned and sequenced (FIG. 59A, right panel). In addition to depicting crossover figures of the shuffled capsids, we used the parental contribution data generated by the Xover software to perform conservation analysis throughout the capsid sequences. The conservation values for each amino acid residue were calculated and graphed (FIG. 59B, FIG. 60B). Using this analysis would allow for evaluation to see if sequence diversity within the libraries was drastically diminished when compared to the parental sequences. In case of the 10 parent library on the plasmid as well as the AAV level conservation patterns closely matched those of the parental sequences (FIG. 59B) while the 18 parent plasmid library exhibited higher conservation levels than the parents throughout most of the capsid (FIG. 60B). Crossover analysis of the capsid amino acid sequences showed that the 10 parent library was well shuffled with an average rate of 11 crossover events per capsid. A small number of clones contained a Glutamine at position 24 originating from the AAV4 derived sequence within chimeric parental LK03. For reasons of consistency LK03 and DJ had not been included as parentals in the crossover analysis figures, thus this residue is marked as a de novo mutation. With an average of 8 crossovers, the 18 parent library was less thoroughly shuffled. This observation can be explained with the large proportion of parental capsids that have low homology to each other throughout large stretches. Crossovers based on an identity of less than 15 bases are difficult to obtain.[13] This is likely due to fragments with low homology to each other do not easily recombine when equimolar amounts of each parent are mixed together. The observation that fewer crossovers were found within the 3' half of the library capsids can also be explained by this limitation as this part of the capsid contains several stretches of low sequence homology between the different serotypes. Complexity of the 10 parent library on the AAV level was found to be similar to that on the plasmid level indicating that capsid assembly during AAV production in 293T cells is not a bottleneck that dramatically reduces diversity (FIG. 59). Moreover, the crossover analysis patterns show that the parents appear to be represented roughly equally and randomly within the libraries, although AAV3B sequences seem to be slightly favoured in the 3' part of the shuffled clones. This can be explained in part by the fact that in addition to AAV3B the chimeric capsid LK03 was used as a parental sequence for shuffling. The entire 3' half of LK03 is derived from AAV3B, thus AAV3B sequence containing fragments were overrepresented in the initial fragment pool. In addition to Sanger sequencing of individual capsids, PacBio sequencing of the 10 parent library on the plasmid level prior to transfection into 293T cells (FIG. 50A) was performed, as well as on the AAV level (FIG. 50B). 21,000 full-length reads were obtained for the 10 parent library on the plasmid level while about half of that number of reads was analysed for the 10 parent AAV library. The graph depicts the contribution of each parental amino acid residue throughout the length of the capsid. As already observed by Sanger sequencing, PacBio sequencing revealed that the 5' half of the capsid gene contained a more even distribution of all parental sequences than the 3' half. Particularly residue contribution from AAV porcine2 and AAV9hu14 were starkly diminished in the sequence stretch between amino acid positions 450 and 650 while AAV3B sequences were overrepresented. An overrepresentation of AAV3B sequences is possibly at least in part due to the fact that LK03 which contains large sequence stretches from AAV3B (FIG. 58B) was used as a parental for shuffling.

Another analysis performed was to see if each capsid was linked to a unique barcode sequence and found very high levels of capsid-BC linkage. According to PacBio sequencing only 0.5% of all sequences had different capsids sharing identical barcodes. No cases in which different barcodes shared a common capsid sequence were detected.

Generation and Analysis of a Parental AAV Pool

Figure 50D:
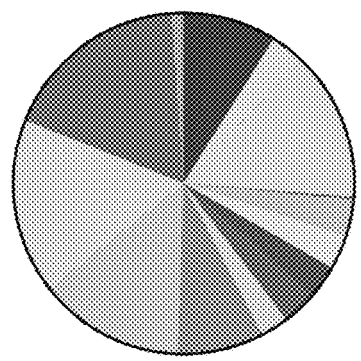

A control AAV pool was generated consisting of equal amounts of each of the 18 barcoded parental AAVs (based on vector genome copy numbers) and then purified this pool by double CsCl centrifugation. The composition of this pool was analysed by high-throughput sequencing of the barcodes (FIG. 50C). Some of the parental AAVs were slightly underrepresented in the pools although equal amounts of each virus were pooled prior to purification. It is possible that those parental AAVs banded at densities outside the collected fractions in the CsCl gradient. Nevertheless, most of the parental sequences were represented fairly equally in the pools. The parental AAV pool was also analysed by PacBio high-throughput sequencing of the amplified capsid plus BC sequence (FIG. 50D). Similar, but not identical data for composition of the pool as compared to the BC NGS data were obtained using PacBio Sequencing. These discrepancies may be due to subtle amplification differences of certain BC sequences or capsid plus BC sequences. Despite its shortcomings the 18 parent pool was found to be useful in a pilot library screen as the first validation for use of barcode sequencing in a capsid selection screen.

Passaging of the 18 Parent Pool on Human Islets

The transduction efficiencies of AAV-2 were first compared with AAV-DJ and AAV-LK03 (FIG. 62A) because of previous unpublished studies showing the latter two vectors as being the most robust in human islets (Song et al., ASGCT abstract). Confirming this result (FIG. 62A), provided the basis of a validation study prior to doing the screening with the shuffled capsid library. The 18 parental pool of AAV capsids were infected onto intact as well as dissociated human islets at MOIs of 20K and 2K, respectively and super-infected with human adenovirus 5 to replicate AAVs. Three consecutive rounds of selection were performed and AAV replication (FIG. 51) as well as composition of the viral pool (FIG. 52) was assessed at each round. For rounds 1 and 2 of selection lower copy numbers of viral genomes were recovered after propagation on intact islets as compared to the input whereas replication picked up at round 3. When a lower MOI of 2K was used to infect dissociated islet cells the amount of virus obtained after islet culture was higher than the input at each round of selection. NGS of the BC sequences was used to assess the composition of AAVs at each round. Between 400,000 and 1,000,000 reads were obtained for each sample. Certain parental AAVs had a clear advantage over others as the diversity of the pool was already diminished after one round of selection, particularly when intact islets were used (FIG. 52). AAV2, AAV3B, as well as shuffled variants DJ and LK03 were enriched already after the first passage. After the third passage on intact islets DJ and LK03 were equally represented while DJ clearly dominated the viral pool after the second passage on dissociated islets further validating our selection screen approach.

Passaging of the Capsid Shuffled Libraries on Human Islets

Figure 61A:
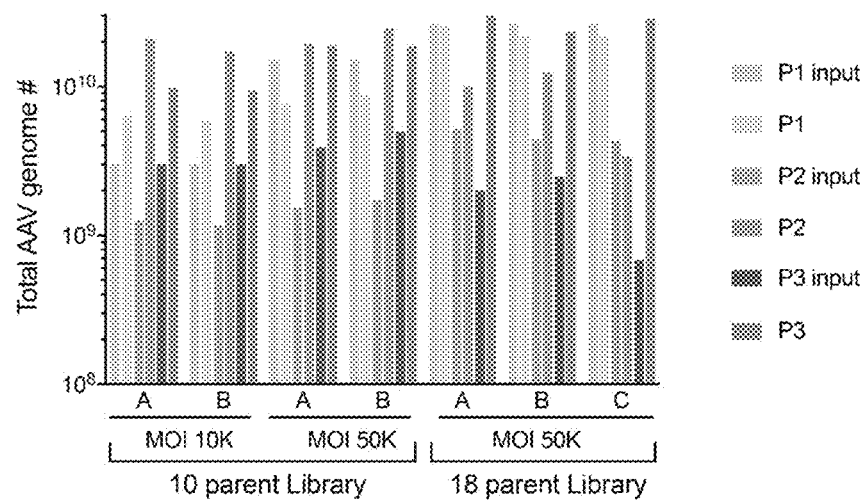
Figure 61B:
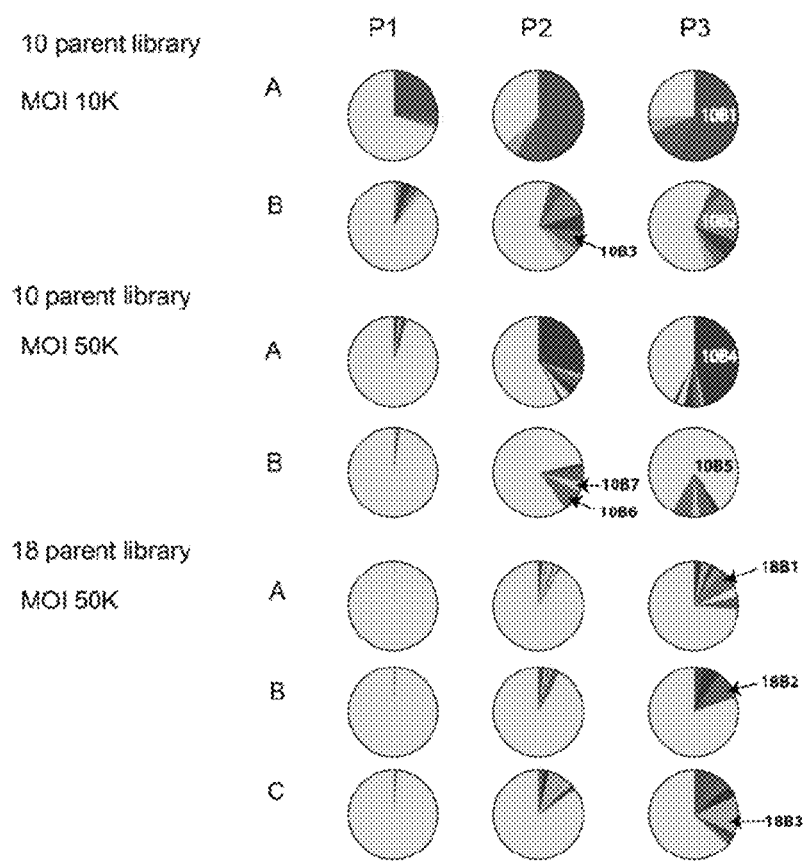

Both libraries were used to infect intact as well as dissociated islets at MOIs of 20K and 2K respectively and Ad5 was used to replicate AAV. After each round virus replication was assessed by qPCR (FIG. 51) and enrichment of variants was tracked by NGS of the BC sequences (FIG. 52). The NGS sample size was between 400,000 and 800,000 sequence reads. In contrast to the 18 parent pool, replication of the libraries at each round of selection was observed which might indicate that certain capsid sequences confer improved tropism, transduction, and/or replication. Distinct capsid variants were selected for as early as round 1 in case of the 18 parent library. A second set of library screens on intact islets using two different MOIs (10K and 50K) were performed in duplicates for the 10 parent library. Furthermore, another 18 parent library screen was performed in triplicates using an MOI of 50K. Replication data for this library screen are shown in FIG. 61A, the BC NGS data are shown in FIG. 61B. Similar levels of replication and enrichment were observed during this second set of library screens. However, this time one variant was found to be enriched in two independent screens (MOI 10K B and MOI 50K B) of the 10 parent library (variant 10B5, highlighted in yellow), indicating that this particular variant may have a significant selection advantage in islets. A different variant was found to be enriched in two of the triplicate screens of the 18 parent library (18B2, highlighted in magenta).

Evaluation of Selected AAV Capsid Variants for Improved Transduction of Islets

Figure 53A:
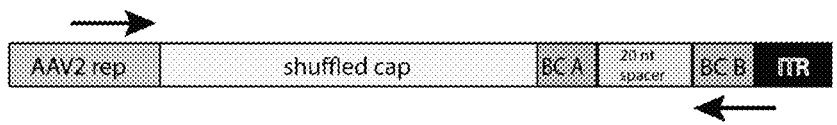
Figure 53B:
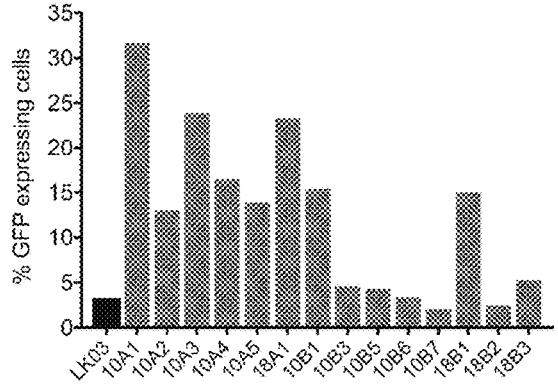
Figure 53C:
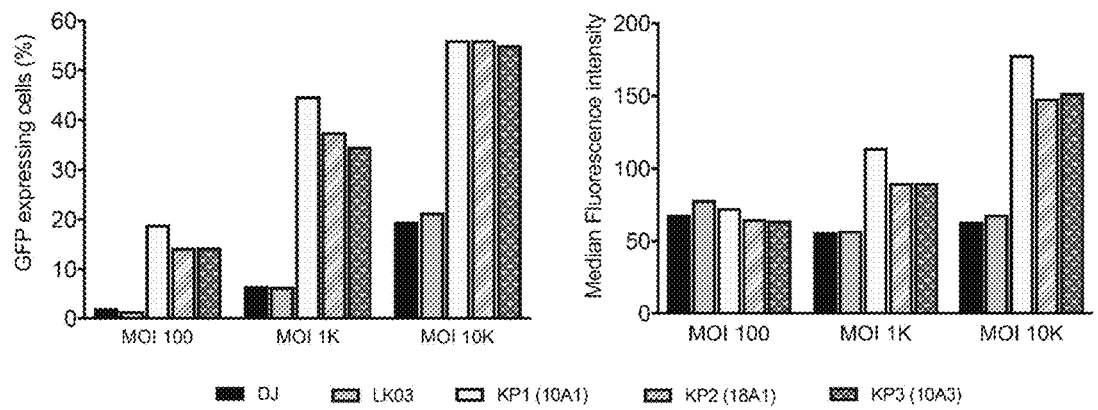
Figure 53D:
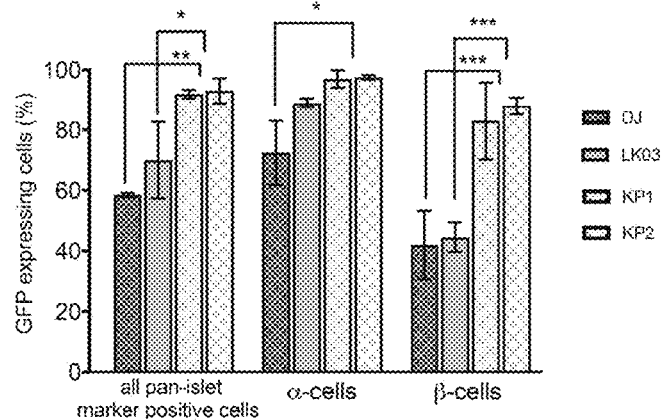

A total of 17 enriched capsid sequences were recovered from the different screens after three rounds of selection (see FIG. 52 and FIG. 61B for enrichment data of those variants) using a BC sequence specific reverse primer (FIG. 53A), TOPO cloned, and sequenced. Several clones for each BC were sequenced to ensure that the left BC sequence matched the sequence obtained by BC NGS. For several of the capsids it was observed that the capsid sequences differed for some of the clones, particularly at the 5' end. This was likely due to template switching after incomplete extension[3-5] and may be alleviated by optimizing PCR conditions and enzymes. It is not believed that it was due to insufficient capsid BC linkage as exhaustive analysis of the input libraries was performed and only found a low level of library clones that contained different capsids linked to identical barcodes. Also, an experiment with two closely related parental sequences revealed that template switching did indeed occur during amplification (data not shown). It was decided to vectorize the capsids that matched the consensus sequence. It was found that all enriched capsids shared large contributions from AAV3B in the 3' half while the 5' half was much more diverse (data not shown). While AAV3B sequence in the 3' half was certainly overrepresented in the input library there was still a fairly good contribution of other parental sequences as shown by Sanger as well as PacBio sequencing. It was established in earlier experiments that DJ and LK03 capsids transduced islets with higher efficiency than AAV2 or AAV3B capsids (FIG. 62A), thus the novel capsids were compared to DJ and LK03 only. All 17 capsid variants as well as one of the previously established best islet capsids (LK03) were used to package a self-complementary AAV vector with GFP as transgene driven by the CAG promoter. Three of the capsids failed to generate high-titer rAAV and were excluded from further evaluation. In an initial pre-screen crude cell lysate derived rAAV was used to transduce dissociated islet cells at a low MOI. Transduction efficiency was determined by flow cytometry of GFP expressing cells two days post transduction. While multiple capsid variants exhibited higher transduction efficiency than AAV-LK03 others were only marginally improved or not improved at all (FIG. 53B). The three most improved capsids (10A1, 18A1, and 10A3) were all derived from the first set of library screening and are referred to as KP1, KP2, and KP3 from now on. Those capsids were used to produce high-titer double CsCl gradient purified rAAV preps. Dissociated islet cells were transduced with those variants as well as with AAV-DJ and AAV-LK03 using three different MOIs and analysed for transduction by FACS. The variants were confirmed to transduce islet cells with considerably higher efficiency than the best parents (FIG. 53C, FIG. 62A). An at least 10-fold higher titer was necessary to transduce the same fraction of islet cells with AAV-DJ or AAV-LK03 as compared to the variant capsid AAVs. The next step was to determine if the novel capsids target α- or β-cells specifically. Subpopulation specific staining of islets that had been transduced with high MOIs of scCAG-GFP vectors packaged with KP1 and KP2 capsids revealed improved β-cell transduction when compared to AAV-DJ and AAV-LK03 while α-cell transduction was marginally improved (FIG. 53D). Moreover, as intact islets were used in this experiment, it was demonstrated that the novel AAVs were capable of penetrating the islets and transduced almost all of the α- and β-cells when a sufficiently high MOI was used.

β-cells were generated from human embryonic stem cells (hESC)s following a recently developed enrichment protocol[75] and tested one of the novel capsids for transduction efficiency as compared to AAV-DJ and AAV-LK03 using three different MOIs. Tomato Red expressing vectors were used in this experiment and cells were stained for the β-cell marker C-peptide (FIG. 66, FIG. 68). Similar to what had been observed in patient derived islet cells a 5- to 10-fold higher titer of AAV-DJ or AAV-LK03 was necessary to achieve similar rates of transduction as with AAV-KP1 in those cells. It should be noted that transduction efficiency is determined both from the percentage of Tomato Red expressing cells and fluorescence intensity of transduced cells AAV-KP1 in those cells.

Figure 5A:
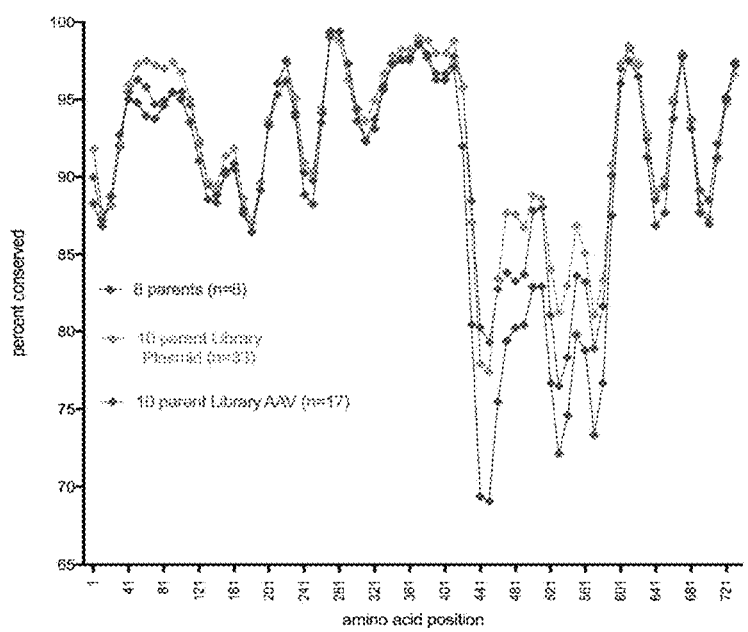
FIG. 5. Parental contributions in the 10 parent library listed by amino acid position. Capsid sequences were amplified from the plasmid library (upper panel) as well as from the AAV library (lower panel) and analyzed by PacBio high-throughput sequencing. (A) Conservation analysis by amino acid position of random 10 parent library clones at the plasmid level and the AAV level as compared to the 10 parents. (B) PacBio high-throughput sequencing of the 10 parent library capsid at the plasmid level (top) as well as the AAV level (bottom) showing parental contributions throughout the capsid sequence.
Figure 5B:
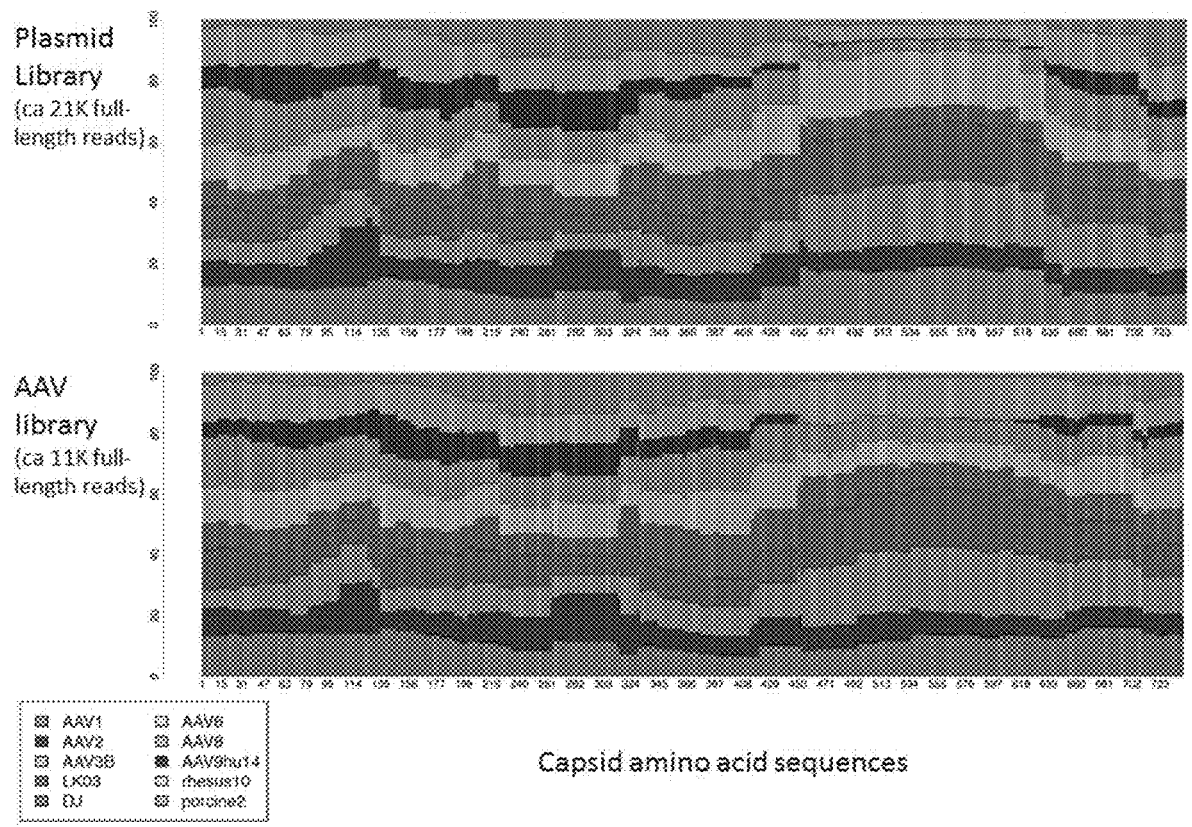
Figure 6:
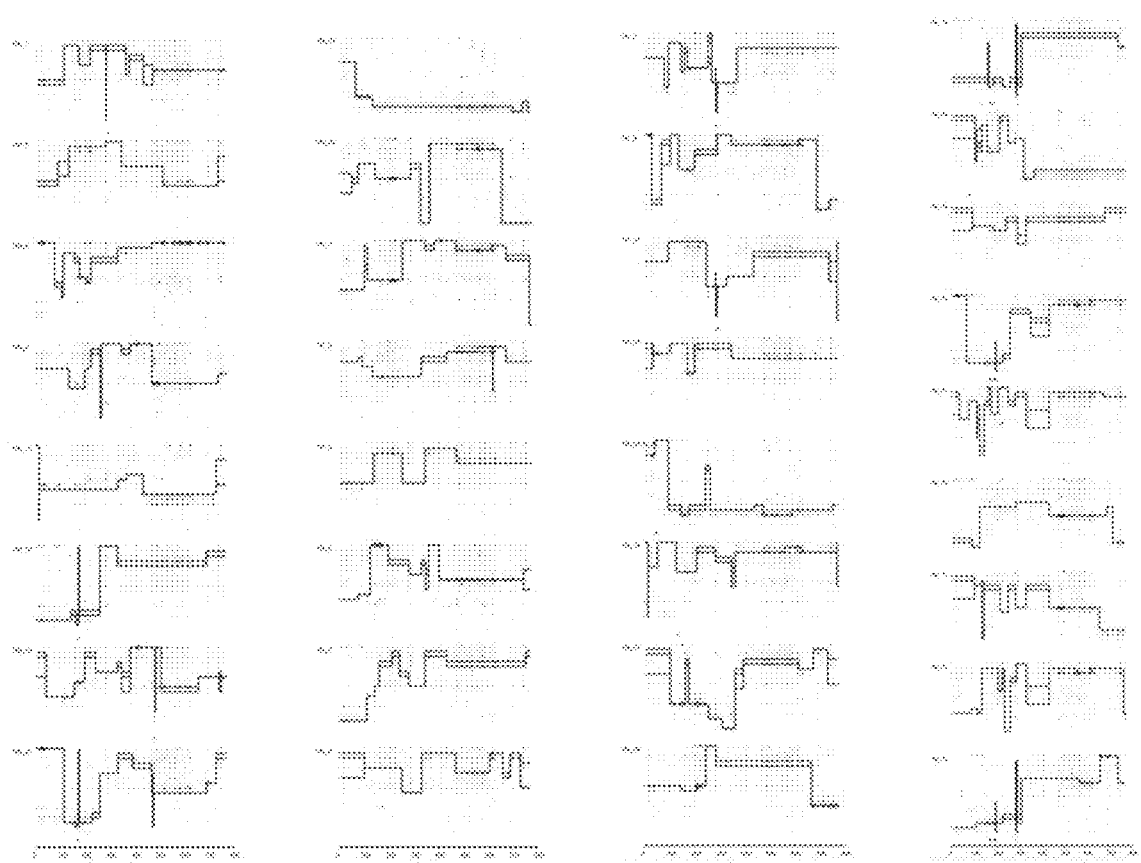
FIG. 6. 18 parent library (plasmid level).
Figure 7:
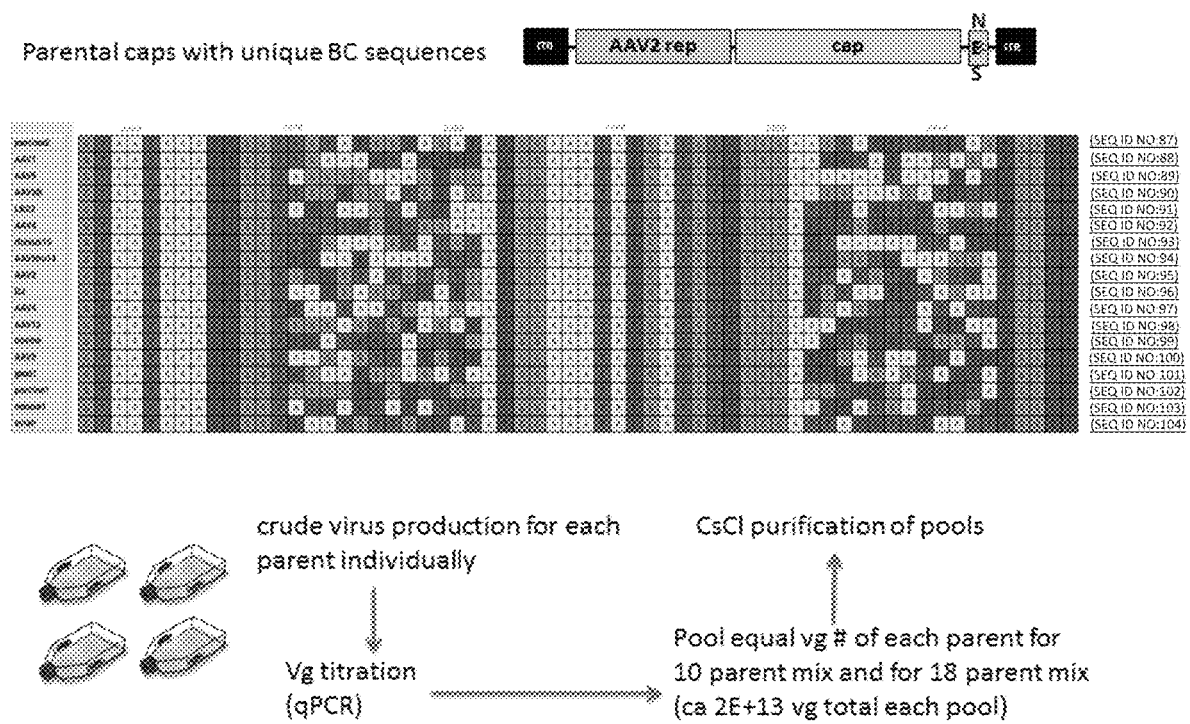
FIG. 7. Production of the 18 parent mix.
Figure 54A:
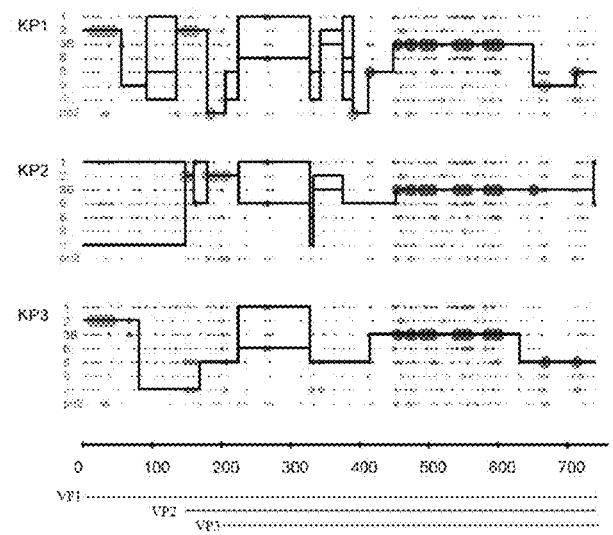
Figure 54B:
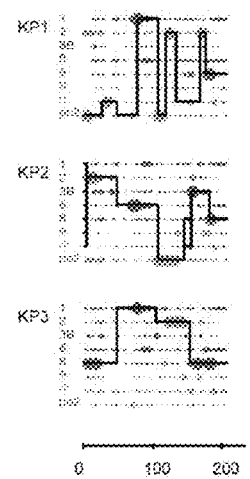
Figure 54C:
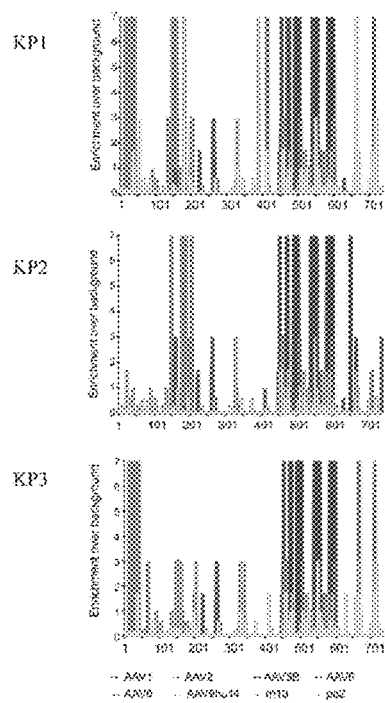
Figure 54D:
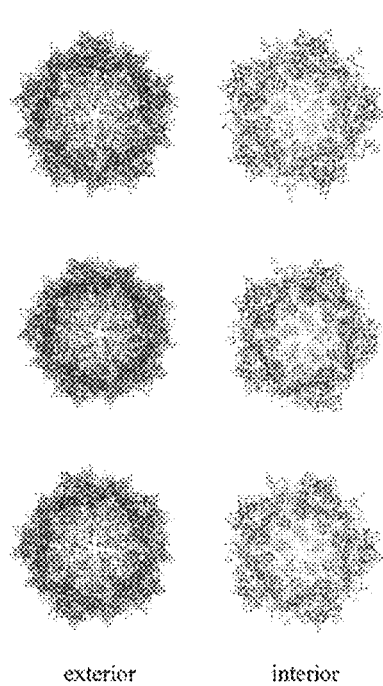
Figure 54E:
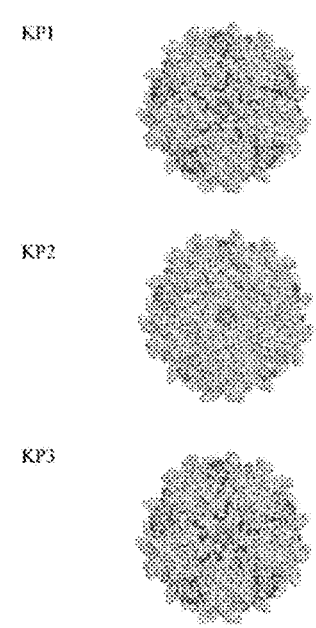
Figure 65A:
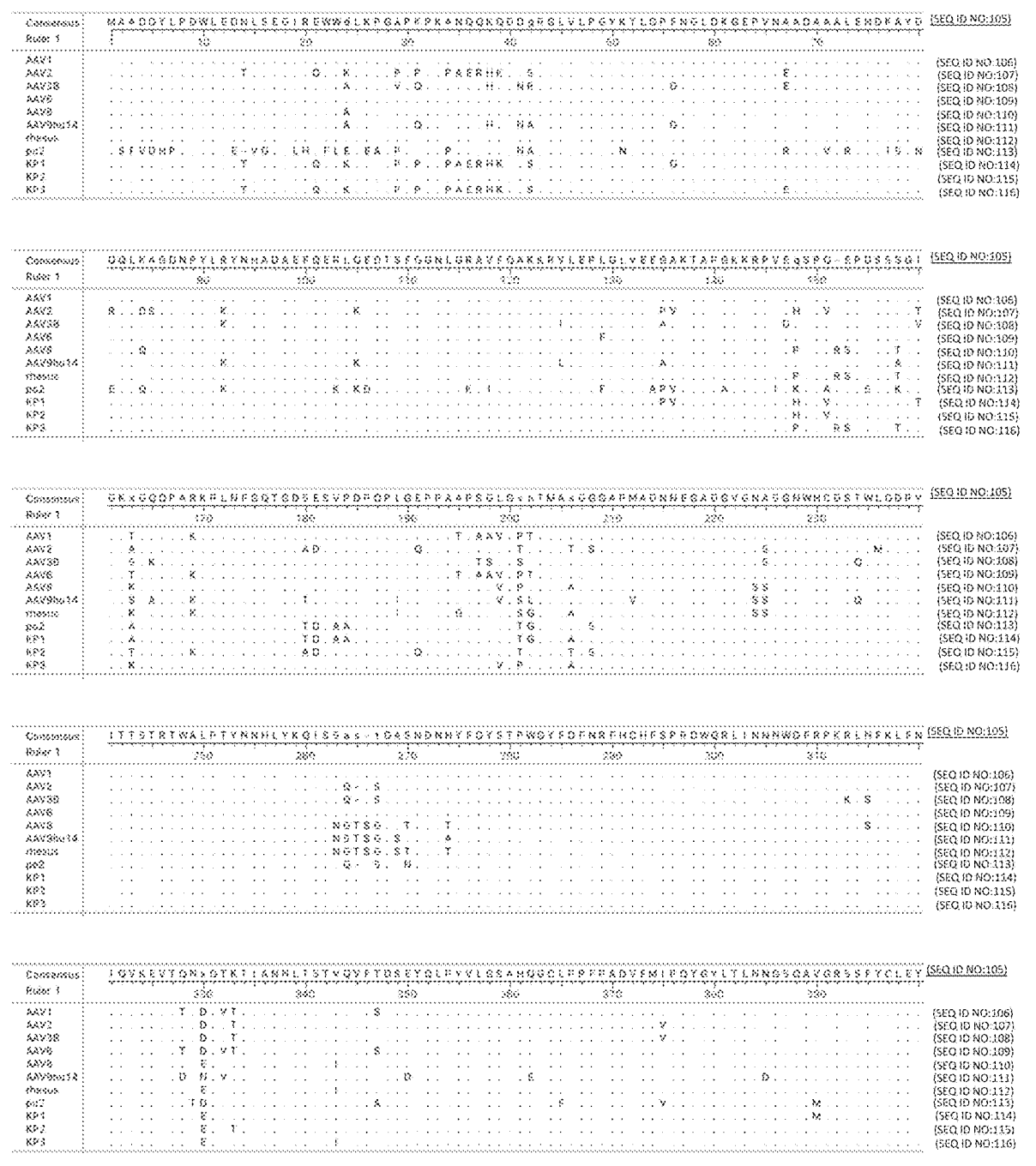

The next step was to try to elucidate common sequence features of the improved capsids. FIG. 54A depicts crossover analyses of the three most improved capsid amino acid capsid sequences with the highest islet cell transduction efficiencies. While the N-terminal part of capsid KP1 contains stretches from many different parental sequences capsids KP2 and KP3 are less diverse in this sequence stretch. However, as seen for all capsids enriched during the islet screen most of the C-terminal half of those capsids was derived from AAV3B, suggesting that this stretch may contain sequence determinants that are crucial for islet cell tropism. AAV3B is the parental capsid that is most closely related to the three novel capsids with 92% sequence identity to KP1 and KP3 and 95% identity to KP2. When performing crossover analysis with the nucleotide sequences (FIG. 63A) the parental contributions were very similar to those found for the amino acid sequences for most part, however some parental contribution patterns differed. As an example in the case of KP2 capsid the region around nucleotide position 900 was derived from AAV-porcine2 capsid rather than AAV1 or AAV6 capsid as the amino acid crossover analysis had suggested. The Xover program will always attempt to minimize the number of crossover events. Since all the parental sequences between amino acid position 275 and 313 share a common amino acid sequence (FIG. 65A), but have different nucleotide sequences, this stretch is shown as being derived from AAV1 or AAV6 when using amino acid sequences, but is shown as being derived from AAV6 and AAV-porcine2 when performing the analysis using the nucleotide sequences. The number of crossovers was also lower for the amino acid sequences as compared to the nucleotide sequences. As an example KP1 capsid has 19 crossovers at the nucleotide level while this was reduced to 15 crossover events on the amino acid level. Since functionality of the capsid is determined by the amino acid sequences focus was put on the amino acid sequence crossover analysis. The fact that all three improved capsids share three residues that are unique to AAV1 and AAV6 in the sequence stretch between aa 225 and 267 may indicate that these residues are important for human islet transduction (FIG. 54A, FIG. 65A). Since AAP uses a different reading frame within the capsid gene crossover analysis for this protein was also performed. It was found that all three novel variants contained chimeric AAP sequences (FIG. 54B, FIG. 65B). As seen for the nucleotide sequence crossover analysis several KP2 AAP residues were derived from AAV-porcine2. Besides the crossover analysis, enrichment analysis was performed that confirmed strong selection pressure for certain amino acid residues in all three capsids (FIG. 54C). In the N-terminus the two most improved variants KP1 and KP3 showed a strong selection of AAV2 residues while they share AAV8 derived residues in the C-terminus. KP2 capsid shows a strong enrichment of several AAV2 residues between positions 150 and 210. All three capsids have an Arginine at the position that has been described to be the key HSPG binding site for AAV3B (position 597 in FIG. S65A)[76]. Predictive three-dimensional structural VP3 capsid mapping of the novel variants was performed to reveal those residues that are displayed on the outside of the capsids (FIG. 5D). All three improved capsids were found to contain Glutamic acid in VP3 hypervariable region (HVR) I (labeling according to[77]) at the 5-fold symmetry pore (position 330 in FIG. S65A) which is derived either from AAV8 or AAV-rhesus10. AAV3B as well as all other parentals except for AAV9hu14 have an Aspartic acid residue at this position. Two other residues shared among all three capsids are the Alanine and the Threonine in HVR I (positions 264 and 266 in FIG. S65A). KP1 and KP3 capsids also contain the surface exposed residue Arginine in HVR II (position 333 in FIG. S65A) which is also shared by parental capsids AAV8, AAV9hu14 and AAV-rhesus10. In addition KP1 and KP3 capsids display residues Aspartic acid, Asparagine, Leucine, and Asparagine within a variable stretch between HVR VIII and IX which was termed HVR 11 by Gao and colleagues[78] (positions 660, 666, 670, and 671 in FIG. S65A). In HVR IX KP1 and KP3 capsids share AAV8 derived surface exposed residues Tyrosine, Threonine, Serine, Alanine, Asparagine, and Glutamic acid (positions 709, 712, 713, 717, 719, and 721 in FIG. S65A). The KP1 capsid displays a surface exposed Methionine which is derived from AAV-porcine2 while KP3 has a AAV3B derived Valin in this position (position 390 in FIG. S65A). Moreover, KP1 contains an Alanine derived from AAV9hu14 at position 664 while KP3 has the same Threonine residue as AAV3B at this position. Surface exposed residues 667 (Lysine) and 668 (Aspartic acid) were derived from AAV9hu14 for KP1 while they originated from AAV8 for KP3 (Glutamine and Serine). In addition to residues displayed on the capsid surface all three novel capsids shared several VP3 residues that are buried inside the capsid (Alanine, Threonine, Arginine, and Asparagine at positions 225, 234, 313, and 315 respectively). Those residues possibly also contribute to the observed strong transduction efficiency as they may be involved in uncoating and other post entry steps.

Figure 63A:
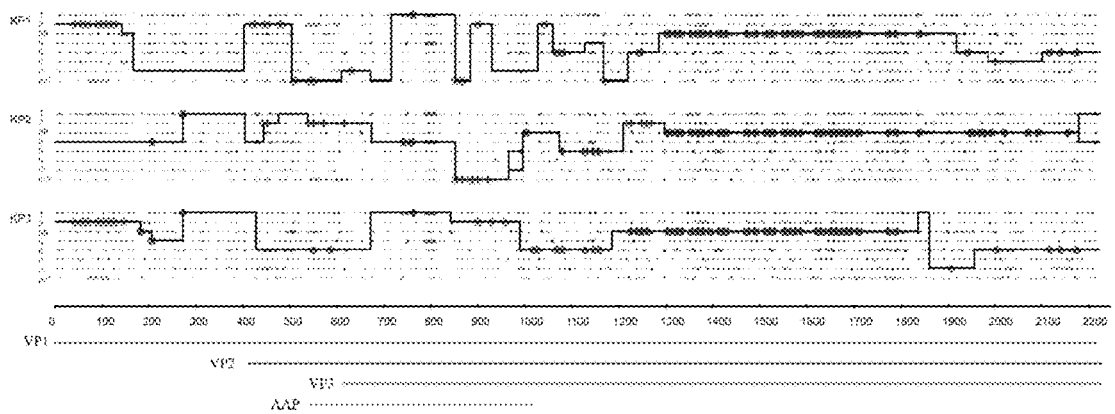
Figure 63B:
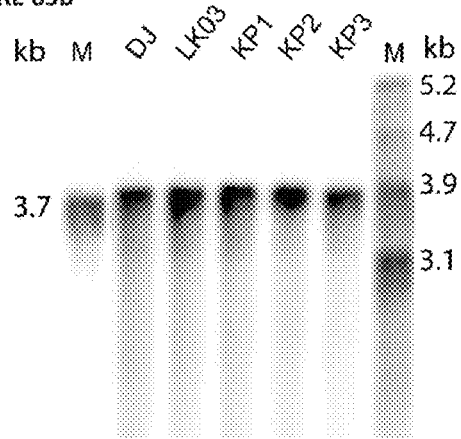
Figure 63C:
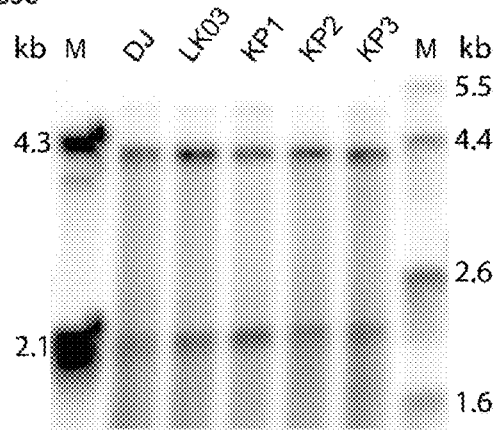
Figure 63D:
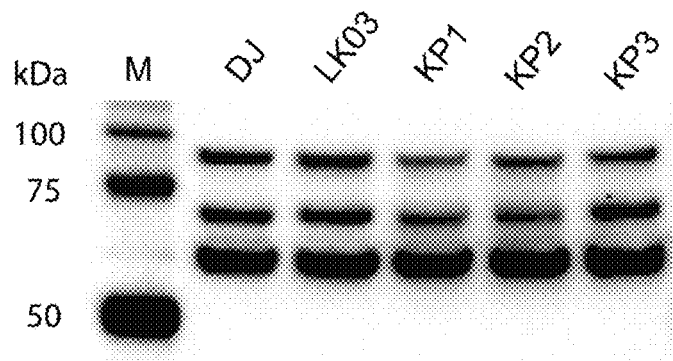

The next step was to evaluate whether the novel capsids would package self-complementary and single stranded vector genomes with similar efficiency as AAV-DJ and AAV-LK03 capsids. Thus Alkaline Southern Blot analysis was performed using isolated vector genomes from CsCl purified rAAV preparations (FIG. 63B) and it was found that a single stranded CAG-Firefly Luciferase genome was packaged at the expected size of 3.7 kb (FIG. 63B). When rAAV preparations packaging self-complementary CAG-GFP genomes were analysed, a band at 4.3 kb was found which represents the self-complementary full-length genome with two expression cassettes joined at the trs deleted ITR. However, in addition to the expected 4.3 kb product, a band of about half the expected size was observed which possibly represents the single stranded vector (FIG. 63C). The reason for this may be the fact that a packaging vector expressing rep with the wild-type ATG start codon was used for virus production as this has been linked to increased levels of ss genome packaging when producing sc vectors. Lower levels of Rep protein expression after mutation of the ATG start codon to the less efficient ACG start codon have been linked to a higher rate of ds genome packaging (Wu et al., 2007).[79] Also incubation times longer than 52 hrs post transfection have been described to increase reversion of double stranded (ds) to single stranded (ss) genomes (Gray et al., 2011).[80] However, for the current study it is of importance to note that the full-length as well as the shorter genome was packaged with equal efficiency for the novel variants as well as AAV-DJ and AAV-LK03. Thus, the improved transduction efficiency of the novel capsids cannot be attributed to increased packaging of full-length functional genomes. Furthermore, the capsid proteins variants consisted of all three capsid proteins VP3, VP1 and VP2 in the expected stoichiometry of 10:1:1 (FIG. 63D).

Evaluation of Transduction Efficiency on a Panel of Diverse Cells Lines

Figure 55A:
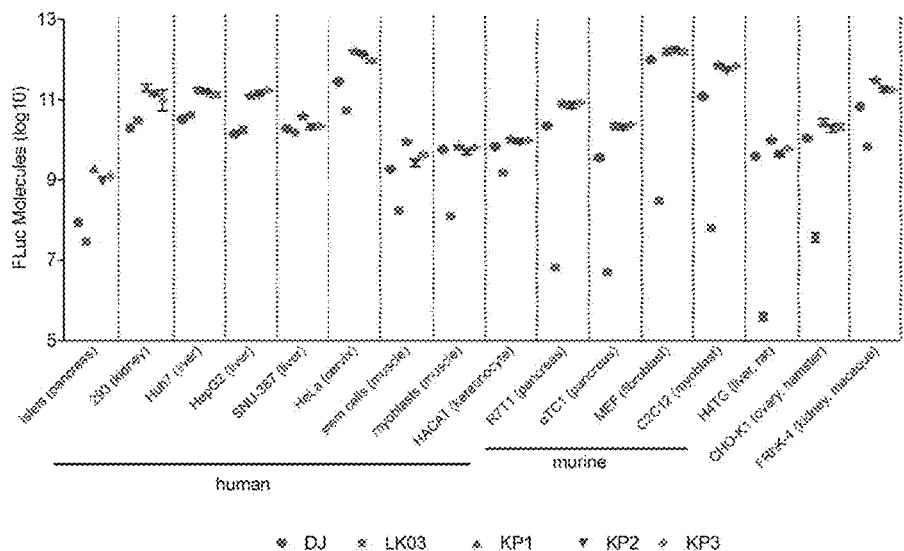
Figure 64A:
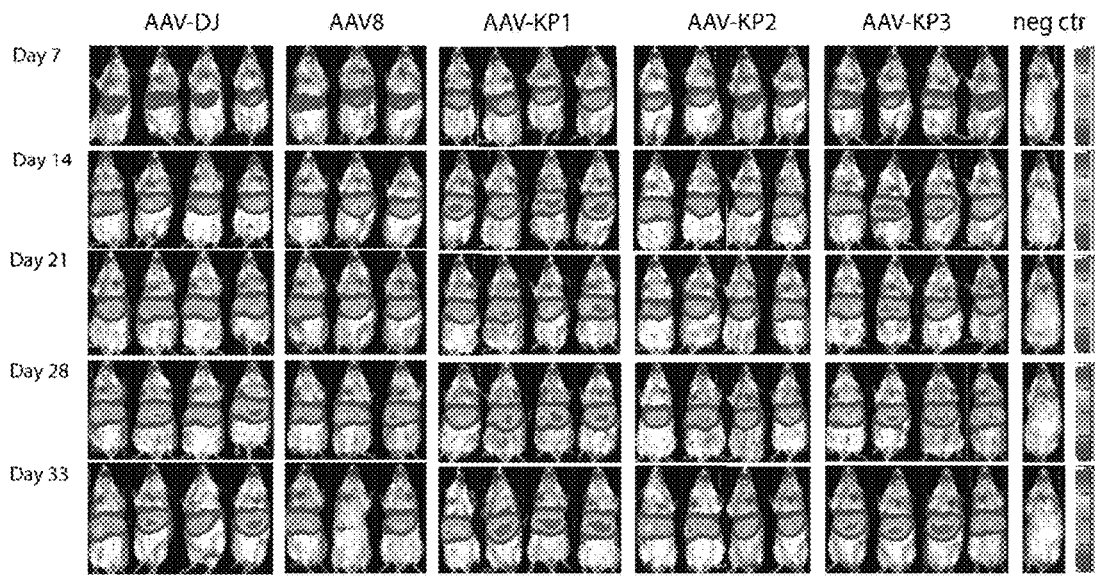

Several primary cells as well as cell lines derived from human as well as animal sources were transduced at an MOI of 1K with a single-stranded firefly luciferase rAAV vector packaged with two parental (DJ, LK03) as well as the three evolved capsids (KP1, KP2, KP3) and analysed for transduction efficiency using a luciferase assay. AAV-LK03 did not transduce murine cells efficiently while AAV-DJ transduced all cell lines with high efficiency. The novel variants showed improved transduction efficiency as compared to AAV-DJ on human islet cells, 293, Hela, HuH7, R7T1, alpha TC1, HepG2, CHO K1, human muscle stem cells, mouse myoblasts, SNU 737, as well as FRhK-4 cells (FIG. 55A, FIG. 64A). AAV-KP1 showed the highest degree of enhancement in general. Transduction of the novel capsid variants as compared to DJ was not or only marginally improved on human keratinocytes, differentiated human myoblasts as well as primary mouse embryonic fibroblasts.

Neutralization Profile of the Novel Capsid Variants

Figure 55B:
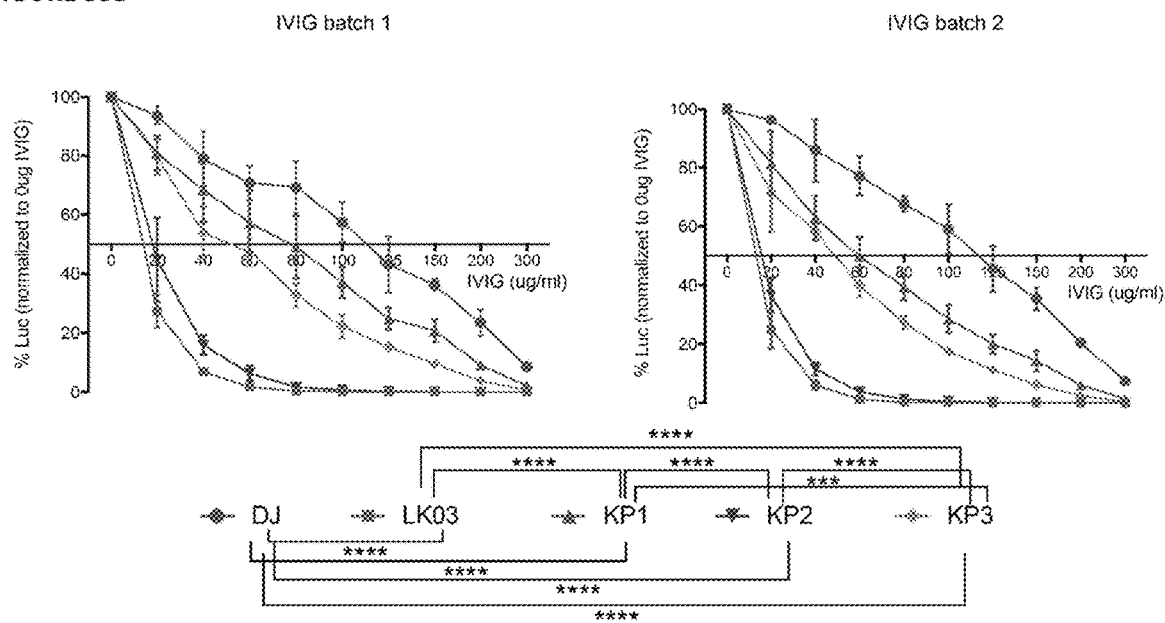

The novel capsid variants as well as AAV-DJ and AAV-LK03 were analysed for sensitivity towards neutralization by two different batches of pooled human immunoglobulin (FIG. 55B). The experiment was performed in seven biological replicates for each sample, split between two independent experiments. While AAV-DJ showed the highest resistance towards neutralization with ~120 ug/ml IVIG needed for 50% inhibition AAV-LK03 was very sensitive with 50% neutralization achieved with only around 15 ug/ml. AAV-KP2 had a neutralization profile similar to that of AAV-LK03 while AAV-KP1 and AAV-KP3 needed more IVIG to be neutralized (45-ug/ml for KP3 and 55-ug/ml for KP1). In summary, when pooled human IVIGs were used for neutralization two of the novel variant capsids performed better than AAV-LK03, but less favourable than AAV-DJ.

In Vivo Biodistribution of the AAV-KP Variants in Mice

Figure 64B:
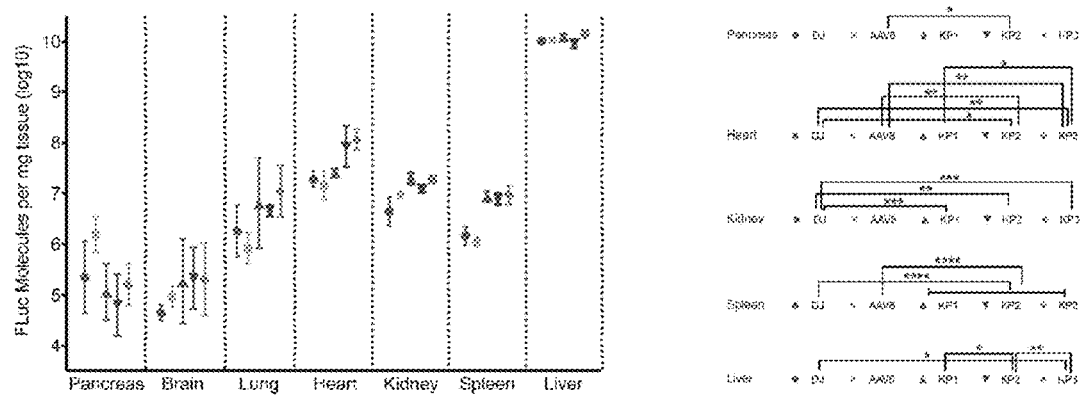
Figure 64C:
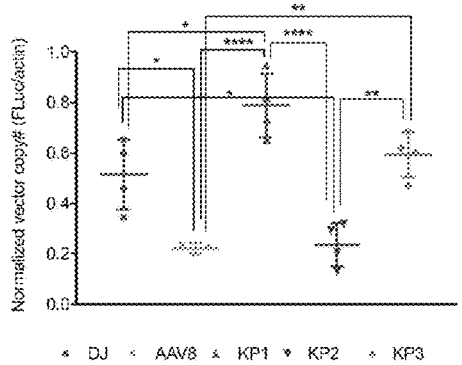

Mice were injected intravenously with 2E10 vg per mouse of firefly luciferase vector rAAV packaged with AAV8, AAV-DJ as well as AAV-KP1, KP2, and KP3 capsids and transgene expression was monitored over several weeks by live imaging (FIG. 56, FIG. 64A). The majority of AAV was found to target the liver. AAV-KP1 appeared to transduce mouse liver more rapidly than AAV-DJ, but expression levels were only slightly higher once steady state expression was achieved at later time points. Thirty-five days post injection several organs were harvested from each mouse and analyzed for luciferase expression. With the exception of liver very low levels of expression with a high variation within each group of mice were detected (FIG. 64B). AAV-KP2 as well as AAV-KP3 injected mice had higher luciferase expression in heart tissue than AAV-DJ or AAV8 injected mice and all three variants had transduced spleen with higher efficiency than DJ or AAV8. Kidney tissue from KP variant AAV injected mice also had higher luciferase expression than that from AAV-DJ injected mice, but levels were not significantly higher when compared to AAV-8 injected mice. Vector genomes were quantified in the organs using qPCR. However, vector genome copies clearly above background were detected only for the liver samples (FIG. 64C). Mice injected with AAV-KP1 contained higher vector copy numbers than the mice that had received AAV-DJ or AAV-8 packaged vectors. AAV-KP3 injected mice contained significantly more vector genomes in their livers than AAV8 injected mice. AAV-KP2 injected mice, however, contained similar levels of rAAV genomes as AAV8 injected mice.

Assessing Functional Hepatocyte Transduction in Xenograft Liver Models In Vivo

Figure 57A:
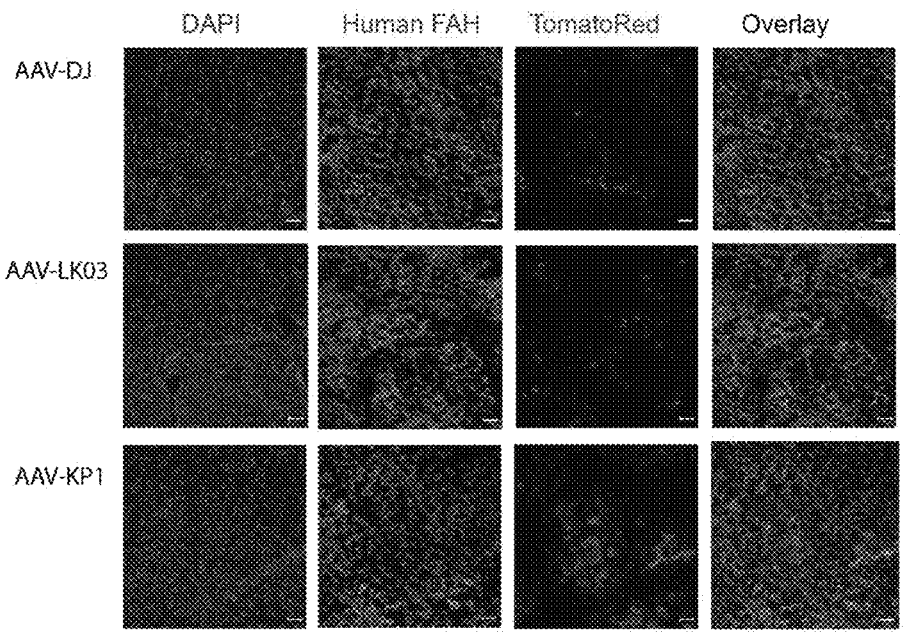
Figure 57B:
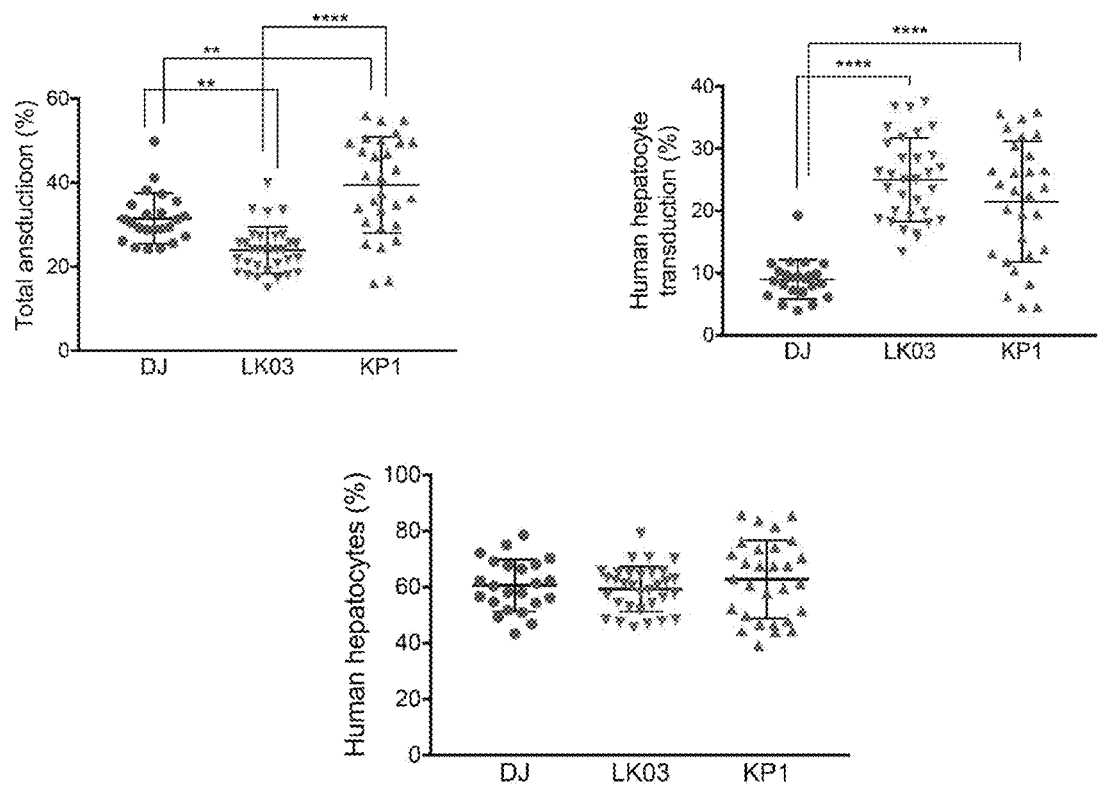

Humanized FRG xenograft mice were transduced to assess the functional human hepatic transduction capabilities of one of our shuffled capsids in an appropriate in vivo setting. Mice were highly re-populated with human hepatocytes as shown by expression of high levels of human albumin (between 5.6 and 8 mg/ml). Humanized mice were administered Tomato Red expressing rAAV packaged with DJ, LK03, or KP1 capsids at a dose of 1E11vg/mouse via the intravenous injection, and assessed for expression of Tomato Red protein in human and mouse hepatocytes 14-days post-AAV administration (FIG. 57). It was observed that LK03 had high transduction efficiency in human hepatocytes, but not mouse hepatocytes while transduction with DJ was not specific towards human cells. KP1 was also found to transduce both human and mouse hepatocytes, however levels were higher than those found with DJ. In three of the four AAV-KP1 injected mice transduction efficiency for human hepatocytes was similar to that found in AAV-LK03 injected mice. However, total transduction was higher in AAV-KP1 injected mice since unlike AAV-LK03, AAV-KP1 transduced both mouse and human cells.

Discussion

The new capsids identified in the current study were at least 10-fold more efficient at transducing human islet cells, particularly β-cells. When one of the variants was tested for transduction efficiency of hESC derived β-cells similar levels of improvements were achieved. In addition, it was confirmed that prior observations that capsid variants AAV-DJ and AAV-LK03 were capable of transducing primary human islets with equal or better efficiency than AAV2 or AAV3B. However, high MOIs are required to efficiently target cells within the center of the islets, and β-cell transduction was less efficient than that of α-cells.

Recently several studies have used retrograde pancreatic intraductal delivery in mice to safely and effectively administer rAAV vectors into the pancreas[49, 81, 82]. Overexpression or inhibition of several transcription factors was found to effectively convert pancreatic islet progenitors and committed islet α-cells into β-cells[50, 52-58]. Endoscopic retrograde cholangio-pancreatography (ERCP) is routinely used in patients to examine the pancreas and bile ducts and could be used to deliver the novel vectors for diabetes treatment.

The method for generation of barcoded capsid shuffled AAV libraries is described in great detail so that other researchers can easily apply this protocol in their own laboratory, either with genes from AAV or any other virus to generate libraries that can be screened for the desired properties. In addition to the protocol for library generation, also described is the generation of a pool containing parental AAVs that proved to be useful as a parental control during the passaging regimen. This pool can be used in any library selection to optimize the selection parameters to isolate AAV capsids with a desired property. The cost and time can be minimized by predetermining the appropriate MOI and number of selection rounds for a particular screen. In contrast to studies in Applicant's lab that routinely employed five rounds of selection, in the current study it was found that three rounds of selection were sufficient to enrich and amplify variants with improved transduction to a level where they could be isolated reliably.

In addition, combining short DNA barcodes and single molecule DNA sequencing approaches will enable one to optimize other important parameters, such as the best MOI to use during the selection process, and the number of screening rounds necessary for efficient enrichment. When generating the AAV libraries from the plasmid libraries by transfection care was given not to overload the cells with library plasmid DNA by reducing the amount of AAV plasmid DNA almost 20-fold as compared to previous protocols for virus production. It had been reported that a transfected copy number of 5000 AAV genomes per cell is sufficiently low to minimize cross-packaging while still achieving high-titer libraries.[83] While the possibility of cross-packaging, characterized by sequence differences between the packaging capsid and the corresponding viral genome, can not be excluded several of the enriched capsids from our screen were found to exhibit the desired phenotype, suggesting that cross-packaging or mosaicism was not a major problem in our libraries. Moreover, previously generated AAV libraries using high concentrations of AAV plasmid during transfection were successful in generating variants with greatly improved phenotypes[8, 37-39], suggesting that for reasons unknown so far there seems to be a strong capsid genotype linkage in case of AAV packaging[11].

When libraries on human islets were screened several capsid sequences were enriched, three of which have improved transduction efficiency not only for human islets, but also for a variety of other cell types. While it is not clear which amino acid residues in the novel capsids are responsible for the improved islet phenotype, several features were noticed in the improved capsid sequences that may confer enhanced transduction of islet cells as well as other cell types. The C-terminal parts of all three improved capsids are strongly enriched for AAV3B residues suggesting that these amino acids may play an important role for islet tropism. In the N-terminus the two most improved variants KP1 and KP3 showed a strong selection of AAV2 residues and all three capsids contain a Threonine originating from either AAV1 or AAV6 at position 265 (FIG. 65A). All three capsids have an Arginine at position 594 (position 597 in FIG. 65A) that has been described to be the key HSPG binding site for AAV3B[6] (Lerch and Chapman).

It is interesting that KP1—despite its similarity to AAV3B and AAVLK03—transduced mouse hepatocytes as well as human hepatocytes in the humanized liver mouse model. This humanized model was used previously to select for several highly human liver AAV transducing vectors (Lisowski Paulk)[37, 39] one of which has been shown to provide robust hFVIII expression in an early human trial[84, 85]. However, all of the vectors selected in the previous screen showed poor transduction of mouse tissues or cells in vitro and in vivo. In contrast, the KP1 variant showed similar transduction of human hepatocytes in the chimeric mouse model but in contrast to AAVLK03 showed efficient transduction of mouse liver. This is intriguing because some have suggested the transduction of human hepatocytes in this mouse model was exaggerated because of the relatively low transduction of mouse cells. If the human hepatocyte results obtained in the humanized mouse model is influenced by the degree of mouse hepatocyte transduction perhaps the KP1 variant will provide even more robust transduction when tested in human trials. At a minimum because this vector transduces both mouse and human liver, a surrogate capsid for preclinical testing is not required. Ultimately, these capsids are good candidates for future study in human clinical liver based gene therapy trials.

A recent report by the Grimm group laid to rest the concern that functionality of AAV capsid libraries generated for directed evolution studies might be severely compromised by inactivation of the assembly activating protein (AAP) in a large proportion of the chimeric variant pool[86]. AAP had previously been described to play an important role in virus assembly[9, 87-89], but appears to be strikingly tolerant towards recombination. Random capsids from other shuffled libraries were previously tested for packaging efficiency and found that surprisingly the vast majority of the capsids produced normal or only slightly reduced titres of rAAV, indicating that the randomized AAP sequence was not detrimental in most cases. The AAP sequences of all the chimeras selected in the present studies are chimeric and the rAAV titres obtained with two of the capsids were lower than those obtained with LK03. Supplying wildtype AAP during virus production was not evaluated to see if it would enhance titres, but this is a possibility to boost rAAV production.

The use of barcoded libraries for molecular evolution studies was found to be highly beneficial as high-throughput analysis of the barcodes of enriched variants is much more cost-effective and thorough than cloning and sequencing of the entire capsids. The libraries generated for this study are currently evaluated in screens on a number of other target cells and may result in the discovery of other AAV capsid variants that are useful for other clinical gene therapy applications.

Methods:

Generation of an AAV Vector Containing a Library of Unique Barcode Sequences.

A wildtype AAV2 vector in which the capsid coding sequences had been replaced by a PacI and AscI containing linker fragment (kindly provided by D. Grimm and S. Grosse, University of Heidelberg, Germany) was used as the starting material for construction of the barcoded AAV library. Two unique restriction sites (AgeI and EagI) were introduced just downstream of the cap polyadenylation signal by mutating two nucleotides in the original sequence (A to T and T to C at positions 6 and 24 when counting the last nucleotide of the cap polyA signal as starting point). Barcodes consisting of two stretches of 12 random nucleotides separated by a 20 nt long spacer sequence were generated as described previously[73]. Briefly, an oligonucleotide with an AgeI restriction site sequence on the 5'-end followed by 12 random nucleotides and the 20nt long spacer sequence (SEQ ID NO: 63) (CTA AAC CGG TNN NNN NNN NNN NAC GGA AAT ACG ATG TCG GGA) was annealed to an oligonucleotide containing an Eag I site on the 5' end followed by 12 random nucleotides as well as the antisense spacer sequence (SEQ ID NO: 64) (TTC TCG GCC GNN NNN NNN NNN NTC CCG ACA TCG TAT TTC CGT) and extended using Klenow Polymerase devoid of exonuclease activity (NEB). Fragments were purified using a Qiaquick PCR purification kit (Qiagen) and subsequently digested with AgeI and EagI and purified using a Qiaquick PCR purification column. Vector was digested with the same restriction enzymes, dephosphorylated, phenol-chloroform purified and Ethanol precipitated. The optimum vector to insert ratio was evaluated by setting up several ligation reactions initially and testing for possible multiple barcode inserts by performing colony PCR with primers rightF (SEQ ID NO: 65) (CGC GCC ACT AGT AAT AAA C) and QSeqRev (SEQ ID NO: 66) (TAG AGC AAC TAG AGT TCG). For the scale-up reaction barcodes were ligated with the vector at a molar vector to insert ratio of 1 to 2.5 in a total volume of 30-ul, de-salted using Strataclean resin according to instruction (Agilent Technologies) and electroporated in 2-ul aliquots into DH10B-MegaX cells (Thermo Fisher). Electroporated cells were pooled and used to inoculate 500-ml LB-Amp medium. An aliquot was plated to assess library size and diversity. After 16-hrs in a 37° C. shaker bacteria were harvested and plasmid DNA was isolated using a Megaprep kit (Qiagen). ITR integrity was confirmed by digestion with XmaI as well as with AhdI. Several individual clones from the test plate were sequenced to assess barcode diversity.

Generation of Capsid Shuffled Barcoded AAV Libraries.

DNAse I mediated family shuffling was essentially performed as described previously[25, 90, 91]. Capsid sequences from 16 AAV serotypes (AAV1, AAV2, AAV3B, AAV4, AAV5, AAV6, AAV8, AAV9hu14, AAV12, AAV rhesus10, AAV porcine1, AAV porcine2, AAV bovine, AAV mouse1, AAV avian, AAV goat1) as well as from shuffled variants AAV DJ and AAV LK03 that had been selected in previous screens[8, 37] were used as parental sequences for the shuffling reactions. The capsid sequences had been obtained from various sources (D. Grimm, University of Heidelberg, Germany, Kay lab, Vector Core, Stanford). All sequences contained a PacI site immediately 5' and an AscI site 3' of cap and had been cloned into pBluescript. Prior to shuffling capsid sequences were amplified individually using primers located in the flanking pBluescript sequences (SEQ ID NO: 67) (outer F: AAT TAA CCC TCA CTA AAG G, outer R: (SEQ ID NO: 68) GTA ATA CGA CTC ACT ATA GGG C). Phusion Hot Start Flex polymerase (NEB) was used for amplification and 25 PCR cycles were employed (30-sec 98° C., 25 cycles of 10-sec 98° C., 15-sec 56° C., 1-min 15-sec 72° C., followed by 10-min 72° C.). PCR products were purified using the Qiaquick PCR purification kit (Qiagen), all 18 capsids (for the 18 parent library) or 10 capsids (for the 10 parent library, AAV1, AAV2, AAV3B, AAV6, AAV8, AAV9hu14, AAV12, AAV rhesus10, DJ, LK03) were pooled in equimolar ratio and fragmented at room temperature (RT) using DNase I (Sigma). At different incubation time points aliquots were analysed on an 1.5% agarose gel while the reaction was temporarily stopped by incubation in a dry ice/ethanol bath. Incubation time and DNAse concentration was adjusted until the majority of the fragments ranged from 100-bp to 500-bp. The entire reaction was then loaded on an 1.5% agarose gel and fragments in the desired size range were electroeluted from the gel, purified using two rounds of phenol-chloroform purification followed by one round of chloroform purification and ethanol precipitated. DNA fragments were then re-assembled in a primer-less PCR using Phusion Hot Start Flex polymerase and the following cycling conditions: 30-sec 98° C., 40 cycles of 10-sec 98° C., 30-sec 42° C., 45-sec 72° C., followed by 10-min 72° C.

Full-length capsid sequences were amplified from the assembly reactions using primers rescueF (SEQ ID NO: 69) (GTC TGA GTG ACT AGC ATT CG) and rescueR (SEQ ID NO: 70) (GTC TAC TGA AGC TCA CTG AG) and the following cycling conditions: 30-sec 98° C., 25 cycles of 10-sec 98° C., 15-sec 57° C., 1-min 15-sec 72° C., followed by 10-min 72° C. Amplicons were diluted 4-fold with fresh PCR mix and subjected to one additional cycle with a 10-min extension to fill up the ends. After concentrating PCR products using a PCR purification kit (Qiagen) they were digested with PacI and AscI and ligated into the BC library vector that had been treated with PacI, AscI, dephosphorylated and phenol-chloroform purified. Ligation reactions were de-salted using the Strataclean resin, electroporated into MegaX DH10B cells and expanded in liquid culture as described above for generation of the BC library vector. Aliquots of transformed cells were plated to assess library size and diversity of the library using Sanger sequencing. 40 clones of the 10 parent library and 20 clones of the 18 parent library were sequenced using primers capF (SEQ ID NO: 71) (TGG ATG ACT GCA TCT TTG AA), capF2 (SEQ ID NO: 72) (ATT GGC ATT GCG ATT CC), and QSeqRev (SEQ ID NO: 73) (TAG AGC AAC TAG AGT TCG).

AAV libraries were generated in HEK 293T cells using the calcium phosphate transfection method. Compared to the regular protocol the amount of transfected library plasmid DNA was reduced almost 20-fold to approximately 5000 copies per cell to minimize the likelihood of cross-packaging events taking place during AAV production. Briefly, 25 T225 flasks were seeded with 8E06 cells per flask in 40 ml media two days prior to transfection. On the day of transfection cells were between 80% and 90% confluent. 20-ml of media per flask was replaced with fresh media 1.5-hrs prior to transfection and a mixture of 40-ug pAd5 helper plasmid and 2-ug library plasmid in 4-ml 300 mM $CaCl_2$) per T225 was prepared. Equal amounts of $CaCl_2$)/DNA mix and 2×HBS (280 mM NaCl, 50 mM HEPES pH 7.28, 1.5 mM $Na_2HPO_4$, pH 7.12) were mixed and 8-ml of the mixture was added to each flask. After 3 days cells were detached with 0.5-ml 500 mM EDTA each flask and the cell pellet was resuspended in Benzonase digestion buffer (2 mM $MgCl_2$, 50 mM Tris-HCl, pH 8.5). AAVs were released from the cells by submitting them to three freeze-thaw cycles, non-encapsidated DNA was removed by digestion with Benzonase (200-U/ml, 1-hr 37° C.), cell debris was pelleted by centrifugation, followed by another $CaCl_2$) precipitation step (25 mM final concentration, l-hr on ice) of the supernatant and an AAV precipitation step using a final concentration of 8% PEG-8000 and 625 mM NaCl. Virus was resuspended in HEPES-EDTA buffer (50 mM HEPES pH 7.28, 150 mM NaCl, 25 mM EDTA) and mixed with CsCl to a final refractory index (RI) of 1.371 followed by centrifugation for 23-hrs at 45000 Rpm in a ultracentrifuge. Fractions were collected after piercing the bottom of the centrifuge tube with a 18 gauge needle and fractions ranging in RI from 1.3766 to 1.3711 were pooled and adjusted to an RI of 1.3710 with HEPES-EDTA resuspension buffer. A second CsCl gradient centrifugation step was carried out for at least 8-hrs at 65000 Rpm. Fractions were collected and fractions with an RI of 1.3766 to 1.3711 were dialyzed overnight against PBS, followed by another 4 hr dialysis against fresh PBS and a 2-hr dialysis against 5% sorbitol in PBS. All dialysis steps were carried out at 4° C. Virus was recovered from the dialysis cassette and pluronic F-68 was added to a final concentration of 0.001%. Virus was sterile-filtered, aliquoted, and stored in aliquots at −80° C. Genomic DNA was extracted from 10-ul of the purified virus using the MinElute Virus Spin Kit (Qiagen Cat #57704), and the viral genome titer was determined by qPCR using an AAV2 rep gene specific primer probe set (SEQ ID NO: 74) (repF: TTC GAT CAA CTA CGC AGA CAG, repR: (SEQ ID NO: 75) GTC CGT GAG TGA AGC AGA TAT T, rep probe: (SEQ ID NO: 76) TCT GAT GCT GTT TCC CTG CAG ACA).

Generation of Barcoded Parental AAV Pools.

Capsids from all 18 parental AAVs were cloned into the BC library vector using PacI and AscI restriction sites. Each parental AAV contained a unique barcode sequence as confirmed by sequence analysis and between 2 and 6 T225 with 293T cells were transfected with each parental AAV (37.5-ug AAV plasmid and 37.5-ug pAd5 helper plasmid per T225). Crude lysates of each barcoded parental cap AAV were generated and 2.8E12 vg of the 10 parents or 1.1E12 vg of the 18 parents were pooled to generate the 10 parent and the 18 parent mix respectively. AAV pools were purified by double CsCl gradient centrifugation as described above.

Sequence Contribution Analysis of Evolved AAV Capsids.

Contigs were assembled using Sequencher 5.3 software and aligned the Muscle multiple sequence alignment software (MacVector, Version 14.5.3). Xover 3.0 DNA/protein shuffling pattern analysis software was used to generate parental fragment crossover maps of shuffled variants. Each parental serotype was color coded as indicated in the figures.

PacBio Sequencing of AAV Pools and Libraries.

For the 10 parent library as well as the 18 parent pool a 2.4 kb fragment containing the capsid as well as the BC sequences was amplified using capF and QSeqRev from extracted viral genomes, loaded onto a 1% agarose gel, visualized by staining with SybrSafe, and gel-purified using a gel extraction kit (Qiagen). The 10 parent library was also assessed at the plasmid level prior to generating the AAV library using restriction enzymes (PacI and XbaI) to release the capsid sequences and gel purified as described above for the amplified capsid sequences. Library preparation and Pacific Biosciences (PacBio) sequencing were performed at the University of Washington PacBio Sequencing Service. Briefly, SMRT bell libraries were prepared following the "Procedure and Checklist-2 kb Template Preparation and Sequencing" protocol from PacBio using the SMRTbell Template Prep Kit v1.0 (PacBio Cat #100-259-100). PacBio 'Binding and Annealing' calculator was used to determine appropriate concentrations for annealing and binding of SMRTbell libraries. SMRTbell libraries were annealed and bound to P6 DNA polymerase for sequencing using the DNA/Polymerase Binding Kit P6 v2.0 (PacBio Cat #100-372-700). Bound SMRTbell libraries were loaded onto SMRT cells using standard MagBead protocols and the MagBead Buffer Kit v2.0 (PacBio Cat #100-642-800). The standard MagBead sequencing protocol was followed with the DNA Sequencing Kit 4.0 v2 (PacBio Cat #100-612-400, also known as P6/C4 chemistry). Sequencing data was collected for 6-hour movie times with 'Stage Start' not enabled. Circular consensus sequence (CCS) reads were generated using the PacBio SMRT portal and the RS_ReadsOfInsert.1 protocol, with filtering set at Minimum Full Pass=3 and Minimum Predicted Accuracy=95%.

Bioinformatic Assessment of PacBio Sequence Reads.

CCS reads with full capsid sequence lengths from 2,250-2,380 nucleotides were included in downstream bioinformatics analyses. Indels in CCS reads were corrected using an in-house algorithm that first assesses parental fragment identity using Xover 3.0 DNA/protein shuffling pattern analysis software. Once the parental identity of each crossover fragment was determined, this information was used to determine indels for correction. Single nucleotide polymorphisms (SNPs) that did not result in indels were maintained. The SNP error rate with the PacBio platform is 1.3-1.7%. SNP frequencies above this rate range were assumed to have arisen from de novo mutations. Corrected sequences in FASTA format were then aligned with MUSCLE. Phylogenetic analyses were conducted using the maximum-likelihood method in RAxML[12133] (Stamatakis et al. 2005).

False-Colored Structural Capsid Mapping.

(FIG. 54D) Chimeric capsids (VP3 sequences only) were false-color mapped onto the AAV2 VLP structure 5IPI (Drouin et al., 2016) using UCSF Chimera version 1.12. Mapped colors correspond to parental serotype colors used in the parental fragment crossover maps. Exterior capsid views have all chains represented, while cross-section views have chains surrounding a cylinder at the 5-fold symmetry axis removed exposing the capsid interior lumen.

Alternative False-Colored Structural Capsid Mapping.

(FIG. 54E) Chimeric capsids (VP3 sequences only) were false-color mapped onto the AAV6 structure 4V86[94] using PyMOL Version 2.3.0. Only surface exposed amino acids that are different from the closest parental AAV3B are shown. With the exception of AAV3B which is shown in gray all mapped amino acid residue colors correspond to parental serotype colors used in the crossover and enrichment figures.

Conservation and Enrichment Calculations.

Amino acid conservation for each position was calculated using the alignment profile obtained with MacVector version 14.5.3. Average conservation values were calculated for stretches of 30 amino acid residues and were used to generate the graphs. Percent parental conservation was determined using an in-house algorithm that identifies the percentage of each parent on each aligned position in the shuffled library. The maximum square size indicates that 100% of variants share that amino acid from that parent at that position. All other square sizes are proportional to the percent of variants from 0-100% that have that amino acid at that position from that parent. Enrichment scores were calculated for each amino acid position in the sequence of each chimera by comparison of sequences from parental serotypes based on maximum likelihood. Xover version 3.0.[74] was used to generate a crossover data analysis set for each chimera. Excel version 16.20 was used to convert those data into enrichment scores. Library parents are depicted in different colors as shown.

Statistics.

Statistical analyses were conducted with Prism v7.0d. Experimental values were assessed via two-way ANOVA using Tukey's multiple comparisons test. P values <0.05 were considered statistically significant.

High Throughput Sequencing of AAV Barcodes.

Barcode sequences were amplified with indexed primers (SEQ ID NO: 77) (F: AAT GAT ACG GCG ACC ACC GAG ATC TAC ACT CTT TCC CTA CAC GAC GCT CTT CCG ATC T (I) (SEQ ID NO: 78) CGC GCC ACT AGT AAT AAA C and R: (SEQ ID NO: 79) CAA GCA GAA GAC GGC ATA CGA GAT CGG TCT CGG CAT TCC TGC TGA ACC GCT CTT CCG ATC T (I) (SEQ ID NO: 80) TAG AGC AAC TAG AGT TCG, with the indices (I) containing between 4 and 6 nucleotides), gel-purified from 2% SybrSafe containing agarose gels, pooled (up to 30 samples), and sequenced on a MiSeq instrument. The number of PCR cycles was minimized to avoid amplification bias and was dependent on the concentration of input AAV genomes as determined by rep qPCR. The following cycling conditions were used: 2-min 98° C., 15 to 30 cycles of 15-sec 98° C., 15-sec 50° C., 20-sec 72° C., with a final 15-min extension at 72° C. Phusion Hot Start Flex (NEB) was used for all amplifications.

Cell Culture Conditions

Human Islet Cultures.

Human pancreatic islets from deceased non-diabetic organ donors were provided by the Integrated Islet Distribution Program (IIDP) or the University of Alberta through the Stanford Islet Research Core and cultured in CMRL-1066 with 10% FBS, Pen-Strep, 1% Insulin Transferrin Selenium (Thermo Fisher), 1 mM sodium pyruvate, 2 mM Glutamax, 2.5 mM HEPES. Ultra-low attachment dishes were used for all islet cell culture experiments.

hESC Derived β-Cells:

Mel1 INS$^{GFP/W}$ human embryonic stem cell (hESC)s were obtained from S. J. Micallef and E. G. Stanley (Monash Immunology and Stem Cell Laboratories, Australia). Cells were maintained and propagated on mouse embryonic fibroblasts (MEFs) in hESC media [DMEM/F12 (Gibco) with 10% KSR (Gibco), 10 ng/ml FGF-2 (R&D Systems)]. A stepwise differentiation of hESC toward β cells was carried out following the protocol described previously[75]. Briefly, confluent hESC were dissociated into single-cell suspensions using TrypLE (Gibco), counted and seeded at $5.5 \times 10^6$ cells per well in 6-well suspension plates in 5.5 ml hESC media supplemented with 10 ng/ml activin A (R&D Systems) and 10 ng/ml heregulinB (Peprotech). The plates were incubated at 37° C. and 5% $CO_2$ on an orbital shaker at 100 rpm to induce 3D sphere formation. After 24 hours, the spheres were washed with PBS and resuspended in day 1 media. From day 1 to day 20, media was changed every day. Media compositions are as follows: Day 1: RPMI (Gibco) containing 0.2% FBS, 1:5,000 ITS (Gibco), 100 ng/ml activin A and 50 ng/ml WNT3a (R&D Systems). Day 2: RPMI containing 0.2% FBS, 1:2,000 ITS and 100 ng/ml activin A. Day 3: RPMI containing 0.2% FBS, 1:1,000 ITS, 2.5 μM TGFbi IV (CalBioChem) and 25 ng/ml KGF (R&D Systems). Day 4-5: RPMI containing 0.4% FBS, 1:1,000 ITS and 25 ng/ml KGF. Day 6-7: DMEM (Gibco) with 25 mM glucose containing 1:100 B27 (Gibco) and 3 nM TTNPB (Sigma). Day 8: DMEM with 25 mM glucose containing 1:100 B27, 3 nM TTNPB and 50 ng/ml EGF (R&D Systems). Day 9-11: DMEM with 25 mM glucose containing 1:100 B27, 50 ng/ml EGF and 50 ng/ml KGF. Day 12-20: DMEM with 25 mM glucose containing 1:100 B27, 1:100 Glutamax (Gibco), 1:100 NEAA (Gibco), 10 μm ALKi II (Axxora), 500 nM LDN—193189 (Stemgent), 1 μm Xxi (Millipore), 1 μM T3 (Sigma-Aldrich), 0.5 mM vitamin C, 1 mM N-acetyl cysteine (Sigma-Aldrich), 10 μM zinc sulfate (Sigma-Aldrich) and 10 µg/ml of heparin sulfate. At day 20, the spheres were collected, incubated with Accumax (innovative cell technologies) for 10 min at 37° C. and dissociated into single cells. Live GFP-high cells were sorted on Aria II at low flow rates and reaggregated in Aggrewell-400 (StemCell Technologies) at 1,000 cells per cluster in CMRL containing 10% FBS, 1:100 Glutamax (Gibco), 1:100 NEAA (Gibco), 10 µm ALKi II (Axxora), 0.5 mM vitamin C, 1 µM T3 (Sigma-Aldrich), 1 mM N-acetyl Cysteine (Sigma-Aldrich), 10 µM zinc sulfate (Sigma-Aldrich) and 10 µg/ml of heparin sulfate. At day 23, the reaggregated enriched β-clusters (eBCs) were transferred from Aggrewells and placed on orbital shakers at 100 rpm, and further cultured for 6 days. Media was changed every third day following reaggregation.

Human Skeletal Muscle Stem Cell and Myotube Cultures.

A pool of primary muscle stem cells isolated from 6 individual donors (kind gift from G. Charville, Stanford) was frozen at an early passage and aliquots were used for experiments. Plates were coated with extracellular matrix protein (Sigma) at 1:500 in DMEM with 1% penicillin/streptomycin. The hMuSC medium was a 1:1 mixture of DMEM:MCDB media supplemented with 20% FBS, 1% insulin-transferrin-selenium, 1% antibiotic/antimycotic, and 10 µM p38i (Cell Signaling Technology Cat #SB203580) to maintain the stem state as described[95]. Media for differentiating primary hMuSCs into myotubes lacked p38i and included a 2% horse serum starve instead of 20% FBS for 7 days. All media was changed every two days.

Mouse Skeletal Muscle Myoblast Cultures.

Wild-type C2C12 mouse myoblasts (ATCC Cat #CRL-1772) were maintained in DMEM supplemented with 10% FBS and 1% antibiotic/antimycotic.

293 and 293T Cell Line Cultures.

HEK 293 cells (ATCC Cat #CRL-1573) and HEK 293T cells (ATCC Cat #CRL-3216) were cultured in DMEM with 10% FBS, 2 mM glutamine, 1% antimycotic-antibiotic, 11 mM HEPES pH 7.28 and 1 mM sodium pyruvate.

HeLa Cell Cultures.

HeLa cells (ATCC Cat #CCL-2) were cultured in DMEM with 10% FBS, 2 mM glutamine, 1% antimycotic-antibiotic.

Mouse Pancreatic β-Cell Cultures.

R7T1 cells (kind gift from H. Moeller, Stanford) were cultured in DMEM with 10% FBS, 2 mM glutamine, 1% antimycotic-antibiotic, 1-ug/ml Doxycyclin.

Mouse Pancreatic α-Cell Cultures.

Alpha TC1 clone 6 cells (ATCC Cat #CRL-2934) were cultured in DMEM with 10% FBS, 2 mM glutamine, 1% antimycotic-antibiotic, 15 mM HEPES, 0.1 mM NEAA.

Rat hepatoma cell cultures. H4TG cells (ATCC Cat #CRL-1578) were cultured in DMEM with 10% FBS, 4 mM glutamine, 1% antimycotic-antibiotic.

Human hepatocellular carcinoma cell cultures. SNU-387 cells (ATCC Cat #CRL-2237) and HepG2 (ATCC Cat #HB-8065) were cultured in RPMI with 10% FBS, 2 mM glutamine, 1% antimycotic-antibiotic, 1% non-essential amino acids. HuH7 cells were cultured in DMEM with 10% FBS, 2 mM glutamine, 1% antimycotic-antibiotic, 1% non-essential amino acids.

Human keratinocyte cell cultures. HaCaT cells (kind gift from A. Oro, Stanford) were cultured in DMEM with 10% FBS, 2 mM glutamine, 1% penicillin/streptomycin.

Hamster ovary cell cultures. CHO-K1 cells (ATCC Cat #CCL-61) were cultured in Ham's F12 with 10% FBS, 1% penicillin/streptomycin.

Rhesus macaque kidney cell cultures. FRhK-4 cells (ATCC Cat #CRL-1688) were cultured in DMEM with 10% FBS, 2 mM glutamine, 1% penicillin/streptomycin.

Mouse fibroblast cell cultures. Primary mouse embryonic fibroblasts derived at E14 were cultured in DMEM with 10% FBS, 2 mM glutamine, 1% non-essential amino acids, 1% antimycotic-antibiotic, 55 uM β-Mercaptoethanol.

Selection of AAV libraries on human islets. Islets were left in a 10 cm Petri Dish with 10 ml complete media to recover overnight prior to AAV infection. Islets were infected either intact or were dissociated into single cell suspensions using Accumax prior to infection (1 ml Accumax per 1000 islet equivalents [IEQ]). Approximately 300 IEQ or 1.7E05 dispersed islet cells were seeded in several wells of an ultra-low attachment 24-well plate, infected with various MOIs of either the 18 parent AAV mix or the AAV libraries and incubated in a 37° C. incubator for 6 hrs. After two PBS washes to remove left over input virus cells were superinfected with human adenovirus 5 obtained from ATCC (Cat #VR-5). For intact islets 8E07 PFU were used, for dissociated islet cells 4E07 PFU were added into 1 ml media per well. After 4 days at 37° C. the cells and supernatant were harvested, subjected to 3 freeze-thaw cycles and incubated for 30 min at 65° C. to inactivate Ad5. Cell debris was removed by centrifugation (2 min, 10,000×g) and viral genomes were isolated from 100-ul clarified supernatant for titration by qPCR using a rep primer-probe set. For subsequent rounds of passaging similar MOIs as for the initial infections were used if sufficiently high titers were achieved. When titers were low a maximum volume of 200 ul was used for infection.

Vector plasmids. A self-complementary rAAV vector expressing GFP under control of a CAG promoter (pscAAV-CAG-GFP, Addgene, Cat #83279) was generated by replacing the CMV promoter in plasmid pscAAV-GFP (gift from John T Gray, Addgene, Cat #32396) with the CAG promoter derived from pAAV-CAG-GFP (gift from Edward Boyden, Addgene, Cat #37825). A single stranded rAAV vector expressing Firefly luciferase under control of the CAG promoter (pAAV-CAG-FLuc, Addgene, Cat #83281) was generated by replacing the GFP sequences in plasmid pAAV-CAG-GFP with Firefly luciferase sequences obtained from plasmid pAAV-EF1α-FLuc-WPRE-HGHpA (Addgene, Cat #87951). A single stranded rAAV vector expressing codon diversified Tomato Red was a gift from Edward Boyden (pAAV-CAG-tdTomato, Addgene, Cat #59462).

Recovery and evaluation of enriched AAV capsid sequences. Capsid sequences were amplified from viral genomes after the third round of selection using primer capF and a reverse primer containing the respective BC specific sequence on its 3' end. The right BC was chosen to be included in the primer sequences so that the left BC served as a control of specific amplification of the desired variant. The number of PCR cycles was adjusted according to viral titer and frequency of the specific variant in the viral pool. The following amplification parameters were used: 2 min 98° C., 25 to 30 cycles of 15 sec 98° C., 20 sec 61° C., 2 min 72° C., with a final 10 min extension at 72° C. PCR products were gel purified, TOPO cloned and sequenced. Several clones for each BC were sequenced to ensure that the left BC sequence matched the sequence obtained by BC NGS. For several of the capsids it was observed that the capsid sequences differed for some of the clones, particularly at the 5' end. This was likely due to template switching after incomplete extension[96-98] and may be alleviated by optimizing PCR conditions and enzymes. The capsid sequences that matched the consensus sequence were used to package a self-complementary CAG promoter driven GFP expression vector by calcium phosphate triple transfection. For each T225 flask 25 ug sc CAG-GFP transfer vector, 25 ug packaging plasmid, and 25 ug pAd5 helper plasmid was used. Crude cell lysates were generated, rAAV titers determined by qPCR using a GFP specific primer-probe set, and tested for transduction efficiency of dissociated human islet cells using an MOI of 1K. 48-hrs post transduction the re-aggregated pseudo islets were dissociated into single-cell suspensions by incubation with Accumax followed by treatment with Dispase. The number of GFP expressing cells was evaluated using a BD FACS Calibur instrument and FlowJo software Version 10 was used to analyse and graph data. Selected capsid variants were used to generate CsCl gradient purified vector preparations packaging different expression vectors.

Analysis of packaged vector genomes by Alkaline Southern Blot. Alkaline Southern Blot analysis was performed to analyze the size of the DNA packaged in rAAV capsids using standard methods. Briefly, 1E09 viral genomes in alkaline loading buffer (50 mM NaOH, 1 mM EDTA, 3% Ficoll, 0.025% Bromcresol, 0.042% Xylene) were loaded onto a 1% alkaline agarose gel with 50 mM NaOH, 1 mM as running buffer. The gel was run at 40 mV for 24 hrs at 4° C. with one buffer exchange after 12 hrs. After gel blotting, the membrane was pre-hybridized with 10 ug/ml salmon sperm DNA in PerfectHyb Plus Hybridization buffer (Sigma) for 2 hrs at 65° C. with rotation. A 300 nt long $^{32}$P-labeled probe containing GFP or FLuc sequences was added and left to hybridize o.n. at 65° C. with rotation. The membrane was washed twice under low-stringent condition (2× salt-sodium citrate, 20 min at 65° C.), followed by one wash under high-stringent condition (2× salt-sodium citrate with 0.1% SDS, 30 min at 65° C.). The membrane was exposed onto a phosphoimager screen and visualized using the Personal Molecular Imager (Biorad). Image analysis was performed using QuantityOne software.

Analysis of capsid proteins by Western Blot. Western Blot analysis was performed using standard methods and equipment. Briefly, proteins were resolved on 4-12% NuPAGE Bis-Tris gels (Life Technologies) using MOPS running buffer. For detection of capsid proteins the membrane was probed with monoclonal antibody B1 (ARP, Cat #03-61058) at a 1:200 dilution for 2 hrs at RT. The membrane was then incubated for 1 hr with a horseradish peroxidase (HRP)-labeled secondary antibody directed against mouse IgG, followed by HRP detection using Pierce ECL2 substrate and the Biorad Chemdoc imager.

Evaluation of cell type specific transduction efficiency of capsid variants. The cold transduction method was performed for those studies. Briefly, approximately 300 intact islets were resuspended in 100-ul CMRL with 2% FBS, rAAV was added at an MOI of 10K (assuming 1,000 cells per islet), and the mixture was incubated on ice while gently rocking on a horizontal shaker in the cold room. After 2-hrs 1-ml pre-warmed complete media (CMRL-1066 with 10 mM HEPES, 0.5% human serum albumin, 2% FBS, 10 mM nicotinamide, 1% antimycotic-antibiotic, 1% Glutamax) was added to each sample and islets were incubated on 24-well ultra-low attachment plates. Media was replaced after 2 days and islets were harvested, dissociated, and analyzed by FACS as described previously using surface antibodies to subdivide into α-, β-, and non-α-/non-β-cells[99].

Evaluation of rAAVs for transduction efficiency on hESC derived β-cells. Recombinant AAVs were mixed with 800,000 GFP-high cells sored from 20 spheres at an MOI of 10, 100, 1000 and reaggregated in Aggrewell-400 in CMRL containing 10% FBS, 1:100 Glutamax, 1:100 NEAA, 10 µm ALKi II, 0.5 mM vitamin C, 1 µM T3, 1 mM N-acetyl Cysteine, 10 µM zinc sulfate and 10 µg/ml of heparin sulfate. Media was replaced after 3 days when the reaggregated eBCs were transferred into 6 well suspension plates. They were placed on orbital shakers at 100 rpm, and further cultured for 3 days. Subsequently, the eBCs were dissociated, fixed, permeabilized and stained for anti-human C-peptide antibody (1: 200), and anti-human RFP antibody (Rockland, 1:500) for analysis on LSRFortessa X20 Dual, as described previously[100]. Data were analyzed with Flowjo software. Anti-human C-peptide antibody was conjugated in-house using the Molecular Probes Antibody Labeling Kits according to manufacturer's instructions. Live images were taken using Leica DMI4000 B.

Evaluation of the variants for transduction efficiency on a variety of cell lines. Capsid sequences of AAV DJ, AAV LK03, as well as the variants AAV KP1, KP2, and KP3 were used to package a single stranded CAG-Firefly Luciferase vector. Recombinant AAV preparations were double CsCl purified and used to transduce a variety of human and mouse primary cells and cell lines at an MOI of 100 and 1000 in triplicates. Except for the differentiated human muscle cells all cells were seeded one day prior to transduction on 48-well plates so that they were about 60-70% confluent at the time of transduction (seeding density of 20,000-80,000 per well, depending on size and proliferation rate). Cells were lysed and assayed for luciferase activity using the Luciferase Assay Kit (Promega) 48-hrs post transduction. Purified recombinant luciferase protein (Promega) was used to generate a standard curve.

Neutralization assay. Two different batches of pooled human immunoglobulin fractions (IVIG, Baxter) were used to evaluate the novel variants for sensitivity to neutralizing antibodies. Neutralization assays were essentially performed as described (Meliani et al., 2015)[101]. Briefly, IVIG preparations were diluted in complement inactivated FBS and incubated for 1-hr at 37° C. with 2E08 vector genomes of each ssCAG-FLuc vector packaged with the different capsids in a total volume of 100 ul. Huh7 cells that had been seeded on 48 well plates the day before (5E04 per well) were transduced with the virus-IVIG mixtures in triplicates (22.5-ul each well, corresponding to MOI of ca 100) and luciferase activity in the cell lysates was determined 24-hrs later.

Mice. Fah/Rag2/Il2rgc (FRG) deficient female mice on a NOD-strain background (FRG/N) were housed and maintained in specific-pathogen-free barrier facilities at Oregon Health & Science University. FRG/N mice were maintained on irradiated high-fat low-protein mouse chow (Lab Diet Cat # Picolab-5LJ5) ad libitum to decrease flux through the tyrosine pathway. Beginning on the day of transplantation, FRG/N mice were maintained for 1 week on acidified water to prevent bacterial growth. The following week, mice were switched to 1 week of 8 mg/L SMX-TMP antibiotic water (supplemented with 0.7-mol/L dextrose for palatability). Thereafter, FRG/N mice were cycled on and off 1 mg/L NTBC water as described. Female Balb/C SCID mice between 6 and 8 weeks of age were purchased from The Jackson Laboratories (Cat #001803) for imaging studies. The Institutional Animal Care & Use Committees of Stanford University, Oregon Health & Science University and the Children's Medical Research Institute approved all mouse procedures.

Hepatocyte transplantation. Donor human hepatocytes for transduction studies were acquired from BioreclarnationIVT (Lot #QIE). Weanling FRG/N mice were pre-conditioned with administration of recombinant human adenovirus expressing urokinase (5E10 PFU retroorbitally) 24 hrs prior to transplant to promote human cell engraftment. Between 5E05 and 1E06 human hepatocytes were injected intrasplenically into anesthetized recipient FRG/N mice and cycled on/off NTBC to promote human hepatocyte engraftment and expansion. Broad-spectrum antibiotic (Ceftiofur 4-mg/kg) was given by intraperitoneal injection immediately prior to surgery and for two days following surgery. Six months post-transplant, circulating human albumin levels as measure of engraftment were determined with the Bethyl Quantitative Human Albumin ELISA kit (Cat #E88-129).

In vivo transduction eperiments. For evaluation of wild-type mouse liver transduction efficiency white Balb/C SCID mice were injected with 2E10 vector genomes of each CAG-Firefly Luciferase vector via normodynamic intravenous lateral tail vein injections. AAV8 was used in place of LK03 as this capsid had previously been shown to be highly human specific. Mice were monitored for Luciferase activity in the liver once a week by intraperitoneal injection of 150 ug per g body weight D-Luciferin (Biosynth Cat #L-8220) and ventral luciferase readings using an Ami Imaging System. On day 35 mice were sacrificed and various organs were recovered (liver, pancreas, heart, lung, spleen, brain, and kidney). Organs were homogenized in Passive lysis buffer (Promega) using a Bullet Storm Homogenizer and luciferase activity from 1 mg each tissue sample was measured as described above. Genomic DNA was isolated from 10 mg each tissue sample and vector copy numbers were determined using qPCR. Primers for Luciferase were FLuc F: (SEQ ID NO: 81) CAC ATA TCG AGG TGG ACA TTA C and FLuc R: (SEQ ID NO: 82) TG TTT GTA TTC AGC CCA TAG. Mouse actin primers (m-actF: (SEQ ID NO: 83) CCT GTA TGC CTC TGG TCG TA and m-actR: (SEQ ID NO: 84) CCT CGT AGA TGG GCA CAG T) were used for normalization.

For evaluation of human hepatocyte transduction in vivo humanized FRG/N mice (3 mice per group) were injected intravenously with 1E11 ssCAG-Td Tomato Red vector genomes pseudotyped with DJ, LK03, or KP1 capsids and maintained on 1 mg/L NTBC during this 14 day transduction. Livers were harvested under inhalation isoflurane anesthesia. Liver tissue was cut into several 2×5-mm pieces from several lobes and fixed in 10× volume of 4% PFA for 5 hrs at 25° C. protected from light. Fixed tissue was washed 1× in PBS and put through a sucrose cryoprotection and rehydration series (10% w/v sucrose for 2 hrs at 25° C., 20% w/v sucrose overnight at 4° C., 30% w/v sucrose for 4 hrs at 25° C.). Liver pieces were rinsed in PBS, blotted dry and mounted in cryomolds (Tissue-Tek Cat #4557) with OCT (Tissue-Tek Cat #4583) and frozen in a liquid nitrogen-cooled isopentane bath. Labeled cryomolds were wrapped in aluminum foil and placed at −80° C. until sectioning.

Liver immunohistochemistry. Each liver sample with four to five lobes was cut in a microtome at 5 μM per section. Slides were fixed in methanol for 1 min at −20° C. and air dried at room temperature (RT). All following steps were done at RT except for notification. Slides were washed in PBT (PBS+0.1% Tween20) for 3×5 min, permeabilized in 0.3% Triton-X-100 in PBS for 1×10 min, and washed in PBT for 2×5 min. Blocking was performed in PBT+10% normal donkey serum (Cat. no. ab7475; Abcam) for 1 hr in a humidified chamber. A rabbit anti-human FAH antibody (Cat. no. HPA041370; Sigma) was added in PBT at 1:200 and incubated overnight at 4° C. Post-staining wash was conducted in PBT for 3×5 min. A secondary antibody for donkey anti-rabbit Alexa Fluor 488 IgG antibody (Cat. no. A-21206; ThermoFisher) was added in PBT (1:500, with DAPI at 80 ng/mL) and incubated at RT for 1 hr. Slides were washed in PBT for 3×5 min and PBS for 1×5 min, followed by mounting with ProLong Gold Antifade Reagent (Cat. no. 9071S; Cell Signaling). Antibody validity controls included secondary-only staining and demonstration on positive control human liver tissue sections (Cat. no. HF-314; Zyagen) and negative control untreated mouse liver sections (Cat. no. MF-314-057; Zyagen). Imaging was performed on an inverted Zeiss laser scanning confocal microscope (LSM 880) by a 20× objective with the Zen Pro software. AAV-RFP signals were scanned and captured directly. Quantification of human hepatocyte transduction was done using the Volocity software (v6.3) and confirmed with counts by eye. Briefly, six to nine different areas of interests across different lobes from different sections of each liver sample were scanned, counting 1,000 cells on average per section. Areas with roughly 30%-80% of FAH-positive staining were chosen for analysis. The percentage of human hepatocytes per scanned area was presented as the number of cells with Alexa Fluor 488 signals (FAH-positive) divided by the number of cells with DAPI signals (total number of cells). Total transduction efficiency was calculated by dividing the number of cells with RFP signals (AAV-positive) by the number of cells with DAPI signals. The overlap of these two numbers represented the transduction efficiency for human hepatocytes for different AAV serotypes.

REFERENCES FOR EXAMPLE 3

1. Kay, M A (2015). Selecting the Best AAV Capsid for Human Studies. Mol Ther 23: 1800-1801.
2. Colella, P, Ronzitti, G, and Mingozzi, F (2018). Emerging Issues in AAV-Mediated In Vivo Gene Therapy. Mol Ther Methods Clin Dev 8: 87-104.
3. Pillay, S, and Carette, J E (2017). Host determinants of adeno-associated viral vector entry. Curr Opin Virol 24: 124-131.
4. Thomas, C E, Storm, T A, Huang, Z, and Kay, M A (2004). Rapid uncoating of vector genomes is the key to efficient liver transduction with pseudotyped adeno-associated virus vectors. J Virol 78: 3110-3122.
5. Keiser, N W, Yan, Z, Zhang, Y, Lei-Butters, D C, and Engelhardt, J F (2011). Unique characteristics of AAV1, 2, and 5 viral entry, intracellular trafficking, and nuclear import define transduction efficiency in HeLa cells. Hum Gene Ther 22: 1433-1444.
6. Grimm, D, and Kay, M A (2003). From virus evolution to vector revolution: use of naturally occurring serotypes of adeno-associated virus (AAV) as novel vectors for human gene therapy. Curr Gene Ther 3: 281-304.
7. Adachi, K, and Nakai, H (2010). A New Recombinant Adeno-Associated Virus (Aav)-Based Random Peptide Display Library System: Infection-Defective Aav1.9-3 as a Novel Detargeted Platform for Vector Evolution. Gene Ther Regul 5: 31-55.
8. Grimm, D, Lee, J S, Wang, L, Desai, T, Akache, B, Storm, T A, et al. (2008). In vitro and in vivo gene therapy vector evolution via multispecies interbreeding and retargeting of adeno-associated viruses. J Virol 82: 5887-5911.
9. Naumer, M, Sonntag, F, Schmidt, K, Nieto, K, Panke, C, Davey, N E, et al. (2012). Properties of the adeno-associated virus assembly-activating protein. J Virol 86: 13038-13048.
10. Munch, R C, Janicki, H, Volker, I, Rasbach, A, Hallek, M, Buning, H, et al. (2013). Displaying high-affinity ligands on adeno-associated viral vectors enables tumor cell-specific and safe gene transfer. Mol Ther 21: 109-118.
11. Grimm, D, and Zolotukhin, S (2015). E Pluribus Unum: 50 Years of Research, Millions of Viruses, and One Goal—Tailored Acceleration of AAV Evolution. Mol Ther 23: 1819-1831.
12. Zinn, E, Pacouret, S, Khaychuk, V, Turunen, H T, Carvalho, L S, Andres-Mateos, E, et al. (2015). In Silico Reconstruction of the Viral Evolutionary Lineage Yields a Potent Gene Therapy Vector. Cell Rep 12: 1056-1068.
13. Stemmer, W P (1994). DNA shuffling by random fragmentation and reassembly: in vitro recombination for molecular evolution. Proc Natl Acad Sci USA 91: 10747-10751.
14. Stemmer, W P (1994). Rapid evolution of a protein in vitro by DNA shuffling. Nature 370: 389-391.
15. Zhao, H, Giver, L, Shao, Z, Affholter, J A, and Arnold, F H (1998). Molecular evolution by staggered extension process (StEP) in vitro recombination. Nat Biotechnol 16: 258-261.
16. Coco, W M, Levinson, W E, Crist, M J, Hektor, H J, Darzins, A, Pienkos, P T, et al. (2001). DNA shuffling method for generating highly recombined genes and evolved enzymes. Nat Biotechnol 19: 354-359.
17. Kikuchi, M, Ohnishi, K, and Harayama, S (1999). Novel family shuffling methods for the in vitro evolution of enzymes. Gene 236: 159-167.
18. Gillam E. M. J., C, J. N., Ackerley, D. F. (2014). Directed Evolution Library Creation, Methods and Protocols, Humana Press.
19. Crameri, A, Raillard, S A, Bermudez, E, and Stemmer, W P (1998). DNA shuffling of a family of genes from diverse species accelerates directed evolution. Nature 391: 288-291.
20. Chang, C C, Chen, T T, Cox, B W, Dawes, G N, Stemmer, W P, Punnonen, J, et al. (1999). Evolution of a cytokine using DNA family shuffling. Nat Biotechnol 17: 793-797.
21. Christians, F C, Scapozza, L, Crameri, A, Folkers, G, and Stemmer, W P (1999). Directed evolution of thymidine kinase for AZT phosphorylation using DNA family shuffling. Nat Biotechnol 17: 259-264.
22. Crameri, A, Dawes, G, Rodriguez, E, Jr., Silver, S, and Stemmer, W P (1997). Molecular evolution of an arsenate detoxification pathway by DNA shuffling. Nat Biotechnol 15: 436-438.
23. Leong, S R, Chang, J C, Ong, R, Dawes, G, Stemmer, W P, and Punnonen, J (2003). Optimized expression and specific activity of IL-12 by directed molecular evolution. Proc Natl Acad Sci USA 100: 1163-1168.
24. Ness, J E, Welch, M, Giver, L, Bueno, M, Cherry, J R, Borchert, T V, et al. (1999). DNA shuffling of subgenomic sequences of subtilisin. Nat Biotechnol 17: 893-896.
25. Pekrun, K, Shibata, R, Igarashi, T, Reed, M, Sheppard, L, Patten, P A, et al. (2002). Evolution of a human immunodeficiency virus type 1 variant with enhanced replication in pig-tailed macaque cells by DNA shuffling. J Virol 76: 2924-2935.
26. Powell, S K, Kaloss, M A, Pinkstaff, A, McKee, R, Burimski, I, Pensiero, M, et al. (2000). Breeding of retroviruses by DNA shuffling for improved stability and processing yields. Nat Biotechnol 18: 1279-1282.
27. Raillard, S, Krebber, A, Chen, Y, Ness, J E, Bermudez, E, Trinidad, R, et al. (2001). Novel enzyme activities and functional plasticity revealed by recombining highly homologous enzymes. Chem Biol 8: 891-898.
28. Soong, N W, Nomura, L, Pekrun, K, Reed, M, Sheppard, L, Dawes, G, et al. (2000). Molecular breeding of viruses. Nat Genet 25: 436-439.
29. Stutzman-Engwall, K, Conlon, S, Fedechko, R, McArthur, H, Pekrun, K, Chen, Y, et al. (2005). Semi-synthetic DNA shuffling of aveC leads to improved industrial scale production of doramectin by *Streptomyces avermitilis*. Metab Eng 7: 27-37.
30. Wright, A, Semyonov, A, Dawes, G, Crameri, A, Lyons, R, Stemmer, W P, et al. (2005). Diverse plasmid DNA vectors by directed molecular evolution of cytomegalovirus promoters. Hum Gene Ther 16: 881-892.
31. Zhang, J H, Dawes, G, and Stemmer, W P (1997). Directed evolution of a fucosidase from a galactosidase by DNA shuffling and screening. Proc Natl Acad Sci USA 94: 4504-4509.
32. Apt, D, Raviprakash, K, Brinkman, A, Semyonov, A, Yang, S, Skinner, C, et al. (2006). Tetravalent neutralizing antibody response against four dengue serotypes by a single chimeric dengue envelope antigen. Vaccine 24: 335-344.
33. Maheshri, N, Koerber, J T, Kaspar, B K, and Schaffer, D V (2006). Directed evolution of adeno-associated virus yields enhanced gene delivery vectors. Nat Biotechnol 24: 198-204.
34. Asuri, P, Bartel, M A, Vazin, T, Jang, J H, Wong, T B, and Schaffer, D V (2012). Directed evolution of adeno-associated virus for enhanced gene delivery and gene targeting in human pluripotent stem cells. Mol Ther 20: 329-338.
35. Koerber, J T, Jang, J H, and Schaffer, D V (2008). DNA shuffling of adeno-associated virus yields functionally diverse viral progeny. Mol Ther 16: 1703-1709.
36. Li, W, Asokan, A, Wu, Z, Van Dyke, T, DiPrimio, N, Johnson, J S, et al. (2008). Engineering and Selection of Shuffled AAV Genomes: A New Strategy for Producing Targeted Biological Nanoparticles. Mol Ther 16: 1252-1260.
37. Lisowski, L, Dane, A P, Chu, K, Zhang, Y, Cunningham, S C, Wilson, E M, et al. (2014). Selection and evaluation of clinically relevant AAV variants in a xenograft liver model. Nature 506: 382-386.
38. Paulk, N K, Pekrun, K, Charville, G W, Maguire-Nguyen, K, Wosczyna, M N, Xu, J, et al. (2018). Bioengineered Viral Platform for Intramuscular Passive Vaccine Delivery to Human Skeletal Muscle. Mol Ther Methods Clin Dev 10: 144-155.
39. Paulk, N K, Pekrun, K, Zhu, E, Nygaard, S, Li, B, Xu, J, et al. (2018). Bioengineered AAV Capsids with Combined High Human Liver Transduction In Vivo and Unique Humoral Seroreactivity. Mol Ther 26: 289-303.
40. Ward, P, and Walsh, C E (2009). Chimeric AAV Cap sequences alter gene transduction. Virology 386: 237-248.
41. Choudhury, S R, Fitzpatrick, Z, Harris, A F, Maitland, S A, Ferreira, J S, Zhang, Y, et al. (2016). In Vivo Selection Yields AAV-B1 Capsid for Central Nervous System and Muscle Gene Therapy. Mol Ther 24: 1247-1257.
42. Dalkara, D, Byrne, L C, Klimczak, R R, Visel, M, Yin, L, Merigan, W H, et al. (2013). In vivo-directed evolution of a new adeno-associated virus for therapeutic outer retinal gene delivery from the vitreous. Sci Transl Med 5: 189ra176.
43. Tervo, D G, Hwang, B Y, Viswanathan, S, Gaj, T, Lavzin, M, Ritola, K D, et al. (2016). A Designer AAV Variant Permits Efficient Retrograde Access to Projection Neurons. Neuron 92: 372-382.
44. Yang, L, Jiang, J, Drouin, L M, Agbandje-McKenna, M, Chen, C, Qiao, C, et al. (2009). A myocardium tropic adeno-associated virus (AAV) evolved by DNA shuffling and in vivo selection. Proc Natl Acad Sci USA 106: 3946-3951.
45. CDC (2017). National Diabetes Statistics Report. U S Department of Health and Human Services.
46. Bruni, A, Gala-Lopez, B, Pepper, A R, Abualhassan, N S, and Shapiro, A J (2014). Islet cell transplantation for the treatment of type 1 diabetes: recent advances and future challenges. Diabetes Metab Syndr Obes 7: 211-223.
47. Wang, X, Meloche, M, Verchere, C B, Ou, D, Mui, A, and Warnock, G L (2011). Improving islet engraftment by gene therapy. J Transplant 2011: 594851.
48. Sakata, N, Yamaguchi, Y, Chen, Y, Shimoda, M, Yoshimatsu, G, Unno, M, et al. (2017). Pleckstrin homology-like domain family A, member 3 (PHLDA3) deficiency improves islets engraftment through the suppression of hypoxic damage. PLoS One 12: e0187927.
49. Mallol, C, Casana, E, Jimenez, V, Casellas, A, Haurigot, V, Jambrina, C, et al. (2017). AAV-mediated pancreatic overexpression of Igf1 counteracts progression to autoimmune diabetes in mice. Mol Metab 6: 664-680.
50. Collombat, P, Xu, X, Ravassard, P, Sosa-Pineda, B, Dussaud, S, Billestrup, N, et al. (2009). The ectopic expression of Pax4 in the mouse pancreas converts progenitor cells into alpha and subsequently beta cells. Cell 138: 449-462.
51. Courtney, M, Gjernes, E, Druelle, N, Ravaud, C, Vieira, A, Ben-Othman, N, et al. (2013). The inactivation of Arx in pancreatic alpha-cells triggers their neogenesis and conversion into functional beta-like cells. PLoS Genet 9: e1003934.
52. Lima, M J, Muir, K R, Docherty, H M, McGowan, N W, Forbes, S, Heremans, Y, et al. (2016). Generation of Functional Beta-Like Cells from Human Exocrine Pancreas. PLoS One 11: e0156204.
53. Wang, Y, Dorrell, C, Naugler, W E, Heskett, M, Spellman, P, Li, B, et al. (2018). Long-Term Correction of Diabetes in Mice by In Vivo Reprogramming of Pancreatic Ducts. Mol Ther 26: 1327-1342.
54. Xiao, X, Guo, P, Shiota, C, Zhang, T, Coudriet, G M, Fischbach, S, et al. (2018). Endogenous Reprogramming of Alpha Cells into Beta Cells, Induced by Viral Gene Therapy, Reverses Autoimmune Diabetes. Cell Stem Cell 22: 78-90 e74.
55. Zhang, Y, Fava, G E, Wang, H, Mauvais-Jarvis, F, Fonseca, V A, and Wu, H (2016). PAX4 Gene Transfer Induces alpha-to-beta Cell Phenotypic Conversion and Confers Therapeutic Benefits for Diabetes Treatment. Mol Ther 24: 251-260.
56. Chakravarthy, H, Gu, X, Enge, M, Dai, X, Wang, Y, Damond, N, et al. (2017). Converting Adult Pancreatic Islet alpha Cells into beta Cells by Targeting Both Dnmt1 and Arx. Cell Metab 25: 622-634.
57. Matsuoka, T A, Kawashima, S, Miyatsuka, T, Sasaki, S, Shimo, N, Katakami, N, et al. (2017). Mafa Enables Pdx1 to Effectively Convert Pancreatic Islet Progenitors and Committed Islet alpha-Cells Into beta-Cells In Vivo. Diabetes 66: 1293-1300.
58. Furuyama, K, Chera, S, van Gurp, L, Oropeza, D, Ghila, L, Damond, N, et al. (2019). Diabetes relief in mice by glucose-sensing insulin-secreting human alpha-cells. Nature.
59. Vieira, A, Courtney, M, Druelle, N, Avolio, F, Napolitano, T, Hadzic, B, et al. (2016). beta-Cell replacement as a treatment for type 1 diabetes: an overview of possible cell sources and current axes of research. Diabetes Obes Metab 18 Suppl 1: 137-143.
60. Zhao, C, Qiao, C, Tang, R H, Jiang, J, Li, J, Martin, C B, et al. (2015). Overcoming Insulin Insufficiency by Forced Follistatin Expression in beta-cells of db/db Mice. Mol Ther 23: 866-874.
61. Flores, R R, Zhou, L, and Robbins, P D (2014). Expression of IL-2 in beta cells by AAV8 gene transfer in pre-diabetic NOD mice prevents diabetes through activation of FoxP3-positive regulatory T cells. Gene Ther 21: 715-722.
62. Wang, Z, Zhu, T, Rehman, K K, Bertera, S, Zhang, J, Chen, C, et al. (2006). Widespread and stable pancreatic gene transfer by adeno-associated virus vectors via different routes. Diabetes 55: 875-884.
63. Martini, S V, Silva, A L, Ferreira, D, Rabelo, R, Ornellas, F M, Gomes, K, et al. (2016). Tyrosine Mutation in AAV9 Capsid Improves Gene Transfer to the Mouse Lung. Cell Physiol Biochem 39: 544-553.
64. Mowat, F M, Gornik, K R, Dinculescu, A, Boye, S L, Hauswirth, W W, Petersen-Jones, S M, et al. (2014). Tyrosine capsid-mutant AAV vectors for gene delivery to the canine retina from a subretinal or intravitreal approach. Gene Ther 21: 96-105.
65. Zhong, L, Li, B, Mah, C S, Govindasamy, L, Agbandje-McKenna, M, Cooper, M, et al. (2008). Next generation of adeno-associated virus 2 vectors: point mutations in tyrosines lead to high-efficiency transduction at lower doses. Proc Natl Acad Sci USA 105: 7827-7832.
66. Song, L, Kauss, M A, Kopin, E, Chandra, M, Ul-Hasan, T, Miller, E, et al. (2013). Optimizing the transduction efficiency of capsid-modified AAV6 serotype vectors in primary human hematopoietic stem cells in vitro and in a xenograft mouse model in vivo. Cytotherapy 15: 986-998.
67. Song, L, Li, X, Jayandharan, G R, Wang, Y, Aslanidi, G V, Ling, C, et al. (2013). High-efficiency transduction of primary human hematopoietic stem cells and erythroid lineage-restricted expression by optimized AAV6 serotype vectors in vitro and in a murine xenograft model in vivo. PLoS One 8: e58757.
68. Chen, M, Maeng, K, Nawab, A, Francois, R A, Bray, J K, Reinhard, M K, et al. (2017). Efficient Gene Delivery and Expression in Pancreas and Pancreatic Tumors by Capsid-Optimized AAV8 Vectors. Hum Gene Ther Methods 28: 49-59.
69. Craig, A T, Gavrilova, o, Dwyer, N K, Jou, W, Pack, S, Liu, E, et al. (2009). Transduction of rat pancreatic islets with pseudotyped adeno-associated virus vectors. Virol J 6: 61.
70. Flotte, T, Agarwal, A, Wang, J, Song, S, Fenjves, E S, Inverardi, L, et al. (2001). Efficient ex vivo transduction of pancreatic islet cells with recombinant adeno-associated virus vectors. Diabetes 50: 515-520.
71. Kapturczak, M R, Flotte, T, and Atkinson, M A (2001). Adeno-associated virus (AAV) as a vehicle for therapeutic gene delivery: improvements in vector design and viral production enhance potential to prolong graft survival in pancreatic islet cell transplantation for the reversal of type 1 diabetes. Curr Mol Med 1: 245-258.
72. Song, Z, Galivo, F H, Adachi, K, Grompe, M, Nakai, H (2017). Strong Alpha Cell Preference of the AAV Strains That Best Transduce Human Pancreatic Islets In Vitro. Molecular Therapy 25: 47.
73. Adachi, K, Enoki, T, Kawano, Y, Veraz, M, and Nakai, H (2014). Drawing a high-resolution functional map of adeno-associated virus capsid by massively parallel sequencing. Nat Commun 5: 3075.

74. Huang, W, Johnston, W A, Boden, M, and Gillam, E M (2016). ReX: A suite of computational tools for the design, visualization, and analysis of chimeric protein libraries. Biotechniques 60: 91-94.
75. Nair, G G, Liu, J S, Russ, H A, Tran, S, Saxton, M S, Chen, R, et al. (2019). Recapitulating endocrine cell clustering in culture promotes maturation of human stem-cell-derived beta cells. Nat Cell Biol 21: 263-274.
76. Lerch, T F, and Chapman, M S (2012). Identification of the heparin binding site on adeno-associated virus serotype 3B (AAV-3B). Virology 423: 6-13.
77. Mays, L E, Wang, L, Tenney, R, Bell, P, Nam, H J, Lin, J, et al. (2013). Mapping the structural determinants responsible for enhanced T cell activation to the immunogenic adeno-associated virus capsid from isolate rhesus 32.33. J Virol 87: 9473-9485.
78. Gao, G, Alvira, M R, Somanathan, S, Lu, Y, Vandenberghe, L H, Rux, J J, et al. (2003). Adeno-associated viruses undergo substantial evolution in primates during natural infections. Proc Natl Acad Sci USA 100: 6081-6086.
79. Wu, J, Zhao, W, Zhong, L, Han, Z, Li, B, Ma, W, et al. (2007). Self-complementary recombinant adeno-associated viral vectors: packaging capacity and the role of rep proteins in vector purity. Hum Gene Ther 18: 171-182.
80. Gray, S J, Choi, V W, Asokan, A, Haberman, R A, McCown, T J, and Samulski, R J (2011). Production of recombinant adeno-associated viral vectors and use in in vitro and in vivo administration. Curr Protoc Neurosci Chapter 4: Unit 4 17.
81. Quirin, K A, Kwon, J J, Alioufi, A, Factora, T, Temm, C J, Jacobsen, M, et al. (2018). Safety and Efficacy of AAV Retrograde Pancreatic Ductal Gene Delivery in Normal and Pancreatic Cancer Mice. Mol Ther Methods Clin Dev 8: 8-20.
82. Jimenez, V, Ayuso, E, Mallol, C, Agudo, J, Casellas, A, Obach, M, et al. (2011). In vivo genetic engineering of murine pancreatic beta cells mediated by single-stranded adeno-associated viral vectors of serotypes 6, 8 and 9. Diabetologia 54: 1075-1086.
83. Nonnenmacher, M, van Bakel, H, Hajjar, R J, and Weber, T (2015). High capsid-genome correlation facilitates creation of AAV libraries for directed evolution. Mol Ther 23: 675-682.
84. Doshi, B S, and Arruda, V R (2018). Gene therapy for hemophilia: what does the future hold? Ther Adv Hematol 9: 273-293.
85. George, L, et al. (2017). Spk-8011: preliminary results from a phase 1/2 dose escalation trial of an investigational AAV-mediated gene therapy for hemophilia A. Blood 130.
86. Herrmann, A K, Grosse, S, Borner, K, Kramer, C, Wiedtke, E, Gunkel, M, et al. (2018). Impact of the assembly-activating protein (AAP) on molecular evolution of synthetic Adeno-associated virus (AAV) capsids. Hum Gene Ther.
87. Sonntag, F, Kother, K, Schmidt, K, Weghofer, M, Raupp, C, Nieto, K, et al. (2011). The assembly-activating protein promotes capsid assembly of different adeno-associated virus serotypes. J Virol 85: 12686-12697.
88. Sonntag, F, Schmidt, K, and Kleinschmidt, J A (2010). A viral assembly factor promotes AAV2 capsid formation in the nucleolus. Proc Natl Acad Sci USA 107: 10220-10225.
89. Grosse, S, Penaud-Budloo, M, Herrmann, A K, Borner, K, Fakhiri, J, Laketa, V, et al. (2017). Relevance of Assembly-Activating Protein for Adeno-associated Virus Vector Production and Capsid Protein Stability in Mammalian and Insect Cells. J Virol 91.
90. Herrmann, A K, Bender, C, Kienle, E, Grosse, S, El Andari, J, Botta, J, et al. (2018). A robust and all-inclusive pipeline for shuffling of Adeno-associated viruses (AAV). ACS Synth Biol.
91. Kienle, E, Senis, E, Borner, K, Niopek, D, Wiedtke, E, Grosse, S, et al. (2012). Engineering and evolution of synthetic adeno-associated virus (AAV) gene therapy vectors via DNA family shuffling. J Vis Exp.
92. Stamatakis, A (2015). Using RAxML to Infer Phylogenies. Curr Protoc Bioinformatics 51: 6 14 11-14.
93. Stamatakis, A, Ludwig, T, and Meier, H (2005). RAxML-III: a fast program for maximum likelihood-based inference of large phylogenetic trees. Bioinformatics 21: 456-463.
94. Xie, Q, Lerch, T F, Meyer, N L, and Chapman, M S (2011). Structure-function analysis of receptor-binding in adeno-associated virus serotype 6 (AAV-6). Virology 420: 10-19.
95. Charville, G W, Cheung, T H, Yoo, B, Santos, P J, Lee, G K, Shrager, J B, et al. (2015). Ex Vivo Expansion and In Vivo Self-Renewal of Human Muscle Stem Cells. Stem Cell Reports 5: 621-632.
96. Chakravarti, D, and Mailander, P C (2008). Formation of template-switching artifacts by linear amplification. J Biomol Tech 19: 184-188.
97. Odelberg, S J, Weiss, R B, Hata, A, and White, R (1995). Template-switching during DNA synthesis by *Thermus aquaticus* DNA polymerase I. Nucleic Acids Res 23: 2049-2057.
98. Paabo, S, Irwin, D M, and Wilson, A C (1990). DNA damage promotes jumping between templates during enzymatic amplification. J Biol Chem 265: 4718-4721.
99. Dorrell, C, Abraham, S L, Lanxon-Cookson, K M, Canaday, P S, Streeter, P R, and Grompe, M (2008). Isolation of major pancreatic cell types and long-term culture-initiating cells using novel human surface markers. Stem Cell Res 1: 183-194.
100. Russ, H A, Parent, A V, Ringler, J J, Hennings, T G, Nair, G G, Shveygert, M, et al. (2015). Controlled induction of human pancreatic progenitors produces functional beta-like cells in vitro. EMBO J 34: 1759-1772.
101. Meliani, A, Leborgne, C, Triffault, S, Jeanson-Leh, L, Veron, P, and Mingozzi, F (2015). Determination of anti-adeno-associated virus vector neutralizing antibody titer with an in vitro reporter system. Hum Gene Ther Methods 26: 45-53.

The examples set forth above are provided to give those of ordinary skill in the art a complete disclosure and description of how to make and use the embodiments of the compositions, systems and methods of the invention, and are not intended to limit the scope of what the inventors regard as their invention. Modifications of the above-described modes for carrying out the invention that are obvious to persons of skill in the art are intended to be within the scope of the following claims. All patents and publications mentioned in the specification are indicative of the levels of skill of those skilled in the art to which the invention pertains. All references cited in this disclosure are incorporated by reference to the same extent as if each reference had been incorporated by reference in its entirety individually.

All headings and section designations are used for clarity and reference purposes only and are not to be considered limiting in any way. For example, those of skill in the art will appreciate the usefulness of combining various aspects from different headings and sections as appropriate according to the spirit and scope of the invention described herein.

All references cited herein are hereby incorporated by reference herein in their entireties and for all purposes to the same extent as if each individual publication or patent or patent application was specifically and individually indicated to be incorporated by reference in its entirety for all purposes.

Many modifications and variations of this application can be made without departing from its spirit and scope, as will be apparent to those skilled in the art. The specific embodiments and examples described herein are offered by way of example only, and the application is to be limited only by the terms of the appended claims, along with the full scope of equivalents to which the claims are entitled.

What is claimed is:

1. An adeno-associated virus (AAV) capsid polypeptide, wherein said AAV capsid polypeptide sequence is selected from the group consisting of AAV-10A1 (SEQ ID NO:1), AAV-10A3 (SEQ ID NO:2), AAV-10A4 (SEQ ID NO:3), AAV-10A5 (SEQ ID NO:4), AAV-18A1 (SEQ ID NO:5), AAV-10B1 (SEQ ID NO:6), AAV-10B3 (SEQ ID NO:7), AAV-10B5 (SEQ ID NO:8), AAV-10B6 (SEQ ID NO:9), AAV-10B7 (SEQ ID NO:10), AAV-18B2 (SEQ ID NO:12), and AAV-18B3 (SEQ ID NO:13).

2. An adeno-associated virus (AAV) vector comprising a nucleic acid sequence encoding an AAV capsid polypeptide, wherein said AAV capsid polypeptide sequence is selected from the group consisting of AAV-10A1 (SEQ ID NO:1), AAV-10A3 (SEQ ID NO:2), AAV-10A4 (SEQ ID NO:3), AAV-10A5 (SEQ ID NO:4), AAV-18A1 (SEQ ID NO:5), AAV-10B1 (SEQ ID NO:6), AAV-10B3 (SEQ ID NO:7), AAV-10B5 (SEQ ID NO:8), AAV-10B6 (SEQ ID NO:9), AAV-10B7 (SEQ ID NO:10), AAV-18B2 (SEQ ID NO:12), and AAV-18B3 (SEQ ID NO:13).

3. The AAV capsid polypeptide of claim 1, wherein the AAV capsid polypeptide sequence comprises AAV-10A1 (SEQ ID NO:1).

4. The AAV capsid polypeptide of claim 1, wherein the AAV capsid polypeptide sequence comprises AAV-10A3 (SEQ ID NO:2).

5. The AAV capsid polypeptide of claim 1, wherein the AAV capsid polypeptide sequence comprises AAV-10A4 (SEQ ID NO:3).

6. The AAV capsid polypeptide of claim 1, wherein the AAV capsid polypeptide sequence comprises AAV-10A5 (SEQ ID NO:4).

7. The AAV capsid polypeptide of claim 1, wherein the AAV capsid polypeptide sequence comprises AAV-18A1 (SEQ ID NO:5).

8. The AAV capsid polypeptide of claim 1, wherein the AAV capsid polypeptide sequence comprises AAV-10B1 (SEQ ID NO:6).

9. The AAV capsid polypeptide of claim 1, wherein the AAV capsid polypeptide sequence comprises AAV-10B3 (SEQ ID NO:7).

10. The AAV capsid polypeptide of claim 1, wherein the AAV capsid polypeptide sequence comprises AAV-10B5 (SEQ ID NO:8).

11. The AAV capsid polypeptide of claim 1, wherein the AAV capsid polypeptide sequence comprises AAV-10B6 (SEQ ID NO:9).

12. The AAV capsid polypeptide of claim 1, wherein the AAV capsid polypeptide sequence comprises AAV-10B7 (SEQ ID NO:10).

13. The AAV capsid polypeptide of claim 1, wherein the AAV capsid polypeptide sequence comprises AAV-18B2 (SEQ ID NO:12).

14. The AAV capsid polypeptide of claim 1, wherein the AAV capsid polypeptide sequence comprises AAV-18B3 (SEQ ID NO:13).

15. The AAV vector of claim 2, wherein the AAV capsid polypeptide sequence comprises AAV-10A1 (SEQ ID NO:1).

16. The AAV vector of claim 2, wherein the AAV capsid polypeptide sequence comprises AAV-10A3 (SEQ ID NO:2).

17. The AAV vector of claim 2, wherein the AAV capsid polypeptide sequence comprises AAV-10A4 (SEQ ID NO:3).

18. The AAV vector of claim 2, wherein the AAV capsid polypeptide sequence comprises AAV-10A5 (SEQ ID NO:4).

19. The AAV vector of claim 2, wherein the AAV capsid polypeptide sequence comprises AAV-18A1 (SEQ ID NO:5).

20. The AAV vector of claim 2, wherein the AAV capsid polypeptide sequence comprises AAV-10B1 (SEQ ID NO:6).

21. The AAV vector of claim 2, wherein the AAV capsid polypeptide sequence comprises AAV-10B3 (SEQ ID NO:7).

22. The AAV vector of claim 2, wherein the AAV capsid polypeptide sequence comprises AAV-10B5 (SEQ ID NO:8).

23. The AAV vector of claim 2, wherein the AAV capsid polypeptide sequence comprises AAV-10B6 (SEQ ID NO:9).

24. The AAV vector of claim 2, wherein the AAV capsid polypeptide sequence comprises AAV-10B7 (SEQ ID NO:10).

25. The AAV vector of claim 2, wherein the AAV capsid polypeptide sequence comprises AAV-18B2 (SEQ ID NO:12).

26. The AAV vector of claim 2, wherein the AAV capsid polypeptide sequence comprises AAV-18B3 (SEQ ID NO:13).

* * * * *